US012492181B2

(12) United States Patent
Han et al.

(10) Patent No.: US 12,492,181 B2
(45) Date of Patent: Dec. 9, 2025

(54) GEM-DISUBSTITUTED PIPERIDINE MELANOCORTIN SUBTYPE-2 RECEPTOR (MC2R) ANTAGONISTS AND USES THEREOF

(71) Applicant: Crinetics Pharmaceuticals, Inc., San Diego, CA (US)

(72) Inventors: Sangdon Han, San Diego, CA (US); Sun Hee Kim, San Diego, CA (US); Yunfei Zhu, San Diego, CA (US)

(73) Assignee: CRINETICS PHARMACEUTICALS, INC., San Diego, CA (US)

( * ) Notice: Subject to any disclaimer, the term of this patent is extended or adjusted under 35 U.S.C. 154(b) by 772 days.

(21) Appl. No.: 17/785,787

(22) PCT Filed: Dec. 11, 2020

(86) PCT No.: PCT/US2020/064493
§ 371 (c)(1),
(2) Date: Jun. 15, 2022

(87) PCT Pub. No.: WO2021/126693
PCT Pub. Date: Jun. 24, 2021

(65) Prior Publication Data

US 2023/0135560 A1 May 4, 2023

Related U.S. Application Data

(60) Provisional application No. 62/949,854, filed on Dec. 18, 2019.

(51) Int. Cl.
*C07D 401/04* (2006.01)
*C07D 211/14* (2006.01)

(52) U.S. Cl.
CPC .......... *C07D 401/04* (2013.01); *C07D 211/14* (2013.01)

(58) Field of Classification Search
CPC ............................ C07D 401/04; C07D 211/14
See application file for complete search history.

(56) References Cited

U.S. PATENT DOCUMENTS

| | | | |
|---|---|---|---|
| 5,284,956 A | 2/1994 | Buchecker et al. | |
| 6,664,273 B2 * | 12/2003 | Burnett | C07D 401/06 546/208 |
| 6,833,369 B2 | 12/2004 | Stokbroekx et al. | |
| 7,208,503 B2 | 4/2007 | Stokbroekx et al. | |
| 7,576,076 B2 | 8/2009 | Clark et al. | |
| 7,880,007 B2 | 2/2011 | Hurley et al. | |
| 10,562,884 B2 | 2/2020 | Han et al. | |
| 10,604,507 B2 | 3/2020 | Han et al. | |
| 10,766,877 B2 | 9/2020 | Han et al. | |
| 10,981,894 B2 | 4/2021 | Han et al. | |
| 11,414,429 B2 | 8/2022 | Yoshida et al. | |
| 2003/0158209 A1 | 8/2003 | Dyck et al. | |
| 2004/0053933 A1 | 3/2004 | Pontillo et al. | |
| 2004/0192676 A1 | 9/2004 | Chen et al. | |
| 2005/0119252 A1 | 6/2005 | Tucci et al. | |
| 2005/0192286 A1 | 9/2005 | Tran et al. | |
| 2006/0258672 A1 * | 11/2006 | Barbosa | A61P 25/00 544/360 |
| 2010/0016340 A1 | 1/2010 | Woodhead et al. | |
| 2013/0184285 A1 | 7/2013 | Brain et al. | |
| 2018/0078548 A1 | 3/2018 | Shoshan-Barmatz et al. | |
| 2018/0118700 A1 | 5/2018 | Shoshan-Barmatz et al. | |
| 2019/0367481 A1 | 12/2019 | Han et al. | |
| 2021/0238164 A1 | 8/2021 | Han et al. | |
| 2023/0015914 A1 | 1/2023 | Han et al. | |
| 2023/0126662 A1 | 4/2023 | Han et al. | |

FOREIGN PATENT DOCUMENTS

| | | |
|---|---|---|
| EP | 2448582 B1 | 4/2017 |
| EP | 3199156 A1 | 8/2017 |
| EP | 3480198 A1 | 5/2019 |
| JP | 2881750 B2 | 4/1999 |
| WO | WO-9858919 A1 | 12/1998 |
| WO | WO-9964002 A1 | 12/1999 |
| WO | WO-0074679 A1 | 12/2000 |
| WO | WO-03009847 A1 | 2/2003 |
| WO | WO-03009850 A1 | 2/2003 |
| WO | WO-03031410 A1 | 4/2003 |
| WO | WO-03045918 A1 | 6/2003 |
| WO | WO-03068738 A1 | 8/2003 |
| WO | WO-03094918 A1 | 11/2003 |
| WO | WO-2004058735 A2 | 7/2004 |
| WO | WO-2004083209 A1 | 9/2004 |
| WO | WO-2005014563 A1 | 2/2005 |
| WO | WO-2005023260 A1 | 3/2005 |

(Continued)

OTHER PUBLICATIONS

Arasasingham et al. Structure-activity relationship of (1-aryl-2-piperazinylethyl)piperazines: antagonists for the AGRP/melanocortin receptor binding. J Med Chem 46:9-11 (2003).
Berge et al. Pharmaceutical Salts. Journal of Pharmaceutical Sciences 66(1):1-19 (Jan. 1977).
Bundgaard. Design and Application of Prodrugs. Textbook of Drug Design and Development. Krosgaard-Larsen and Bundgaard. Chapter 5. pp. 113-191 (1991).
Bundgaard. Means to Enhance Penetration: Prodrugs as a Means to Improve the Delivery of Peptide Drugs. Advanced Drug Delivery Review 8:1-38 (1992).
Chen et al. Identification and characterization of pyrrolidine diastereoisomers as potent functional agonists and antagonists of the human melanocortin-4 receptor. Bioorg Med Chem Lett 18:129-136 (2008).

(Continued)

*Primary Examiner* — Rebecca L Anderson
(74) *Attorney, Agent, or Firm* — WILSON SONSINI GOODRICH & ROSATI

(57) ABSTRACT

Described herein are compounds that are melanocortin subtype-2 receptor (MC2R) modulators, methods of making such compounds, pharmaceutical compositions and medicaments comprising such compounds, and methods of using such compounds in the treatment of conditions, diseases, or disorders that would benefit from modulation of MC2R activity.

21 Claims, No Drawings

(56) References Cited

FOREIGN PATENT DOCUMENTS

| | | | |
|---|---|---|---|
| WO | WO-2005040109 | A1 | 5/2005 |
| WO | WO-2005040136 | A1 | 5/2005 |
| WO | WO-2005042516 | A2 | 5/2005 |
| WO | WO-2005047253 | A1 | 5/2005 |
| WO | WO-2006113704 | A2 | 10/2006 |
| WO | WO-2007047496 | A2 | 4/2007 |
| WO | WO-2007076070 | A2 | 7/2007 |
| WO | WO-2007125325 | A1 | 11/2007 |
| WO | WO-2009124692 | A1 | 10/2009 |
| WO | WO-2010026124 | A1 | 3/2010 |
| WO | WO-2012163354 | A1 | 12/2012 |
| WO | WO-2013047144 | A1 | 4/2013 |
| WO | WO-2017046794 | A1 | 3/2017 |
| WO | WO-2018116307 | A1 | 6/2018 |
| WO | WO-2019014460 | A1 | 1/2019 |
| WO | WO-2019079373 | A1 | 4/2019 |
| WO | WO-2019236699 | A1 | 12/2019 |
| WO | WO-2021091788 | A1 | 5/2021 |
| WO | WO-2021126693 | A1 | 6/2021 |
| WO | WO-2021133563 | A1 | 7/2021 |

OTHER PUBLICATIONS

Chen et al. Pharmacological and pharmacokinetic characterization of 2-piperazine-a-isopropyl benzylamine derivatives as melanocortin-4 receptor antagonists. Bioorg Med Chem 16:5606-5618 (2008).

Fukuoka et al. The Mechanisms Underlying Autonomous Adrenocorticotropic Hormone Secretion in Cushing's Disease. Int J Mol Sci. 21(23):9132 (2020).

Gantz et al. The melanocortin system. Am. J. Physiol. Endocrinol. Metab. 284:E468-E474 (2003).

PCT/US2020/064493 International Search Report and Written Opinion dated Apr. 12, 2021.

Richardson et al. Synthesis and structure-activity relationships of novel arylpiperazines as potent and selective agonists of the melanocortin subtype-4 receptor. J Med Chem 47:744-755 (2004).

Science IP Report dated Jun. 7, 2019 (135 pgs).

Science IP Report dated Mar. 29, 2018 (129 pgs).

Sebhat et al., Melanocortin subtype 4 receptor agonists: Structure-activity relationships about the 4-alkyl piperidine core. Bioorg. Med. Chem. Lett. 17:5720-5723 (2007).

Tian et al. Design, Synthesis, and Evaluation of Proline and Pyrrolidine Based Melanocortin Receptor Agonists. A Conformationally Restricted Dipeptide Mimic Approach. J Med Chem 49:4745-4761 (2006).

Tran et al. Syntheses of tetrahydrothiophenes and tetrahydrofurans and studies of their derivatives as melanocortin-4 receptor ligands. Bioorg Med Chem Lett 18:1124-1130 (2008).

Widder et al. Section III: Prodrugs Kinetics. Method in Enzymology. 112:309-396 (1985).

* cited by examiner

GEM-DISUBSTITUTED PIPERIDINE MELANOCORTIN SUBTYPE-2 RECEPTOR (MC2R) ANTAGONISTS AND USES THEREOF

CROSS-REFERENCE TO RELATED APPLICATIONS

This application claims the benefit of U.S. Provisional Patent Application No. 62/949,854 filed on Dec. 18, 2019, which is herein incorporated by reference in its entirety.

FIELD OF THE INVENTION

Described herein are compounds that modulate the activity of one or more melanocortin receptors, methods of making such compounds, pharmaceutical compositions and medicaments comprising such compounds, and methods of using such compounds in the treatment of conditions, diseases, or disorders that would benefit from modulating melanocortin subtype-2 receptor (MC2R) activity.

BACKGROUND OF THE INVENTION

The melanocortin receptors form a family of G protein-coupled receptor (GPCRs) (MC1R, MC2R, MC3R, MC4R, and MC5R) that are selectively activated by different melanocortin peptides adrenocorticotropic hormone (ACTH), and the melanocortin peptides α-, β-, and γ-melanocyte-stimulating hormone (α-MSH, β-MSH, and γ-MSH) that are all derived proteolytically from proopiomelanocortin hormone, or POMC. ACTH is a 39 amino acid peptide that is the primary regulator of adrenal glucocorticoid synthesis and secretion and only has affinity for MC2R. As the central actor in this hypothalamic-pituitary-adrenal (HPA) axis, ACTH is secreted by the pituitary in response to stressful stimuli and acts at the adrenal gland to stimulate the synthesis and secretion of cortisol. Modulation of MC2R is attractive for the treatment of conditions, diseases, or disorders that would benefit from modulating melanocortin receptor activity.

SUMMARY OF THE INVENTION

Compounds described herein are melanocortin receptor modulator compounds. In some embodiments, compounds described herein modulate one or more of the subtype melanocortin receptor proteins. In some embodiments, compounds described herein modulate two or more of the subtype melanocortin receptor proteins. In some embodiments, compounds described herein modulate MC2R.

In one aspect, described herein is a compound of Formula (I), or a pharmaceutically acceptable salt, or solvate thereof:

Formula (I)

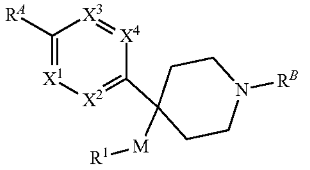

wherein:

$R^A$ is unsubstituted or substituted heteroaryl or unsubstituted or substituted aryl, wherein if $R^A$ is substituted then $R^A$ is substituted with 1, 2, 3 or 4 groups selected from $R^a$, $R^b$, and $R^c$;

$R^a$, $R^b$, and $R^c$ are independently selected from the group consisting of hydrogen, halogen, —$OR^4$, —CN, —$N(R^4)_2$, —C(═O)$R^7$, unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted $C_3$-$C_6$ cycloalkyl, unsubstituted or substituted $C_2$-$C_7$ heterocycloalkyl, unsubstituted or substituted phenyl, and unsubstituted or substituted heteroaryl, wherein any substituted group of $R^a$, $R^b$, and $R^c$ is substituted with one or more $R^6$ groups;

or one $R^a$ and one $R^b$, when present on adjacent atoms of $R^A$, are taken together with the intervening atoms connecting $R^a$ to $R^b$ to form a 5- to 6-membered monocyclic carbocycle or 5- to 6-membered monocyclic heterocycle, wherein the carbocycle or heterocycle is unsubstituted or substituted with one or more $R^6$ groups;

wherein, if $R^a$, $R^b$, or $R^c$ is attached to the N atom of a heteroaryl, then it is hydrogen, —C(═O)$R^7$, unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted $C_3$-$C_6$ cycloalkyl, or unsubstituted or substituted $C_2$-$C_7$ heterocycloalkyl;

$R^B$ is unsubstituted or substituted aryl or unsubstituted or substituted heteroaryl, wherein if $R^B$ is substituted then $R^B$ is substituted with 1, 2, 3 or 4 groups selected from $R^d$, $R^e$, and $R^f$;

$R^d$, $R^e$, and $R^f$ are independently selected from the group consisting of hydrogen, halogen, —$OR^4$, —CN, —$N(R^4)_2$, —C(═O)$R^7$, —C(═O)$N(R^4)_2$, unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted $C_3$-$C_6$ cycloalkyl, unsubstituted or substituted $C_2$-$C_7$ heterocycloalkyl, unsubstituted or substituted phenyl, and unsubstituted or substituted heteroaryl, wherein any substituted group of $R^d$, $R^e$, and $R^f$ is substituted with one or more $R^6$ groups;

wherein, if $R^d$, $R^e$, or $R^f$ is attached to the N atom of a heteroaryl, then it is hydrogen, —C(═O)$R^7$, unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted $C_3$-$C_6$ cycloalkyl, or unsubstituted or substituted $C_2$-$C_7$ heterocycloalkyl;

$X^1$ is $CR^{11}$ or N;

$X^2$ is $CR^{12}$ or N;

$X^3$ is $CR^{13}$ or N;

$X^4$ is $CR^{14}$ or N;

$R^{11}$, $R^{12}$, $R^{13}$, and $R^{14}$ are each independently hydrogen, halogen, unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted $C_3$-$C_6$cycloalkyl, —CN, —$OR^4$, —$SR^4$, —$CO_2R^4$, —C(═O)$N(R^4)_2$, or —$N(R^4)_2$;

M is —(C═O)—, —$NR^3$—, —O—, —S—, —$SO_2$—, *—$NR^3$—(C═O)—, *—(C═O)—$NR^3$—, *—O—(C═O)$NR^3$—, *—$NR^3$—(C═O)O—, —$NR^3$—(C═O)$NR^3$—, *—$NR^3(SO_2)$—, *—$SO_2NR^3$—, or 5-membered heterocycle, wherein * indicates the attachment point to $R^1$;

$R^1$ is unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted $C_3$-$C_6$ cycloalkyl, unsubstituted or substituted $C_2$-$C_7$ heterocycloalkyl, unsubstituted or substituted —($C_1$-$C_6$ alkyl)-($C_3$-$C_6$ cycloalkyl), or unsubstituted or substituted —($C_1$-$C_6$ alkyl)-($C_2$-$C_7$ heterocycloalkyl), wherein any substituted group of $R^1$ is substituted with one or more halogen, unsubstituted or substituted $C_1$-$C_6$ alkyl, unsubstituted or substituted monocyclic heterocycle, —$N(R^4)_2$, —$OR^5$, —CN, —$CO_2R^5$, —$C(=O)N(R^4)_2$, —$SR^5$, —$S(=O)R^7$, —$S(=O)_2R^7$, —$NR^4C(=O)R^5$, —$NR^4SO_2R^7$, —$SO_2R^7$, or —$SO_2N(R^4)_2$;

each $R^3$ is independently hydrogen, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl;

each $R^4$ is independently selected from the group consisting of hydrogen, unsubstituted or substituted $C_1$-$C_6$ alkyl, unsubstituted or substituted $C_3$-$C_6$ cycloalkyl, unsubstituted or substituted $C_1$-$C_6$fluoroalkyl, unsubstituted or substituted aryl, and unsubstituted or substituted heteroaryl;

or two $R^4$ are taken together with the nitrogen atom to which they are attached to form an unsubstituted or substituted 3- to 6-membered monocyclic heterocycle;

each $R^5$ is independently selected from the group consisting of hydrogen, substituted $C_1$-$C_6$ alkyl, unsubstituted or substituted $C_3$-$C_6$ cycloalkyl, unsubstituted or substituted $C_1$-$C_6$fluoroalkyl, unsubstituted or substituted aryl, and unsubstituted or substituted heteroaryl;

each $R^6$ is independently hydrogen, halogen, unsubstituted or substituted $C_1$-$C_4$alkyl, unsubstituted or substituted $C_1$-$C_4$alkoxy, unsubstituted or substituted $C_1$-$C_4$fluoroalkyl, unsubstituted or substituted $C_1$-$C_4$fluoroalkoxy, unsubstituted or substituted monocyclic carbocycle, unsubstituted or substituted monocyclic heterocycle, —CN, —OH, —$CO_2R^5$, —$CH_2CO_2R^5$, —$C(=O)N(R^4)_2$, —$C(=O)N(R^4)OR^5$, —$CH_2C(=O)N(R^4)_2$, —$N(R^4)_2$, —$CH_2N(R^4)_2$, —$C(R^5)_2N(R^4)_2$, —$NR^4C(=O)R^5$, —$CH_2NR^4C(=O)R^5$, —$NR^4C(=O)N(R^5)_2$, —$NR^4C(=O)N(R^4)_2$, $C(R^5)=N(R^4)$—$OR^5$, —$SR^5$, —$S(=O)R^7$, —$SO_2R^7$, or —$SO_2N(R^4)_2$; and each $R^7$ is independently selected from the group consisting substituted $C_1$-$C_6$ alkyl, unsubstituted or substituted $C_3$-$C_6$ cycloalkyl, unsubstituted or substituted $C_1$-$C_6$fluoroalkyl, unsubstituted or substituted phenyl, and unsubstituted or substituted heteroaryl.

Also described herein is a pharmaceutical composition comprising a compound described herein, or a pharmaceutically acceptable salt, or solvate thereof, and at least one pharmaceutically acceptable excipient. In some embodiments, the pharmaceutical composition is formulated for administration to a mammal by intravenous administration, subcutaneous administration, oral administration, inhalation, nasal administration, dermal administration, or ophthalmic administration. In some embodiments, the pharmaceutical composition is formulated for administration to a mammal by oral administration. In some embodiments, the pharmaceutical composition is in the form of a tablet, a pill, a capsule, a liquid, a suspension, a gel, a dispersion, a solution, an emulsion, an ointment, or a lotion. In some embodiments, the pharmaceutical composition is in the form of a tablet, a pill, or a capsule.

In any of the aforementioned aspects are further embodiments in which the effective amount of the compound of Formula (I), or a pharmaceutically acceptable salt thereof, is: (a) systemically administered to the mammal; and/or (b) administered orally to the mammal; and/or (c) intravenously administered to the mammal; and/or (d) administered by inhalation; and/or (e) administered by nasal administration; or and/or (f) administered by injection to the mammal; and/or (g) administered topically to the mammal; and/or (h) administered by ophthalmic administration; and/or (i) administered rectally to the mammal; and/or (j) administered non-systemically or locally to the mammal.

In any of the aforementioned aspects are further embodiments comprising single administrations of the effective amount of the compound, including further embodiments in which the compound is administered once a day to the mammal or the compound is administered to the mammal multiple times over the span of one day. In some embodiments, the compound is administered on a continuous dosing schedule. In some embodiments, the compound is administered on a continuous daily dosing schedule.

In any of the embodiments disclosed herein, the mammal is a human.

In some embodiments, compounds provided herein are orally administered to a human.

Articles of manufacture, which include packaging material, a compound of Formula (I), or a pharmaceutically acceptable salt thereof, within the packaging material, and a label that indicates that the compound or composition, or pharmaceutically acceptable salt, tautomers, pharmaceutically acceptable N-oxide, pharmaceutically active metabolite, pharmaceutically acceptable prodrug, or pharmaceutically acceptable solvate thereof, is used for modulating one or more subtype melanocortin receptor proteins, or for the treatment, prevention or amelioration of one or more symptoms of a disease or condition that would benefit from modulating one or more subtype melanocortin receptor proteins, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Adrenocorticotropic hormone (ACTH) is a 39 amino acid peptide synthesized by anterior pituitary corticotrophic cells by proteolytic cleavage of the proopiomelanocortin hormone (POMC). ACTH is the primary regulator of adrenal glucocorticoid (GC; cortisol in humans and most other species; corticosterone in rodents) synthesis and secretion. As the central actor in this hypothalamic-pituitary-adrenal (HPA) axis, ACTH is secreted by the pituitary in response to stressful stimuli and acts at the adrenal gland to stimulate the synthesis and secretion of cortisol. This stimulation is mediated through a highly specific G protein-coupled receptor (GPCR) which is expressed almost uniquely in the adrenal cortex. The receptor is the melanocortin 2 receptor (MC2R), and, along with ACTH, is part of the larger melanocortin system.

The melanocortin system comprises a family of five GPCRs (MC1R, MC2R, MC3R, MC4R, and MC5R); their natural agonists, the melanocortin peptides α-, β-, and γ-melanocyte-stimulating hormone (α-MSH, β-MSH, and γ-MSH) and ACTH; and endogenous melanocortin antagonists agouti and agouti-related protein (AGRP). The melanocortin receptors (MCRs) have different selectivities for endogenous agonist and antagonist peptides and are expressed in diverse tissues where they serve varied and discreet physiological functions (Gantz, I. and T. M. Fong, *Am. J. Physiol. Endocrinol. Metab.,* 284: E468-E474, 2003).

It is possible to selectively modulate any one of the MCRs, or combinations thereof. In some embodiments, selectively modulating any one of the MCRs relative to the other MCRs, or combinations thereof, is useful in a variety of clinical applications. In some embodiments, selectively modulating any one of the MCRs relative to the other MCRs, or combinations thereof, reduces unwanted side effects in a variety of clinical applications. In one aspect, compounds described herein are antagonists of MC2R. In some embodiments, compounds described herein are selective antagonists for MC2R relative or other MCRs.

MC2R is a highly selective receptor for ACTH. Although ACTH can activate all five MCRs, at physiological levels, the sensitivity of the other receptors is not high enough to be activated, and ACTH selectively activates MC2R. Importantly, the other naturally occurring agonists α-MSH, β-MSH, and γ-MSH have no affinity for MC2R (Gantz, I. and T. M. Fong, *Am. J. Physiol. Endocrinol. Metab.,* 284: E468-E474, 2003). The major function of MC2R is to stimulate the fasciculata cells of the adrenal cortex to synthesize and secret cortisol. MC2R requires the GPCR accessory protein MRAP (melanocortin 2 receptor protein) to be successfully secreted to the cell surface and as well as to function. MRAP is a small protein with a single transmembrane domain that forms an antiparallel homodimer in stable complex with MC2R and is necessary for both cell surface expression of MC2R and its ability to bind ACTH. MRAP can bind to any of the MCRs and affect their activities, but is only essential for MC2R activity. Binding of ACTH to the MC2R/MRAP complex on adrenal cortical cells activates Gs to elevate intracellular cAMP levels which in turn stimulates cortisol synthesis and secretion by regulating multiple steps in the steroidogenic pathway.

Cushing's syndrome is a rare disorder characterized by chronic, excess glucocorticoid exposure. Clinical signs of Cushing's syndrome include growth of fat pads (collarbone, back of neck, face and trunk), excessive sweating, dilation of capillaries, thinning of the skin, muscle weakness, hirsutism, depression/anxiety, hypertension, osteoporosis, insulin resistance, hyperglycemia, heart disease, and a range of other metabolic disturbances resulting in high morbidity. If inadequately controlled in its severe forms, Cushing's syndrome is associated with high mortality. Although glucocorticoid excess can sometimes be ACTH independent, for example from excessive autonomous secretion of cortisol from a hyperfunctioning adrenal adenoma, carcinoma, or steroid abuse, about 60-80% of all cases are ACTH dependent Cushing's syndrome, known as Cushing's disease. Cushing's disease is caused by microadenomas of pituitary corticotropic cells that secrete excess ACTH. Corticotroph adenomas are small, usually slow growing, benign tumors that normally come to clinical attention as a result of the effects of glucocorticoid excess, rather than because of the physical effects of an expanding tumor. First line treatments for Cushing's disease are surgical and involve removal of either the ACTH-secreting tumor in the pituitary or the adrenal glands themselves. As surgery is often unsuccessful, contraindicated, or delayed, medical therapy for these patients becomes necessary. Current treatment options include inhibitors of steroid synthesis enzymes that can prevent the production of cortisol and improve symptoms, but these treatments also induce a host of unwanted side effects due to the accumulation of other steroid products. In one aspect, an MC2R antagonist is used in the treatment of Cushing's syndrome. In some embodiments, an MC2R antagonist is used in the treatment of Cushing's disease. In some embodiments, glucocorticoid excess is ACTH independent. In some embodiments, glucocorticoid excess is ACTH dependent.

Ectopic ACTH syndrome, or ectopic Cushing's syndrome or disease, is essentially the same as Cushing's disease, except that the underlying tumor expressing ACTH is outside the pituitary gland. In some embodiments, the tumors are small carcinoid tumors that occur anywhere in the lungs or gastrointestinal tract. In some embodiments, an MC2R antagonist is used in the treatment of ectopic ACTH syndrome.

Congenital adrenal hyperplasia (CAH) is characterized by a reduction or loss of cortisol synthesis and excessive ACTH and corticotropin-releasing hormone. CAH can result from a variety of genetic defects in the adrenal steroidal biosynthesis pathway. In some embodiments, CAH is due to a mutation in 21β-hydroxylase. The lack of cortisol removes the negative feedback to the pituitary which leads to excessive ACTH secretion. The resulting excessive adrenal stimulation causes overproduction of steroid precursors which also have negative consequences (e.g., hyperandrogenism). Administration of replacement glucocorticoids typically does not adequately suppress ACTH without also causing Cushing's-like symptoms. In some embodiments, an MC2R antagonist is used in the treatment of CAH.

In addition to Cushing's disease, Ectopic ACTH syndrome and CAH it has also been hypothesized that there might be a role for an MC2R antagonist in the treatment of ACTH driven adrenal tumors, Functional Adrenal Hyperandrogenism (FAH), stress disorders, psychiatric disorders, type 2 diabetes and septic shock. In some embodiments, an MC2R antagonist is used in the treatment of ACTH driven adrenal tumors. In some embodiments, an MC2R antagonist is used in the treatment of Functional Adrenal Hyperandrogenism. In some embodiments, an MC2R antagonist is used in the treatment of stress disorders. In some embodiments, an MC2R antagonist is used in the treatment of psychiatric disorders. In some embodiments, an MC2R antagonist is used in the treatment of type 2 diabetes. In some embodiments, an MC2R antagonist is used in the treatment of septic shock.

In some embodiments, an MC2R antagonist is used in the treatment of septic shock.

In some embodiments, compounds described herein are amenable to administration to a mammal in need of treatment with an MC2R antagonist.

Compounds

Compounds of Formula (I), including pharmaceutically acceptable salts, prodrugs, active metabolites and pharmaceutically acceptable solvates thereof, are melanocortin receptor modulators. In some embodiments, the compounds of Formula (I), including pharmaceutically acceptable salts, prodrugs, active metabolites and pharmaceutically acceptable solvates thereof, are MC2R modulators. In some embodiments, the MC2R modulators are MC2R antagonists.

In one aspect, provided herein is a compound of Formula (I), or a pharmaceutically acceptable salt, or solvate thereof:

Formula (I)

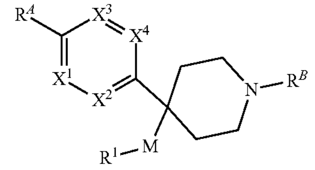

wherein:

$R^A$ is unsubstituted or substituted heteroaryl or unsubstituted or substituted aryl, wherein if $R^A$ is substituted then $R^A$ is substituted with 1, 2, 3 or 4 groups selected from $R^a$, $R^b$, and $R^c$;

$R^a$, $R^b$, and $R^c$ are independently selected from the group consisting of hydrogen, halogen, —$OR^4$, —CN, —$N(R^4)_2$, —C(═O)$R^7$, unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted $C_3$-$C_6$ cycloalkyl, unsubstituted or substituted $C_2$-$C_7$ heterocycloalkyl, unsubstituted or substituted phenyl, and unsubstituted or substituted heteroaryl, wherein any substituted group of $R^a$, $R^b$, and $R^c$ is substituted with one or more $R^6$ groups;

or one $R^a$ and one $R^b$, when present on adjacent atoms of $R^A$, are taken together with the intervening atoms connecting $R^a$ to $R^b$ to form a 5- to 6-membered monocyclic carbocycle or 5- to 6-membered monocyclic heterocycle, wherein the carbocycle or heterocycle is unsubstituted or substituted with one or more $R^6$ groups;

wherein, if $R^a$, $R^b$, or $R^c$ is attached to the N atom of a heteroaryl, then it is hydrogen, —C(═O)$R^7$, unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted $C_3$-$C_6$ cycloalkyl, or unsubstituted or substituted $C_2$-$C_7$ heterocycloalkyl;

$R^B$ is unsubstituted or substituted aryl or unsubstituted or substituted heteroaryl, wherein if $R^B$ is substituted then $R^B$ is substituted with 1, 2, 3 or 4 groups selected from $R^d$, $R^e$, and $R^f$;

$R^d$, $R^e$, and $R^f$ are independently selected from the group consisting of hydrogen, halogen, —$OR^4$, —CN, —$N(R^4)_2$, —C(═O)$R^7$, —C(═O)$N(R^4)_2$, unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted $C_3$-$C_6$ cycloalkyl, unsubstituted or substituted $C_2$-$C_7$ heterocycloalkyl, unsubstituted or substituted phenyl, and unsubstituted or substituted heteroaryl, wherein any substituted group of $R^d$, $R^e$, and $R^f$ is substituted with one or more $R^6$ groups;

wherein, if $R^d$, $R^e$, or $R^f$ is attached to the N atom of a heteroaryl, then it is hydrogen, —C(═O)$R^7$, unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted $C_3$-$C_6$ cycloalkyl, or unsubstituted or substituted $C_2$-$C_7$ heterocycloalkyl;

$X^1$ is $CR^{11}$ or N;

$X^2$ is $CR^{12}$ or N;

$X^3$ is $CR^{13}$ or N;

$X^4$ is $CR^{14}$ or N;

$R^{11}$, $R^{12}$, $R^{13}$, and $R^{14}$ are each independently hydrogen, halogen, unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted $C_3$-$C_6$cycloalkyl, —CN, —$OR^4$, —$SR^4$, —$CO_2R^4$, —C(═O)$N(R^4)_2$, or —$N(R^4)_2$;

M is —(C═O)—, —$NR^3$—, —O—, —S—, —$SO_2$—, *—$NR^3$—(C═O)—, *—(C═O)—$NR^3$—, *—O—(C═O)$NR^3$—, *—$NR^3$—(C═O)O—, —$NR^3$—(C═O)$NR^3$—, *—$NR^3(SO_2)$—, *—$SO_2NR^3$—, or 5-membered heterocycle, wherein * indicates the attachment point to $R^1$;

$R^1$ is unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted $C_3$-$C_6$ cycloalkyl, unsubstituted or substituted $C_2$-$C_7$ heterocycloalkyl, unsubstituted or substituted —($C_1$-$C_6$ alkyl)-($C_3$-$C_6$ cycloalkyl), or unsubstituted or substituted —($C_1$-$C_6$ alkyl)-($C_2$-$C_7$ heterocycloalkyl), wherein any substituted group of $R^1$ is substituted with one or more halogen, unsubstituted or substituted $C_1$-$C_6$ alkyl, unsubstituted or substituted monocyclic heterocycle, —$N(R^4)_2$, —$OR^5$, —CN, —$CO_2R^5$, —C(═O)$N(R^4)_2$, —$SR^5$, —S(═O)$R^7$, —S(═O)$_2R^7$, —$NR^4$C(═O)$R^5$, —$NR^4SO_2R^7$, —$SO_2R^7$, or —$SO_2N(R^4)_2$;

each $R^3$ is independently hydrogen, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl;

each $R^4$ is independently selected from the group consisting of hydrogen, unsubstituted or substituted $C_1$-$C_6$ alkyl, unsubstituted or substituted $C_3$-$C_6$ cycloalkyl, unsubstituted or substituted $C_1$-$C_6$fluoroalkyl, unsubstituted or substituted aryl, and unsubstituted or substituted heteroaryl;

or two $R^4$ are taken together with the nitrogen atom to which they are attached to form an unsubstituted or substituted 3- to 6-membered monocyclic heterocycle;

each $R^5$ is independently selected from the group consisting of hydrogen, substituted $C_1$-$C_6$ alkyl, unsubstituted or substituted $C_3$-$C_6$ cycloalkyl, unsubstituted or substituted $C_1$-$C_6$fluoroalkyl, unsubstituted or substituted aryl, and unsubstituted or substituted heteroaryl;

each $R^6$ is independently hydrogen, halogen, unsubstituted or substituted $C_1$-$C_4$alkyl, unsubstituted or substituted $C_1$-$C_4$alkoxy, unsubstituted or substituted $C_1$-$C_4$fluoroalkyl, unsubstituted or substituted $C_1$-$C_4$fluoroalkoxy, unsubstituted or substituted monocyclic carbocycle, unsubstituted or substituted monocyclic heterocycle, —CN, —OH, —$CO_2R^5$, —$CH_2CO_2R^5$, —C(═O)$N(R^4)_2$, —C(═O)$N(R^4)OR^5$, —$CH_2$C(═O)$N(R^4)_2$, —$N(R^4)_2$, —$CH_2N(R^4)_2$, —$C(R^5)_2N(R^4)_2$, —$NR^4$C(═O)$R^5$, —$CH_2NR^4$C(═O)$R^5$, —$NR^4$C(═O)$N(R^5)_2$, —$NR^4$C(═O)$N(R^4)_2$, $C(R^5)$═$N(R^4)$—$OR^5$, —$SR^5$, —S(═O)$R^7$, —$SO_2R^7$, or —$SO_2N(R^4)_2$; and each $R^7$ is independently selected from the group consisting substituted $C_1$-$C_6$ alkyl, unsubstituted or substituted $C_3$-$C_6$ cycloalkyl, unsubstituted or substituted $C_1$-$C_6$fluoroalkyl, unsubstituted or substituted phenyl, and unsubstituted or substituted heteroaryl.

In some embodiments, M is —C(═O)—, —$NR^3$—, —O—, —S—, —$SO_2$—, *—$NR^3$—(C═O)—, *—(C═O)—$NR^3$—, *—$NR^3SO_2$—, or 5-membered heterocycle, wherein * indicates the attachment point to $R^1$. In some embodiments, M is —C(═O)—, —$NR^3$—, —O—, —S—, —$SO_2$—, *—(C═O)—$NR^3$—, *—$NR^3$—(C═O)—, *—$NR^3SO_2$—, or 5-membered heteroaryl, wherein * indicates the attachment point to $R^1$.

In some embodiments, M is —O—, *—$NR^3$—C(═O)—, —S—, —$SO_2$—, *—$NR^3SO_2$—, or 5-membered heteroaryl, wherein * indicates the attachment point to $R^1$.

In some embodiments, M is 5-membered heterocycle. In some embodiments, M is 5-membered heteroaryl. In some embodiments, M is furanyl, thienyl, pyrrolyl, oxazolyl, thiazolyl, imidazolyl, pyrazolyl, triazolyl, isoxazolyl, isothiazolyl, oxadiazolyl, or thiadiazolyl. In some embodiments, M is oxazolyl, imidazolyl, or triazolyl.

In some embodiments, M is —$NR^3$—, —O—, *—$NR^3$—(C═O)—, *—(C═O)—$NR^3$—, *—O—(C═O)$NR^3$—, *—$NR^3$—(C═O)O—, or —$NR^3$—(C═O)$NR^3$—, wherein * indicates the attachment point to $R^1$. In some embodiments, M is *—$NR^3$—(C═O)—, *—(C═O)—$NR^3$—, *—O—(C═O)$NR^3$— *—$NR^3$—(C═O)O—, or —$NR^3$—(C═O)$NR^3$—, wherein * indicates the attachment point to $R^1$. In some embodiments, M is *—$NR^3$—(C═O)— or *—(C═O)—$NR_3$—, wherein * indicates the attachment point to $R^1$.

In some embodiments, M is *—(C═O)—$NR^3$—, wherein * indicates the attachment point to $R^1$. In some embodiments, M is *—$NR^3$—(C═O)—, wherein * indicates the attachment point to $R^1$.

In some embodiments, each $R^3$ is independently hydrogen or unsubstituted or substituted $C_1$-$C_6$ alkyl. In some embodiments, each $R^3$ is independently hydrogen or $C_1$-$C_6$ alkyl. In some embodiments, each $R^3$ is independently hydrogen, —$CH_3$, —$CH_2CH_3$, —$CH_2CH_2CH_3$, or —$CH(CH_3)_2$. In some embodiments, each $R^3$ is independently hydrogen or —$CH_3$. In some embodiments, each $R^3$ is —$CH_3$. In some embodiments, each $R^3$ is hydrogen.

In some embodiments, M is —$NR^3$—, —O—, *—$NR^3$—(C═O)—, *—(C═O)—$NR^3$—, *—O—(C═O)$NR^3$—, *—$NR^3$—(C═O)O—, or —$NR^3$—(C═O)$NR^3$—, wherein * indicates the attachment point to $R^1$; and each $R^3$ is independently hydrogen, —$CH_3$, —$CH_2CH_3$, —$CH_2CH_2CH_3$, or —$CH(CH_3)_2$. In some embodiments, M is *—$NR^3$—(C═O)— or *—(C═O)—$NR^3$—, wherein * indicates the attachment point to $R^1$; and $R^3$ is hydrogen.

In some embodiments, M comprises an N atom and the N atom of M is attached to $R^1$, wherein $R^1$ also comprises an N atom. In some embodiments, the N atom of M is connected to the N atom of $R^1$ through one carbon atom, two carbon atoms, three carbon atoms, or four carbon atoms. In some embodiments, the N atom of M is connected to the N atom of $R^1$ through a two carbon atom spacer. In some embodiments, the N atom of $R^1$ is part of an unsubstituted or substituted aliphatic alkyl chain. In some embodiments, the N atom of $R^1$ is part of an unsubstituted or substituted cyclic ring. In some embodiments, the N-containing cyclic ring of $R^1$ is an unsubstituted or substituted monocyclic $C_2$-$C_7$ heterocycloalkyl or unsubstituted or substituted bicyclic $C_2$-$C_7$ heterocycloalkyl.

In some embodiments, the compound has the structure of Formula (IIa), or a pharmaceutically acceptable salt, or solvate thereof:

Formula (IIa)

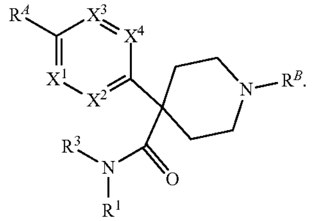

In some embodiments, the compound has the structure of Formula (IIb), or a pharmaceutically acceptable salt, or solvate thereof:

Formula (IIb)

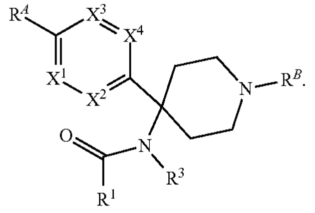

In some embodiments, $R^A$ is unsubstituted or substituted monocyclic 6-membered heteroaryl, unsubstituted or substituted phenyl, or unsubstituted or substituted monocyclic 5-membered heteroaryl, wherein if $R^A$ is substituted then $R^A$ is substituted with 1, 2, 3 or 4 groups selected from $R^a$, $R^b$, and $R^c$. In some embodiments, $R^A$ is unsubstituted or substituted monocyclic 6-membered heteroaryl, unsubstituted or substituted phenyl, or unsubstituted or substituted monocyclic 5-membered heteroaryl, wherein if $R^A$ is substituted then $R^A$ is substituted with 1, 2, or 3 groups selected from $R^a$, $R^b$, and $R^c$. In some embodiments, $R^A$ is unsubstituted or substituted monocyclic 6-membered heteroaryl, unsubstituted or substituted phenyl, or unsubstituted or substituted monocyclic 5-membered heteroaryl, wherein if $R^A$ is substituted then $R^A$ is substituted with 1 or 2 groups selected from $R^a$, $R^b$, and $R^c$. In some embodiments, $R^A$ is unsubstituted or substituted monocyclic 6-membered heteroaryl, unsubstituted or substituted phenyl, or unsubstituted or substituted monocyclic 5-membered heteroaryl, wherein if $R^A$ is substituted then $R^A$ is substituted with 1 $R^a$, $R^b$, or $R^c$ group.

In some embodiments, $R^A$ is substituted with 1, 2, 3 or 4 groups selected from $R^a$, $R^b$, and $R^c$. In some embodiments, $R^A$ is substituted with 1, 2, or 3 groups selected from $R^a$, $R^b$, and $R^c$. In some embodiments, $R^A$ is substituted with 1 or 2 groups selected from $R^a$, $R^b$, and $R^c$. In some embodiments, $R^A$ is substituted with 1 group selected from $R^a$, $R^b$, and $R^c$. In some embodiments, $R^A$ is substituted with one $R^a$. In some embodiments, $R^A$ is substituted with one $R^c$.

In some embodiments, $R^A$ is unsubstituted or substituted pyrrolyl, unsubstituted or substituted furanyl, unsubstituted or substituted thienyl, unsubstituted or substituted oxazolyl, unsubstituted or substituted thiazolyl, unsubstituted or substituted imidazolyl, unsubstituted or substituted pyrazolyl, unsubstituted or substituted triazolyl, unsubstituted or substituted tetrazolyl, unsubstituted or substituted isoxazolyl, unsubstituted or substituted isothiazolyl, unsubstituted or substituted oxadiazolyl, or unsubstituted or substituted thiadiazolyl, unsubstituted or substituted pyridinyl, unsubstituted or substituted pyrimidinyl, unsubstituted or substituted pyrazinyl, unsubstituted or substituted pyridazinyl, unsubstituted or substituted triazinyl, or unsubstituted or substituted phenyl, wherein if $R^A$ is substituted then $R^A$ is substituted with 1, 2, or 3 groups selected from $R^a$, $R^b$, and $R^c$. In some embodiments, if $R^A$ is substituted then $R^A$ is substituted with 1 or 2 groups selected from $R^a$, $R^b$, and $R^c$. In some embodiments, if $R^A$ is substituted then $R^A$ is substituted with 1 $R^a$, $R^b$, or $R^c$ group.

In some embodiments, $R^A$ is unsubstituted or substituted monocyclic 5-membered heteroaryl, wherein if $R^A$ is substituted then $R^A$ is substituted with 1, 2 or 3 groups selected from $R^a$, $R^b$, and $R^c$. In some embodiments, $R^A$ is unsubstituted or substituted monocyclic 5-membered heteroaryl, wherein if $R^A$ is substituted then $R^A$ is substituted with 1 or 2 groups selected from $R^a$, $R^b$, and $R^c$. In some embodiments, $R^A$ is unsubstituted or substituted monocyclic 5-membered heteroaryl containing one heteroatom selected from N, O, and S, wherein if $R^A$ is substituted then $R^A$ is substituted with 1 or 2 groups selected from $R^a$, $R^b$, and $R^c$. In some embodiments, $R^A$ is unsubstituted or substituted monocyclic 5-membered heteroaryl containing one heteroatom selected from N, O, and S, wherein if $R^A$ is substituted then $R^A$ is substituted with 1 or 2 groups selected from $R^a$, $R^b$, and $R^c$. In some embodiments, $R^A$ is unsubstituted or substituted monocyclic 5-membered heteroaryl containing one heteroatom selected from N, O, and S, wherein if $R^A$ is substituted then $R^A$ is substituted with 1 $R^a$, $R^b$, or $R^c$ group.

In some embodiments, $R^A$ is unsubstituted or substituted pyrrolyl, unsubstituted or substituted furanyl, unsubstituted or substituted thienyl, unsubstituted or substituted oxazolyl, unsubstituted or substituted thiazolyl, unsubstituted or substituted imidazolyl, unsubstituted or substituted pyrazolyl, unsubstituted or substituted triazolyl, unsubstituted or substituted tetrazolyl, unsubstituted or substituted isoxazolyl, unsubstituted or substituted isothiazolyl, unsubstituted or substituted oxadiazolyl, or unsubstituted or substituted thiadiazolyl, wherein if $R^A$ is substituted then $R^A$ is substituted with 1, 2, or 3 groups selected from $R^a$, $R^b$, and $R^c$. In some embodiments, if $R^A$ is substituted then $R^A$ is substituted with 1 or 2 groups selected from $R^a$, $R^b$, and $R^c$. In some embodiments, if $R^A$ is substituted then $R^A$ is substituted with 1 $R^a$, $R^b$, or $R^c$ group.

In some embodiments, $R^A$ is unsubstituted or substituted pyrrolyl, unsubstituted or substituted furanyl, unsubstituted or substituted thienyl, unsubstituted or substituted pyrazolyl, unsubstituted or substituted isoxazolyl, wherein if $R^A$ is substituted then $R^A$ is substituted with 1, 2, or 3 groups selected from $R^a$, $R^b$, and $R^c$. In some embodiments, if $R^A$ is substituted then $R^A$ is substituted with 1 or 2 groups selected from $R^a$, $R^b$, and $R^c$. In some embodiments, if $R^A$ is substituted then $R^A$ is substituted with 1 $R^a$, $R^b$, or $R^c$ group.

In some embodiments, $R^A$ is unsubstituted or substituted pyrrolyl, unsubstituted or substituted furanyl, or unsubstituted or substituted thienyl, wherein if $R^A$ is substituted then $R^A$ is substituted with 1, 2, or 3 groups selected from $R^a$, $R^b$, and $R^c$. In some embodiments, if $R^A$ is substituted then $R^A$ is substituted with 1 or 2 groups selected from $R^a$, $R^b$, and $R^c$. In some embodiments, if $R^A$ is substituted then $R^A$ is substituted with 1 $R^a$, $R^b$, or $R^c$ group.

In some embodiments, $R^A$ is

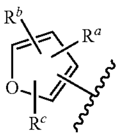, 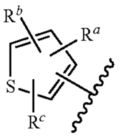, 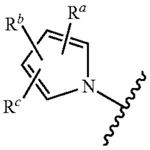,

-continued

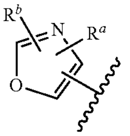, 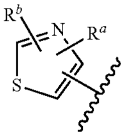, 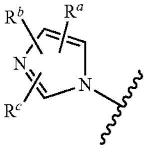,

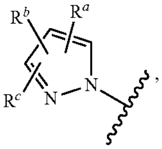, 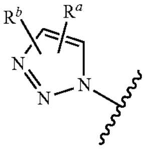, 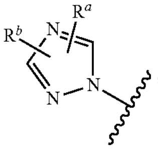,

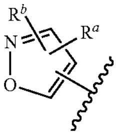, 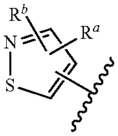, 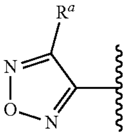,

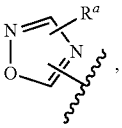, 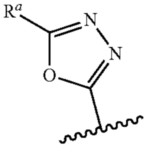, 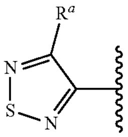,

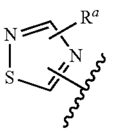, 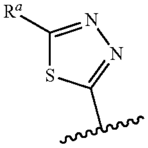, 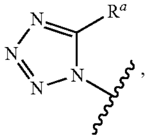, or

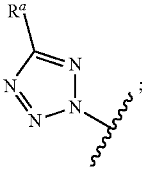; or $R^A$ is 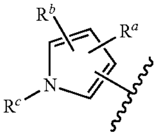,

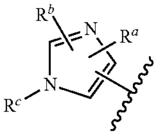, 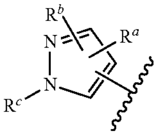, 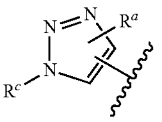,

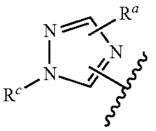, 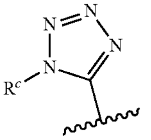, or 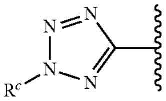, where $R^c$ is hydrogen, —C(=O)$R^7$, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl.

In some embodiments, $R^A$ is

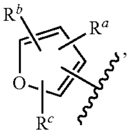, 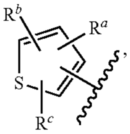, 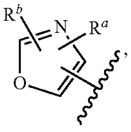,

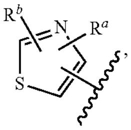, 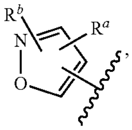, or 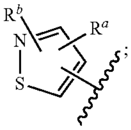;

or $R^A$ is

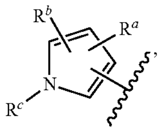
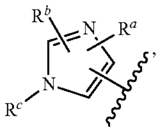
or
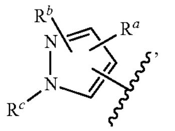

where $R^c$ is hydrogen, —C(=O)$R^7$, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl.

In some embodiments, $R^A$ is

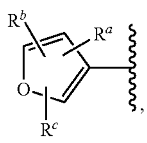
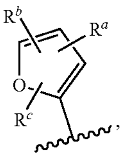
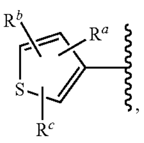
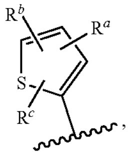
or
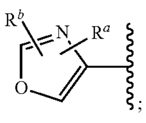

or $R^A$ is

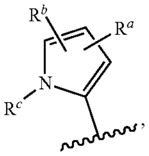
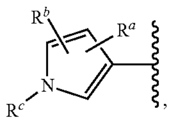
or
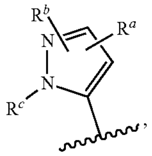

where $R^c$ is hydrogen, —C(=O)$R^7$, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl.

In some embodiments, $R^A$ is

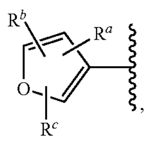
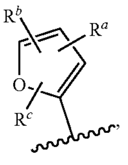
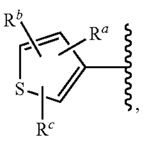
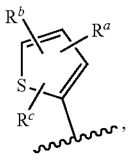
or
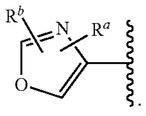

In some embodiments, $R^A$ is

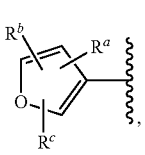
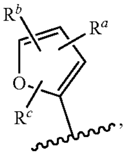
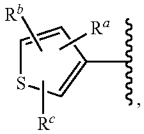
or
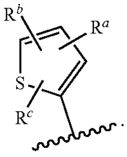

In some embodiments, $R^A$ is

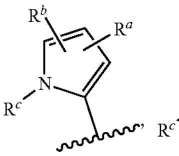
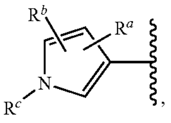
or
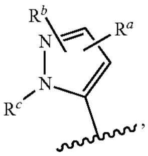

where $R^c$ is hydrogen, —C(=O)$R^7$, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl. In some embodiments, $R^A$ is

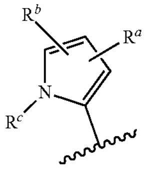
or
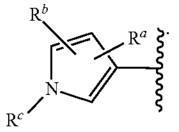

In some embodiments, $R^A$ is

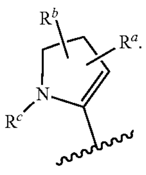

In some embodiments, $R^A$ is

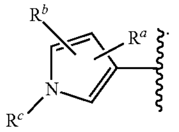

In some embodiments, $R^A$ is

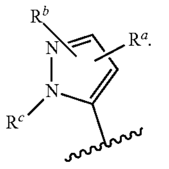

In some embodiments, $R^A$ is

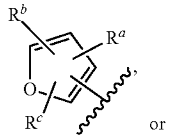

or

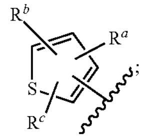

or $R^A$ is

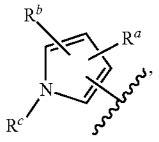

where $R^c$ is hydrogen, —C(=O)$R^7$, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl.

In some embodiments, $R^A$ is

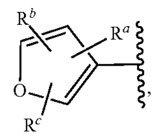

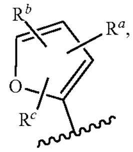

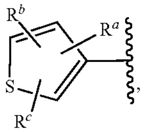

or

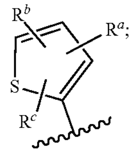

or $R^A$ is

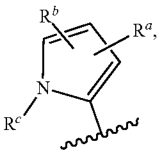

or

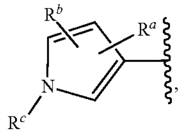

where $R^c$ is hydrogen, —C(=O)$R^7$, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl.

In some embodiments, $R^A$ is

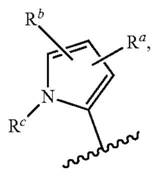

where $R^c$ is hydrogen, —C(=O)$R^7$, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl. In some embodiments, $R^c$ is hydrogen, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl. In some embodiments, $R^c$ is hydrogen or unsubstituted or substituted $C_1$-$C_6$ alkyl. In some embodiments, $R^c$ is hydrogen or $C_1$-$C_6$ alkyl. In some embodiments, $R^c$ is hydrogen, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$, —$CH_2CH_2CH_2CH_2CH_3$, or —$CH_2CH_2CH(CH_3)_2$. In some embodiments, $R^c$ is hydrogen, —$CH_3$, —$CH_2CH_3$, —$CH_2CH_2CH_3$, or —$CH(CH_3)_2$. In some embodiments, $R^c$ is hydrogen or —$CH_3$. In some embodiments, $R^c$ is —$CH_3$. In some embodiments, $R^c$ is hydrogen. In some embodiments, $R^c$ is unsubstituted or substituted $C_1$-$C_6$ alkyl. In some embodiments, $R^c$ is $C_1$-$C_6$ alkyl. In some embodiments, $R^c$ is —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$, —$CH_2CH_2CH_2CH_2CH_3$, or —$CH_2CH_2CH(CH_3)_2$. In some embodiments, R is —$CH_3$, —$CH_2CH_3$, —$CH_2CH_2CH_3$, or —$CH(CH_3)_2$. In some embodiments, $R^c$ is hydrogen, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$, —$CH_2CH_2CH(CH_3)_2$, or unsubstituted $C_3$-$C_6$ cycloalkyl.

In some embodiments, $R^A$ is

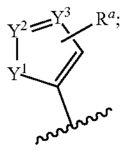

$Y^1$ is $NR^c$, O, or S; $Y^2$ and $Y^3$ are independently CH, $CR^a$, $CR^b$, or N; and $R^c$ is hydrogen, —C(=O)$R^7$, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl. In some embodiments, $R^A$ is

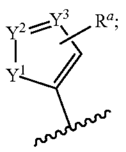

$Y^1$ is $NR^c$; $Y^2$ and $Y^3$ are independently CH, $CR^a$, $CR^b$, or N; and $R^c$ is hydrogen, —C(=O)$R^7$, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl. In some embodiments, $R^A$ is

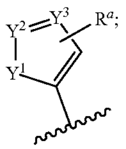

$Y^1$ is $NR^c$; $Y^2$ and $Y^3$ are independently CH, $CR^a$, or $CR^b$; and $R^c$ is hydrogen, —C(=O)$R^7$, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl. In some embodiments, $R^A$ is

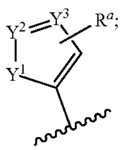

$Y^1$ is $NR^c$; $Y^2$ and $Y^3$ are each CH; and $R^c$ is hydrogen, —C(=O)$R^7$, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl.

In some embodiments, $R^A$ is

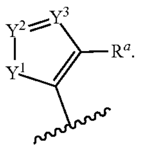

In some embodiments, $R^A$ is

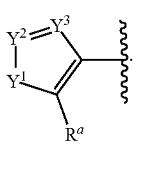

In some embodiments, $R^A$ is

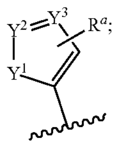

$Y^1$ is $NR^c$, O, or S; $Y^2$ and $Y^3$ are independently CH, $CR^a$, $CR^b$, or N; and $R^c$ is hydrogen, —C(=O)$R^7$, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl. In some embodiments, $R^A$ is

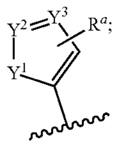

$Y^1$ is $NR^c$; $Y^2$ and $Y^3$ are independently CH, $CR^a$, $CR^b$, or N; and $R^c$ is hydrogen, —C(=O)$R^7$, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl. In some embodiments, $R^A$ is

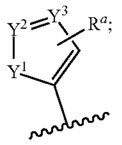

$Y^1$ is $NR^c$; $Y^2$ and $Y^3$ are independently CH, $CR^a$, or $CR^b$; and $R^c$ is hydrogen, —C(=O)$R^7$, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl. In some embodiments, $R^A$ is

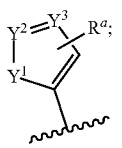

$Y^1$ is $NR^c$; $Y^2$ and $Y^3$ are each CH; and $R^c$ is hydrogen, —C(=O)$R^7$, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl.

In some embodiments, the compound has the structure of Formula (III), or a pharmaceutically acceptable salt, or solvate thereof:

Formula (III)

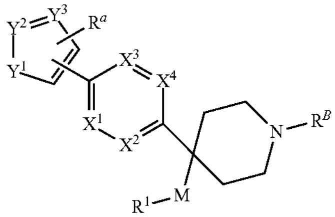

wherein: $Y^1$ is $NR^c$, O, or S; $Y^2$ and $Y^3$ are independently CH, $CR^a$, $CR^b$, or N; and $R^c$ is hydrogen, —C(═O)$R^7$, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl.

In some embodiments, the compound has the structure of Formula (IIIa), or a pharmaceutically acceptable salt, or solvate thereof:

Formula (IIIa)

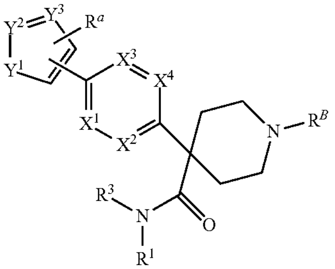

wherein: $Y^1$ is $NR^c$, O, or S; $Y^2$ and $Y^3$ are independently CH, $CR^a$, $CR^b$, or N; and $R^c$ is hydrogen, —C(═O)$R^7$, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl.

In some embodiments, the compound has the structure of Formula (IIIb), or a pharmaceutically acceptable salt, or solvate thereof:

Formula (IIIb)

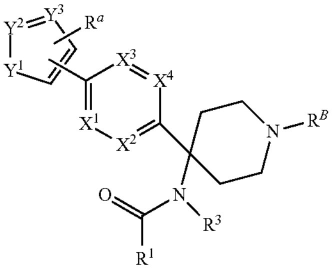

wherein: $Y^1$ is $NR^c$, O, or S; $Y^2$ and $Y^3$ are independently CH, $CR^a$, $CR^b$, or N; and $R^c$ is hydrogen, —C(═O)$R^7$, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl.

In some embodiments, $R^A$ is unsubstituted or substituted monocyclic 6-membered heteroaryl or unsubstituted or substituted phenyl, wherein if $R^A$ is substituted then $R^A$ is substituted with 1, 2, 3 or 4 groups selected from $R^a$, $R^b$, and $R^c$. In some embodiments, $R^A$ is unsubstituted or substituted pyridinyl, unsubstituted or substituted pyrimidinyl, unsubstituted or substituted pyrazinyl, or unsubstituted or substituted pyridazinyl, or unsubstituted or substituted phenyl, wherein if $R^A$ is substituted then $R^A$ is substituted with 1, 2, 3 or 4 groups selected from $R^a$, $R^b$, and $R^c$. In some embodiments, if $R^A$ is substituted then $R^A$ is substituted with 1 or 2 groups selected from $R^a$, $R^b$, and $R^c$.

In some embodiments, $R^A$ is unsubstituted or substituted pyridinyl or unsubstituted or substituted phenyl, wherein if $R^A$ is substituted then $R^A$ is substituted with 1, 2, 3 or 4 groups selected from $R^a$, $R^b$, and $R^c$. In some embodiments, if $R^A$ is substituted then $R^A$ is substituted with 1 or 2 groups selected from $R^a$, $R^b$, and $R^c$.

In some embodiments, $R^A$ is

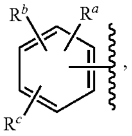,
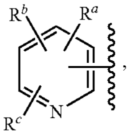,
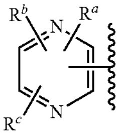,
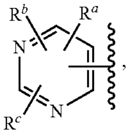, or
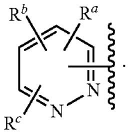.

In some embodiments, $R^A$ is

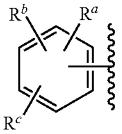 or
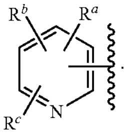.

In some embodiments, $R^A$ is

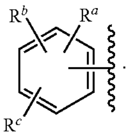.

In some embodiments, $R^A$ is

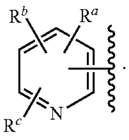.

In some embodiments, $R^A$ is

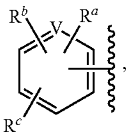, where V is CH, $CR^a$, $CR^b$, or N. In some embodiments, V is CH or N.

In some embodiments, $R^A$ is

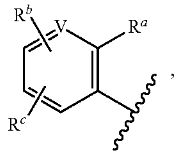

where V is CH, $CR^a$, $CR^b$, or N. In some embodiments, V is CH or N.

In some embodiments, the compound has the structure of Formula (IV), or a pharmaceutically acceptable salt, or solvate thereof:

Formula (IV)

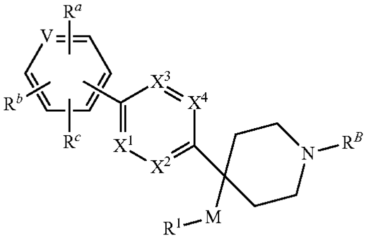

wherein V is CH, $CR^a$, $CR^b$, or N. In some embodiments, V is CH or N.

In some embodiments, the compound has the structure of Formula (IVa), or a pharmaceutically acceptable salt, or solvate thereof.

Formula (IVa)

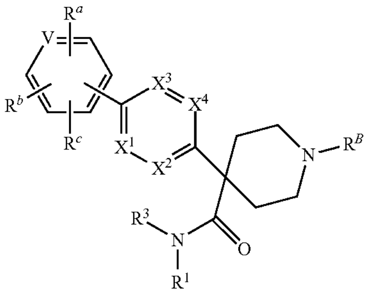

wherein V is CH, $CR^a$, $CR^b$, or N. In some embodiments, V is CH or N.

In some embodiments, the compound has the structure of Formula (IVb), or a pharmaceutically acceptable salt, or solvate thereof.

Formula (IVb)

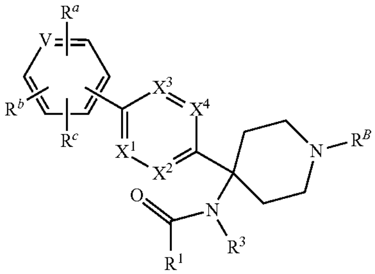

wherein V is CH, $CR^a$, $CR^b$, or N. In some embodiments, V is CH or N.

In some embodiments, $R^A$ is unsubstituted or substituted bicyclic 9- to 10-membered heteroaryl, wherein if $R^A$ is substituted then $R^A$ is substituted with 1, 2, 3 or 4 groups selected from $R^a$, $R^b$, and $R^c$. $R^A$ is unsubstituted or substituted bicyclic 9- to 10-membered heteroaryl, wherein if $R^A$ is substituted then $R^A$ is substituted with 1 or 2 groups selected from $R^a$, $R^b$, and $R^c$.

In some embodiments, $R^A$ is unsubstituted or substituted quinolinyl, unsubstituted or substituted isoquinolinyl, unsubstituted or substituted cinnolinyl, unsubstituted or substituted phthalazinyl, unsubstituted or substituted quinazolinyl, unsubstituted or substituted quinoxalinyl, unsubstituted or substituted naphthyridinyl, unsubstituted or substituted pteridinyl, unsubstituted or substituted indolizinyl, unsubstituted or substituted azaindolizinyl, unsubstituted or substituted indolyl, unsubstituted or substituted azaindolyl, unsubstituted or substituted indazolyl, unsubstituted or substituted azaindazolyl, unsubstituted or substituted benzimidazolyl, unsubstituted or substituted azabenzimidazolyl, unsubstituted or substituted benzotriazolyl, unsubstituted or substituted azabenzotriazolyl, unsubstituted or substituted benzoxazolyl, unsubstituted or substituted azabenzoxazolyl, unsubstituted or substituted benzisoxazolyl, unsubstituted or substituted azabenzisoxazolyl, unsubstituted or substituted benzofuranyl, unsubstituted or substituted azabenzofuranyl, unsubstituted or substituted benzothienyl, unsubstituted or substituted azabenzothienyl, unsubstituted or substituted benzothiazolyl, unsubstituted or substituted azabenzothiazolyl, or unsubstituted or substituted purinyl, wherein if $R^A$ is substituted then $R^A$ is substituted with 1, 2, 3 or 4 groups selected from $R^a$, $R^b$, and $R^c$. In some embodiments, if $R^A$ is substituted then $R^A$ is substituted with 1 or 2 groups selected from $R^a$, $R^b$, and $R^c$.

In some embodiments, $R^A$ is unsubstituted or substituted quinolinyl, unsubstituted or substituted indolyl, unsubstituted or substituted indazolyl, or unsubstituted or substituted benzofuranyl, wherein if $R^A$ is substituted then $R^A$ is substituted with 1, 2, 3 or 4 groups selected from $R^a$, $R^b$, and $R^c$. In some embodiments, if $R^A$ is substituted then $R^A$ is substituted with 1 or 2 groups selected from $R^a$, $R^b$, and $R^c$.

In some embodiments, $R^A$ is unsubstituted or substituted indazolyl or unsubstituted or substituted benzofuranyl, wherein if $R^A$ is substituted then $R^A$ is substituted with 1, 2, 3 or 4 groups selected from $R^a$, $R^b$, and $R^c$. In some embodiments, if $R^A$ is substituted then $R^A$ is substituted with 1 or 2 groups selected from $R^a$, $R^b$, and $R^c$.

In some embodiments, $R^B$ is an unsubstituted or substituted phenyl, unsubstituted or substituted naphthyl, unsubstituted or substituted monocyclic 6-membered heteroaryl, unsubstituted or substituted monocyclic 5-membered heteroaryl, or unsubstituted or substituted bicyclic heteroaryl, wherein if $R^B$ is substituted then $R^B$ is substituted with 1, 2, 3 or 4 groups selected from $R^d$, $R^e$, and $R^f$. In some embodiments, if $R^B$ is substituted then $R^B$ is substituted with 1, 2, or 3 groups selected from $R^d$, $R^e$, and $R^f$.

In some embodiments, $R^B$ is an unsubstituted or substituted phenyl, unsubstituted or substituted naphthyl, unsubstituted or substituted furanyl, unsubstituted or substituted thienyl, unsubstituted or substituted pyrrolyl, unsubstituted or substituted oxazolyl, unsubstituted or substituted thiazolyl, unsubstituted or substituted imidazolyl, unsubstituted or substituted pyrazolyl, unsubstituted or substituted triazolyl, unsubstituted or substituted tetrazolyl, unsubstituted or substituted isoxazolyl, unsubstituted or substituted isothiazolyl, unsubstituted or substituted oxadiazolyl, unsubstituted or substituted thiadiazolyl, unsubstituted or substituted pyridinyl, unsubstituted or substituted pyrimidinyl, unsubstituted or substituted pyrazinyl, unsubstituted or substituted pyridazinyl, unsubstituted or substituted triazinyl, unsubstituted or substituted quinolinyl, unsubstituted or substituted isoquinolinyl, unsubstituted or substituted cinnolinyl, unsubstituted or substituted phthalazinyl, unsubstituted or substituted quinazolinyl, unsubstituted or substituted quinoxalinyl, unsubstituted or substituted naphthyridinyl, unsubstituted or substituted pteridinyl, unsubstituted or substituted indolizinyl, unsubstituted or substituted azaindolizinyl, unsubstituted or substituted indolyl, unsubstituted or substituted azaindolyl, unsubstituted or substituted indazolyl, unsubstituted or substituted azaindazolyl, unsubstituted or substituted benzimidazolyl, unsubstituted or substituted azabenzimidazolyl, unsubstituted or substituted benzotriazolyl, unsubstituted or substituted azabenzotriazolyl, unsubstituted or substituted benzoxazolyl, unsubstituted or substituted azabenzoxazolyl, unsubstituted or substituted benzisoxazolyl, unsubstituted or substituted azabenzisoxazolyl, unsubstituted or substituted benzofuranyl, unsubstituted or substituted azabenzofuranyl, unsubstituted or substituted benzothienyl, unsubstituted or substituted azabenzothienyl, unsubstituted or substituted benzothiazolyl, unsubstituted or substituted azabenzothiazolyl, or unsubstituted or substituted purinyl, wherein if $R^B$ is substituted then $R^B$ is substituted with 1, 2, 3 or 4 groups selected from $R^d$, $R^e$, and $R^f$. In some embodiments, if $R^B$ is substituted then $R^B$ is substituted with 1, 2, or 3 groups selected from $R^d$, $R^e$, and $R^f$.

In some embodiments, $R^B$ is an unsubstituted or substituted phenyl or unsubstituted or substituted monocyclic 6-membered heteroaryl, wherein if $R^B$ is substituted then $R^B$ is substituted with 1, 2, 3 or 4 groups selected from $R^d$, $R^e$, and $R^f$. In some embodiments, $R^B$ is unsubstituted or substituted phenyl, unsubstituted or substituted pyridinyl, unsubstituted or substituted pyrimidinyl, unsubstituted or substituted pyrazinyl, or unsubstituted or substituted pyridazinyl, wherein if $R^B$ is substituted then $R^B$ is substituted with 1, 2, 3 or 4 groups selected from $R^d$, $R^e$, and $R^f$. In some embodiments, if $R^B$ is substituted then $R^B$ is substituted with 1, 2, or 3 groups selected from $R^d$, $R^e$, and $R^f$.

In some embodiments, $R^B$ is unsubstituted or substituted phenyl or unsubstituted or substituted pyridinyl, wherein if $R^B$ is substituted then $R^B$ is substituted with 1, 2, 3 or 4 groups selected from $R^d$, $R^e$, and $R^f$. In some embodiments, if $R^B$ is substituted then $R^B$ is substituted with 1, 2, or 3 groups selected from $R^d$, $R^e$, and $R^f$.

In some embodiments, $R^B$ is

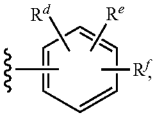 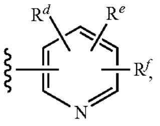 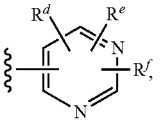

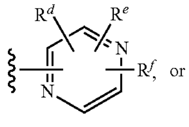 or 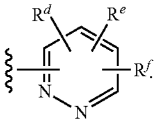

In some embodiments, $R^B$ is

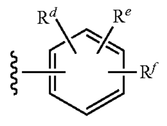 or 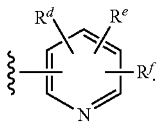

In some embodiments, $R^B$ is

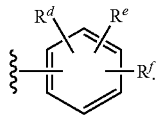

In some embodiments, $R^B$ is

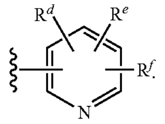

In some embodiments, $R^B$ is

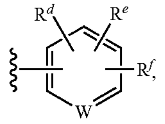

where W is CH, $CR^d$, $CR^e$, or N. In some embodiments, W is CH or N.

In some embodiments, the compound has the structure of Formula (V), or a pharmaceutically acceptable salt, or solvate thereof:

Formula (V)

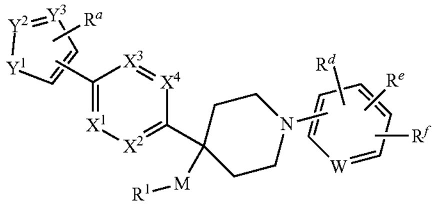

wherein:

$Y^1$ is $NR^c$, O, or S;

$Y^2$ and $Y^3$ are independently CH, $CR^a$, $CR^b$, or N;

$R^c$ is hydrogen, —C(═O)$R^7$, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl; and W is CH, $CR^d$, $CR^e$, or N.

In some embodiments, the compound of Formula (V) has one of the following structures, or a pharmaceutically acceptable salt, or solvate thereof:

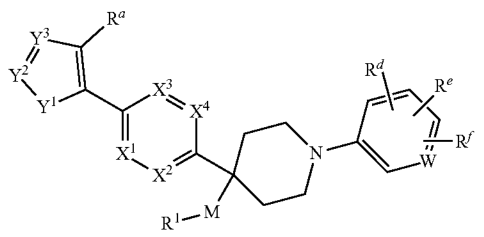

or

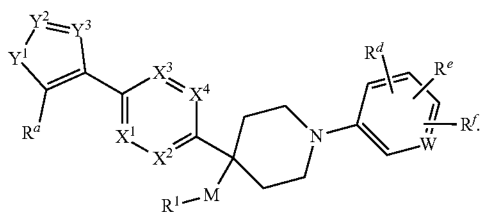

In some embodiments, M is *—$NR^3$—(C═O)—, wherein * indicates the attachment point to $R^1$.

In some embodiments, W is CH or N.

In some embodiments, $Y^1$ is $NR^c$; and $Y^2$ and $Y^3$ are independently CH, $CR^a$, $CR^b$, or N. In some embodiments, $Y^1$ is $NR^c$; $Y^2$ and $Y^3$ are independently CH, $CR^a$, or $CR^b$. In some embodiments; $Y^1$ is $NR^c$; $Y^2$ and $Y^3$ are each CH.

In some embodiments, the compound has the structure of Formula (Va), or a pharmaceutically acceptable salt, or solvate thereof:

Formula (Va)

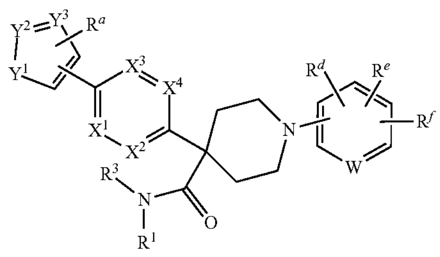

wherein: $Y^1$ is $NR^c$, O, or S; $Y^2$ and $Y^3$ are independently CH, $CR^a$, $CR^b$, or N; $R^c$ is hydrogen, —C(═O)$R^7$, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl; and W is CH, $CR^d$, $CR^e$, or N.

In some embodiments, W is CH or N.

In some embodiments, $Y^1$ is $NR^c$; and $Y^2$ and $Y^3$ are independently CH, $CR^a$, $CR^b$, or N. In some embodiments, $Y^1$ is $NR^c$; $Y^2$ and $Y^3$ are independently CH, $CR^a$, or $CR^b$. In some embodiments; $Y^1$ is $NR^c$; $Y^2$ and $Y^3$ are each CH.

In some embodiments, the compound has the structure of Formula (Vb), or a pharmaceutically acceptable salt, or solvate thereof:

Formula (Vb)

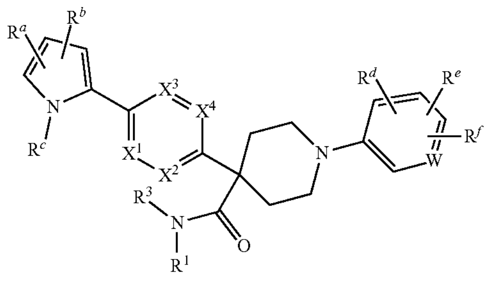

wherein: $R^c$ is hydrogen, —C(═O)$R^7$, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl; and W is CH, $CR^d$, $CR^e$, or N.

In some embodiments, W is CH or N.

In some embodiments, $R^c$ is hydrogen, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl. In some embodiments, $R^c$ is hydrogen or unsubstituted or substituted $C_1$-$C_6$ alkyl. In some embodiments, $R^c$ is hydrogen or $C_1$-$C_6$ alkyl. In some embodiments, $R^c$ is unsubstituted or substituted $C_1$-$C_6$ alkyl. In some embodiments, $R^c$ is $C_1$-$C_6$ alkyl.

In some embodiments, the compound has the structure of Formula (Vc), or a pharmaceutically acceptable salt, or solvate thereof:

Formula (Vc)

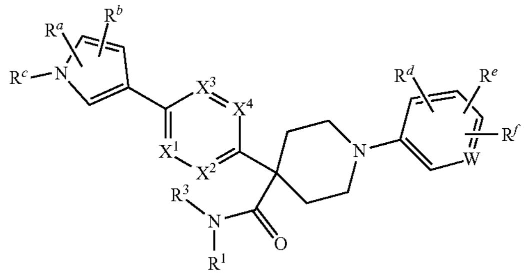

wherein: $R^c$ is hydrogen, —C(═O)$R^7$, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl; and W is CH, $CR^d$, $CR^e$, or N.

In some embodiments, W is CH or N.

In some embodiments, $R^c$ is hydrogen, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl. In some embodiments, $R^c$ is hydrogen or unsubstituted or substituted $C_1$-$C_6$ alkyl. In some embodiments, $R^c$ is hydrogen or $C_1$-$C_6$ alkyl. In some embodiments, $R^c$ is unsubstituted or substituted $C_1$-$C_6$ alkyl. In some embodiments, $R^c$ is $C_1$-$C_6$ alkyl.

In some embodiments, the compound has the structure of Formula (Vd), or a pharmaceutically acceptable salt, or solvate thereof:

Formula (Vd)

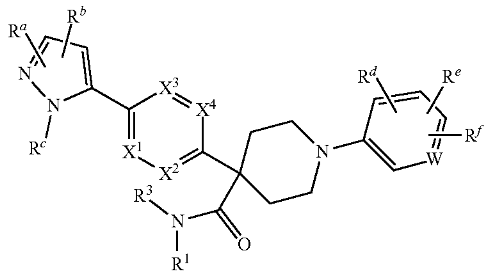

wherein: $R^c$ is hydrogen, —C(═O)$R^7$, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl; and W is CH, $CR^d$, $CR^e$, or N.

In some embodiments, W is CH or N.

In some embodiments, $R^c$ is hydrogen, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl. In some embodiments, $R^c$ is hydrogen or unsubstituted or substituted $C_1$-$C_6$ alkyl. In some embodiments, $R^c$ is hydrogen or $C_1$-$C_6$ alkyl. In some embodiments, $R^c$ is unsubstituted or substituted $C_1$-$C_6$ alkyl. In some embodiments, $R^c$ is $C_1$-$C_6$ alkyl.

In some embodiments, the compound has the structure of Formula (Ve), or a pharmaceutically acceptable salt, or solvate thereof:

Formula (Ve)

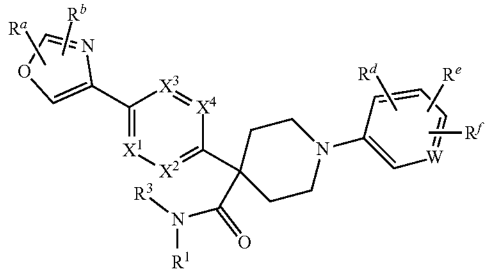

wherein W is CH, $CR^d$, $CR^e$, or N. In some embodiments, W is CH or N.

In some embodiments, the compound has the structure of Formula (Vf), or a pharmaceutically acceptable salt, or solvate thereof:

Formula (Vf)

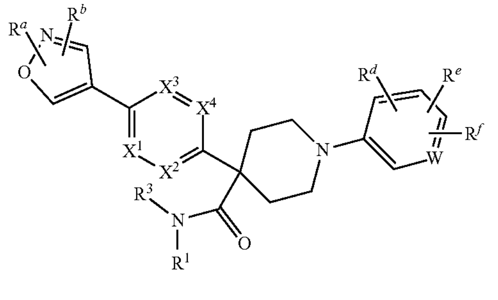

wherein W is CH, $CR^d$, $CR^e$, or N. In some embodiments, W is CH or N.

In some embodiments, the compound has the structure of Formula (Vg), or a pharmaceutically acceptable salt, or solvate thereof:

Formula (Vg)

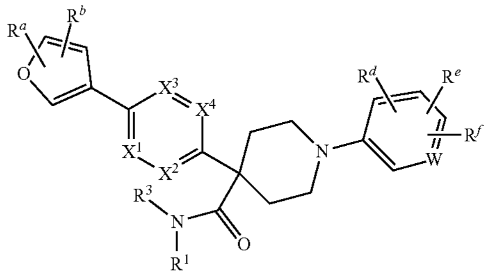

wherein W is CH, $CR^d$, $CR^e$, or N. In some embodiments, W is CH or N.

In some embodiments, the compound has the structure of Formula (Vh), or a pharmaceutically acceptable salt, or solvate thereof:

Formula (Vh)

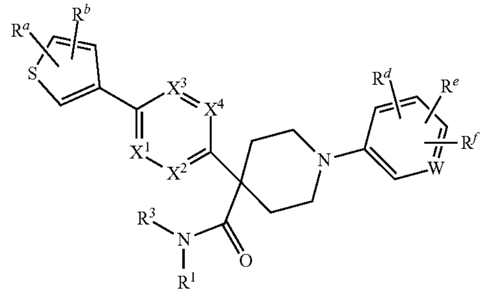

wherein W is CH, $CR^d$, $CR^e$, or N. In some embodiments, W is CH or N.

In some embodiments, the compound has the structure of Formula (Vi), or a pharmaceutically acceptable salt, or solvate thereof:

Formula (Vi)

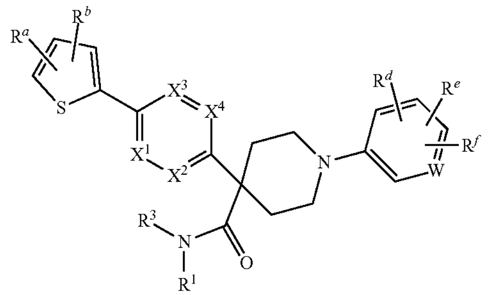

wherein W is CH, $CR^d$, $CR^e$, or N. In some embodiments, W is CH or N.

In some embodiments, the compound has the structure of Formula (Vj), or a pharmaceutically acceptable salt, or solvate thereof:

Formula (Vj)

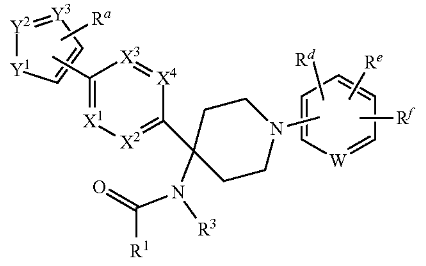

wherein:

$Y^1$ is $NR^c$, O, or S;

$Y^2$ and $Y^3$ are independently CH, $CR^a$, $CR^b$, or N;

$R^c$ is hydrogen, —C(═O)$R^7$, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl; and W is CH, $CR^d$, $CR^e$, or N.

In some embodiments, W is CH or N.

In some embodiments, $Y^1$ is $NR^c$; and $Y^2$ and $Y^3$ are independently CH, $CR^a$, $CR^b$, or N. In some embodiments, $Y^1$ is $NR^c$; $Y^2$ and $Y^3$ are independently CH, $CR^a$, or $CR^b$. In some embodiments; $Y^1$ is $NR^c$; $Y^2$ and $Y^3$ are each CH.

In some embodiments, the compound has the structure of Formula (Vk), or a pharmaceutically acceptable salt, or solvate thereof:

Formula (Vk)

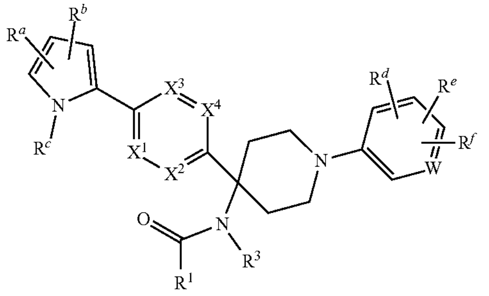

wherein:

$R^c$ is hydrogen, —C(═O)$R^7$, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl; and W is CH, $CR^d$, $CR^e$, or N.

In some embodiments, W is CH or N.

In some embodiments, $R^c$ is hydrogen, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl. In some embodiments, $R^c$ is hydrogen or unsubstituted or substituted $C_1$-$C_6$ alkyl. In some embodiments, $R^c$ is hydrogen or $C_1$-$C_6$ alkyl. In some embodiments, $R^c$ is unsubstituted or substituted $C_1$-$C_6$ alkyl. In some embodiments, $R^c$ is $C_1$-$C_6$ alkyl.

In some embodiments, the compound has the structure of Formula (Vl), or a pharmaceutically acceptable salt, or solvate thereof:

Formula (Vl)

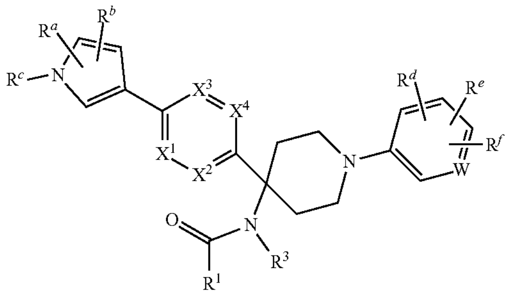

wherein:

$R^c$ is hydrogen, —C(═O)$R^7$, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl; and W is CH, $CR^d$, $CR^e$, or N.

In some embodiments, W is CH or N.

In some embodiments, $R^c$ is hydrogen, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl. In some embodiments, $R^c$ is hydrogen or unsubstituted or substituted $C_1$-$C_6$ alkyl. In some embodiments, $R^c$ is hydrogen or $C_1$-$C_6$ alkyl. In some embodiments, $R^c$ is unsubstituted or substituted $C_1$-$C_6$ alkyl. In some embodiments, $R^c$ is $C_1$-$C_6$ alkyl.

In some embodiments, the compound has the structure of Formula (Vm), or a pharmaceutically acceptable salt, or solvate thereof:

Formula (Vm)

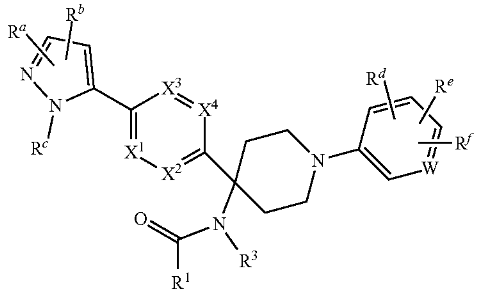

wherein:

$R^c$ is hydrogen, —C(═O)$R^7$, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl; and W is CH, $CR^d$, $CR^e$, or N.

In some embodiments, W is CH or N.

In some embodiments, $R^c$ is hydrogen, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl. In some embodiments, $R^c$ is hydrogen or unsubstituted or substituted $C_1$-$C_6$ alkyl. In some embodiments, $R^c$ is hydrogen or $C_1$-$C_6$ alkyl. In some embodiments, $R^c$ is unsubstituted or substituted $C_1$-$C_6$ alkyl. In some embodiments, $R^c$ is $C_1$-$C_6$ alkyl.

In some embodiments, the compound has the structure of Formula (Ve), or a pharmaceutically acceptable salt, or solvate thereof:

Formula (Vn)

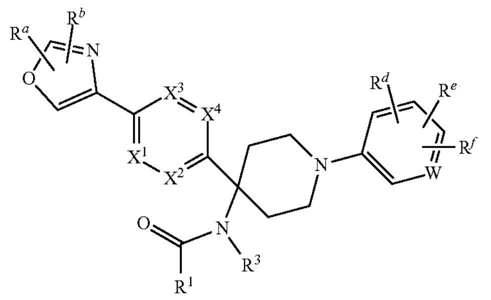

wherein W is CH, $CR^d$, $CR^e$, or N. In some embodiments, W is CH or N.

In some embodiments, the compound has the structure of Formula (Vf), or a pharmaceutically acceptable salt, or solvate thereof:

Formula (Vn)

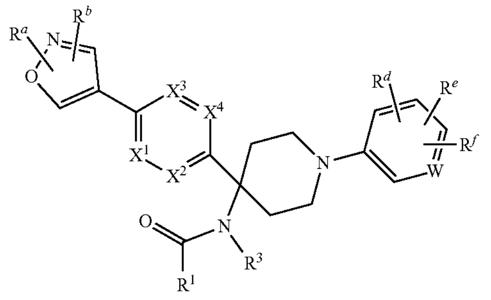

wherein W is CH, $CR^d$, $CR^e$, or N. In some embodiments, W is CH or N.

In some embodiments, the compound has the structure of Formula (Vg), or a pharmaceutically acceptable salt, or solvate thereof:

Formula (Vo)

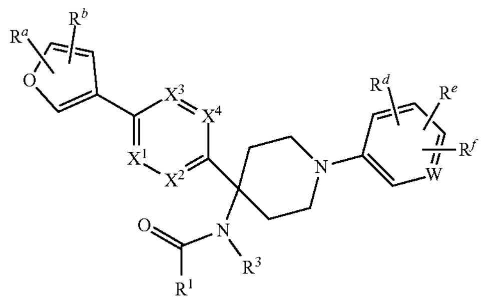

wherein W is CH, $CR^d$, $CR^e$, or N. In some embodiments, W is CH or N.

In some embodiments, the compound has the structure of Formula (Vh), or a pharmaceutically acceptable salt, or solvate thereof:

Formula (Vo)

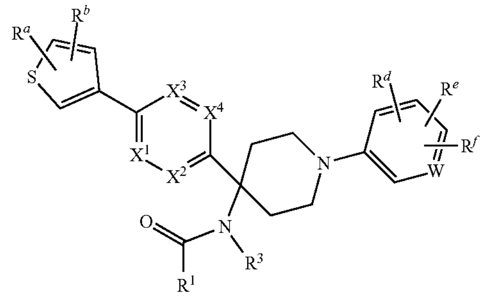

wherein W is CH, $CR^d$, $CR^e$, or N. In some embodiments, W is CH or N.

In some embodiments, the compound has the structure of Formula (Vp), or a pharmaceutically acceptable salt, or solvate thereof:

Formula (Vp)

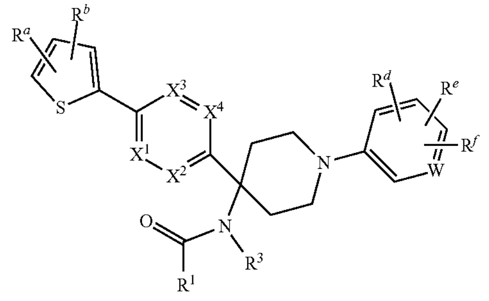

wherein W is CH, $CR^d$, $CR^e$, or N. In some embodiments, W is CH or N.

In some embodiments, the compound has the structure of Formula (VI), or a pharmaceutically acceptable salt, or solvate thereof:

Formula (VI)

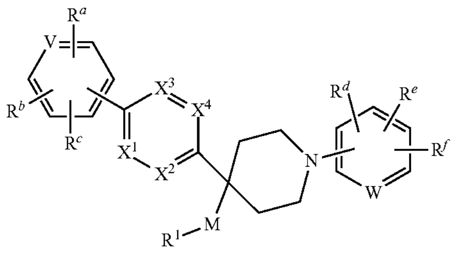

wherein V is CH, $CR^a$, $CR^b$, or N; and W is CH, $CR^d$, $CR^e$, or N.

In some embodiments, the compound of Formula (VI) has the following structure, or a pharmaceutically acceptable salt, or solvate thereof:

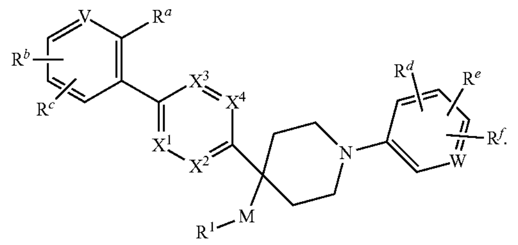

In some embodiments, M is *—$NR^3$—(C═O)—, wherein * indicates the attachment point to $R^1$. In some embodiments, M is *—(C═O)—$NR^3$—, wherein * indicates the attachment point to $R^1$.

In some embodiments, V is CH or N. In some embodiments, W is CH or N. In some embodiments, V is CH or N; and W is CH or N.

In some embodiments, the compound has the structure of Formula (VIa), or a pharmaceutically acceptable salt, or solvate thereof:

Formula (VIa)

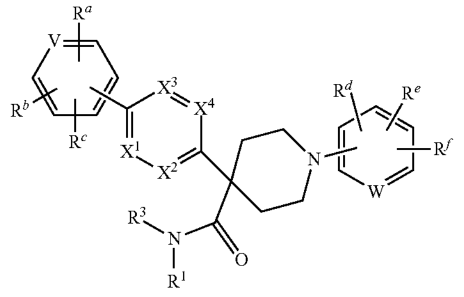

wherein V is CH, $CR^a$, $CR^b$, or N; and W is CH, $CR^d$, $CR^e$, or N.

In some embodiments, V is CH or N. In some embodiments, W is CH or N. In some embodiments, V is CH or N; and W is CH or N.

In some embodiments, the compound has the structure of Formula (VIb), or a pharmaceutically acceptable salt, or solvate thereof:

Formula (VIb)

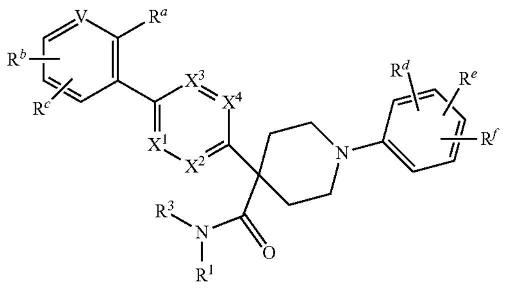

wherein V is CH, $CR^a$, $CR^b$, or N. In some embodiments, V is CH or N.

In some embodiments, the compound has the structure of Formula (VIc), or a pharmaceutically acceptable salt, or solvate thereof:

Formula (VIc)

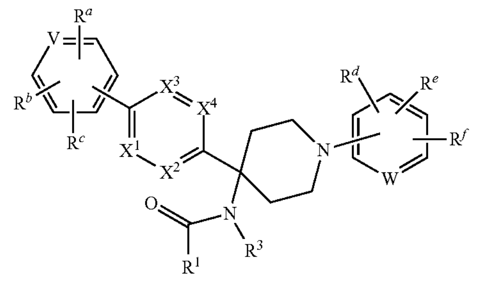

wherein V is CH, $CR^a$, $CR^b$, or N; and W is CH, $CR^d$, $CR^e$, or N.

In some embodiments, V is CH or N. In some embodiments, W is CH or N. In some embodiments, V is CH or N; and W is CH or N.

In some embodiments, the compound has the structure of Formula (VId), or a pharmaceutically acceptable salt, or solvate thereof:

Formula (VId)

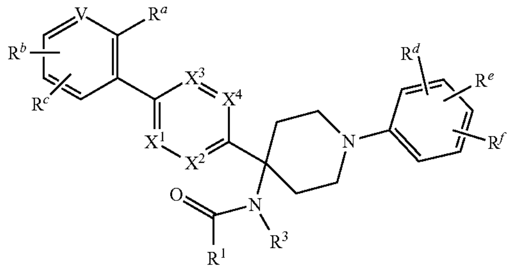

wherein V is CH, $CR^a$, $CR^b$, or N. In some embodiments, V is CH or N.

In some embodiments, $R^B$ is an unsubstituted or substituted monocyclic 5-membered heteroaryl, wherein if $R^B$ is substituted then $R^B$ is substituted with 1, 2, or 3 groups selected from $R^d$, $R^e$, and $R^f$.

In some embodiments, $R^B$ is unsubstituted or substituted monocyclic 5-membered heteroaryl, wherein if $R^B$ is substituted then $R^B$ is substituted with 1, 2, or 3 groups selected from $R^d$, $R^e$, and $R^f$. In some embodiments, $R^B$ is unsubstituted or substituted monocyclic 5-membered heteroaryl, wherein if $R^B$ is substituted then $R^B$ is substituted with 1 or 2 groups selected from $R^d$, $R^e$, and $R^f$. In some embodiments, $R^B$ is unsubstituted or substituted monocyclic 5-membered heteroaryl containing one heteroatom selected from N, O, and S, wherein if $R^B$ is substituted then $R^B$ is substituted with 1 or 2 groups selected from $R^d$, $R^e$, and $R^f$. In some embodiments, $R^B$ is unsubstituted or substituted monocyclic 5-membered heteroaryl containing one heteroatom selected from N, O, and S, wherein if $R^B$ is substituted then $R^B$ is substituted with 1 or 2 groups selected from $R^d$, $R^e$, and $R^f$. In some embodiments, $R^B$ is unsubstituted or substituted furanyl, unsubstituted or substituted thienyl, unsubstituted or substituted pyrrolyl, unsubstituted or substituted oxazolyl, unsubstituted or substituted thiazolyl, unsubstituted or substituted imidazolyl, unsubstituted or substituted pyrazolyl, unsubstituted or substituted triazolyl, unsubstituted or substituted tetrazolyl, unsubstituted or substituted isoxazolyl, unsubstituted or substituted isothiazolyl, unsubstituted or substituted oxadiazolyl, or unsubstituted or substituted thiadiazolyl, wherein if $R^B$ is substituted then $R^B$ is substituted with 1, 2, or 3 groups selected from $R^d$, $R^e$, and $R^f$.

In some embodiments, $R^B$ is

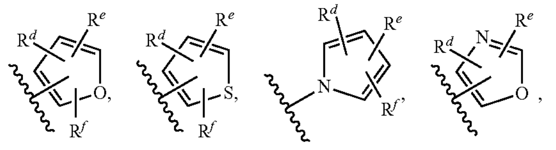

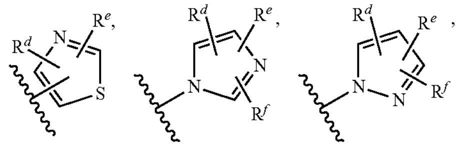

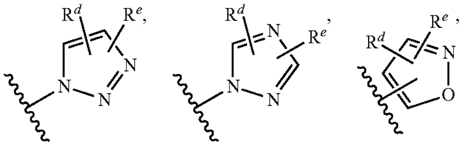

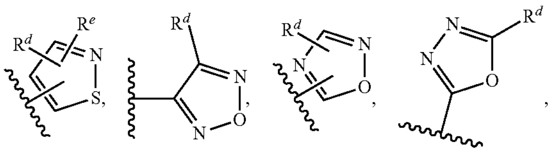

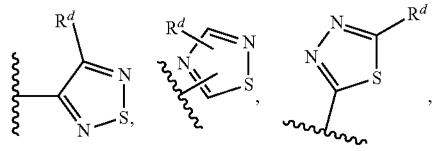

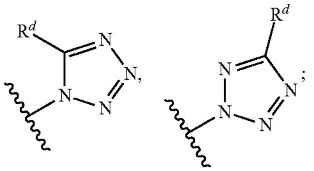

; or $R^B$ is

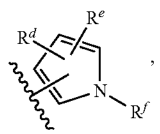

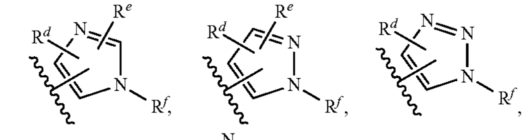

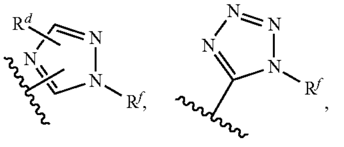

, or

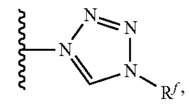

where $R^f$ is hydrogen, —C(=O)$R^7$, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl.

In some embodiments, $R^1$ is unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted $C_3$-$C_6$ cycloalkyl, unsubstituted or substituted $C_2$-$C_7$ heterocycloalkyl, unsubstituted or substituted —($C_1$-$C_6$ alkyl)-($C_3$-$C_6$ cycloalkyl), or unsubstituted or substituted —($C_1$-$C_6$ alkyl)-($C_2$-$C_7$ heterocycloalkyl), wherein any substituted group of $R^1$ is substituted with one or more halogen, unsubstituted or substituted $C_1$-$C_6$ alkyl, unsubstituted or substituted monocyclic heterocycle, —N($R^4$)$_2$, —O$R^5$, —CN, —CO$_2$$R^5$, —C(=O)N($R^4$)$_2$, —S$R^5$, —S(=O)$R^7$, —S(=O)$_2$$R^7$, —N$R^4$C(=O)$R^5$, —N$R^4$SO$_2$$R^7$, —SO$_2$$R^7$, or —SO$_2$N($R^4$)$_2$; wherein $R^1$ comprises a basic amine group.

In some embodiments, $R^1$ is unsubstituted or substituted $C_1$-$C_6$ alkyl, unsubstituted or substituted $C_1$-$C_6$ heteroalkyl containing 1 N atom, unsubstituted or substituted monocyclic 4-, 5- or 6-membered heterocycloalkyl containing 1-4 N atoms and 0 or 1 O or S atoms, unsubstituted or substituted bridged $C_2$-$C_7$ heterocycloalkyl containing 1-2 N atoms, or unsubstituted or substituted —($C_1$-$C_6$ alkyl)-($C_2$-$C_7$ heterocycloalkyl), wherein any substituted group of $R^1$ is substituted with one or more halogen, unsubstituted or substituted $C_1$-$C_6$ alkyl, unsubstituted or substituted monocyclic heterocycle, —N($R^4$)$_2$, —O$R^5$, —CN, —CO$_2$$R^5$, —C(=O)N($R^4$)$_2$, —S$R^5$, —S(=O)$R^7$, —S(=O)$_2$$R^7$, —N$R^4$C(=O)$R^5$, —N$R^4$SO$_2$$R^7$, —SO$_2$$R^7$, or —SO$_2$N($R^4$)$_2$.

In some embodiments, $R^1$ is unsubstituted or substituted $C_1$-$C_6$ alkyl, unsubstituted or substituted $C_1$-$C_6$ heteroalkyl containing 1 N atom, wherein any substituted group of $R^1$ is substituted with one or more halogen, unsubstituted or substituted $C_1$-$C_6$ alkyl, unsubstituted or substituted monocyclic heterocycle, —N($R^4$)$_2$, —O$R^5$, —CN, —CO$_2$$R^5$, —C(=O)N($R^4$)$_2$, —S$R^5$, —S(=O)$R^7$, —S(=O)$_2$$R^7$, —N$R^4$C(=O)$R^5$, —N$R^4$SO$_2$$R^7$, —SO$_2$$R^7$, or —SO$_2$N($R^4$)$_2$; or $R^1$ is unsubstituted or substituted monocyclic 4-, 5- or 6-membered heterocycle containing 1-4 N atoms and 0 or 1 O or S atoms; or $R^1$ is unsubstituted or substituted bridged $C_2$-$C_7$ heterocycloalkyl containing 1-2 N atoms; or $R^1$ is unsubstituted or substituted —($C_1$-$C_6$ alkyl)-($C_2$-$C_7$ heterocycloalkyl), wherein the heterocycloalkyl is an unsubstituted or substituted monocyclic 4-, 5- or 6-membered heterocycloalkyl containing 1-4 N atoms and 0 or 1 O or S atoms.

In some embodiments, $R^1$ is unsubstituted or substituted $C_1$-$C_6$ heteroalkyl containing 1 N atom; or $R^1$ is unsubstituted or substituted monocyclic 4-, 5- or 6-membered heterocycle containing 1-4 N atoms and 0 or 1 O or S atoms; or $R^1$ is unsubstituted or substituted —($C_1$-$C_6$ alkyl)-($C_2$-$C_7$ heterocycloalkyl), wherein the heterocycloalkyl is an unsubstituted or substituted monocyclic 4-, 5- or 6-membered heterocycloalkyl containing 1-4 N atoms and 0 or 1 O or S atoms.

In some embodiments, $R^1$ is unsubstituted or substituted $C_1$-$C_6$ alkyl, unsubstituted or substituted $C_1$-$C_6$ heteroalkyl containing 1 N atom, wherein any substituted group of $R^1$ is substituted with one or more halogen, unsubstituted or substituted $C_1$-$C_6$ alkyl, unsubstituted or substituted monocyclic heterocycle, —N($R^4$)$_2$, —O$R^5$, —CN, —CO$_2$$R^5$, —C(=O)N($R^4$)$_2$, —S$R^5$, —S(=O)$R^7$, —S(=O)$_2$$R^7$, —N$R^4$C(=O)$R^5$, —N$R^4$SO$_2$$R^7$, —SO$_2$$R^7$, or —SO$_2$N($R^4$)$_2$.

In some embodiments, $R^1$ is unsubstituted or substituted $C_1$-$C_6$ heteroalkyl containing 1 N atom. In some embodiments, $R^1$ is unsubstituted or substituted $C_1$-$C_6$ heteroalkyl containing 1 N atom; wherein any substituted group of $R^1$ is substituted with one or more halogen, unsubstituted or substituted $C_1$-$C_6$ alkyl, unsubstituted or substituted monocyclic heterocycle, —N($R^4$)$_2$, —O$R^5$, —CN, —CO$_2$$R^5$, —C(=O)N($R^4$)$_2$, —S$R^5$, —S(=O)$R^7$, —S(=O)$_2$$R^7$, —N$R^4$C(=O)$R^5$, —N$R^4$SO$_2$$R^7$, —SO$_2$$R^7$, or —SO$_2$N($R^4$)$_2$.

In some embodiments, $R^1$ is unsubstituted or substituted monocyclic 4-, 5- or 6-membered heterocycle containing 1-4 N atoms and 0 or 1 O or S atoms.

In some embodiments, $R^1$ is unsubstituted or substituted bridged $C_2$-$C_7$ heterocycloalkyl containing 1-2 N atoms.

In some embodiments, $R^1$ is unsubstituted or substituted —($C_1$-$C_6$ alkyl)-($C_2$-$C_7$ heterocycloalkyl), wherein the heterocycloalkyl is an unsubstituted or substituted monocyclic 4-, 5- or 6-membered heterocycloalkyl containing 1-4 N atoms and 0 or 1 O or S atoms.

In some embodiments, $R^1$ is unsubstituted or substituted $C_1$-$C_6$ heteroalkyl containing 1 N atom, wherein any substituted group of $R^1$ is substituted with one or more halogen, $C_1$-$C_4$ alkyl, —$N(R^4)_2$, or —$OR^5$; or $R^1$ is unsubstituted or substituted azetidinyl, unsubstituted or substituted pyrrolidinyl, or unsubstituted or substituted piperidinyl; or $R^1$ is unsubstituted or substituted —($C_1$-$C_6$ alkyl)-($C_2$-$C_7$ heterocycloalkyl), wherein the heterocycloalkyl is an unsubstituted or substituted azetidinyl, unsubstituted or substituted pyrrolidinyl, or unsubstituted or substituted piperidinyl.

In some embodiments, $R^1$ is unsubstituted or substituted azetidinyl, unsubstituted or substituted pyrrolidinyl, or unsubstituted or substituted piperidinyl.

In some embodiments, $R^1$ is unsubstituted or substituted $C_1$-$C_6$ heteroalkyl containing 1 N atom, wherein any substituted group of $R^1$ is substituted with one or more halogen, $C_1$-$C_4$ alkyl, —$N(R^4)_2$, or —$OR^5$.

In some embodiments, the compound has the structure of Formula (VIIa), or a pharmaceutically acceptable salt, or solvate thereof:

Formula (VIIa)

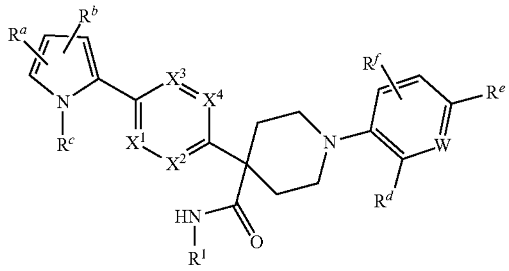

wherein W is CH, $CR^a$, $CR^b$, or N. In some embodiments, W is CH or N.

In some embodiments, the compound has the structure of Formula (VIIb), or a pharmaceutically acceptable salt, or solvate thereof:

Formula (VIIb)

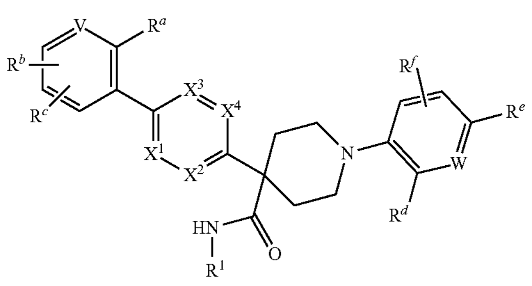

wherein V is CH, $CR^a$, $CR^b$, or N; and W is CH, $CR^d$, $CR^e$, or N.

In some embodiments, the compound has the structure of Formula (VIIc), or a pharmaceutically acceptable salt, or solvate thereof:

Formula (VIIc)

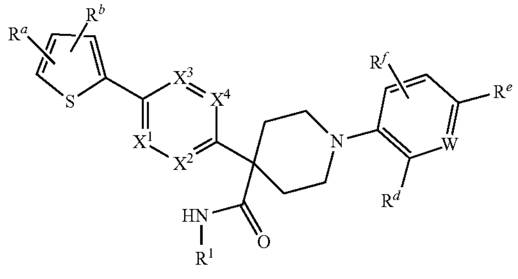

wherein W is CH, $CR^a$, $CR^b$, or N. In some embodiments, W is CH or N.

In some embodiments, V is CH or N. In some embodiments, W is CH or N. In some embodiments, V is CH or N; and W is CH or N.

In some embodiments, the compound has the structure of Formula (VIId), or a pharmaceutically acceptable salt, or solvate thereof:

Formula (VIId)

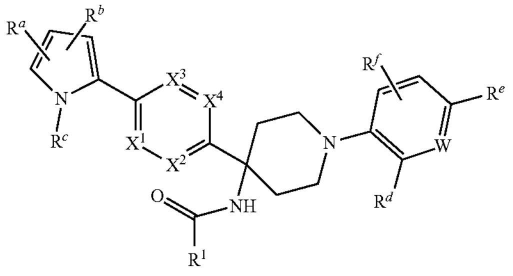

wherein W is CH, $CR^a$, $CR^b$, or N. In some embodiments, W is CH or N.

In some embodiments, the compound has the structure of Formula (VIIe), or a pharmaceutically acceptable salt, or solvate thereof:

Formula (VIIe)

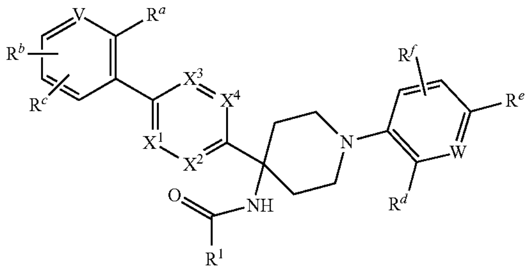

wherein V is CH, $CR^a$, $CR^b$, or N; and W is CH, $CR^d$, $CR^e$, or N.

In some embodiments, the compound has the structure of Formula (VIIf), or a pharmaceutically acceptable salt, or solvate thereof:

Formula (VIIf)

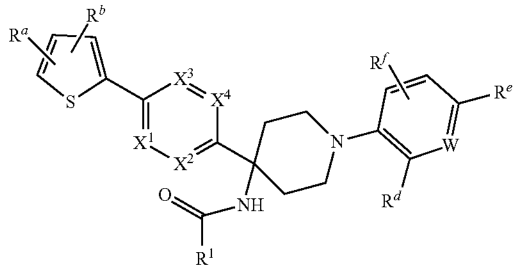

wherein W is CH, $CR^a$, $CR^b$, or N. In some embodiments, W is CH or N.

In some embodiments, V is CH or N. In some embodiments, W is CH or N. In some embodiments, V is CH or N; and W is CH or N.

In some embodiments, the compound has the structure of Formula (VIII), or a pharmaceutically acceptable salt, or solvate thereof:

Formula (VIII)

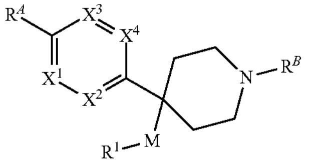

wherein:

$R^A$ is unsubstituted or substituted phenyl, unsubstituted or substituted pyridinyl, unsubstituted or substituted furanyl, unsubstituted or substituted thienyl, unsubstituted or substituted pyrrolyl, unsubstituted or substituted pyrazolyl, unsubstituted or substituted isoxazolyl, unsubstituted or substituted quinolinyl, unsubstituted or substituted indolyl, unsubstituted or substituted indazolyl, or unsubstituted or substituted benzofuranyl, wherein if $R^A$ is substituted then $R^A$ is substituted with 1 or 2 groups selected from $R^a$, $R^b$, and $R^c$;

$R^B$ is unsubstituted or substituted phenyl or unsubstituted or substituted pyridinyl, wherein if $R^B$ is substituted then $R^B$ is substituted with 1, 2, or 3 groups selected from $R^d$, $R^e$, and $R^f$; and M is —$NR^3$—, —O—, *—$NR^3$—(C═O)—, *—(C═O)—$NR^3$—, *—O—(C═O)$NR^3$—, *—$NR^3$—(C═O)O—, or —$NR^3$—(C═O)$NR^3$—, wherein * indicates the attachment point to $R^1$.

In some embodiments, $X^1$ is $CR^{11}$; $X^2$ is $CR^{12}$; $X^3$ is $CR^{13}$; and $X^4$ is $CR^{14}$. In some embodiments, $X^1$ is N; $X^2$ is $CR^{12}$; $X^3$ is $CR^{13}$; and $X^4$ is $CR^{14}$. In some embodiments, $X^1$ is $CR^{11}$; $X^2$ is N; $X^3$ is $CR^{13}$; and $X^4$ is $CR^{14}$. In some embodiments, $X^1$ is N; $X^2$ is $CR^{12}$; $X^3$ is $CR^{13}$; and $X^4$ is N. In some embodiments, $X^1$ is N; $X^2$ is N; $X^3$ is $CR^{13}$; and $X^4$ is $CR^{14}$. In some embodiments, $X^1$ is N; $X^2$ is $CR^{12}$; $X^3$ is N; and $X^4$ is $CR^{14}$. In some embodiments, $X^1$ is $CR^{11}$; $X^2$ is $CR^{12}$; $X^3$ is $CR^{13}$; and $X^4$ is $CR^{14}$.

In some embodiments, $X^1$ is $CR^{11}$ or N; $X^2$ is $CR^{12}$; $X^3$ is $CR^{13}$; and $X^4$ is $CR^{14}$.

In some embodiments, $X^1$ is $CR^{11}$ or N; $X^2$ is $CR^{12}$ or N; $X^3$ is $CR^{13}$; and $X^4$ is $CR^{14}$.

In some embodiments, $R^{11}$, $R^{12}$, $R^{13}$, and $R^{14}$ are each independently hydrogen, halogen, unsubstituted or substituted $C_1$-$C_6$ alkyl, unsubstituted or substituted $C_1$-$C_6$ fluoroalkyl, unsubstituted or substituted $C_3$-$C_6$cycloalkyl, —CN, or —$OR^4$. In some embodiments, $R^{11}$, $R^{12}$, $R^{13}$, and $R^{14}$ are each independently hydrogen, halogen, $C_1$-$C_6$ alkyl, fluoroalkyl, unsubstituted $C_3$-$C_6$cycloalkyl, —CN, or —$OR^4$. In some embodiments, $R^{11}$, $R^{12}$, $R^{13}$, and $R^{14}$ are each independently hydrogen, F, Cl, Br, —CN, —$OCH_3$, —$OCH_2CH_3$, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$, —$CH_2F$, —$CHF_2$, —$CF_3$, or cyclopropyl. In some embodiments, $R^{11}$, $R^{12}$, $R^{13}$, and $R^{14}$ are each independently hydrogen or F.

In some embodiments, $X^1$ is CH or CF; $X^2$ is CH or CF; $X^3$ is CH or CF; and $X^4$ is CH or CF. In some embodiments, $X^1$ is N; $X^2$ is CH or CF; $X^3$ is CH or CF; and $X^4$ is CH or CF. In some embodiments, $X^1$ is CH or CF; $X^2$ is N; $X^3$ is CH or CF; and $X^4$ is CH or CF. In some embodiments, $X^1$ is N; $X^2$ is CH or CF; $X^3$ is CH or CF; and $X^4$ is N. In some embodiments, $X^1$ is N; $X^2$ is N; $X^3$ is CH or CF; and $X^4$ is CH or CF. In some embodiments, $X^1$ is N; $X^2$ is CH or CF; $X^3$ is N; and $X^4$ is CH or CF. In some embodiments, $X^1$ is CH or CF; $X^2$ is CH or CF; $X^3$ is $CR^{13}$; and $X^4$ is $CR^{14}$.

In some embodiments, $X^1$ is CH, CF, or N; $X^2$ is CH or CF; $X^3$ is CH or CF; and $X^4$ is CH or CF. In some embodiments, $X^1$ is $CR^{11}$ or N; $X^2$ is CH; $X^3$ is CH; and $X^4$ is CH. In some embodiments, $X^1$ is CH, CF, or N; $X^2$ is CH; $X^3$ is CH; and $X^4$ is CH.

In some embodiments, $X^1$ is CH, CF, or N; $X^2$ is CH, CF, or N; $X^3$ is CH or CF; and $X^4$ is CH or CF. In some embodiments, $X^1$ is $CR^{11}$ or N; $X^2$ is $CR^{12}$ or N; $X^3$ is CH; and $X^4$ is CH. In some embodiments, $X^1$ is CH, CF, or N; $X^2$ is CH, CF, or N; $X^3$ is CH; and $X^4$ is CH.

In some embodiments, $X^1$ is CH, CF, or N; $X^2$ is CH or CF; $X^3$ is $CR^{13}$; and $X^4$ is CH or CF. In some embodiments, $X^1$ is CH, CF, or N; $X^2$ is CH; $X^3$ is $CR^{13}$; and $X^4$ is CH. In some embodiments, $X^1$ is N; $X^2$ is CH; $X^3$ is $CR^{13}$; and $X^4$ is CH.

In some embodiments, $X^1$ is CH or N; $X^2$ is CH or N; $X^3$ is CH, CF, or N; and $X^4$ is CH or N. In some embodiments, $X^1$ is CH or N; $X^2$ is CH or N; $X^3$ is CH or CF; and $X^4$ is CH. In some embodiments, $X^1$ is N; $X^2$ is CH; $X^3$ is CH or CF; and $X^4$ is CH. In some embodiments, $X^1$ is N; $X^2$ is CH; $X^3$ is CH; and $X^4$ is CH. In some embodiments, $X^1$ is N; $X^2$ is CH; $X^3$ is CF; and $X^4$ is CH.

In some embodiments, $R^{13}$ is hydrogen, halogen, unsubstituted or substituted $C_1$-$C_6$ alkyl, unsubstituted or substituted $C_1$-$C_6$ fluoroalkyl, unsubstituted or substituted $C_3$-$C_6$cycloalkyl, —CN, or —$OR^4$. In some embodiments, $R^{13}$ is hydrogen, halogen, $C_1$-$C_6$ alkyl, fluoroalkyl, unsubstituted $C_3$-$C_6$cycloalkyl, —CN, or —$OR^4$. In some embodiments, $R^{13}$ is hydrogen, F, Cl, Br, —CN, —$OCH_3$, —$OCH_2CH_3$, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$, —$CH_2F$, —$CHF_2$, —$CF_3$, or cyclopropyl. In some embodiments, $R^{13}$ is hydrogen or F. In some embodiments, $R^{13}$ is hydrogen. In some embodiments, $R^{13}$ is F.

In some embodiments, M is *—$NR^3$—(C═O)— or *—(C═O)—$NR^3$—, wherein * indicates the attachment point to $R^1$ In some embodiments, $R^A$ is unsubstituted or substituted pyridinyl or unsubstituted or substituted phenyl, wherein if $R^A$ is substituted then $R^A$ is substituted with 1 or 2 groups selected from $R^a$, $R^b$, and $R^c$.

In some embodiments, $R^B$ is unsubstituted or substituted phenyl, wherein if $R^B$ is substituted then $R^B$ is substituted with 1, 2, or 3 groups selected from $R^d$, $R^e$, and $R^f$.

In some embodiments, $R^a$, $R^b$, and $R^c$ are independently selected from the group consisting of hydrogen, halogen, —$OR^4$, —CN, —$N(R^4)_2$, —C(═O)$R^7$, unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted $C_3$-$C_6$ cycloalkyl, unsubstituted or substituted $C_2$-$C_7$ heterocycloalkyl, unsubstituted or substituted phenyl, unsubstituted or substituted monocyclic heteroaryl, and unsubstituted or substituted bicyclic heteroaryl, wherein any substituted group of $R^a$, $R^b$, and $R^c$ is substituted with one or more $R^6$ groups; or one $R^a$ and one $R^b$, when present on adjacent atoms of $R^A$, are taken together with the intervening atoms connecting $R^a$ to $R^b$ to form a 5- to 6-membered monocyclic carbocycle or 5- to 6-membered monocyclic heterocycle, wherein the carbocycle or heterocycle is unsubstituted or substituted with one or more $R^6$ groups; wherein, if $R^a$, $R^b$, or $R^c$ is attached to the N atom of a heteroaryl, then it is hydrogen, —C(═O)$R^7$, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl; and $R^d$, $R^e$, and $R^f$ are independently selected from the group consisting of hydrogen, halogen, —$OR^4$, —CN, —$N(R^4)_2$, —C(═O)$R^7$, —C(═O)$N(R^4)_2$, unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted $C_3$-$C_6$ cycloalkyl, unsubstituted or substituted $C_2$-$C_7$ heterocycloalkyl, unsubstituted or substituted phenyl, unsubstituted or substituted monocyclic heteroaryl, and unsubstituted or substituted bicyclic heteroaryl, wherein any substituted group of $R^d$, $R^e$, and $R^f$ is substituted with one or more $R^6$ groups; wherein, if $R^d$, $R^e$, or R is attached to the N atom of a heteroaryl, then it is hydrogen, —C(═O)$R^7$, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl.

In some embodiments, $R^a$ is selected from the group consisting of hydrogen, halogen, —$OR^4$, —CN, —$N(R^4)_2$, —C(═O)$R^7$, unsubstituted or substituted $C_1$-$C_6$ alkyl, unsubstituted or substituted $C_1$-$C_6$ fluoroalkyl, unsubstituted or substituted $C_1$-$C_6$ heteroalkyl, and unsubstituted or substituted $C_3$-$C_6$ cycloalkyl, wherein any substituted group of $R^a$ is substituted with one or more $R^6$ groups; and $R^b$ and $R^c$ are independently selected from the group consisting of hydrogen, halogen, —$OR^4$, —CN, —$N(R^4)_2$, —C(═O)$R^7$, unsubstituted or substituted $C_1$-$C_6$ alkyl, unsubstituted or substituted $C_1$-$C_6$ fluoroalkyl, and unsubstituted or substituted $C_1$-$C_6$ heteroalkyl, wherein any substituted group of $R^b$ and $R^c$ is substituted with one or more $R^6$ groups; wherein, if $R^a$, $R^b$, or $R^c$ is attached to the N atom of a heteroaryl, then it is hydrogen, —C(═O)$R^7$, or unsubstituted or substituted $C_1$-$C_6$ alkyl.

In some embodiments, $R^a$ is selected from the group consisting of hydrogen, F, Cl, Br, —CN, —OH, —$OCH_3$, —$OCH_2CH_3$, —C(O)$CH_3$, —C(O)$CH_2CH_3$, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)(CH_2CH_3)$, —$C(CH_3)_3$, —$CH_2CH_2CH(CH_3)_2$, —$CH_2OH$, —$CH_2CN$, —$CH_2F$, —$CHF_2$, —$CF_3$, —$CH_2CH_2OH$, —$CH_2CH_2CN$, —$CH_2CH_2F$, —$CH_2CHF_2$, —$CH_2CF_3$, —$CH_2OCH_3$, —$CH_2CH_2OCH_3$, —$CH_2NH_2$, —$CH_2NHCH_3$, —$CH_2N(CH_3)_2$, —$CH_2CH_2NH_2$, —$CH_2CH_2NHCH_3$, —$CH_2CH_2N(CH_3)_2$, cyclopropyl, cyclobutyl, cyclopentyl, and cyclohexyl; and $R^b$ and $R^c$ are independently selected from the group consisting of hydrogen, F, Cl, Br, —CN, —OH, —$OCH_3$, —$OCH_2CH_3$, —C(O)$CH_3$, —C(O)$CH_2CH_3$, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)(CH_2CH_3)$, —$C(CH_3)_3$, —$CH_2CH_2CH(CH_3)_2$, —$CH_2OH$, —$CH_2CN$, —$CH_2F$, —$CHF_2$, —$CF_3$, —$CH_2CH_2OH$, —$CH_2CH_2CN$, —$CH_2CH_2F$, —$CH_2CHF_2$, —$CH_2CF_3$, —$CH_2OCH_3$, —$CH_2CH_2OCH_3$, —$CH_2NH_2$, —$CH_2NHCH_3$, —$CH_2N(CH_3)_2$, —$CH_2CH_2NH_2$, —$CH_2CH_2NHCH_3$, and —$CH_2CH_2N(CH_3)_2$; wherein, if $R^a$, $R^b$, or $R^c$ is attached to the N atom of a heteroaryl, then it is hydrogen, —C(O)$CH_3$, —C(O)$CH_2CH_3$, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)(CH_2CH_3)$, —$C(CH_3)_3$, —$CH_2CH_2CH(CH_3)_2$, —$CH_2OH$, —$CH_2CN$, —$CH_2F$, —$CHF_2$, —$CF_3$, —$CH_2CH_2OH$, —$CH_2CH_2CN$, —$CH_2CH_2F$, —$CH_2CHF_2$, —$CH_2CF_3$, —$CH_2OCH_3$, —$CH_2CH_2OCH_3$, —$CH_2NH_2$, —$CH_2NHCH_3$, —$CH_2N(CH_3)_2$, —$CH_2CH_2NH_2$, —$CH_2CH_2NHCH_3$, and —$CH_2CH_2N(CH_3)_2$.

In some embodiments, one $R^a$ and one $R^b$ on adjacent atoms of $R^A$ are taken together with the intervening atoms connecting $R^a$ to $R^b$ to form a 5- to 6-membered monocyclic cycloalkyl or 5- to 6-membered monocyclic heterocycloalkyl, wherein the cycloalkyl or heterocycloalkyl is unsubstituted or substituted with one or more $R^6$ groups. In some embodiments, one $R^a$ and one $R^b$ on adjacent atoms of $R^A$ are taken together with the intervening atoms connecting $R^a$ to $R^b$ to form a 5-membered monocyclic heterocycloalkyl, wherein the heterocycloalkyl is unsubstituted or substituted with one or more $R^6$ groups.

In some embodiments, $R^d$ is selected from the group consisting of hydrogen, halogen, —$OR^4$, —CN, —$N(R^4)_2$, unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted $C_3$-$C_6$ cycloalkyl, unsubstituted or substituted $C_2$-$C_7$ heterocycloalkyl, unsubstituted or substituted phenyl, unsubstituted or substituted monocyclic heteroaryl, and unsubstituted or substituted bicyclic heteroaryl, wherein any substituted group of $R^d$ is substituted with one or more $R^6$ groups; and $R^e$ and $R^f$ are independently selected from the group consisting of hydrogen, halogen, —$OR^4$, —CN, —$N(R^4)_2$, unsubstituted or substituted $C_1$-$C_6$ alkyl, unsubstituted or substituted $C_1$-$C_6$ fluoroalkyl, and unsubstituted or substituted $C_1$-$C_6$ heteroalkyl; wherein, if $R^d$, $R^e$, or $R^f$ is attached to the N atom of a heteroaryl, then it is hydrogen, —C(═O)$R^7$, or unsubstituted or substituted $C_1$-$C_6$ alkyl.

In some embodiments, $R^d$ is selected from the group consisting of hydrogen, F, Cl, Br, —CN, —OH, —$OCH_3$, —$OCH_2CH_3$, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)(CH_2CH_3)$, —$C(CH_3)_3$, —$CH_2CH_2CH(CH_3)_2$, —$CH_2OH$, —$CH_2CN$, —$CH_2F$, —$CHF_2$, —$CF_3$, —$CH_2CH_2OH$, —$CH_2CH_2CN$, —$CH_2CH_2F$, —$CH_2CHF_2$, —$CH_2CF_3$, —$CH_2OCH_3$, —$CH_2CH_2OCH_3$, —$CH_2NH_2$, —$CH_2NHCH_3$, —$CH_2N(CH_3)_2$, —$CH_2CH_2NH_2$, —$CH_2CH_2NHCH_3$, —$CH_2CH_2N(CH_3)_2$, unsubstituted or substituted cyclopropyl, unsubstituted or substituted cyclobutyl, unsubstituted or substituted cyclopentyl, unsubstituted or substituted cyclohexyl, unsubstituted or substituted $C_2$-$C_7$ heterocycloalkyl, unsubstituted or substituted phenyl, unsubstituted or substituted monocyclic heteroaryl, and unsubstituted or substituted bicyclic heteroaryl, wherein any substituted group of $R^d$ is substituted with one or more $R^6$ groups; and $R^e$ and $R^f$ are independently selected from the group consisting of hydrogen, F, Cl, Br, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)(CH_2CH_3)$, —$C(CH_3)_3$, —$CH_2CH_2CH(CH_3)_2$, —$CH_2OH$, —$CH_2CN$, —$CH_2F$, —$CHF_2$, —$CF_3$, —CN, —OH, —$OCH_3$, and —$OCH_2CH_3$; wherein, if $R^d$, $R^e$, or $R^f$ is attached to the N atom of a heteroaryl, then it is hydrogen, —C(O)$CH_3$, —C(O)$CH_2CH_3$, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)(CH_2CH_3)$, —$C(CH_3)_3$, —$CH_2CH_2CH(CH_3)_2$, —$CH_2OH$, —$CH_2CN$, —$CH_2F$, —$CHF_2$, —$CF_3$, —$CH_2CH_2OH$, —$CH_2CH_2CN$, —$CH_2CH_2F$, —$CH_2CHF_2$, —$CH_2CF_3$, —$CH_2OCH_3$, —$CH_2CH_2OCH_3$, —$CH_2NH_2$, —$CH_2NHCH_3$, —$CH_2N(CH_3)_2$, —$CH_2CH_2NH_2$, —$CH_2CH_2NHCH_3$, and —$CH_2CH_2N(CH_3)_2$.

In some embodiments, $R^A$ is unsubstituted or substituted 5- or 6-membered heteroaryl containing 1 or 2 N atoms or unsubstituted or substituted phenyl, wherein if $R^A$ is substituted then $R^A$ is substituted with 1, or 2 groups selected from $R^a$, $R^b$, and $R^c$;

$R^a$ is selected from the group consisting of hydrogen, halogen, —$OR^4$, —CN, —$N(R^4)_2$, —C(═O)$R^7$, unsubstituted or substituted $C_1$-$C_6$ alkyl, unsubstituted or substituted $C_1$-$C_6$ fluoroalkyl, unsubstituted or substituted $C_1$-$C_6$ heteroalkyl, and unsubstituted or substituted $C_3$-$C_6$ cycloalkyl, wherein any substituted group of $R^a$ is substituted with one or more $R^6$ groups;

$R^b$ and $R^c$ are independently selected from the group consisting of hydrogen, halogen, —$OR^4$, —CN, —$N(R^4)_2$, —C(═O)$R^7$, unsubstituted or substituted $C_1$-$C_6$ alkyl, unsubstituted or substituted $C_1$-$C_6$ fluoroalkyl, and unsubstituted or substituted $C_1$-$C_6$ heteroalkyl, wherein any substituted group of $R^b$ and $R^c$ is substituted with one or more $R^6$ groups;

wherein, if $R^a$, $R^b$, or $R^c$ is attached to the N atom of a heteroaryl, then it is hydrogen, —C(═O)$R^7$, or unsubstituted or substituted $C_1$-$C_6$ alkyl;

$R^B$ is unsubstituted or substituted phenyl or unsubstituted or substituted 5- or 6-membered heteroaryl containing 1 or 2 N atoms, wherein if $R^B$ is substituted then $R^B$ is substituted with 1, 2, or 3 groups selected from $R^d$, $R^e$, and $R^f$;

$R^d$ is selected from the group consisting of hydrogen, halogen, —$OR^4$, —CN, —$N(R^4)_2$, unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted $C_3$-$C_6$ cycloalkyl, unsubstituted or substituted $C_2$-$C_7$ heterocycloalkyl, unsubstituted or substituted phenyl, unsubstituted or substituted monocyclic heteroaryl, and unsubstituted or substituted bicyclic heteroaryl, wherein any substituted group of $R^d$ is substituted with one or more $R^6$ groups;

$R^e$ and $R^f$ are independently selected from the group consisting of hydrogen, halogen, —$OR^4$, —CN, —$N(R^4)_2$, unsubstituted or substituted $C_1$-$C_6$ alkyl, unsubstituted or substituted $C_1$-$C_6$ fluoroalkyl, and unsubstituted or substituted $C_1$-$C_6$ heteroalkyl;

wherein, if $R^d$, $R^e$, or $R^f$ is attached to the N atom of a heteroaryl, then it is hydrogen, —C(═O)$R^7$, or unsubstituted or substituted $C_1$-$C_6$ alkyl;

$X^1$ is $CR^{11}$ or N;

$X^2$ is $CR^{12}$ or N;

$X^3$ is $CR^{13}$ or N;

$X^4$ is $CR^{14}$ or N;

$R^{11}$, $R^{12}$, $R^{13}$, and $R^{14}$ are each independently hydrogen, halogen, $C_1$-$C_6$ alkyl, $C_1$-$C_6$ fluoroalkyl, or $C_1$-$C_6$ heteroalkyl, —CN, —$OR^4$, or —$N(R^4)_2$;

M is *—$NR^3$—(C═O)— or *—(C═O)—$NR^3$—, wherein * indicates the attachment point to $R^1$;

$R^1$ is unsubstituted or substituted $C_1$-$C_6$ alkyl, unsubstituted or substituted $C_1$-$C_6$ heteroalkyl containing 1 N atom, wherein any substituted group of $R^1$ is substituted with one or more halogen, unsubstituted or substituted $C_1$-$C_6$ alkyl, unsubstituted or substituted monocyclic heterocycle, —$N(R^4)_2$, —$OR^5$, —CN, —$CO_2R^5$, —C(═O)$N(R^4)_2$, —$SR^5$, —S(═O)$R^7$, —S(═O)$_2R^7$, —$NR^4$C(═O)$R^5$, —$NR^4SO_2R^7$, —$SO_2R^7$, or —$SO_2N(R^4)_2$;

or $R^1$ is unsubstituted or substituted monocyclic 4-, 5- or 6-membered heterocycle containing 1-4 N atoms and 0 or 1 O or S atoms;

or $R^1$ is unsubstituted or substituted bridged $C_2$-$C_7$ heterocycloalkyl containing 1-2 N atoms;

or $R^1$ is unsubstituted or substituted —($C_1$-$C_6$ alkyl)-($C_2$-$C_7$ heterocycloalkyl), wherein the heterocycloalkyl is an unsubstituted or substituted monocyclic 4-, 5- or 6-membered heterocycloalkyl containing 1-2 N atoms.

In some embodiments, $R^A$ is unsubstituted or substituted pyrrolyl, unsubstituted or substituted pyridinyl, or unsubstituted or substituted phenyl, wherein if $R^A$ is substituted then $R^A$ is substituted with 1, or 2 groups selected from $R^a$, $R^b$, and $R^c$;

$R^B$ is unsubstituted or substituted phenyl or unsubstituted or substituted pyridinyl, wherein if $R^B$ is substituted then $R^B$ is substituted with 1, 2, or 3 groups selected from $R^d$, $R^e$, and $R^f$;

$X^1$ is CH or N;

$X^2$ is CH or N;

$X^3$ is $CR^{13}$ or N;

$X^4$ is CH or N;

M is *—$NR^3$—(C═O)— or *—(C═O)—$NR^3$—, wherein * indicates the attachment point to $R^1$;

$R^{11}$, $R^{12}$, $R^{13}$, and $R^{14}$ are each independently hydrogen, F, Cl, —$CH_3$, $CF_3$, —CN, —$OR^4$, or —$N(R^4)_2$;

$R^1$ is unsubstituted or substituted $C_1$-$C_6$ heteroalkyl containing 1 N atom, wherein any substituted group of $R^1$ is substituted with one or more halogen, $C_1$-$C_4$ alkyl, —$N(R^4)_2$, or —$OR^5$;

or $R^1$ is unsubstituted or substituted azetidinyl, unsubstituted or substituted pyrrolidinyl, or unsubstituted or substituted piperidinyl;

or $R^1$ is unsubstituted or substituted bridged $C_2$-$C_7$ heterocycloalkyl containing 1-2 N atoms;

or $R^1$ is unsubstituted or substituted —($C_1$-$C_6$ alkyl)-($C_2$-$C_7$ heterocycloalkyl), wherein the heterocycloalkyl is an unsubstituted or substituted monocyclic 4-, 5- or 6-membered heterocycloalkyl containing 1-2 N atoms.

In some embodiments, $R^A$ is

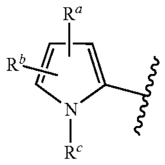

;

or $R^A$ is

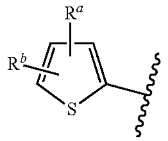

;

or $R^A$ is

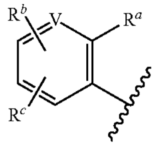

, where V is CH or N;

$R^a$ is selected from the group consisting of hydrogen, halogen, —$OR^4$, —CN, unsubstituted or substituted $C_1$-$C_6$ alkyl, unsubstituted or substituted $C_1$-$C_6$ fluoroalkyl, and unsubstituted or substituted $C_3$-$C_6$ cycloalkyl; and $R^b$ and $R^c$ are independently selected from the group consisting of hydrogen, halogen, —$OR^4$, —CN, unsubstituted or substituted $C_1$-$C_6$ alkyl, and unsubstituted or substituted $C_1$-$C_6$ fluoroalkyl;

$R^B$ is

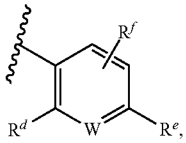

where W is CH or N;

$R^d$ is selected from the group consisting of hydrogen, halogen, —$OR^4$, —CN, unsubstituted or substituted $C_1$-$C_6$ alkyl, unsubstituted or substituted $C_1$-$C_6$ fluoroalkyl, and unsubstituted or substituted $C_3$-$C_6$ cycloalkyl; and $R^e$ and $R^f$ are independently selected from the group consisting of hydrogen, halogen, —$OR^4$, —CN, unsubstituted or substituted $C_1$-$C_6$ alkyl, and unsubstituted or substituted $C_1$-$C_6$ fluoroalkyl;

$X^1$ is CH, CF, or N;

$X^2$ is CH, CF, or N;

$X^3$ is CH, CF, or N;

$X^4$ is CH, CF, or N;

M is *—NH—(C=O)— or *—(C=O)—NH—, wherein * indicates the attachment point to $R^1$;

$R^1$ is unsubstituted or substituted $C_1$-$C_6$ alkyl, unsubstituted or substituted $C_1$-$C_6$ heteroalkyl containing 1 N atom, wherein any substituted group of $R^1$ is substituted with one or more halogen, unsubstituted or substituted $C_1$-$C_6$ alkyl, unsubstituted or substituted monocyclic heterocycle, —$N(R^4)_2$, —$OR^5$, —CN, —$CO_2R^5$, —$C(=O)N(R^4)_2$, —$SR^5$, —$S(=O)R^7$, —$S(=O)_2R^7$, —$NR^4C(=O)R^5$, —$NR^4SO_2R^7$, —$SO_2R^7$, or —$SO_2N(R^4)_2$;

or $R^1$ is unsubstituted or substituted monocyclic 4-, 5- or 6-membered heterocycle containing 1-4 N atoms and 0 or 1 O or S atoms;

or $R^1$ is unsubstituted or substituted bridged $C_2$-$C_7$ heterocycloalkyl containing 1-2 N atoms;

or $R^1$ is unsubstituted or substituted —($C_1$-$C_6$ alkyl)-($C_2$-$C_7$ heterocycloalkyl), wherein the heterocycloalkyl is an unsubstituted or substituted monocyclic 4-, 5- or 6-membered heterocycloalkyl containing 1-2 N atoms.

In some embodiments, $R^A$ is

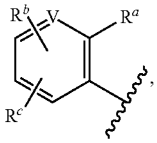

, where V is CH or N;

$R^a$ is selected from the group consisting of hydrogen, F, Cl, Br, —CN, —$OCH_3$, —$OCH_2CH_3$, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)(CH_2CH_3)$, —$C(CH_3)_3$, —$CH_2F$, —$CHF_2$, and —$CF_3$; and $R^b$ and $R^c$ are independently selected from the group consisting of hydrogen, F, Cl, —$CH_3$, —$CH_2F$, —$CHF_2$, —$CF_3$, —CN, and —$OCH_3$;

$R^B$ is

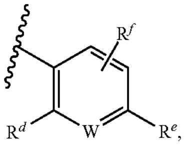

where W is CH or N;

$R^d$ is selected from the group consisting of hydrogen, F, Cl, Br, —CN, —$OCH_3$, —$OCH_2CH_3$, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)(CH_2CH_3)$, —$C(CH_3)_3$, —$CH_2F$, —$CHF_2$, and —$CF_3$;

$R^e$ and $R^f$ are independently selected from the group consisting of hydrogen, F, Cl, Br, —$CH_3$, —$CH_2F$, —$CHF_2$, —$CF_3$, —CN, —OH, and —$OCH_3$;

$X^1$ is CH or N;

$X^2$ is CH or N;

$X^3$ is CH, CF, or N;

$X^4$ is CH or N;

M is *—NH—(C=O)— or *—(C=O)—NH—, wherein * indicates the attachment point to $R^1$;

$R^1$ is unsubstituted or substituted $C_1$-$C_6$ alkyl, unsubstituted or substituted $C_1$-$C_6$ heteroalkyl containing 1 N atom, wherein any substituted group of $R^1$ is substituted with one or more halogen, unsubstituted or substituted $C_1$-$C_6$ alkyl, unsubstituted or substituted monocyclic heterocycle, —$N(R^4)_2$, —$OR^5$, —CN, —$CO_2R^5$, —$C(=O)N(R^4)_2$, —$SR^5$, —$S(=O)R^7$, —$S(=O)_2R^7$, —$NR^4C(=O)R^5$, —$NR^4SO_2R^7$, —$SO_2R^7$, or —$SO_2N(R^4)_2$;

or $R^1$ is unsubstituted or substituted monocyclic 4-, 5- or 6-membered heterocycle containing 1-4 N atoms and 0 or 1 O or S atoms;

or $R^1$ is unsubstituted or substituted bridged $C_2$-$C_7$ heterocycloalkyl containing 1-2 N atoms;

or $R^1$ is unsubstituted or substituted —($C_1$-$C_6$ alkyl)-($C_2$-$C_7$ heterocycloalkyl), wherein the heterocycloalkyl is an unsubstituted or substituted monocyclic 4-, 5- or 6-membered heterocycloalkyl containing 1-2 N atoms.

In some embodiments, the compound has the structure of Formula (IX), or a pharmaceutically acceptable salt, or solvate thereof:

Formula (IX)

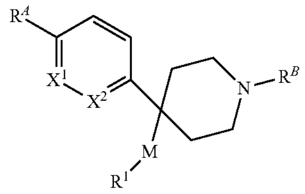

wherein, $R^A$ is unsubstituted or substituted 5- or 6-membered heteroaryl containing 1 or 2 N atoms or unsubstituted or substituted phenyl, wherein if $R^A$ is substituted then $R^A$ is substituted with 1, or 2 groups selected from $R^a$, $R^b$, and $R^c$;

$R^a$ is selected from the group consisting of hydrogen, halogen, —$OR^4$, —CN, —$N(R^4)_2$, —C(═O)$R^7$, unsubstituted or substituted $C_1$-$C_6$ alkyl, unsubstituted or substituted $C_1$-$C_6$ fluoroalkyl, unsubstituted or substituted $C_1$-$C_6$ heteroalkyl, and unsubstituted or substituted $C_3$-$C_6$ cycloalkyl, wherein any substituted group of $R^a$ is substituted with one or more $R^6$ groups; and $R^b$ and $R^c$ are independently selected from the group consisting of hydrogen, halogen, —$OR^4$, —CN, —$N(R^4)_2$, —C(═O)$R^7$, unsubstituted or substituted $C_1$-$C_6$ alkyl, unsubstituted or substituted $C_1$-$C_6$ fluoroalkyl, and unsubstituted or substituted $C_1$-$C_6$ heteroalkyl, wherein any substituted group of $R^b$ and $R^c$ is substituted with one or more $R^6$ groups;

wherein, if $R^a$, $R^b$, or $R^c$ is attached to the N atom of a heteroaryl, then it is hydrogen, —C(═O)$R^7$, or unsubstituted or substituted $C_1$-$C_6$ alkyl;

$R^B$ is unsubstituted or substituted phenyl or unsubstituted or substituted 5- or 6-membered heteroaryl containing 1 or 2 N atoms, wherein if $R^B$ is substituted then $R^B$ is substituted with 1, 2, or 3 groups selected from $R^d$, $R^e$, and $R^f$;

$R^d$ is selected from the group consisting of hydrogen, halogen, —$OR^4$, —CN, —$N(R^4)_2$, unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted $C_3$-$C_6$ cycloalkyl, unsubstituted or substituted $C_2$-$C_7$ heterocycloalkyl, unsubstituted or substituted phenyl, unsubstituted or substituted monocyclic heteroaryl, and unsubstituted or substituted bicyclic heteroaryl, wherein any substituted group of $R^d$ is substituted with one or more $R^6$ groups; and $R^e$ and $R^f$ are independently selected from the group consisting of hydrogen, halogen, —$OR^4$, —CN, —$N(R^4)_2$, unsubstituted or substituted $C_1$-$C_6$ alkyl, unsubstituted or substituted $C_1$-$C_6$ fluoroalkyl, and unsubstituted or substituted $C_1$-$C_6$ heteroalkyl;

wherein, if $R^d$, $R^e$, or $R^f$ is attached to the N atom of a heteroaryl, then it is hydrogen, —C(═O)$R^7$, or unsubstituted or substituted $C_1$-$C_6$ alkyl;

$X^1$ is $CR^{11}$ or N;

$X^2$ is $CR^{12}$ or N;

$R^{11}$ and $R^{12}$ are each independently hydrogen, halogen, $C_1$-$C_6$ alkyl, $C_1$-$C_6$ fluoroalkyl, or $C_1$-$C_6$ heteroalkyl, —CN, —$OR^4$, or —$N(R^4)_2$;

M is —$NR^3$—, —O—, *—$NR^3$—(C═O)—, *—(C═O)—$NR^3$—, *—O—(C═O)$NR^3$—, *—$NR^3$—(C═O)O—, or —$NR^3$—(C═O)$NR^3$—, wherein * indicates the attachment point to $R^1$; and $R^1$ is unsubstituted or substituted $C_1$-$C_6$ alkyl, unsubstituted or substituted $C_1$-$C_6$ heteroalkyl containing 1 N atom, wherein any substituted group of $R^1$ is substituted with one or more halogen, unsubstituted or substituted $C_1$-$C_6$ alkyl, unsubstituted or substituted monocyclic heterocycle, —$N(R^4)_2$, —$OR^5$, —CN, —$CO_2R^5$, —C(═O)$N(R^4)_2$, —$SR^5$, —S(═O)$R^7$, —$S(═O)_2R^7$, —$NR^4C$(═O)$R^5$, —$NR^4SO_2R^7$, —$SO_2R^7$, or —$SO_2N(R^4)_2$;

or $R^1$ is unsubstituted or substituted monocyclic 4-, 5- or 6-membered heterocycle containing 1-4 N atoms and 0 or 1 O or S atoms;

or $R^1$ is unsubstituted or substituted bridged $C_2$-$C_7$ heterocycloalkyl containing 1-2 N atoms;

or $R^1$ is unsubstituted or substituted —($C_1$-$C_6$ alkyl)-($C_2$-$C_7$ heterocycloalkyl), wherein the heterocycloalkyl is an unsubstituted or substituted monocyclic 4-, 5- or 6-membered heterocycloalkyl containing 1-2 N atoms.

In some embodiments, $R^A$ is unsubstituted or substituted pyrrolyl, unsubstituted or substituted pyridinyl, or unsubstituted or substituted phenyl, wherein if $R^A$ is substituted then $R^A$ is substituted with 1, or 2 groups selected from $R^a$, $R^b$, and $R^c$;

wherein, if $R^a$, $R^b$, or $R^c$ is attached to the N atom of a heteroaryl, then it is hydrogen, —C(═O)$R^7$, or unsubstituted or substituted $C_1$-$C_6$ alkyl;

$R^B$ is unsubstituted or substituted phenyl or unsubstituted or substituted pyridinyl, wherein if $R^B$ is substituted then $R^B$ is substituted with 1, 2, or 3 groups selected from $R^d$, $R^e$, and $R^f$;

$X^1$ is $CR^{11}$ or N;

$X^2$ is $CR^{12}$ or N;

$R^{11}$ and $R^{12}$ are each independently hydrogen, F, Cl, —$CH_3$, $CF_3$, —CN, —$OR^4$, or —$N(R^4)_2$;

$R^1$ is unsubstituted or substituted $C_1$-$C_6$ heteroalkyl containing 1 N atom, wherein any substituted group of $R^1$ is substituted with one or more halogen, $C_1$-$C_4$ alkyl, —$N(R^4)_2$, or —$OR^5$;

or $R^1$ is unsubstituted or substituted azetidinyl, unsubstituted or substituted pyrrolidinyl, or unsubstituted or substituted piperidinyl;

or $R^1$ is unsubstituted or substituted bridged $C_2$-$C_7$ heterocycloalkyl containing 1-2 N atoms;

or $R^1$ is unsubstituted or substituted —($C_1$-$C_6$ alkyl)-($C_2$-$C_7$ heterocycloalkyl), wherein the heterocycloalkyl is an unsubstituted or substituted monocyclic 4-, 5- or 6-membered heterocycloalkyl containing 1-2 N atoms.

In some embodiments, the compound has the structure of Formula (IXa), or a pharmaceutically acceptable salt, or solvate thereof:

Formula (IXa)

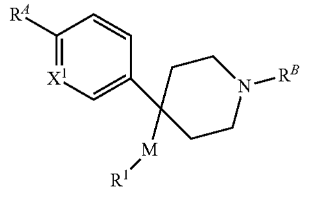

wherein, $R^A$ is unsubstituted or substituted 5- or 6-membered heteroaryl containing 1 or 2 N atoms or unsubstituted or substituted phenyl, wherein if $R^A$ is substituted then $R^A$ is substituted with 1, or 2 groups selected from $R^a$, $R^b$, and $R^c$;

$R^a$ is selected from the group consisting of hydrogen, halogen, —$OR^4$, —CN, —$N(R^4)_2$, —C(═O)$R^7$, unsubstituted or substituted $C_1$-$C_6$ alkyl, unsubstituted or substituted $C_1$-$C_6$ fluoroalkyl, unsubstituted or substituted $C_1$-$C_6$ heteroalkyl, and unsubstituted or substituted $C_3$-$C_6$ cycloalkyl, wherein any substituted group of $R^a$ is substituted with one or more $R^6$ groups; and $R^b$ and $R^c$ are independently selected from the group consisting of hydrogen, halogen, —$OR^4$, —CN, —$N(R^4)_2$, —C(═O)$R^7$, unsubstituted or substituted $C_1$-$C_6$ alkyl, unsubstituted or substituted $C_1$-$C_6$ fluoroalkyl, and unsubstituted or substituted $C_1$-$C_6$ heteroalkyl, wherein any substituted group of $R^b$ and $R^c$ is substituted with one or more $R^6$ groups;

wherein, if $R^a$, $R^b$, or $R^c$ is attached to the N atom of a heteroaryl, then it is hydrogen, —C(═O)$R^7$, or unsubstituted or substituted $C_1$-$C_6$ alkyl;

$R^B$ is unsubstituted or substituted phenyl or unsubstituted or substituted 5- or 6-membered heteroaryl containing 1 or 2 N atoms, wherein if $R^B$ is substituted then $R^B$ is substituted with 1, 2, or 3 groups selected from $R^d$, $R^e$, and $R^f$;

$R^d$ is selected from the group consisting of hydrogen, halogen, —$OR^4$, —CN, —$N(R^4)_2$, unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted $C_3$-$C_6$ cycloalkyl, unsubstituted or substituted $C_2$-$C_7$ heterocycloalkyl, unsubstituted or substituted phenyl, unsubstituted or substituted monocyclic heteroaryl, and unsubstituted or substituted bicyclic heteroaryl, wherein any substituted group of $R^d$ is substituted with one or more $R^6$ groups; and $R^e$ and $R^f$ are independently selected from the group consisting of hydrogen, halogen, —$OR^4$, —CN, —$N(R^4)_2$, unsubstituted or substituted $C_1$-$C_6$ alkyl, unsubstituted or substituted $C_1$-$C_6$ fluoroalkyl, and unsubstituted or substituted $C_1$-$C_6$ heteroalkyl;

wherein, if $R^d$, $R^e$, or $R^f$ is attached to the N atom of a heteroaryl, then it is hydrogen, —C(═O)$R^7$, or unsubstituted or substituted $C_1$-$C_6$ alkyl;

$X^1$ is $CR^{11}$ or N;

$R^{11}$ is hydrogen, halogen, $C_1$-$C_6$ alkyl, $C_1$-$C_6$ fluoroalkyl, or $C_1$-$C_6$ heteroalkyl, —CN, —$OR^4$, or —$N(R^4)_2$;

M is —$NR^3$—, —O—, *—$NR^3$—(C═O)—, *—(C═O)—$NR^3$—, *—O—(C═O)$NR^3$—, *—$NR^3$—(C═O)O—, or —$NR^3$—(C═O)$NR^3$—, wherein * indicates the attachment point to $R^1$; and $R^1$ is unsubstituted or substituted $C_1$-$C_6$ alkyl, unsubstituted or substituted $C_1$-$C_6$ heteroalkyl containing 1 N atom, wherein any substituted group of $R^1$ is substituted with one or more halogen, unsubstituted or substituted $C_1$-$C_6$ alkyl, unsubstituted or substituted monocyclic heterocycle, —$N(R^4)_2$, —$OR^5$, —CN, —$CO_2R^5$, —C(═O)$N(R^4)_2$, —$SR^5$, —S(═O)$R^7$, —S(═O)$_2R^7$, —$NR^4$C(═O)$R^5$, —$NR^4SO_2R^7$, —$SO_2R^7$, or —$SO_2N(R^4)_2$;

or $R^1$ is unsubstituted or substituted monocyclic 4-, 5- or 6-membered heterocycle containing 1-4 N atoms and 0 or 1 O or S atoms;

or $R^1$ is unsubstituted or substituted bridged $C_2$-$C_7$ heterocycloalkyl containing 1-2 N atoms;

or $R^1$ is unsubstituted or substituted —($C_1$-$C_6$ alkyl)-($C_2$-$C_7$ heterocycloalkyl), wherein the heterocycloalkyl is an unsubstituted or substituted monocyclic 4-, 5- or 6-membered heterocycloalkyl containing 1-2 N atoms.

In some embodiments, $R^A$ is unsubstituted or substituted pyrrolyl, unsubstituted or substituted pyridinyl, or unsubstituted or substituted phenyl, wherein if $R^A$ is substituted then $R^A$ is substituted with 1, or 2 groups selected from $R^a$, $R^b$, and $R^c$;

wherein, if $R^a$, $R^b$, or $R^c$ is attached to the N atom of a heteroaryl, then it is hydrogen, —C(═O)$R^7$, or unsubstituted or substituted $C_1$-$C_6$ alkyl;

$R^B$ is unsubstituted or substituted phenyl or unsubstituted or substituted pyridinyl, wherein if $R^B$ is substituted then $R^B$ is substituted with 1, 2, or 3 groups selected from $R^d$, $R^e$, and $R^f$;

$X^1$ is $CR^{11}$ or N;

$R^{11}$ is hydrogen, F, Cl, —$CH_3$, $CF_3$, —CN, —$OR^4$, or —$N(R^4)_2$;

$R^1$ is unsubstituted or substituted $C_1$-$C_6$ heteroalkyl containing 1 N atom, wherein any substituted group of $R^1$ is substituted with one or more halogen, $C_1$-$C_4$ alkyl, —$N(R^4)_2$, or —$OR^5$;

or $R^1$ is unsubstituted or substituted azetidinyl, unsubstituted or substituted pyrrolidinyl, or unsubstituted or substituted piperidinyl;

or $R^1$ is unsubstituted or substituted bridged $C_2$-$C_7$ heterocycloalkyl containing 1-2 N atoms;

or $R^1$ is unsubstituted or substituted —($C_1$-$C_6$ alkyl)-($C_2$-$C_7$ heterocycloalkyl), wherein the heterocycloalkyl is an unsubstituted or substituted monocyclic 4-, 5- or 6-membered heterocycloalkyl containing 1-2 N atoms.

In some embodiments, $R^A$ is

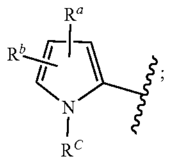

or $R^A$ is

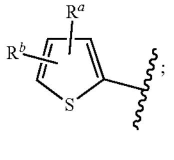

or $R^A$ is

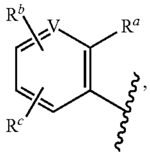

where V is CH or N; and $R^B$ is

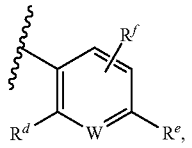

where W is CH or N.

In some embodiments, $R^A$ is

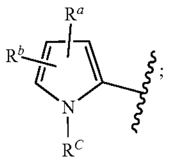

or $R^A$ is

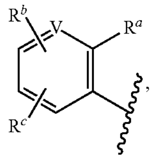

where V is CH or N; and $R^B$ is

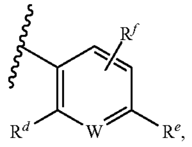

where W is CH or N.

In some embodiments, $R^A$ is

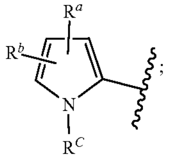

and $R^B$ is

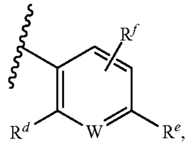

where W is CH or N.

In some embodiments, $R^A$ is

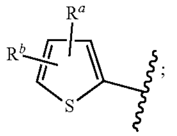

and $R^B$ is

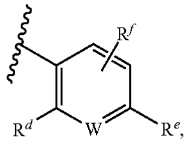

where W is CH or N.

In some embodiments, $R^A$ is

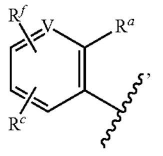

where V is CH or N; and $R^B$ is

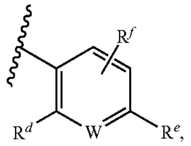

where W is CH or N.

In some embodiments, the compound has the structure of Formula (X), or a pharmaceutically acceptable salt, or solvate thereof:

Formula (X)

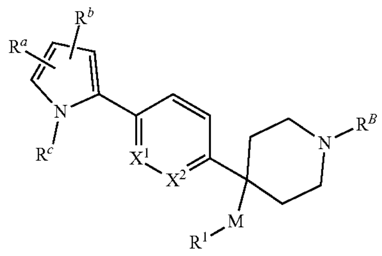

wherein:

$R^c$ is hydrogen, —C(═O)$R^7$, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl.

In some embodiments, the compound has the structure of Formula (Xa), or a pharmaceutically acceptable salt, or solvate thereof:

Formula (Xa)

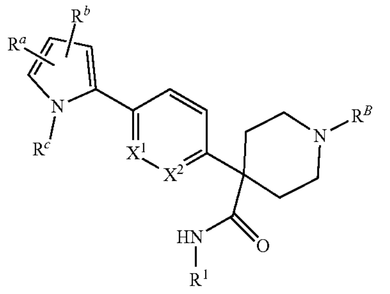

wherein:

$R^a$ and $R^b$ are independently selected from the group consisting of hydrogen, halogen, —$OR^4$, —CN, unsubstituted or substituted $C_1$-$C_6$ alkyl, unsubstituted or substituted $C_1$-$C_6$ fluoroalkyl, and unsubstituted or substituted $C_3$-$C_6$ cycloalkyl;

$R^c$ is hydrogen, —C(═O)$R^7$, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl.

In some embodiments, $R^a$ and $R^b$ are independently selected from the group consisting of hydrogen, F, Cl, Br, —CN, —$OCH_3$, —$OCH_2CH_3$, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$, —$CH_2F$, —$CHF_2$, —$CF_3$, and cyclopropyl; $R^c$ is hydrogen, —C(═O)$R^7$, unsubstituted or substituted $C_1$-$C_6$ alkyl, unsubstituted or substituted $C_3$-$C_6$ cycloalkyl.

In some embodiments, the compound has the structure of Formula (Xb), or a pharmaceutically acceptable salt, or solvate thereof:

Formula (Xb)

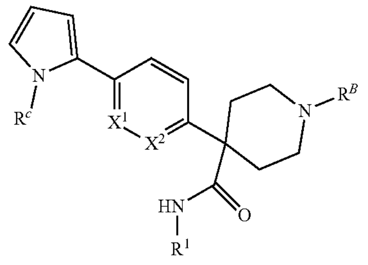

wherein: $X^1$ is N; $X^2$ is CH or N; and $R^c$ is hydrogen, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$, —$CH_2CH_2CH(CH_3)_2$, or unsubstituted $C_3$-$C_6$ cycloalkyl.

In some embodiments, $X^2$ is N. In some embodiments, $X^2$ is CH.

In some embodiments, the compound has the structure of Formula (Xc), or a pharmaceutically acceptable salt, or solvate thereof:

Formula (Xc)

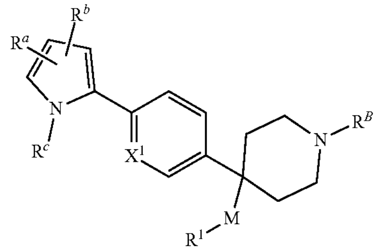

wherein: $R^c$ is hydrogen, —C(═O)$R^7$, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl.

In some embodiments, the compound has the structure of Formula (Xd), or a pharmaceutically acceptable salt, or solvate thereof:

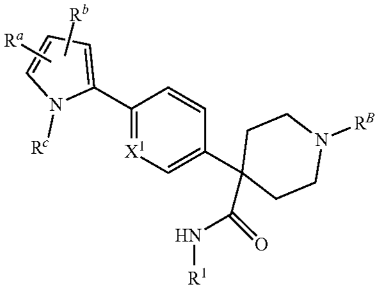

wherein: $R^a$ and $R^b$ are independently selected from the group consisting of hydrogen, halogen, —$OR^4$, —CN, unsubstituted or substituted $C_1$-$C_6$ alkyl, unsubstituted or substituted $C_1$-$C_6$ fluoroalkyl, and unsubstituted or substituted $C_3$-$C_6$ cycloalkyl; $R^c$ is hydrogen, —C(═O)$R^7$, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl.

In some embodiments, $R^a$ and $R^b$ are independently selected from the group consisting of hydrogen, F, Cl, Br, —CN, —$OCH_3$, —$OCH_2CH_3$, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$, —$CH_2F$, —$CHF_2$, —$CF_3$, and cyclopropyl; $R^c$ is hydrogen, —C(═O)$R^7$, unsubstituted or substituted $C_1$-$C_6$ alkyl, unsubstituted or substituted $C_3$-$C_6$ cycloalkyl.

In some embodiments, the compound has the structure of Formula (Xe), or a pharmaceutically acceptable salt, or solvate thereof:

Formula (Xe)

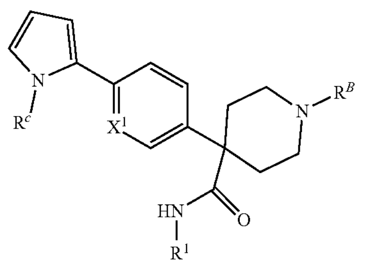

wherein: $X^1$ is N; and $R^c$ is hydrogen, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$, —$CH_2CH_2CH(CH_3)_2$, or unsubstituted $C_3$-$C_6$ cycloalkyl.

In some embodiments, the compound has the structure of Formula (XI), or a pharmaceutically acceptable salt, or solvate thereof:

Formula (XI)

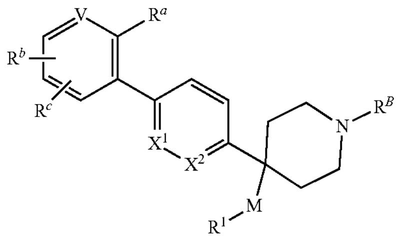

wherein V is CH or N.

In some embodiments, the compound has the structure of Formula (XIa), or a pharmaceutically acceptable salt, or solvate thereof:

Formula (XIa)

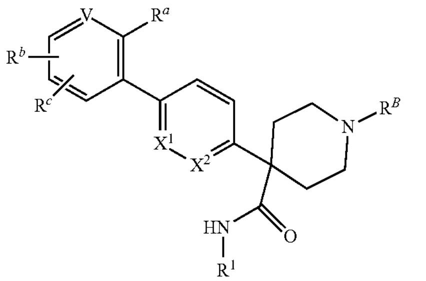

wherein V is CH or N; $R^a$ is selected from the group consisting of hydrogen, halogen, —$OR^4$, —CN, unsubstituted or substituted $C_1$-$C_6$ alkyl, unsubstituted or substituted $C_1$-$C_6$ fluoroalkyl, and unsubstituted or substituted $C_3$-$C_6$ cycloalkyl; and $R^b$ and $R^c$ are independently selected from the group consisting of hydrogen, halogen, —$OR^4$, —CN, unsubstituted or substituted $C_1$-$C_6$ alkyl, and unsubstituted or substituted $C_1$-$C_6$ fluoroalkyl.

In some embodiments, $R^a$ is selected from the group consisting of hydrogen, F, Cl, Br, —CN, —$OCH_3$, —$OCH_2CH_3$, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)(CH_2CH_3)$, —$C(CH_3)_3$, —$CH_2F$, —$CHF_2$, and —$CF_3$; $R^b$ and $R^c$ are independently selected from the group consisting of hydrogen, F, Cl, —$CH_3$, —$CH_2F$, —$CHF_2$, —$CF_3$, —CN, and —$OCH_3$.

In some embodiments, the compound has the structure of Formula (XIb), or a pharmaceutically acceptable salt, or solvate thereof:

Formula (XIb)

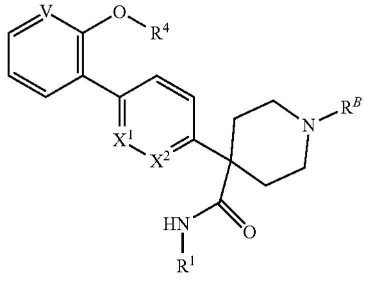

wherein: V is CH or N; $X^1$ is N; and $X^2$ is CH or N.

In some embodiments, $X^2$ is N. In some embodiments, $X^2$ is CH.

In some embodiments, the compound has the structure of Formula (XIc), or a pharmaceutically acceptable salt, or solvate thereof:

Formula (XIc)

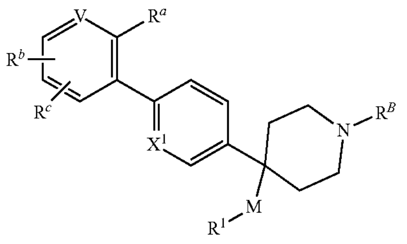

wherein V is CH or N.

In some embodiments, the compound has the structure of Formula (XId), or a pharmaceutically acceptable salt, or solvate thereof.

Formula (XId)

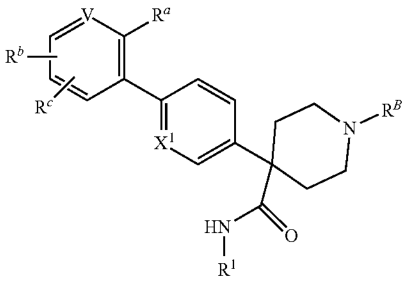

wherein V is CH or N;

$R^a$ is selected from the group consisting of hydrogen, halogen, —$OR^4$, —CN, unsubstituted or substituted $C_1$-$C_6$ alkyl, unsubstituted or substituted $C_1$-$C_6$ fluoroalkyl, and unsubstituted or substituted $C_3$-$C_6$ cycloalkyl; and $R^b$ and $R^c$ are independently selected from the group consisting of hydrogen, halogen, —$OR^4$, —CN, unsubstituted or substituted $C_1$-$C_6$ alkyl, and unsubstituted or substituted $C_1$-$C_6$ fluoroalkyl.

In some embodiments, $R^a$ is selected from the group consisting of hydrogen, F, Cl, Br, —CN, —$OCH_3$, —$OCH_2CH_3$, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)(CH_2CH_3)$, —$C(CH_3)_3$, —$CH_2F$, —$CHF_2$, and —$CF_3$; and $R^b$ and $R^c$ are independently selected from the group consisting of hydrogen, F, Cl, —$CH_3$, —$CH_2F$, —$CHF_2$, —$CF_3$, —CN, and —$OCH_3$.

In some embodiments, the compound has the structure of Formula (XIe), or a pharmaceutically acceptable salt, or solvate thereof:

Formula (XIe)

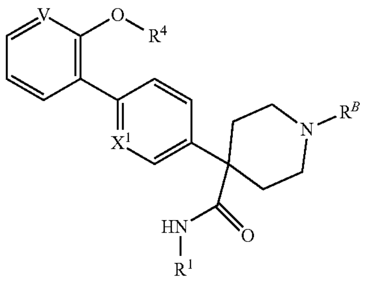

wherein: V is CH or N; and $X^1$ is N.

In some embodiments, the compound has the structure of Formula (XII), or a pharmaceutically acceptable salt, or solvate thereof:

Formula (XII)

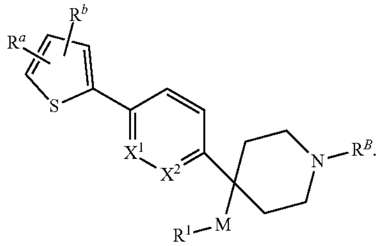

In some embodiments, the compound has the structure of Formula (XIIa), or a pharmaceutically acceptable salt, or solvate thereof:

Formula (XIIa)

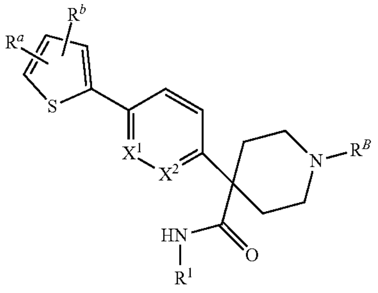

wherein:

$R^a$ is selected from the group consisting of hydrogen, halogen, —$OR^4$, —CN, unsubstituted or substituted $C_1$-$C_6$ alkyl, unsubstituted or substituted $C_1$-$C_6$ fluoroalkyl, and unsubstituted or substituted $C_3$-$C_6$ cycloalkyl; and $R^b$ is selected from the group consisting of hydrogen, halogen, —$OR^4$, —CN, unsubstituted or substituted $C_1$-$C_6$ alkyl, and unsubstituted or substituted $C_1$-$C_6$ fluoroalkyl.

In some embodiments, $R^a$ is selected from the group consisting of hydrogen, F, Cl, Br, —CN, —$OCH_3$, —$OCH_2CH_3$, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)(CH_2CH_3)$, —$C(CH_3)_3$, —$CH_2F$, —$CHF_2$, and —$CF_3$; and $R^b$ is selected from the group consisting of hydrogen, F, Cl, —$CH_3$, —$CH_2F$, —$CHF_2$, —$CF_3$, —CN, and —$OCH_3$.

In some embodiments, $X^1$ is N; and $X^2$ is CH or N. In some embodiments, $X^2$ is N. In some embodiments, $X^2$ is CH.

In some embodiments, the compound has the structure of Formula (XIIb), or a pharmaceutically acceptable salt, or solvate thereof:

Formula (XIIb)

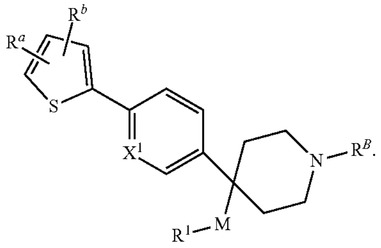

In some embodiments, the compound has the structure of Formula (XIIc), or a pharmaceutically acceptable salt, or solvate thereof:

Formula (XIIc)

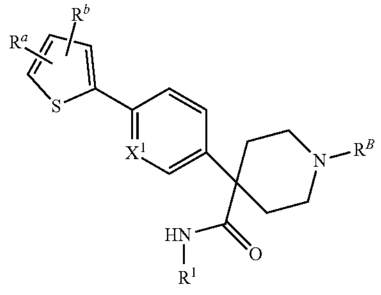

wherein:

$R^a$ is selected from the group consisting of hydrogen, halogen, —$OR^4$, —CN, unsubstituted or substituted $C_1$-$C_6$ alkyl, unsubstituted or substituted $C_1$-$C_6$ fluoroalkyl, and unsubstituted or substituted $C_3$-$C_6$ cycloalkyl; and $R^b$ is selected from the group consisting of hydrogen, halogen, —$OR^4$, —CN, unsubstituted or substituted $C_1$-$C_6$ alkyl, and unsubstituted or substituted $C_1$-$C_6$ fluoroalkyl.

In some embodiments, $R^a$ is selected from the group consisting of hydrogen, F, Cl, Br, —CN, —$OCH_3$, —$OCH_2CH_3$, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)(CH_2CH_3)$, —$C(CH_3)_3$, —$CH_2F$, —$CHF_2$, and —$CF_3$; and $R^b$ is selected from the group consisting of hydrogen, F, Cl, —$CH_3$, —$CH_2F$, —$CHF_2$, —$CF_3$, —CN, and —$OCH_3$.

In some embodiments, $X^1$ is N; and $X^2$ is CH or N. In some embodiments, $X^2$ is N. In some embodiments, $X^2$ is CH.

In some embodiments, the compound has the structure of Formula (XIII), or a pharmaceutically acceptable salt, or solvate thereof:

Formula (XIII)

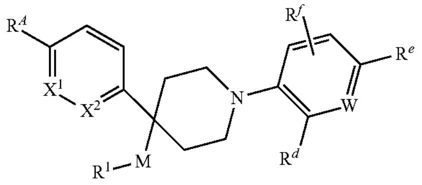

wherein W is CH or N.

In some embodiments, the compound has the structure of Formula (XIIIa), or a pharmaceutically acceptable salt, or solvate thereof:

Formula (XIIIa)

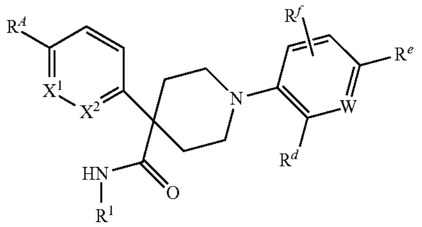

wherein:

W is CH or N;

$R^d$ is selected from the group consisting of hydrogen, halogen, —$OR^4$, —CN, unsubstituted or substituted $C_1$-$C_6$ alkyl, unsubstituted or substituted $C_1$-$C_6$ fluoroalkyl, and unsubstituted or substituted $C_3$-$C_6$ cycloalkyl; and $R^e$ and $R^f$ are independently selected from the group consisting of hydrogen, halogen, —$OR^4$, —CN, unsubstituted or substituted $C_1$-$C_6$ alkyl, and unsubstituted or substituted $C_1$-$C_6$ fluoroalkyl.

In some embodiments, $R^d$ is selected from the group consisting of hydrogen, F, Cl, Br, —CN, —$OCH_3$, —$OCH_2CH_3$, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)(CH_2CH_3)$, —$C(CH_3)_3$, —$CH_2F$, —$CHF_2$, and —$CF_3$; $R^e$ and $R^f$ are independently selected from the group consisting of hydrogen, F, Cl, Br, —$CH_3$, —$CH_2F$, —$CHF_2$, —$CF_3$, —CN, —OH, and —$OCH_3$.

In some embodiments, the compound has the structure of Formula (XIIIb), or a pharmaceutically acceptable salt, or solvate thereof:

Formula (XIIIb)

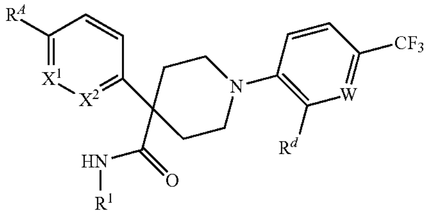

wherein: $X^1$ is N; $X^2$ is CH or N; W is CH or N; and $R^d$ is selected from the group consisting of F, Cl, —CN, —$OCH_3$, —$CH_3$, —$CH_2F$, —$CHF_2$, and —$CF_3$.

In some embodiments, $X^2$ is N. In some embodiments, $X^2$ is CH.

In some embodiments, the compound has the structure of Formula (XIIIc), or a pharmaceutically acceptable salt, or solvate thereof:

Formula (XIIIc)

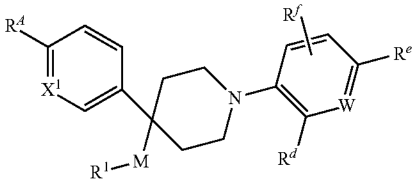

wherein W is CH or N.

In some embodiments, the compound has the structure of Formula (XIIId), or a pharmaceutically acceptable salt, or solvate thereof:

Formula (XIIId)

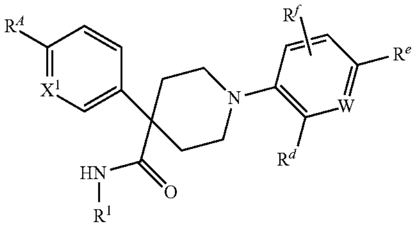

wherein: W is CH or N; $R^d$ is selected from the group consisting of hydrogen, halogen, —$OR^4$, —CN, unsubstituted or substituted $C_1$-$C_6$ alkyl, unsubstituted or substituted $C_1$-$C_6$ fluoroalkyl, and unsubstituted or substituted $C_3$-$C_6$ cycloalkyl; and $R^e$ and $R^f$ are independently selected from the group consisting of hydrogen, halogen, —$OR^4$, —CN, unsubstituted or substituted $C_1$-$C_6$ alkyl, and unsubstituted or substituted $C_1$-$C_6$ fluoroalkyl.

In some embodiments, $R^d$ is selected from the group consisting of hydrogen, F, Cl, Br, —CN, —$OCH_3$, —$OCH_2CH_3$, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)(CH_2CH_3)$, —$C(CH_3)_3$, —$CH_2F$, —$CHF_2$, and —$CF_3$; $R^e$ and $R^f$ are independently selected from the group consisting of hydrogen, F, Cl, Br, —$CH_3$, —$CH_2F$, —$CHF_2$, —$CF_3$, —CN, —OH, and —$OCH_3$.

In some embodiments, the compound has the structure of Formula (XIIIe), or a pharmaceutically acceptable salt, or solvate thereof:

Formula (XIIIe)

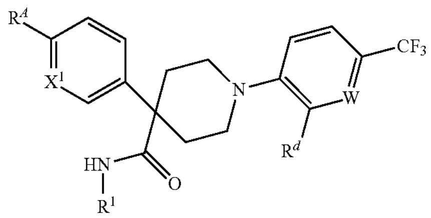

wherein: $X^1$ is N; W is CH or N; and R is selected from the group consisting of F, Cl, —CN, —$OCH_3$, —$CH_3$, —$CH_2F$, —$CHF_2$, and —$CF_3$.

In some embodiments, $R^1$ is unsubstituted or substituted $C_1$-$C_6$ heteroalkyl containing 1 N atom, wherein any substituted group of $R^1$ is substituted with one or more halogen, $C_1$-$C_4$ alkyl, —$N(R^4)_2$, or —$OR^5$; or $R^1$ is unsubstituted or substituted azetidinyl, unsubstituted or substituted pyrrolidinyl, or unsubstituted or substituted piperidinyl; or $R^1$ is unsubstituted or substituted —($C_1$-$C_6$ alkyl)-($C_2$-$C_7$ heterocycloalkyl), wherein the heterocycloalkyl is an unsubstituted or substituted azetidinyl, unsubstituted or substituted pyrrolidinyl, or unsubstituted or substituted piperidinyl.

In some embodiments, $R^1$ is unsubstituted or substituted azetidinyl, unsubstituted or substituted pyrrolidinyl, or unsubstituted or substituted piperidinyl.

In some embodiments, $R^1$ is unsubstituted or substituted $C_1$-$C_6$ heteroalkyl containing 1 N atom, wherein any substituted group of $R^1$ is substituted with one or more halogen, $C_1$-$C_4$ alkyl, —$N(R^4)_2$, or —$OR^5$.

In some embodiments, compounds described herein have the following structure:

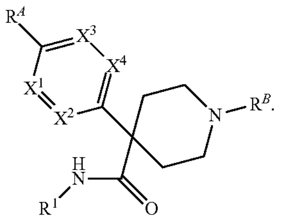

In some embodiments, $R^A$, $R^B$, $X^1$, $X^2$, $X^3$, $X^4$, and $R^1$ are as described herein.

In some embodiments, $R^A$, $R^B$, $X^1$, $X^2$, $X^3$, $X^4$, and $R^1$ are as described in Table 1.

In some embodiments, $R^A$ is

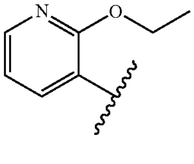 , 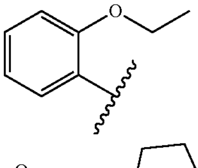 ,

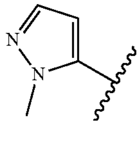 , 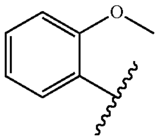 , 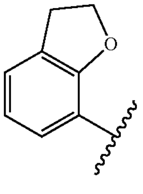 ,

-continued

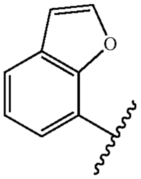 , 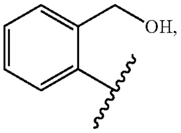 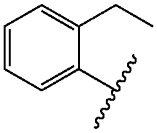 ,

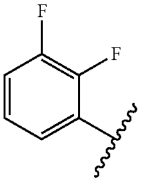 , 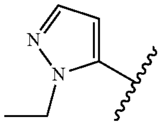 ,

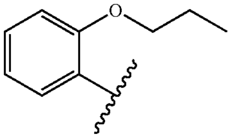 , 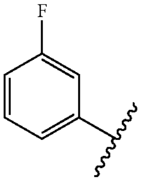 ,

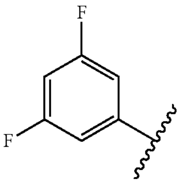 , 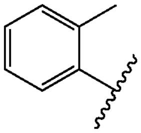 , 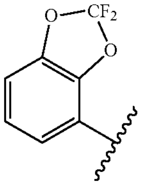 ,

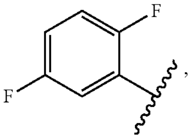 , 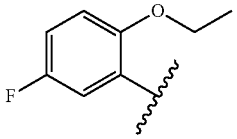 ,

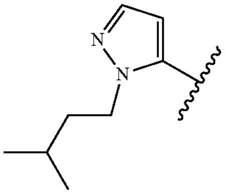 , 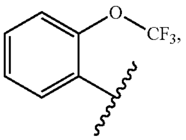

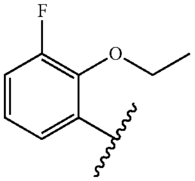 , 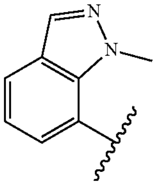 , 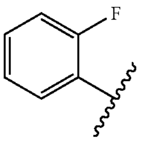 ,

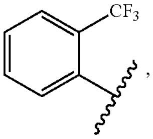 , 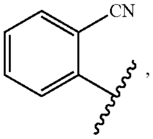 , 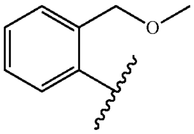 ,

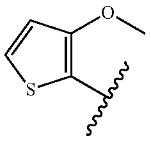 , 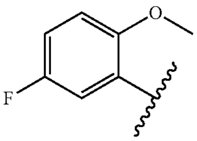 , 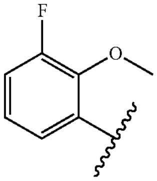 ,

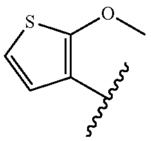 , 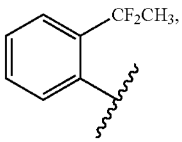 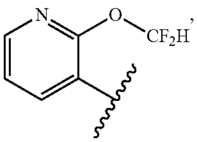

-continued
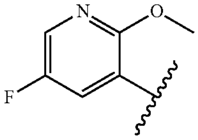, 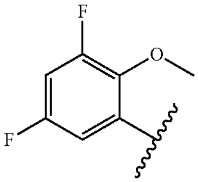,
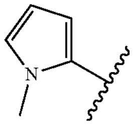, 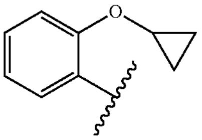, 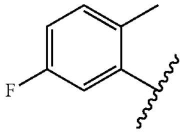,
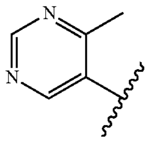, 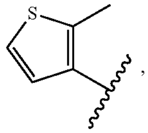, 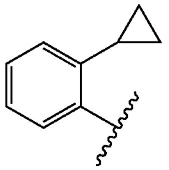,
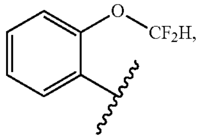 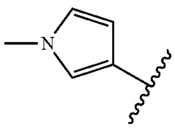, 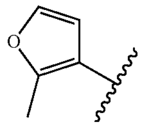,
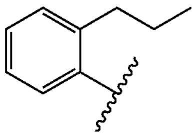, 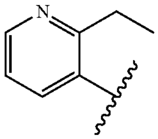, 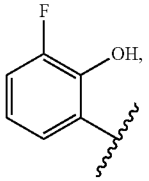
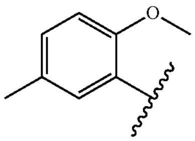, 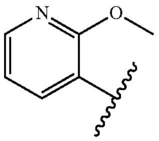,
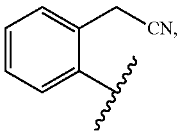 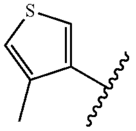, 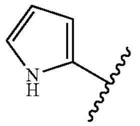,
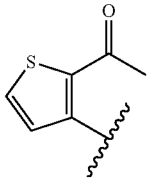, 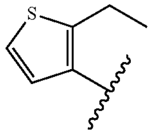, 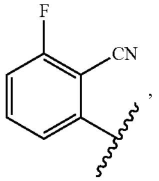,
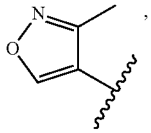, 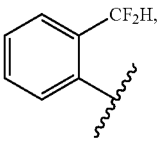 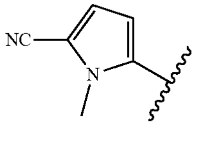,
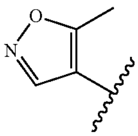, 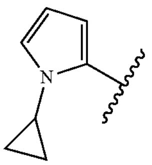, 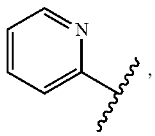,
-continued
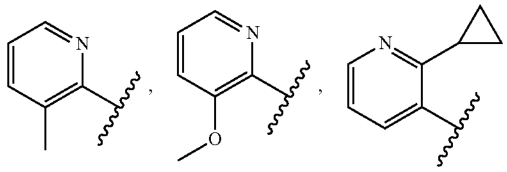
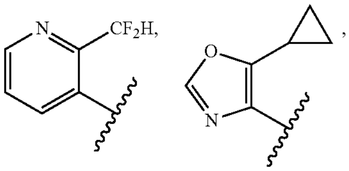
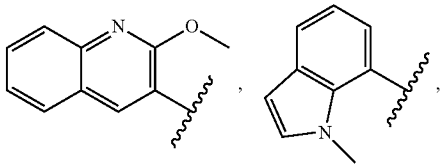
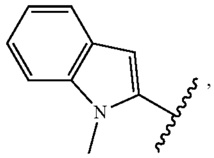, or 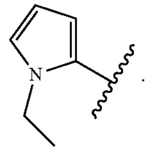.
In some embodiments, $R^B$ is
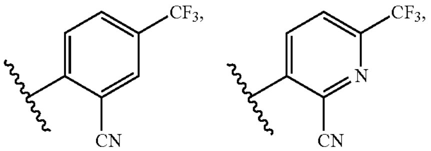
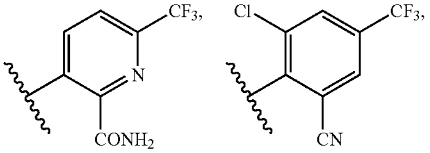
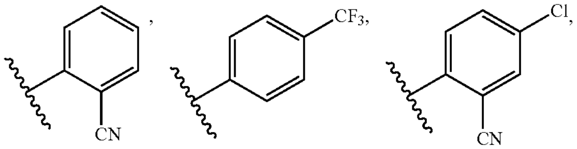
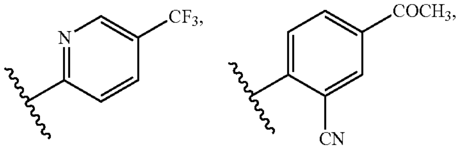
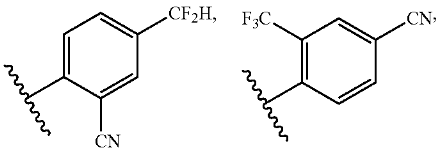
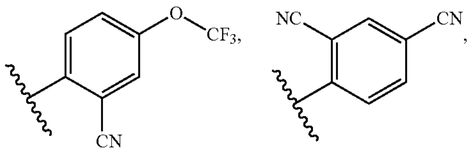

-continued
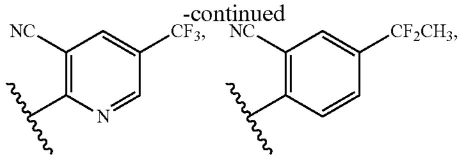
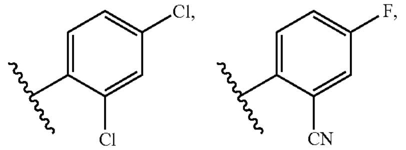
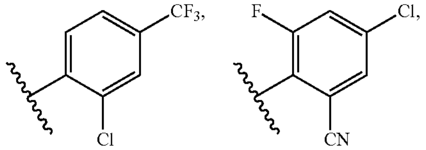
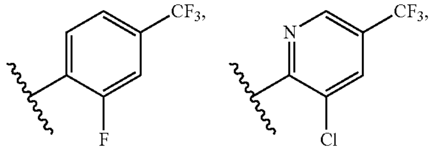
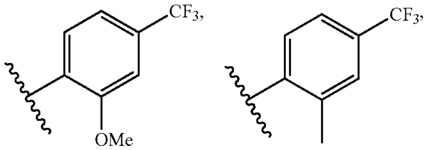
or
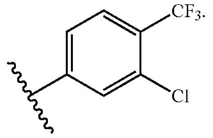
In some embodiments, $X^1$ is CH or N. In some embodiments, $X^2$ is CH or N. In some embodiments, $X^3$ is CH, CF, or N. In some embodiments, $X^4$ is CH or N.
In some embodiments, $X^1$ is CH or N; $X^2$ is CH or N; $X^3$ is CH, or CF; and $X^4$ is CH. In some embodiments, $X^1$ is CH or N; $X^2$ is CH; $X^3$ is CH, or CF; and $X^4$ is CH.
In some embodiments, $R^1$ is
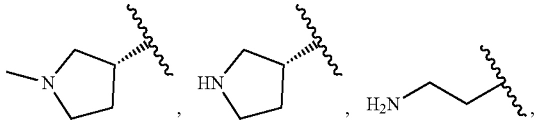
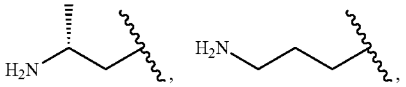
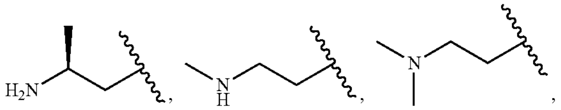
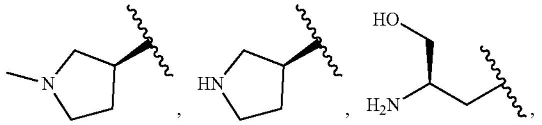
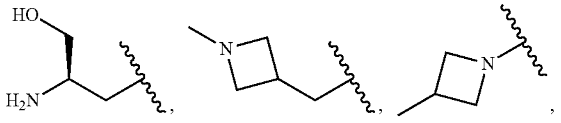
-continued
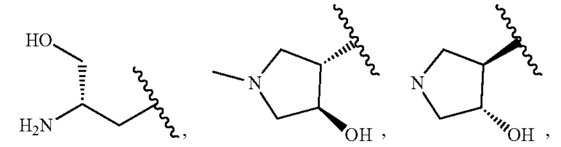
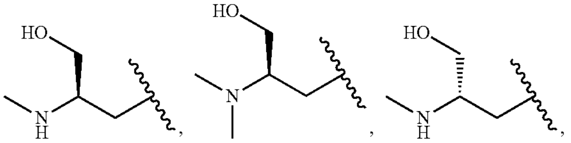
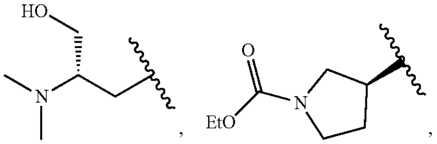
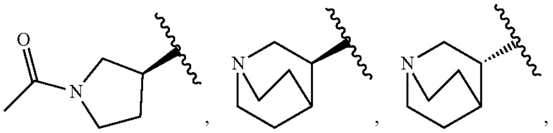
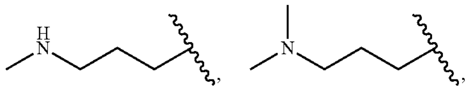
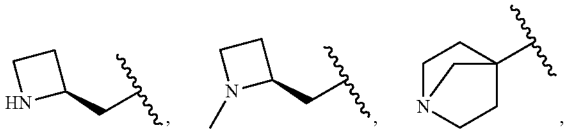
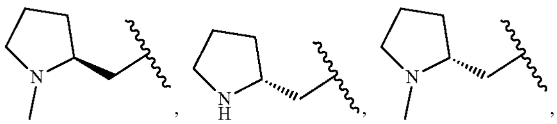
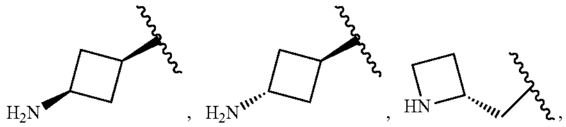
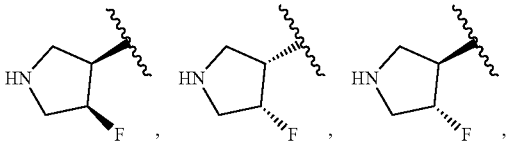
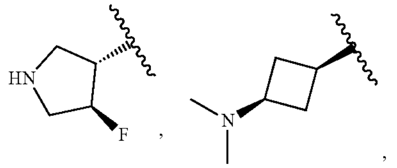
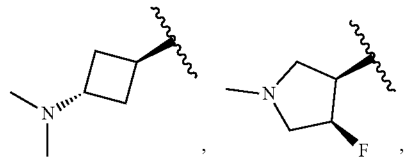
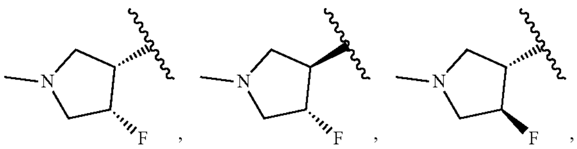

-continued

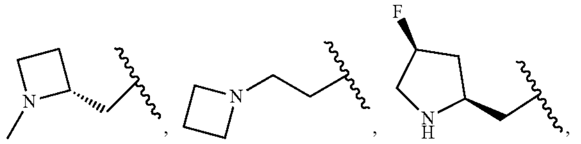
,

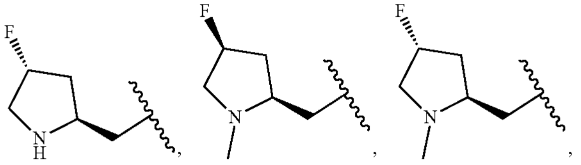
,

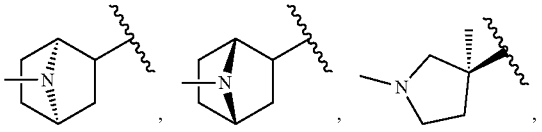
,

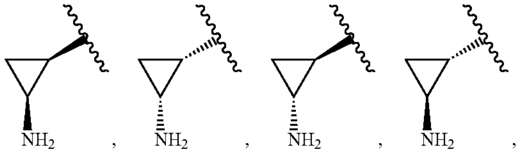
,

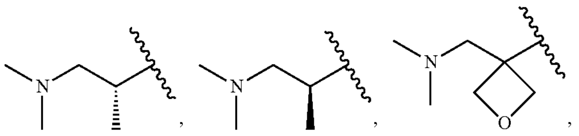
,

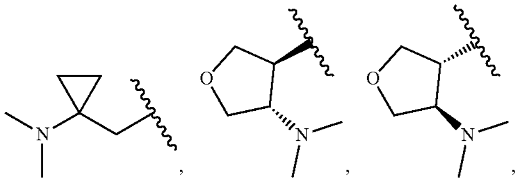
,

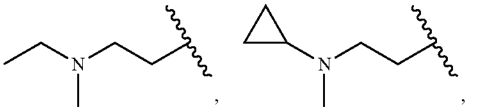
,

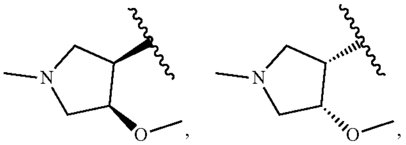
,

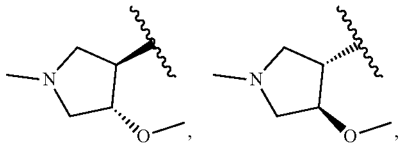
,

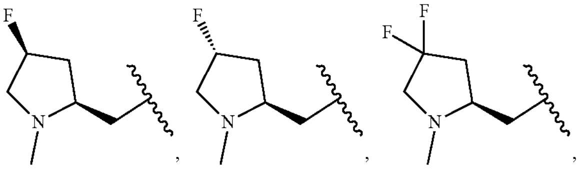
,

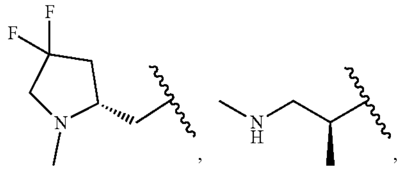
,

-continued

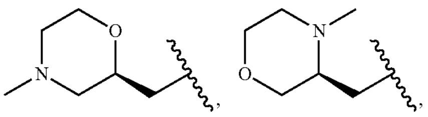
,

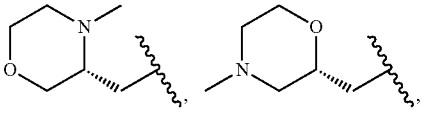
,

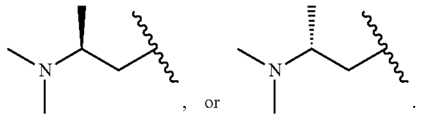
, or .

In some embodiments, compounds described herein have the following structure:

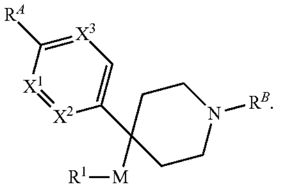

In some embodiments, $R^A$, $R^B$, $X^1$, $X^2$, $X^3$, M and $R^1$ are as described herein. In some embodiments, $R^A$, $R^B$, $X^1$, $X^2$, $X^3$, M and $R^1$ are as described in Table 2.

In some embodiments, $R^A$ is

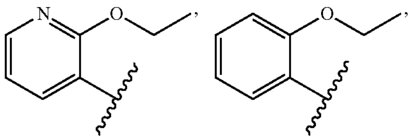

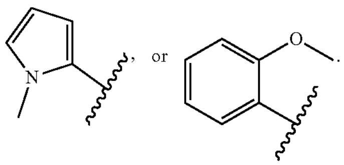
, or .

In some embodiments, $R^B$ is

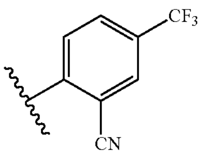
or
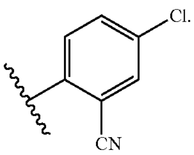

In some embodiments, $X^1$ is CH or N.

In some embodiments, $X^2$ is CH or N.

In some embodiments, $X^3$ is CH or CF.

In some embodiments, M is —O—, —NH—,

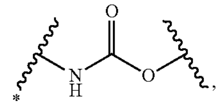, 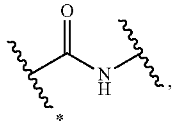,

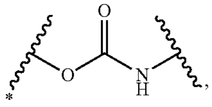, 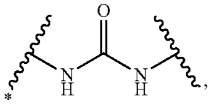, wherein * indicates the attachment point to $R^1$.

In some embodiments, $R^1$ is

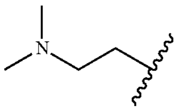, 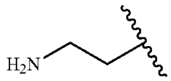,

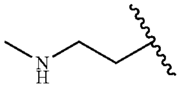, 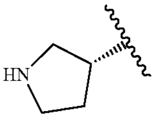, 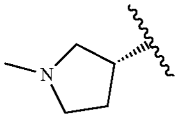,

-continued

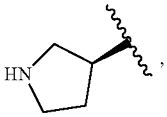, 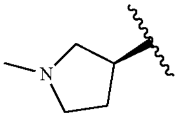, 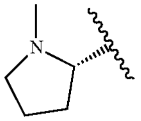,

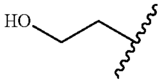, 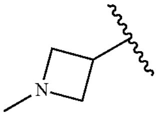, 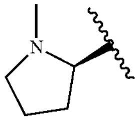,

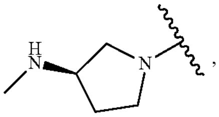, 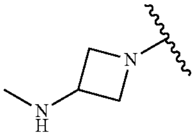,

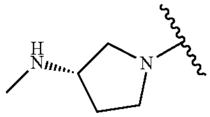, or 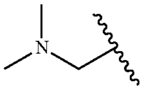.

Any combination of the groups described above for the various variables is contemplated herein. Throughout the specification, groups and substituents thereof are chosen by one skilled in the field to provide stable moieties and compounds.

Exemplary compounds of Formula (I) include the compounds described in the following Tables:

TABLE 1

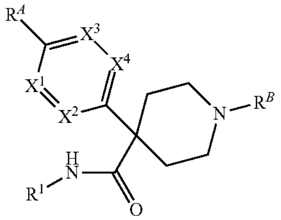

| Cpd No. | $R^A$ | $X^1$ | $X^2$ | $X^3$ | $X^4$ | $R^B$ | $R^1$ |
|---|---|---|---|---|---|---|---|
| 1-1 | 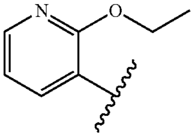 [SMILES: *c1cccnc1OCC] | CH | CH | CH | CH | 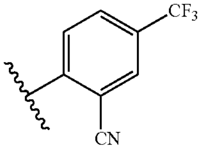 | 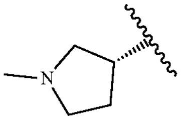 [SMILES: *[C@@H]1CCN(C)C1] |
| 1-2 | 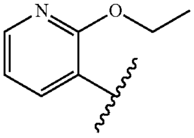 [SMILES: *c1cccnc1OCC] | CH | CH | CH | CH | 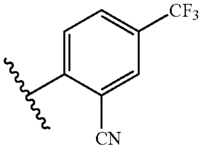 | 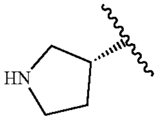 |
| 1-3 | 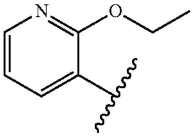 [SMILES: *c1cccnc1OCC] | CH | CH | CH | CH | 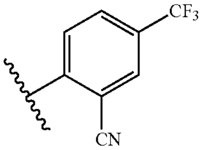 | 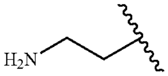 |

TABLE 1-continued
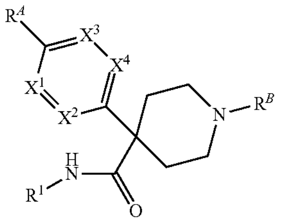
| Cpd No. | $R^A$ | $X^1$ | $X^2$ | $X^3$ | $X^4$ | $R^B$ | $R^1$ |
|---|---|---|---|---|---|---|---|
| 1-4 | 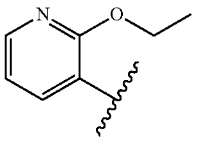 [SMILES: *c1cccnc1OCC] | CH | CH | CH | CH | 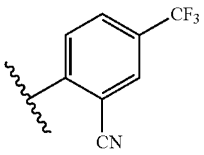 | 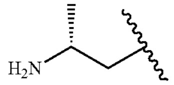 |
| 1-5 | 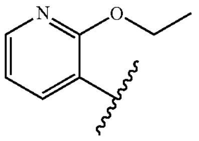 [SMILES: *c1cccnc1OCC] | CH | CH | CH | CH | 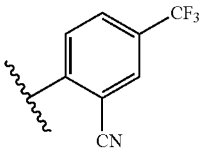 | 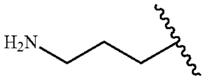 |
| 1-6 | 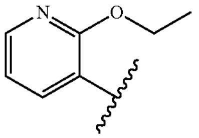 [SMILES: *c1cccnc1OCC] | CH | CH | CH | CH | 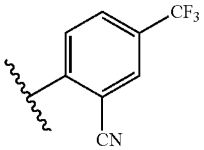 | 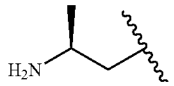 |
| 1-7 | 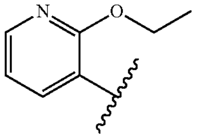 [SMILES: *c1cccnc1OCC] | CH | CH | CH | CH | 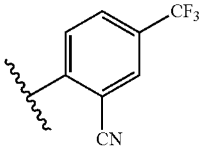 | 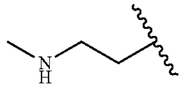 [SMILES: *CCNC] |
| 1-8 | 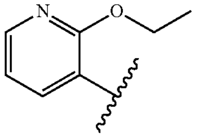 [SMILES: *c1cccnc1OCC] | CH | CH | CH | CH | 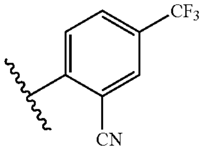 | 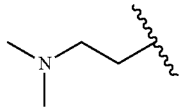 [SMILES: *CCN(C)C] |
| 1-9 | 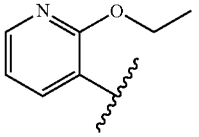 [SMILES: *c1cccnc1OCC] | N | CH | CH | CH | 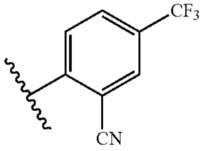 | 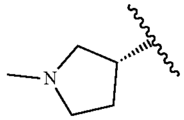 [SMILES: *[C@@H]1CCN(C)C1] |
| 1-10 | 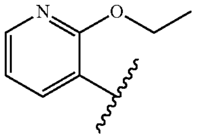 [SMILES: *c1cccnc1OCC] | N | CH | CH | CH | 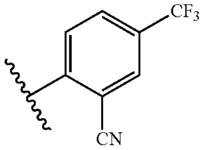 | 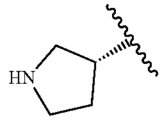 [SMILES: *[C@@H]1CCNC1] |
| 1-11 | 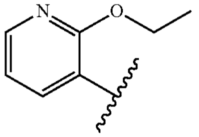 [SMILES: *c1cccnc1OCC] | N | CH | CH | CH | 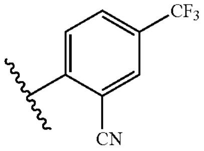 | 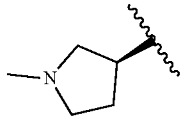 [SMILES: *[C@H]1CCN(C)C1] |

TABLE 1-continued
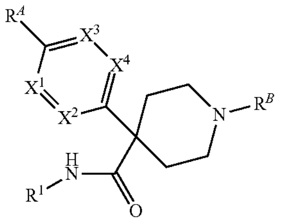
| Cpd No. | $R^A$ | $X^1$ | $X^2$ | $X^3$ | $X^4$ | $R^B$ | $R^1$ |
|---|---|---|---|---|---|---|---|
| 1-12 | 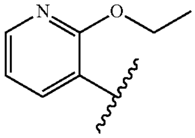 [SMILES: *c1cccnc1OCC] | N | CH | CH | CH | 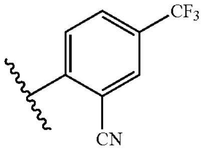 | 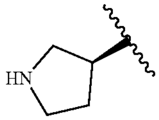 [SMILES: *[C@H]1CCNC1] |
| 1-13 | 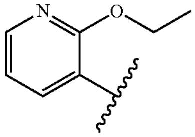 [SMILES: *c1cccnc1OCC] | N | CH | CH | CH | 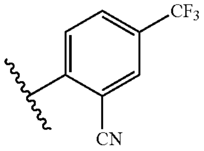 | 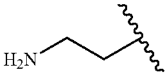 |
| 1-14 | 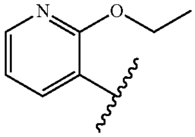 [SMILES: *c1cccnc1OCC] | N | CH | CH | CH | 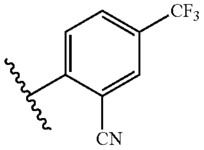 | 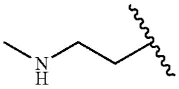 [SMILES: *CCNC] |
| 1-15 | 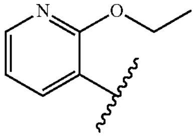 [SMILES: *c1cccnc1OCC] | N | CH | CH | CH | 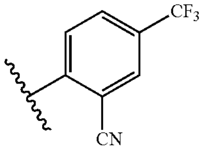 | 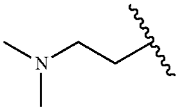 [SMILES: *CCN(C)C] |
| 1-16 | 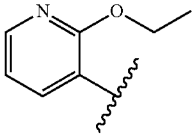 [SMILES: *c1cccnc1OCC] | N | CH | CH | CH | 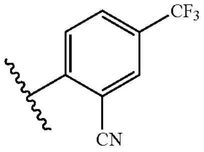 | 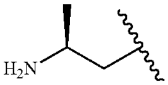 |
| 1-17 | 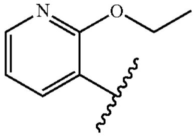 [SMILES: *c1cccnc1OCC] | N | CH | CH | CH | 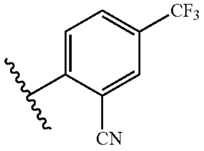 | 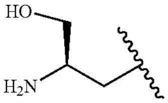 |
| 1-18 | 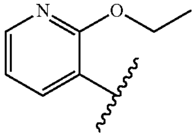 [SMILES: *c1cccnc1OCC] | N | CH | CH | CH | 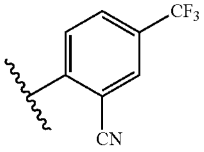 | 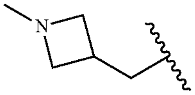 [SMILES: *CC1CN(C)C1] |
| 1-19 | 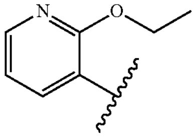 [SMILES: *c1cccnc1OCC] | N | CH | CH | CH | 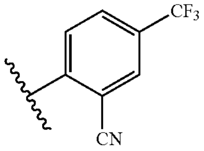 | 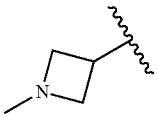 [SMILES: *C1CN(C)C1] |

TABLE 1-continued
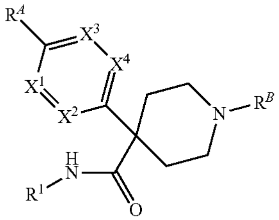
| Cpd No. | $R^A$ | $X^1$ | $X^2$ | $X^3$ | $X^4$ | $R^B$ | $R^1$ |
|---|---|---|---|---|---|---|---|
| 1-20 | 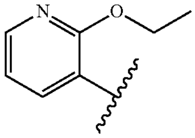 [SMILES: *c1cccnc1OCC] | N | CH | CH | CH | 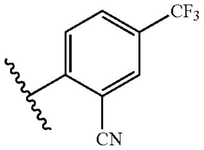 | 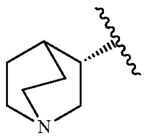 [SMILES: *[C@@H]1CN2CCC1CC2] |
| 1-21 | 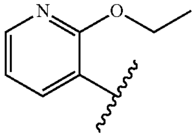 [SMILES: *c1cccnc1OCC] | CH | N | CH | CH | 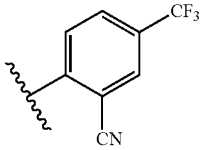 | 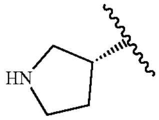 [SMILES: *[C@@H]1CCNC1] |
| 1-22 | 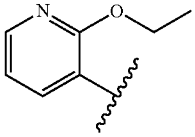 [SMILES: *c1cccnc1OCC] | CH | N | CH | CH | 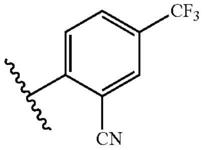 | 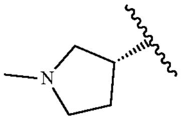 [SMILES: *[C@@H]1CCN(C)C1] |
| 1-23 | 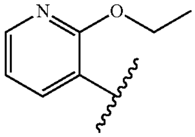 [SMILES: *c1cccnc1OCC] | CH | CH | CH | CH | 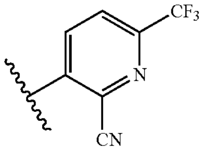 | 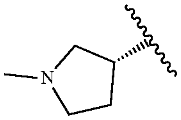 [SMILES: *[C@@H]1CCN(C)C1] |
| 1-24 | 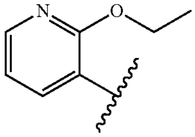 [SMILES: *c1cccnc1OCC] | N | CH | CH | CH | 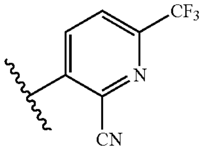 | 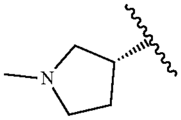 [SMILES: *[C@@H]1CCN(C)C1] |
| 1-25 | 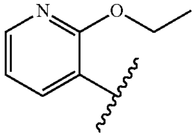 [SMILES: *c1cccnc1OCC] | N | CH | CH | CH | 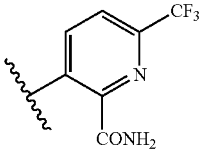 [SMILES: *c1ccc(C(F)(F)F)nc1C(N)=O] | 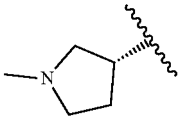 [SMILES: *[C@@H]1CCN(C)C1] |
| 1-26 | 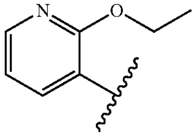 [SMILES: *c1cccnc1OCC] | N | CH | CH | CH | 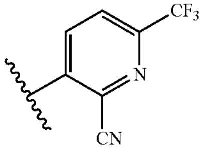 | 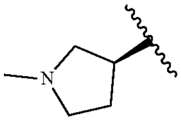 [SMILES: *[C@H]1CCN(C)C1] |
| 1-27 | 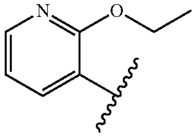 | N | CH | CH | CH | 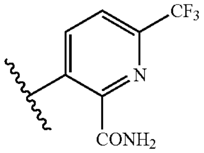 [SMILES: *c1ccc(C(F)(F)F)nc1C(N)=O] | 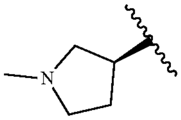 [SMILES: *[C@H]1CCN(C)C1] |

TABLE 1-continued
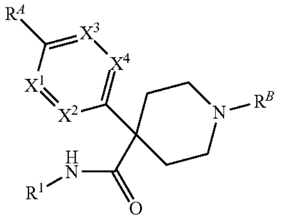
| Cpd No. | $R^A$ | $X^1$ | $X^2$ | $X^3$ | $X^4$ | $R^B$ | $R^1$ |
|---|---|---|---|---|---|---|---|
| 1-28 | 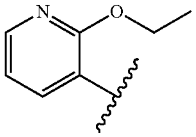 [SMILES: *c1cccnc1OCC] | N | CH | CH | CH | 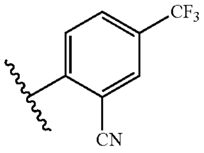 | 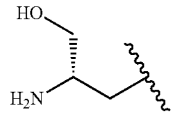 |
| 1-29 | 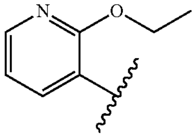 | CH | CH | CH | CH | 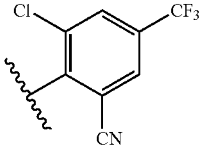 [SMILES: *c1c(Cl)cc(C(F)(F)F)cc1C#N] | 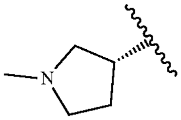 [SMILES: *[C@@H]1CCN(C)C1] |
| 1-30 | 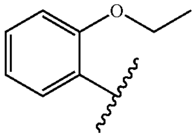 [SMILES: *c1ccccc1OCC] | N | CH | CH | CH | 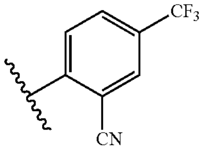 | 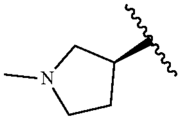 [SMILES: *[C@H]1CCN(C)C1] |
| 1-31 | 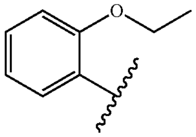 [SMILES: *c1ccccc1OCC] | N | CH | CH | CH | 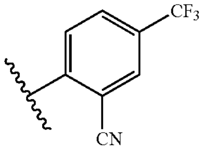 | 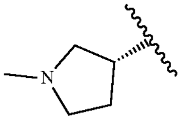 [SMILES: *[C@@H]1CCN(C)C1] |
| 1-32 | 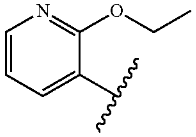 [SMILES: *c1cccnc1OCC] | N | CH | CH | CH | 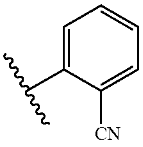 [SMILES: *c1ccccc1C#N] | 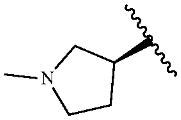 [SMILES: *[C@H]1CCN(C)C1] |
| 1-33 | 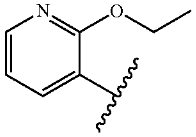 [SMILES: *c1cccnc1OCC] | N | CH | CH | CH | 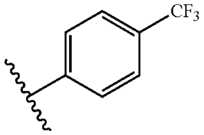 [SMILES: *c1ccc(C(F)(F)F)cc1] | 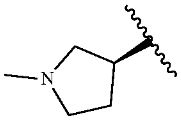 [SMILES: *[C@H]1CCN(C)C1] |
| 1-34 | 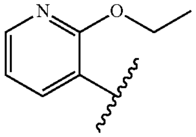 [SMILES: *c1cccnc1OCC] | N | CH | CH | CH | 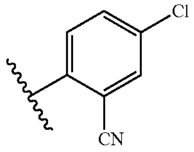 [SMILES: *c1ccc(Cl)cc1C#N] | 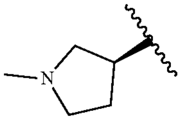 [SMILES: *[C@H]1CCN(C)C1] |
| 1-35 | 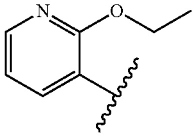 | N | CH | CH | CH | 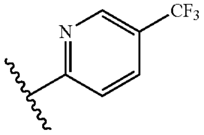 [SMILES: *c1ccc(C(F)(F)F)cn1] | 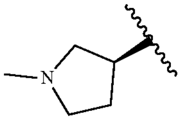 [SMILES: *[C@H]1CCN(C)C1] |

TABLE 1-continued
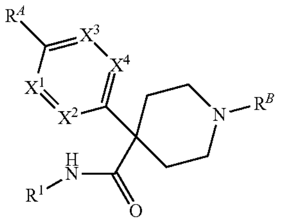
| Cpd No. | $R^A$ | $X^1$ | $X^2$ | $X^3$ | $X^4$ | $R^B$ | $R^1$ |
|---|---|---|---|---|---|---|---|
| 1-36 | 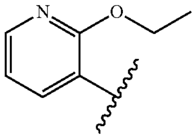 [SMILES: *c1cccnc1OCC] | N | CH | CH | CH | 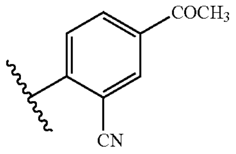 [SMILES: *c1ccc(C(C)=O)cc1C#N] | 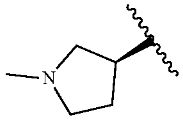 [SMILES: *[C@H]1CCN(C)C1] |
| 1-37 | 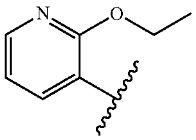 [SMILES: *c1cccnc1OCC] | N | CH | CH | CH | 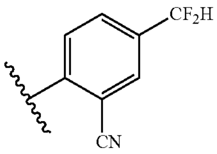 [SMILES: *c1ccc(C(F)F)cc1C#N] | 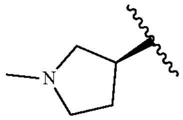 [SMILES: *[C@H]1CCN(C)C1] |
| 1-38 | 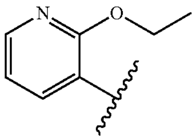 [SMILES: *c1cccnc1OCC] | N | CH | CH | CH | 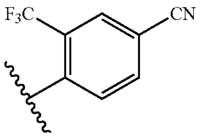 [SMILES: *c1ccc(C#N)cc1C(F)(F)F] | 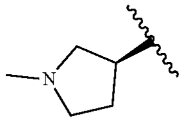 [SMILES: *[C@H]1CCN(C)C1] |
| 1-39 | 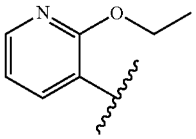 [SMILES: *c1cccnc1OCC] | N | CH | CH | CH | 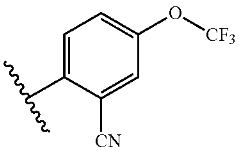 [SMILES: *c1ccc(OC(F)(F)F)cc1C#N] | 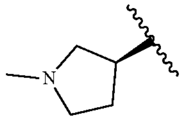 [SMILES: *[C@H]1CCN(C)C1] |
| 1-40 | 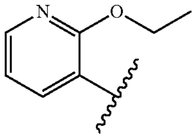 [SMILES: *c1cccnc1OCC] | N | CH | CH | CH | 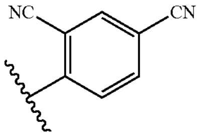 [SMILES: *c1ccc(C#N)cc1C#N] | 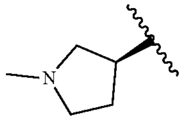 [SMILES: *[C@H]1CCN(C)C1] |
| 1-41 | 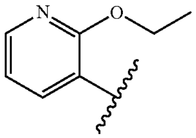 [SMILES: *c1cccnc1OCC] | N | CH | CH | CH | 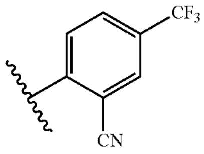 | *trans- 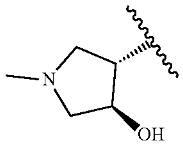 |
| 1-42 | 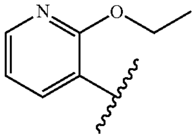 [SMILES: *c1cccnc1OCC] | N | CH | CH | CH | 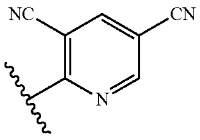 [SMILES: *c1ncc(C#N)cc1C#N] | 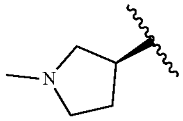 [SMILES: *[C@H]1CCN(C)C1] |
| 1-43 | 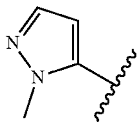 [SMILES: *c1ccnn1C] | N | CH | CH | CH | 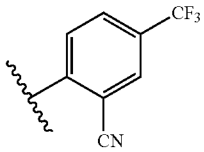 | 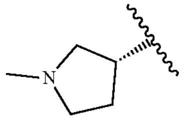 [SMILES: *[C@@H]1CCN(C)C1] |

TABLE 1-continued
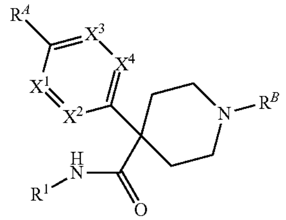
| Cpd No. | $R^A$ | $X^1$ | $X^2$ | $X^3$ | $X^4$ | $R^B$ | $R^1$ |
|---|---|---|---|---|---|---|---|
| 1-44 | 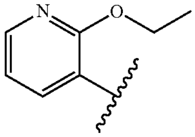 [SMILES: *c1cccnc1OCC] | N | CH | CH | CH | 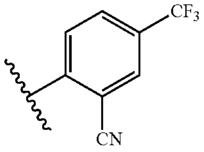 | 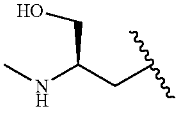 [SMILES: *C[C@H](CO)NC] |
| 1-45 | 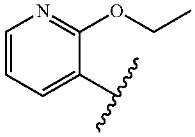 [SMILES: *c1cccnc1OCC] | N | CH | CH | CH | 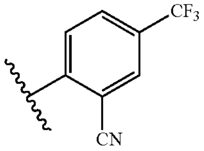 | 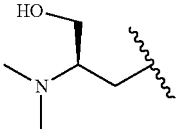 [SMILES: *C[C@H](CO)N(C)C] |
| 1-46 | 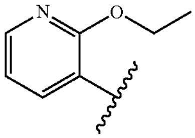 [SMILES: *c1cccnc1OCC] | N | CH | CH | CH | 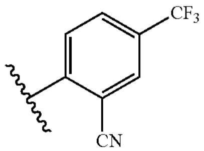 | *trans- 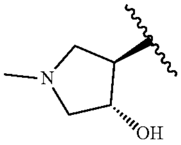 |
| 1-47 | 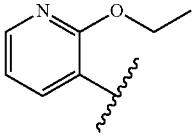 [SMILES: *c1cccnc1OCC] | N | CH | CH | CH | 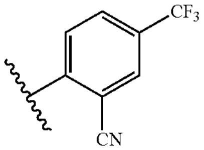 | 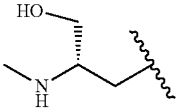 [SMILES: *C[C@@H](CO)NC] |
| 1-48 | 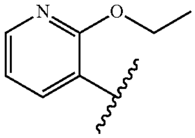 [SMILES: *c1cccnc1OCC] | N | CH | CH | CH | 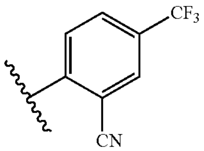 | 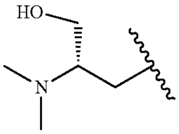 [SMILES: *C[C@@H](CO)N(C)C] |
| 1-51 | 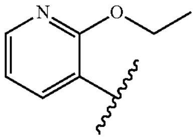 [SMILES: *c1cccnc1OCC] | N | CH | CH | N | 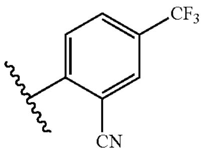 | 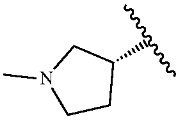 [SMILES: *[C@@H]1CCN(C)C1] |
| 1-52 | 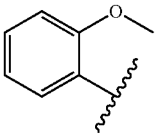 [SMILES: *c1ccccc1OC] | N | CH | CH | CH | 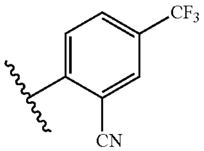 | 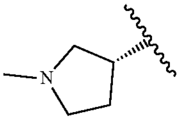 [SMILES: *[C@@H]1CCN(C)C1] |
| 1-53 | 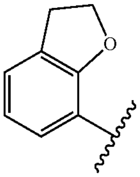 [SMILES: *c1cccc2c1OCC2] | N | CH | CH | CH | 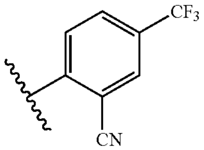 | 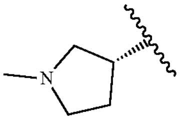 [SMILES: *[C@@H]1CCN(C)C1] |

TABLE 1-continued
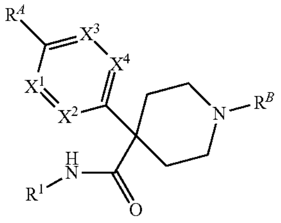
| Cpd No. | $R^A$ | $X^1$ | $X^2$ | $X^3$ | $X^4$ | $R^B$ | $R^1$ |
|---|---|---|---|---|---|---|---|
| 1-54 | 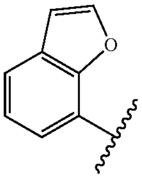 [SMILES: *c1cccc2ccoc12] | N | CH | CH | CH | 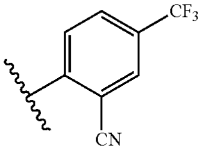 | 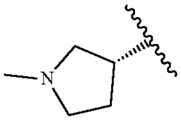 [SMILES: *[C@@H]1CCN(C)C1] |
| 1-55 | 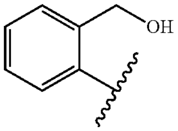 [SMILES: *c1ccccc1CO] | N | CH | CH | CH | 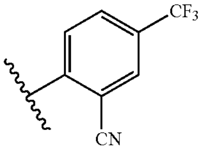 | 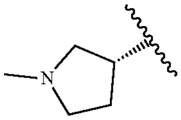 [SMILES: *[C@@H]1CCN(C)C1] |
| 1-56 | 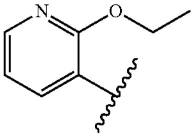 [SMILES: *c1cccnc1OCC] | N | N | CH | CH | 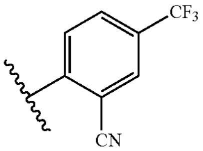 | 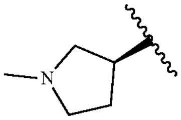 [SMILES: *[C@H]1CCN(C)C1] |
| 1-57 | 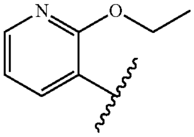 [SMILES: *c1cccnc1OCC] | N | N | CH | CH | 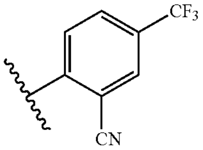 | 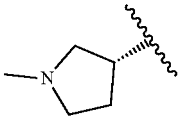 [SMILES: *[C@@H]1CCN(C)C1] |
| 1-58 | 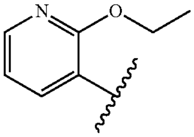 [SMILES: *c1cccnc1OCC] | N | CH | CH | N | 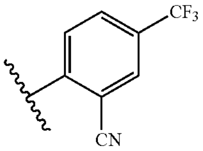 | 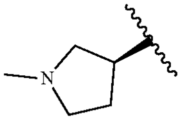 [SMILES: *[C@H]1CCN(C)C1] |
| 1-59 | 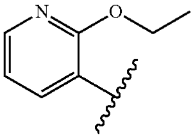 [SMILES: *c1cccnc1OCC] | N | CH | CH | CH | 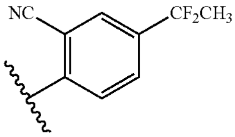 | 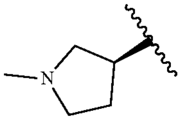 [SMILES: *[C@H]1CCN(C)C1] |
| 1-60 | 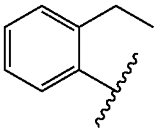 [SMILES: *c1ccccc1CC] | N | CH | CH | CH | 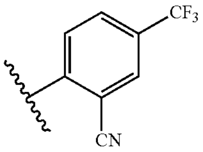 | 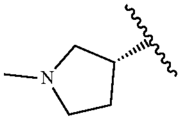 [SMILES: *[C@@H]1CCN(C)C1] |

TABLE 1-continued
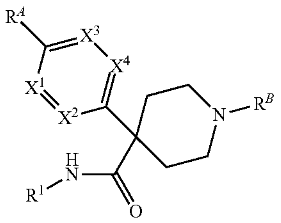
| Cpd No. | $R^A$ | $X^1$ | $X^2$ | $X^3$ | $X^4$ | $R^B$ | $R^1$ |
|---|---|---|---|---|---|---|---|
| 1-61 | 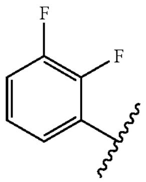 [SMILES: *c1cccc(F)c1F] | N | CH | CH | CH | 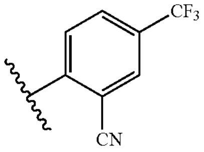 | 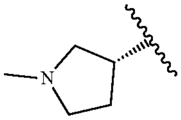 [SMILES: *[C@@H]1CCN(C)C1] |
| 1-62 | 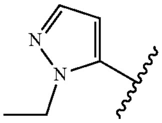 [SMILES: *c1ccnn1CC] | N | CH | CH | CH | 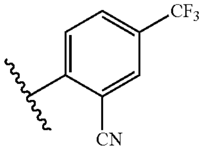 | 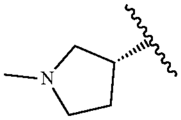 [SMILES: *[C@@H]1CCN(C)C1] |
| 1-63 | 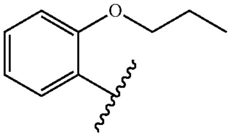 [SMILES: *c1ccccc1OCCC] | N | CH | CH | CH | 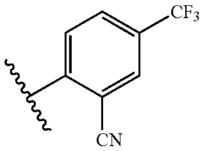 | 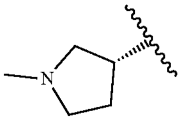 [SMILES: *[C@@H]1CCN(C)C1] |
| 1-64 | 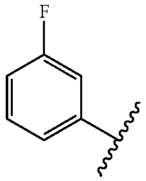 [SMILES: *c1cccc(F)c1] | N | CH | CH | CH | 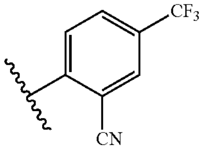 | 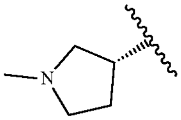 [SMILES: *[C@@H]1CCN(C)C1] |
| 1-65 | 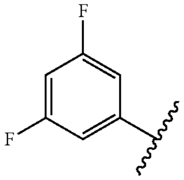 | N | CH | CH | CH | 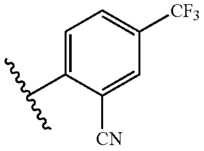 | 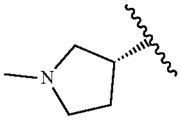 [SMILES: *[C@@H]1CCN(C)C1] |
| 1-66 | 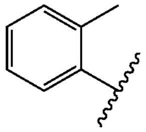 [SMILES: *c1ccccc1C] | N | CH | CH | CH | 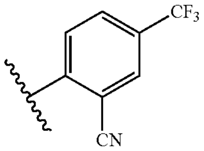 | 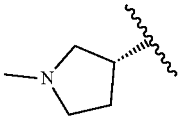 [SMILES: *[C@@H]1CCN(C)C1] |
| 1-67 | 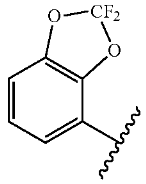 [SMILES: *c1cccc2c1OC(F)(F)O2] | N | CH | CH | CH | 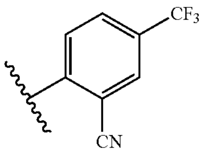 | 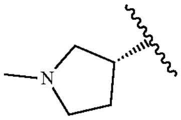 [SMILES: *[C@@H]1CCN(C)C1] |

TABLE 1-continued
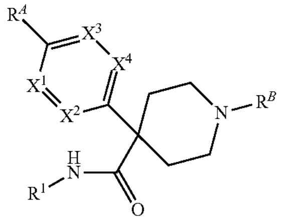
| Cpd No. | $R^A$ | $X^1$ | $X^2$ | $X^3$ | $X^4$ | $R^B$ | $R^1$ |
|---|---|---|---|---|---|---|---|
| 1-68 | 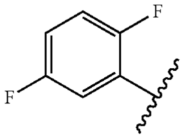 | N | CH | CH | CH | 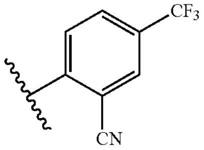 | 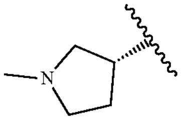 [SMILES: *[C@@H]1CCN(C)C1] |
| 1-69 | 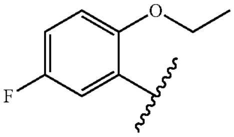 [SMILES: *c1cc(F)ccc1OCC] | N | CH | CH | CH | 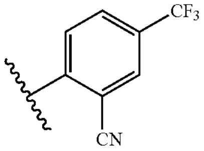 | 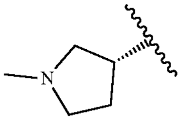 [SMILES: *[C@@H]1CCN(C)C1] |
| 1-70 | 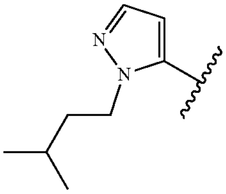 [SMILES: *c1ccnn1CCC(C)C] | N | CH | CH | CH | 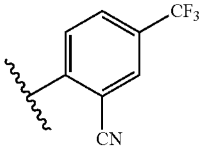 | 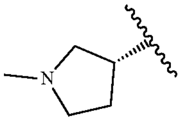 [SMILES: *[C@@H]1CCN(C)C1] |
| 1-71 | 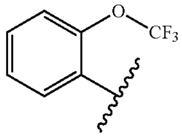 [SMILES: *c1ccccc1OC(F)(F)F] | N | CH | CH | CH | 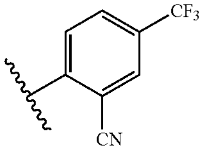 | 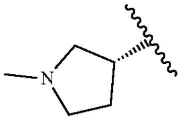 [SMILES: *[C@@H]1CCN(C)C1] |
| 1-72 | 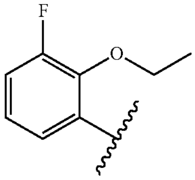 [SMILES: *c1cccc(F)c1OCC] | N | CH | CH | CH | 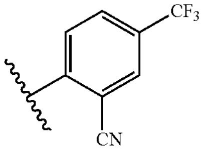 | 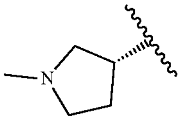 [SMILES: *[C@@H]1CCN(C)C1] |
| 1-73 | 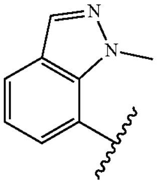 [SMILES: *c1cccc2cnn(C)c12] | N | CH | CH | CH | 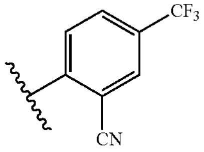 | 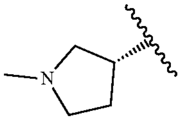 [SMILES: *[C@@H]1CCN(C)C1] |
| 1-74 | 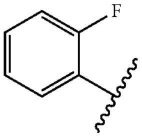 [SMILES: *c1ccccc1F] | N | CH | CH | CH | 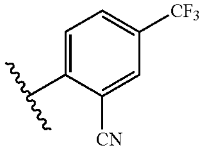 | 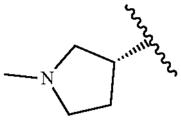 [SMILES: *[C@@H]1CCN(C)C1] |

TABLE 1-continued
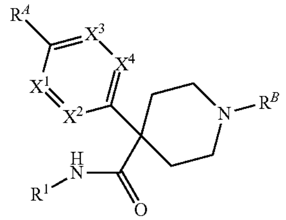
| Cpd No. | $R^A$ | $X^1$ | $X^2$ | $X^3$ | $X^4$ | $R^B$ | $R^1$ |
|---|---|---|---|---|---|---|---|
| 1-75 | 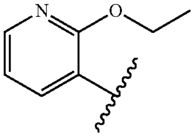 [SMILES: *c1cccnc1OCC] | CH | CH | CF | CH | 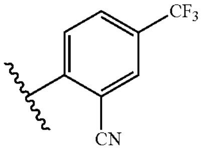 | 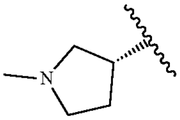 [SMILES: *[C@@H]1CCN(C)C1] |
| 1-76 | 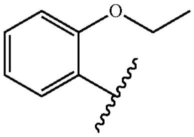 [SMILES: *c1ccccc1OCC] | N | CH | CH | CH | 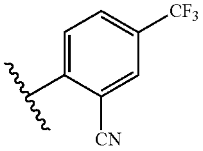 | 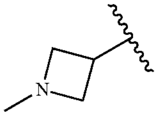 [SMILES: *C1CN(C)C1] |
| 1-77 | 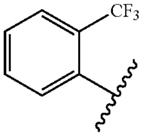 [SMILES: *c1ccccc1C(F)(F)F] | N | CH | CH | CH | 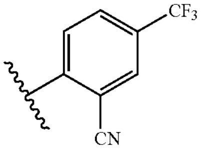 | 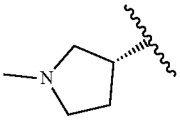 [SMILES: *[C@@H]1CCN(C)C1] |
| 1-78 | 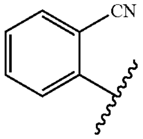 [SMILES: *c1ccccc1C#N] | N | CH | CH | CH | 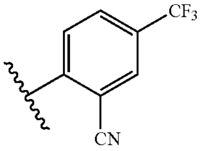 | 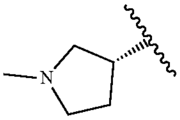 [SMILES: *[C@@H]1CCN(C)C1] |
| 1-79 | 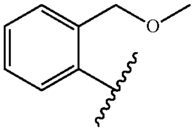 [SMILES: *c1ccccc1COC] | N | CH | CH | CH | 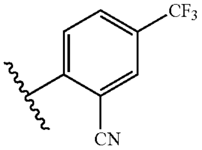 | 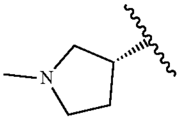 [SMILES: *[C@@H]1CCN(C)C1] |
| 1-80 | 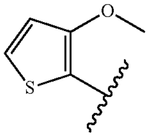 [SMILES: *c1sccc1OC] | N | CH | CH | CH | 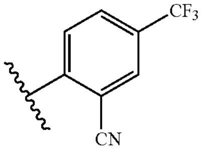 | 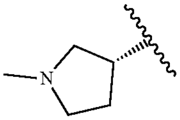 [SMILES: *[C@@H]1CCN(C)C1] |
| 1-81 | 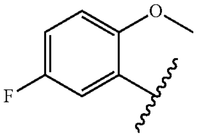 [SMILES: *c1cc(F)ccc1OC] | N | CH | CH | CH | 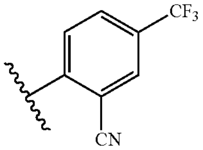 | 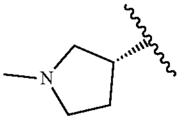 [SMILES: *[C@@H]1CCN(C)C1] |
| 1-82 | 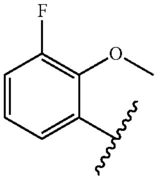 [SMILES: *c1cccc(F)c1OC] | N | CH | CH | CH | 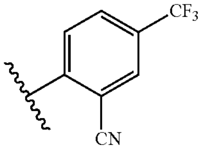 | 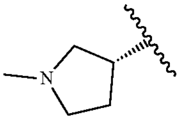 [SMILES: *[C@@H]1CCN(C)C1] |

TABLE 1-continued
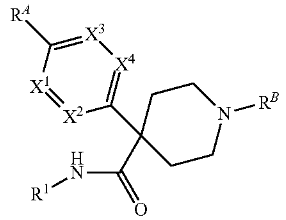
| Cpd No. | $R^A$ | $X^1$ | $X^2$ | $X^3$ | $X^4$ | $R^B$ | $R^1$ |
|---|---|---|---|---|---|---|---|
| 1-83 | 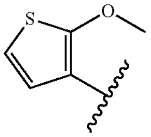 [SMILES: *c1ccsc1OC] | N | CH | CH | CH | 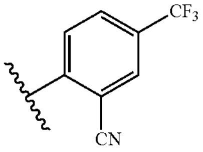 | 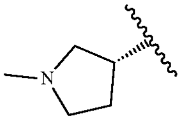 [SMILES: *[C@@H]1CCN(C)C1] |
| 1-84 | 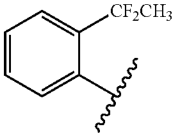 | N | CH | CH | CH | 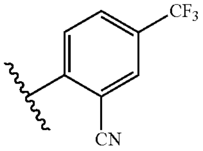 | 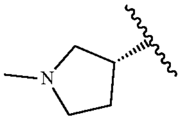 [SMILES: *[C@@H]1CCN(C)C1] |
| 1-85 | 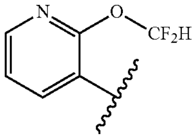 [SMILES: *c1cccnc1OC(F)F] | N | CH | CH | CH | 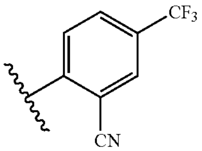 | 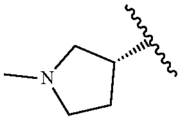 [SMILES: *[C@@H]1CCN(C)C1] |
| 1-86 | 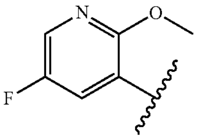 [SMILES: *c1cc(F)cnc1OC] | N | CH | CH | CH | 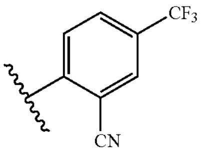 | 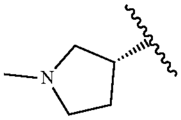 [SMILES: *[C@@H]1CCN(C)C1] |
| 1-87 | 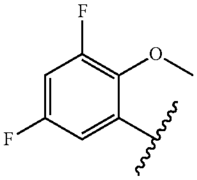 [SMILES: *c1cc(F)cc(F)c1OC] | N | CH | CH | CH | 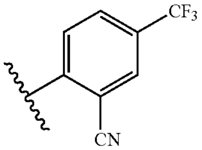 | 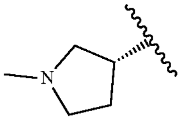 [SMILES: *[C@@H]1CCN(C)C1] |
| 1-88 | 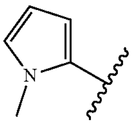 [SMILES: *c1cccn1C] | N | CH | CH | CH | 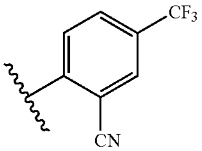 | 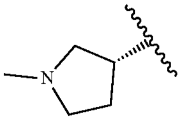 [SMILES: *[C@@H]1CCN(C)C1] |
| 1-89 | 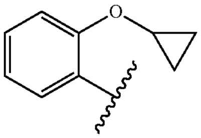 [SMILES: *c1ccccc1OC1CC1] | N | CH | CH | CH | 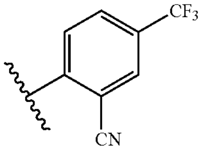 | 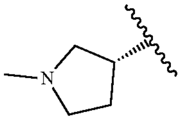 [SMILES: *[C@@H]1CCN(C)C1] |
| 1-90 | 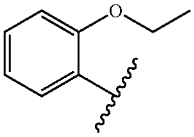 [SMILES: *c1ccccc1OCC] | N | CH | CH | CH | 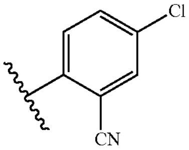 | 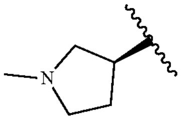 [SMILES: *[C@H]1CCN(C)C1] |

TABLE 1-continued
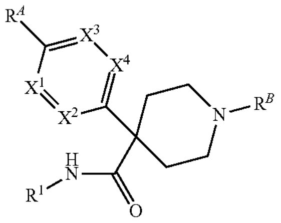
| Cpd No. | $R^A$ | $X^1$ | $X^2$ | $X^3$ | $X^4$ | $R^B$ | $R^1$ |
|---|---|---|---|---|---|---|---|
| 1-91 | 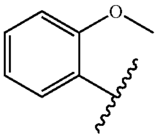 [SMILES: *c1ccccc1OC] | N | CH | CH | CH | 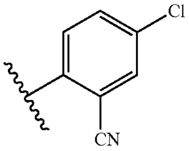 | 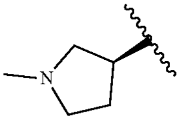 [SMILES: *[C@H]1CCN(C)C1] |
| 1-92 | 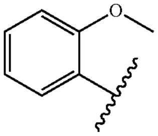 [SMILES: *c1ccccc1OC] | N | CH | CH | CH | 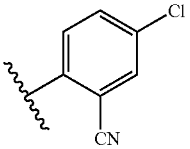 | 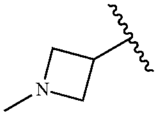 [SMILES: *C1CN(C)C1] |
| 1-93 | 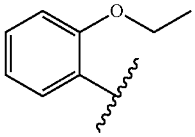 [SMILES: *c1ccccc1OCC] | N | CH | CH | CH | 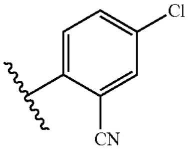 [SMILES: *c1ccc(Cl)cc1C#N] | 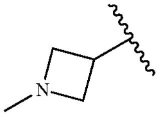 [SMILES: *C1CN(C)C1] |
| 1-94 | 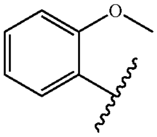 [SMILES: *c1ccccc1OC] | N | CH | CH | CH | 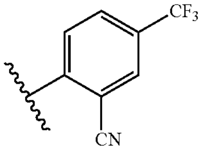 [SMILES: *c1ccc(C(F)(F)F)cc1C#N] | 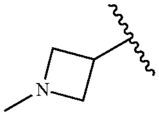 |
| 1-95 | 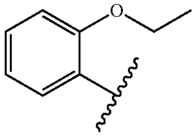 [SMILES: *c1ccccc1OCC] | N | CH | CH | CH | 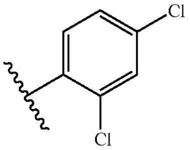 [SMILES: *c1ccc(Cl)cc1Cl] | 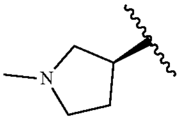 [SMILES: *[C@H]1CCN(C)C1] |
| 1-96 | 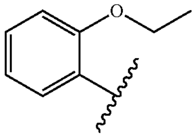 [SMILES: *c1ccccc1OCC] | N | CH | CH | CH | 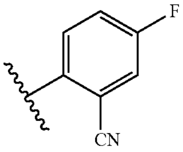 [SMILES: *c1ccc(F)cc1C#N] | 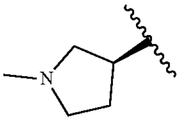 [SMILES: *[C@H]1CCN(C)C1] |
| 1-97 | 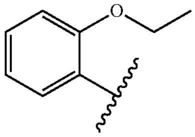 [SMILES: *c1ccccc1OCC] | N | CH | CH | CH | 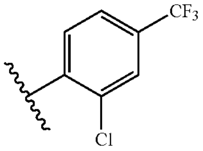 [SMILES: *c1ccc(C(F)(F)F)cc1Cl] | 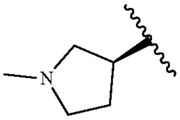 [SMILES: *[C@H]1CCN(C)C1] |
| 1-98 | 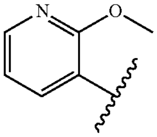 [SMILES: *c1cccnc1OC] | N | CH | CH | CH | 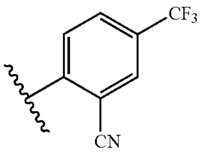 | 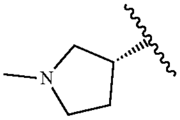 [SMILES: *[C@@H]1CCN(C)C1] |

TABLE 1-continued
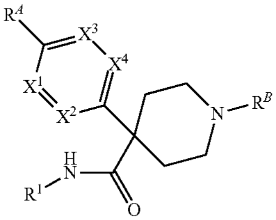
| Cpd No. | $R^A$ | $X^1$ | $X^2$ | $X^3$ | $X^4$ | $R^B$ | $R^1$ |
|---|---|---|---|---|---|---|---|
| 1-99 | 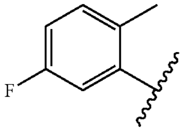 | N | CH | CH | CH | 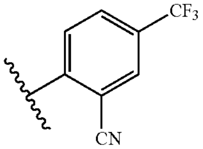 | 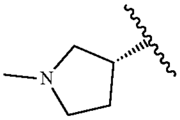 [SMILES: *[C@@H]1CCN(C)C1] |
| 1-100 | 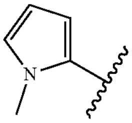 [SMILES: *c1cccn1C] | N | CH | CH | CH | 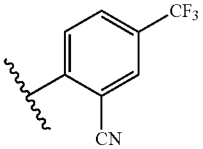 | 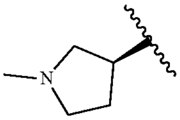 [SMILES: *[C@H]1CCN(C)C1] |
| 1-101 | 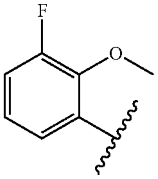 [SMILES: *c1cccc(F)c1OC] | N | CH | CH | CH | 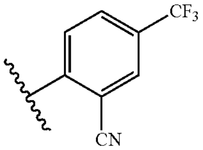 | 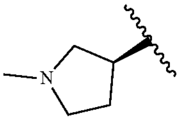 [SMILES: *[C@H]1CCN(C)C1] |
| 1-102 | 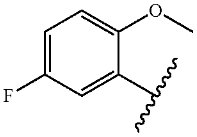 [SMILES: *c1cc(F)ccc1OC] | N | CH | CH | CH | 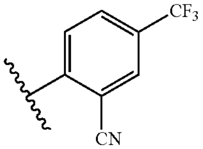 | 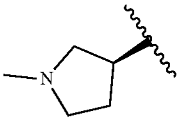 [SMILES: *[C@H]1CCN(C)C1] |
| 1-103 | 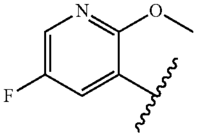 [SMILES: *c1cc(F)cnc1OC] | N | CH | CH | CH | 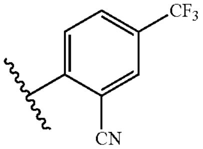 | 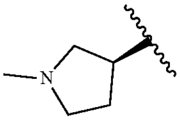 [SMILES: *[C@H]1CCN(C)C1] |
| 1-104 | 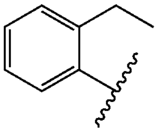 [SMILES: *c1ccccc1CC] | N | CH | CH | CH | 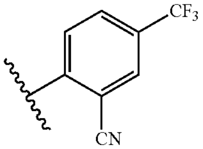 | 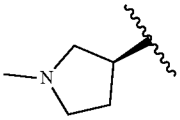 [SMILES: *[C@H]1CCN(C)C1] |
| 1-105 | 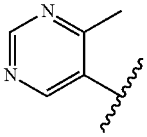 | N | CH | CH | CH | 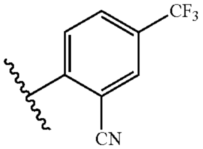 | 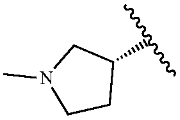 [SMILES: *[C@@H]1CCN(C)C1] |
| 1-106 | 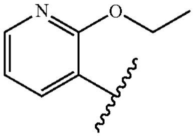 [SMILES: *c1cccnc1OCC] | N | CH | N | CH | 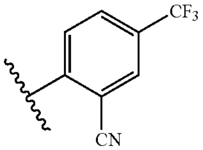 | 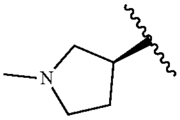 [SMILES: *[C@H]1CCN(C)C1] |

TABLE 1-continued
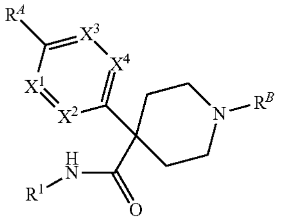
| Cpd No. | $R^A$ | $X^1$ | $X^2$ | $X^3$ | $X^4$ | $R^B$ | $R^1$ |
|---|---|---|---|---|---|---|---|
| 1-107 | 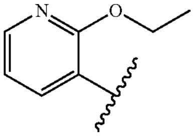 [SMILES: *c1cccnc1OCC] | N | CH | N | CH | 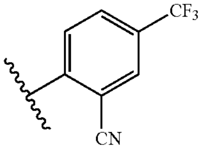 | 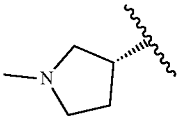 [SMILES: *[C@@H]1CCN(C)C1] |
| 1-108 | 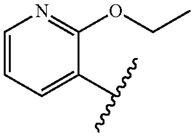 [SMILES: *c1cccnc1OCC] | N | CH | CF | CH | 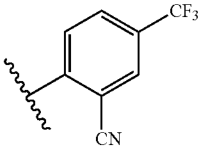 | 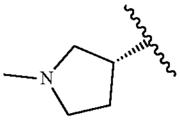 [SMILES: *[C@@H]1CCN(C)C1] |
| 1-109 | 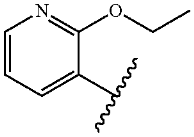 [SMILES: *c1cccnc1OCC] | N | CH | CF | CH | 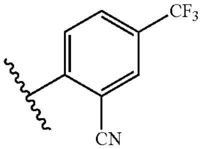 | 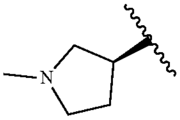 [SMILES: *[C@H]1CCN(C)C1] |
| 1-110 | 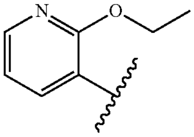 [SMILES: *c1cccnc1OCC] | N | CH | CF | CH | 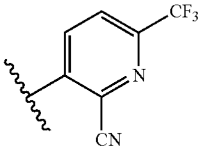 | 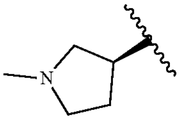 [SMILES: *[C@H]1CCN(C)C1] |
| 1-111 | 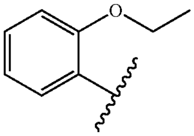 [SMILES: *c1ccccc1OCC] | N | CH | CH | CH | 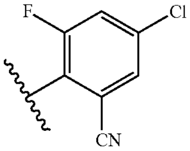 [SMILES: *c1c(F)cc(Cl)cc1C#N] | 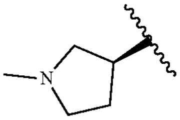 [SMILES: *[C@H]1CCN(C)C1] |
| 1-112 | 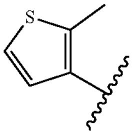 [SMILES: *c1ccsc1C] | N | CH | CH | CH | 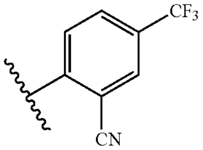 | 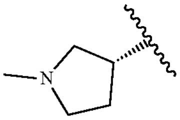 [SMILES: *[C@@H]1CCN(C)C1] |
| 1-113 | 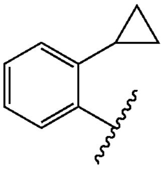 [SMILES: *c1ccccc1C1CC1] | N | CH | CH | CH | 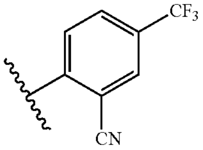 | 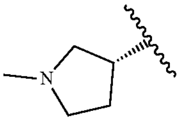 [SMILES: *[C@@H]1CCN(C)C1] |
| 1-114 | 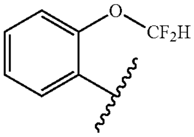 [SMILES: *c1ccccc1OC(F)F] | N | CH | CH | CH | 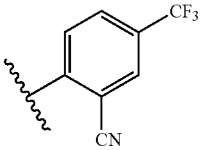 | 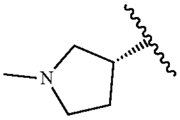 [SMILES: *[C@@H]1CCN(C)C1] |

TABLE 1-continued
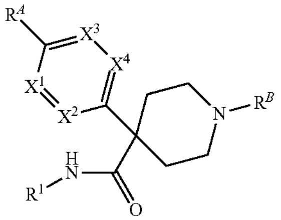
| Cpd No. | $R^A$ | $X^1$ | $X^2$ | $X^3$ | $X^4$ | $R^B$ | $R^1$ |
|---|---|---|---|---|---|---|---|
| 1-115 | 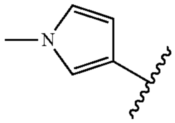 [SMILES: *c1ccn(C)c1] | N | CH | CH | CH | 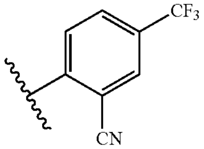 | 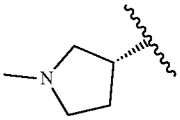 [SMILES: *[C@@H]1CCN(C)C1] |
| 1-116 | 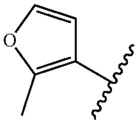 [SMILES: *c1ccoc1C] | N | CH | CH | CH | 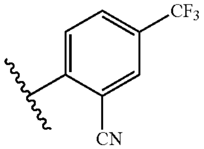 | 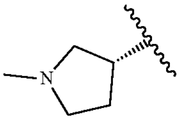 [SMILES: *[C@@H]1CCN(C)C1] |
| 1-117 | 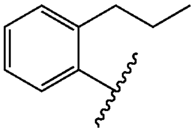 [SMILES: *c1ccccc1CCC] | N | CH | CH | CH | 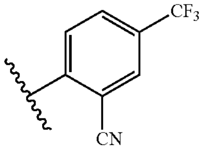 | 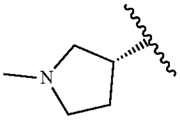 [SMILES: *[C@@H]1CCN(C)C1] |
| 1-118 | 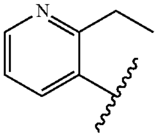 [SMILES: *c1cccnc1CC] | N | CH | CH | CH | 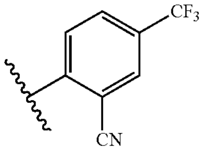 | 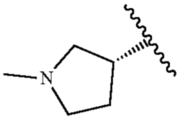 [SMILES: *[C@@H]1CCN(C)C1] |
| 1-119 | 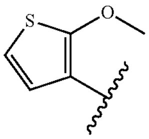 [SMILES: *c1ccsc1OC] | N | CH | CH | CH | 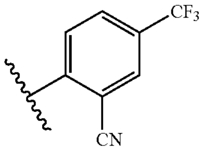 | 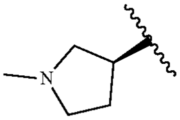 [SMILES: *[C@H]1CCN(C)C1] |
| 1-120 | 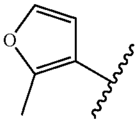 [SMILES: *c1ccoc1C] | N | CH | CH | CH | 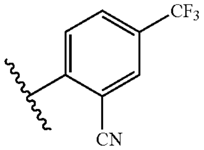 | 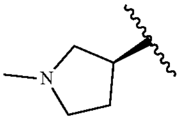 [SMILES: *[C@H]1CCN(C)C1] |
| 1-121 | 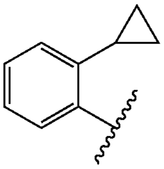 [SMILES: *c1ccccc1C1CC1] | N | CH | CH | CH | 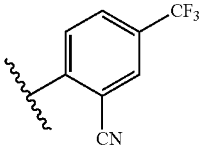 | 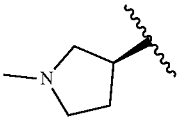 [SMILES: *[C@H]1CCN(C)C1] |
| 1-122 | 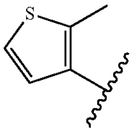 [SMILES: *c1ccsc1C] | N | CH | CH | CH | 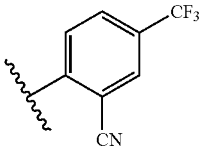 | 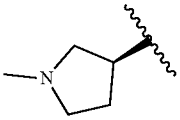 [SMILES: *[C@H]1CCN(C)C1] |

TABLE 1-continued
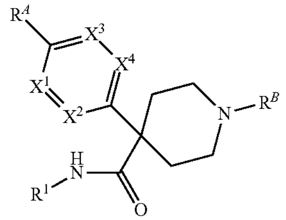
| Cpd No. | $R^A$ | $X^1$ | $X^2$ | $X^3$ | $X^4$ | $R^B$ | $R^1$ |
|---|---|---|---|---|---|---|---|
| 1-123 | 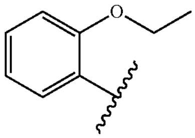 [SMILES: *c1ccccc1OCC] | N | CH | CF | CH | 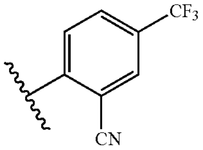 [SMILES: *c1ccc(C(F)(F)F)cc1C#N] | 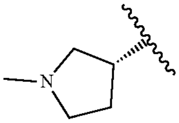 [SMILES: *[C@@H]1CCN(C)C1] |
| 1-124 | 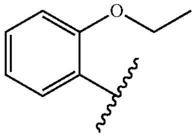 [SMILES: *c1ccccc1OCC] | N | CH | CF | CH | 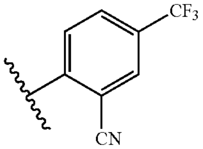 [SMILES: *c1ccc(C(F)(F)F)cc1C#N] | 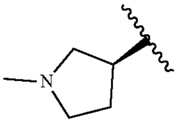 [SMILES: *[C@H]1CCN(C)C1] |
| 1-125 | 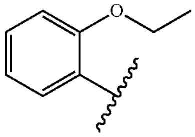 [SMILES: *c1ccccc1OCC] | N | CH | CF | CH | 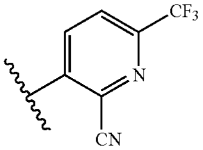 [SMILES: *c1ccc(C(F)(F)F)nc1C#N] | 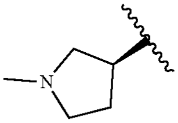 [SMILES: *[C@H]1CCN(C)C1] |
| 1-126 | 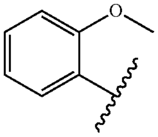 [SMILES: *c1ccccc1OC] | N | CH | CF | CH | 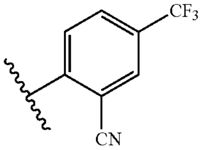 [SMILES: *c1ccc(C(F)(F)F)cc1C#N] | 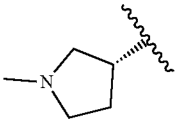 [SMILES: *[C@@H]1CCN(C)C1] |
| 1-127 | 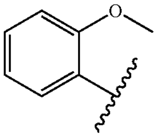 [SMILES: *c1ccccc1OC] | N | CH | CF | CH | 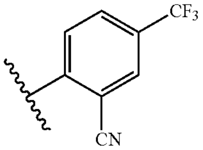 [SMILES: *c1ccc(C(F)(F)F)cc1C#N] | 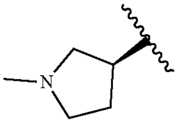 [SMILES: *[C@H]1CCN(C)C1] |
| 1-128 | 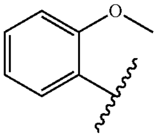 [SMILES: *c1ccccc1OC] | N | CH | CF | CH | 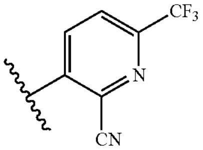 [SMILES: *c1ccc(C(F)(F)F)nc1C#N] | 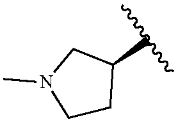 [SMILES: *[C@H]1CCN(C)C1] |
| 1-129 | 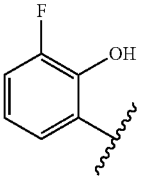 [SMILES: *c1cccc(F)c1O] | N | CH | CH | CH | 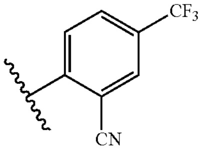 [SMILES: *c1ccc(C(F)(F)F)cc1C#N] | 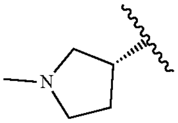 [SMILES: *[C@@H]1CCN(C)C1] |
| 1-130 | 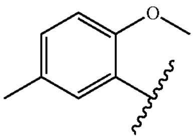 | N | CH | CH | CH | 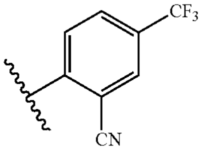 [SMILES: *c1ccc(C(F)(F)F)cc1C#N] | 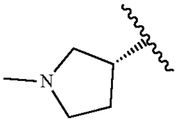 [SMILES: *[C@@H]1CCN(C)C1] |

TABLE 1-continued
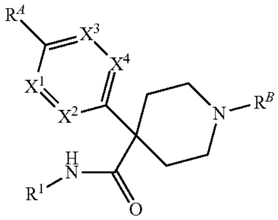
| Cpd No. | $R^A$ | $X^1$ | $X^2$ | $X^3$ | $X^4$ | $R^B$ | $R^1$ |
|---|---|---|---|---|---|---|---|
| 1-131 | 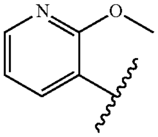 [SMILES: *c1cccnc1OC] | N | CH | CF | CH | 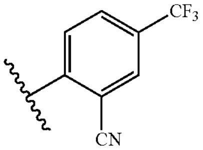 [SMILES: *c1ccc(C(F)(F)F)cc1C#N] | 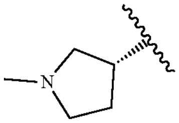 |
| 1-132 | 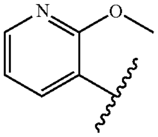 [SMILES: *c1cccnc1OC] | N | CH | CF | CH | 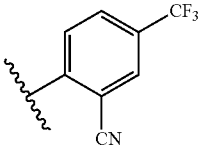 [SMILES: *c1ccc(C(F)(F)F)cc1C#N] | 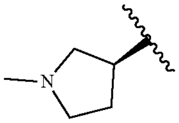 [SMILES: *[C@H]1CCN(C)C1] |
| 1-133 | 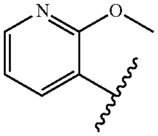 [SMILES: *c1cccnc1OC] | N | CH | CF | CH | 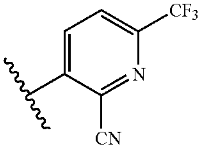 [SMILES: *c1ccc(C(F)(F)F)nc1C#N] | 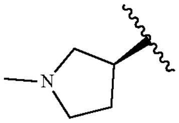 [SMILES: *[C@H]1CCN(C)C1] |
| 1-134 | 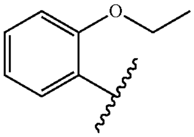 [SMILES: *c1ccccc1OCC] | N | N | CH | CH | 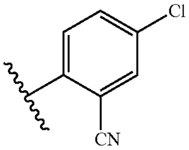 | 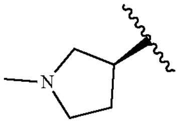 [SMILES: *[C@H]1CCN(C)C1] |
| 1-135 | 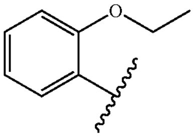 [SMILES: *c1ccccc1OCC] | N | N | CH | CH | 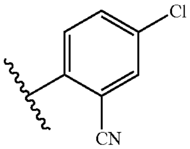 [SMILES: *c1ccc(Cl)cc1C#N] | 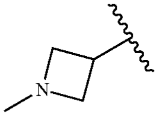 [SMILES: *C1CN(C)C1] |
| 1-136 | 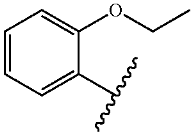 [SMILES: *c1ccccc1OCC] | N | N | CH | CH | 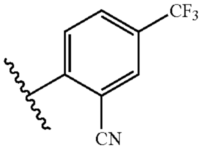 | 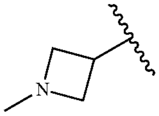 [SMILES: *C1CN(C)C1] |
| 1-137 | 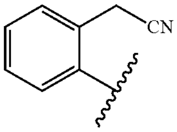 [SMILES: *c1ccccc1CC#N] | N | CH | CH | CH | 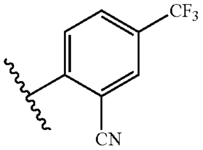 | 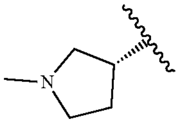 [SMILES: *[C@@H]1CCN(C)C1] |
| 1-138 | 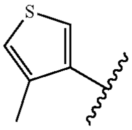 [SMILES: *c1cscc1C] | N | CH | CH | CH | 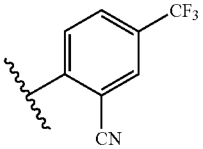 | 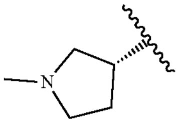 |

TABLE 1-continued
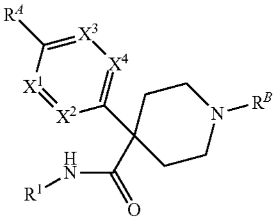
| Cpd No. | $R^A$ | $X^1$ | $X^2$ | $X^3$ | $X^4$ | $R^B$ | $R^1$ |
|---|---|---|---|---|---|---|---|
| 1-139 | 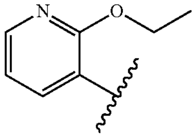 [SMILES: *c1cccnc1OCC] | N | N | CH | CH | 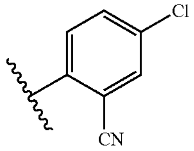 [SMILES: *c1ccc(Cl)cc1C#N] | 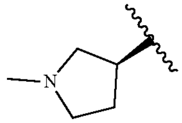 [SMILES: *[C@H]1CCN(C)C1] |
| 1-140 | 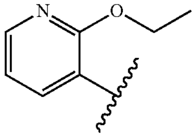 [SMILES: *c1cccnc1OCC] | N | N | CH | CH | 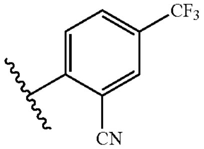 | 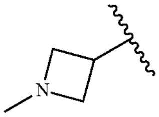 |
| 1-141 | 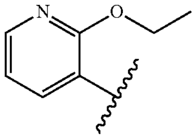 [SMILES: *c1cccnc1OCC] | N | CH | CH | CH | 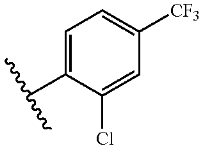 | 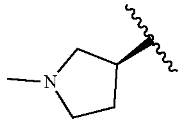 [SMILES: *[C@H]1CCN(C)C1] |
| 1-142 | 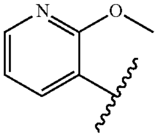 [SMILES: *c1cccnc1OC] | N | CH | CH | CH | 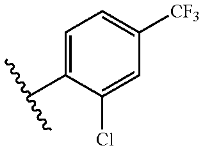 | 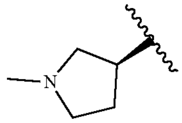 [SMILES: *[C@H]1CCN(C)C1] |
| 1-143 | 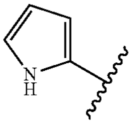 [SMILES: *c1ccc[nH]1] | N | CH | CH | CH | 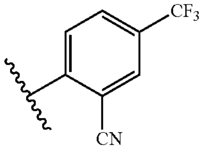 | 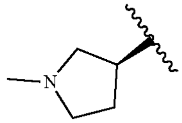 [SMILES: *[C@H]1CCN(C)C1] |
| 1-144 | 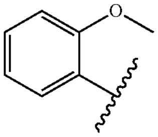 [SMILES: *c1ccccc1OC] | N | CH | CH | CH | 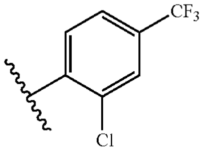 | 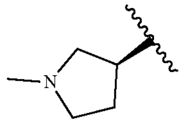 [SMILES: *[C@H]1CCN(C)C1] |
| 1-145 | 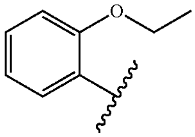 [SMILES: *c1ccccc1OCC] | N | CH | CH | CH | 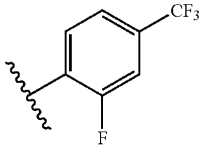 [SMILES: *c1ccc(C(F)(F)F)cc1F] | 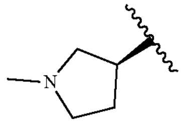 [SMILES: *[C@H]1CCN(C)C1] |
| 1-146 | 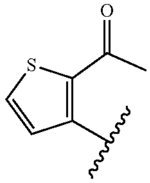 [SMILES: *c1ccsc1C(C)=O] | N | CH | CH | CH | 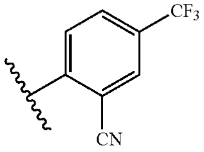 | 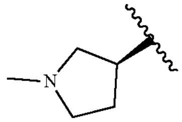 [SMILES: *[C@H]1CCN(C)C1] |

TABLE 1-continued
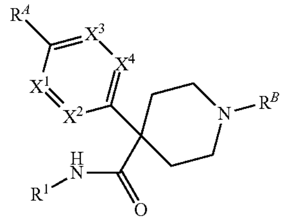
| Cpd No. | $R^A$ | $X^1$ | $X^2$ | $X^3$ | $X^4$ | $R^B$ | $R^1$ |
|---|---|---|---|---|---|---|---|
| 1-147 | 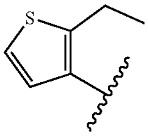 [SMILES: *c1ccsc1CC] | N | CH | CH | CH | 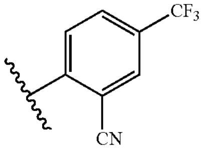 | 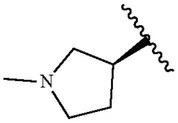 [SMILES: *[C@H]1CCN(C)C1] |
| 1-148 | 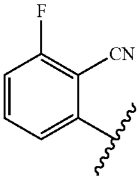 [SMILES: *c1cccc(F)c1C#N] | N | CH | CH | CH | 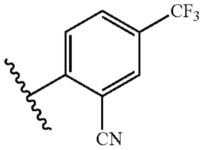 | 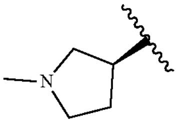 [SMILES: *[C@H]1CCN(C)C1] |
| 1-149 | 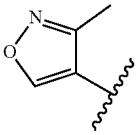 [SMILES: *c1conc1C] | N | CH | CH | CH | 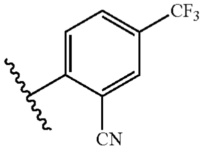 | 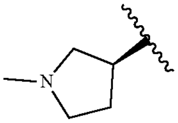 [SMILES: *[C@H]1CCN(C)C1] |
| 1-150 | 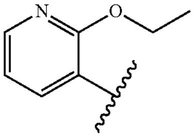 [SMILES: *c1cccnc1OCC] | N | CH | CH | CH | 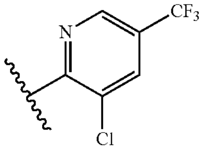 | 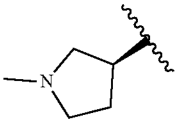 [SMILES: *[C@H]1CCN(C)C1] |
| 1-151 | 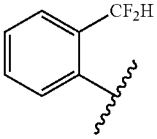 [SMILES: *c1ccccc1C(F)F] | N | CH | CH | CH | 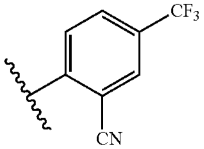 | 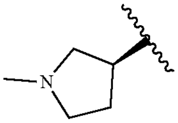 [SMILES: *[C@H]1CCN(C)C1] |
| 1-152 | 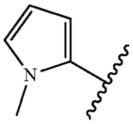 [SMILES: *c1cccn1C] | N | CH | CH | CH | 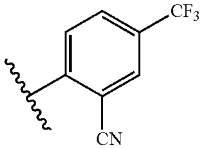 | 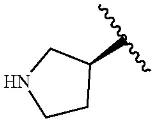 [SMILES: *[C@H]1CCNC1] |
| 1-153 | 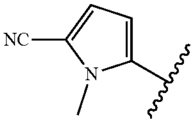 [SMILES: *c1ccc(C#N)n1C] | N | CH | CH | CH | 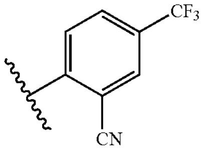 | 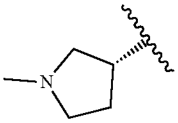 |
| 1-154 | 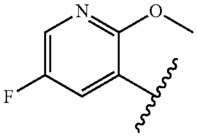 [SMILES: *c1cc(F)cnc1OC] | N | CH | CH | CH | 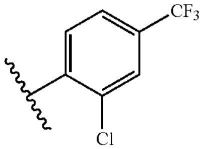 | 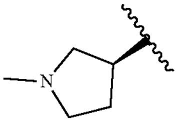 [SMILES: *[C@H]1CCN(C)C1] |

TABLE 1-continued
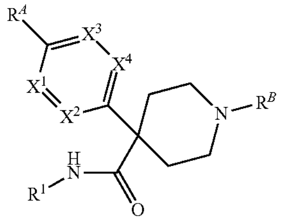
| Cpd No. | $R^A$ | $X^1$ | $X^2$ | $X^3$ | $X^4$ | $R^B$ | $R^1$ |
|---|---|---|---|---|---|---|---|
| 1-155 | 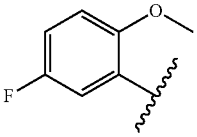 [SMILES: *c1cc(F)ccc1OC] | N | CH | CH | CH | 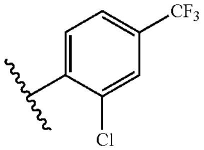 | 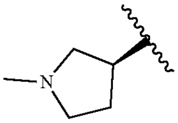 [SMILES: *[C@H]1CCN(C)C1] |
| 1-156 | 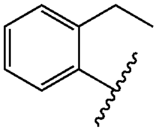 [SMILES: *c1ccccc1CC] | N | CH | CH | CH | 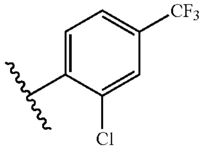 [SMILES: *c1ccc(C(F)(F)F)cc1Cl] | 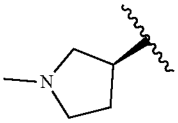 |
| 1-157 | 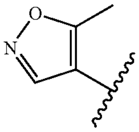 | N | CH | CH | CH | 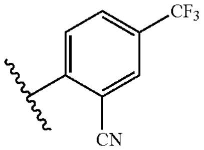 | 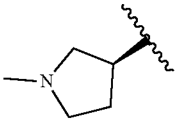 [SMILES: *[C@H]1CCN(C)C1] |
| 1-158 | 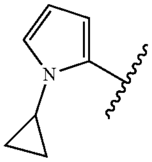 [SMILES: *c1cccn1C1CC1] | N | CH | CH | CH | 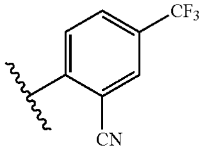 [SMILES: *c1ccc(C(F)(F)F)cc1C#N] | 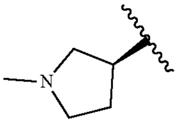 [SMILES: *[C@H]1CCN(C)C1] |
| 1-159 | 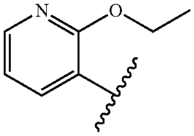 [SMILES: *c1cccnc1OCC] | CH | CH | CH | CH | 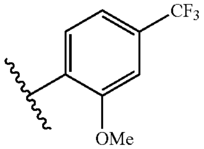 | 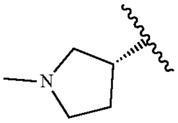 [SMILES: *[C@@H]1CCN(C)C1] |
| 1-160 | 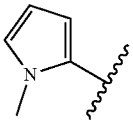 [SMILES: *c1cccn1C] | N | CH | CH | CH | 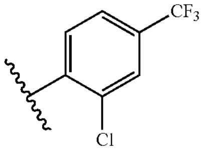 | 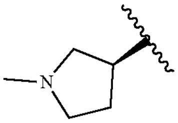 [SMILES: *[C@H]1CCN(C)C1] |
| 1-161 | 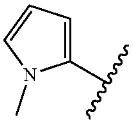 [SMILES: *c1cccn1C] | N | CH | CF | CH | 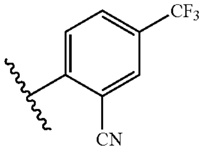 | 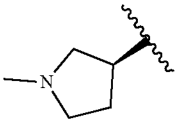 [SMILES: *[C@H]1CCN(C)C1] |
| 1-162 | 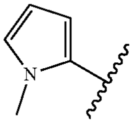 [SMILES: *c1cccn1C] | N | CH | CF | CH | 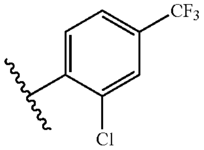 | 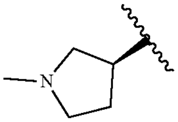 [SMILES: *[C@H]1CCN(C)C1] |

TABLE 1-continued
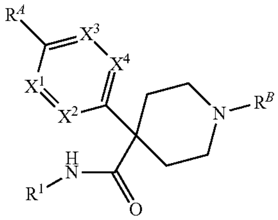
| Cpd No. | $R^A$ | $X^1$ | $X^2$ | $X^3$ | $X^4$ | $R^B$ | $R^1$ |
|---|---|---|---|---|---|---|---|
| 1-163 | 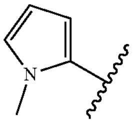 [SMILES: *c1cccn1C] | N | CH | CF | CH | 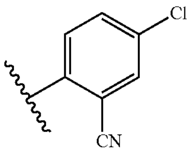 [SMILES: *c1ccc(Cl)cc1C#N] | 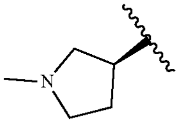 [SMILES: *[C@H]1CCN(C)C1] |
| 1-164 | 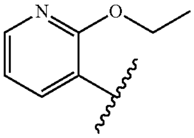 | CH | CH | CH | CH | 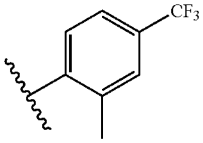 [SMILES: *c1ccc(C(F)(F)F)cc1C] | 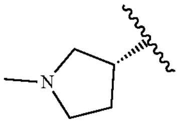 [SMILES: *[C@@H]1CCN(C)C1] |
| 1-165 | 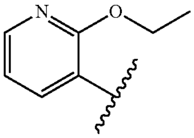 | CH | CH | CH | CH | 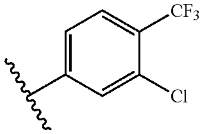 [SMILES: *c1ccc(C(F)(F)F)c(Cl)c1] | 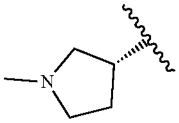 [SMILES: *[C@@H]1CCN(C)C1] |
| 1-166 | 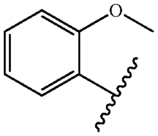 [SMILES: *c1ccccc1OC] | N | CH | CH | CH | 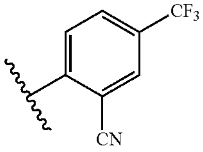 | 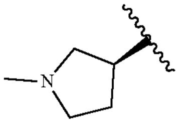 [SMILES: *[C@H]1CCN(C)C1] |
| 1-167 | 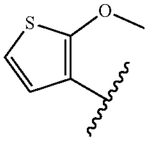 [SMILES: *c1ccsc1OC] | N | CH | CH | CH | 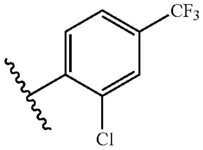 | 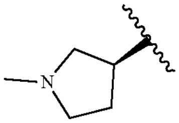 [SMILES: *[C@H]1CCN(C)C1] |
| 1-168 | 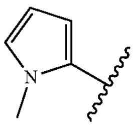 [SMILES: *c1cccn1C] | N | N | CH | CH | 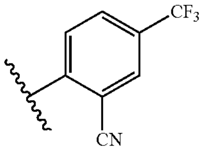 | 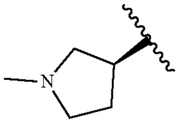 [SMILES: *[C@H]1CCN(C)C1] |
| 1-169 | 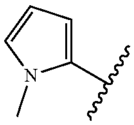 [SMILES: *c1cccn1C] | N | N | CH | CH | 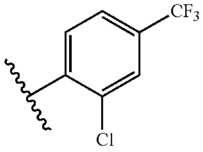 | 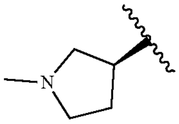 [SMILES: *[C@H]1CCN(C)C1] |
| 1-170 | 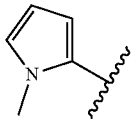 [SMILES: *c1cccn1C] | N | N | CH | CH | 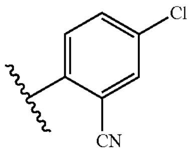 [SMILES: *c1ccc(Cl)cc1C#N] | 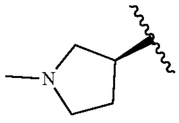 [SMILES: *[C@H]1CCN(C)C1] |

TABLE 1-continued
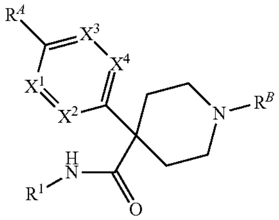
| Cpd No. | $R^A$ | $X^1$ | $X^2$ | $X^3$ | $X^4$ | $R^B$ | $R^1$ |
| --- | --- | --- | --- | --- | --- | --- | --- |
| 1-171 | 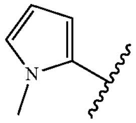 [SMILES: *c1cccn1C] | N | N | CH | CH | 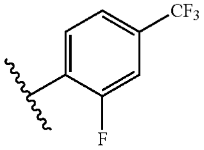 [SMILES: *c1ccc(C(F)(F)F)cc1F] | 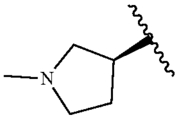 [SMILES: *[C@H]1CCN(C)C1] |
| 1-172 | 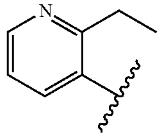 [SMILES: *c1cccnc1CC] | N | CH | CH | CH | 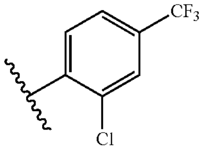 [SMILES: *c1ccc(C(F)(F)F)cc1Cl] | 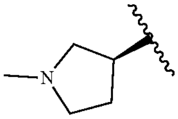 [SMILES: *[C@H]1CCN(C)C1] |
| 1-173 | 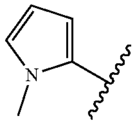 [SMILES: *c1cccn1C] | N | CH | CH | CH | 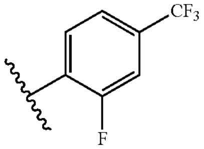 [SMILES: *c1ccc(C(F)(F)F)cc1F] | 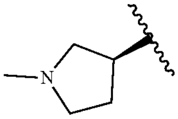 [SMILES: *[C@H]1CCN(C)C1] |
| 1-174 | 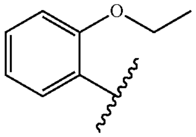 [SMILES: *c1ccccc1OCC] | N | N | CH | CH | 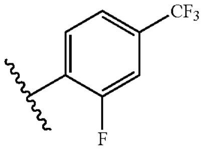 [SMILES: *c1ccc(C(F)(F)F)cc1F] | 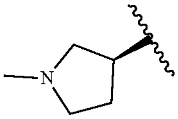 [SMILES: *[C@H]1CCN(C)C1] |
| 1-175 | 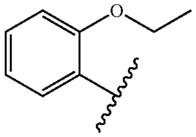 [SMILES: *c1ccccc1OCC] | N | N | CH | CH | 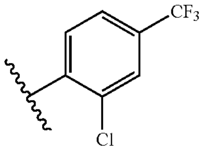 [SMILES: *c1ccc(C(F)(F)F)cc1Cl] | 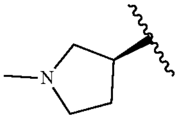 [SMILES: *[C@H]1CCN(C)C1] |
| 1-176 | 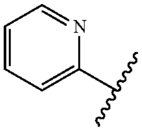 | N | CH | CH | CH | 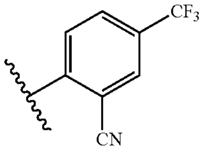 [SMILES: *c1ccc(C(F)(F)F)cc1C#N] | 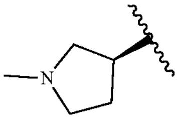 [SMILES: *[C@H]1CCN(C)C1] |
| 1-177 | 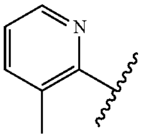 [SMILES: *c1ncccc1C] | N | CH | CH | CH | 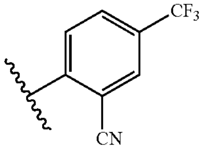 [SMILES: *c1ccc(C(F)(F)F)cc1C#N] | 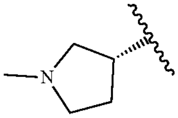 [SMILES: *[C@@H]1CCN(C)C1] |
| 1-178 | 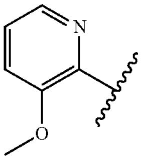 [SMILES: *c1ncccc1OC] | N | CH | CH | CH | 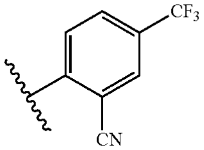 | 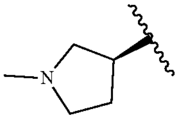 [SMILES: *[C@H]1CCN(C)C1] |

TABLE 1-continued
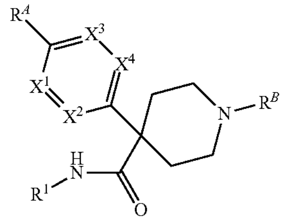
| Cpd No. | $R^A$ | $X^1$ | $X^2$ | $X^3$ | $X^4$ | $R^B$ | $R^1$ |
|---|---|---|---|---|---|---|---|
| 1-179 | 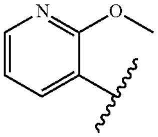 [SMILES: *c1cccnc1OC] | N | CH | CH | CH | 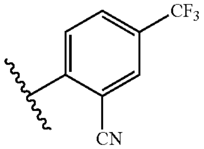 | 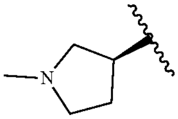 [SMILES: *[C@H]1CCN(C)C1] |
| 1-180 | 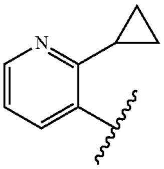 [SMILES: *c1cccnc1C1CC1] | N | CH | CH | CH | 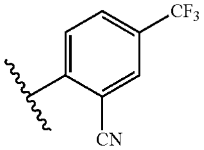 | 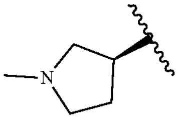 [SMILES: *[C@H]1CCN(C)C1] |
| 1-181 | 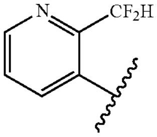 [SMILES: *c1cccnc1C(F)F] | N | CH | CH | CH | 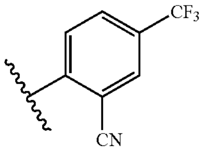 | 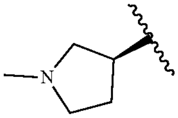 [SMILES: *[C@H]1CCN(C)C1] |
| 1-182 | 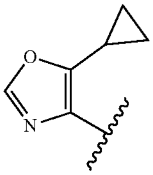 [SMILES: *c1ncoc1C1CC1] | N | CH | CH | CH | 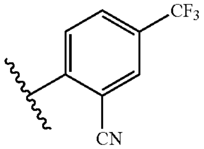 | 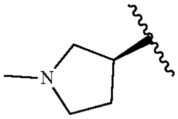 [SMILES: *[C@H]1CCN(C)C1] |
| 1-183 | 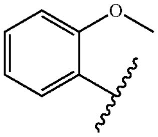 [SMILES: *c1ccccc1OC] | N | N | CH | CH | 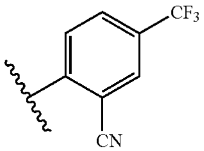 | 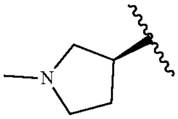 [SMILES: *[C@H]1CCN(C)C1] |
| 1-184 | 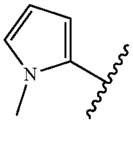 [SMILES: *c1cccn1C] | N | CH | CH | CH | 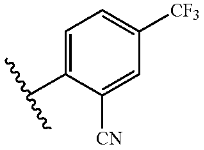 | 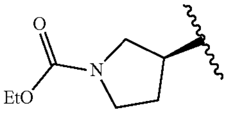 [SMILES: *[C@H]1CCN(C(=O)OCC)C1] |
| 1-185 | 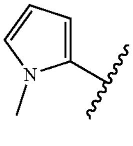 [SMILES: *c1cccn1C] | N | CH | CH | CH | 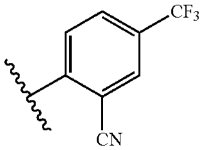 | 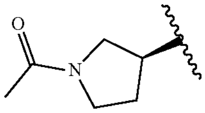 [SMILES: *[C@H]1CCN(C(C)=O)C1] |
| 1-186 | 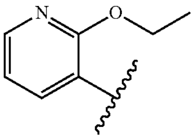 [SMILES: *c1cccnc1OCC] | N | CH | CH | CH | 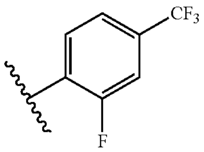 | 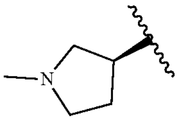 [SMILES: *[C@H]1CCN(C)C1] |

TABLE 1-continued
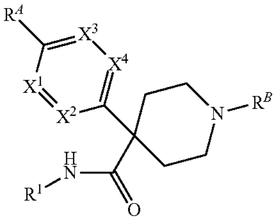
| Cpd No. | $R^A$ | $X^1$ | $X^2$ | $X^3$ | $X^4$ | $R^B$ | $R^1$ |
|---|---|---|---|---|---|---|---|
| 1-187 | 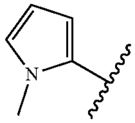 [SMILES: *c1cccn1C] | N | CH | CH | CH | 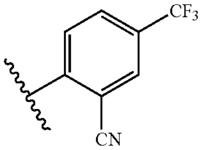 | 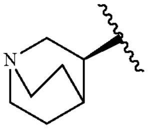 [SMILES: *[C@@H]1CN2CCC1CC2] |
| 1-188 | 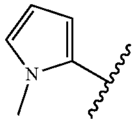 [SMILES: *c1cccn1C] | N | CH | CH | CH | 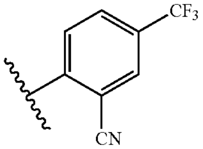 | 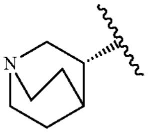 |
| 1-189 | 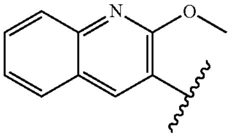 [SMILES: *c1cc2ccccc2nc1OC] | N | CH | CH | CH | 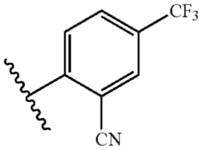 | 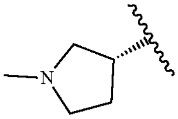 [SMILES: *[C@@H]1CCN(C)C1] |
| 1-190 | 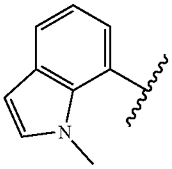 [SMILES: *c1cccc2ccn(C)c12] | N | CH | CH | CH | 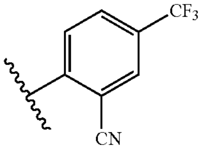 | 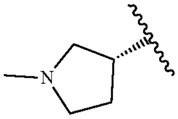 [SMILES: *[C@@H]1CCN(C)C1] |
| 1-191 | 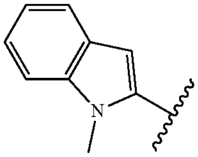 [SMILES: *c1cc2ccccc2n1C] | N | CH | CH | CH | 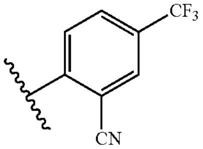 | 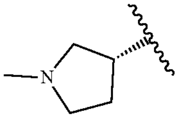 [SMILES: *[C@@H]1CCN(C)C1] |
| 1-192 | 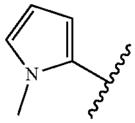 [SMILES: *c1cccn1C] | N | CH | CF | CH | 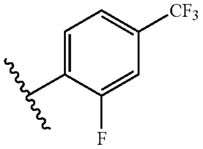 | 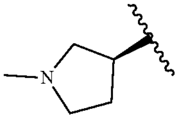 [SMILES: *[C@H]1CCN(C)C1] |
| 1-193 | 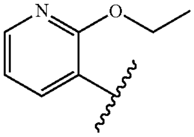 [SMILES: *c1cccnc1OCC] | N | N | CH | CH | 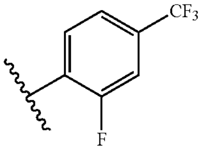 | 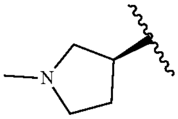 [SMILES: *[C@H]1CCN(C)C1] |
| 1-194 | 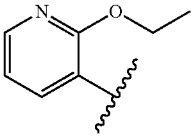 [SMILES: *c1cccnc1OCC] | N | N | CH | CH | 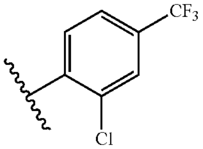 | 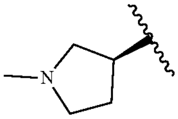 [SMILES: *[C@H]1CCN(C)C1] |

TABLE 1-continued
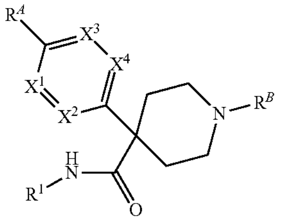
| Cpd No. | $R^A$ | $X^1$ | $X^2$ | $X^3$ | $X^4$ | $R^B$ | $R^1$ |
|---|---|---|---|---|---|---|---|
| 1-195 | 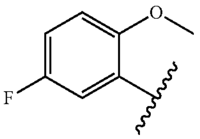 [SMILES: *c1cc(F)ccc1OC] | N | CH | CF | CH | 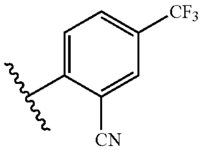 [SMILES: *c1ccc(C(F)(F)F)cc1C#N] | 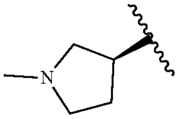 [SMILES: *[C@H]1CCN(C)C1] |
| 1-196 | 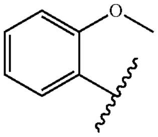 [SMILES: *c1ccccc1OC] | N | CH | CF | CH | 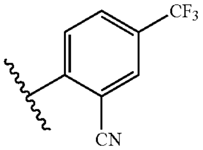 [SMILES: *c1ccc(C(F)(F)F)cc1C#N] | 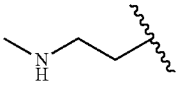 [SMILES: *CCNC] |
| 1-197 | 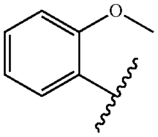 [SMILES: *c1ccccc1OC] | N | CH | CF | CH | 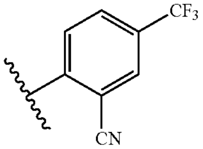 [SMILES: *c1ccc(C(F)(F)F)cc1C#N] | 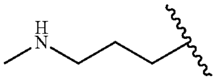 [SMILES: *CCCNC] |
| 1-198 | 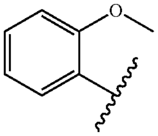 [SMILES: *c1ccccc1OC] | N | CH | CF | CH | 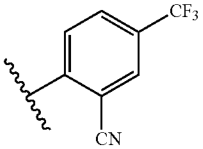 [SMILES: *c1ccc(C(F)(F)F)cc1C#N] | 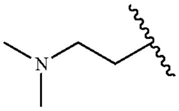 [SMILES: *CCN(C)C] |
| 1-199 | 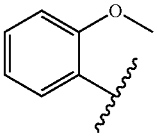 [SMILES: *c1ccccc1OC] | N | CH | CF | CH | 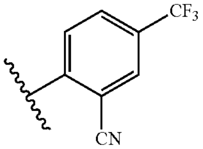 [SMILES: *c1ccc(C(F)(F)F)cc1C#N] | 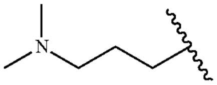 [SMILES: *CCCN(C)C] |
| 1-200 | 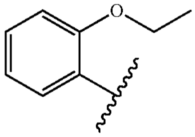 [SMILES: *c1ccccc1OCC] | N | CH | CF | CH | 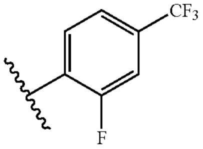 [SMILES: *c1ccc(C(F)(F)F)cc1F] | 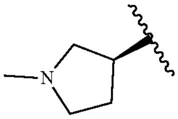 [SMILES: *[C@H]1CCN(C)C1] |
| 1-201 | 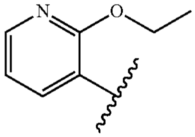 [SMILES: *c1cccnc1OCC] | N | CH | CF | CH | 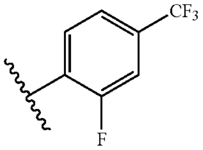 [SMILES: *c1ccc(C(F)(F)F)cc1F] | 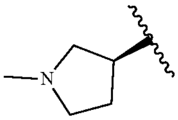 [SMILES: *[C@H]1CCN(C)C1] |
| 1-202 | 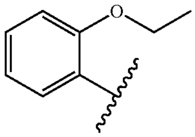 [SMILES: *c1ccccc1OCC] | N | CH | CF | CH | 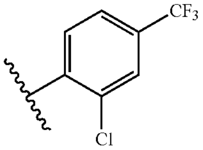 [SMILES: *c1ccc(C(F)(F)F)cc1Cl] | 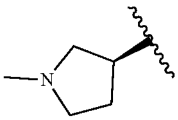 [SMILES: *[C@H]1CCN(C)C1] |

TABLE 1-continued
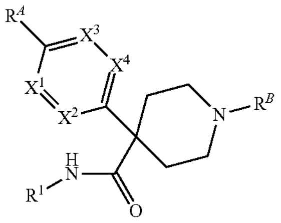
| Cpd No. | $R^A$ | $X^1$ | $X^2$ | $X^3$ | $X^4$ | $R^B$ | $R^1$ |
|---|---|---|---|---|---|---|---|
| 1-203 | 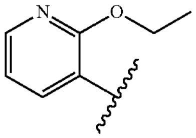 [SMILES: *c1cccnc1OCC] | N | CH | CF | CH | 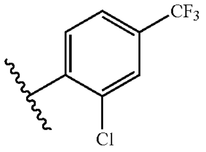 [SMILES: *c1ccc(C(F)(F)F)cc1Cl] | 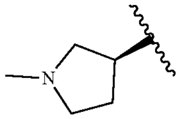 [SMILES: *[C@H]1CCN(C)C1] |
| 1-204 | 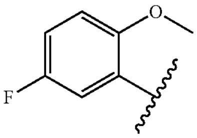 [SMILES: *c1cc(F)ccc1OC] | N | CH | CF | CH | 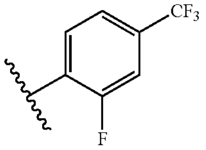 [SMILES: *c1ccc(C(F)(F)F)cc1F] | 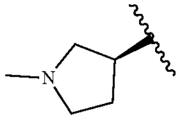 [SMILES: *[C@H]1CCN(C)C1] |
| 1-205 | 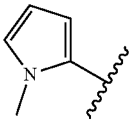 [SMILES: *c1cccn1C] | N | CH | CH | CH | 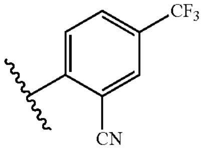 [SMILES: *c1ccc(C(F)(F)F)cc1C#N] | 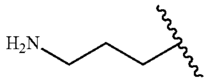 |
| 1-206 | 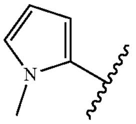 | N | CH | CH | CH | 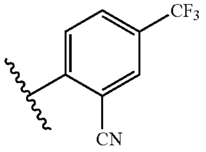 [SMILES: *c1ccc(C(F)(F)F)cc1C#N] | 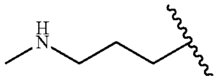 [SMILES: *CCCNC] |
| 1-207 | 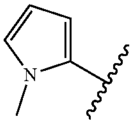 [SMILES: *c1cccn1C] | N | CH | CH | CH | 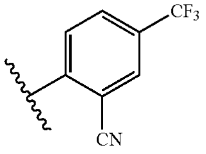 [SMILES: *c1ccc(C(F)(F)F)cc1C#N] | 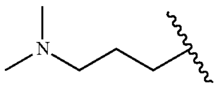 [SMILES: *CCCN(C)C] |
| 1-208 | 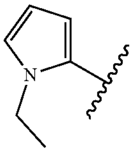 [SMILES: *c1cccn1CC] | N | CH | CH | CH | 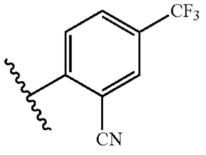 [SMILES: *c1ccc(C(F)(F)F)cc1C#N] | 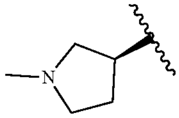 [SMILES: *[C@H]1CCN(C)C1] |
| 1-209 | 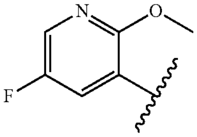 [SMILES: *c1cc(F)cnc1OC] | N | CH | CF | CH | 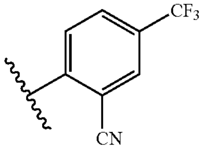 [SMILES: *c1ccc(C(F)(F)F)cc1C#N] | 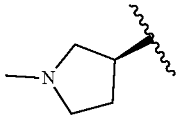 [SMILES: *[C@H]1CCN(C)C1] |
| 1-210 | 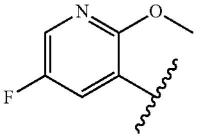 [SMILES: *c1cc(F)cnc1OC] | N | CH | CF | CH | 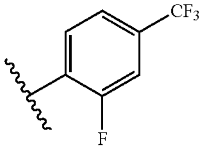 [SMILES: *c1ccc(C(F)(F)F)cc1F] | 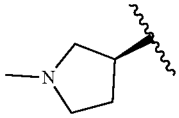 [SMILES: *[C@H]1CCN(C)C1] |

TABLE 1-continued
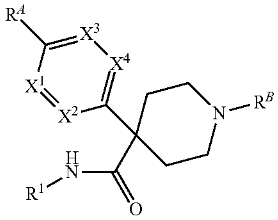
| Cpd No. | $R^A$ | $X^1$ | $X^2$ | $X^3$ | $X^4$ | $R^B$ | $R^1$ |
|---|---|---|---|---|---|---|---|
| 1-211 | 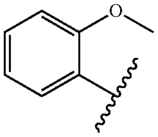 [SMILES: *c1ccccc1OC] | N | CH | CH | CH | 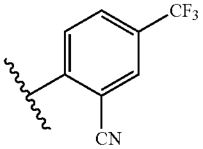 [SMILES: *c1ccc(C(F)(F)F)cc1C#N] | 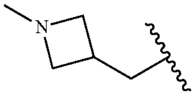 |
| 1-212 | 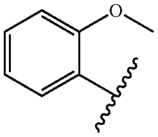 [SMILES: *c1ccccc1OC] | N | CH | CH | CH | 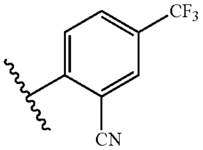 [SMILES: *c1ccc(C(F)(F)F)cc1C#N] | 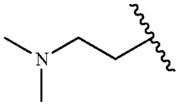 [SMILES: *CCN(C)C] |
| 1-213 | 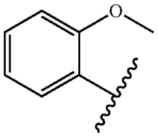 [SMILES: *c1ccccc1OC] | N | CH | CH | CH | 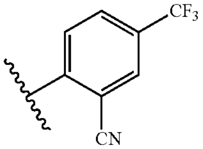 [SMILES: *c1ccc(C(F)(F)F)cc1C#N] | 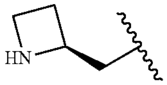 [SMILES: *C[C@@H]1CCN1] |
| 1-214 | 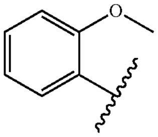 [SMILES: *c1ccccc1OC] | N | CH | CH | CH | 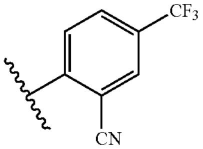 [SMILES: *c1ccc(C(F)(F)F)cc1C#N] | 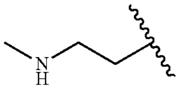 [SMILES: *CCNC] |
| 1-215 | 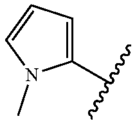 [SMILES: *c1cccn1C] | N | CH | CH | CH | 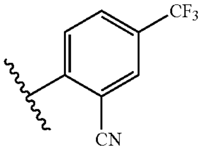 [SMILES: *c1ccc(C(F)(F)F)cc1C#N] | 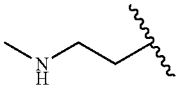 |
| 1-216 | 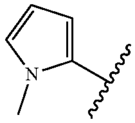 [SMILES: *c1cccn1C] | N | CH | CH | CH | 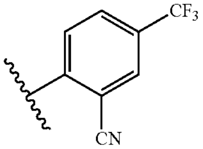 [SMILES: *c1ccc(C(F)(F)F)cc1C#N] | 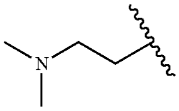 [SMILES: *CCN(C)C] |
| 1-217 | 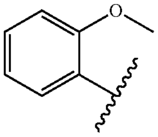 [SMILES: *c1ccccc1OC] | N | CH | CH | CH | 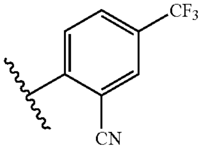 [SMILES: *c1ccc(C(F)(F)F)cc1C#N] | 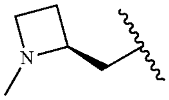 [SMILES: *C[C@@H]1CCN1C] |
| 1-218 | 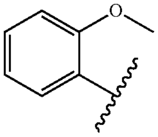 [SMILES: *c1ccccc1OC] | N | CH | CH | CH | 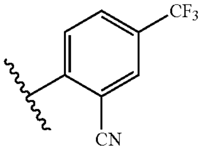 [SMILES: *c1ccc(C(F)(F)F)cc1C#N] | 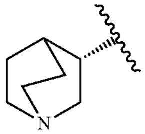 [SMILES: *[C@@H]1CN2CCC1CC2] |

TABLE 1-continued
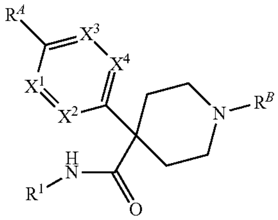
| Cpd No. | $R^A$ | $X^1$ | $X^2$ | $X^3$ | $X^4$ | $R^B$ | $R^1$ |
|---|---|---|---|---|---|---|---|
| 1-219 | 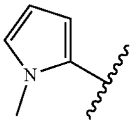 [SMILES: *c1cccn1C] | N | CH | CH | CH | 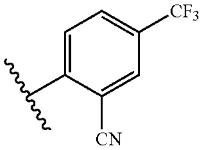 [SMILES: *c1ccc(C(F)(F)F)cc1C#N] | 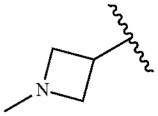 [SMILES: *C1CN(C)C1] |
| 1-220 | 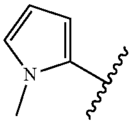 [SMILES: *c1cccn1C] | N | CH | CH | CH | 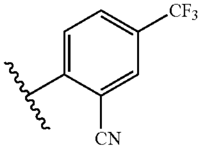 [SMILES: *c1ccc(C(F)(F)F)cc1C#N] | 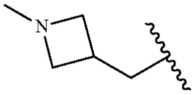 [SMILES: *CC1CN(C)C1] |
| 1-221 | 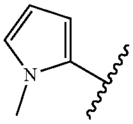 [SMILES: *c1cccn1C] | N | CH | CH | CH | 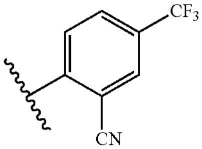 | 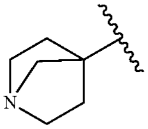 [SMILES: *C12CCN(CC1)C2] |
| 1-222 | 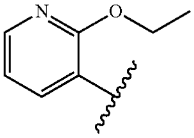 [SMILES: *c1cccnc1OCC] | N | CH | CH | CH | 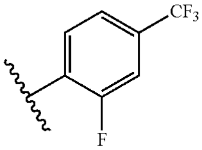 | 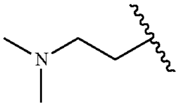 [SMILES: *CCN(C)C] |
| 1-223 | 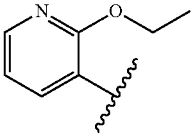 [SMILES: *c1cccnc1OCC] | N | CH | CH | CH | 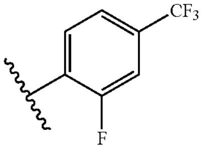 | 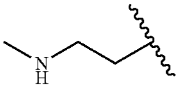 [SMILES: *CCNC] |
| 1-224 | 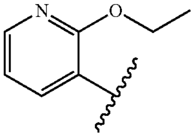 [SMILES: *c1cccnc1OCC] | N | CH | CH | CH | 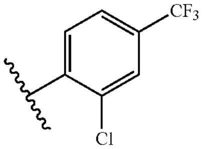 | 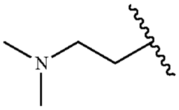 [SMILES: *CCN(C)C] |
| 1-225 | 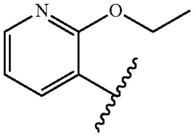 [SMILES: *c1cccnc1OCC] | N | CH | CH | CH | 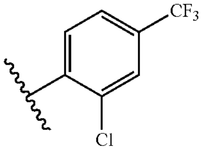 | 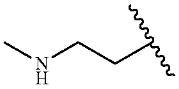 |
| 1-226 | 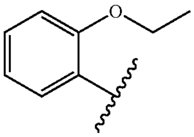 [SMILES: *c1ccccc1OCC] | N | CH | CH | CH | 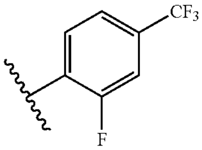 | 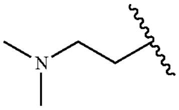 [SMILES: *CCN(C)C] |

TABLE 1-continued
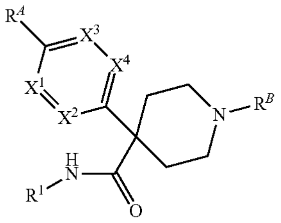
| Cpd No. | $R^A$ | $X^1$ | $X^2$ | $X^3$ | $X^4$ | $R^B$ | $R^1$ |
|---|---|---|---|---|---|---|---|
| 1-227 | 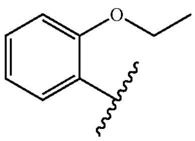 [SMILES: *c1ccccc1OCC] | N | CH | CH | CH | 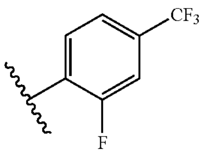 | 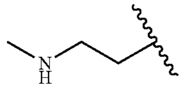 [SMILES: *CCNC] |
| 1-228 | 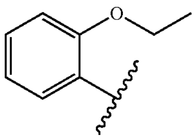 [SMILES: *c1ccccc1OCC] | N | CH | CH | CH | 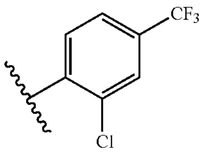 | 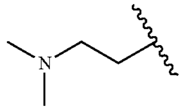 [SMILES: *CCN(C)C] |
| 1-229 | 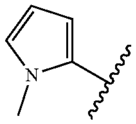 [SMILES: *c1cccn1C] | N | CH | CH | CH | 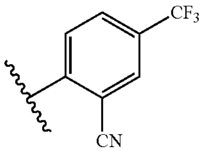 | 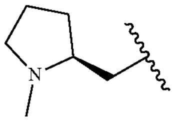 [SMILES: *C[C@@H]1CCCN1C] |
| 1-230 | 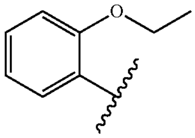 [SMILES: *c1ccccc1OCC] | N | CH | CH | CH | 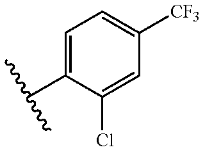 | 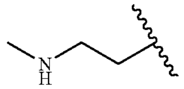 |
| 1-231 | 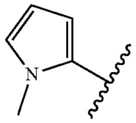 [SMILES: *c1cccn1C] | N | CH | CH | CH | 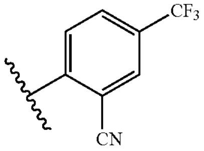 | 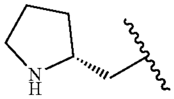 [SMILES: *C[C@H]1CCCN1] |
| 1-232 | 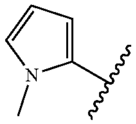 [SMILES: *c1cccn1C] | N | CH | CH | CH | 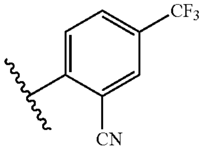 | 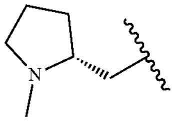 [SMILES: *C[C@H]1CCCN1C] |
| 1-233 | 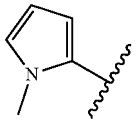 [SMILES: *c1cccn1C] | N | CH | CH | CH | 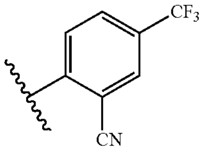 | 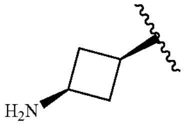 [SMILES: *[C@H]1C[C@@H](N)C1] |
| 1-234 | 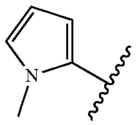 | N | CH | CH | CH | 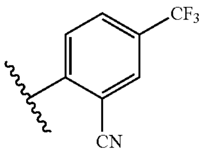 | 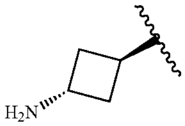 [SMILES: *[C@H]1C[C@H](N)C1] |

TABLE 1-continued
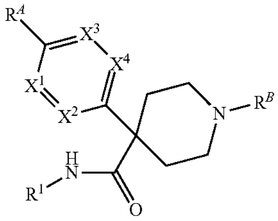
| Cpd No. | $R^A$ | $X^1$ | $X^2$ | $X^3$ | $X^4$ | $R^B$ | $R^1$ |
|---|---|---|---|---|---|---|---|
| 1-235 | 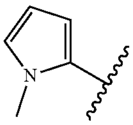 | N | CH | CH | CH | 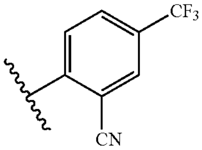 | 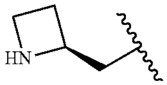 |
| 1-236 | 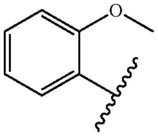 [SMILES: *c1ccccc1OC] | N | CH | CH | CH | 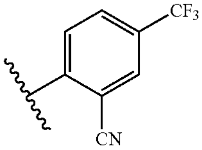 | 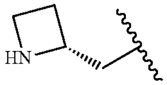 |
| 1-237 | 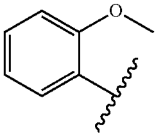 [SMILES: *c1ccccc1OC] | N | CH | CH | CH | 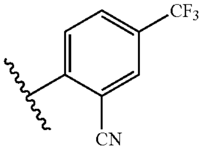 | *cis- 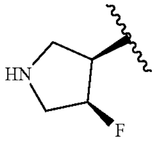 |
| 1-238 | 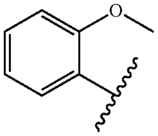 [SMILES: *c1ccccc1OC] | N | CH | CH | CH | 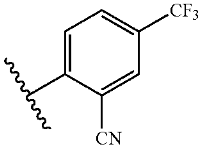 | *trans- 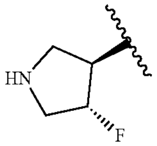 |
| 1-239 | 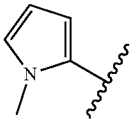 [SMILES: *c1cccn1C] | N | CH | CH | CH | 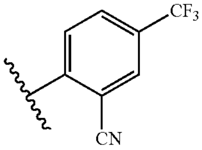 | 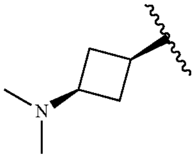 [SMILES: *[C@H]1C[C@@H](N(C)C)C1] |
| 1-240 | 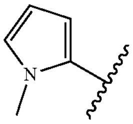 [SMILES: *c1cccn1C] | N | CH | CH | CH | 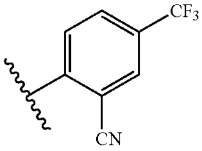 | 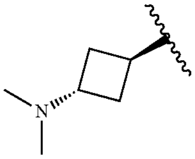 [SMILES: *[C@H]1C[C@H](N(C)C)C1] |
| 1-241 | 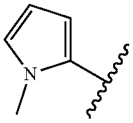 [SMILES: *c1cccn1C] | N | CH | CH | CH | 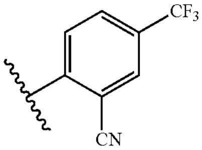 | 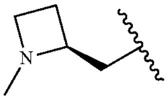 [SMILES: *C[C@@H]1CCN1C] |

TABLE 1-continued
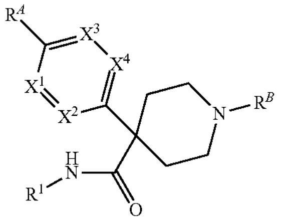
| Cpd No. | $R^A$ | $X^1$ | $X^2$ | $X^3$ | $X^4$ | $R^B$ | $R^1$ |
|---|---|---|---|---|---|---|---|
| 1-242 | 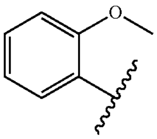 [SMILES: *c1ccccc1OC] | N | CH | CH | CH | 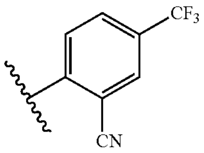 | *cis- 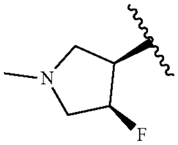 |
| 1-243 | 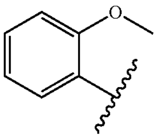 [SMILES: *c1ccccc1OC] | N | CH | CH | CH | 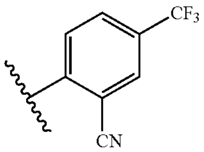 | *trans- 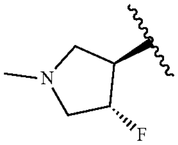 |
| 1-244 | 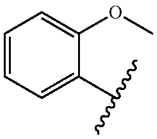 [SMILES: *c1ccccc1OC] | N | CH | CH | CH | 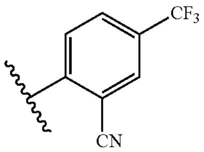 | 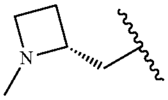 [SMILES: *C[C@H]1CCN1C] |
| 1-245 | 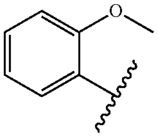 [SMILES: *c1ccccc1OC] | N | CH | CH | CH | 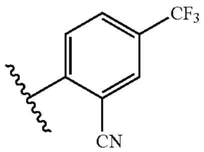 | 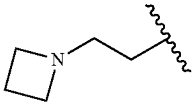 [SMILES: *CCN1CCC1] |
| 1-246 | 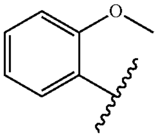 [SMILES: *c1ccccc1OC] | N | CH | CH | CH | 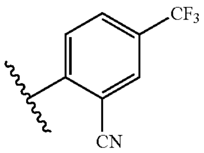 [SMILES: *c1ccc(C(F)(F)F)cc1C#N] | 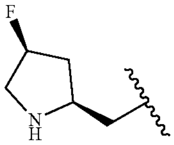 [SMILES: *C[C@@H]1C[C@H](F)CN1] |
| 1-247 | 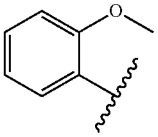 [SMILES: *c1ccccc1OC] | N | CH | CH | CH | 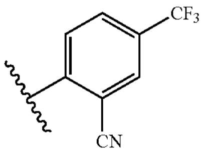 [SMILES: *c1ccc(C(F)(F)F)cc1C#N] | 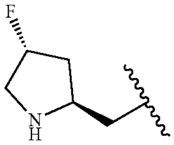 [SMILES: *C[C@@H]1C[C@@H](F)CN1] |
| 1-248 | 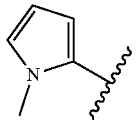 [SMILES: *c1cccn1C] | N | CH | CH | CH | 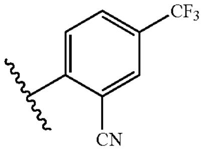 [SMILES: *c1ccc(C(F)(F)F)cc1C#N] | 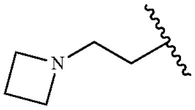 [SMILES: *CCN1CCC1] |

TABLE 1-continued
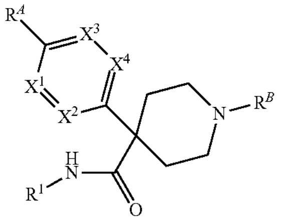
| Cpd No. | $R^A$ | $X^1$ | $X^2$ | $X^3$ | $X^4$ | $R^B$ | $R^1$ |
|---|---|---|---|---|---|---|---|
| 1-249 | 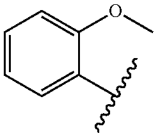 [SMILES: *c1ccccc1OC] | N | CH | CH | CH | 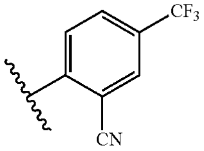 [SMILES: *c1ccc(C(F)(F)F)cc1C#N] | 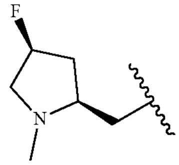 [SMILES: *C[C@@H]1C[C@H](F)CN1C] |
| 1-250 | 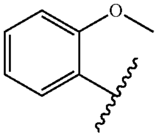 [SMILES: *c1ccccc1OC] | N | CH | CH | CH | 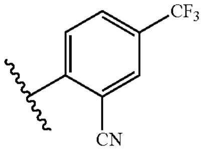 [SMILES: *c1ccc(C(F)(F)F)cc1C#N] | 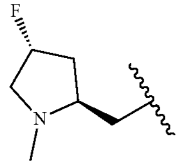 [SMILES: *C[C@@H]1C[C@@H](F)CN1C] |
| 1-251 | 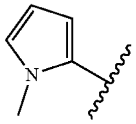 [SMILES: *c1cccn1C] | N | CH | CH | CH | 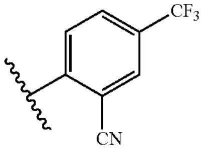 [SMILES: *c1ccc(C(F)(F)F)cc1C#N] | 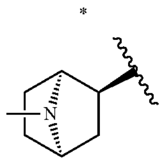 [SMILES: *[C@H]1C[C@H]2CC[C@@H]1N2C] |
| 1-252 | 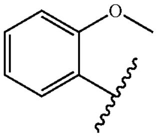 [SMILES: *c1ccccc1OC] | N | CH | CH | CH | 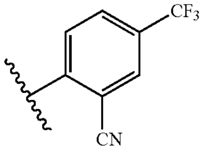 [SMILES: *c1ccc(C(F)(F)F)cc1C#N] | 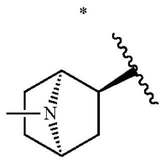 [SMILES: *[C@H]1C[C@H]2CC[C@@H]1N2C] |
| 1-253 | 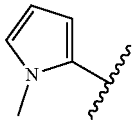 [SMILES: *c1cccn1C] | N | CH | CH | CH | 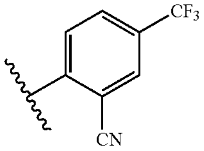 [SMILES: *c1ccc(C(F)(F)F)cc1C#N] | 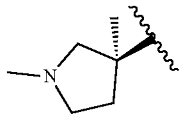 [SMILES: *[C@@]1(C)CCN(C)C1] |
| 1-254 | 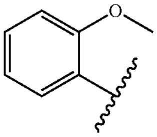 [SMILES: *c1ccccc1OC] | N | CH | CH | CH | 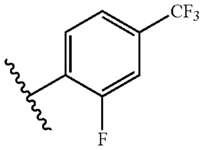 [SMILES: *c1ccc(C(F)(F)F)cc1F] | 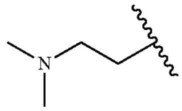 [SMILES: *CCN(C)C] |
| 1-255 | 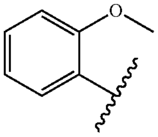 [SMILES: *c1ccccc1OC] | N | CH | CH | CH | 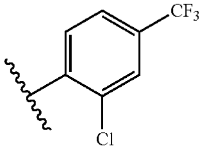 [SMILES: *c1ccc(C(F)(F)F)cc1Cl] | 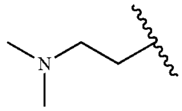 [SMILES: *CCN(C)C] |
| 1-256 | 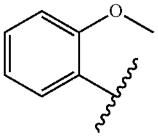 [SMILES: *c1ccccc1OC] | N | CH | CH | CH | 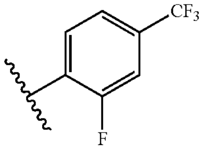 [SMILES: *c1ccc(C(F)(F)F)cc1F] | 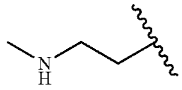 [SMILES: *CCNC] |

TABLE 1-continued
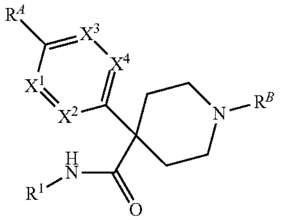
| Cpd No. | $R^A$ | $X^1$ | $X^2$ | $X^3$ | $X^4$ | $R^B$ | $R^1$ |
|---|---|---|---|---|---|---|---|
| 1-257 | 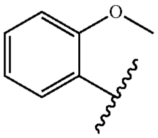 [SMILES: *c1ccccc1OC] | N | CH | CH | CH | 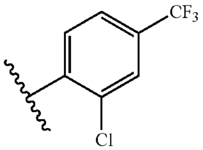 [SMILES: *c1ccc(C(F)(F)F)cc1Cl] | 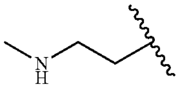 [SMILES: *CCNC] |
| 1-258 | 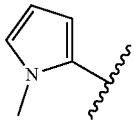 [SMILES: *c1cccn1C] | N | CH | CH | CH | 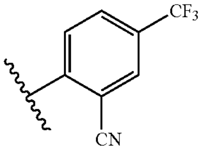 [SMILES: *c1ccc(C(F)(F)F)cc1C#N] | *cis- 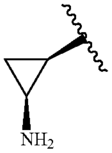 |
| 1-259 | 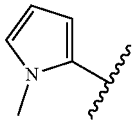 [SMILES: *c1cccn1C] | N | CH | CH | CH | 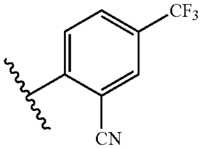 [SMILES: *c1ccc(C(F)(F)F)cc1C#N] | *cis- 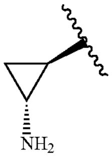 |
| 1-260 | 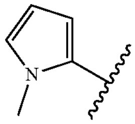 | N | CH | CH | CH | 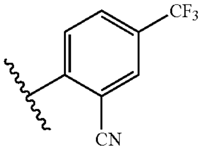 [SMILES: *c1ccc(C(F)(F)F)cc1C#N] | 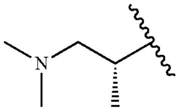 [SMILES: *[C@H](C)CN(C)C] |
| 1-261 | 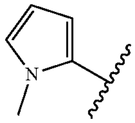 [SMILES: *c1cccn1C] | N | CH | CH | CH | 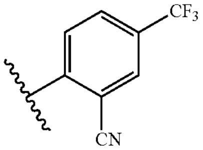 [SMILES: *c1ccc(C(F)(F)F)cc1C#N] | 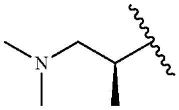 [SMILES: *[C@@H](C)CN(C)C] |
| 1-262 | 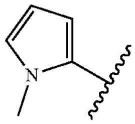 [SMILES: *c1cccn1C] | N | CH | CH | CH | 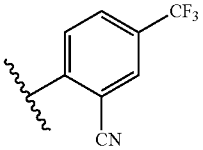 [SMILES: *c1ccc(C(F)(F)F)cc1C#N] | 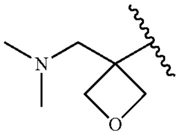 [SMILES: *C1(CN(C)C)COC1] |
| 1-263 | 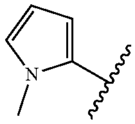 [SMILES: *c1cccn1C] | N | CH | CH | CH | 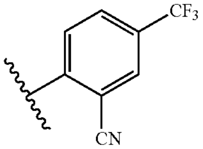 [SMILES: *c1ccc(C(F)(F)F)cc1C#N] | 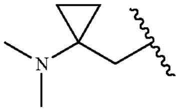 [SMILES: *CC1(N(C)C)CC1] |

TABLE 1-continued
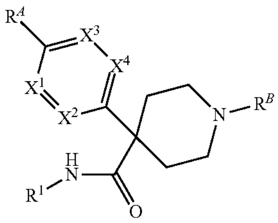
| Cpd No. | $R^A$ | $X^1$ | $X^2$ | $X^3$ | $X^4$ | $R^B$ | $R^1$ |
|---|---|---|---|---|---|---|---|
| 1-264 | 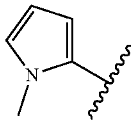 [SMILES: *c1cccn1C] | N | CH | CH | CH | 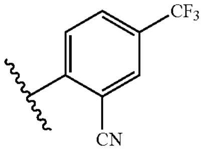 [SMILES: *c1ccc(C(F)(F)F)cc1C#N] | *trans- 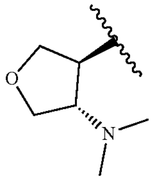 |
| 1-265 | 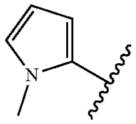 [SMILES: *c1cccn1C] | N | CH | CH | CH | 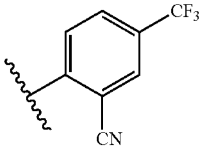 [SMILES: *c1ccc(C(F)(F)F)cc1C#N] | 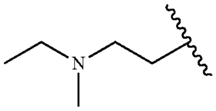 [SMILES: *CCN(C)CC] |
| 1-266 | 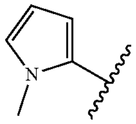 [SMILES: *c1cccn1C] | N | CH | CH | CH | 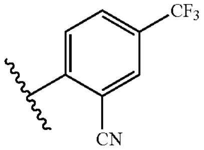 [SMILES: *c1ccc(C(F)(F)F)cc1C#N] | 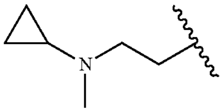 [SMILES: *CCN(C)C1CC1] |
| 1-267 | 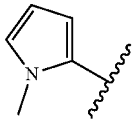 [SMILES: *c1cccn1C] | N | CH | CH | CH | 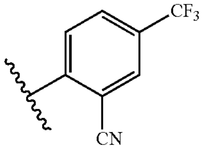 [SMILES: *c1ccc(C(F)(F)F)cc1C#N] | *cis- 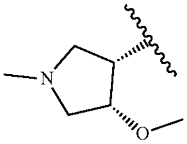 |
| 1-268 | 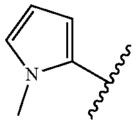 [SMILES: *c1cccn1C] | N | CH | CH | CH | 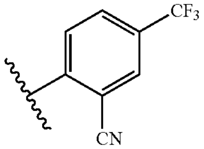 [SMILES: *c1ccc(C(F)(F)F)cc1C#N] | *trans- 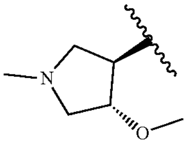 |
| 1-269 | 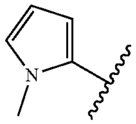 [SMILES: *c1cccn1C] | N | CH | CH | CH | 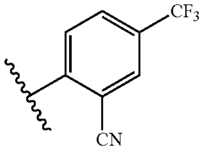 [SMILES: *c1ccc(C(F)(F)F)cc1C#N] | 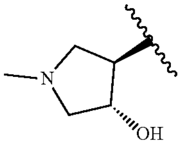 [SMILES: *[C@@H]1CN(C)C[C@H]1O] |
| 1-270 | 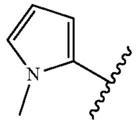 [SMILES: *c1cccn1C] | N | CH | CH | CH | 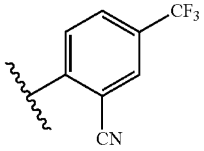 | 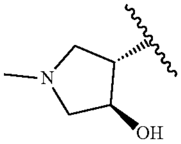 [SMILES: *[C@H]1CN(C)C[C@@H]1O] |

TABLE 1-continued
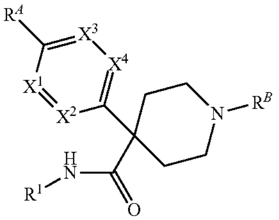
| Cpd No. | $R^A$ | $X^1$ | $X^2$ | $X^3$ | $X^4$ | $R^B$ | $R^1$ |
|---|---|---|---|---|---|---|---|
| 1-271 | 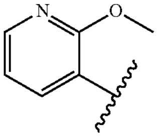 [SMILES: *c1cccnc1OC] | N | CH | CH | CH | 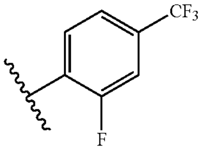 [SMILES: *c1ccc(C(F)(F)F)cc1F] | 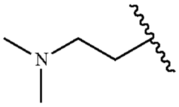 [SMILES: *CCN(C)C] |
| 1-272 | 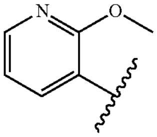 [SMILES: *c1cccnc1OC] | N | CH | CH | CH | 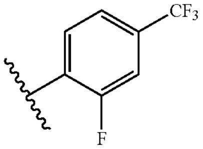 [SMILES: *c1ccc(C(F)(F)F)cc1F] | 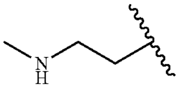 [SMILES: *CCNC] |
| 1-273 | 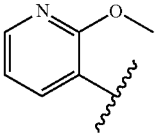 [SMILES: *c1cccnc1OC] | N | CH | CH | CH | 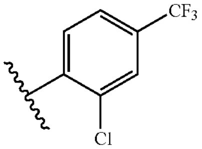 | 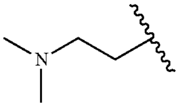 [SMILES: *CCN(C)C] |
| 1-274 | 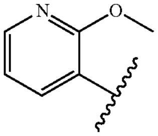 [SMILES: *c1cccnc1OC] | N | CH | CH | CH | 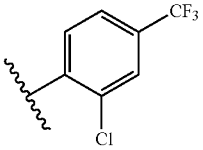 [SMILES: *c1ccc(C(F)(F)F)cc1Cl] | 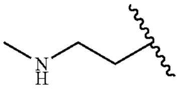 |
| 1-275 | 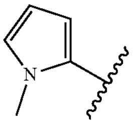 [SMILES: *c1cccn1C] | N | CH | CH | CH | 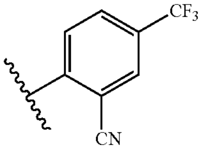 [SMILES: *c1ccc(C(F)(F)F)cc1C#N] | 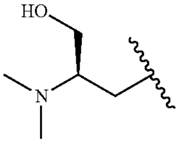 [SMILES: *C[C@H](CO)N(C)C] |
| 1-276 | 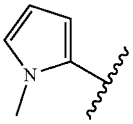 [SMILES: *c1cccn1C] | N | CH | CH | CH | 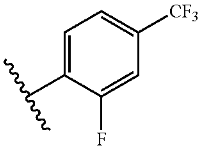 [SMILES: *c1ccc(C(F)(F)F)cc1F] | 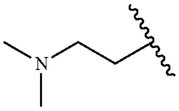 [SMILES: *CCN(C)C] |
| 1-277 | 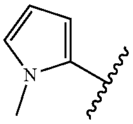 [SMILES: *c1cccn1C] | N | CH | CH | CH | 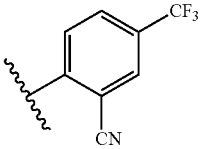 [SMILES: *c1ccc(C(F)(F)F)cc1C#N] | 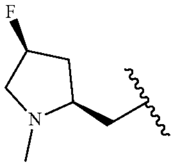 [SMILES: *C[C@@H]1C[C@H](F)CN1C] |
| 1-278 | 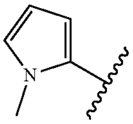 [SMILES: *c1cccn1C] | N | CH | CH | CH | 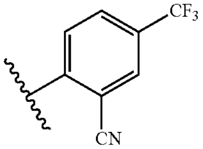 [SMILES: *c1ccc(C(F)(F)F)cc1C#N] | 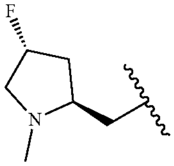 [SMILES: *C[C@@H]1C[C@@H](F)CN1C] |

TABLE 1-continued
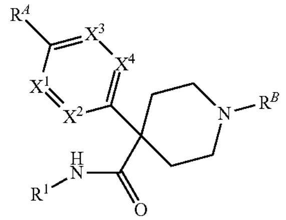
| Cpd No. | $R^A$ | $X^1$ | $X^2$ | $X^3$ | $X^4$ | $R^B$ | $R^1$ |
|---|---|---|---|---|---|---|---|
| 1-279 | 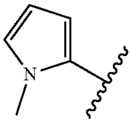 [SMILES: *c1cccn1C] | N | CH | CH | CH | 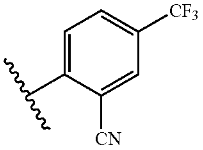 [SMILES: *c1ccc(C(F)(F)F)cc1C#N] | 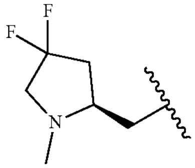 [SMILES: *C[C@@H]1CC(F)(F)CN1C] |
| 1-280 | 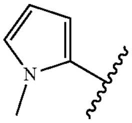 [SMILES: *c1cccn1C] | N | CH | CH | CH | 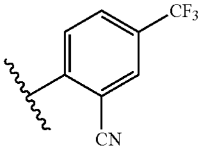 [SMILES: *c1ccc(C(F)(F)F)cc1C#N] | 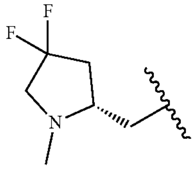 [SMILES: *C[C@H]1CC(F)(F)CN1C] |
| 1-281 | 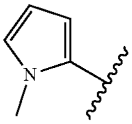 [SMILES: *c1cccn1C] | N | CH | CH | CH | 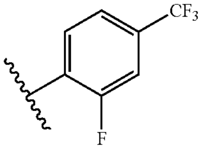 [SMILES: *c1ccc(C(F)(F)F)cc1F] | 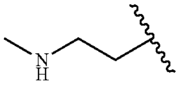 [SMILES: *CCNC] |
| 1-282 | 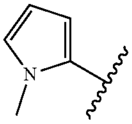 [SMILES: *c1cccn1C] | N | CH | CH | CH | 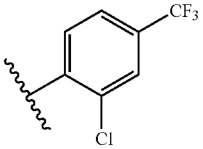 [SMILES: *c1ccc(C(F)(F)F)cc1Cl] | 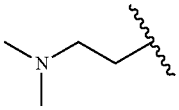 [SMILES: *CCN(C)C] |
| 1-283 | 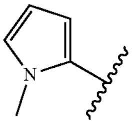 [SMILES: *c1cccn1C] | N | CH | CH | CH | 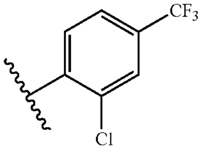 [SMILES: *c1ccc(C(F)(F)F)cc1Cl] | 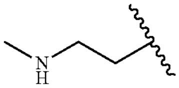 [SMILES: *CCNC] |
| 1-284 | 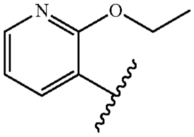 [SMILES: *c1cccnc1OCC] | N | CH | CF | CH | 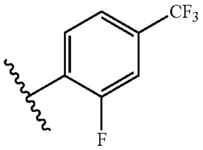 [SMILES: *c1ccc(C(F)(F)F)cc1F] | 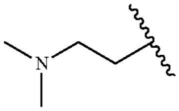 [SMILES: *CCN(C)C] |
| 1-285 | 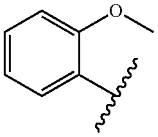 [SMILES: *c1ccccc1OC] | N | CH | CF | CH | 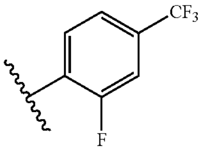 [SMILES: *c1ccc(C(F)(F)F)cc1F] | 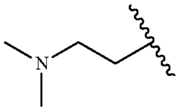 [SMILES: *CCN(C)C] |
| 1-286 | 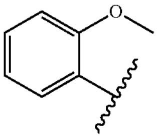 [SMILES: *c1ccccc1OC] | N | CH | CF | CH | 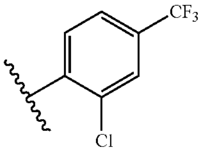 [SMILES: *c1ccc(C(F)(F)F)cc1Cl] | 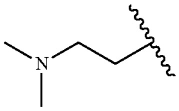 [SMILES: *CCN(C)C] |

TABLE 1-continued
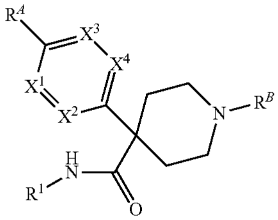
| Cpd No. | $R^A$ | $X^1$ | $X^2$ | $X^3$ | $X^4$ | $R^B$ | $R^1$ |
|---|---|---|---|---|---|---|---|
| 1-287 | 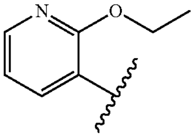 [SMILES: *c1cccnc1OCC] | N | CH | CF | CH | 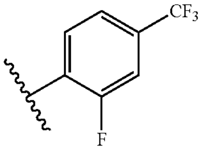 [SMILES: *c1ccc(C(F)(F)F)cc1F] | 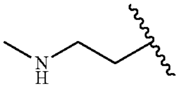 [SMILES: *CCNC] |
| 1-288 | 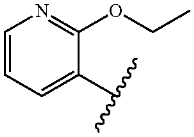 [SMILES: *c1cccnc1OCC] | N | CH | CF | CH | 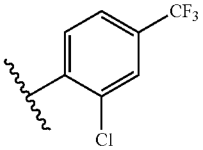 [SMILES: *c1ccc(C(F)(F)F)cc1Cl] | 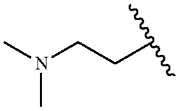 [SMILES: *CCN(C)C] |
| 1-289 | 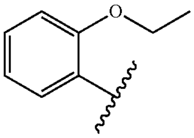 [SMILES: *c1ccccc1OCC] | N | CH | CF | CH | 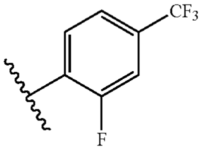 [SMILES: *c1ccc(C(F)(F)F)cc1F] | 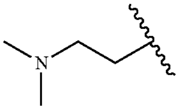 [SMILES: *CCN(C)C] |
| 1-290 | 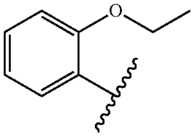 [SMILES: *c1ccccc1OCC] | N | CH | CF | CH | 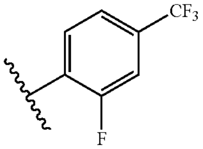 [SMILES: *c1ccc(C(F)(F)F)cc1F] | 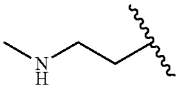 [SMILES: *CCNC] |
| 1-291 | 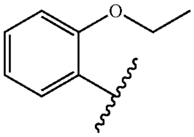 [SMILES: *c1ccccc1OCC] | N | CH | CF | CH | 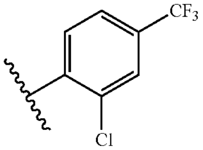 [SMILES: *c1ccc(C(F)(F)F)cc1Cl] | 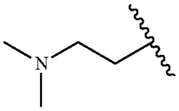 [SMILES: *CCN(C)C] |
| 1-292 | 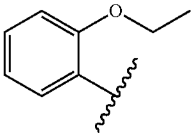 [SMILES: *c1ccccc1OCC] | N | CH | CF | CH | 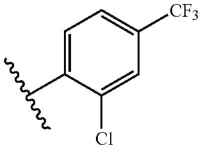 [SMILES: *c1ccc(C(F)(F)F)cc1Cl] | 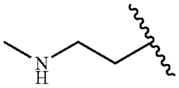 [SMILES: *CCNC] |
| 1-293 | 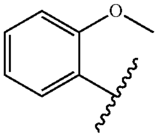 [SMILES: *c1ccccc1OC] | N | CH | CF | CH | 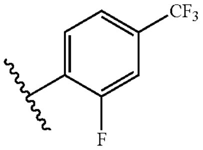 [SMILES: *c1ccc(C(F)(F)F)cc1F] | 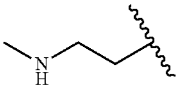 [SMILES: *CCNC] |
| 1-294 | 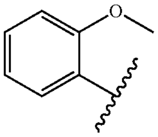 [SMILES: *c1ccccc1OC] | N | CH | CF | CH | 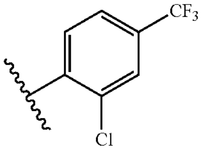 [SMILES: *c1ccc(C(F)(F)F)cc1Cl] | 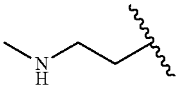 |

TABLE 1-continued
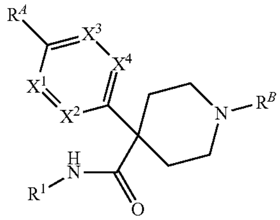
| Cpd No. | $R^A$ | $X^1$ | $X^2$ | $X^3$ | $X^4$ | $R^B$ | $R^1$ |
|---|---|---|---|---|---|---|---|
| 1-295 | 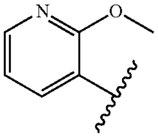 [SMILES: *c1cccnc1OC] | N | CH | CH | CH | 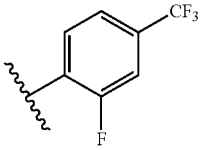 [SMILES: *c1ccc(C(F)(F)F)cc1F] | 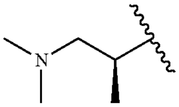 [SMILES: *[C@@H](C)CN(C)C] |
| 1-296 | 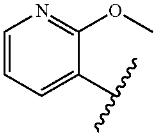 [SMILES: *c1cccnc1OC] | N | CH | CH | CH | 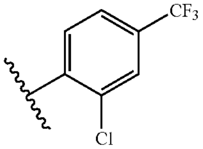 [SMILES: *c1ccc(C(F)(F)F)cc1Cl] | 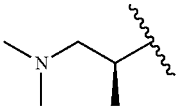 [SMILES: *[C@@H](C)CN(C)C] |
| 1-297 | 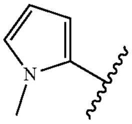 [SMILES: *c1cccn1C] | N | CH | CH | CH | 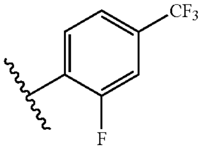 [SMILES: *c1ccc(C(F)(F)F)cc1F] | 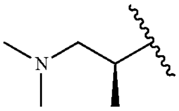 [SMILES: *[C@@H](C)CN(C)C] |
| 1-298 | 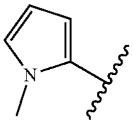 [SMILES: *c1cccn1C] | N | CH | CH | CH | 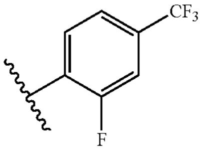 [SMILES: *c1ccc(C(F)(F)F)cc1F] | 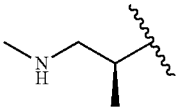 [SMILES: *[C@@H](C)CNC] |
| 1-299 | 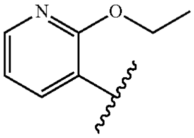 [SMILES: *c1cccnc1OCC] | N | CH | CF | CH | 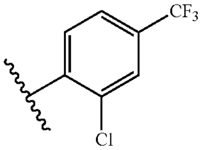 [SMILES: *c1ccc(C(F)(F)F)cc1Cl] | 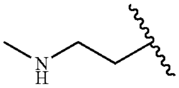 [SMILES: *CCNC] |
| 1-300 | 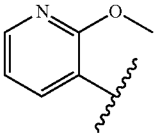 | N | CH | CF | CH | 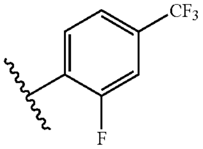 [SMILES: *c1ccc(C(F)(F)F)cc1F] | 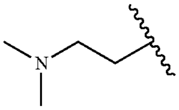 [SMILES: *CCN(C)C] |
| 1-301 | 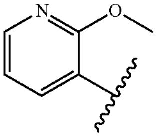 | N | CH | CF | CH | 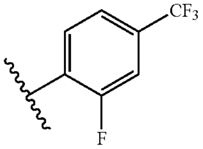 [SMILES: *c1ccc(C(F)(F)F)cc1F] | 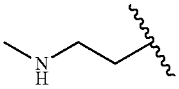 [SMILES: *CCNC] |
| 1-302 | 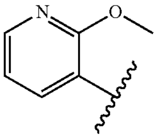 [SMILES: *c1cccnc1OC] | N | CH | CF | CH | 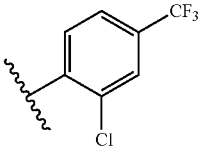 [SMILES: *c1ccc(C(F)(F)F)cc1Cl] | 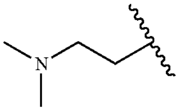 [SMILES: *CCN(C)C] |

TABLE 1-continued
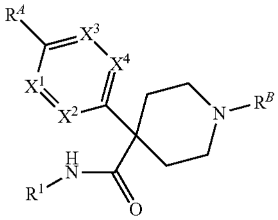
| Cpd No. | $R^A$ | $X^1$ | $X^2$ | $X^3$ | $X^4$ | $R^B$ | $R^1$ |
|---|---|---|---|---|---|---|---|
| 1-303 | 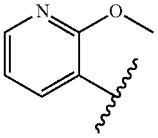 [SMILES: *c1cccnc1OC] | N | CH | CF | CH | 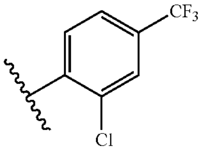 [SMILES: *c1ccc(C(F)(F)F)cc1Cl] | 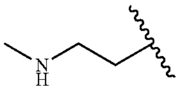 |
| 1-304 | 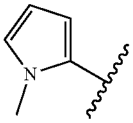 [SMILES: *c1cccn1C] | N | CH | CF | CH | 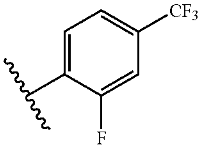 [SMILES: *c1ccc(C(F)(F)F)cc1F] | 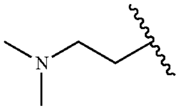 [SMILES: *CCN(C)C] |
| 1-305 | 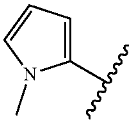 [SMILES: *c1cccn1C] | N | CH | CF | CH | 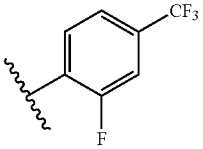 [SMILES: *c1ccc(C(F)(F)F)cc1F] | 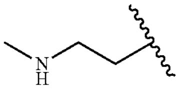 [SMILES: *CCNC] |
| 1-306 | 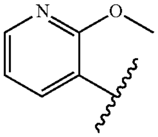 [SMILES: *c1cccnc1OC] | N | CH | CH | CH | 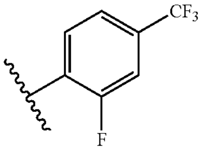 [SMILES: *c1ccc(C(F)(F)F)cc1F] | 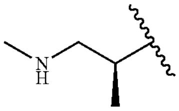 |
| 1-307 | 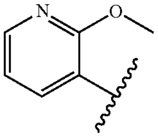 | N | CH | CH | CH | 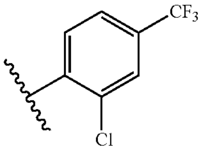 [SMILES: *c1ccc(C(F)(F)F)cc1Cl] | 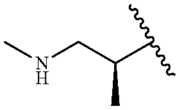 |
| 1-308 | 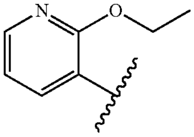 [SMILES: *c1cccnc1OCC] | N | CH | CF | CH | 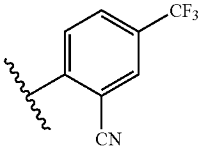 [SMILES: *c1ccc(C(F)(F)F)cc1C#N] | 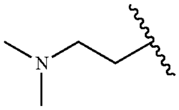 [SMILES: *CCN(C)C] |
| 1-309 | 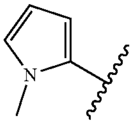 [SMILES: *c1cccn1C] | N | CH | CF | CH | 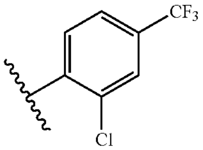 [SMILES: *c1ccc(C(F)(F)F)cc1Cl] | 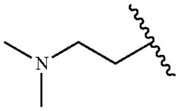 [SMILES: *CCN(C)C] |
| 1-310 | 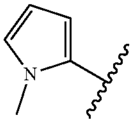 [SMILES: *c1cccn1C] | N | CH | CF | CH | 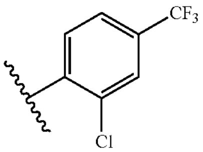 [SMILES: *c1ccc(C(F)(F)F)cc1Cl] | 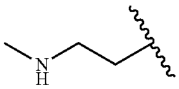 [SMILES: *CCNC] |

TABLE 1-continued
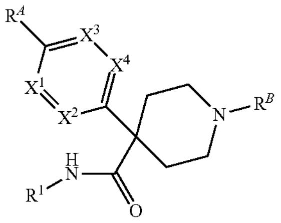
| Cpd No. | $R^A$ | $X^1$ | $X^2$ | $X^3$ | $X^4$ | $R^B$ | $R^1$ |
|---|---|---|---|---|---|---|---|
| 1-311 | 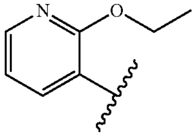 [SMILES: *c1cccnc1OCC] | N | CH | CF | CH | 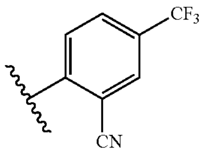 | 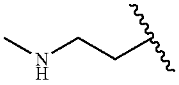 [SMILES: *CCNC] |
| 1-312 | 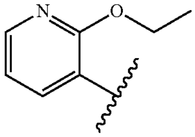 [SMILES: *c1cccnc1OCC] | N | CH | CF | CH | 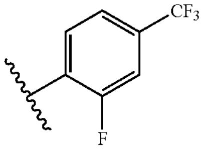 | 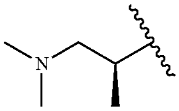 [SMILES: *[C@@H](C)CN(C)C] |
| 1-313 | 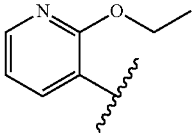 [SMILES: *c1cccnc1OCC] | N | CH | CH | CH | 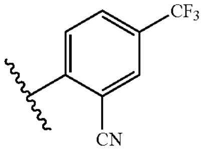 | 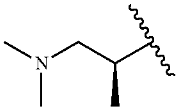 [SMILES: *[C@@H](C)CN(C)C] |
| 1-314 | 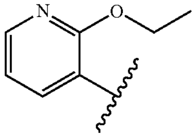 [SMILES: *c1cccnc1OCC] | N | CH | CH | CH | 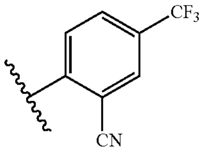 | 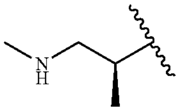 [SMILES: *[C@@H](C)CNC] |
| 1-315 | 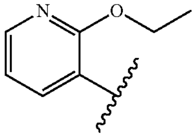 [SMILES: *c1cccnc1OCC] | N | CH | CF | CH | 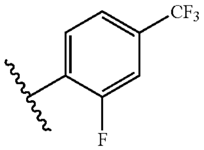 | 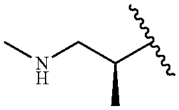 [SMILES: *[C@@H](C)CNC] |
| 1-316 | 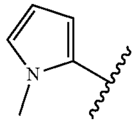 [SMILES: *c1cccn1C] | N | CH | CH | CH | 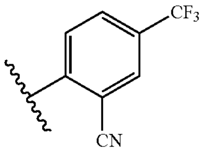 | 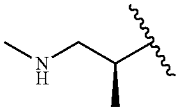 [SMILES: *[C@@H](C)CNC] |
| 1-317 | 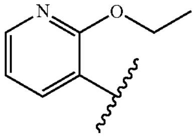 [SMILES: *c1cccnc1OCC] | N | CH | CH | CH | 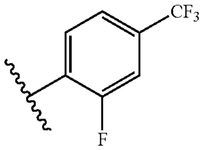 | 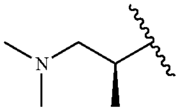 [SMILES: *[C@@H](C)CN(C)C] |
| 1-318 | 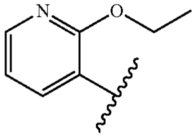 [SMILES: *c1cccnc1OCC] | N | CH | CH | CH | 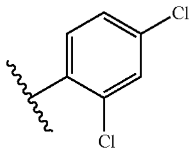 [SMILES: *c1ccc(Cl)cc1Cl] | 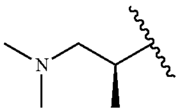 [SMILES: *[C@@H](C)CN(C)C] |

TABLE 1-continued
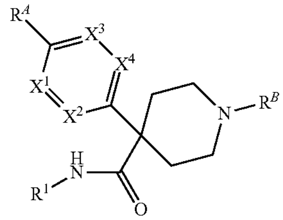
| Cpd No. | $R^A$ | $X^1$ | $X^2$ | $X^3$ | $X^4$ | $R^B$ | $R^1$ |
|---|---|---|---|---|---|---|---|
| 1-319 | 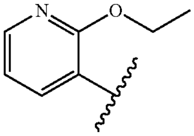 [SMILES: *c1cccnc1OCC] | N | CH | CF | CH | 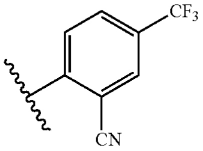 | 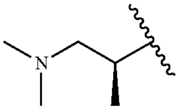 [SMILES: *[C@@H](C)CN(C)C] |
| 1-320 | 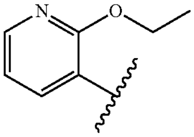 [SMILES: *c1cccnc1OCC] | N | CH | CF | CH | 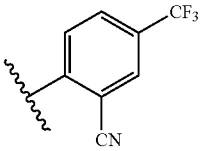 | 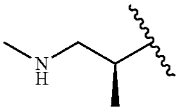 [SMILES: *[C@@H](C)CNC] |
| 1-321 | 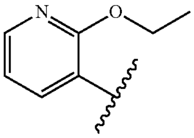 [SMILES: *c1cccnc1OCC] | N | CH | CH | CH | 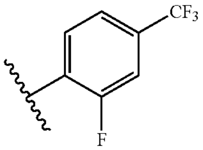 | 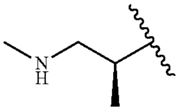 [SMILES: *[C@@H](C)CNC] |
| 1-322 | 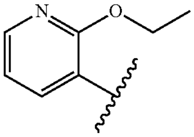 [SMILES: *c1cccnc1OCC] | N | CH | CH | CH | 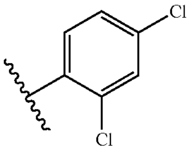 [SMILES: *c1ccc(Cl)cc1Cl] | 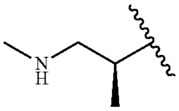 [SMILES: *[C@@H](C)CNC] |
| 1-323 | 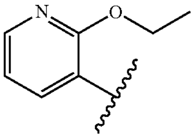 [SMILES: *c1cccnc1OCC] | N | CH | CF | CH | 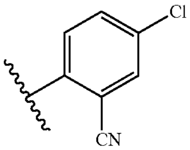 [SMILES: *c1ccc(Cl)cc1C#N] | 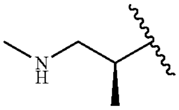 [SMILES: *[C@@H](C)CNC] |
| 1-324 | 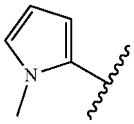 [SMILES: *c1cccn1C] | N | CH | CF | CH | 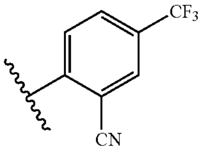 | 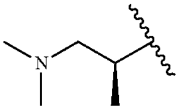 [SMILES: *[C@@H](C)CN(C)C] |
| 1-325 | 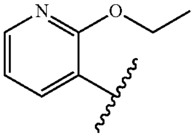 [SMILES: *c1cccnc1OCC] | N | CH | CF | CH | 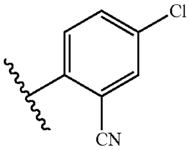 [SMILES: *c1ccc(Cl)cc1C#N] | 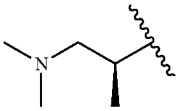 [SMILES: *[C@@H](C)CN(C)C] |
| 1-326 | 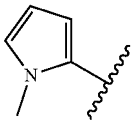 [SMILES: *c1cccn1C] | N | CH | CF | CH | 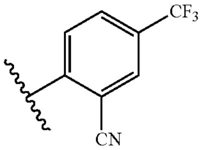 | 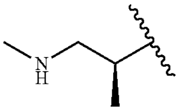 [SMILES: *[C@@H](C)CNC] |

TABLE 1-continued
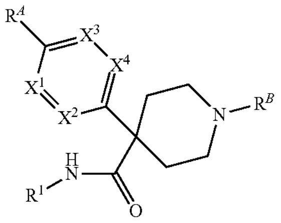
| Cpd No. | $R^A$ | $X^1$ | $X^2$ | $X^3$ | $X^4$ | $R^B$ | $R^1$ |
|---|---|---|---|---|---|---|---|
| 1-327 | 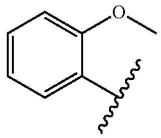 [SMILES: *c1ccccc1OC] | N | CH | CH | CH | 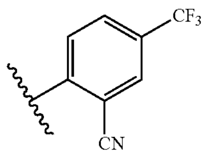 | 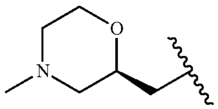 [SMILES: *C[C@H]1CN(C)CCO1] |
| 1-328 | 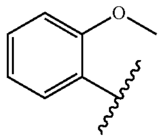 [SMILES: *c1ccccc1OC] | N | CH | CH | CH | 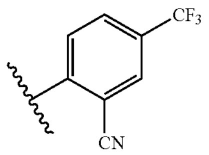 | 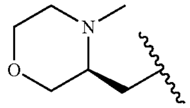 [SMILES: *C[C@H]1COCCN1C] |
| 1-329 | 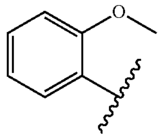 [SMILES: *c1ccccc1OC] | N | CH | CH | CH | 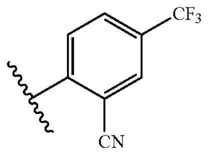 | 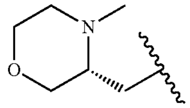 [SMILES: *C[C@@H]1COCCN1C] |
| 1-330 | 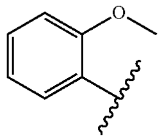 [SMILES: *c1ccccc1OC] | N | CH | CH | CH | 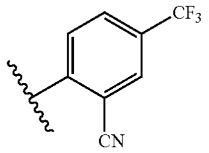 | 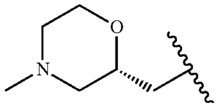 [SMILES: *C[C@@H]1CN(C)CCO1] |
| 1-331 | 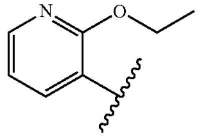 [SMILES: *c1cccnc1OCC] | N | N | CH | CH | 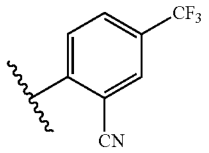 | 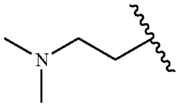 [SMILES: *CCN(C)C] |
| 1-332 | 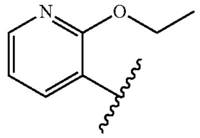 [SMILES: *c1cccnc1OCC] | N | CH | CH | CH | 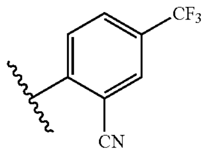 | 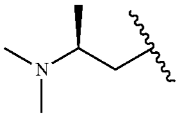 [SMILES: *C[C@H](C)N(C)C] |
| 1-333 | 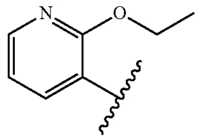 [SMILES: *c1cccnc1OCC] | N | CH | CH | CH | 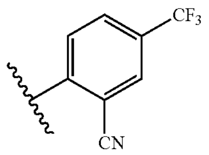 | 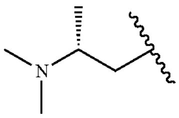 [SMILES: *C[C@@H](C)N(C)C] |
| 1-334 | 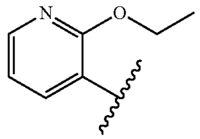 [SMILES: *c1cccnc1OCC] | N | CH | CF | CH | 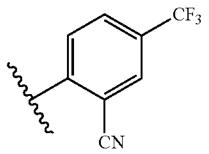 | 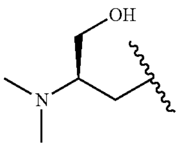 [SMILES: *C[C@H](CO)N(C)C] |

TABLE 1-continued

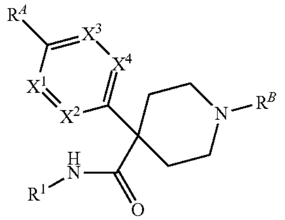

| Cpd No. | $R^A$ | $X^1$ | $X^2$ | $X^3$ | $X^4$ | $R^B$ | $R^1$ |
|---|---|---|---|---|---|---|---|
| 1-335 | 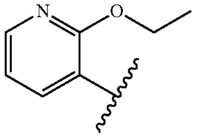 [SMILES: *c1cccnc1OCC] | N | N | CH | CH | 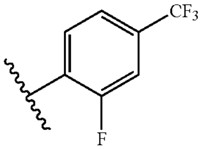 | 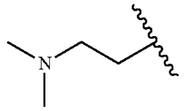 [SMILES: *CCN(C)C] |

*absolute stereochemistry has not been determined.
**cis- & trans- were assigned tentatively.

Compounds in Table 1 are named:

1-1: 1-[2-cyano-4-(trifluoromethyl)phenyl]-4-[4-(2-ethoxypyridin-3-yl)phenyl]-N-[(3R)-1-methylpyrrolidin-3-yl]piperidine-4-carboxamide;

1-2: 1-[2-cyano-4-(trifluoromethyl)phenyl]-4-[4-(2-ethoxypyridin-3-yl)phenyl]-N-[(3R)-pyrrolidin-3-yl]piperidine-4-carboxamide;

1-3: N-(2-aminoethyl)-1-[2-cyano-4-trifluoromethyl)phenyl]-4-[4-(2-ethoxypyridin-3-yl)phenyl]piperidine-4-carboxamide;

1-4: N-[(2R)-2-aminopropyl]-1-[2-cyano-4-(trifluoromethyl)phenyl]-4-[4-(2-ethoxypyridin-3-yl)phenyl]piperidine-4-carboxamide;

1-5: N-(3-aminopropyl)-1-[2-cyano-4-(trifluoromethyl)phenyl]-4-[4-(2-ethoxypyridin-3-yl)phenyl]piperidine-4-carboxamide;

1-6: N-[(2S)-2-aminopropyl]-1-[2-cyano-4-(trifluoromethyl)phenyl]-4-[4-(2-ethoxypyridin-3-yl)phenyl]piperidine-4-carboxamide;

1-7: 1-[2-cyano-4-(trifluoromethyl)phenyl]-4-[4-(2-ethoxypyridin-3-yl)phenyl]-N-[2-(methylamino)ethyl]piperidine-4-carboxamide;

1-8: 1-[2-cyano-4-(trifluoromethyl)phenyl]-N-[2-(dimethylamino)ethyl]-4-[4-(2-ethoxypyridin-3-yl)phenyl]piperidine-4-carboxamide;

1-9: 1-[2-cyano-4-(trifluoromethyl)phenyl]-4-{2'-ethoxy-[2,3'-bipyridin]-5-yl}-N-[(3R)-1-methylpyrrolidin-3-yl]piperidine-4-carboxamide;

1-10: 1-[2-cyano-4-(trifluoromethyl)phenyl]-4-{2'-ethoxy-[2,3'-bipyridin]-5-yl}-N-[(3R)-pyrrolidin-3-yl]piperidine-4-carboxamide;

1-11: 1-[2-cyano-4-(trifluoromethyl)phenyl]-4-{2'-ethoxy-[2,3'-bipyridin]-5-yl}-N-[(3S)-1-methylpyrrolidin-3-yl]piperidine-4-carboxamide;

1-12: 1-[2-cyano-4-(trifluoromethyl)phenyl]-4-{2'-ethoxy-[2,3'-bipyridin]-5-yl}-N-[(3S)-pyrrolidin-3-yl]piperidine-4-carboxamide;

1-13: N-(2-aminoethyl)-1-[2-cyano-4-(trifluoromethyl)phenyl]-4-{2'-ethoxy-[2,3'-bipyridin]-5-yl}piperidine-4-carboxamide;

1-14: 1-[2-cyano-4-(trifluoromethyl)phenyl]-4-{2'-ethoxy-[2,3'-bipyridin]-5-yl}-N-[2-(methylamino)ethyl]piperidine-4-carboxamide;

1-15: 1-[2-cyano-4-(trifluoromethyl)phenyl]-N-[2-(dimethylamino)ethyl]-4-{2'-ethoxy-[2,3'-bipyridin]-5-yl}piperidine-4-carboxamide;

1-16: N-[(2S)-2-aminopropyl]-1-[2-cyano-4-(trifluoromethyl)phenyl]-4-{2'-ethoxy-[2,3'-bipyridin]-5-yl}piperidine-4-carboxamide;

1-17: N-[(2R)-2-amino-3-hydroxypropyl]-1-[2-cyano-4-(trifluoromethyl)phenyl]-4-{2'-ethoxy-[2,3'-bipyridin]-5-yl}piperidine-4-carboxamide;

1-18: 1-[2-cyano-4-(trifluoromethyl)phenyl]-4-{2'-ethoxy-[2,3'-bipyridin]-5-yl}-N-[(1-methylazetidin-3-yl)methyl]piperidine-4-carboxamide;

1-19: 1-[2-cyano-4-(trifluoromethyl)phenyl]-4-{2'-ethoxy-[2,3'-bipyridin]-5-yl}-N-(1-methylazetidin-3-yl)piperidine-4-carboxamide;

1-20: N-[(3S)-1-azabicyclo[2.2.2]octan-3-yl]-1-[2-cyano-4-(trifluoromethyl)phenyl]-4-{2'-ethoxy-[2,3'-bipyridin]-5-yl}piperidine-4-carboxamide;

1-21: 1-[2-cyano-4-(trifluoromethyl)phenyl]-4-{2'-ethoxy-[3,3'-bipyridin]-6-yl}-N-[(3R)-pyrrolidin-3-yl]piperidine-4-carboxamide;

1-22: 1-[2-cyano-4-(trifluoromethyl)phenyl]-4-{2'-ethoxy-[3,3'-bipyridin]-6-yl}-N-[(3R)-1-methylpyrrolidin-3-yl]piperidine-4-carboxamide;

1-23: 1-[2-cyano-6-(trifluoromethyl)pyridin-3-yl]-4-[4-(2-ethoxypyridin-3-yl)phenyl]-N-[(3R)-1-methylpyrrolidin-3-yl]piperidine-4-carboxamide;

1-24: 1-[2-cyano-6-(trifluoromethyl)pyridin-3-yl]-4-{2'-ethoxy-[2,3'-bipyridin]-5-yl}-N-[(3R)-1-methylpyrrolidin-3-yl]piperidine-4-carboxamide;

1-25: 3-(4-{2'-ethoxy-[2,3'-bipyridin]-5-yl}-4-{[(3R)-1-methylpyrrolidin-3-yl]carbamoyl}piperidin-1-yl)-6-(trifluoromethyl)pyridine-2-carboxamide;

1-26: 1-[2-cyano-6-(trifluoromethyl)pyridin-3-yl]-4-{2'-ethoxy-[2,3'-bipyridin]-5-yl}-N-[(3S)-1-methylpyrrolidin-3-yl]piperidine-4-carboxamide;

1-27: 3-(4-{2'-ethoxy-[2,3'-bipyridin]-5-yl}-4-{[(3S)-1-methylpyrrolidin-3-yl]carbamoyl}piperidin-1-yl)-6-(trifluoromethyl)pyridine-2-carboxamide;

1-28: N-[(2S)-2-amino-3-hydroxypropyl]-1-[2-cyano-4-(trifluoromethyl)phenyl]-4-{2'-ethoxy-[2,3'-bipyridin]-5-yl}piperidine-4-carboxamide;

1-29: 1-[2-chloro-6-cyano-4-(trifluoromethyl)phenyl]-4-[4-(2-ethoxypyridin-3-yl)phenyl]-N-[(3R)-1-methylpyrrolidin-3-yl]piperidine-4-carboxamide;

1-30: 1-[2-cyano-4-(trifluoromethyl)phenyl]-4-[6-(2-ethoxyphenyl)pyridin-3-yl]-N-[(3S)-1-methylpyrrolidin-3-yl]piperidine-4-carboxamide;

1-31: 1-[2-cyano-4-(trifluoromethyl)phenyl]-4-[6-(2-ethoxyphenyl)pyridin-3-yl]-N-[(3R)-1-methylpyrrolidin-3-yl]piperidine-4-carboxamide;

1-32: 1-(2-cyanophenyl)-4-{2'-ethoxy-[2,3'-bipyridin]-5-yl}-N-[(3S)-1-methylpyrrolidin-3-yl]piperidine-4-carboxamide;

1-33: 4-{2'-ethoxy-[2,3'-bipyridin]-5-yl}-N-[(3S)-1-methylpyrrolidin-3-yl]-1-[4-(trifluoromethyl)phenyl]piperidine-4-carboxamide;

1-34: 1-(4-chloro-2-cyanophenyl)-4-{2'-ethoxy-[2,3'-bipyridin]-5-yl}-N-[(3S)-1-methylpyrrolidin-3-yl]piperidine-4-carboxamide;

1-35: 4-{2'-ethoxy-[2,3'-bipyridin]-5-yl}-N-[(3S)-1-methylpyrrolidin-3-yl]-1-[5-(trifluoromethyl)pyridin-2-yl]piperidine-4-carboxamide;

1-36: 1-(4-acetyl-2-cyanophenyl)-4-{2'-ethoxy-[2,3'-bipyridin]-5-yl}-N-[(3S)-1-methylpyrrolidin-3-yl]piperidine-4-carboxamide;

1-37: 1-[2-cyano-4-(difluoromethyl)phenyl]-4-{2'-ethoxy-[2,3'-bipyridin]-5-yl}-N-[(3S)-1-methylpyrrolidin-3-yl]piperidine-4-carboxamide;

1-38: 1-[4-cyano-2-(trifluoromethyl)phenyl]-4-{2'-ethoxy-[2,3'-bipyridin]-5-yl}-N-[(3S)-1-methylpyrrolidin-3-yl]piperidine-4-carboxamide;

1-39: 1-[2-cyano-4-(trifluoromethoxy)phenyl]-4-{2'-ethoxy-[2,3'-bipyridin]-5-yl}-N-[(3S)-1-methylpyrrolidin-3-yl]piperidine-4-carboxamide;

1-40: 1-(2,4-dicyanophenyl)-4-{2'-ethoxy-[2,3'-bipyridin]-5-yl}-N-[(3S)-1-methylpyrrolidin-3-yl]piperidine-4-carboxamide;

1-41: 1-[2-cyano-4-(trifluoromethyl)phenyl]-4-{2'-ethoxy-[2,3'-bipyridin]-5-yl}-N-[(3S,4S)*-4-hydroxy-1-methylpyrrolidin-3-yl]piperidine-4-carboxamide;

1-42: 1-[3-cyano-5-(trifluoromethyl)pyridin-2-yl]-4-{2'-ethoxy-[2,3'-bipyridin]-5-yl}-N-[(3S)-1-methylpyrrolidin-3-yl]piperidine-4-carboxamide;

1-43: 1-[2-cyano-4-(trifluoromethyl)phenyl]-4-[6-(1-methyl-1H-pyrazol-5-yl)pyridin-3-yl]-N-[(3R)-1-methylpyrrolidin-3-yl]piperidine-4-carboxamide;

1-44: 1-[2-cyano-4-(trifluoromethyl)phenyl]-4-{2'-ethoxy-[2,3'-bipyridin]-5-yl}-N-[(2R)-3-hydroxy-2-(methylamino)propyl]piperidine-4-carboxamide;

1-45: 1-[2-cyano-4-(trifluoromethyl)phenyl]-N-[(2R)-2-(dimethylamino)-3-hydroxypropyl]-4-{2'-ethoxy-[2,3'-bipyridin]-5-yl}piperidine-4-carboxamide;

1-46: 1-[2-cyano-4-(trifluoromethyl)phenyl]-4-{2'-ethoxy-[2,3'-bipyridin]-5-yl}-N-[(3R,4R)*-4-hydroxy-1-methylpyrrolidin-3-yl]piperidine-4-carboxamide;

1-47: 1-[2-cyano-4-(trifluoromethyl)phenyl]-4-{2'-ethoxy-[2,3'-bipyridin]-5-yl}-N-[(2S)-3-hydroxy-2-(methylamino)propyl]piperidine-4-carboxamide;

1-48: 1-[2-cyano-4-(trifluoromethyl)phenyl]-N-[(2S)-2-(dimethylamino)-3-hydroxypropyl]-4-{2'-ethoxy-[2,3'-bipyridin]-5-yl}piperidine-4-carboxamide;

1-51: 1-[2-cyano-4-(trifluoromethyl)phenyl]-4-[5-(2-ethoxypyridin-3-yl)pyrazin-2-yl]-N-[(3R)-1-methylpyrrolidin-3-yl]piperidine-4-carboxamide;

1-52: 1-[2-cyano-4-(trifluoromethyl)phenyl]-4-[6-(2-methoxyphenyl)pyridin-3-yl]-N-[(3R)-1-methylpyrrolidin-3-yl]piperidine-4-carboxamide;

1-53: 1-[2-cyano-4-(trifluoromethyl)phenyl]-4-[6-(2,3-dihydro-1-benzofuran-7-yl)pyridin-3-yl]-N-[(3R)-1-methylpyrrolidin-3-yl]piperidine-4-carboxamide;

1-54: 4-[6-(1-benzofuran-7-yl)pyridin-3-yl]-1-[2-cyano-4-(trifluoromethyl)phenyl]-N-[(3R)-1-methylpyrrolidin-3-yl]piperidine-4-carboxamide;

1-55: 1-[2-cyano-4-(trifluoromethyl)phenyl]-4-{6-[2-(hydroxymethyl)phenyl]pyridin-3-yl}-N-[(3R)-1-methylpyrrolidin-3-yl]piperidine-4-carboxamide;

1-56: 1-[2-cyano-4-(trifluoromethyl)phenyl]-4-[6-(2-ethoxypyridin-3-yl)pyridazin-3-yl]-N-[(3S)-1-methylpyrrolidin-3-yl]piperidine-4-carboxamide;

1-57: 1-[2-cyano-4-(trifluoromethyl)phenyl]-4-[6-(2-ethoxypyridin-3-yl)pyridazin-3-yl]-N-[(3R)-1-methylpyrrolidin-3-yl]piperidine-4-carboxamide;

1-58: 1-[2-cyano-4-(trifluoromethyl)phenyl]-4-[5-(2-ethoxypyridin-3-yl)pyrazin-2-yl]-N-[(3S)-1-methylpyrrolidin-3-yl]piperidine-4-carboxamide;

1-59: 1-[2-cyano-4-(1,1-difluoroethyl)phenyl]-4-{2'-ethoxy-[2,3'-bipyridin]-5-yl}-N-[(3S)-1-methylpyrrolidin-3-yl]piperidine-4-carboxamide;

1-60: 1-[2-cyano-4-(trifluoromethyl)phenyl]-4-[6-(2-ethylphenyl)pyridin-3-yl]-N-[(3R)-1-methylpyrrolidin-3-yl]piperidine-4-carboxamide;

1-61: 1-[2-cyano-4-(trifluoromethyl)phenyl]-4-[6-(2,3-difluorophenyl)pyridin-3-yl]-N-[(3R)-1-methylpyrrolidin-3-yl]piperidine-4-carboxamide;

1-62: 1-[2-cyano-4-(trifluoromethyl)phenyl]-4-[6-(1-ethyl-1H-pyrazol-5-yl)pyridin-3-yl]-N-[(3R)-1-methylpyrrolidin-3-yl]piperidine-4-carboxamide;

1-63: 1-[2-cyano-4-(trifluoromethyl)phenyl]-N-[(3R)-1-methylpyrrolidin-3-yl]-4-[6-(2-propoxyphenyl)pyridin-3-yl]piperidine-4-carboxamide;

1-64: 1-[2-cyano-4-(trifluoromethyl)phenyl]-4-[6-(3-fluorophenyl)pyridin-3-yl]-N-[(3R)-1-methylpyrrolidin-3-yl]piperidine-4-carboxamide;

1-65: 1-[2-cyano-4-(trifluoromethyl)phenyl]-4-[6-(3,5-difluorophenyl)pyridin-3-yl]-N-[(3R)-1-methylpyrrolidin-3-yl]piperidine-4-carboxamide;

1-66: 1-[2-cyano-4-(trifluoromethyl)phenyl]-4-[6-(2-methylphenyl)pyridin-3-yl]-N-[(3R)-1-methylpyrrolidin-3-yl]piperidine-4-carboxamide;

1-67: 1-[2-cyano-4-(trifluoromethyl)phenyl]-4-[6-(2,2-difluoro-2H-1,3-benzodioxol-4-yl)pyridin-3-yl]-N-[(3R)-1-methylpyrrolidin-3-yl]piperidine-4-carboxamide;

1-68: 1-[2-cyano-4-(trifluoromethyl)phenyl]-4-[6-(2,5-difluorophenyl)pyridin-3-yl]-N-[(3R)-1-methylpyrrolidin-3-yl]piperidine-4-carboxamide;

1-69: 1-[2-cyano-4-(trifluoromethyl)phenyl]-4-[6-(2-ethoxy-5-fluorophenyl)pyridin-3-yl]-N-[(3R)-1-methylpyrrolidin-3-yl]piperidine-4-carboxamide;

1-70: 1-[2-cyano-4-(trifluoromethyl)phenyl]-4-{6-[1-(3-methylbutyl)-1H-pyrazol-5-yl]pyridin-3-yl}-N-[(3R)-1-methylpyrrolidin-3-yl]piperidine-4-carboxamide;

1-71: 1-[2-cyano-4-(trifluoromethyl)phenyl]-N-[(3R)-1-methylpyrrolidin-3-yl]-4-{6-[2-(trifluoromethoxy)phenyl]pyridin-3-yl}piperidine-4-carboxamide;

1-72: 1-[2-cyano-4-(trifluoromethyl)phenyl]-4-[6-(2-ethoxy-3-fluorophenyl)pyridin-3-yl]-N-[(3R)-1-methylpyrrolidin-3-yl]piperidine-4-carboxamide;

1-73: 1-[2-cyano-4-(trifluoromethyl)phenyl]-4-[6-(1-methyl-1H-indazol-7-yl)pyridin-3-yl]-N-[(3R)-1-methylpyrrolidin-3-yl]piperidine-4-carboxamide;

1-74: 1-[2-cyano-4-(trifluoromethyl)phenyl]-4-[6-(2-fluorophenyl)pyridin-3-yl]-N-[(3R)-1-methylpyrrolidin-3-yl]piperidine-4-carboxamide;

1-75: 1-[2-cyano-4-(trifluoromethyl)phenyl]-4-[4-(2-ethoxypyridin-3-yl)-3-fluorophenyl]-N-[(3R)-1-methylpyrrolidin-3-yl]piperidine-4-carboxamide;

1-76: 1-[2-cyano-4-(trifluoromethyl)phenyl]-4-[6-(2-ethoxyphenyl)pyridin-3-yl]-N-(1-methylazetidin-3-yl)piperidine-4-carboxamide;
1-77: 1-[2-cyano-4-(trifluoromethyl)phenyl]-N-[(3R)-1-methylpyrrolidin-3-yl]-4-{6-[2-(trifluoromethyl)phenyl]pyridin-3-yl}piperidine-4-carboxamide;
1-78: 1-[2-cyano-4-(trifluoromethyl)phenyl]-4-[6-(2-cyanophenyl)pyridin-3-yl]-N-[(3R)-1-methylpyrrolidin-3-yl]piperidine-4-carboxamide;
1-79: 1-[2-cyano-4-(trifluoromethyl)phenyl]-4-{6-[2-(methoxymethyl)phenyl]pyridin-3-yl}-N-[(3R)-1-methylpyrrolidin-3-yl]piperidine-4-carboxamide;
1-80: 1-[2-cyano-4-(trifluoromethyl)phenyl]-4-[6-(3-methoxythiophen-2-yl)pyridin-3-yl]-N-[(3R)-1-methylpyrrolidin-3-yl]piperidine-4-carboxamide;
1-81: 1-[2-cyano-4-(trifluoromethyl)phenyl]-4-[6-(5-fluoro-2-methoxyphenyl)pyridin-3-yl]-N-[(3R)-1-methylpyrrolidin-3-yl]piperidine-4-carboxamide;
1-82: 1-[2-cyano-4-(trifluoromethyl)phenyl]-4-[6-(3-fluoro-2-methoxyphenyl)pyridin-3-yl]-N-[(3R)-1-methylpyrrolidin-3-yl]piperidine-4-carboxamide;
1-83: 1-[2-cyano-4-(trifluoromethyl)phenyl]-4-[6-(2-methoxythiophen-3-yl)pyridin-3-yl]-N-[(3R)-1-methylpyrrolidin-3-yl]piperidine-4-carboxamide;
1-84: 1-[2-cyano-4-(trifluoromethyl)phenyl]-4-{6-[2-(1,1-difluoroethyl)phenyl]pyridin-3-yl}-N-[(3R)-1-methylpyrrolidin-3-yl]piperidine-4-carboxamide;
1-85: 1-[2-cyano-4-(trifluoromethyl)phenyl]-4-[2'-(difluoromethoxy)-[2,3'-bipyridin]-5-yl]-N-[(3R)-1-methylpyrrolidin-3-yl]piperidine-4-carboxamide;
1-86: 1-[2-cyano-4-(trifluoromethyl)phenyl]-4-{5'-fluoro-2'-methoxy-[2,3'-bipyridin]-5-yl}-N-[(3R)-1-methylpyrrolidin-3-yl]piperidine-4-carboxamide;
1-87: 1-[2-cyano-4-(trifluoromethyl)phenyl]-4-[6-(3,5-difluoro-2-methoxyphenyl)pyridin-3-yl]-N-[(3R)-1-methylpyrrolidin-3-yl]piperidine-4-carboxamide;
1-88: 1-[2-cyano-4-(trifluoromethyl)phenyl]-4-[6-(1-methyl-1H-pyrrol-2-yl)pyridin-3-yl]-N-[(3R)-1-methylpyrrolidin-3-yl]piperidine-4-carboxamide;
1-89: 1-[2-cyano-4-(trifluoromethyl)phenyl]-4-[6-(2-cyclopropoxyphenyl)pyridin-3-yl]-N-[(3R)-1-methylpyrrolidin-3-yl]piperidine-4-carboxamide;
1-90: 1-(4-chloro-2-cyanophenyl)-4-[6-(2-ethoxyphenyl)pyridin-3-yl]-N-[(3S)-1-methylpyrrolidin-3-yl]piperidine-4-carboxamide;
1-91: 1-(4-chloro-2-cyanophenyl)-4-[6-(2-methoxyphenyl)pyridin-3-yl]-N-[(3S)-1-methylpyrrolidin-3-yl]piperidine-4-carboxamide;
1-92: 1-(4-chloro-2-cyanophenyl)-4-[6-(2-methoxyphenyl)pyridin-3-yl]-N-(1-methylazetidin-3-yl)piperidine-4-carboxamide;
1-93: 1-(4-chloro-2-cyanophenyl)-4-[6-(2-ethoxyphenyl)pyridin-3-yl]-N-(1-methylazetidin-3-yl)piperidine-4-carboxamide;
1-94: 1-[2-cyano-4-(trifluoromethyl)phenyl]-4-[6-(2-methoxyphenyl)pyridin-3-yl]-N-(1-methylazetidin-3-yl)piperidine-4-carboxamide;
1-95: 1-(2,4-dichlorophenyl)-4-[6-(2-ethoxyphenyl)pyridin-3-yl]-N-[(3S)-1-methylpyrrolidin-3-yl]piperidine-4-carboxamide;
1-96: 1-(2-cyano-4-fluorophenyl)-4-[6-(2-ethoxyphenyl)pyridin-3-yl]-N-[(3S)-1-methylpyrrolidin-3-yl]piperidine-4-carboxamide;
1-97: 1-[2-chloro-4-(trifluoromethyl)phenyl]-4-[6-(2-ethoxyphenyl)pyridin-3-yl]-N-[(3S)-1-methylpyrrolidin-3-yl]piperidine-4-carboxamide;
1-98: 1-[2-cyano-4-(trifluoromethyl)phenyl]-4-{2'-methoxy-[2,3'-bipyridin]-5-yl}-N-[(3R)-1-methylpyrrolidin-3-yl]piperidine-4-carboxamide;
1-99: 1-[2-cyano-4-(trifluoromethyl)phenyl]-4-[6-(5-fluoro-2-methylphenyl)pyridin-3-yl]-N-[(3R)-1-methylpyrrolidin-3-yl]piperidine-4-carboxamide;
1-100: 1-[2-cyano-4-(trifluoromethyl)phenyl]-4-[6-(1-methyl-1H-pyrrol-2-yl)pyridin-3-yl]-N-[(3S)-1-methylpyrrolidin-3-yl]piperidine-4-carboxamide;
1-101: 1-[2-cyano-4-(trifluoromethyl)phenyl]-4-[6-(3-fluoro-2-methoxyphenyl)pyridin-3-yl]-N-[(3S)-1-methylpyrrolidin-3-yl]piperidine-4-carboxamide;
1-102: 1-[2-cyano-4-(trifluoromethyl)phenyl]-4-[6-(5-fluoro-2-methoxyphenyl)pyridin-3-yl]-N-[(3S)-1-methylpyrrolidin-3-yl]piperidine-4-carboxamide;
1-103: 1-[2-cyano-4-(trifluoromethyl)phenyl]-4-{5'-fluoro-2'-methoxy-[2,3'-bipyridin]-5-yl}-N-[(3S)-1-methylpyrrolidin-3-yl]piperidine-4-carboxamide;
1-104: 1-[2-cyano-4-(trifluoromethyl)phenyl]-4-[6-(2-ethylphenyl)pyridin-3-yl]-N-[(3S)-1-methylpyrrolidin-3-yl]piperidine-4-carboxamide;
1-105: 1-[2-cyano-4-(trifluoromethyl)phenyl]-4-[6-(4-methylpyrimidin-5-yl)pyridin-3-yl]-N-[(3R)-1-methylpyrrolidin-3-yl]piperidine-4-carboxamide;
1-106: 1-[2-cyano-4-(trifluoromethyl)phenyl]-4-[2-(2-ethoxypyridin-3-yl)pyrimidin-5-yl]-N-[(3S)-1-methylpyrrolidin-3-yl]piperidine-4-carboxamide;
1-107: 1-[2-cyano-4-(trifluoromethyl)phenyl]-4-[2-(2-ethoxypyridin-3-yl)pyrimidin-5-yl]-N-[(3R)-1-methylpyrrolidin-3-yl]piperidine-4-carboxamide;
1-108: 1-[2-cyano-4-(trifluoromethyl)phenyl]-4-{2'-ethoxy-3-fluoro-[2,3'-bipyridin]-5-yl}-N-[(3R)-1-methylpyrrolidin-3-yl]piperidine-4-carboxamide;
1-109: 1-[2-cyano-4-(trifluoromethyl)phenyl]-4-{2'-ethoxy-3-fluoro-[2,3'-bipyridin]-5-yl}-N-[(3S)-1-methylpyrrolidin-3-yl]piperidine-4-carboxamide;
1-110: 1-[2-cyano-6-(trifluoromethyl)pyridin-3-yl]-4-{2'-ethoxy-3-fluoro-[2,3'-bipyridin]-5-yl}-N-[(3S)-1-methylpyrrolidin-3-yl]piperidine-4-carboxamide;
1-111: 1-(4-chloro-2-cyano-6-fluorophenyl)-4-[6-(2-ethoxyphenyl)pyridin-3-yl]-N-[(3S)-1-methylpyrrolidin-3-yl]piperidine-4-carboxamide;
1-112: 1-[2-cyano-4-(trifluoromethyl)phenyl]-N-[(3R)-1-methylpyrrolidin-3-yl]-4-[6-(2-methylthiophen-3-yl)pyridin-3-yl]piperidine-4-carboxamide;
1-113: 1-[2-cyano-4-(trifluoromethyl)phenyl]-4-[6-(2-cyclopropylphenyl)pyridin-3-yl]-N-[(3R)-1-methylpyrrolidin-3-yl]piperidine-4-carboxamide;
1-114: 1-[2-cyano-4-(trifluoromethyl)phenyl]-4-{6-[2-(difluoromethoxy)phenyl]pyridin-3-yl}-N-[(3R)-1-methylpyrrolidin-3-yl]piperidine-4-carboxamide;
1-115: 1-[2-cyano-4-(trifluoromethyl)phenyl]-4-[6-(1-methyl-1H-pyrrol-3-yl)pyridin-3-yl]-N-[(3R)-1-methylpyrrolidin-3-yl]piperidine-4-carboxamide;
1-116: 1-[2-cyano-4-(trifluoromethyl)phenyl]-4-[6-(2-methylfuran-3-yl)pyridin-3-yl]-N-[(3R)-1-methylpyrrolidin-3-yl]piperidine-4-carboxamide;
1-117: 1-[2-cyano-4-(trifluoromethyl)phenyl]-N-[(3R)-1-methylpyrrolidin-3-yl]-4-[6-(2-propylphenyl)pyridin-3-yl]piperidine-4-carboxamide;
1-118: 1-[2-cyano-4-(trifluoromethyl)phenyl]-4-{2'-ethyl-[2,3'-bipyridin]-5-yl}-N-[(3R)-1-methylpyrrolidin-3-yl]piperidine-4-carboxamide;
1-119: 1-[2-cyano-4-(trifluoromethyl)phenyl]-4-[6-(2-methoxythiophen-3-yl)pyridin-3-yl]-N-[(3S)-1-methylpyrrolidin-3-yl]piperidine-4-carboxamide;

1-120: 1-[2-cyano-4-(trifluoromethyl)phenyl]-4-[6-(2-methylfuran-3-yl)pyridin-3-yl]-N-[(3S)-1-methylpyrrolidin-3-yl]piperidine-4-carboxamide;

1-121: 1-[2-cyano-4-(trifluoromethyl)phenyl]-4-[6-(2-cyclopropylphenyl)pyridin-3-yl]-N-[(3S)-1-methylpyrrolidin-3-yl]piperidine-4-carboxamide;

1-122: 1-[2-cyano-4-(trifluoromethyl)phenyl]-N-[(3S)-1-methylpyrrolidin-3-yl]-4-[6-(2-methylthiophen-3-yl) pyridin-3-yl]piperidine-4-carboxamide;

1-123: 1-[2-cyano-4-(trifluoromethyl)phenyl]-4-[6-(2-ethoxyphenyl)-5-fluoropyridin-3-yl]-N-[(3R)-1-methylpyrrolidin-3-yl]piperidine-4-carboxamide;

1-124: 1-[2-cyano-4-(trifluoromethyl)phenyl]-4-[6-(2-ethoxyphenyl)-5-fluoropyridin-3-yl]-N-[(3S)-1-methylpyrrolidin-3-yl]piperidine-4-carboxamide;

1-125: 1-[2-cyano-6-(trifluoromethyl)pyridin-3-yl]-4-[6-(2-ethoxyphenyl)-5-fluoropyridin-3-yl]-N-[(3S)-1-methylpyrrolidin-3-yl]piperidine-4-carboxamide;

1-126: 1-[2-cyano-4-(trifluoromethyl)phenyl]-4-[5-fluoro-6-(2-methoxyphenyl)pyridin-3-yl]-N-[(3R)-1-methylpyrrolidin-3-yl]piperidine-4-carboxamide;

1-127: 1-[2-cyano-4-(trifluoromethyl)phenyl]-4-[5-fluoro-6-(2-methoxyphenyl)pyridin-3-yl]-N-[(3S)-1-methylpyrrolidin-3-yl]piperidine-4-carboxamide;

1-128: 1-[2-cyano-6-(trifluoromethyl)pyridin-3-yl]-4-[5-fluoro-6-(2-methoxyphenyl)pyridin-3-yl]-N-[(3S)-1-methylpyrrolidin-3-yl]piperidine-4-carboxamide;

1-129: 1-[2-cyano-4-(trifluoromethyl)phenyl]-4-[6-(3-fluoro-2-hydroxyphenyl)pyridin-3-yl]-N-[(3R)-1-methylpyrrolidin-3-yl]piperidine-4-carboxamide;

1-130: 1-[2-cyano-4-(trifluoromethyl)phenyl]-4-[6-(2-methoxy-5-methylphenyl)pyridin-3-yl]-N-[(3R)-1-methylpyrrolidin-3-yl]piperidine-4-carboxamide;

1-131: 1-[2-cyano-4-(trifluoromethyl)phenyl]-4-{3-fluoro-2'-methoxy-[2,3'-bipyridin]-5-yl}-N-[(3R)-1-methylpyrrolidin-3-yl]piperidine-4-carboxamide;

1-132: 1-[2-cyano-4-(trifluoromethyl)phenyl]-4-{3-fluoro-2'-methoxy-[2,3'-bipyridin]-5-yl}-N-[(3S)-1-methylpyrrolidin-3-yl]piperidine-4-carboxamide;

1-133: 1-[2-cyano-6-(trifluoromethyl)pyridin-3-yl]-4-{3-fluoro-2'-methoxy-[2,3'-bipyridin]-5-yl}-N-[(3S)-1-methylpyrrolidin-3-yl]piperidine-4-carboxamide;

1-134: 1-(4-chloro-2-cyanophenyl)-4-[6-(2-ethoxyphenyl) pyridazin-3-yl]-N-[(3S)-1-methylpyrrolidin-3-yl]piperidine-4-carboxamide;

1-135: 1-(4-chloro-2-cyanophenyl)-4-[6-(2-ethoxyphenyl) pyridazin-3-yl]-N-(1-methylazetidin-3-yl)piperidine-4-carboxamide;

1-136: 1-[2-cyano-4-(trifluoromethyl)phenyl]-4-[6-(2-ethoxyphenyl)pyridazin-3-yl]-N-(1-methylazetidin-3-yl) piperidine-4-carboxamide;

1-137: 1-[2-cyano-4-(trifluoromethyl)phenyl]-4-{6-[2-(cyanomethyl)phenyl]pyridin-3-yl}-N-[(3R)-1-methylpyrrolidin-3-yl]piperidine-4-carboxamide;

1-138: 1-[2-cyano-4-(trifluoromethyl)phenyl]-N-[(3R)-1-methylpyrrolidin-3-yl]-4-[6-(4-methylthiophen-3-yl) pyridin-3-yl]piperidine-4-carboxamide;

1-139: 1-(4-chloro-2-cyanophenyl)-4-[6-(2-ethoxypyridin-3-yl)pyridazin-3-yl]-N-[(3S)-1-methylpyrrolidin-3-yl]piperidine-4-carboxamide;

1-140: 1-[2-cyano-4-(trifluoromethyl)phenyl]-4-[6-(2-ethoxypyridin-3-yl)pyridazin-3-yl]-N-(1-methylazetidin-3-yl)piperidine-4-carboxamide;

1-141: 1-[2-chloro-4-(trifluoromethyl)phenyl]-4-{2'-ethoxy-[2,3'-bipyridin]-5-yl}-N-[(3S)-1-methylpyrrolidin-3-yl]piperidine-4-carboxamide;

1-142: 1-[2-chloro-4-(trifluoromethyl)phenyl]-4-{2'-methoxy-[2,3'-bipyridin]-5-yl}-N-[(3S)-1-methylpyrrolidin-3-yl]piperidine-4-carboxamide;

1-143: 1-[2-cyano-4-(trifluoromethyl)phenyl]-N-[(3S)-1-methylpyrrolidin-3-yl]-4-[6-(1H-pyrrol-2-yl)pyridin-3-yl]piperidine-4-carboxamide;

1-144: 1-[2-chloro-4-(trifluoromethyl)phenyl]-4-[6-(2-methoxyphenyl)pyridin-3-yl]-N-[(3S)-1-methylpyrrolidin-3-yl]piperidine-4-carboxamide;

1-145: 4-[6-(2-ethoxyphenyl)pyridin-3-yl]-1-[2-fluoro-4-(trifluoromethyl)phenyl]-N-[(3S)-1-methylpyrrolidin-3-yl]piperidine-4-carboxamide;

1-146: 4-[6-(2-acetylthiophen-3-yl)pyridin-3-yl]-1-[2-cyano-4-(trifluoromethyl)phenyl]-N-[(3S)-1-methylpyrrolidin-3-yl]piperidine-4-carboxamide;

1-147: 1-[2-cyano-4-(trifluoromethyl)phenyl]-4-[6-(2-ethylthiophen-3-yl)pyridin-3-yl]-N-[(3S)-1-methylpyrrolidin-3-yl]piperidine-4-carboxamide;

1-148: 4-[6-(2-cyano-3-fluorophenyl)pyridin-3-yl]-1-[2-cyano-4-(trifluoromethyl)phenyl]-N-[(3S)-1-methylpyrrolidin-3-yl]piperidine-4-carboxamide;

1-149: 1-[2-cyano-4-(trifluoromethyl)phenyl]-4-[6-(3-methyl-1,2-oxazol-4-yl)pyridin-3-yl]-N-[(3S)-1-methylpyrrolidin-3-yl]piperidine-4-carboxamide;

1-150: 1-[3-chloro-5-(trifluoromethyl)pyridin-2-yl]-4-{2'-ethoxy-[2,3'-bipyridin]-5-yl}-N-[(3S)-1-methylpyrrolidin-3-yl]piperidine-4-carboxamide;

1-151: 1-[2-cyano-4-(trifluoromethyl)phenyl]-4-{6-[2-(difluoromethyl)phenyl]pyridin-3-yl}-N-[(3S)-1-methylpyrrolidin-3-yl]piperidine-4-carboxamide;

1-152: 1-[2-cyano-4-(trifluoromethyl)phenyl]-4-[6-(1-methyl-1H-pyrrol-2-yl)pyridin-3-yl]-N-[(3S)-pyrrolidin-3-yl]piperidine-4-carboxamide;

1-153: 4-[6-(5-cyano-1-methyl-1H-pyrrol-2-yl)pyridin-3-yl]-1-[2-cyano-4-(trifluoromethyl)phenyl]-N-[(3R)-1-methylpyrrolidin-3-yl]piperidine-4-carboxamide;

1-154: 1-[2-chloro-4-(trifluoromethyl)phenyl]-4-{5'-fluoro-2'-methoxy-[2,3'-bipyridin]-5-yl}-N-[(3S)-1-methylpyrrolidin-3-yl]piperidine-4-carboxamide;

1-155: 1-[2-chloro-4-(trifluoromethyl)phenyl]-4-[6-(5-fluoro-2-methoxyphenyl)pyridin-3-yl]-N-[(3S)-1-methylpyrrolidin-3-yl]piperidine-4-carboxamide;

1-156: 1-[2-chloro-4-(trifluoromethyl)phenyl]-4-[6-(2-ethylphenyl)pyridin-3-yl]-N-[(3S)-1-methylpyrrolidin-3-yl] piperidine-4-carboxamide;

1-157: 1-[2-cyano-4-(trifluoromethyl)phenyl]-4-[6-(5-methyl-1,2-oxazol-4-yl)pyridin-3-yl]-N-[(3R)-1-methylpyrrolidin-3-yl]piperidine-4-carboxamide;

1-158: 1-[2-cyano-4-(trifluoromethyl)phenyl]-4-[6-(1-cyclopropyl-1H-pyrrol-2-yl)pyridin-3-yl]-N-[(3S)-1-methylpyrrolidin-3-yl]piperidine-4-carboxamide;

1-159: 4-[4-(2-ethoxypyridin-3-yl)phenyl]-1-[2-methoxy-4-(trifluoromethyl)phenyl]-N-[(3R)-1-methylpyrrolidin-3-yl]piperidine-4-carboxamide;

1-160: 1-[2-chloro-4-(trifluoromethyl)phenyl]-4-[6-(1-methyl-1H-pyrrol-2-yl)pyridin-3-yl]-N-[(3S)-1-methylpyrrolidin-3-yl]piperidine-4-carboxamide;

1-161: 1-[2-cyano-4-(trifluoromethyl)phenyl]-4-[5-fluoro-6-(1-methyl-1H-pyrrol-2-yl)pyridin-3-yl]-N-[(3S)-1-methylpyrrolidin-3-yl]piperidine-4-carboxamide;

1-162: 1-[2-chloro-4-(trifluoromethyl)phenyl]-4-[5-fluoro-6-(1-methyl-1H-pyrrol-2-yl)pyridin-3-yl]-N-[(3S)-1-methylpyrrolidin-3-yl]piperidine-4-carboxamide;

1-163: 1-(4-chloro-2-cyanophenyl)-4-[5-fluoro-6-(1-methyl-1H-pyrrol-2-yl)pyridin-3-yl]-N-[(3S)-1-methylpyrrolidin-3-yl]piperidine-4-carboxamide;

1-164: 4-[4-(2-ethoxypyridin-3-yl)phenyl]-1-[2-methyl-4-(trifluoromethyl)phenyl]-N-[(3R)-1-methylpyrrolidin-3-yl]piperidine-4-carboxamide;
1-165: 1-[3-chloro-4-(trifluoromethyl)phenyl]-4-[4-(2-ethoxypyridin-3-yl)phenyl]-N-[(3R)-1-methylpyrrolidin-3-yl]piperidine-4-carboxamide;
1-166: 1-[2-cyano-4-(trifluoromethyl)phenyl]-4-[6-(2-methoxyphenyl)pyridin-3-yl]-N-[(3S)-1-methylpyrrolidin-3-yl]piperidine-4-carboxamide;
1-167: 1-[2-chloro-4-(trifluoromethyl)phenyl]-4-[6-(2-methoxythiophen-3-yl)pyridin-3-yl]-N-[(3S)-1-methylpyrrolidin-3-yl]piperidine-4-carboxamide;
1-168: 1-[2-cyano-4-(trifluoromethyl)phenyl]-4-[6-(1-methyl-1H-pyrrol-2-yl)pyridazin-3-yl]-N-[(3S)-1-methylpyrrolidin-3-yl]piperidine-4-carboxamide;
1-169: 1-[2-chloro-4-(trifluoromethyl)phenyl]-4-[6-(1-methyl-1H-pyrrol-2-yl)pyridazin-3-yl]-N-[(3S)-1-methylpyrrolidin-3-yl]piperidine-4-carboxamide;
1-170: 1-(4-chloro-2-cyanophenyl)-4-[6-(1-methyl-1H-pyrrol-2-yl)pyridazin-3-yl]-N-[(3S)-1-methylpyrrolidin-3-yl]piperidine-4-carboxamide;
1-171: 1-[2-fluoro-4-(trifluoromethyl)phenyl]-4-[6-(1-methyl-1H-pyrrol-2-yl)pyridazin-3-yl]-N-[(3S)-1-methylpyrrolidin-3-yl]piperidine-4-carboxamide;
1-172: 1-[2-chloro-4-(trifluoromethyl)phenyl]-4-{2'-ethyl-[2,3'-bipyridin]-5-yl}-N-[(3S)-1-methylpyrrolidin-3-yl]piperidine-4-carboxamide;
1-173: 1-[2-fluoro-4-(trifluoromethyl)phenyl]-4-[6-(1-methyl-1H-pyrrol-2-yl)pyridin-3-yl]-N-[(3S)-1-methylpyrrolidin-3-yl]piperidine-4-carboxamide;
1-174: 4-[6-(2-ethoxyphenyl)pyridazin-3-yl]-1-[2-fluoro-4-(trifluoromethyl)phenyl]-N-[(3S)-1-methylpyrrolidin-3-yl]piperidine-4-carboxamide;
1-175: 1-[2-chloro-4-(trifluoromethyl)phenyl]-4-[6-(2-ethoxyphenyl)pyridazin-3-yl]-N-[(3S)-1-methylpyrrolidin-3-yl]piperidine-4-carboxamide;
1-176: 4-{[2,2'-bipyridin]-5-yl}-1-[2-cyano-4-(trifluoromethyl)phenyl]-N-[(3S)-1-methylpyrrolidin-3-yl]piperidine-4-carboxamide;
1-177: 1-[2-cyano-4-(trifluoromethyl)phenyl]-4-{3'-methyl-[2,2'-bipyridin]-5-yl}-N-[(3R)-1-methylpyrrolidin-3-yl]piperidine-4-carboxamide;
1-178: 1-[2-cyano-4-(trifluoromethyl)phenyl]-4-{3'-methoxy-[2,2'-bipyridin]-5-yl}-N-[(3S)-1-methylpyrrolidin-3-yl]piperidine-4-carboxamide;
1-179: 1-[2-cyano-4-(trifluoromethyl)phenyl]-4-{2'-methoxy-[2,3'-bipyridin]-5-yl}-N-[(3S)-1-methylpyrrolidin-3-yl]piperidine-4-carboxamide;
1-180: 1-[2-cyano-4-(trifluoromethyl)phenyl]-4-{2'-cyclopropyl-[2,3'-bipyridin]-5-yl}-N-[(3S)-1-methylpyrrolidin-3-yl]piperidine-4-carboxamide;
1-181: 1-[2-cyano-4-(trifluoromethyl)phenyl]-4-[2'-(difluoromethyl)-[2,3'-bipyridin]-5-yl]-N-[(3S)-1-methylpyrrolidin-3-yl]piperidine-4-carboxamide;
1-182: 1-[2-cyano-4-(trifluoromethyl)phenyl]-4-[6-(5-cyclopropyl-1,3-oxazol-4-yl)pyridin-3-yl]-N-[(3S)-1-methylpyrrolidin-3-yl]piperidine-4-carboxamide;
1-183: 1-[2-cyano-4-(trifluoromethyl)phenyl]-4-[6-(2-methoxyphenyl)pyridazin-3-yl]-N-[(3S)-1-methylpyrrolidin-3-yl]piperidine-4-carboxamide;
1-184: ethyl (3S)-3-{1-[2-cyano-4-(trifluoromethyl)phenyl]-4-[6-(1-methyl-1H-pyrrol-2-yl)pyridin-3-yl]piperidine-4-amido}pyrrolidine-1-carboxylate;
1-185: N-[(3S)-1-acetylpyrrolidin-3-yl]-1-[2-cyano-4-(trifluoromethyl)phenyl]-4-[6-(1-methyl-1H-pyrrol-2-yl)pyridin-3-yl]piperidine-4-carboxamide;
1-186: 4-{2'-ethoxy-[2,3'-bipyridin]-5-yl}-1-[2-fluoro-4-(trifluoromethyl)phenyl]-N-[(3S)-1-methylpyrrolidin-3-yl]piperidine-4-carboxamide;
1-187: N-[(3S)-1-azabicyclo[2.2.2]octan-3-yl]-1-[2-cyano-4-(trifluoromethyl)phenyl]-4-[6-(1-methyl-1H-pyrrol-2-yl)pyridin-3-yl]piperidine-4-carboxamide;
1-188: N-[(3R)-1-azabicyclo[2.2.2]octan-3-yl]-1-[2-cyano-4-(trifluoromethyl)phenyl]-4-[6-(1-methyl-1H-pyrrol-2-yl)pyridin-3-yl]piperidine-4-carboxamide;
1-189: 1-[2-cyano-4-(trifluoromethyl)phenyl]-4-[6-(2-methoxyquinolin-3-yl)pyridin-3-yl]-N-[(3R)-1-methylpyrrolidin-3-yl]piperidine-4-carboxamide;
1-190: 1-[2-cyano-4-(trifluoromethyl)phenyl]-4-[6-(1-methyl-1H-indol-7-yl)pyridin-3-yl]-N-[(3R)-1-methylpyrrolidin-3-yl]piperidine-4-carboxamide;
1-191: 1-[2-cyano-4-(trifluoromethyl)phenyl]-4-[6-(1-methyl-1H-indol-2-yl)pyridin-3-yl]-N-[(3R)-1-methylpyrrolidin-3-yl]piperidine-4-carboxamide;
1-192: 1-[2-fluoro-4-(trifluoromethyl)phenyl]-4-[5-fluoro-6-(1-methyl-1H-pyrrol-2-yl)pyridin-3-yl]-N-[(3S)-1-methylpyrrolidin-3-yl]piperidine-4-carboxamide;
1-193: 4-[6-(2-ethoxypyridin-3-yl)pyridazin-3-yl]-1-[2-fluoro-4-(trifluoromethyl)phenyl]-N-[(3S)-1-methylpyrrolidin-3-yl]piperidine-4-carboxamide;
1-194: 1-[2-chloro-4-(trifluoromethyl)phenyl]-4-[6-(2-ethoxypyridin-3-yl)pyridazin-3-yl]-N-[(3S)-1-methylpyrrolidin-3-yl]piperidine-4-carboxamide;
1-195: 1-[2-cyano-4-(trifluoromethyl)phenyl]-4-[5-fluoro-6-(5-fluoro-2-methoxyphenyl)pyridin-3-yl]-N-[(3S)-1-methylpyrrolidin-3-yl]piperidine-4-carboxamide;
1-196: 1-[2-cyano-4-(trifluoromethyl)phenyl]-4-[5-fluoro-6-(2-methoxyphenyl)pyridin-3-yl]-N-[2-(methylamino)ethyl]piperidine-4-carboxamide;
1-197: 1-[2-cyano-4-(trifluoromethyl)phenyl]-4-[5-fluoro-6-(2-methoxyphenyl)pyridin-3-yl]-N-[3-(methylamino)propyl]piperidine-4-carboxamide;
1-198: 1-[2-cyano-4-(trifluoromethyl)phenyl]-N-[2-(dimethylamino)ethyl]-4-[5-fluoro-6-(2-methoxyphenyl)pyridin-3-yl]piperidine-4-carboxamide;
1-199: 1-[2-cyano-4-(trifluoromethyl)phenyl]-N-[3-(dimethylamino)propyl]-4-[5-fluoro-6-(2-methoxyphenyl)pyridin-3-yl]piperidine-4-carboxamide;
1-200: 4-[6-(2-ethoxyphenyl)-5-fluoropyridin-3-yl]-1-[2-fluoro-4-(trifluoromethyl)phenyl]-N-[(3S)-1-methylpyrrolidin-3-yl]piperidine-4-carboxamide;
1-201: 4-{2'-ethoxy-3-fluoro-[2,3'-bipyridin]-5-yl}-1-[2-fluoro-4-(trifluoromethyl)phenyl]-N-[(3S)-1-methylpyrrolidin-3-yl]piperidine-4-carboxamide;
1-202: 1-[2-chloro-4-(trifluoromethyl)phenyl]-4-[6-(2-ethoxyphenyl)-5-fluoropyridin-3-yl]-N-[(3S)-1-methylpyrrolidin-3-yl]piperidine-4-carboxamide;
1-203: 1-[2-chloro-4-(trifluoromethyl)phenyl]-4-{2'-ethoxy-3-fluoro-[2,3'-bipyridin]-5-yl}-N-[(3S)-1-methylpyrrolidin-3-yl]piperidine-4-carboxamide;
1-204: 1-[2-fluoro-4-(trifluoromethyl)phenyl]-4-[5-fluoro-6-(5-fluoro-2-methoxyphenyl)pyridin-3-yl]-N-[(3S)-1-methylpyrrolidin-3-yl]piperidine-4-carboxamide;
1-205: N-(3-aminopropyl)-1-[2-cyano-4-(trifluoromethyl)phenyl]-4-[6-(1-methyl-1H-pyrrol-2-yl)pyridin-3-yl]piperidine-4-carboxamide;
1-206: 1-[2-cyano-4-(trifluoromethyl)phenyl]-4-[6-(1-methyl-1H-pyrrol-2-yl)pyridin-3-yl]-N-[3-(methylamino)propyl]piperidine-4-carboxamide;
1-207: 1-[2-cyano-4-(trifluoromethyl)phenyl]-N-[3-(dimethylamino)propyl]-4-[6-(1-methyl-1H-pyrrol-2-yl)pyridin-3-yl]piperidine-4-carboxamide;

1-208: 1-[2-cyano-4-(trifluoromethyl)phenyl]-4-[6-(1-ethyl-1H-pyrrol-2-yl)pyridin-3-yl]-N-[(3S)-1-methylpyrrolidin-3-yl]piperidine-4-carboxamide;

1-209: 1-[2-cyano-4-(trifluoromethyl)phenyl]-4-{3,5'-difluoro-2'-methoxy-[2,3'-bipyridin]-5-yl}-N-[(3S)-1-methylpyrrolidin-3-yl]piperidine-4-carboxamide;

1-210: 4-{3,5'-difluoro-2'-methoxy-[2,3'-bipyridin]-5-yl}-1-[2-fluoro-4-(trifluoromethyl)phenyl]-N-[(3S)-1-methylpyrrolidin-3-yl]piperidine-4-carboxamide;

1-211: 1-[2-cyano-4-(trifluoromethyl)phenyl]-4-[6-(2-methoxyphenyl)pyridin-3-yl]-N-[(1-methylazetidin-3-yl)methyl]piperidine-4-carboxamide;

1-212: 1-[2-cyano-4-(trifluoromethyl)phenyl]-N-[2-(dimethylamino)ethyl]-4-[6-(2-methoxyphenyl)pyridin-3-yl]piperidine-4-carboxamide;

1-213: N-{[(2S)-azetidin-2-yl]methyl}-1-[2-cyano-4-(trifluoromethyl)phenyl]-4-[6-(2-methoxyphenyl)pyridin-3-yl]piperidine-4-carboxamide;

1-214: 1-[2-cyano-4-(trifluoromethyl)phenyl]-4-[6-(2-methoxyphenyl)pyridin-3-yl]-N-[2-(methylamino)ethyl]piperidine-4-carboxamide;

1-215: 1-[2-cyano-4-(trifluoromethyl)phenyl]-4-[6-(1-methyl-1H-pyrrol-2-yl)pyridin-3-yl]-N-[2-(methylamino)ethyl]piperidine-4-carboxamide;

1-216: 1-[2-cyano-4-(trifluoromethyl)phenyl]-N-[2-(dimethylamino)ethyl]-4-[6-(1-methyl-1H-pyrrol-2-yl)pyridin-3-yl]piperidine-4-carboxamide;

1-217: 1-[2-cyano-4-(trifluoromethyl)phenyl]-4-[6-(2-methoxyphenyl)pyridin-3-yl]-N-{[(2S)-1-methylazetidin-2-yl]methyl}piperidine-4-carboxamide;

1-218: N-[(3S)-1-azabicyclo[2.2.2]octan-3-yl]-1-[2-cyano-4-(trifluoromethyl)phenyl]-4-[6-(2-methoxyphenyl)pyridin-3-yl]piperidine-4-carboxamide;

1-219: 1-[2-cyano-4-(trifluoromethyl)phenyl]-4-[6-(1-methyl-1H-pyrrol-2-yl)pyridin-3-yl]-N-(1-methylazetidin-3-yl)piperidine-4-carboxamide;

1-220: 1-[2-cyano-4-(trifluoromethyl)phenyl]-4-[6-(1-methyl-1H-pyrrol-2-yl)pyridin-3-yl]-N-[(1-methylazetidin-3-yl)methyl]piperidine-4-carboxamide;

1-221: N-{1-azabicyclo[2.2.1]heptan-4-yl}-1-[2-cyano-4-(trifluoromethyl)phenyl]-4-[6-(1-methyl-1H-pyrrol-2-yl)pyridin-3-yl]piperidine-4-carboxamide;

1-222: N-[2-(dimethylamino)ethyl]-4-{2'-ethoxy-[2,3'-bipyridin]-5-yl}-1-[2-fluoro-4-(trifluoromethyl)phenyl]piperidine-4-carboxamide;

1-223: 4-{2'-ethoxy-[2,3'-bipyridin]-5-yl}-1-[2-fluoro-4-(trifluoromethyl)phenyl]-N-[2-(methylamino)ethyl]piperidine-4-carboxamide;

1-224: 1-[2-chloro-4-(trifluoromethyl)phenyl]-N-[2-(dimethylamino)ethyl]-4-{2'-ethoxy-[2,3'-bipyridin]-5-yl}piperidine-4-carboxamide;

1-225: 1-[2-chloro-4-(trifluoromethyl)phenyl]-4-{2'-ethoxy-[2,3'-bipyridin]-5-yl}-N-[2-(methylamino)ethyl]piperidine-4-carboxamide;

1-226: N-[2-(dimethylamino)ethyl]-4-[6-(2-ethoxyphenyl)pyridin-3-yl]-1-[2-fluoro-4-(trifluoromethyl)phenyl]piperidine-4-carboxamide;

1-227: 4-[6-(2-ethoxyphenyl)pyridin-3-yl]-1-[2-fluoro-4-(trifluoromethyl)phenyl]-N-[2-(methylamino)ethyl]piperidine-4-carboxamide;

1-228: 1-[2-chloro-4-(trifluoromethyl)phenyl]-N-[2-(dimethylamino)ethyl]-4-[6-(2-ethoxyphenyl)pyridin-3-yl]piperidine-4-carboxamide;

1-229: 1-[2-cyano-4-(trifluoromethyl)phenyl]-4-[6-(1-methyl-1H-pyrrol-2-yl)pyridin-3-yl]-N-{[(2S)-1-methylpyrrolidin-2-yl]methyl}piperidine-4-carboxamide;

1-230: 1-[2-chloro-4-(trifluoromethyl)phenyl]-4-[6-(2-ethoxyphenyl)pyridin-3-yl]-N-[2-(methylamino)ethyl]piperidine-4-carboxamide;

1-231: 1-[2-cyano-4-(trifluoromethyl)phenyl]-4-[6-(1-methyl-1H-pyrrol-2-yl)pyridin-3-yl]-N-{[(2R)-pyrrolidin-2-yl]methyl}piperidine-4-carboxamide;

1-232: 1-[2-cyano-4-(trifluoromethyl)phenyl]-4-[6-(1-methyl-1H-pyrrol-2-yl)pyridin-3-yl]-N-{[(2R)-1-methylpyrrolidin-2-yl]methyl}piperidine-4-carboxamide;

1-233: 1-[2-cyano-4-(trifluoromethyl)phenyl]-4-[6-(1-methyl-1H-pyrrol-2-yl)pyridin-3-yl]-N-[(1S,3S)-3-aminocyclobutyl]piperidine-4-carboxamide;

1-234: 1-[2-cyano-4-(trifluoromethyl)phenyl]-4-[6-(1-methyl-1H-pyrrol-2-yl)pyridin-3-yl]-N-[(1R,3R)-3-aminocyclobutyl]piperidine-4-carboxamide;

1-235: N-{[(2S)-azetidin-2-yl]methyl}-1-[2-cyano-4-(trifluoromethyl)phenyl]-4-[6-(1-methyl-1H-pyrrol-2-yl)pyridin-3-yl]piperidine-4-carboxamide;

1-236: N-{[(2R)-azetidin-2-yl]methyl}-1-[2-cyano-4-(trifluoromethyl)phenyl]-4-[6-(2-methoxyphenyl)pyridin-3-yl]piperidine-4-carboxamide;

1-237: 1-[2-cyano-4-(trifluoromethyl)phenyl]-N-[(3R,4S)-4-fluoropyrrolidin-3-yl]-4-[6-(2-methoxyphenyl)pyridin-3-yl]piperidine-4-carboxamide;

1-238: 1-[2-cyano-4-(trifluoromethyl)phenyl]-N-[(3R,4R)-4-fluoropyrrolidin-3-yl]-4-[6-(2-methoxyphenyl)pyridin-3-yl]piperidine-4-carboxamide;

1-239: 1-[2-cyano-4-(trifluoromethyl)phenyl]-4-[6-(1-methyl-1H-pyrrol-2-yl)pyridin-3-yl]-N-[(1S,3S)-3-(dimethylamino)cyclobutyl]piperidine-4-carboxamide;

1-240: 1-[2-cyano-4-(trifluoromethyl)phenyl]-4-[6-(1-methyl-1H-pyrrol-2-yl)pyridin-3-yl]-N-[(1R,3R)-3-(dimethylamino)cyclobutyl]piperidine-4-carboxamide;

1-241: 1-[2-cyano-4-(trifluoromethyl)phenyl]-4-[6-(1-methyl-1H-pyrrol-2-yl)pyridin-3-yl]-N-{[(2S)-1-methylazetidin-2-yl]methyl}piperidine-4-carboxamide;

1-242: 1-[2-cyano-4-(trifluoromethyl)phenyl]-N-[(3R,4S)-4-fluoro-1-methylpyrrolidin-3-yl]-4-[6-(2-methoxyphenyl)pyridin-3-yl]piperidine-4-carboxamide;

1-243: 1-[2-cyano-4-(trifluoromethyl)phenyl]-N-[(3R,4R)-4-fluoro-1-methylpyrrolidin-3-yl]-4-[6-(2-methoxyphenyl)pyridin-3-yl]piperidine-4-carboxamide;

1-244: 1-[2-cyano-4-(trifluoromethyl)phenyl]-4-[6-(2-methoxyphenyl)pyridin-3-yl]-N-{[(2R)-1-methylazetidin-2-yl]methyl}piperidine-4-carboxamide;

1-245: N-[2-(azetidin-1-yl)ethyl]-1-[2-cyano-4-(trifluoromethyl)phenyl]-4-[6-(2-methoxyphenyl)pyridin-3-yl]piperidine-4-carboxamide;

1-246: 1-[2-cyano-4-(trifluoromethyl)phenyl]-N-{[(2S,4S)-4-fluoropyrrolidin-2-yl]methyl}-4-[6-(2-methoxyphenyl)pyridin-3-yl]piperidine-4-carboxamide;

1-247: 1-[2-cyano-4-(trifluoromethyl)phenyl]-N-{[(2S,4R)-4-fluoropyrrolidin-2-yl]methyl}-4-[6-(2-methoxyphenyl)pyridin-3-yl]piperidine-4-carboxamide;

1-248: N-[2-(azetidin-1-yl)ethyl]-1-[2-cyano-4-(trifluoromethyl)phenyl]-4-[6-(1-methyl-1H-pyrrol-2-yl)pyridin-3-yl]piperidine-4-carboxamide;

1-249: 1-[2-cyano-4-(trifluoromethyl)phenyl]-N-{[(2S,4S)-4-fluoro-1-methylpyrrolidin-2-yl]methyl}-4-[6-(2-methoxyphenyl)pyridin-3-yl]piperidine-4-carboxamide;

1-250: 1-[2-cyano-4-(trifluoromethyl)phenyl]-N-{[(2S,4R)-4-fluoro-1-methylpyrrolidin-2-yl]methyl}-4-[6-(2-methoxyphenyl)pyridin-3-yl]piperidine-4-carboxamide;

1-251: rac-1-[2-cyano-4-(trifluoromethyl)phenyl]-4-[6-(1-methyl-1H-pyrrol-2-yl)pyridin-3-yl]-N-[(1S,2S,4R)-7-methyl-7-azabicyclo[2.2.1]heptan-2-yl]piperidine-4-carboxamide;

1-252: rac-1-[2-cyano-4-(trifluoromethyl)phenyl]-4-[6-(2-methoxyphenyl)pyridin-3-yl]-N-[(1S,2S,4R)-7-methyl-7-azabicyclo[2.2.1]heptan-2-yl]piperidine-4-carboxamide;

1-253: 1-[2-cyano-4-(trifluoromethyl)phenyl]-N-[(3S)-1,3-dimethylpyrrolidin-3-yl]-4-[6-(1-methyl-1H-pyrrol-2-yl)pyridin-3-yl]piperidine-4-carboxamide;

1-254: N-[2-(dimethylamino)ethyl]-1-[2-fluoro-4-(trifluoromethyl)phenyl]-4-[6-(2-methoxyphenyl)pyridin-3-yl]piperidine-4-carboxamide;

1-255: 1-[2-chloro-4-(trifluoromethyl)phenyl]-N-[2-(dimethylamino)ethyl]-4-[6-(2-methoxyphenyl)pyridin-3-yl]piperidine-4-carboxamide;

1-256: 1-[2-fluoro-4-(trifluoromethyl)phenyl]-4-[6-(2-methoxyphenyl)pyridin-3-yl]-N-[2-(methylamino)ethyl]piperidine-4-carboxamide;

1-257: 1-[2-chloro-4-(trifluoromethyl)phenyl]-4-[6-(2-methoxyphenyl)pyridin-3-yl]-N-[2-(methylamino)ethyl]piperidine-4-carboxamide;

1-258: rac-N-[(1R,2S)-2-aminocyclopropyl]-1-[2-cyano-4-(trifluoromethyl)phenyl]-4-[6-(1-methyl-1H-pyrrol-2-yl)pyridin-3-yl]piperidine-4-carboxamide;

1-259: rac-N-[(1R,2R)-2-aminocyclopropyl]-1-[2-cyano-4-(trifluoromethyl)phenyl]-4-[6-(1-methyl-1H-pyrrol-2-yl)pyridin-3-yl]piperidine-4-carboxamide;

1-260: 1-[2-cyano-4-(trifluoromethyl)phenyl]-N-[(2R)-1-(dimethylamino)propan-2-yl]-4-[6-(1-methyl-1H-pyrrol-2-yl)pyridin-3-yl]piperidine-4-carboxamide;

1-261: 1-[2-cyano-4-(trifluoromethyl)phenyl]-N-[(2S)-1-(dimethylamino)propan-2-yl]-4-[6-(1-methyl-1H-pyrrol-2-yl)pyridin-3-yl]piperidine-4-carboxamide;

1-262: 1-[2-cyano-4-(trifluoromethyl)phenyl]-N-{3-[(dimethylamino)methyl]oxetan-3-yl}-4-[6-(1-methyl-1H-pyrrol-2-yl)pyridin-3-yl]piperidine-4-carboxamide;

1-263: 1-[2-cyano-4-(trifluoromethyl)phenyl]-N-{[1-(dimethylamino)cyclopropyl]methyl}-4-[6-(1-methyl-1H-pyrrol-2-yl)pyridin-3-yl]piperidine-4-carboxamide;

1-264: 1-[2-cyano-4-(trifluoromethyl)phenyl]-N-[(3S,4S)-4-(dimethylamino)oxolan-3-yl]-4-[6-(1-methyl-1H-pyrrol-2-yl)pyridin-3-yl]piperidine-4-carboxamide;

1-265: 1-[2-cyano-4-(trifluoromethyl)phenyl]-N-{2-[ethyl(methyl)amino]ethyl}-4-[6-(1-methyl-1H-pyrrol-2-yl)pyridin-3-yl]piperidine-4-carboxamide;

1-266: 1-[2-cyano-4-(trifluoromethyl)phenyl]-N-{2-[cyclopropyl(methyl)amino]ethyl}-4-[6-(1-methyl-1H-pyrrol-2-yl)pyridin-3-yl]piperidine-4-carboxamide;

1-267: rac-1-[2-cyano-4-(trifluoromethyl)phenyl]-N-[(3S,4R)-4-methoxy-1-methylpyrrolidin-3-yl]-4-[6-(1-methyl-1H-pyrrol-2-yl)pyridin-3-yl]piperidine-4-carboxamide;

1-268: rac-1-[2-cyano-4-(trifluoromethyl)phenyl]-N-[(3R,4R)-4-methoxy-1-methylpyrrolidin-3-yl]-4-[6-(1-methyl-1H-pyrrol-2-yl)pyridin-3-yl]piperidine-4-carboxamide;

1-269: 1-[2-cyano-4-(trifluoromethyl)phenyl]-N-[(3R,4R)-4-hydroxy-1-methylpyrrolidin-3-yl]-4-[6-(1-methyl-1H-pyrrol-2-yl)pyridin-3-yl]piperidine-4-carboxamide;

1-270: 1-[2-cyano-4-(trifluoromethyl)phenyl]-N-[(3S,4S)-4-hydroxy-1-methylpyrrolidin-3-yl]-4-[6-(1-methyl-1H-pyrrol-2-yl)pyridin-3-yl]piperidine-4-carboxamide;

1-271: N-[2-(dimethylamino)ethyl]-1-[2-fluoro-4-(trifluoromethyl)phenyl]-4-{2'-methoxy-[2,3'-bipyridin]-5-yl}piperidine-4-carboxamide;

1-272: 1-[2-fluoro-4-(trifluoromethyl)phenyl]-4-{2'-methoxy-[2,3'-bipyridin]-5-yl}-N-[2-(methylamino)ethyl]piperidine-4-carboxamide;

1-273: 1-[2-chloro-4-(trifluoromethyl)phenyl]-N-[2-(dimethylamino)ethyl]-4-{2'-methoxy-[2,3'-bipyridin]-5-yl}piperidine-4-carboxamide;

1-274: 1-[2-chloro-4-(trifluoromethyl)phenyl]-4-{2'-methoxy-[2,3'-bipyridin]-5-yl}-N-[2-(methylamino)ethyl]piperidine-4-carboxamide;

1-275: 1-[2-cyano-4-(trifluoromethyl)phenyl]-N-[(2R)-2-(dimethylamino)-3-hydroxypropyl]-4-[6-(1-methyl-1H-pyrrol-2-yl)pyridin-3-yl]piperidine-4-carboxamide;

1-276: N-[2-(dimethylamino)ethyl]-1-[2-fluoro-4-(trifluoromethyl)phenyl]-4-[6-(1-methyl-1H-pyrrol-2-yl)pyridin-3-yl]piperidine-4-carboxamide;

1-277: 1-[2-cyano-4-(trifluoromethyl)phenyl]-N-{[(2S,4S)-4-fluoro-1-methylpyrrolidin-2-yl]methyl}-4-[6-(1-methyl-1H-pyrrol-2-yl)pyridin-3-yl]piperidine-4-carboxamide;

1-278: 1-[2-cyano-4-(trifluoromethyl)phenyl]-N-{[(2S,4R)-4-fluoro-1-methylpyrrolidin-2-yl]methyl}-4-[6-(1-methyl-1H-pyrrol-2-yl)pyridin-3-yl]piperidine-4-carboxamide;

1-279: 1-[2-cyano-4-(trifluoromethyl)phenyl]-N-{[(2S)-4,4-difluoro-1-methylpyrrolidin-2-yl]methyl}-4-[6-(1-methyl-1H-pyrrol-2-yl)pyridin-3-yl]piperidine-4-carboxamide;

1-280: 1-[2-cyano-4-(trifluoromethyl)phenyl]-N-{[(2R)-4,4-difluoro-1-methylpyrrolidin-2-yl]methyl}-4-[6-(1-methyl-1H-pyrrol-2-yl)pyridin-3-yl]piperidine-4-carboxamide;

1-281: 1-[2-fluoro-4-(trifluoromethyl)phenyl]-4-[6-(1-methyl-1H-pyrrol-2-yl)pyridin-3-yl]-N-[2-(methylamino)ethyl]piperidine-4-carboxamide;

1-282: 1-[2-chloro-4-(trifluoromethyl)phenyl]-N-[2-(dimethylamino)ethyl]-4-[6-(1-methyl-1H-pyrrol-2-yl)pyridin-3-yl]piperidine-4-carboxamide;

1-283: 1-[2-chloro-4-(trifluoromethyl)phenyl]-4-[6-(1-methyl-1H-pyrrol-2-yl)pyridin-3-yl]-N-[2-(methylamino)ethyl]piperidine-4-carboxamide;

1-284: N-[2-(dimethylamino)ethyl]-4-{2'-ethoxy-3-fluoro-[2,3'-bipyridin]-5-yl}-1-[2-fluoro-4-(trifluoromethyl)phenyl]piperidine-4-carboxamide;

1-285: N-[2-(dimethylamino)ethyl]-1-[2-fluoro-4-(trifluoromethyl)phenyl]-4-[5-fluoro-6-(2-methoxyphenyl)pyridin-3-yl]piperidine-4-carboxamide;

1-286: 1-[2-chloro-4-(trifluoromethyl)phenyl]-N-[2-(dimethylamino)ethyl]-4-[5-fluoro-6-(2-methoxyphenyl)pyridin-3-yl]piperidine-4-carboxamide;

1-287: 4-{2'-ethoxy-3-fluoro-[2,3'-bipyridin]-5-yl}-1-[2-fluoro-4-(trifluoromethyl)phenyl]-N-[2-(methylamino)ethyl]piperidine-4-carboxamide;

1-288: 1-[2-chloro-4-(trifluoromethyl)phenyl]-N-[2-(dimethylamino)ethyl]-4-{2'-ethoxy-3-fluoro-[2,3'-bipyridin]-5-yl}piperidine-4-carboxamide;

1-289: N-[2-(dimethylamino)ethyl]-4-[6-(2-ethoxyphenyl)-5-fluoropyridin-3-yl]-1-[2-fluoro-4-(trifluoromethyl)phenyl]piperidine-4-carboxamide;

1-290: 4-[6-(2-ethoxyphenyl)-5-fluoropyridin-3-yl]-1-[2-fluoro-4-(trifluoromethyl)phenyl]-N-[2-(methylamino)ethyl]piperidine-4-carboxamide;

1-291: 1-[2-chloro-4-(trifluoromethyl)phenyl]-N-[2-(dimethylamino)ethyl]-4-[6-(2-ethoxyphenyl)-5-fluoropyridin-3-yl]piperidine-4-carboxamide;

1-292: 1-[2-chloro-4-(trifluoromethyl)phenyl]-4-[6-(2-ethoxyphenyl)-5-fluoropyridin-3-yl]-N-[2-(methylamino)ethyl]piperidine-4-carboxamide;

1-293: 1-[2-fluoro-4-(trifluoromethyl)phenyl]-4-[5-fluoro-6-(2-methoxyphenyl)pyridin-3-yl]-N-[2-(methylamino)ethyl]piperidine-4-carboxamide;

1-294: 1-[2-chloro-4-(trifluoromethyl)phenyl]-4-[5-fluoro-6-(2-methoxyphenyl)pyridin-3-yl]-N-[2-(methylamino)ethyl]piperidine-4-carboxamide;

1-295: N-[(2S)-1-(dimethylamino)propan-2-yl]-1-[2-fluoro-4-(trifluoromethyl)phenyl]-4-{2'-methoxy-[2,3'-bipyridin]-5-yl}piperidine-4-carboxamide;

1-296: 1-[2-chloro-4-(trifluoromethyl)phenyl]-N-[(2S)-1-(dimethylamino)propan-2-yl]-4-{2'-methoxy-[2,3'-bipyridin]-5-yl}piperidine-4-carboxamide;

1-297: N-[(2S)-1-(dimethylamino)propan-2-yl]-1-[2-fluoro-4-(trifluoromethyl)phenyl]-4-[6-(1-methyl-1H-pyrrol-2-yl)pyridin-3-yl]piperidine-4-carboxamide;

1-298: 1-[2-fluoro-4-(trifluoromethyl)phenyl]-4-[6-(1-methyl-1H-pyrrol-2-yl)pyridin-3-yl]-N-[(2S)-1-(methylamino)propan-2-yl]piperidine-4-carboxamide;

1-299: 1-[2-chloro-4-(trifluoromethyl)phenyl]-4-{2'-ethoxy-3-fluoro-[2,3'-bipyridin]-5-yl}-N-[2-(methylamino)ethyl]piperidine-4-carboxamide;

1-300: N-[2-(dimethylamino)ethyl]-4-{3-fluoro-2'-methoxy-[2,3'-bipyridin]-5-yl}-1-[2-fluoro-4-(trifluoromethyl)phenyl]piperidine-4-carboxamide;

1-301: 4-{3-fluoro-2'-methoxy-[2,3'-bipyridin]-5-yl}-1-[2-fluoro-4-(trifluoromethyl)phenyl]-N-[2-(methylamino)ethyl]piperidine-4-carboxamide;

1-302: 1-[2-chloro-4-(trifluoromethyl)phenyl]-N-[2-(dimethylamino)ethyl]-4-{3-fluoro-2'-methoxy-[2,3'-bipyridin]-5-yl}piperidine-4-carboxamide;

1-303: 1-[2-chloro-4-(trifluoromethyl)phenyl]-4-{3-fluoro-2'-methoxy-[2,3'-bipyridin]-5-yl}-N-[2-(methylamino)ethyl]piperidine-4-carboxamide;

1-304: N-[2-(dimethylamino)ethyl]-1-[2-fluoro-4-(trifluoromethyl)phenyl]-4-[5-fluoro-6-(1-methyl-1H-pyrrol-2-yl)pyridin-3-yl]piperidine-4-carboxamide;

1-305: 1-[2-fluoro-4-(trifluoromethyl)phenyl]-4-[5-fluoro-6-(1-methyl-1H-pyrrol-2-yl)pyridin-3-yl]-N-[2-(methylamino)ethyl]piperidine-4-carboxamide;

1-306: 1-[2-fluoro-4-(trifluoromethyl)phenyl]-4-{2'-methoxy-[2,3'-bipyridin]-5-yl}-N-[(2S)-1-(methylamino)propan-2-yl]piperidine-4-carboxamide;

1-307: 1-[2-chloro-4-(trifluoromethyl)phenyl]-4-{2'-methoxy-[2,3'-bipyridin]-5-yl}-N-[(2S)-1-(methylamino)propan-2-yl]piperidine-4-carboxamide;

1-308: 1-[2-cyano-4-(trifluoromethyl)phenyl]-N-[2-(dimethylamino)ethyl]-4-{2'-ethoxy-3-fluoro-[2,3'-bipyridin]-5-yl}piperidine-4-carboxamide;

1-309: 1-[2-chloro-4-(trifluoromethyl)phenyl]-N-[2-(dimethylamino)ethyl]-4-[5-fluoro-6-(1-methyl-1H-pyrrol-2-yl)pyridin-3-yl]piperidine-4-carboxamide;

1-310: 1-[2-chloro-4-(trifluoromethyl)phenyl]-4-[5-fluoro-6-(1-methyl-1H-pyrrol-2-yl)pyridin-3-yl]-N-[2-(methylamino)ethyl]piperidine-4-carboxamide;

1-311: 1-[2-cyano-4-(trifluoromethyl)phenyl]-4-{2'-ethoxy-3-fluoro-[2,3'-bipyridin]-5-yl}-N-[2-(methylamino)ethyl]piperidine-4-carboxamide;

1-312: N-[(2S)-1-(dimethylamino)propan-2-yl]-4-{2'-ethoxy-3-fluoro-[2,3'-bipyridin]-5-yl}-1-[2-fluoro-4-(trifluoromethyl)phenyl]piperidine-4-carboxamide;

1-313: 1-[2-cyano-4-(trifluoromethyl)phenyl]-N-[(2S)-1-(dimethylamino)propan-2-yl]-4-{2'-ethoxy-[2,3'-bipyridin]-5-yl}piperidine-4-carboxamide;

1-314: 1-[2-cyano-4-(trifluoromethyl)phenyl]-4-{2'-ethoxy-[2,3'-bipyridin]-5-yl}-N-[(2S)-1-(methylamino)propan-2-yl]piperidine-4-carboxamide;

1-315: 4-{2'-ethoxy-3-fluoro-[2,3'-bipyridin]-5-yl}-1-[2-fluoro-4-(trifluoromethyl)phenyl]-N-[(2S)-1-(methylamino)propan-2-yl]piperidine-4-carboxamide;

1-316: 1-[2-cyano-4-(trifluoromethyl)phenyl]-4-[6-(1-methyl-1H-pyrrol-2-yl)pyridin-3-yl]-N-[(2S)-1-(methylamino)propan-2-yl]piperidine-4-carboxamide;

1-317: N-[(2S)-1-(dimethylamino)propan-2-yl]-4-{2'-ethoxy-[2,3'-bipyridin]-5-yl}-1-[2-fluoro-4-(trifluoromethyl)phenyl]piperidine-4-carboxamide;

1-318: 1-(2,4-dichlorophenyl)-N-[(2S)-1-(dimethylamino)propan-2-yl]-4-{2'-ethoxy-[2,3'-bipyridin]-5-yl}piperidine-4-carboxamide;

1-319: 1-[2-cyano-4-(trifluoromethyl)phenyl]-N-[(2S)-1-(dimethylamino)propan-2-yl]-4-{2'-ethoxy-3-fluoro-[2,3'-bipyridin]-5-yl}piperidine-4-carboxamide;

1-320: 1-[2-cyano-4-(trifluoromethyl)phenyl]-4-{2'-ethoxy-3-fluoro-[2,3'-bipyridin]-5-yl}-N-[(2S)-1-(methylamino)propan-2-yl]piperidine-4-carboxamide;

1-321: 4-{2'-ethoxy-[2,3'-bipyridin]-5-yl}-1-[2-fluoro-4-(trifluoromethyl)phenyl]-N-[(2S)-1-(methylamino)propan-2-yl]piperidine-4-carboxamide;

1-322: 1-(2,4-dichlorophenyl)-4-{2'-ethoxy-[2,3'-bipyridin]-5-yl}-N-[(2S)-1-(methylamino)propan-2-yl]piperidine-4-carboxamide;

1-323: 1-(4-chloro-2-cyanophenyl)-4-{2'-ethoxy-3-fluoro-[2,3'-bipyridin]-5-yl}-N-[(2S)-1-(methylamino)propan-2-yl]piperidine-4-carboxamide;

1-324: 1-[2-cyano-4-(trifluoromethyl)phenyl]-N-[(2S)-1-(dimethylamino)propan-2-yl]-4-[5-fluoro-6-(1-methyl-1H-pyrrol-2-yl)pyridin-3-yl]piperidine-4-carboxamide;

1-325: 1-(4-chloro-2-cyanophenyl)-N-[(2S)-1-(dimethylamino)propan-2-yl]-4-{2'-ethoxy-3-fluoro-[2,3'-bipyridin]-5-yl}piperidine-4-carboxamide;

1-326: 1-[2-cyano-4-(trifluoromethyl)phenyl]-4-[5-fluoro-6-(1-methyl-1H-pyrrol-2-yl)pyridin-3-yl]-N-[(2S)-1-(methylamino)propan-2-yl]piperidine-4-carboxamide;

1-327: 1-[2-cyano-4-(trifluoromethyl)phenyl]-4-[6-(2-methoxyphenyl)pyridin-3-yl]-N-{[(2S)-4-methylmorpholin-2-yl]methyl}piperidine-4-carboxamide;

1-328: 1-[2-cyano-4-(trifluoromethyl)phenyl]-4-[6-(2-methoxyphenyl)pyridin-3-yl]-N-{[(3S)-4-methylmorpholin-3-yl]methyl}piperidine-4-carboxamide;

1-329: 1-[2-cyano-4-(trifluoromethyl)phenyl]-4-[6-(2-methoxyphenyl)pyridin-3-yl]-N-{[(3R)-4-methylmorpholin-3-yl]methyl}piperidine-4-carboxamide;

1-330: 1-[2-cyano-4-(trifluoromethyl)phenyl]-4-[6-(2-methoxyphenyl)pyridin-3-yl]-N-{[(2R)-4-methylmorpholin-2-yl]methyl}piperidine-4-carboxamide;

1-331: 1-[2-cyano-4-(trifluoromethyl)phenyl]-N-[2-(dimethylamino)ethyl]-4-[6-(2-ethoxypyridin-3-yl)pyridazin-3-yl]piperidine-4-carboxamide;

1-332: 1-[2-cyano-4-(trifluoromethyl)phenyl]-N-[(2S)-2-(dimethylamino)propyl]-4-{2'-ethoxy-[2,3'-bipyridin]-5-yl}piperidine-4-carboxamide;

1-333: 1-[2-cyano-4-(trifluoromethyl)phenyl]-N-[(2R)-2-(dimethylamino)propyl]-4-{2'-ethoxy-[2,3'-bipyridin]-5-yl}piperidine-4-carboxamide;

1-334: 1-[2-cyano-4-(trifluoromethyl)phenyl]-N-[(2R)-2-(dimethylamino)-3-hydroxypropyl]-4-{2'-ethoxy-3-fluoro-[2,3'-bipyridin]-5-yl}piperidine-4-carboxamide;

1-335: N-[2-(dimethylamino)ethyl]-4-[6-(2-ethoxypyridin-3-yl)pyridazin-3-yl]-1-[2-fluoro-4-(trifluoromethyl)phenyl]piperidine-4-carboxamide.

TABLE 2
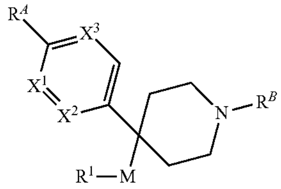
| Cpd No. | $R^A$ | $X^1$ | $X^2$ | $X^3$ | $R^B$ | $R^1$ | —M— |
|---|---|---|---|---|---|---|---|
| 2-1 | 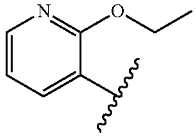 [SMILES: *c1cccnc1OCC] | CH | CH | CH | 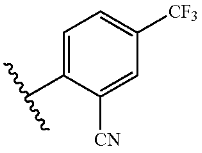 [SMILES: *c1ccc(C(F)(F)F)cc1C#N] | 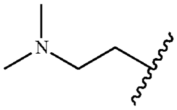 [SMILES: *CCN(C)C] | —O— |
| 2-2 | 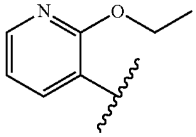 | CH | CH | CH | 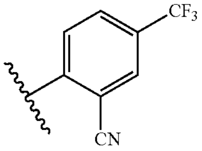 [SMILES: *c1ccc(C(F)(F)F)cc1C#N] | 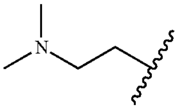 [SMILES: *CCN(C)C] | 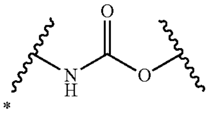 |
| 2-3 | 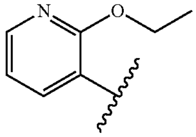 [SMILES: *c1cccnc1OCC] | CH | CH | CH | 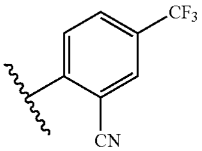 [SMILES: *c1ccc(C(F)(F)F)cc1C#N] | 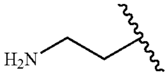 | 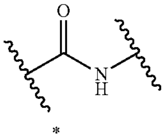 |
| 2-4 | 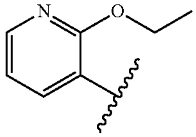 [SMILES: *c1cccnc1OCC] | N | CH | CH | 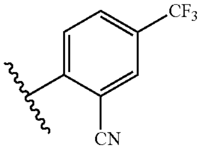 [SMILES: *c1ccc(C(F)(F)F)cc1C#N] | 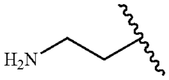 | 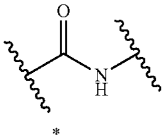 [SMILES: *NC(*)=O] |
| 2-5 | 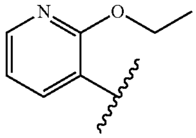 [SMILES: *c1cccnc1OCC] | N | CH | CH | 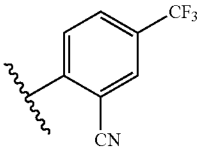 [SMILES: *c1ccc(C(F)(F)F)cc1C#N] | 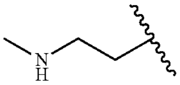 | 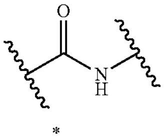 |
| 2-6 | 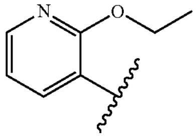 [SMILES: *c1cccnc1OCC] | N | CH | CH | 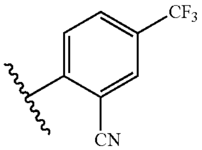 [SMILES: *c1ccc(C(F)(F)F)cc1C#N] | 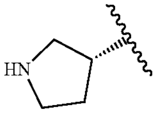 [SMILES: *[C@@H]1CCNC1] | 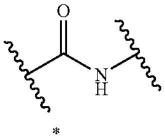 [SMILES: *NC(*)=O] |
| 2-7 | 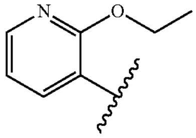 [SMILES: *c1cccnc1OCC] | N | CH | CH | 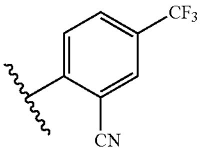 [SMILES: *c1ccc(C(F)(F)F)cc1C#N] | 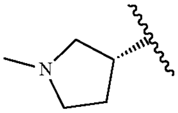 [SMILES: *[C@@H]1CCN(C)C1] | 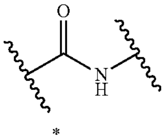 [SMILES: *NC(*)=O] |
| 2-8 | 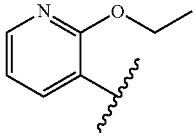 [SMILES: *c1cccnc1OCC] | N | CH | CH | 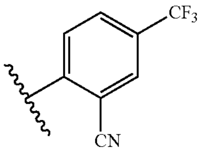 [SMILES: *c1ccc(C(F)(F)F)cc1C#N] | 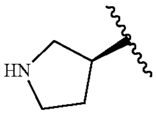 [SMILES: *[C@H]1CCNC1] | 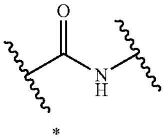 |

TABLE 2-continued
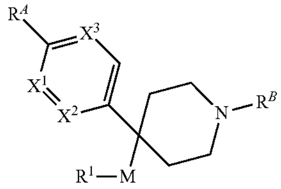
| Cpd No. | $R^A$ | $X^1$ | $X^2$ | $X^3$ | $R^B$ | $R^1$ | —M— |
|---|---|---|---|---|---|---|---|
| 2-9 | 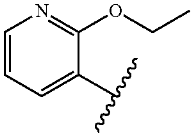 [SMILES: *c1cccnc1OCC] | N | CH | CH | 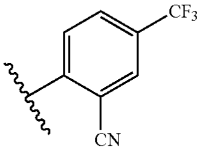 [SMILES: *c1ccc(C(F)(F)F)cc1C#N] | 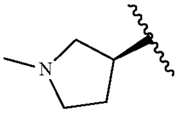 [SMILES: *[C@H]1CCN(C)C1] | 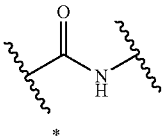 [SMILES: *NC(*)=O] |
| 2-10 | 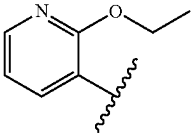 | N | CH | CH | 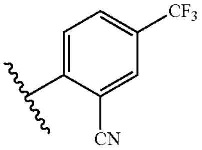 [SMILES: *c1ccc(C(F)(F)F)cc1C#N] | 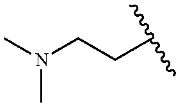 [SMILES: *CCN(C)C] | 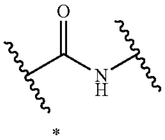 |
| 2-11 | 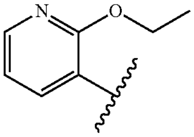 [SMILES: *c1cccnc1OCC] | CH | CH | CH | 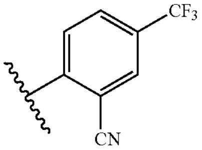 [SMILES: *c1ccc(C(F)(F)F)cc1C#N] | 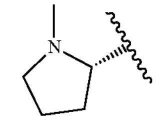 [SMILES: *[C@@H]1CCCN1C] | 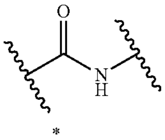 |
| 2-12 | 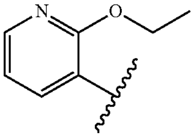 [SMILES: *c1cccnc1OCC] | CH | CH | CH | 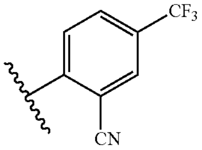 [SMILES: *c1ccc(C(F)(F)F)cc1C#N] | 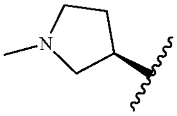 [SMILES: *[C@@H]1CCN(C)C1] | 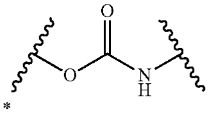 |
| 2-13 | 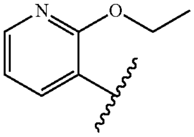 [SMILES: *c1cccnc1OCC] | CH | CH | CH | 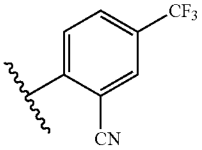 [SMILES: *c1ccc(C(F)(F)F)cc1C#N] | 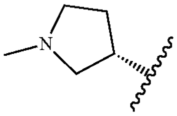 [SMILES: *[C@H]1CCN(C)C1] | 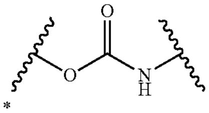 |
| 2-14 | 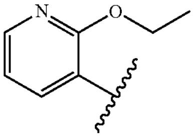 [SMILES: *c1cccnc1OCC] | N | CH | CH | 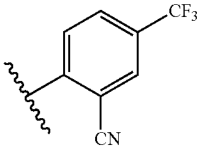 [SMILES: *c1ccc(C(F)(F)F)cc1C#N] | 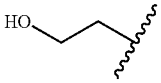 | —NH— |
| 2-15 | 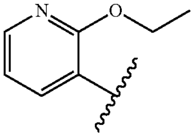 [SMILES: *c1cccnc1OCC] | N | CH | CH | 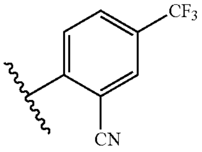 [SMILES: *c1ccc(C(F)(F)F)cc1C#N] | 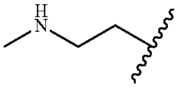 | —NH— |
| 2-16 | 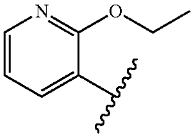 [SMILES: *c1cccnc1OCC] | CH | CH | CH | 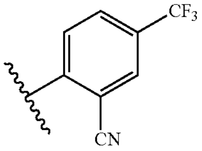 [SMILES: *c1ccc(C(F)(F)F)cc1C#N] | 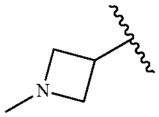 [SMILES: *C1CN(C)C1] | 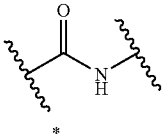 [SMILES: *NC(*)=O] |

TABLE 2-continued
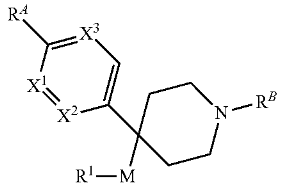
| Cpd No. | $R^A$ | $X^1$ | $X^2$ | $X^3$ | $R^B$ | $R^1$ | —M— |
|---|---|---|---|---|---|---|---|
| 2-17 | 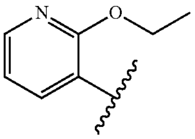 [SMILES: *c1cccnc1OCC] | CH | CH | CH | 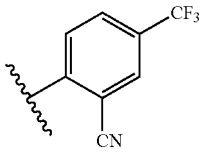 [SMILES: *c1ccc(C(F)(F)F)cc1C#N] | 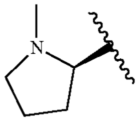 [SMILES: *[C@H]1CCCN1C] | 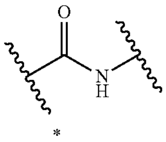 |
| 2-18 | 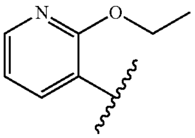 [SMILES: *c1cccnc1OCC] | N | CH | CH | 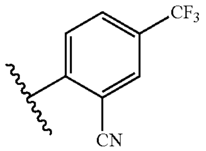 [SMILES: *c1ccc(C(F)(F)F)cc1C#N] | 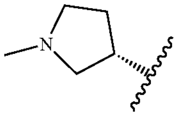 | 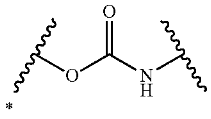 |
| 2-19 | 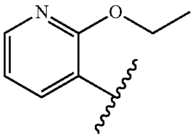 [SMILES: *c1cccnc1OCC] | N | CH | CH | 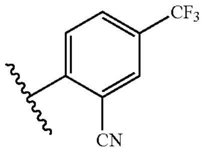 [SMILES: *c1ccc(C(F)(F)F)cc1C#N] | 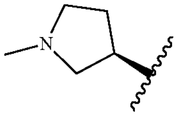 [SMILES: *[C@@H]1CCN(C)C1] | 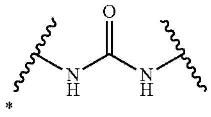 [SMILES: *NC(=O)N*] |
| 2-20 | 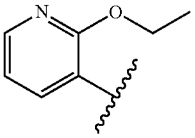 [SMILES: *c1cccnc1OCC] | N | CH | CH | 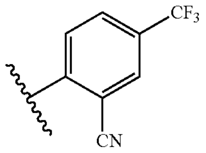 [SMILES: *c1ccc(C(F)(F)F)cc1C#N] | 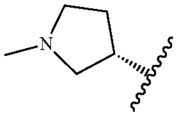 [SMILES: *[C@H]1CCN(C)C1] | 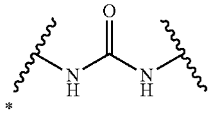 |
| 2-21 | 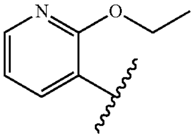 [SMILES: *c1cccnc1OCC] | N | CH | CH | 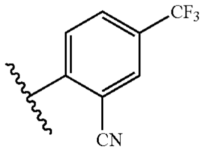 [SMILES: *c1ccc(C(F)(F)F)cc1C#N] | 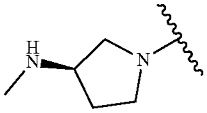 [SMILES: *N1CC[C@@H](NC)C1] | 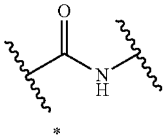 |
| 2-22 | 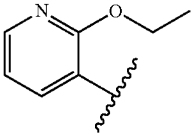 [SMILES: *c1cccnc1OCC] | N | CH | CH | 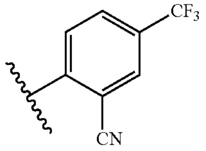 [SMILES: *c1ccc(C(F)(F)F)cc1C#N] | 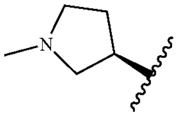 [SMILES: *[C@@H]1CCN(C)C1] | 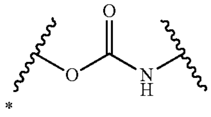 |
| 2-23 | 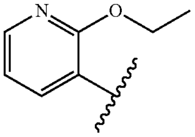 [SMILES: *c1cccnc1OCC] | N | CH | CH | 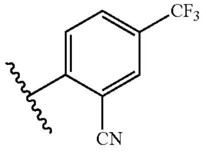 [SMILES: *c1ccc(C(F)(F)F)cc1C#N] | 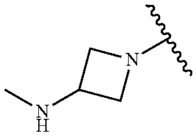 [SMILES: *N1CC(NC)C1] | 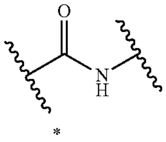 |
| 2-24 | 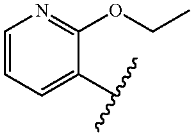 [SMILES: *c1cccnc1OCC] | N | CH | CH | 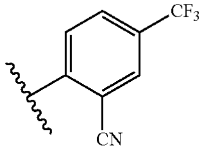 [SMILES: *c1ccc(C(F)(F)F)cc1C#N] | 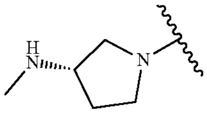 [SMILES: *N1CC[C@H](NC)C1] | 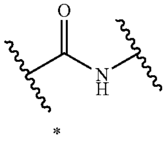 [SMILES: *NC(*)=O] |

TABLE 2-continued
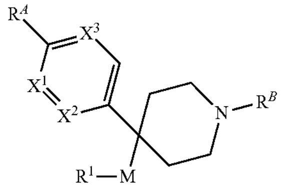
| Cpd No. | $R^A$ | $X^1$ | $X^2$ | $X^3$ | $R^B$ | $R^1$ | —M— |
|---|---|---|---|---|---|---|---|
| 2-25 | 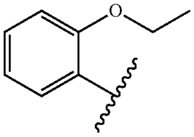 [SMILES: *c1ccccc1OCC] | N | CH | CH | 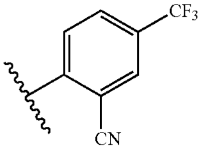 [SMILES: *c1ccc(C(F)(F)F)cc1C#N] | 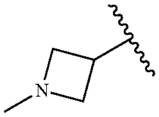 [SMILES: *C1CN(C)C1] | 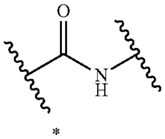 |
| 2-26 | 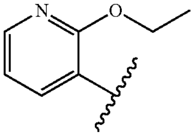 [SMILES: *c1cccnc1OCC] | N | CH | CH | 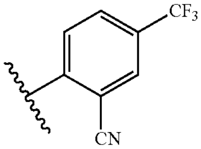 [SMILES: *c1ccc(C(F)(F)F)cc1C#N] | 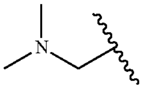 [SMILES: *CN(C)C] | 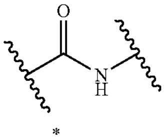 [SMILES: *NC(*)=O] |
| 2-27 | 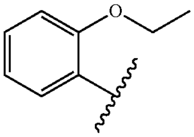 [SMILES: *c1ccccc1OCC] | N | CH | CH | 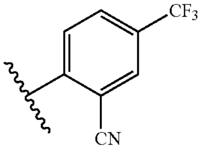 [SMILES: *c1ccc(C(F)(F)F)cc1C#N] | 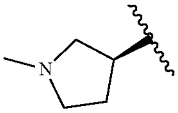 [SMILES: *[C@H]1CCN(C)C1] | 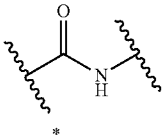 |
| 2-28 | 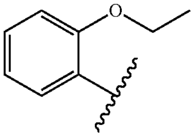 [SMILES: *c1ccccc1OCC] | N | CH | CH | 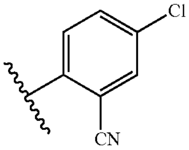 [SMILES: *c1ccc(Cl)cc1C#N] | 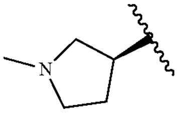 [SMILES: *[C@H]1CCN(C)C1] | 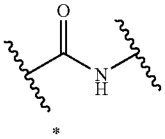 |
| 2-29 | 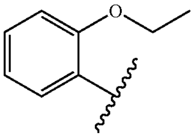 [SMILES: *c1ccccc1OCC] | N | CH | CH | 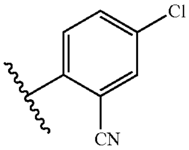 | 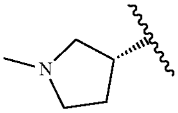 [SMILES: *[C@@H]1CCN(C)C1] | 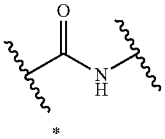 |
| 2-30 | 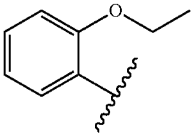 [SMILES: *c1ccccc1OCC] | N | CH | CH | 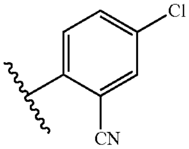 [SMILES: *c1ccc(Cl)cc1C#N] | 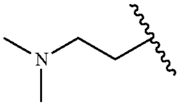 [SMILES: *CCN(C)C] | 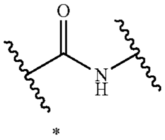 |
| 2-31 | 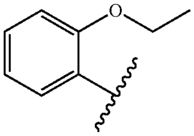 [SMILES: *c1ccccc1OCC] | N | CH | CH | 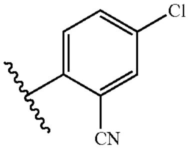 | 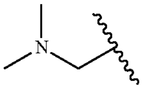 [SMILES: *CN(C)C] | 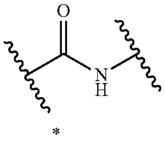 |
| 2-32 | 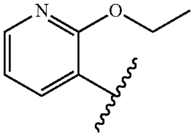 [SMILES: *c1cccnc1OCC] | N | CH | CH | 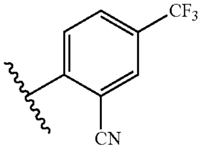 [SMILES: *c1ccc(C(F)(F)F)cc1C#N] | 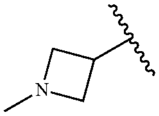 [SMILES: *C1CN(C)C1] | 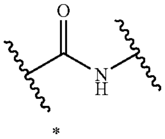 |

TABLE 2-continued
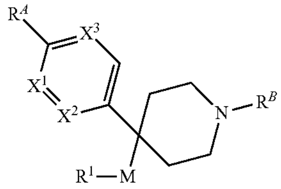
| Cpd No. | $R^A$ | $X^1$ | $X^2$ | $X^3$ | $R^B$ | $R^1$ | —M— |
|---|---|---|---|---|---|---|---|
| 2-33 | 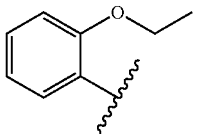 [SMILES: *c1ccccc1OCC] | N | CH | CH | 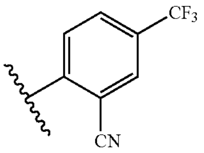 [SMILES: *c1ccc(C(F)(F)F)cc1C#N] | 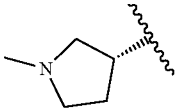 [SMILES: *[C@@H]1CCN(C)C1] | 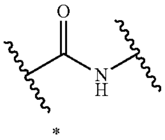 |
| 2-34 | 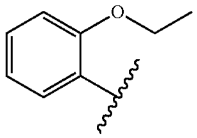 [SMILES: *c1ccccc1OCC] | N | CH | CH | 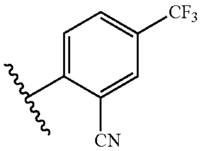 [SMILES: *c1ccc(C(F)(F)F)cc1C#N] | 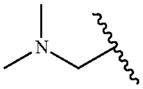 | 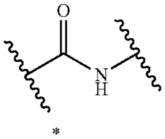 |
| 2-35 | 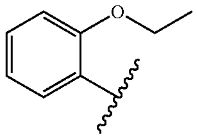 [SMILES: *c1ccccc1OCC] | N | CH | CH | 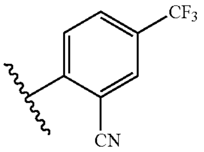 [SMILES: *c1ccc(C(F)(F)F)cc1C#N] | 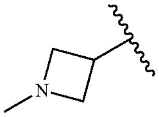 | 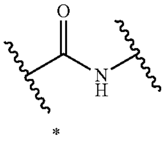 |
| 2-36 | 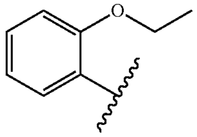 [SMILES: *c1ccccc1OCC] | N | CH | CH | 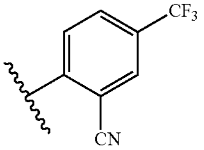 [SMILES: *c1ccc(C(F)(F)F)cc1C#N] | 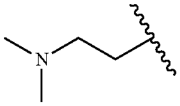 [SMILES: *CCN(C)C] | 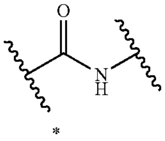 |
| 2-37 | 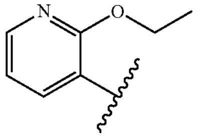 [SMILES: *c1cccnc1OCC] | N | CH | CH | 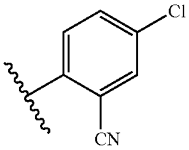 | 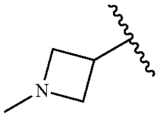 [SMILES: *C1CN(C)C1] | 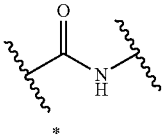 |
| 2-38 | 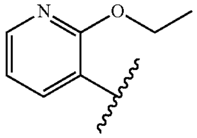 [SMILES: *c1cccnc1OCC] | N | CH | CH | 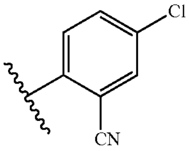 [SMILES: *c1ccc(Cl)cc1C#N] | 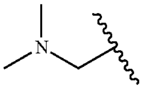 | 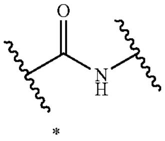 |
| 2-39 | 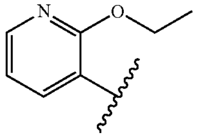 [SMILES: *c1cccnc1OCC] | N | CH | CH | 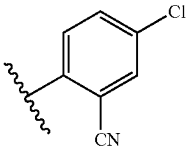 | 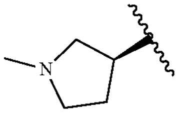 [SMILES: *[C@H]1CCN(C)C1] | 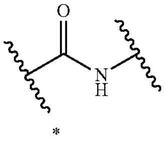 |
| 2-40 | 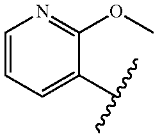 [SMILES: *c1cccnc1OC] | N | CH | CH | 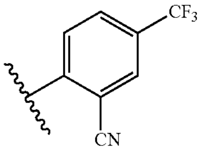 [SMILES: *c1ccc(C(F)(F)F)cc1C#N] | 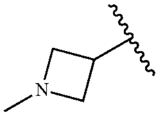 [SMILES: *C1CN(C)C1] | 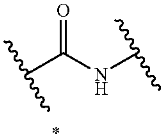 |

TABLE 2-continued
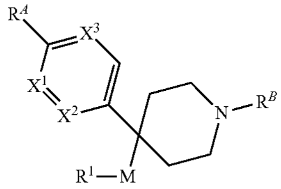
| Cpd No. | $R^A$ | $X^1$ | $X^2$ | $X^3$ | $R^B$ | $R^1$ | —M— |
|---|---|---|---|---|---|---|---|
| 2-41 | 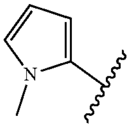 [SMILES: *c1cccn1C] | N | CH | CH | 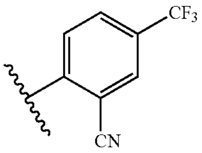 [SMILES: *c1ccc(C(F)(F)F)cc1C#N] | 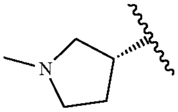 [SMILES: *[C@@H]1CCN(C)C1] | 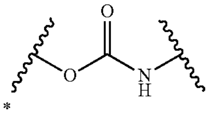 [SMILES: *NC(=O)O*] |
| 2-42 | 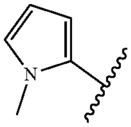 [SMILES: *c1cccn1C] | N | CH | CH | 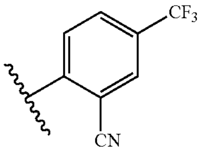 [SMILES: *c1ccc(C(F)(F)F)cc1C#N] | 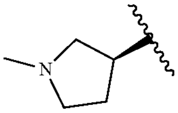 [SMILES: *[C@H]1CCN(C)C1] | 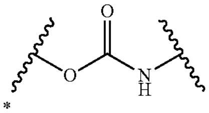 |
| 2-43 | 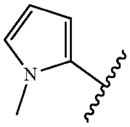 [SMILES: *c1cccn1C] | N | CH | CH | 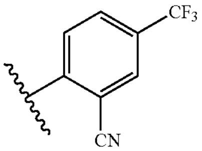 [SMILES: *c1ccc(C(F)(F)F)cc1C#N] | 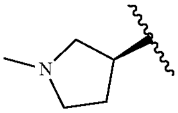 [SMILES: *[C@H]1CCN(C)C1] | 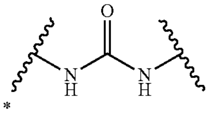 |
| 2-44 | 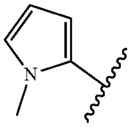 [SMILES: *c1cccn1C] | N | CH | CH | 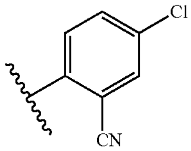 [SMILES: *c1ccc(Cl)cc1C#N] | 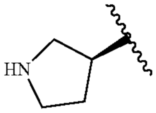 | 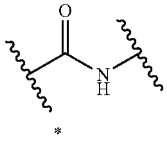 |
| 2-45 | 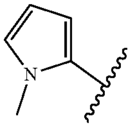 [SMILES: *c1cccn1C] | N | CH | CH | 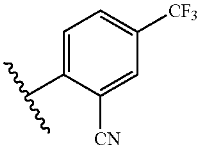 [SMILES: *c1ccc(C(F)(F)F)cc1C#N] | 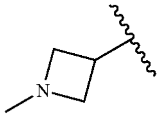 [SMILES: *C1CN(C)C1] | 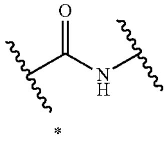 |
| 2-46 | 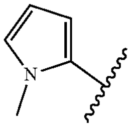 [SMILES: *c1cccn1C] | N | CH | CH | 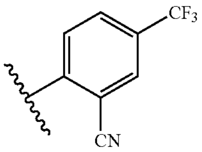 [SMILES: *c1ccc(C(F)(F)F)cc1C#N] | 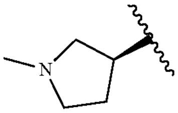 [SMILES: *[C@H]1CCN(C)C1] | 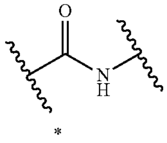 |
| 2-47 | 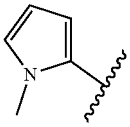 [SMILES: *c1cccn1C] | N | CH | CH | 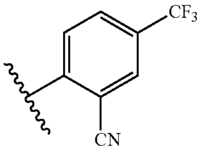 [SMILES: *c1ccc(C(F)(F)F)cc1C#N] | 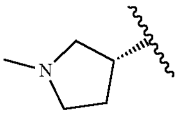 [SMILES: *[C@@H]1CCN(C)C1] | 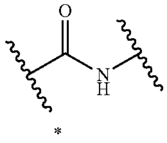 |
| 2-48 | 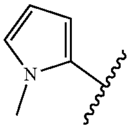 | N | CH | CH | 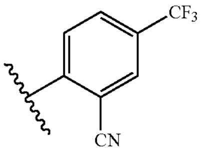 [SMILES: *c1ccc(C(F)(F)F)cc1C#N] | 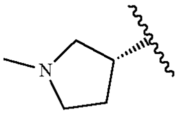 [SMILES: *[C@@H]1CCN(C)C1] | 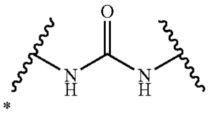 |

TABLE 2-continued
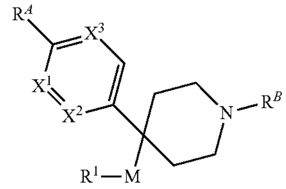
| Cpd No. | $R^A$ | $X^1$ | $X^2$ | $X^3$ | $R^B$ | $R^1$ | —M— |
|---|---|---|---|---|---|---|---|
| 2-49 | 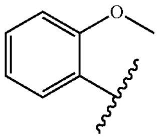 [SMILES: *c1ccccc1OC] | N | CH | CF | 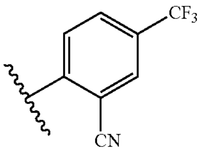 [SMILES: *c1ccc(C(F)(F)F)cc1C#N] | 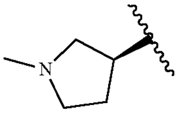 [SMILES: *[C@H]1CCN(C)C1] | 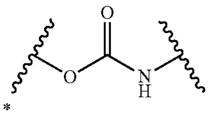 [SMILES: *NC(=O)O*] |
| 2-50 | 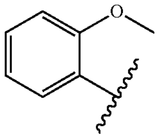 [SMILES: *c1ccccc1OC] | N | CH | CF | 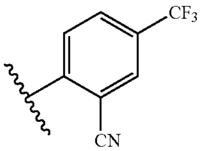 [SMILES: *c1ccc(C(F)(F)F)cc1C#N] | 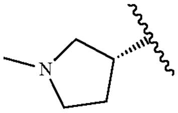 [SMILES: *[C@@H]1CCN(C)C1] | 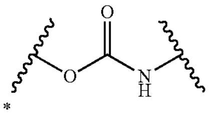 |
| 2-51 | 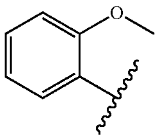 [SMILES: *c1ccccc1OC] | N | CH | CF | 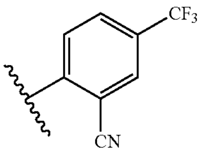 [SMILES: *c1ccc(C(F)(F)F)cc1C#N] | 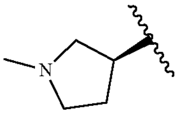 [SMILES: *[C@H]1CCN(C)C1] | 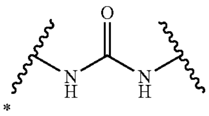 [SMILES: *NC(=O)N*] |
| 2-52 | 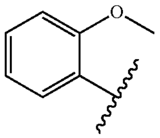 [SMILES: *c1ccccc1OC] | N | CH | CF | 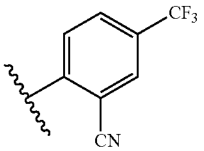 [SMILES: *c1ccc(C(F)(F)F)cc1C#N] | 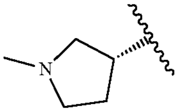 [SMILES: *[C@@H]1CCN(C)C1] | 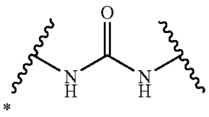 |
| 2-53 | 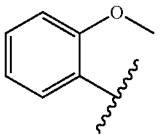 [SMILES: *c1ccccc1OC] | N | CH | CH | 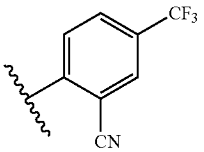 [SMILES: *c1ccc(C(F)(F)F)cc1C#N] | 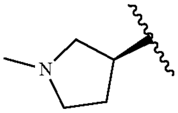 [SMILES: *[C@H]1CCN(C)C1] | 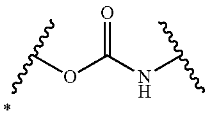 [SMILES: *NC(=O)O*] |
| 2-54 | 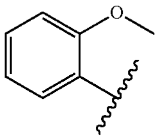 [SMILES: *c1ccccc1OC] | N | CH | CH | 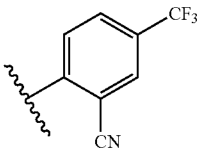 [SMILES: *c1ccc(C(F)(F)F)cc1C#N] | 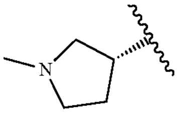 [SMILES: *[C@@H]1CCN(C)C1] | 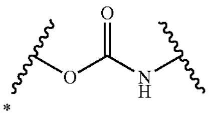 |
| 2-55 | 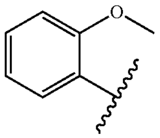 [SMILES: *c1ccccc1OC] | N | CH | CH | 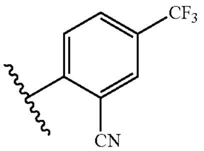 [SMILES: *c1ccc(C(F)(F)F)cc1C#N] | 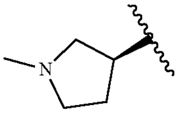 [SMILES: *[C@H]1CCN(C)C1] | 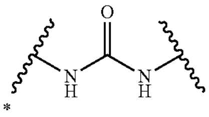 [SMILES: *NC(=O)N*] |
| 2-56 | 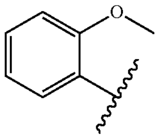 [SMILES: *c1ccccc1OC] | N | CH | CH | 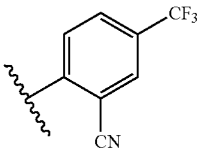 [SMILES: *c1ccc(C(F)(F)F)cc1C#N] | 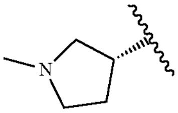 [SMILES: *[C@@H]1CCN(C)C1] | 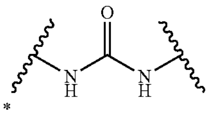 |

TABLE 2-continued
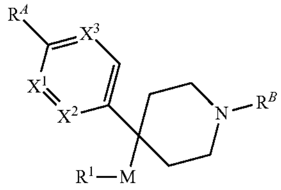
| Cpd No. | $R^A$ | $X^1$ | $X^2$ | $X^3$ | $R^B$ | $R^1$ | —M— |
|---|---|---|---|---|---|---|---|
| 2-57 | 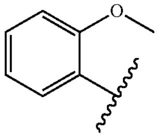 [SMILES: *c1ccccc1OC] | N | CH | CH | 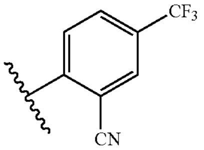 [SMILES: *c1ccc(C(F)(F)F)cc1C#N] | 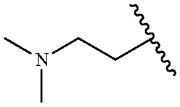 [SMILES: *CCN(C)C] | 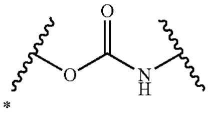 |
| 2-58 | 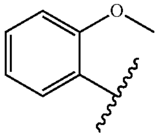 [SMILES: *c1ccccc1OC] | N | CH | CH | 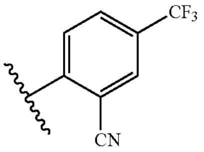 [SMILES: *c1ccc(C(F)(F)F)cc1C#N] | 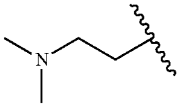 [SMILES: *CCN(C)C] | 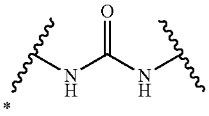 |
| 2-59 | 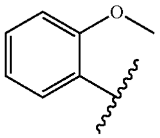 [SMILES: *c1ccccc1OC] | N | CH | CH | 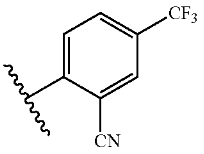 [SMILES: *c1ccc(C(F)(F)F)cc1C#N] | 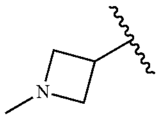 [SMILES: *C1CN(C)C1] | 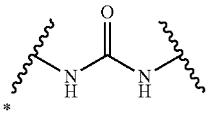 [SMILES: *NC(=O)N*] |
| 2-60 | 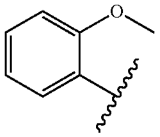 [SMILES: *c1ccccc1OC] | N | CH | CH | 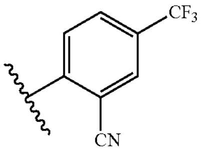 [SMILES: *c1ccc(C(F)(F)F)cc1C#N] | 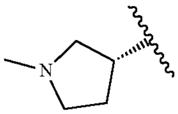 [SMILES: *[C@@H]1CCN(C)C1] | 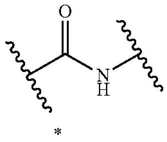 |
| 2-61 | 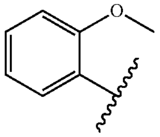 [SMILES: *c1ccccc1OC] | N | CH | CF | 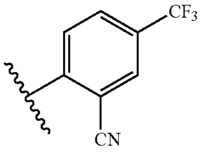 [SMILES: *c1ccc(C(F)(F)F)cc1C#N] | 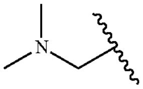 [SMILES: *CN(C)C] | 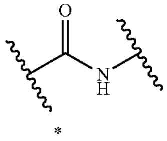 |
| 2-62 | 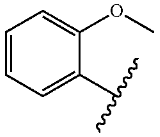 [SMILES: *c1ccccc1OC] | N | CH | CF | 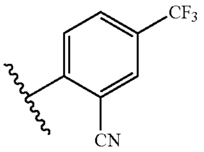 [SMILES: *c1ccc(C(F)(F)F)cc1C#N] | 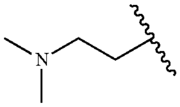 | 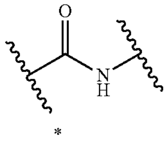 |
| 2-63 | 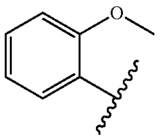 [SMILES: *c1ccccc1OC] | N | CH | CF | 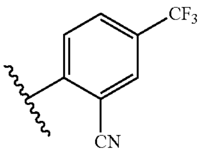 [SMILES: *c1ccc(C(F)(F)F)cc1C#N] | 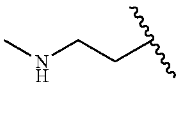 [SMILES: *CCNC] | 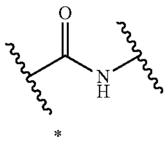 [SMILES: *NC(*)=O] |
| 2-64 | 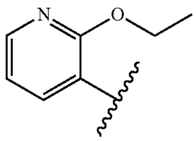 [SMILES: *c1cccnc1OCC] | N | N | CH | 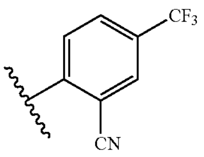 [SMILES: *c1ccc(C(F)(F)F)cc1C#N] | 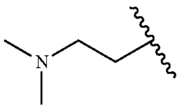 [SMILES: *CCN(C)C] | 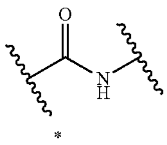 |
*attachment point to $R^1$ Compounds in Table 2 are named:

2-1: 2-{4-[2-(dimethylamino)ethoxy]-4-[4-(2-ethoxypyridin-3-yl)phenyl]piperidin-1-yl}-5-(trifluoromethyl)benzonitrile;

2-2: 1-[2-cyano-4-(trifluoromethyl)phenyl]-4-[4-(2-ethoxypyridin-3-yl)phenyl]piperidin-4-yl N-[2-(dimethylamino)ethyl]carbamate;

2-3: 3-amino-N-{1-[2-cyano-4-(trifluoromethyl)phenyl]-4-[4-(2-ethoxypyridin-3-yl)phenyl]piperidin-4-yl}propanamide;

2-4: 3-amino-N-{1-[2-cyano-4-(trifluoromethyl)phenyl]-4-{2'-ethoxy-[2,3'-bipyridin]-5-yl}piperidin-4-yl}propanamide;

2-5: N-{1-[2-cyano-4-(trifluoromethyl)phenyl]-4-{2'-ethoxy-[2,3'-bipyridin]-5-yl}piperidin-4-yl}-3-(methylamino)propanamide;

2-6: (3R)—N-{1-[2-cyano-4-(trifluoromethyl)phenyl]-4-{2'-ethoxy-[2,3'-bipyridin]-5-yl}piperidin-4-yl}pyrrolidine-3-carboxamide;

2-7: (3R)—N-{1-[2-cyano-4-(trifluoromethyl)phenyl]-4-{2'-ethoxy-[2,3'-bipyridin]-5-yl}piperidin-4-yl}-1-methylpyrrolidine-3-carboxamidev;

2-8: (3S)—N-{1-[2-cyano-4-(trifluoromethyl)phenyl]-4-{2'-ethoxy-[2,3'-bipyridin]-5-yl}piperidin-4-yl}pyrrolidine-3-carboxamide;

2-9: (3S)—N-{1-[2-cyano-4-(trifluoromethyl)phenyl]-4-{2'-ethoxy-[2,3'-bipyridin]-5-yl}piperidin-4-yl}-1-methylpyrrolidine-3-carboxamide;

2-10: N-{1-[2-cyano-4-(trifluoromethyl)phenyl]-4-{2'-ethoxy-[2,3'-bipyridin]-5-yl}piperidin-4-yl}-3-(dimethylamino)propanamide;

2-11: (2S)—N-{1-[2-cyano-4-(trifluoromethyl)phenyl]-4-[4-(2-ethoxypyridin-3-yl)phenyl]piperidin-4-yl}-1-methylpyrrolidine-2-carboxamide;

2-12: (3R)-1-methylpyrrolidin-3-yl N-{1-[2-cyano-4-(trifluoromethyl)phenyl]-4-[4-(2-ethoxypyridin-3-yl)phenyl]piperidin-4-yl}carbamate;

2-13: (3S)-1-methylpyrrolidin-3-yl N-{1-[2-cyano-4-(trifluoromethyl)phenyl]-4-[4-(2-ethoxypyridin-3-yl)phenyl]piperidin-4-yl}carbamate;

2-14: 2-(4-{2'-ethoxy-[2,3'-bipyridin]-5-yl}-4-[(2-hydroxyethyl)amino]piperidin-1-yl)-5-(trifluoromethyl)benzonitrile;

2-15: 2-(4-{2'-ethoxy-[2,3'-bipyridin]-5-yl}-4-{[2-(methylamino)ethyl]amino}piperidin-1-yl)-5-(trifluoromethyl)benzonitrile;

2-16: N-{1-[2-cyano-4-(trifluoromethyl)phenyl]-4-[4-(2-ethoxypyridin-3-yl)phenyl]piperidin-4-yl}-1-methylazetidine-3-carboxamide;

2-17: (2R)—N-{1-[2-cyano-4-(trifluoromethyl)phenyl]-4-[4-(2-ethoxypyridin-3-yl)phenyl]piperidin-4-yl}-1-methylpyrrolidine-2-carboxamide;

2-18: (3S)-1-methylpyrrolidin-3-yl N-{1-[2-cyano-4-(trifluoromethyl)phenyl]-4-{2'-ethoxy-[2,3'-bipyridin]-5-yl}piperidin-4-yl}carbamate;

2-19: 1-{1-[2-cyano-4-(trifluoromethyl)phenyl]-4-{2'-ethoxy-[2,3'-bipyridin]-5-yl}piperidin-4-yl}-3-[(3R)-1-methylpyrrolidin-3-yl]urea;

2-20: 1-{1-[2-cyano-4-(trifluoromethyl)phenyl]-4-{2'-ethoxy-[2,3'-bipyridin]-5-yl}piperidin-4-yl}-3-[(3S)-1-methylpyrrolidin-3-yl]urea;

2-21: (3R)—N-{1-[2-cyano-4-(trifluoromethyl)phenyl]-4-{2'-ethoxy-[2,3'-bipyridin]-5-yl}piperidin-4-yl}-3-(methylamino)pyrrolidine-1-carboxamide;

2-22: (3R)-1-methylpyrrolidin-3-yl N-{1-[2-cyano-4-(trifluoromethyl)phenyl]-4-{2'-ethoxy-[2,3'-bipyridin]-5-yl}piperidin-4-yl}carbamate;

2-23: N-{1-[2-cyano-4-(trifluoromethyl)phenyl]-4-{2'-ethoxy-[2,3'-bipyridin]-5-yl}piperidin-4-yl}-3-(methylamino)azetidine-1-carboxamide;

2-24: (3S)—N-{1-[2-cyano-4-(trifluoromethyl)phenyl]-4-{2'-ethoxy-[2,3'-bipyridin]-5-yl}piperidin-4-yl}-3-(methylamino)pyrrolidine-1-carboxamide;

2-25: N-[1-(4-chloro-2-cyanophenyl)-4-[6-(2-ethoxyphenyl)pyridin-3-yl]piperidin-4-yl]-1-methylazetidine-3-carboxamide;

2-26: N-{1-[2-cyano-4-(trifluoromethyl)phenyl]-4-{2'-ethoxy-[2,3'-bipyridin]-5-yl}piperidin-4-yl}-2-(dimethylamino)acetamide;

2-27: (3S)—N-{1-[2-cyano-4-(trifluoromethyl)phenyl]-4-[6-(2-ethoxyphenyl)pyridin-3-yl]piperidin-4-yl}-1-methylpyrrolidine-3-carboxamide;

2-28: (3S)—N-[1-(4-chloro-2-cyanophenyl)-4-[6-(2-ethoxyphenyl)pyridin-3-yl]piperidin-4-yl]-1-methylpyrrolidine-3-carboxamide;

2-29: (3R)—N-[1-(4-chloro-2-cyanophenyl)-4-[6-(2-ethoxyphenyl)pyridin-3-yl]piperidin-4-yl]-1-methylpyrrolidine-3-carboxamide;

2-30: N-[1-(4-chloro-2-cyanophenyl)-4-[6-(2-ethoxyphenyl)pyridin-3-yl]piperidin-4-yl]-3-(dimethylamino)propanamide;

2-31: N-[1-(4-chloro-2-cyanophenyl)-4-[6-(2-ethoxyphenyl)pyridin-3-yl]piperidin-4-yl]-2-(dimethylamino)acetamide;

2-32: N-{1-[2-cyano-4-(trifluoromethyl)phenyl]-4-{2'-ethoxy-[2,3'-bipyridin]-5-yl}piperidin-4-yl}-1-methylazetidine-3-carboxamide;

2-33: (3R)—N-{1-[2-cyano-4-(trifluoromethyl)phenyl]-4-[6-(2-ethoxyphenyl)pyridin-3-yl]piperidin-4-yl}-1-methylpyrrolidine-3-carboxamide;

2-34: N-{1-[2-cyano-4-(trifluoromethyl)phenyl]-4-[6-(2-ethoxyphenyl)pyridin-3-yl]piperidin-4-yl}-2-(dimethylamino)acetamide;

2-35: N-{1-[2-cyano-4-(trifluoromethyl)phenyl]-4-[6-(2-ethoxyphenyl)pyridin-3-yl]piperidin-4-yl}-1-methylazetidine-3-carboxamide;

2-36: N-{1-[2-cyano-4-(trifluoromethyl)phenyl]-4-[6-(2-ethoxyphenyl)pyridin-3-yl]piperidin-4-yl}-3-(dimethylamino)propanamide;

2-37: N-[1-(4-chloro-2-cyanophenyl)-4-{2'-ethoxy-[2,3'-bipyridin]-5-yl}piperidin-4-yl]-1-methylazetidine-3-carboxamide;

2-38: N-[1-(4-chloro-2-cyanophenyl)-4-{2'-ethoxy-[2,3'-bipyridin]-5-yl}piperidin-4-yl]-2-(dimethylamino)acetamide;

2-39: (3S)—N-[1-(4-chloro-2-cyanophenyl)-4-{2'-ethoxy-[2,3'-bipyridin]-5-yl}piperidin-4-yl]-1-methylpyrrolidine-3-carboxamide;

2-40: N-{1-[2-cyano-4-(trifluoromethyl)phenyl]-4-{2'-methoxy-[2,3'-bipyridin]-5-yl}piperidin-4-yl}-1-methylazetidine-3-carboxamide;

2-41: (3R)-1-methylpyrrolidin-3-yl N-{1-[2-cyano-4-(trifluoromethyl)phenyl]-4-[6-(1-methyl-1H-pyrrol-2-yl)pyridin-3-yl]piperidin-4-yl}carbamate;

2-42: (3S)-1-methylpyrrolidin-3-yl N-{1-[2-cyano-4-(trifluoromethyl)phenyl]-4-[6-(1-methyl-1H-pyrrol-2-yl)pyridin-3-yl]piperidin-4-yl}carbamate;

2-43: 1-{1-[2-cyano-4-(trifluoromethyl)phenyl]-4-[6-(1-methyl-1H-pyrrol-2-yl)pyridin-3-yl]piperidin-4-yl}-3-[(3S)-1-methylpyrrolidin-3-yl]urea;

2-44: (3S)—N-{1-[2-cyano-4-(trifluoromethyl)phenyl]-4-[6-(1-methyl-1H-pyrrol-2-yl)pyridin-3-yl]piperidin-4-yl}pyrrolidine-3-carboxamide;

2-45: N-{1-[2-cyano-4-(trifluoromethyl)phenyl]-4-[6-(1-methyl-1H-pyrrol-2-yl)pyridin-3-yl]piperidin-4-yl}-1-methylazetidine-3-carboxamide;

2-46: (3S)—N-{1-[2-cyano-4-(trifluoromethyl)phenyl]-4-[6-(1-methyl-1H-pyrrol-2-yl)pyridin-3-yl]piperidin-4-yl}-1-methylpyrrolidine-3-carboxamide;

2-47: (3R)—N-{1-[2-cyano-4-(trifluoromethyl)phenyl]-4-[6-(1-methyl-1H-pyrrol-2-yl)pyridin-3-yl]piperidin-4-yl}-1-methylpyrrolidine-3-carboxamide;

2-48: 1-{1-[2-cyano-4-(trifluoromethyl)phenyl]-4-[6-(1-methyl-1H-pyrrol-2-yl)pyridin-3-yl]piperidin-4-yl}-3-[(3R)-1-methylpyrrolidin-3-yl]urea;

2-49: (3S)-1-methylpyrrolidin-3-yl N-{1-[2-cyano-4-(trifluoromethyl)phenyl]-4-[5-fluoro-6-(2-methoxyphenyl)pyridin-3-yl]piperidin-4-yl}carbamate;

2-50: (3R)-1-methylpyrrolidin-3-yl N-{1-[2-cyano-4-(trifluoromethyl)phenyl]-4-[5-fluoro-6-(2-methoxyphenyl)pyridin-3-yl]piperidin-4-yl}carbamate;

2-51: 1-{1-[2-cyano-4-(trifluoromethyl)phenyl]-4-[5-fluoro-6-(2-methoxyphenyl)pyridin-3-yl]piperidin-4-yl}-3-[(3S)-1-methylpyrrolidin-3-yl]urea;

2-52: 1-{1-[2-cyano-4-(trifluoromethyl)phenyl]-4-[5-fluoro-6-(2-methoxyphenyl)pyridin-3-yl]piperidin-4-yl}-3-[(3R)-1-methylpyrrolidin-3-yl]urea;

2-53: (3S)-1-methylpyrrolidin-3-yl N-{1-[2-cyano-4-(trifluoromethyl)phenyl]-4-[6-(2-methoxyphenyl)pyridin-3-yl]piperidin-4-yl}carbamate;

2-54: (3R)-1-methylpyrrolidin-3-yl N-{1-[2-cyano-4-(trifluoromethyl)phenyl]-4-[6-(2-methoxyphenyl)pyridin-3-yl]piperidin-4-yl}carbamate;

2-55: 1-{1-[2-cyano-4-(trifluoromethyl)phenyl]-4-[6-(2-methoxyphenyl)pyridin-3-yl]piperidin-4-yl}-3-[(3S)-1-methylpyrrolidin-3-yl]urea;

2-56: 1-{1-[2-cyano-4-(trifluoromethyl)phenyl]-4-[6-(2-methoxyphenyl)pyridin-3-yl]piperidin-4-yl}-3-[(3R)-1-methylpyrrolidin-3-yl]urea;

2-57: 2-(dimethylamino)ethyl N-{1-[2-cyano-4-(trifluoromethyl)phenyl]-4-[6-(2-methoxyphenyl)pyridin-3-yl]piperidin-4-yl}carbamate;

2-58: 1-{1-[2-cyano-4-(trifluoromethyl)phenyl]-4-[6-(2-methoxyphenyl)pyridin-3-yl]piperidin-4-yl}-3-[2-(dimethylamino)ethyl]urea;

2-59: 1-{1-[2-cyano-4-(trifluoromethyl)phenyl]-4-[6-(2-methoxyphenyl)pyridin-3-yl]piperidin-4-yl}-3-(1-methylazetidin-3-yl)urea;

2-60: (3R)—N-{1-[2-cyano-4-(trifluoromethyl)phenyl]-4-[6-(2-methoxyphenyl)pyridin-3-yl]piperidin-4-yl}-1-methylpyrrolidine-3-carboxamide;

2-61: N-{1-[2-cyano-4-(trifluoromethyl)phenyl]-4-[5-fluoro-6-(2-methoxyphenyl)pyridin-3-yl]piperidin-4-yl}-2-(dimethylamino)acetamide;

2-62: N-{1-[2-cyano-4-(trifluoromethyl)phenyl]-4-[5-fluoro-6-(2-methoxyphenyl)pyridin-3-yl]piperidin-4-yl}-3-(dimethylamino)propanamide;

2-63: N-{1-[2-cyano-4-(trifluoromethyl)phenyl]-4-[5-fluoro-6-(2-methoxyphenyl)pyridin-3-yl]piperidin-4-yl}-3-(methylamino)propanamide;

2-64: N-{1-[2-cyano-4-(trifluoromethyl)phenyl]-4-[6-(2-ethoxypyridin-3-yl)pyridazin-3-yl]piperidin-4-yl}-3-(dimethylamino)propanamide.

In one aspect, compounds described herein are in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

"Pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zürich:Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviours. Also, because the salt-forming molecule can be in equilibrium with a neutral form, passage through biological membranes can be adjusted.

In some embodiments, pharmaceutically acceptable salts are obtained by reacting a compound of Formula (I) with an acid. In some embodiments, the compound of Formula (I) (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid.

In some embodiments, a compound of Formula (I) is prepared as a chloride salt, sulfate salt, bromide salt, mesylate salt, maleate salt, citrate salt or phosphate salt.

In some embodiments, pharmaceutically acceptable salts are obtained by reacting a compound of Formula (I) with a base. In some embodiments, the compound of Formula (I) is acidic and is reacted with a base. In such situations, an acidic proton of the compound of Formula (I) is replaced by a metal ion, e.g., lithium, sodium, potassium, magnesium, calcium, or an aluminum ion. In some cases, compounds described herein coordinate with an organic base, such as, but not limited to, ethanolamine, diethanolamine, triethanolamine, tromethamine, meglumine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

The methods and formulations described herein include the use of N-oxides (if appropriate), or pharmaceutically acceptable salts of compounds having the structure of Formula (I), as well as active metabolites of these compounds having the same type of activity.

In some embodiments, sites on the organic radicals (e.g. alkyl groups, aromatic rings) of compounds of Formula (I) are susceptible to various metabolic reactions. Incorporation of appropriate substituents on the organic radicals will reduce, minimize or eliminate this metabolic pathway. In specific embodiments, the appropriate substituent to decrease or eliminate the susceptibility of the aromatic ring to metabolic reactions is, by way of example only, a halogen, deuterium, an alkyl group, a haloalkyl group, or a deuteroalkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine chlorine, iodine, phosphorus, such as, for example, $^{2}H$, $^{3}H$, $^{13}C$, $^{14}C$, $^{15}N$, $^{18}O$, $^{17}O$, $^{35}S$, $^{18}F$, $^{36}Cl$, $^{123}I$, $^{124}I$, $^{125}I$, $^{131}I$, $^{32}P$ and $^{33}P$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In some embodiments, the compounds of Formula (I) possess one or more stereocenters and each stereocenter exists independently in either the R or S configuration. In some embodiments, the compound of Formula (I) exists in the R configuration. In some embodiments, the compound of Formula (I) exists in the S configuration. The compounds presented herein include all diastereomeric, individual enantiomers, atropisomers, and epimeric forms as well as the appropriate mixtures thereof. The compounds and methods provided herein include all cis, trans, syn, anti, entgegen (E), and zusammen (Z) isomers as well as the appropriate mixtures thereof.

Individual stereoisomers are obtained, if desired, by methods such as, stereoselective synthesis and/or the separation of stereoisomers by chiral chromatographic columns or the separation of diastereomers by either non-chiral or chiral chromatographic columns or crystallization and recrystallization in a proper solvent or a mixture of solvents. In certain embodiments, compounds of Formula (I) are prepared as their individual stereoisomers by reacting a racemic mixture of the compound with an optically active resolving agent to form a pair of diastereoisomeric compounds/salts, separating the diastereomers and recovering the optically pure individual enantiomers. In some embodiments, resolution of individual enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In some embodiments, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they are easier to administer than the parent drug. They are, for instance, bioavailable by oral administration whereas the parent is not. Further or alternatively, the prodrug also has improved solubility in pharmaceutical compositions over the parent drug. In some embodiments, the design of a prodrug increases the effective water solubility. An example, without limitation, of a prodrug is a compound described herein, which is administered as an ester (the "prodrug") but then is metabolically hydrolyzed to provide the active entity. A further example of a prodrug is a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, N-alkyloxyacyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like. In some embodiments, a hydroxyl group in the compounds disclosed herein is a prodrug wherein the hydroxyl is then metabolized in vivo to provide a carboxylic acid group. In some embodiments, a carboxyl group is used to provide an ester or amide (i.e. the prodrug), which is then metabolized in vivo to provide a carboxylic acid group. In some embodiments, compounds described herein are prepared as alkyl ester prodrugs.

Prodrug forms of the herein described compounds, wherein the prodrug is metabolized in vivo to produce a compound of Formula (I) as set forth herein are included within the scope of the claims. In some cases, some of the herein-described compounds is a prodrug for another derivative or active compound.

In some embodiments, any one of the hydroxyl group(s), amino group(s) and/or carboxylic acid group(s) are functionalized in a suitable manner to provide a prodrug moiety. In some embodiments, the prodrug moiety is as described above.

In additional or further embodiments, the compounds described herein are metabolized upon administration to an organism in need to produce a metabolite that is then used to produce a desired effect, including a desired therapeutic effect.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

Synthesis of Compounds

Compounds of Formula (I) described herein are synthesized using standard synthetic techniques or using methods known in the art in combination with methods described herein.

Unless otherwise indicated, conventional methods of mass spectroscopy, NMR, HPLC, protein chemistry, biochemistry, recombinant DNA techniques and pharmacology are employed.

Compounds are prepared using standard organic chemistry techniques such as those described in, for example, March's Advanced Organic Chemistry, 6th Edition, John Wiley and Sons, Inc. Alternative reaction conditions for the synthetic transformations described herein may be employed such as variation of solvent, reaction temperature, reaction time, as well as different chemical reagents and other reaction conditions.

In some embodiments, compounds described herein are prepared as described in Scheme A.

Scheme A

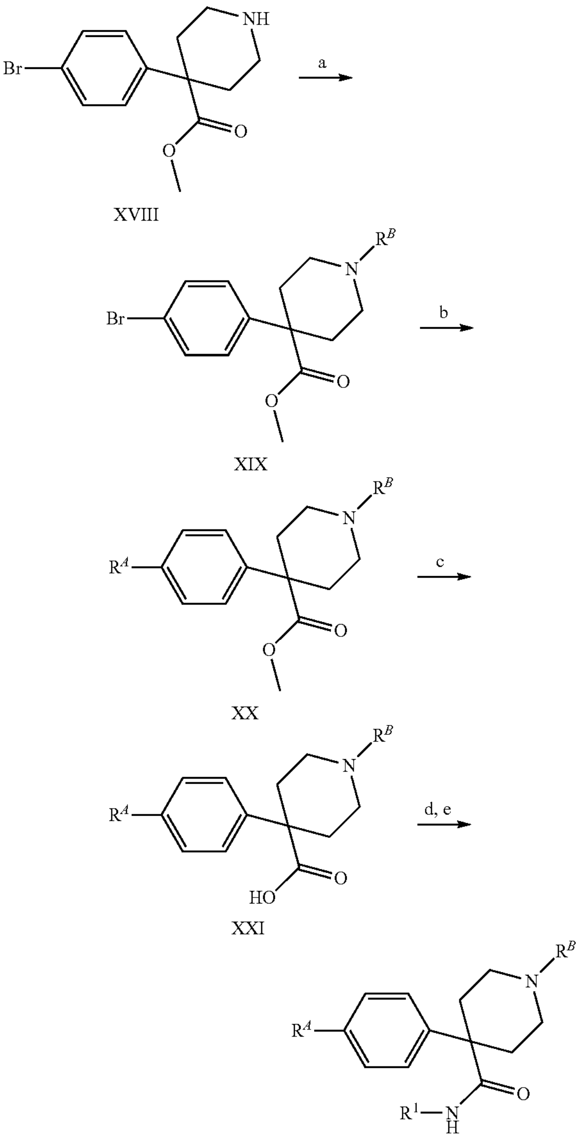

XVIII

XIX

XX

XXI

XXII a) $R^BX$, Pd(II), or $R^BX$, DIEA; b) $R^AB(OH)_2$, Pd(DtBPF)$Cl_2$, $K_2CO_3$, Dioxane/$H_2O$; c) LiOH, EtOH; c) $R^1NH_2$, HATU, TEA; e) deprotection Commercially available XVIII is converted to compound XIX by either a standard $S_NAr$ reaction with $R^BX$ or Buchwald-Hartwig cross coupling reaction with $R^BX$. Subsequently, introduction of $R^A$ by Suzuki-Miyaura coupling reaction with $R^AB(OH)_2$ or Stille coupling with $R^ASnBu_3$ yield compound XX. Hydrolysis of the ester to the acid XXI and then HATU-mediated amide coupling reaction with $R^1NH_2$ produce the final compound XXII. If R, contains a protecting group, then an additional deprotection step takes place to produce XXII.

In some embodiments, compounds described herein are prepared as described in Scheme B.

$S_NAr$ reaction with $R^BX$ or Buchwald-Hartwig cross coupling reaction with $R^BX$ and followed by hydrolysis to yield the acid XXV. Variation of $R^1$ in the final XXX is achieved by HATU-mediated coupling reaction with $R^1NH_2$. Starting from the intermediate XXIII, introduction of various 5- and Scheme B

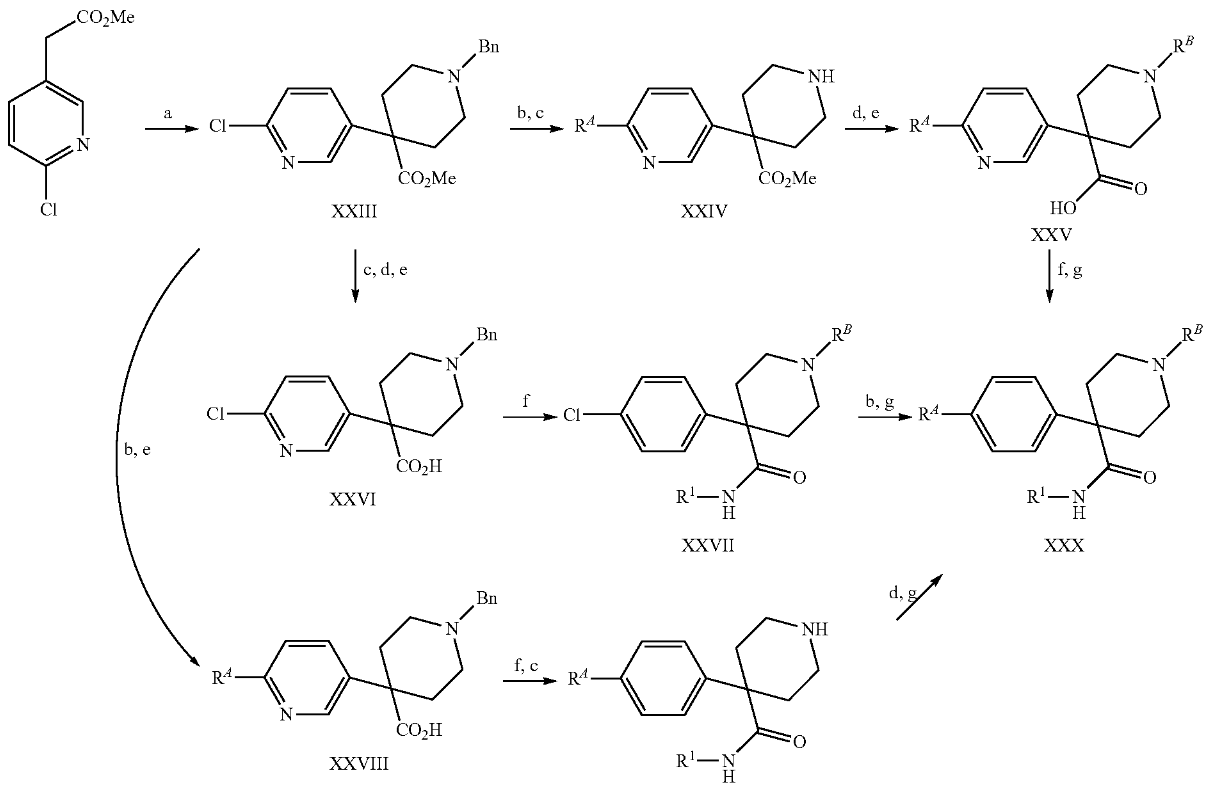

XXIII XXIV XXV XXVI XXVII XXX XXVIII XXIX a) N-benzyl-2-bromo-N-(2-bromoethyl)ethan-1-amine, KOH; b) $R^AB(OH)_2$, Pd(DtBPFCl$_2$, $K_2CO_3$, Dioxane/$H_2O$; c) $Pd(PH)_2$, Pd/C, $H_2$; d) $R^BX$, DIEA, or $R^BX$, Pd(II); e) LiOH, MeOH; f) $R^1NH_2$, HATU, TEA; g) deprotection Methyl 2-(6-chloropyridin-3-yl)acetate efficiently undergoes a one-pot reaction with N-benzyl-2-bromo-N-(2-bromoethyl)ethan-1-amine in the presence of a strong inorganic base such as KOH to produce the piperidinyl intermediate XXIII. Subsequently, introduction of $R^A$ by Suzuki-Miyaura coupling reaction with $R^AB(OH)_2$ and then de-benzylation yield compound XXIV. $R^B$ is introduced by either a standard 6-membered aromatic rings for $R^A$ (XXVI-XXVII-XXX) and diverse $R^B$ (XXVIII-XXIX-XXX) is accomplished by change of the reaction sequence as described in the scheme. If $R^1$ contains a protecting group, then an additional deprotection step takes place to produce XX.

In some embodiments, compounds described herein are prepared as described in Scheme C.

Scheme C

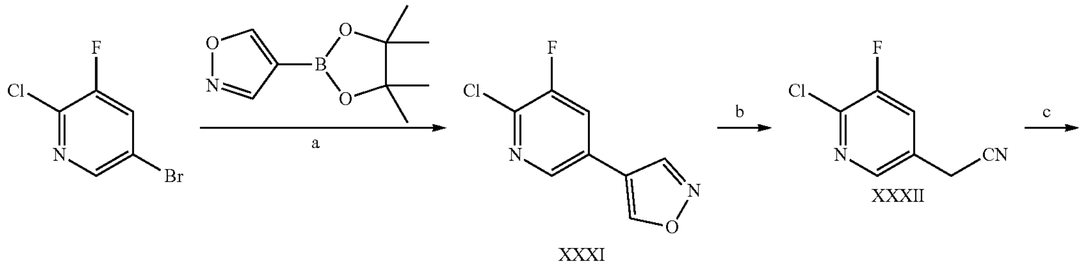

XXXI XXXII

-continued

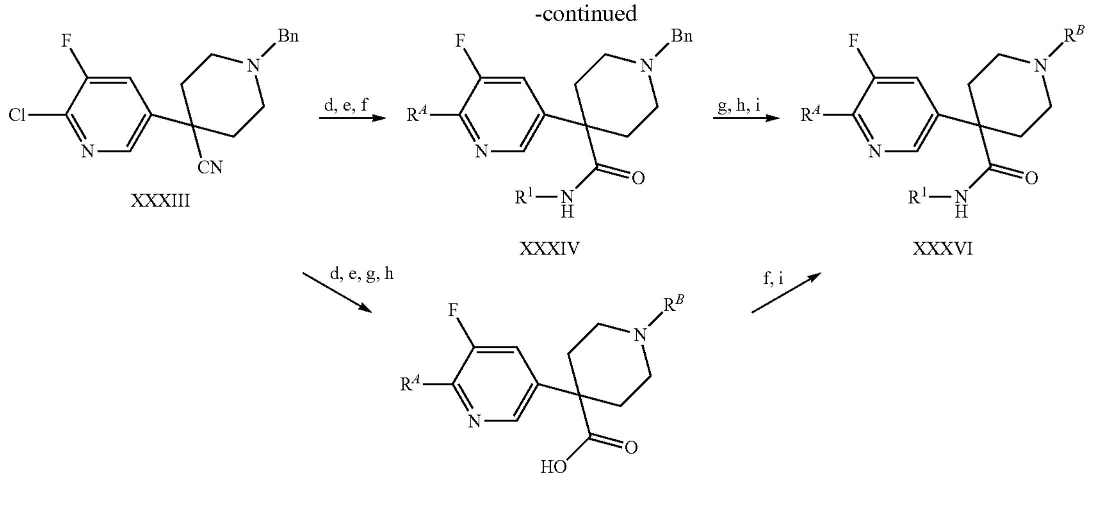

XXXV a) Pd(DTBPF)$Cl_2$, KF, DMSP/$H_2O$; b) KF, MeOH/$H_2O$; c) N-benzyl-2-bromo-N-(2-bromoethyl) ethan-1-amine, KOH; d) $R^A B(OH)_2$, PdAMPhos, $K_2CO_3$, Dioxane/$H_2O$; e) KOH EtOH, $H_2O$; f) $R^1NH_2$, HATU, TEA; g) $Pd(OH)_2$, Pd/C, $H_2$; h) $R^B X$, DIEA, or $R^B X$, Pd(II); i) deprotection The cyanomethylation of 5-bromo-2-chloro-3-fluoropyridine to XXXII efficiently proceeds through Suzuki-Miyaura coupling reaction with isoxazole-4-boronic acid pinacol ester, base-induced fragmentation, and deformylation. The nitrogen-containing heterocycle XXXIII is obtained from cyclocondensation of XXXII with N-benzyl-2-bromo-N-(2-bromoethyl)ethan-1-amine in a strong alkaline medium. Starting from the intermediate XXXIII, introduction of various $R^B$ and $R^1$ in the final XXXVI is achieved through the intermediate XXXIV and XXXV, respectively. The reaction conditions for each route are similar to those described in the previous scheme. If $R^1$ contains a protecting group, then an additional deprotection step takes place to produce XXXVI.

In some embodiments, compounds described herein are prepared as described in Scheme D.

Scheme D

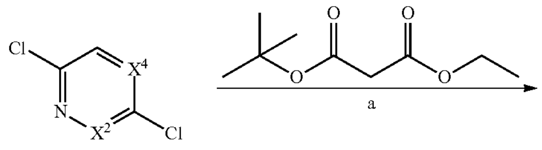

If $X^2$ = N, $X^4$ = CH
If $X^2$ = CH, $X^4$ = N

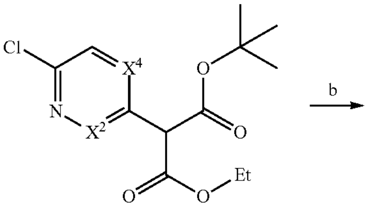

XXXVI

-continued

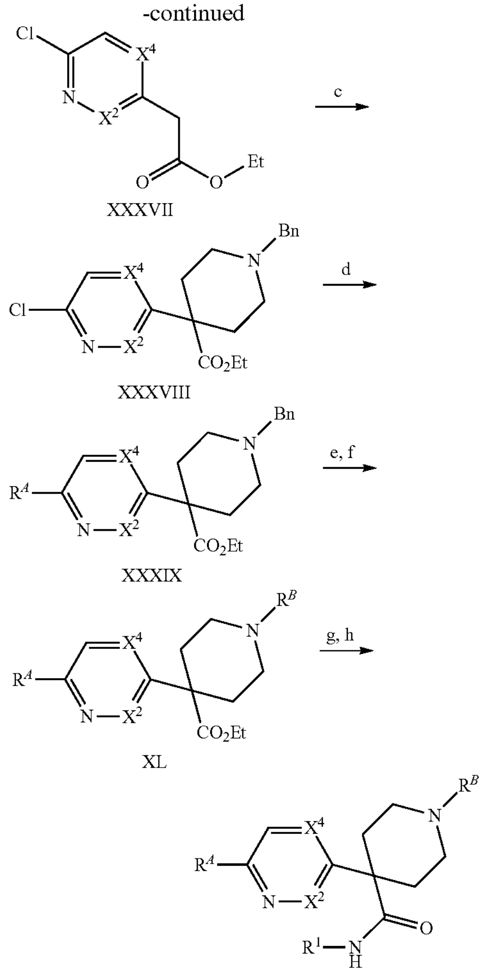

XLI a) $Cs_2CO_3$, DMSO; b) TFA, DCM; c) N-benzyl-2-bromo-N-(2-bromoethyl)ethan-1-amine, KOH; d) $R^A B(OH)_2$, PdAMPhos, $K_2CO_3$, Dioxane/$H_2O$; e) $Pd(OH)_2$, Pd/C, $H_2$; f) $R^B X$, DIEA, or $R^B X$, Pd(II); g) $R^1NH_2$, LiHMDS; h) deprotection Dichloro pyridazine or pyrazine is converted to the acetate XXXVII through formation of the malonate adduct and then removal of tert-butyloxycarbonyl group in an acidic condition. Starting from XXXVII, the intermediate XL is prepared by a similar manner as described in Scheme B. Due to chemical instability of the acid of XL, the amide bond is directly introduced by $S_N2$ reaction of the ester with $R^1NH_2$/LiHIDS. If $R^1$ contains a protecting group, then an additional deprotection step takes place to produce XLI.

In some embodiments, compounds described herein are prepared as described in Scheme E.

Scheme E

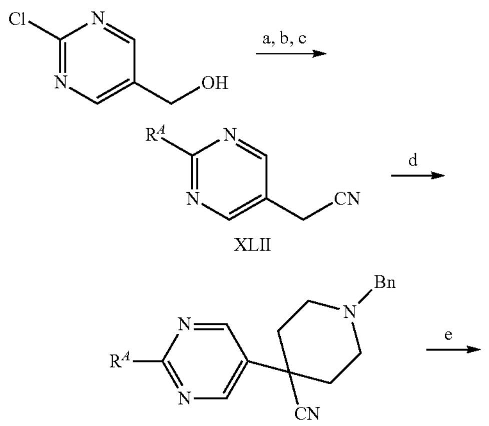

XLII

XLIII

-continued

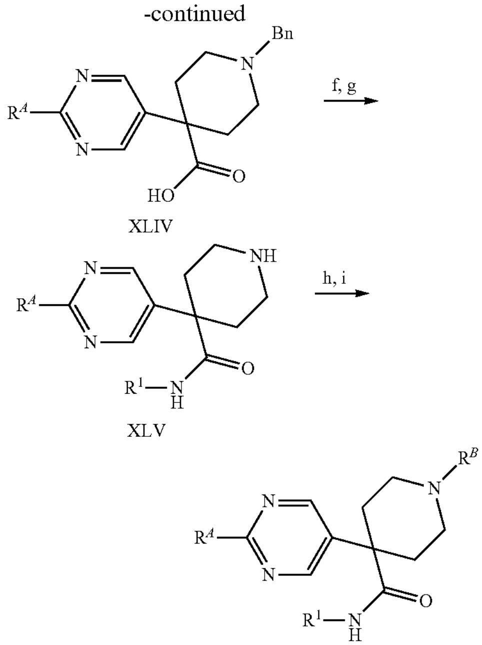

XLIV

XLV

XLVI a) $R^AB(OH)_2$, PdAMPhos, $K_2CO_3$, Dioxane/$H_2O$; b) MsCl, TEA, c) NaCN, DMSO; d) N-benzyl-2-bromo-N-(2-bromoethyl)ethan-1-amine, KOH; e) KOH, EtOH; f) $R^1NH_2$, HATU, TEA; g) $Pd(OH)_2$, Pd/C, $H_2$; h) $R^BX$, DIEA, or $R^BX$, Pd(II); i) deprotection The cyanomethyl substituted pyrimidine XLII is obtained from a three-step sequence, Suzuki coupling, mesylation, and cyanation. Starting from XLII, the final compound XLVI is prepared by a similar manner as described in Scheme C. If $R^1$ contains a protecting group, then an additional deprotection step takes place to produce XLVI.

Scheme F

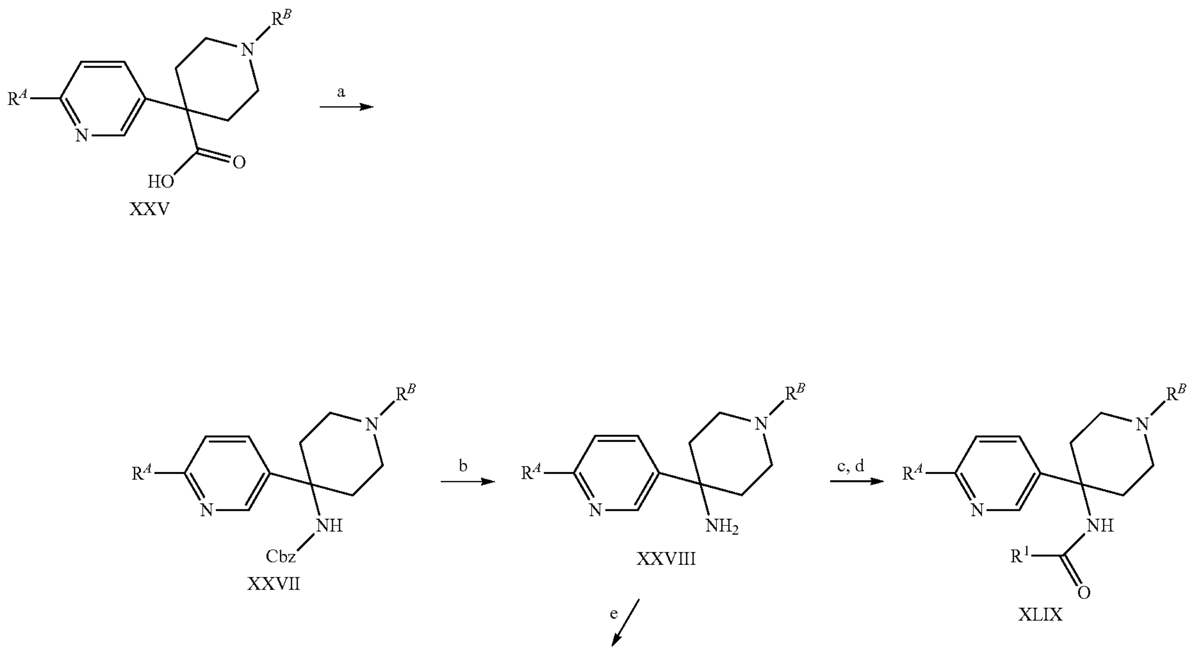

XXV

XXVII

XXVIII

XLIX

-continued

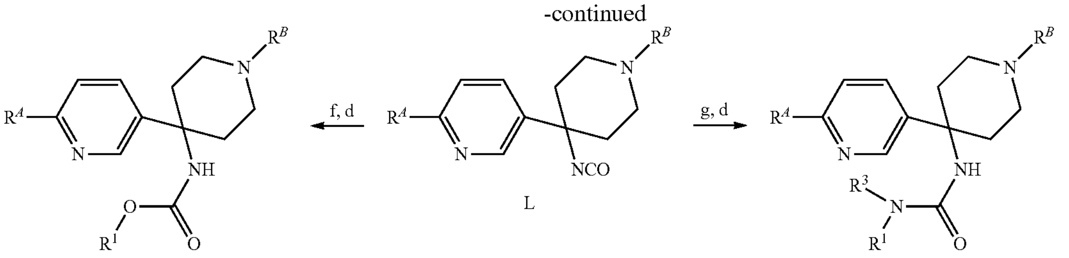

LI L LII a) DPPA, TEA, tol, BnOH, 4Å MS; b) $Pd(OH)_2$, Pd/C, $H_2$; c) $R^1NH_2$, HATU, TEA; d) deprotection; e) triphosgene, tol; f) $R^1OH$, 4Å MS; g) $R^1R^3NH$, TEA, toluene.

In some embodiments, compounds described herein are prepared as described in Scheme F.

Curtius Rearrangement by the reaction of XXV with diphenylphosphoryl azide (DPPA) yields the isocyanate intermediate, which is subjected to in situ trapping of benzyl alcohol to produce XLVII. Deprotection to XLVIII and then HATU-mediated coupling reaction with $R^1NH_2$ yield the final XLIX. The isocyanate L derived from XLVIII undergoes $S_N2$ reaction with various nucleophiles such as alcohols ($R^1OH$) and amines ($R^1R^3NH$) to yield carbamate (LI) or urea (LII) derivatives, respectively. If $R^1$ contains a protecting group in XLLX, LI, and LII, then an additional deprotection step is required for the final product.

In some embodiments, compounds described herein are synthesized as outlined in the Examples.

Certain Terminology

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

As used herein, $C_1$-$C_x$ includes $C_1$-$C_2$, $C_1$-$C_3$ . . . $C_1$-$C_x$. By way of example only, a group designated as "$C_1$-$C_6$" indicates that there are one to six carbon atoms in the moiety, i.e. groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

An "alkyl" group refers to an aliphatic hydrocarbon group. The alkyl group is branched or straight chain. In some embodiments, the "alkyl" group has 1 to 10 carbon atoms, i.e. a $C_1$-$C_{10}$alkyl. Whenever it appears herein, a numerical range such as "1 to 10" refers to each integer in the given range; e.g., "1 to 10 carbon atoms" means that the alkyl group consist of 1 carbon atom, 2 carbon atoms, 3 carbon atoms, etc., up to and including 10 carbon atoms, although the present definition also covers the occurrence of the term "alkyl" where no numerical range is designated. In some embodiments, an alkyl is a $C_1$-$C_6$alkyl. In one aspect the alkyl is methyl, ethyl, propyl, iso-propyl, n-butyl, iso-butyl, sec-butyl, or t-butyl. Typical alkyl groups include, but are in no way limited to, methyl, ethyl, propyl, isopropyl, butyl, isobutyl, sec-butyl, tertiary butyl, pentyl, neopentyl, or hexyl.

An "alkylene" group refers to a divalent alkyl radical. Any of the above mentioned monovalent alkyl groups may be an alkylene by abstraction of a second hydrogen atom from the alkyl. In some embodiments, an alkylene is a $C_1$-$C_6$alkylene. In other embodiments, an alkylene is a $C_1$-$C_4$alkylene. Typical alkylene groups include, but are not limited to, $—CH_2—$, $—CH_2CH_2—$, $—CH_2CH_2CH_2—$, $—CH_2CH_2CH_2CH_2—$, and the like. In some embodiments, an alkylene is $—CH_2—$.

An "alkoxy" group refers to a (alkyl)O— group, where alkyl is as defined herein.

The term "alkylamine" refers to the $—N(alkyl)_xH_y$ group, where x is 0 and y is 2, or where x is 1 and y is 1, or where x is 2 and y is 0.

An "hydroxyalkyl" refers to an alkyl in which one hydrogen atom is replaced by a hydroxyl. In some embodiments, a hydroxyalkyl is a $C_1$-$C_4$hydroxyalkyl. Typical hydroxyalkyl groups include, but are not limited to, $—CH_2OH$, $—CH_2CH_2OH$, $—CH_2CH_2CH_2OH$, $—CH_2CH_2CH_2CH_2OH$, and the like.

An "aminoalkyl" refers to an alkyl in which one hydrogen atom is replaced by an amino. In some embodiments, aminoalkyl is a $C_1$-$C_4$aminoalkyl. Typical aminoalkyl groups include, but are not limited to, $—CH_2NH_2$, $—CH_2CH_2NH_2$, $—CH_2CH_2CH_2NH_2$, $—CH_2CH_2CH_2CH_2NH_2$, and the like.

The term "alkenyl" refers to a type of alkyl group in which at least one carbon-carbon double bond is present. In one embodiment, an alkenyl group has the formula $—C(R)=CR_2$, wherein R refers to the remaining portions of the alkenyl group, which may be the same or different. In some embodiments, R is H or an alkyl. In some embodiments, an alkenyl is selected from ethenyl (i.e., vinyl), propenyl (i.e., allyl), butenyl, pentenyl, pentadienyl, and the like. Non-limiting examples of an alkenyl group include $—CH=CH_2$, $—C(CH_3)=CH_2$, $—CH=CHCH_3$, $—C(CH_3)=CHCH_3$, and $—CH_2CH=CH_2$.

The term "alkynyl" refers to a type of alkyl group in which at least one carbon-carbon triple bond is present. In one embodiment, an alkenyl group has the formula $—C≡C—R$, wherein R refers to the remaining portions of the alkynyl group. In some embodiments, R is H or an alkyl. In some embodiments, an alkynyl is selected from ethynyl, propynyl, butynyl, pentynyl, hexynyl, and the like. Non-limiting examples of an alkynyl group include $—C≡CH$, $—C≡CCH_3—C≡CCH_2CH_3$, $—CH_2C≡CH$.

The term "heteroalkyl" refers to an alkyl group in which one or more skeletal atoms of the alkyl are selected from an atom other than carbon, e.g., oxygen, nitrogen (e.g. —NH—, —N(alkyl)-, sulfur, or combinations thereof. A heteroalkyl is attached to the rest of the molecule at a carbon atom of the heteroalkyl. In one aspect, a heteroalkyl is a $C_1$-$C_6$heteroalkyl.

The term "aromatic" refers to a planar ring having a delocalized π-electron system containing 4n+2π electrons, where n is an integer. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" or "carbocycle" refers to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, a carbocycle is a monocyclic carbocycle or a bicyclic carbocycle. In some embodiments, a carbocycle is a monocyclic carbocycle. Carbocycles are non-aromatic or aromatic. Non-aromatic carbocycles are saturated or partially unsaturated. In some embodiments, a carbocycle is a bicyclic carbocycle. In some embodiments, at least one of the two rings of a bicyclic carbocycle is aromatic. In some embodiments, both rings of a bicyclic carbocycle are aromatic. Carbocycles include aryls and cycloalkyls.

As used herein, the term "aryl" refers to an aromatic ring wherein each of the atoms forming the ring is a carbon atom. In one aspect, aryl is phenyl or a naphthyl. In some embodiments, an aryl is a phenyl. In some embodiments, an aryl is a phenyl, naphthyl, indanyl, indenyl, or tetrahyodronaphthyl. In some embodiments, an aryl is a $C_6$-$C_{10}$aryl. Depending on the structure, an aryl group is a monoradical or a diradical (i.e., an arylene group).

The term "cycloalkyl" refers to a monocyclic, bicyclic or polycyclic aliphatic, non-aromatic radical, wherein each of the atoms forming the ring (i.e. skeletal atoms) is a carbon atom. In some embodiments, cycloalkyls are spirocyclic or bridged compounds. In some embodiments, cycloalkyls are optionally fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, norbornyl, norbornenyl, bicycle[1.1.1]pentyl, adamantyl, norbornyl, norbornenyl, decalinyl, or 7,7-dimethyl-bicyclo[2.2.1]heptanyl. In some embodiments, a cycloalkyl is a $C_3$-$C_6$cycloalkyl. In some embodiments, a cycloalkyl is a monocyclic cycloalkyl. Monocyclic cycloalkyls include, but are not limited to, cyclopropyl, cyclobutyl, cyclopentyl, cyclohexyl, cycloheptyl, and cyclooctyl. Polycyclic cycloalkyls include, for example, adamantyl, norbornyl (i.e., bicyclo[2.2.1]heptanyl), norbornenyl, decalinyl, 7,7-dimethyl-bicyclo[2.2.1]heptanyl, and the like.

The term "halo" or, alternatively, "halogen" or "halide" means fluoro, chloro, bromo or iodo. In some embodiments, halo is fluoro, chloro, or bromo.

The term "fluoroalkyl" refers to an alkyl in which one or more hydrogen atoms are replaced by a fluorine atom. In one aspect, a fluoroalkyl is a $C_1$-$C_6$fluoroalkyl.

The term "heterocycle" or "heterocyclic" refers to heteroaromatic rings (also known as heteroaryls) and heterocycloalkyl rings containing one to four heteroatoms in the ring(s), where each heteroatom in the ring(s) is selected from O, S and N, wherein each heterocyclic group has from 3 to 10 atoms in its ring system, and with the proviso that any ring does not contain two adjacent O or S atoms. Non-aromatic heterocyclic groups (also known as heterocycloalkyls) include rings having 3 to 10 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (=O) moieties, such as pyrrolidin-2-one. In some embodiments, at least one of the two rings of a bicyclic heterocycle is aromatic. In some embodiments, both rings of a bicyclic heterocycle are aromatic.

The terms "heteroaryl" or, alternatively, "heteroaromatic" refers to an aryl group that includes one or more ring heteroatoms selected from nitrogen, oxygen and sulfur. Illustrative examples of heteroaryl groups include monocyclic heteroaryls and bicyclic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Monocyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl.

A "heterocycloalkyl" group refers to a cycloalkyl group that includes at least one heteroatom selected from nitrogen, oxygen and sulfur. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. The term heterocycloalkyl also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "optionally substituted" or "substituted" means that the referenced group is optionally substituted with one or more additional group(s) individually and independently selected from halogen, —CN, —$NH_2$, —NH(alkyl), —N(alkyl)$_2$, —OH, —$CO_2H$, —$CO_2$alkyl, —C(═O)$NH_2$, —C(═O)NH(alkyl), —C(═O)N(alkyl)$_2$, —S(═O)$_2NH_2$, —S(═O)$_2$NH(alkyl), —S(═O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from halogen, —CN, —$NH_2$, —NH($CH_3$), —N($CH_3$)$_2$, —OH, —$CO_2H$, —$CO_2$($C_1$-$C_4$alkyl), —C(═O)$NH_2$, —C(═O)NH($C_1$-$C_4$alkyl), —C(═O)N($C_1$-$C_4$alkyl)$_2$, —S(═O)$_2NH_2$, —S(═O)$_2$NH($C_1$-$C_4$alkyl), —S(═O)$_2$N($C_1$-$C_4$alkyl)$_2$, $C_1$-$C_4$alkyl, $C_3$-$C_6$cycloalkyl, $C_1$-$C_4$fluoroalkyl, $C_1$-$C_4$heteroalkyl, $C_1$-$C_4$alkoxy, $C_1$-$C_4$fluoroalkoxy, —S$C_1$-$C_4$alkyl, —S(═O)$C_1$-$C_4$alkyl, and —S(═O)$_2C_1$-$C_4$alkyl. In some other embodiments, optional substituents are independently selected from halogen, —CN, —$NH_2$, —NH($CH_3$), —N($CH_3$)$_2$, —OH, —$CO_2H$, —$CO_2$($C_1$-$C_4$alkyl), —C(═O)$NH_2$, —C(═O)NH($C_1$-$C_4$alkyl), —C(═O)N($C_1$-$C_4$alkyl)$_2$, —S(═O)$_2$$NH_2$, —S(═O)$_2$NH($C_1$-$C_4$alkyl), —S(═O)$_2$N($C_1$-$C_4$ alkyl)$_2$, $C_1$-$C_4$alkyl, $C_3$-$C_6$cycloalkyl, $C_2$-$C_6$heterocycloalkyl, $C_1$-$C_4$fluoroalkyl, $C_1$-$C_4$heteroalkyl, $C_1$-$C_4$alkoxy, $C_1$-$C_4$fluoroalkoxy, —S$C_1$-$C_4$alkyl, —S(═O)$C_1$-$C_4$alkyl, and —S(═O)$_2C_1$-$C_4$alkyl. In some embodiments, optional substituents are independently selected from halogen, —CN, —$NH_2$, —OH, —NH($CH_3$), —N($CH_3$)$_2$, —$CH_3$, —$CH_2CH_3$, —$CF_3$, —$OCH_3$, and —$OCF_3$. In some embodiments, substituted groups are substituted with one or two of the preceding groups. In some embodiments, an optional substituent on an aliphatic carbon atom (acyclic or cyclic) includes oxo (═O).

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an agonist.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula (I), or a pharmaceutically acceptable salt thereof, and a co-agent, are both administered to a patient simultaneously in the form of a single entity or dosage. The term "non-fixed combination" means that the active ingredients, e.g. a compound of Formula (I), or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "article of manufacture" and "kit" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, compounds described herein can be administered locally to the area in need of treatment, by for example, local infusion during surgery, topical application such as creams or ointments, injection, catheter, or implant. The administration can also be by direct injection at the site of a diseased tissue or organ.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical compositions may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical compositions suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation.

Pharmaceutical compositions for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

It should be understood that in addition to the ingredients particularly mentioned above, the compounds and compositions described herein may include other agents conventional in the art having regard to the type of formulation in question, for example those suitable for oral administration may include flavoring agents.

Methods of Dosing and Treatment Regimens

In one embodiment, the compounds of Formula (I), or a pharmaceutically acceptable salt thereof, are used in the preparation of medicaments for the treatment of diseases or conditions in a mammal that would benefit from modulation of melanocortin receptor activity. Methods for treating any of the diseases or conditions described herein in a mammal in need of such treatment, involves administration of pharmaceutical compositions that include at least one compound of Formula (I) or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound of Formula (I), or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-2000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound of Formula (I), or a pharmaceutically acceptable salt thereof, described herein are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound of Formula (I), or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

Combination Treatments

In certain instances, it is appropriate to administer at least one compound of Formula (I), or a pharmaceutically acceptable salt thereof, in combination with one or more other therapeutic agents.

In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

In one specific embodiment, a compound of Formula (I), or a pharmaceutically acceptable salt thereof, is co-administered with a second therapeutic agent, wherein the compound of Formula (I), or a pharmaceutically acceptable salt thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient is simply be additive of the two therapeutic agents or the patient experiences a synergistic benefit.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds of Formula (I), or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject.

Abbreviations

DIEA: N,N-diisopropylethylamine;

DMSO: dimethyl sulfoxide;

CuI: copper(I) iodide;

TBAF: tetra-n-butylammonium fluoride;

$P(t\text{-}Bu)_3$: tri-tert-butylphosphine;

$HBF_4$: tetrafluoroboric acid;

DBU: 1,8-diazabicyclo[5.4.0]undec-7-ene;

Prep-HPLC: preparative high performance liquid chromatography;

TFA: trifluoroacetic acid;

$CH_3CN$: acetonitrile;

MeOD: deuterated methanol;

$CDCl_3$: deuterated chloroform;

DME: 1,2-dimethoxyethane;

$H_2O$: water;

KOAc: potassium acetate;

NaOAc: sodium acetate;

$Cs_2CO_3$: cesium carbonate;

P-TsOH: p-toluenesulfonic acid;

$NaNO_2$: sodium nitrate;

THF: tetrahydrofuran;

NBS: N-bromosuccinimide;

4 Å MS: 4 Å molecular sieves;

DPPA: diphenyl phosphoryl azide;

$Br_2$: bromine;

AgF: silver fluoride;

$LiAlH_4$: lithium aluminium hydride;

LiHMDS: lithium bis(trimethylsilyl)amide;

IBX: 2-iodoxybenzoic acid;

CDI: 1,1'-carbonyldiimidazole;

TEA: trimethylamine;

HOBT: hydroxybenzotriazole;

EDCI: 1-ethyl-3-(3-dimethylaminopropyl)carbodiimide;

$Pd(PPh_3)_4$: tetrakis(triphenylphosphine)palladium(O);

$Pd(OH)_2$: palladium hydroxide;

$Pd(PPh_3)_2Cl_2$: bis(triphenylphosphine)palladium(II) dichloride;

$Pd(dppf)Cl_2$: [1,1'-Bis(diphenylphosphino)ferrocene]dichloropalladium(II);

PdAMphos or Pd $(amphos)Cl_2$ or: bis(di-tert-butyl(4-dimethylaminophenyl)phosphine)dichloropalladium (II);

$Pd(DTBPF)Cl_2$: [1,1'-bis(di-tert-butylphosphino)ferrocene]dichloropalladium(II);

$Pd_2(dba)_3{\cdot}CHCl_3$: tris(dibenzylideneacetone)dipalladium (O)-chloroform adduct;

XPhos: 2-dicyclohexylphosphino-2',4',6'-triisopropylbiphenyl;

RuPhos-Pd-G3: dicyclohexyl-[2-[2,6-di(propan-2-yloxy) phenyl]phenyl]phosphane methanesulfonic acid palladium 2-phenylaniline;

XPhos-Pd-G2: chloro(2-dicyclohexnylphosphino-2',4',6'-triisopropyl-1,1'-biphenyl)[2-(2'-amino-1,1'-biphenyl)] palladium(II);

rt: room temperature;

h: hour or hours;

Cpd: compound.

EXAMPLES

The following examples are provided for illustrative purposes only and not to limit the scope of the claims provided herein.

Synthesis of Compounds

Example 1: N-(2-aminoethyl)-1-[2-cyano-4-(trifluoromethyl)phenyl]-4-[4-(2-ethoxypyridin-3-yl)phenyl]piperidine-4-carboxamide (Cpd 1-3)

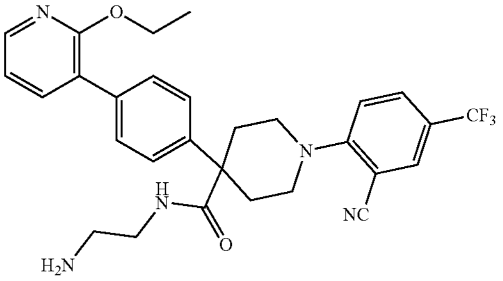 [SMILES: CCOc1ncccc1-c1ccc(C2(C(=O)NCCN)CCN(c3ccc(C(F)(F)F)cc3C#N)CC2)cc1]

Step 1-1, preparation of methyl 4-(4-bromophenyl)-1-[2-cyano-4-(trifluoromethyl)phenyl]piperidine-4-carboxylate: Methyl 4-(4-bromophenyl)piperidine-4-carboxylate hydrochloride (500 mg, 1.49 mmol), 2-fluoro-5-(trifluoromethyl) benzonitrile (706 mg, 3.74 mmol), DIEA (772 mg, 5.98 mmol), and DMSO (5 mL) were charged into a heavy-wall tube. The tube was sealed, and then the resulting solution was stirred at 125° C. for 16 h and cooled to rt. The reaction was directly purified by reverse phase C18 column chromatography to afford the title compound (600 mg, 86%). LCMS $(M+H)^+=467.3$.

Step 1-2, preparation of methyl 1-[2-cyano-4-(trifluoromethyl)phenyl]-4-[4-(2-ethoxypyridin-3-yl)phenyl]piperidine-4-carboxylate: Methyl 4-(4-bromophenyl)-1-[2-cyano-4-(trifluoromethyl)phenyl]piperidine-4-carboxylate (480 mg, 1.03 mmol), (2-ethoxypyridin-3-yl)boronic acid (343 mg, 2.05 mmol), PdAMphos (73 mg, 0.103 mmol), potassium carbonate (284 mg, 2.05 mmol), and dioxane/$H_2O$ (5 mL/0.5 mL) were charged into a heavy-wall tube. The resulting mixture was degassed with $N_2$ for 5 min, sealed, and stirred at 80° C. for 1 h. The reaction was cooled to rt, and concentrated. The residue was directly purified by reverse phase C18 column chromatography to afford the title compound (450 mg, 86%). LCMS $(M+H)^+=510.3$.

Step 1-3, preparation of 1-[2-cyano-4-(trifluoromethyl) phenyl]-4-[4-(2-ethoxypyridin-3-yl)phenyl]piperidine-4-carboxylic acid: To a suspension of methyl 1-[2-cyano-4-(trifluoromethyl)phenyl]-4-[4-(2-ethoxypyridin-3-yl) phenyl]piperidine-4-carboxylate (450 mg, 0.883 mmol) in EtOH (8 mL) was added 2N-lithium hydroxide (4 mL, 8.83 mmol) at rt. The resulting mixture was stirred at 85° C. for 3 h and cooled to rt. After removal of the volatile solvent, the aqueous layer was filtered to remove inorganic solid. The aqueous filtrate was acidified to ~pH 4 with 1N-HCl to form ppts. The solid ppts were collected, washed with $H_2O$, and dried to afford the title compound (270 mg, 62%). LCMS $(M+H)^+=496.1$.

Step 1-4, preparation of tert-butyl N-[2-({1-[2-cyano-4-(trifluoromethyl)phenyl]-4-[4-(2-ethoxypyridin-3-yl)phenyl]piperidin-4-yl}formamido)ethyl]arbamate: To a solution of 1-[2-cyano-4-(trifluoromethyl)phenyl]-4-[4-(2-ethoxypyridin-3-yl)phenyl]piperidine-4-carboxylic acid (30 mg, 0.061 mmol) in ACN (1 mL) was added HATU (25 mg, 0.067 mmol) and TEA (12 mg, 0.12 mmol) at rt. After stirring for 5 min at rt, the reaction was treated with tert-butyl (2-aminoethyl)carbamate (12 mg, 0.073 mmol). The resulting solution was stirred at rt for 30 min, and then directly purified by reverse phase C18 column chromatography to afford the title compound (30 mg, 78%). LCMS $(M+H)^+$=638.1.

Step 1-5, preparation of N-(2-aminoethyl)-1-[2-cyano-4-(trifluoromethyl)phenyl]-4-[4-(2-ethoxypyridin-3-yl)phenyl]piperidine-4-carboxamide: To a solution of tert-butyl N-[2-({1-[2-cyano-4-(trifluoromethyl)phenyl]-4-[4-(2-ethoxypyridin-3-yl)phenyl]piperidin-4-yl}formamido)ethyl]carbamate (30 mg, 0.047 mmol) in DCM (0.4 mL) was added TFA (0.1 mL) at rt. The reaction was stirred at rt for 1 h and concentrated under vacuum. The residue was purified by reverse phase C18 column chromatography to afford the title compound (18.5 mg, 73%). LCMS $(M+H)^+$= 538.4.

The following compounds were prepared similarly to Example 1 with appropriate substituting reagents and substrates at different steps. Some examples do not require deprotection in the final step.

| Compound no. | MS $(M + H)^+$ |
|---|---|
| 1-1 | 578.3 |
| 1-2 | 564.4 |
| 1-4 | 552.3 |
| 1-5 | 552.3 |
| 1-6 | 552.2 |
| 1-7 | 552.4 |
| 1-8 | 566.3 |
| 1-23 | 579.4 |
| 1-29 | 612.3 |
| 1-75 | 596.4 |
| 1-159 | 583.6 |
| 1-164 | 567.4 |
| 1-165 | 587.2 |

Example 2: 1-[2-cyano-4-(trifluoromethyl)phenyl]-4-{2'-ethoxy-[3,3'-bipyridin]-6-yl}-N-[(3R)-1-methylpyrrolidin-3-yl]piperidine-4-carboxamide (Cpd 1-22)

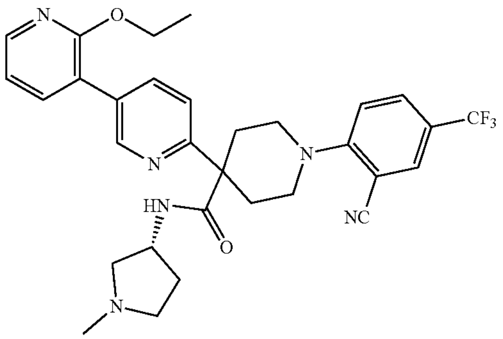 [SMILES: CCOc1ncccc1-c1ccc(C2(C(=O)N[C@@H]3CCN(C)C3)CCN(c3ccc(C(F)(F)F)cc3C#N)CC2)nc1]

Step 2-1, preparation of 2-(5-chloropyridin-2-yl)acetonitrile: Into a 250-mL round-bottom flask, were placed 5-chloro-2-(chloromethyl)pyridine (8.0 g, 49 mmol), potassium cyanide (4.5 g, 69 mmol), EtOH (80 mL) and $H_2O$ (60 mL). The resulting mixture was stirred at 100° C. for 1 h and cooled to room temperature. The reaction was quenched with water (200 mL) and then extracted with ethyl acetate (3×). The combined organic layers were washed with brine, dried over anhydrous sodium sulfate and concentrated under vacuum. The residue was applied onto a silica gel column with ethyl acetate/petroleum ether (1:1) to afford the title compound (4.3 g, 57%) as a yellow oil. LCMS $(M+H)^+$= 153.2.

Step 2-2, preparation of 1-benzyl-4-(5-chloropyridin-2-yl)piperidine-4-carbonitrile: To a solution of 2-(5-chloropyridin-2-yl)acetonitrile (2.0 g, 13 mmol) and N-benzyl-2-bromo-N-(2-bromoethyl)ethan-1-amine (5.0 g, 16 mmol) in DMSO (20 mL) was added KOH (2.0 g, 36 mmol) at rt. The resulting mixture was stirred at 30° C. for 1 h and then quenched with water (50 mL). The resulting solution was extracted with ethyl acetate (3×).

The combined organic layers were washed with brine, dried over anhydrous sodium sulfate and concentrated under vacuum. The residue was applied onto a silica gel column with ethyl acetate/petroleum ether (1:1). This resulted in the title compound (2.0 g, 49%) as a yellow oil. LCMS $(M+H)^+$= 312.0.

Step 2-3, preparation of 1-benzyl-4-{2'-ethoxy-[3,3'-bipyridin]-6-yl}piperidine-4-carbonitrile: Into a 50 mL round-bottom flask purged and maintained with an inert atmosphere of nitrogen, were placed 1-benzyl-4-(5-chloropyridin-2-yl)piperidine-4-carbonitrile (1.0 g, 3.2 mmol), (2-ethoxypyridin-3-yl)boronic acid (1.0 g, 6.0 mmol), Pd(dppf)$Cl_2$ (0.3 g, 0.4 mmol), $K_2CO_3$ (1.2 g, 8.7 mmol), and dioxane/$H_2O$ (10 mL/1 mL). The resulting solution was stirred at 80° C. for 1 h under $N_2$ and cooled to room temperature. The reaction was quenched with water (50 mL) and extracted with ethyl acetate (3×). The combined organic layers were washed with brine, dried over anhydrous sodium sulfate and concentrated under vacuum. The residue was applied onto a silica gel column with ethyl acetate/petroleum ether (30:70) to afford the title compound (1.0 g, 78%) as a yellow oil. LCMS $(M+H)^+$=399.1.

Step 2-4, preparation of 1-benzyl-4-{2'-ethoxy-[3,3'-bipyridin]-6-yl}piperidine-4-carboxylic acid: Into a 50-mL round-bottom flask, were placed 1-benzyl-4-{2'-ethoxy-[3,3'-bipyridin]-6-yl}piperidine-4-carbonitrile (1.0 g, 2.5 mmol), KOH (1.0 g, 17.8 mmol), EtOH (10 mL) and $H_2O$ (10 mL). The resulting solution was stirred at 100° C. for 30 h, cooled to rt, and concentrated under vacuum. The residue was diluted with $H_2O$, and then pH of the solution was adjusted to ~4 with 4M-HCl. The solid ppts were collected, washed with water, and dried to afford the title compound as a white solid (800 mg, 80%). LCMS $(M+H)^+$=418.3.

Step 2-5, preparation of tert-butyl (3R)-3-(1-benzyl-4-{2'-ethoxy-[3,3'-bipyridin]-6-yl}piperidine-4-amido)pyrrolidine-1-carboxylate: To a solution of 1-benzyl-4-{2'-ethoxy-[3,3'-bipyridin]-6-yl}piperidine-4-carboxylic acid (230 mg, 0.55 mmol) in DMF (4 mL) was added HATU (251 mg, 0.66 mmol) and DIEA (427 mg, 3.3 mmol) at rt. After stirring at rt for 5 min, the reaction was treated with tert-butyl (R)-3-aminopyrrolidine-1-carboxylate (123 mg, 0.66 mmol). The resulting solution was stirred at rt for 2 h and directly purified by Prep-HPLC to afford the title compound (230 mg, 71%) as a yellow solid. LCMS $(M+H)^+$=586.3.

Step 2-6, preparation of tert-butyl (3R)-3-(4-{2'-ethoxy-[3,3'-bipyridin]-6-yl}piperidine-4-amido)pyrrolidine-1-carboxylate: Into a 50-mL round-bottom flask, were placed tert-butyl (3R)-3-(1-benzyl-4-{2'-ethoxy-[3,3'-bipyridin]-6-yl}piperidine-4-amido)pyrrolidine-1-carboxylate (230 mg, 0.39 mmol), MeOH (10 mL), wet 10%-Pd/C (30 mg), and $Pd(OH)_2$ (30 mg, 0.21 mmol). The reaction flask was evacuated and flushed three times with nitrogen, followed by flushing with hydrogen. The mixture was stirred at rt for 2 h under hydrogen (balloon). The reaction was diluted with MeOH, and filtered through a pad of Celite. The filtrate was concentrated under vacuum to afford the title compound (180 mg, 92%) as a yellow oil. LCMS $(M+H)^+$=496.4.

Step 2-7, preparation of tert-butyl (3R)-3-{1-[2-cyano-4-(trifluoromethyl)phenyl]-4-{2'-ethoxy-[3,3'-bipyridin]-6-yl}piperidine-4-amido}pyrrolidine-1-carboxylate: A solution of tert-butyl (3R)-3-(4-{2'-ethoxy-[3,3'-bipyridin]-6-yl}piperidine-4-amido)pyrrolidine-1-carboxylate (180 mg, 0.36 mmol), 2-fluoro-5-(trifluoromethyl)benzonitrile (83 mg, 0.44 mmol), and DIEA (142 mg, 1.1 mmol) in DMSO (2 mL) was stirred 70° C. for 2 h. The reaction was cooled to rt and directly purified by Prep-HPLC to afford the title compound (190 mg, 78%) as a yellow solid. LCMS $(M+H)^+$= 665.3.

Step 2-8, preparation of 1-[2-cyano-4-(trifluoromethyl)phenyl]-4-{2'-ethoxy-[3,3'-bipyridin]-6-yl}-N-[(3R)-pyrrolidin-3-yl]piperidine-4-carboxamide (cpd 2-21): To a solution of tert-butyl (3R)-3-{1-[2-cyano-4-(trifluoromethyl)phenyl]-4-{2'-ethoxy-[3,3'-bipyridin]-6-yl}piperidine-4-amido}pyrrolidine-1-carboxylate (190 mg, 0.28 mmol) in DCM (2 mL) was added TFA (0.4 mL) at rt. The resulting mixture was stirred at rt for 2 h and then diluted with $H_2O$. The pH of the solution was adjusted to 8-9 with sat-$NaHCO_3$. The solution was extracted with ethyl acetate (3×). The combined organic layers were washed with brine, dried over anhydrous sodium sulfate, and concentrated to afford the title compound (130 mg, 80%) as a yellow solid. LCMS $(M+H)^+$=565.2.

Step 2-9, preparation of 1-[2-cyano-4-(trifluoromethyl)phenyl]-4-{2'-ethoxy-[3,3'-bipyridin]-6-yl}-N-[(3R)-1-methylpyrrolidin-3-yl]piperidine-4-carboxamide formate: To a solution of 1-[2-cyano-4-(trifluoromethyl)phenyl]-4-{2'-ethoxy-[3,3'-bipyridin]-6-yl}-N-[(3R)-pyrrolidin-3-yl]piperidine-4-carboxamide (55 mg, 0.097 mmol) in MeOH (2 mL) was added formaldehyde (20 mg, 0.67 mmol) and AcOH (6.0 mg, 0.10 mmol), and followed by sodium cyanotrihydroborate (12 mg, 0.19 mmol) at rt. The resulting solution was stirred at rt for 2 h, and then concentrated under vacuum. The residue was purified by Prep-HPLC to afford the title compound (20 mg, 33%) as a white solid. LCMS $(M+H)^+$=579.3.

Example 3: 1-[2-cyano-4-(trifluoromethyl)phenyl]-4-[5-(2-ethoxypyridin-3-yl)pyrazin-2-yl]-N-[(3R)-1-methylpyrrolidin-3-yl]piperidine-4-carboxamide (Cpd 1-51)

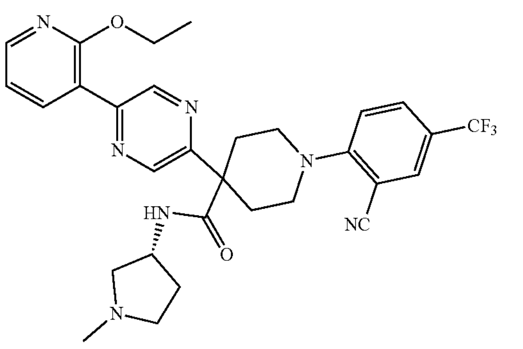 [SMILES: CCOc1ncccc1-c1cnc(C2(C(=O)N[C@@H]3CCN(C)C3)CCN(c3ccc(C(F)(F)F)cc3C#N)CC2)cn1]

Step 3-1, preparation of 1-tert-butyl 3-ethyl 2-(5-chloropyrazin-2-yl)propanedioate: Into a 100-mL round-bottom flask purged and maintained with an inert atmosphere of nitrogen, were placed 2,5-dichloropyrazine (4.0 g, 27 mmol), cesium carbonate (26 g, 80 mmol), tert-butyl ethyl malonate (5.6 g, 30 mmol) and DMSO (40 mL). The resulting mixture was stirred 100° C. for 2 h and cooled to room temperature. The reaction was quenched with water (200 mL) and then extracted with ethyl acetate (3×). The combined organic layers were washed with brine, dried over anhydrous sodium sulfate and concentrated under vacuum. The residue was applied onto a silica gel column with ethyl acetate/petroleum ether (1:3). This resulted in the title compound (4.6 g, 57%) as a yellow oil. LCMS $(M+H)^+$=301.1.

Step 3-2, preparation of ethyl 2-(5-chloropyrazin-2-yl)acetate: To a solution of 1-tert-butyl 3-ethyl 2-(5-chloropyrazin-2-yl)propanedioate (4.6 g, 15 mmol) in DCM (40 mL) was added TFA (10 mL) in an ice bath. The reaction was stirred at 0° C. for 1 h and quenched with water (100 mL). The resulting solution was extracted with ethyl acetate (3×). The combined organic layers were washed with brine, dried over anhydrous sodium sulfate and concentrated under vacuum. The residue was applied onto a silica gel column with ethyl acetate/petroleum ether (1:3) to afford the title compound (2.6 g, 85%) as yellow oil. LCMS $(M+H)^+$=201.1.

Step 3-3, preparation of ethyl 1-benzyl-4-(5-chloropyrazin-2-yl)piperidine-4-carboxylate: Into a 50 mL round-bottom flask. were placed ethyl 2-(5-chloropyrazin-2-yl)acetate (1.0 g, 5.0 mmol), 18-crown-6 (300 mg, 1.13 mmol) and DMF (10 mL). The reaction mixture was cooled to 0° C. and then treated with 60%-NaH (600 mg, 15 mmol). After stirring at 0° C. for 0.5 h, the reaction was treated with N-benzyl-2-bromo-N-(2-bromoethyl)ethan-1-amine (1.8 g, 5.6 mmol). The resulting mixture was stirred at rt for 2 h and then quenched with water (50 mL). The resulting solution was extracted with ethyl acetate (3×). The combined organic layers were washed with brine, dried over anhydrous sodium sulfate and concentrated under vacuum. The residue was applied onto a silica gel column with ethyl acetate/petroleum ether (1:3). This resulted in the title compound (800 mg, 45%) as a yellow oil. LCMS $(M+H)^+$=360.2.

Step 3-4, preparation of ethyl 1-benzyl-4-[5-(2-ethoxypyridin-3-yl)pyrazin-2-yl]piperidine-4-carboxylate: Into a 50 mL three-neck bottle, purged and maintained with an inert atmosphere of nitrogen, were added ethyl 1-benzyl-4-(5-chloropyrazin-2-yl)piperidine-4-carboxylate (800 mg, 2.22 mmol), (2-ethoxypyridin-3-yl)boronic acid (557 mg, 3.34 mmol), $Pd(DTBPF)Cl_2$ (145 mg, 0.22 mmol), $K_2CO_3$ (922 mg, 6.67 mmol), and dioxane/$H_2O$ (8 mL/0.8 mL). The resulting mixture was stirred 90° C. for 2 h under $N_2$ and then cooled to room temperature. The reaction was quenched with water (50 mL) and extracted with ethyl acetate (3×). The combined organic layers were washed with brine, dried over anhydrous sodium sulfate and concentrated under vacuum. The residue was applied onto a silica gel column with ethyl acetate/petroleum ether (1:1) to afford the title compound (800 mg, 80%) as yellow oil. LCMS $(M+H)^+$= 447.5.

Step 3-5, preparation of ethyl 4-[5-(2-ethoxypyridin-3-yl)pyrazin-2-yl]piperidine-4-carboxylate: To a solution of ethyl 1-benzyl-4-[5-(2-ethoxypyridin-3-yl)pyrazin-2-yl]piperidine-4-carboxylate (800 mg, 1.79 mmol) in MeOH (20 mL) was added 10%-Pd/C (191 mg) and $Pd(OH)_2$ (252 mg, 1.79 mmol). The flask was evacuated and flushed three times with nitrogen, followed by flushing with hydrogen. The mixture was stirred at rt 40 min under an atmosphere of hydrogen (balloon). The resulting solution was diluted with MeOH and filtered through a pad of Celite. The filtrate was concentrated under vacuum to afford the title compound (580 mg, 91%) as a white oil. LCMS $(M+H)^+$=357.3.

Step 3-6, preparation of ethyl 1-[2-cyano-4-(trifluoromethyl)phenyl]-4-[5-(2-ethoxypyridin-3-yl)pyrazin-2-yl]piperidine-4-carboxylate: Into a 8-mL vial, were placed ethyl 4-[5-(2-ethoxypyridin-3-yl)pyrazin-2-yl]piperidine-4-carboxylate (200 mg, 0.56 mmol), DIEA (218 mg, 1.69 mmol), 2-fluoro-5-(trifluoromethyl)benzonitrile (212 mg, 1.12 mmol) and DMSO (2 mL). The resulting mixture was stirred at 60° C. for 2 h and then cooled to room temperature. The crude product was purified by Prep-HPLC to afford the title compound (220 mg, 74%). LCMS $(M+H)^+$=526.5.

Step 3-7, preparation of 1-[2-cyano-4-(trifluoromethyl)phenyl]-4-[5-(2-ethoxypyridin-3-yl)pyrazin-2-yl]-N-[(3R)-1-methylpyrrolidin-3-yl]piperidine-4-carboxamide: Into a 8-mL vial purged and maintained with an inert atmosphere of nitrogen, were placed ethyl 1-[2-cyano-4-(trifluoromethyl)phenyl]-4-[5-(2-ethoxypyridin-3-yl)pyrazin-2-yl]piperidine-4-carboxylate (40 mg, 0.076 mmol), (R)-1-methylpyrrolidine-3-amine (23 mg, 0.23 mmol), LHMDS (130 mg, 0.77 mmol), and THE (1.3 mL). The resulting mixture was stirred at rt for 1 h under $N_2$ and then quenched with sat-$NH_4C_1$ (20 mL). The resulting solution was extracted with ethyl acetate (3×). The combined organic layers were washed with brine, dried over anhydrous sodium sulfate and concentrated under vacuum. The residue was purified by Prep-HPLC to afford the title compound (13 mg, 28%). LCMS $(M+H)^+$=580.2.

The following compounds were prepared similarly to Example 3 with appropriate substituting reagents and substrates at different steps.

| Compound no. | MS $(M + H)^+$ |
|---|---|
| 1-58 | 580.2 |

Example 4: 1-[2-cyano-4-(trifluoromethyl)phenyl]-4-[6-(2-ethoxypyridin-3-yl)pyridazin-3-yl]-N-[(3S)-1-methylpyrrolidin-3-yl]piperidine-4-carboxamide (Cpd 1-56)

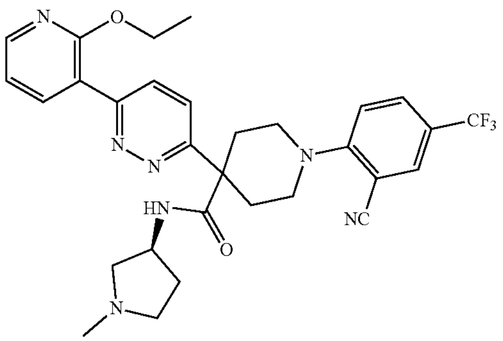 [SMILES: CCOc1ncccc1-c1ccc(C2(C(=O)N[C@H]3CCN(C)C3)CCN(c3ccc(C(F)(F)F)cc3C#N)CC2)nn1]

Step 4-1, preparation of ethyl 1-benzyl-4-[6-(2-ethoxypyridin-3-yl)pyridazin-3-yl]piperidine-4-carboxylate: Starting from 3,6-dichloropyridazine, the title compound was prepared by a similar manner described from step 3-1 to 3-4 in Example 3. LCMS $(M+H)^+$=447.3.

Step 4-2, preparation of 1-tert-butyl 4-ethyl 4-[6-(2-ethoxypyridin-3-yl)pyridazin-3-yl]piperidine-1,4-dicarboxylate: Into a 100-mL round bottom flask, was placed ethyl 1-benzyl-4-[6-(2-ethoxypyridin-3-yl)pyridazin-3-yl]piperidine-4-carboxylate (240 mg, 0.54 mmol), di-tert-butyl decarbonate (350 mg, 1.60 mmol), MeOH (30 mL), TEA (160 mg, 1.58 mmol), 10%-Pd/C (20 mg) and $Pd(OH)_2$ (20 mg, 0.14 mmol). The flask was evacuated and flushed three times with nitrogen, followed by flushing with hydrogen. The reaction mixture was stirred at rt for 2 h under an atmosphere of hydrogen (balloon). The reaction was filtered through a pad of Celite, and the filtrate was concentrated. The residue was purified by Prep-HPLC to afford the title compound (200 mg, 81%) as a light yellow oil. LCMS $(M+H)^+$=457.4.

Step 4-3, preparation of ethyl 4-[6-(2-ethoxypyridin-3-yl)pyridazin-3-yl]piperidine-4-carboxylate trifluoroacetate: To a solution of 1-tert-butyl 4-ethyl 4-[6-(2-ethoxypyridin-3-yl)pyridazin-3-yl]piperidine-1,4-dicarboxylate (200 mg, 0.44 mmol) in DCM (3 mL) was added TFA (1 mL). The resulting mixture was stirred at rt for 1 h and then concentrated under vacuum. This resulted in the title compound (200 mg, 96%) as yellow oil. LCMS $(M+H)^+$=357.2.

Step 4-4, preparation of ethyl 1-[2-cyano-4-(trifluoromethyl)phenyl]-4-[6-(2-ethoxypyridin-3-yl)pyridazin-3-yl]piperidine-4-carboxylate formate: Into a 8-mL vial, was placed ethyl 4-[6-(2-ethoxypyridin-3-yl)pyridazin-3-yl]piperidine-4-carboxylate trifluoroacetate (200 mg, 0.42 mmol), 2-fluoro-5-(trifluoromethyl)benzonitrile (96 mg, 51 mmol), DIEA (200 mg, 1.55 mmol) and DMSO (3 mL). The resulting solution was stirred at 60° C. for 1 h and cooled to rt. The reaction was directly purified by Prep-HPLC to afford the title compound (145 mg, 60%) as a light yellow oil. LCMS $(M+H)^+$=526.3.

Step 4-5, preparation of 1-[2-cyano-4-(trifluoromethyl)phenyl]-4-[6-(2-ethoxypyridin-3-yl)pyridazin-3-yl]-N-[(3S)-1-methylpyrrolidin-3-yl]piperidine-4-carboxamide: Into a 8-mL vial, were placed ethyl 1-[2-cyano-4-(trifluoromethyl)phenyl]-4-[6-(2-ethoxypyridin-3-yl)pyridazin-3-yl]piperidine-4-carboxylate (60 mg, 0.11 mmol), (S)-1-methylpyrrolidine-3-amine (30 mg, 0.30 mmol), and 1M-LiHMDS in THE (1.0 mL, 1.0 mmol) under $N_2$ atmosphere. The resulting mixture was stirred at rt for 1 h and then quenched with sat-$NH_4Cl$. The resulting solution was extracted with EtOAc (3×). The combined organic layers were washed with brine, dried over anhydrous sodium sulfate and concentrated under vacuum. The residue was purified by Prep-HPLC to afford the title compound (16 mg, 22%). LCMS $(M+H)^+$=580.2.

The following compounds were prepared similarly to Example 4 with appropriate substituting reagents and substrates at different steps.

| Compound no. | MS $(M + H)^+$ |
|---|---|
| 1-57 | 580.2 |
| 1-134 | 545.3 |
| 1-135 | 531.2 |
| 1-136 | 565.3 |
| 1-139 | 546.3 |
| 1-140 | 566.3 |
| 1-168 | 538.2 |
| 1-169 | 547.2 |
| 1-170 | 504.3 |
| 1-171 | 531.2 |
| 1-174 | 572.2 |
| 1-175 | 588.2 |
| 1-183 | 565.5 |
| 1-331 | 568.4 |

Example 5: 1-[2-cyano-4-(trifluoromethyl)phenyl]-4-[2-(2-ethoxypyridin-3-yl)pyrimidin-5-yl]-N-[(3S)-1-methylpyrrolidin-3-yl]piperidine-4-carboxamide (Cpd 1-106)

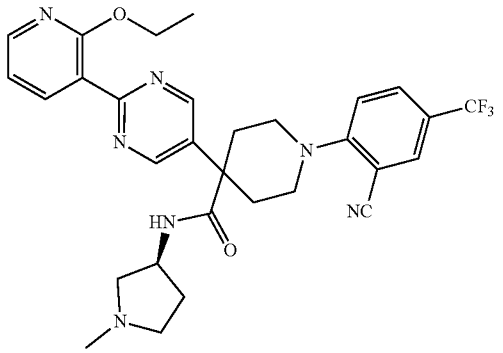 [SMILES: CCOc1ncccc1-c1ncc(C2(C(=O)N[C@H]3CCN(C)C3)CCN(c3ccc(C(F)(F)F)cc3C#N)CC2)cn1]

Step 5-1, preparation of [2-(2-ethoxypyridin-3-yl)pyrimidin-5-yl]methanol: Into a 100 mL three-neck bottle, purged and maintained with an inert atmosphere of nitrogen, were added (2-chloropyrimidin-5-yl)methanol (3.0 g, 21 mmol), (2-ethoxypyridin-3-yl)boronic acid (4.0 g, 21 mmol), Pd(DTBPF)$Cl_2$ (1.4 g, 2.1 mmol), $K_2CO_3$ (9.0 g, 65 mmol) and dioxane (30 mL)/$H_2O$ (3 mL) at rt. The resulting reaction mixture was stirred at 60° C. for 1 h and cooled to room temperature. The reaction was quenched with water and extracted with ethyl acetate (3×). The combined organic layers were washed with brine, dried over anhydrous sodium sulfate and concentrated under vacuum. The residue was applied onto a silica gel column with ethyl acetate/petroleum ether (2:1) to afford the title compound (4.2 g, 88%). LCMS $(M+H)^+$=232.1.

Step 5-2, preparation of [2-(2-ethoxypyridin-3-yl)pyrimidin-5-yl]methyl methanesulfonate: To a solution of [2-(2-ethoxypyridin-3-yl)pyrimidin-5-yl]methanol (2.0 g, 8.6 mmol) and TEA (3.0 g, 30 mmol) in DCM (20 mL) was slowly added MsCl (1.0 g, 8.7 mmol) in an ice bath. The reaction was stirred at 0° C. for 1 h, quenched with water (30 mL), and extracted with DCM (3×). The combined organic layers were washed with brine, dried over anhydrous sodium sulfate and concentrated under vacuum. This resulted in the title compound (2.3 g, 86%) as a yellow oil. LCMS $(M+H)^+$= 310.1.

Step 5-3, preparation of 2-[2-(2-ethoxypyridin-3-yl)pyrimidin-5-yl]acetonitrile: Into a 50-mL round-bottom flask, were placed [2-(2-ethoxypyridin-3-yl)pyrimidin-5-yl]methyl methanesulfonate (2.3 g, 7.4 mmol), sodium cyanide (1.1 g, 22 mmol) and DMSO (20 mL). The resulting mixture was at rt stirred for 1 h, quenched with aq-$FeSO_4$ (~100 mL), and then extracted with ethyl acetate (3×). The combined organic layers were washed with brine, dried over anhydrous sodium sulfate and concentrated under vacuum. The residue was applied onto a silica gel column with DCM/MeOH (10:1) to afford the title compound (1.3 g, 73%) as a yellow oil. LCMS $(M+H)^+$=241.1.

Step 5-4, preparation of 1-benzyl-4-[2-(2-ethoxypyridin-3-yl)pyrimidin-5-yl]piperidine-4-carbonitrile: Into a 50-mL round-bottom flask, were placed 2-[2-(2-ethoxypyridin-3-yl)pyrimidin-5-yl]acetonitrile (600 mg, 2.5 mmol), N-benzyl-2-bromo-N-(2-bromoethyl)ethan-1-amine (962 mg, 3.0 mmol), KOH (420 mg, 7.49 mmol), and DMSO (10 mL). The resulting mixture was stirred at rt for 1 h, quenched with water (50 mL) and extracted with ethyl acetate (3×). The combined organic layers were washed with brine, dried over anhydrous sodium sulfate and concentrated under vacuum. The residue was applied onto a silica gel column with ethyl acetate/petroleum ether (1:1). This resulted in the title compound (450 mg, 45%) as a yellow oil. LCMS $(M+H)^+$= 400.2.

Step 5-5, preparation of 1-benzyl-4-[2-(2-ethoxypyridin-3-yl)pyrimidin-5-yl]piperidine-4-carboxylic acid: Into a 50-mL round-bottom flask. were placed 1-benzyl-4-[2-(2-ethoxypyridin-3-yl)pyrimidin-5-yl]piperidine-4-carbonitrile (450 mg, 1.13 mmol), KOH (632 mg, 11.3 mmol), and EtOH (5 mL)/$H_2O$ (2.5 mL). The resulting mixture was stirred at 100° C. for 16 h and cooled to room temperature. The reaction was diluted with water (20 ml), then adjusted to pH 6~7 with 3N-HCl and extracted with ethyl acetate (3×). The combined organic layers were washed with brine, dried over anhydrous sodium sulfate and concentrated under vacuum. This resulted in the title compound (400 mg, 85%) as a yellow oil. LCMS $(M+H)^+$=419.2.

Step 5-6, preparation of 1-benzyl-4-[2-(2-ethoxypyridin-3-yl)pyrimidin-5-yl]-N-[(3S)-1-methylpyrrolidin-3-yl]piperidine-4-carboxamide: To a solution of 1-benzyl-4-[2-(2-ethoxypyridin-3-yl)pyrimidin-5-yl]piperidine-4-carboxylic acid (180 mg, 0.43 mmol) in DMF (2 mL) was added HATU (164 mg, 0.43 mmol) and DIEA (167 mg, 1.29 mmol) at rt. After stirring for 10 min at rt, the reaction was treated with (S)-1-methylpyrrolidine-3-amine (52 mg, 0.52 mmol). The resulting mixture was stirred at rt for 1 h and then directly purified by prep-HPLC to afford the title compound (150 mg, 70%) as a white oil. LCMS $(M+H)^+$=501.3.

Step 5-7, preparation of tert-butyl 4-[2-(2-ethoxypyridin-3-yl)pyrimidin-5-yl]-4-{[(3S)-1-methylpyrrolidin-3-yl]carbamoyl}piperidine-1-carboxylate: Into a 50-mL round-bottom flask. were placed 1-benzyl-4-[2-(2-ethoxypyridin-3-yl)pyrimidin-5-yl]-N-[(3S)-1-methylpyrrolidin-3-yl]piperidine-4-carboxamide (160 mg, 0.32 mmol), TEA (98 mg, 0.97 mmol), $(Boc)_2O$ (209 mg, 0.96 mmol), wet 10%-Pd/C (34 mg), $Pd(OH)_2$ (45 mg, 0.32 mmol) and MeOH (10 mL). The flask was evacuated and flushed three times with nitrogen, followed by flushing with hydrogen. The mixture was stirred at rt 30 min under an atmosphere of hydrogen (balloon). The reaction was diluted with MeOH and filtered through a pad of Celite. The filtrate was concentrated under vacuum. The residue was purified by prep-HPLC to afford the title compound (40 mg, 25%) as a white oil. LCMS $(M+H)^+$=511.3.

Step 5-8, preparation of 4-[2-(2-ethoxypyridin-3-yl)pyrimidin-5-yl]-N-[(3S)-1-methylpyrrolidin-3-yl]piperidine-4-carboxamide bistrifluoracetate: To a solution of tert-butyl 4-[2-(2-ethoxypyridin-3-yl)pyrimidin-5-yl]-4-{[(3S)-1-methylpyrrolidin-3-yl]carbamoyl}piperidine-1-carboxylate (40 mg, 0.078 mmol) in DCM (1 mL) was added TFA (0.3 mL). The resulting solution was stirred at rt for 1 h and then concentrated under vacuum. This resulted in the title compound (30 mg, 60%) as yellow oil. LCMS $(M+H)^+$=411.3.

Step 5-9, preparation of 1-[2-cyano-4-(trifluoromethyl)phenyl]-4-[2-(2-ethoxypyridin-3-yl)pyrimidin-5-yl]-N-[(3S)-1-methylpyrrolidin-3-yl]piperidine-4-carboxamide bistrifluoracetate: Into a 8-mL vial, were placed 4-[2-(2-ethoxypyridin-3-yl)pyrimidin-5-yl]-N-[(3S)-1-methylpyrrolidin-3-yl]piperidine-4-carboxamide bistrifluoracetate (30 mg, 0.047 mmol), DIEA (28 mg, 0.22 mmol), 2-fluoro-5-(trifluoromethyl)benzonitrile (28 mg, 0.15 mmol), and DMSO (1 mL). The resulting mixture was stirred at 60° C. for 2 h and cooled to room temperature. The reaction was purified by Prep-HPLC to afford the title compound (14 mg, 38%). LCMS $(M+H)^+$=580.3.

The following compounds were prepared similarly to Example 5 with appropriate substituting reagents and substrates at different steps:

| Compound no. | MS (M + H)$^+$ |
|---|---|
| 1-107 | 580.3 |

Example 6: 1-[2-cyano-4-(trifluoromethyl)phenyl]-4-[6-(2-ethoxyphenyl)-5-fluoropyridin-3-yl]-N-[(3S)-1-methylpyrrolidin-3-yl]piperidine-4-carboxamide (Cpd 1-124)

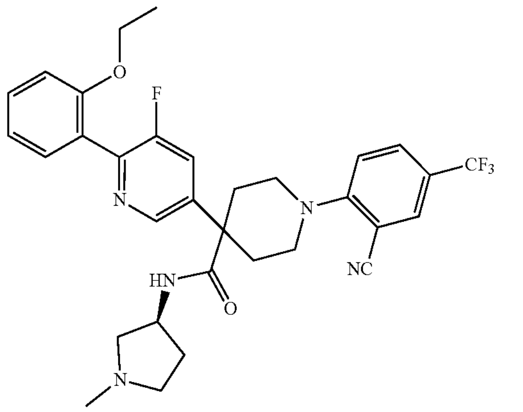 [SMILES: CCOc1ccccc1-c1ncc(C2(C(=O)N[C@H]3CCN(C)C3)CCN(c3ccc(C(F)(F)F)cc3C#N)CC2)cc1F]

Step 6-1, preparation of 2-chloro-3-fluoro-5-(1,2-oxazol-4-yl)pyridine: Into a 250 mL three-neck bottle, purged and maintained with an inert atmosphere of nitrogen, were added 5-bromo-2-chloro-3-fluoropyridine (5.0 g, 24 mmol), 4-(4,4,5,5-tetramethyl-1,3,2-dioxaborolan-2-yl)isoxazole (5.6 g, 29 mmol), Pd(DTBPF)$Cl_2$ (1.5 g, 2.3 mmol), KF (4.1 g, 71 mmol), and DMSO (50 mL)/$H_2O$ (5 mL). The resulting mixture was stirred at 100° C. for 1 h and cooled to room temperature. The reaction was diluted with $H_2O$ and extracted with EtOAc (3×). The combined organic layers were washed with brine, dried over anhydrous sodium sulfate and concentrated under vacuum. The residue was purified by prep-HPLC to afford the title compound (3.5 g, 74%) as yellow solid. LCMS $(M+H)^+$=199.0.

Step 6-2, preparation of 2-(6-chloro-5-fluoropyridin-3-yl) acetonitrile: To a solution of 2-chloro-3-fluoro-5-(1,2-oxazol-4-yl)pyridine (3.5 g, 18 mmol) in MeOH (35 mL)/$H_2O$ (3.5 mL) was added KF (0.2 g, 3.0 mmol). The resulting solution was stirred at 90° C. for 1 h and cooled to room temperature. The reaction was diluted with water (100 mL) and extracted with ethyl acetate (3×). The combined organic layers were washed with brine, dried over anhydrous sodium sulfate and concentrated under vacuum. The residue was applied onto a silica gel column with ethyl acetate/petroleum ether (1:1) to afford the title compound (2.3 g, 77%) as yellow solid. LCMS $(M+H)^+$=171.1.

Step 6-3, preparation of 1-benzyl-4-(6-chloro-5-fluoropyridin-3-yl)piperidine-4-carbonitrile: Into a 50-mL round-bottom flask, were placed 2-(6-chloro-5-fluoropyridin-3-yl) acetonitrile (2.3 g, 13 mmol), N-benzyl-2-bromo-N-(2-bromoethyl)ethan-1-amine (4.3 g, 13 mmol), KOH (2.3 g, 41 mmol), and DMSO (25 mL). The resulting mixture was stirred at rt for 1 h, quenched with water (100 mL) and extracted with ethyl acetate (3×). The combined organic layers were washed with brine, dried over anhydrous sodium sulfate and concentrated under vacuum. The residue was applied onto a silica gel column with ethyl acetate/petroleum ether (1:1). This resulted in the title compound (2.7 g, 61%) as a yellow oil. LCMS $(M+H)^+$=330.2.

Step 6-4, preparation of 1-benzyl-4-[6-(2-ethoxyphenyl)-5-fluoropyridin-3-yl]piperidine-4-carbonitrile: Into a 50 mL three-neck bottle, purged and maintained with an inert atmosphere of nitrogen, were added 1-benzyl-4-(6-chloro-5-fluoropyridin-3-yl)piperidine-4-carbonitrile (500 mg, 1.52 mmol), (2-ethoxyphenyl)boronic acid (300 mg, 1.81 mmol), Pd(DTBPF)$Cl_2$ (99 mg, 0.15 mmol), $K_2CO_3$ (630 mg, 4.56 mmol) and dioxane (5 mL)/$H_2O$ (0.5 mL) at rt. The resulting reaction mixture was stirred at 100° C. for 1 h and cooled to room temperature. The reaction was quenched with water and extracted with ethyl acetate (3×). The combined organic layers were washed with brine, dried over anhydrous sodium sulfate and concentrated under vacuum. The residue was applied onto a silica gel column with ethyl acetate/petroleum ether (1:1) to afford the title compound (500 mg, 79%) as light yellow oil. LCMS $(M+H)^+$=416.3.

Step 6-5, preparation of 1-benzyl-4-[6-(2-ethoxyphenyl)-5-fluoropyridin-3-yl]piperidine-4-carboxylic acid: Into a 50-mL round-bottom flask, were placed 1-benzyl-4-[6-(2-ethoxyphenyl)-5-fluoropyridin-3-yl]piperidine-4-carbonitrile (500 mg, 1.2 mmol), KOH (675 mg, 12.0 mmol), and EtOH (10 mL)/$H_2O$ (5 mL). The resulting mixture was stirred at 100° C. for 24 h and cooled to room temperature. The reaction was diluted with water (20 ml), then adjusted to pH 6~7 with 3N-HCl and extracted with ethyl acetate (3×). The combined organic layers were washed with brine, dried over anhydrous sodium sulfate and concentrated under vacuum. This resulted in the title compound (450 mg, 86%) as a yellow solid. LCMS $(M+H)^+$=435.2.

Step 6-6, preparation of 1-benzyl-4-[6-(2-ethoxyphenyl)-5-fluoropyridin-3-yl]-N-[(3S)-1-methylpyrrolidin-3-yl]piperidine-4-carboxamide: To a solution of 1-benzyl-4-[6-(2-ethoxyphenyl)-5-fluoropyridin-3-yl]piperidine-4-carboxylic acid (140 mg, 0.32 mmol) in DMF (2 mL) was added HATU (123 mg, 0.32 mmol) and DIEA (125 mg, 0.97 mmol). After stirring for 10 min at rt, the reaction was treated with (S)-1-methylpyrrolidine-3-amine dihydrochloride (56 mg, 0.32 mmol). The resulting mixture was stirred at rt for 1 h and then directly purified by prep-HPLC to afford the title compound (130 mg, 73%) as a white solid. LCMS $(M+H)^+$=517.4.

Step 6-7, preparation of 4-[6-(2-ethoxyphenyl)-5-fluoropyridin-3-yl]-N-[(3S)-1-methylpyrrolidin-3-yl]piperidine-4-carboxamide: Into a 50-mL round-bottom flask, were placed 1-benzyl-4-[6-(2-ethoxyphenyl)-5-fluoropyridin-3-yl]-N-[(3S)-1-methylpyrrolidin-3-yl]piperidine-4-carboxamide (130 mg, 0.25 mmol), wet 10%-Pd/C (27 mg), $Pd(OH)_2$ (35 mg, 0.25 mmol) and MeOH (5 mL). The flask was evacuated and flushed three times with nitrogen, followed by flushing with hydrogen. The mixture was stirred at rt 30 min under an atmosphere of hydrogen (balloon). The reaction was diluted with MeOH and filtered through a pad of Celite. The filtrate was concentrated under vacuum. This resulted in the title compound (90 mg, 84%) as a white oil. LCMS $(M+H)^+$=427.5.

Step 6-8, preparation of 1-[2-cyano-4-(trifluoromethyl) phenyl]-4-[6-(2-ethoxyphenyl)-5-fluoropyridin-3-yl]-N-[(3S)-1-methylpyrrolidin-3-yl]piperidine-4-carboxamide formate: Into a 8-mL vial, were placed 4-[6-(2-ethoxyphenyl)-5-fluoropyridin-3-yl]-N-[(3S)-1-methylpyrrolidin-3-yl]piperidine-4-carboxamide (45 mg, 0.11 mmol), DIEA (41 mg, 0.32 mmol), 2-fluoro-5-(trifluoromethyl)benzonitrile (40 mg, 0.21 mmol), and DMSO (1 mL). The resulting mixture was stirred at 60° C. for 2 h and cooled to room temperature. The reaction was purified by Prep-HPLC to afford the title compound (29 mg, 43%) as a white solid. LCMS $(M+H)^+$=596.3.

The following compounds were prepared similarly to Example 6 with appropriate substituting reagents and substrates at different steps. Some examples require deprotection in the final step:

| Compound no. | MS $(M + H)^+$ |
|---|---|
| 1-108 | 597.3 |
| 1-109 | 597.3 |
| 1-110 | 598.3 |
| 1-123 | 596.3 |
| 1-125 | 597.3 |
| 1-126 | 582.3 |
| 1-127 | 582.3 |
| 1-128 | 583.3 |
| 1-131 | 583.3 |
| 1-132 | 583.3 |
| 1-133 | 584.3 |
| 1-161 | 555.2 |
| 1-162 | 564.5 |
| 1-163 | 522.2 |
| 1-195 | 600.3 |
| 1-196 | 556.3 |
| 1-197 | 570.3 |
| 1-334 | 615.3 |

Example 7: 1-[2-cyano-4-(trifluoromethyl)phenyl]-4-{2'-ethoxy-[2,3'-bipyridin]-5-yl}-N-[(3R)-1-methylpyrrolidin-3-yl]piperidine-4-carboxamide (Cpd 1-9)

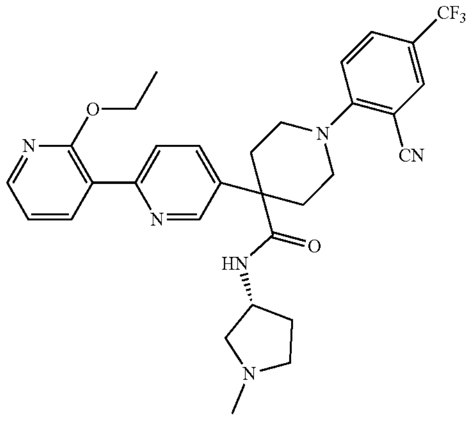 [SMILES: CCOc1ncccc1-c1ccc(C2(C(=O)N[C@@H]3CCN(C)C3)CCN(c3ccc(C(F)(F)F)cc3C#N)CC2)cn1]

Step 7-1, preparation of methyl 1-benzyl-4-(6-chloropyridin-3-yl)piperidine-4-carboxylate: To a solution of methyl 6-chloropyridine-3-carboxylate (4.0 g, 22 mmol) and 18-Crown-6 (1.1 g, 4.2 mmol) in DMF (30 mL) at 0° C. was added 60% sodium hydride in mineral oil (2.2 g, 55 mmol) in portions. The mixture was stirred at 0° C. for 2 h. To this was added a solution of benzylbis(2-bromoethyl)amine (8.3 g, 26 mmol) in DMF (10 mL). The mixture was stirred at rt for 2 h. The mixture was quenched with water and extracted with EtOAc (3×). The combined organics were dried over anhydrous $Na_2SO_4$ and concentrated to dryness to give the title compound (4.8 g, 65%) as a yellow solid. LCMS $(M+H)^+$=345.2.

Step 7-2, preparation of methyl 1-benzyl-4-{2'-ethoxy-[2,3'-bipyridin]-5-yl}piperidine-4-carboxylate: To a suspension of methyl 1-benzyl-4-(6-chloropyridin-3-yl)piperidine-4-carboxylate (1.8 g, 5.2 mmol) in 1,4-dioxane (20 mL) and water (2 mL) under nitrogen was added potassium carbonate (2.2 g, 16 mmol), (2-ethoxypyridin-3-yl)boronic acid (1.7 g, 10 mmol) and Pd(dtbpf)$Cl_2$ (0.10 g, 0.15 mmol). The mixture was heated at 90° C. for 2 h. The mixture was quenched with water and extracted with EtOAc (2×). The combined organics were concentrated to dryness and the residue was purified by silica gel CC to give the title compound (1.8 g, 80%) as a light yellow solid. LCMS $(M+H)^+$=432.3.

Step 7-3, preparation of methyl 4-{2'-ethoxy-[2,3'-bipyridin]-5-yl}piperidine-4-carboxylate: To a solution of methyl 1-benzyl-4-{2'-ethoxy-[2,3'-bipyridin]-5-yl}piperidine-4-carboxylate (1.8 g, 4.2 mmol) in MeOH (25 mL) was added 10 wt. % of Pd on carbon (100 mg) and 20 wt. % of $Pd(OH)_2$ on carbon (100 mg). The mixture was charged with hydrogen (g) and stirred at rt for 2 h. The mixture was filtered and the filtrate was concentrated to dryness to give the title compound (1.2 g, 60%) as yellow oil. LCMS $(M+H)^+$=342.2.

Step 7-4, preparation of methyl 1-[2-cyano-4-(trifluoromethyl)phenyl]-4-{2'-ethoxy-[2,3'-bipyridin]-5-yl}piperidine-4-carboxylate: To a solution of methyl 4-{2'-ethoxy-[2,3'-bipyridin]-5-yl}piperidine-4-carboxylate (1.2 g, 3.5 mmol) and 2-fluoro-5-(trifluoromethyl)benzonitrile (0.8 g, 4 mmol) in DMSO (15 mL) was added DIEA (1.4 g, 11 mmol). The mixture was heated at 60° C. for 2 h. The mixture was quenched with water and extracted with EtOAc (3×). The combined organics were concentrated to dryness and the residue was purified by silica gel CC to give the title compound (1.1 g, 61%) as a white solid. LCMS $(M+H)^+$=511.3.

Step 7-5, preparation of 1-[2-cyano-4-(trifluoromethyl)phenyl]-4-{2'-ethoxy-[2,3'-bipyridin]-5-yl}piperidine-4-carboxylic acid: To a suspension of methyl 1-[2-cyano-4-(trifluoromethyl)phenyl]-4-{2'-ethoxy-[2,3'-bipyridin]-5-yl}piperidine-4-carboxylate (1.4 g, 2.7 mmol) in a mixed solvent of EtOH and water (2:1, 12 mL) was added lithium hydroxide (0.60 g, 25 mmol). The mixture was heated at 60° C. for 2 h. The mixture was concentrated to remove the organics and the aqueous residue was adjusted to pH 6-7 with 1N HCl (aq). The solution was extracted with EtOAc (3×) and the combined organics were dried over anhydrous $Na_2SO_4$ and concentrated to dryness to give the title compound (1.2 g, 88%) as a light yellow solid. LCMS $(M+H)^+$=497.3.

Step 7-6, preparation of 1-[2-cyano-4-(trifluoromethyl)phenyl]-4-{2'-ethoxy-[2,3'-bipyridin]-5-yl}-N-[(3R)-1-methylpyrrolidin-3-yl]piperidine-4-carboxamide: To a solution of 1-[2-cyano-4-(trifluoromethyl)phenyl]-4-{2'-ethoxy-[2,3'-bipyridin]-5-yl}piperidine-4-carboxylic acid (60 mg, 0.12 mmol) and HATU (55 mg, 0.14 mmol) in DMF (1 mL) was added DIEA (94 mg, 0.73 mmol). After stirring at rt for 5 min, (3R)-1-methylpyrrolidin-3-amine dihydrochloride (31 mg, 0.18 mmol) was added to the above HATU-activated solution. The mixture was stirred at rt for 1 h and purified by reversed-phase CC to give the title compound (42 mg, 56%) as a white solid. LCMS $(M+H)^+$=579.3.

The following compounds were prepared similarly to Example 7 with appropriate substituting reagents and substrates at different steps:

| Compound no. | MS (M + H)$^+$ |
|---|---|
| 1-11 | 579.3 |
| 1-15 | 567.4 |
| 1-18 | 579.3 |
| 1-19 | 565.3 |
| 1-20 | 605.3 |
| 1-41 | 595.3 |
| 1-45 | 597.2 |
| 1-46 | 595.2 |
| 1-48 | 597.2 |
| 1-166 | 564.5 |
| 1-176 | 535.5 |
| 1-178 | 565.7 |
| 1-179 | 565.4 |

Example 8: 1-[2-cyano-4-(trifluoromethyl)phenyl]-4-{2'-ethoxy-[2,3'-bipyridin]-5-yl}-N-[(3R)-pyrrolidin-3-yl]piperidine-4-carboxamide (Cpd 1-10)

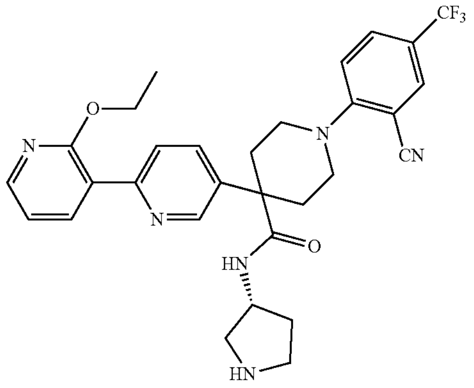 [SMILES: CCOc1ncccc1-c1ccc(C2(C(=O)N[C@@H]3CCNC3)CCN(c3ccc(C(F)(F)F)cc3C#N)CC2)cn1]

Step 8-1, preparation of tert-butyl (3R)-3-{1-[2-cyano-4-(trifluoromethyl)phenyl]-4-{2'-ethoxy-[2,3'-bipyridin]-5-yl}piperidine-4-amido}pyrrolidine-1-carboxylate: To a solution of 1-[2-cyano-4-(trifluoromethyl)phenyl]-4-{2'-ethoxy-[2,3'-bipyridin]-5-yl}piperidine-4-carboxylic acid (60 mg, 0.10 mmol) from Step 7-5 and HATU (58 mg, 0.15 mmol) in DMF (1 mL) was added DIEA (0.10 mL, 0.57 mmol). After stirring at rt for 5 min, tert-butyl (3R)-3-aminopyrrolidine-1-carboxylate (45 mg, 0.24 mmol) was added to the above HATU-activated solution. The mixture was stirred at rt for 1 h and purified by reversed-phase CC to give the title compound (69 mg, 100%) as light brown oil. LCMS (M+H)$^+$=665.3.

Step 8-2, preparation of 1-[2-cyano-4-(trifluoromethyl)phenyl]-4-{2'-ethoxy-[2,3'-bipyridin]-5-yl}-N-[(3R)-pyrrolidin-3-yl]piperidine-4-carboxamide: To a solution of tert-butyl (3R)-3-{1-[2-cyano-4-(trifluoromethyl)phenyl]-4-{2'-ethoxy-[2,3'-bipyridin]-5-yl}piperidine-4-amido}pyrrolidine-1-carboxylate (69 mg, 0.10 mmol) in DCM (4 mL) was added TFA (1 mL). The mixture was stirred at rt for 1 h. The mixture was concentrated to dryness and the residue was purified by reversed-phase CC to give the title compound (32 mg, 51%) as light brown oil. LCMS (M+H)$^+$=565.3.

The following compounds were prepared similarly to Example 8 with appropriate substituting reagents and substrates at different steps:

| Compound no. | MS (M + H)$^+$ |
|---|---|
| 1-12 | 565.3 |
| 1-13 | 539.3 |
| 1-14 | 553.3 |
| 1-16 | 553.3 |
| 1-17 | 569.3 |
| 1-28 | 569.2 |
| 1-44 | 583.3 |
| 1-47 | 583.3 |
| 1-21 | 565.3 |

Example 9: 1-(2-cyanophenyl)-4-{2'-ethoxy-[2,3'-bipyridin]-5-yl}-N-[(3S)-1-methylpyrrolidin-3-yl]piperidine-4-carboxamide (Cpd 1-32)

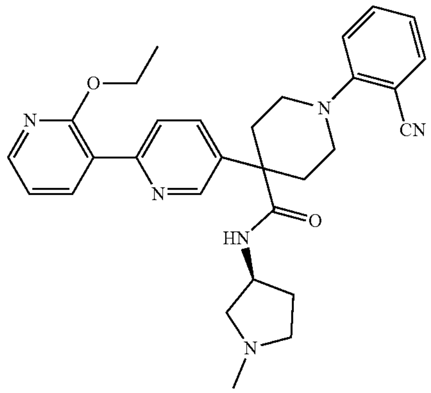 [SMILES: CCOc1ncccc1-c1ccc(C2(C(=O)N[C@H]3CCN(C)C3)CCN(c3ccccc3C#N)CC2)cn1]

Step 9-1, preparation of ethyl 1-benzyl-4-(6-chloropyridin-3-yl)piperidine-4-carboxylate: To a solution of ethyl 6-chloropyridine-3-carboxylate (9.5 g, 48 mmol) in DMF (100 mL) at 0° C. was added 60% sodium hydride in mineral oil (3.4 g, 0.14 mol) in portions. The mixture was stirred at 0° C. for 0.5 h. To this was added benzylbis(2-bromoethyl)amine (8.3 g, 26 mmol) and the mixture was stirred at rt for 2 h. The mixture was quenched with water and extracted with EtOAc (3×). The combined organics were dried over anhydrous $Na_2SO_4$ and concentrated to dryness. The residue was purified by silica gel CC to give the title compound (12 g, 70%) as yellow oil. LCMS (M+H)$^+$=359.2.

Step 9-2, preparation of ethyl 1-benzyl-4-{2'-ethoxy-[2,3'-bipyridin]-5-yl}piperidine-4-carboxylate: To a suspension of ethyl 1-benzyl-4-(6-chloropyridin-3-yl)piperidine-4-carboxylate (5.0 g, 14 mmol) in 1,4-dioxane (50 mL) and water (5 mL) under nitrogen was added potassium carbonate (5.8 g, 42 mmol), (2-ethoxypyridin-3-yl)boronic acid (3.5 g, 21 mmol) and Pd(dtbpf)$Cl_2$ (0.91 g, 1.4 mmol). The mixture was heated at 90° C. for 2 h. The mixture was quenched with water and extracted with EtOAc (3×). The combined organics were concentrated to dryness and the residue was purified by silica gel CC to give the title compound (5.5 g, 89%) as a yellow solid. LCMS (M+H)$^+$=446.3.

Step 9-3, preparation of 1-benzyl-4-{2'-ethoxy-[2,3'-bipyridin]-5-yl}piperidine-4-carboxylic acid: To a suspension of ethyl 1-(4-chloro-2-cyanophenyl)-4-[6-(2-ethoxyphenyl)pyridin-3-yl]piperidine-4-carboxylate (2.0 g, 4.5 mmol) in a mixed solvent of EtOH and water (2:1, 45 mL) was added lithium hydroxide (1.1 g, 46 mmol). The mixture was heated at 60° C. for 1 h. The mixture was diluted with water and adjusted to pH 6-7 with 3N HCl (aq). The mixture was extracted with EtOAc (3×) and the combined organics were dried over anhydrous $Na_2SO_4$ and concentrated to dryness to give the title compound (1.5 g, 80%) as yellow oil. LCMS $(M+H)^+$=418.1.

Step 9-4, preparation of 1-benzyl-4-{2'-ethoxy-[2,3'-bipyridin]-5-yl}-N-[(3S)-1-methylpyrrolidin-3-yl]piperidine-4-carboxamide: To a solution of 1-benzyl-4-{2'-ethoxy-[2,3'-bipyridin]-5-yl}piperidine-4-carboxylic acid (1.2 g, 2.9 mmol) and HATU (1.1 g, 2.9 mmol) in DMF (12 mL) was added DIEA (1.5 mL, 8.5 mmol). After stirring at rt for 5 min, (3S)-1-methylpyrrolidin-3-amine (0.30 g, 3.0 mmol) was added to the above HATU-activated solution. The mixture was stirred at rt for 2 h. The mixture was quenched with water and extracted with EtOAc (3×). The combined organics were concentrated to dryness and the residue was purified by silica gel CC to give the title compound (1.1 g, 77%) as yellow oil. LCMS $(M+H)^+$=500.4.

Step 9-5, preparation of 4-{2'-ethoxy-[2,3'-bipyridin]-5-yl}-N-[(3S)-1-methylpyrrolidin-3-yl]piperidine-4-carboxamide: To a solution of 1-benzyl-4-{2'-ethoxy-[2,3'-bipyridin]-5-yl}-N-[(3S)-1-methylpyrrolidin-3-yl]piperidine-4-carboxamide (1.1 g, 2.2 mmol) in MeOH (20 mL) was added 10 wt. % of Pd on carbon (0.23 g) and 20 wt. % of $Pd(OH)_2$ on carbon (0.31 g). The mixture was charged with hydrogen (g) and stirred at rt for 1 h. The mixture was filtered and the filtrate was concentrated to dryness to give the title compound (0.70 g, 78%) as white oil. LCMS $(M+H)^+$=410.3.

Step 9-6, preparation of 1-(2-cyanophenyl)-4-{2'-ethoxy-[2,3'-bipyridin]-5-yl}-N-[(3S)-1-methylpyrrolidin-3-yl]piperidine-4-carboxamide: To a solution of 4-{2'-ethoxy-[2,3'-bipyridin]-5-yl}-N-[(3S)-1-methylpyrrolidin-3-yl] piperidine-4-carboxamide (45 mg, 0.11 mmol) and 2-fluorobenzonitrile (40 mg, 0.33 mmol) in DMSO (1 mL) was added DIEA (28 mg, 0.22 mmol). The mixture was heated at 120° C. for 1 h. The mixture was purified by revered-phase CC to give the title compound (18 mg, 31%) as a white solid. LCMS $(M+H)^+$=511.2.

The following compounds were prepared similarly to Example 9 with appropriate substituting reagents and substrates at different steps:

| Compound no. | MS $(M + H)^+$ |
| --- | --- |
| 1-34 | 545.2 |
| 1-35 | 555.3 |
| 1-36 | 553.2 |
| 1-37 | 561.3 |
| 1-38 | 579.2 |
| 1-39 | 595.2 |
| 1-40 | 536.2 |
| 1-42 | 580.3 |
| 1-59 | 575.3 |
| 1-150 | 588.4 |
| 1-308 | 585.3 |
| 1-311 | 571.3 |

Example 10: 4-{2'-ethoxy-[2,3'-bipyridin]-5-yl}-N-[(3S)-1-methylpyrrolidin-3-yl]-1-[4-(trifluoromethyl)phenyl]piperidine-4-carboxamide (Cpd 1-33)

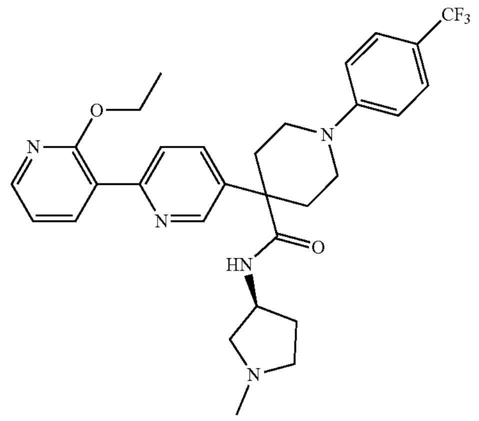 [SMILES: CCOc1ncccc1-c1ccc(C2(C(=O)N[C@H]3CCN(C)C3)CCN(c3ccc(C(F)(F)F)cc3)CC2)cn1]

Step 10-1, preparation of 4-{2'-ethoxy-[2,3'-bipyridin]-5-yl}-N-[(3S)-1-methylpyrrolidin-3-yl]-1-[4-(trifluoromethyl)phenyl]piperidine-4-carboxamide formate: To a mixture of 4-{2'-ethoxy-[2,3'-bipyridin]-5-yl}-N-[(3S)-1-methylpyrrolidin-3-yl]piperidine-4-carboxamide (40 mg, 0.098 mmol), 1-bromo-4-(trifluoromethyl)benzene (33 mg, 0.115 mmol), XPhos (17 mg, 0.020 mmol), $Pd_2(dba)_3$ (9.0 mg, 0.0098 mmol), and sodium tert-butoxide (28 mg, 0.29 mmol) under nitrogen was added toluene (1 mL). The mixture was heated at 80° C. for 1 h. The mixture was filtered and the filtrate was concentrated to dryness. The residue was purified by reversed-phase CC to give the title compound (25 mg, 43%) as yellow oil. LCMS $(M+H)^+$=554.2.

The following compounds were prepared similarly to Example 10 with appropriate substituting reagents and substrates at different steps:

| Compound no. | MS $(M + H)^+$ |
| --- | --- |
| 1-154 | 592.2 |
| 1-155 | 591.2 |
| 1-156 | 571.2 |
| 1-186 | 572.3 |

Example 11: 1-[2-cyano-6-(trifluoromethyl)pyridin-3-yl]-4-{2'-ethoxy-[2,3'-bipyridin]-5-yl}-N-[(3R)-1-methylpyrrolidin-3-yl]piperidine-4-carboxamide & 3-(4-{2'-ethoxy-[2,3'-bipyridin]-5-yl}-4-{[(3R)-1-methylpyrrolidin-3-yl]carbamoyl}piperidin-1-yl)-6-(trifluoromethyl)pyridine-2-carboxamide (Cpd 1-24 & 1-25)

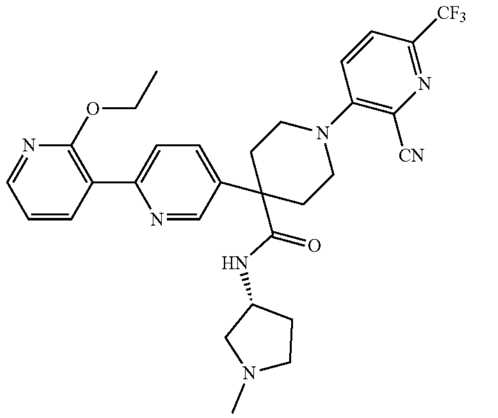

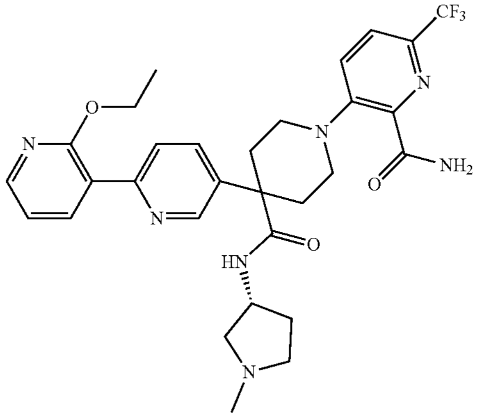

Step 11-1, preparation of ethyl 4-{2'-ethoxy-[2,3'-bipyridin]-5-yl}piperidine-4-carboxylate: To a solution of ethyl 1-benzyl-4-{2'-ethoxy-[2,3'-bipyridin]-5-yl}piperidine-4-carboxylate (2.0 g, 4.5 mmol) in MeOH (100 mL) was added 10 wt. % of Pd on carbon (100 mg) and 20 wt. % of $Pd(OH)_2$ on carbon (100 mg). The mixture was stirred at rt for 3 h under hydrogen (3 bar). The mixture was filtered and the filtrate was concentrated to dryness to give the title compound (1.0 g, 62%) as light yellow oil. LCMS $(M+H)^+$=356.2.

Step 11-2, preparation of ethyl 1-[2-cyano-6-(trifluoromethyl)pyridin-3-yl]-4-{2'-ethoxy-[2,3'-bipyridin]-5-yl}piperidine-4-carboxylate: To a solution of ethyl 4-{2'-ethoxy-[2,3'-bipyridin]-5-yl}piperidine-4-carboxylate (0.2 g, 0.6 mmol) and 3-fluoro-6-(trifluoromethyl)pyridine-2-carbonitrile (0.16 g, 0.84 mmol) in DMSO (5 mL) was added DIEA (0.4 mL, 2 mmol). The mixture was heated at 60° C. for 2 h. The mixture was purified by reversed-phase CC to give the title compound (0.21 g, 70%) as light yellow oil. LCMS $(M+H)^+$=526.5.

Step 11-3, preparation of 1-[2-cyano-6-(trifluoromethyl)pyridin-3-yl]-4-{2'-ethoxy-[2,3'-bipyridin]-5-yl}piperidine-4-carboxylic acid & 1-[2-carbamoyl-6-(trifluoromethyl)pyridin-3-yl]-4-{2'-ethoxy-[2,3'-bipyridin]-5-yl}piperidine-4-carboxylic acid: To a suspension of ethyl 1-[2-cyano-6-(trifluoromethyl)pyridin-3-yl]-4-{2'-ethoxy-[2,3'-bipyridin]-5-yl}piperidine-4-carboxylate (0.21 g, 0.40 mmol) in a mixed solvent of EtOH and water (2:1, 6 mL) was added lithium hydroxide (0.10 g, 4.2 mmol). The mixture was heated at 60° C. for 1 h. The mixture was adjusted to pH 6-7 with 1N HCl (aq). The solution was extracted with EtOAc (3×) and the combined organics were dried over anhydrous $Na_2SO_4$ and concentrated to dryness to give the mixture of title compounds (0.17 g) in a ratio of 47:53 as a light yellow solid. LCMS $(M+H)^+$=498.3 & 516.3.

Step 11-4, preparation of 1-[2-cyano-6-(trifluoromethyl)pyridin-3-yl]-4-{2'-ethoxy-[2,3'-bipyridin]-5-yl}-N-[(3R)-1-methylpyrrolidin-3-yl]piperidine-4-carboxamide & 3-(4-{2'-ethoxy-[2,3'-bipyridin]-5-yl}-4-{[(3R)-1-methylpyrrolidin-3-yl]carbamoyl}piperidin-1-yl)-6-(trifluoromethyl)pyridine-2-carboxamide: To a solution of a mixture of 1-[2-cyano-6-(trifluoromethyl)pyridin-3-yl]-4-{2'-ethoxy-[2,3'-bipyridin]-5-yl}piperidine-4-carboxylic acid & 1-[2-carbamoyl-6-(trifluoromethyl)pyridin-3-yl]-4-{2'-ethoxy-[2,3'-bipyridin]-5-yl}piperidine-4-carboxylic acid (85 mg, 0.17 mmol) and HATU (79 mg, 0.21 mmol) in DMF (1 mL) was added DIEA (0.1 mL, 0.8 mmol). After stirring at rt for 5 min, (3R)-1-methylpyrrolidin-3-amine (64 mg, 0.64 mmol) was added to the above HATU-activated solution. The mixture was stirred at rt for 1 h and purified by reversed-phase CC to give the first title compound (32 mg, 33% yield) as a white solid; LCMS $(M+H)^+$=580.3 and the second title compound (44 mg, 43%) as a white solid; LCMS $(M+H)^+$=598.3.

The following compounds were prepared similarly to Example 1 with appropriate substituting reagents and substrates at different steps:

| Compound no. | MS $(M + H)^+$ |
|---|---|
| 1-26 | 580.3 |
| 1-27 | 598.3 |

Example 12: 1-[2-cyano-4-(trifluoromethyl)phenyl]-4-[6-(1-methyl-1H-pyrrol-2-yl)pyridin-3-yl]-N-[(3R)-1-methylpyrrolidin-3-yl]piperidine-4-carboxamide (Cpd 1-88)

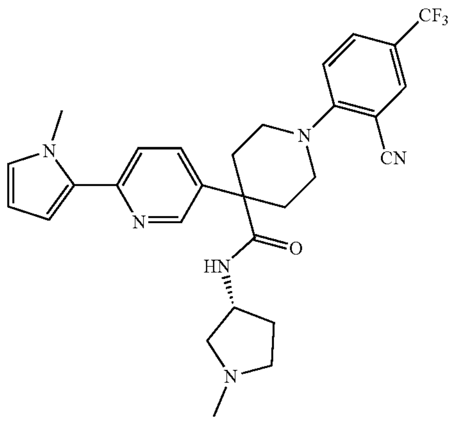 [SMILES: CN1CC[C@@H](NC(=O)C2(c3ccc(-c4cccn4C)nc3)CCN(c3ccc(C(F)(F)F)cc3C#N)CC2)C1]

Step 12-1, preparation of methyl 4-(6-chloropyridin-3-yl) piperidine-4-carboxylate: To a solution of methyl 1-benzyl-4-(6-chloropyridin-3-yl)piperidine-4-carboxylate (2.9 g, 8.4 mmol) from step 7-1 in DCM (30 mL) at 0° C. was added chloroethyl chloroformate (2.3 mL, 21 mmol). The mixture was stirred at rt for 2 h and then MeOH (15 mL) was added. The resulting mixture was heated at reflux for 2 h. The mixture was concentrated to dryness and the residue was triturated with a mixed solvent of hexanes and ether (5:1, 40 mL). The solid was collected by vacuum filtration to give the title compound (1.7 g, 79%) as a white solid. LCMS $(M+H)^+$=255.0.

Step 12-2, preparation of methyl 4-(6-chloropyridin-3-yl)-1-[2-cyano-4-(trifluoromethyl)phenyl]piperidine-4-carboxylate: To a solution of methyl 4-(6-chloropyridin-3-yl) piperidine-4-carboxylate (1.7 g, 6.7 mmol) and 2-fluoro-5-(trifluoromethyl)benzonitrile (1.3 g, 7.0 mmol) in DMSO (17 mL) was added DIEA (3.6 mL, 21 mmol). The mixture was heated at 60° C. for 2 h. The mixture was diluted with 10% citric acid (aq) (50 mL) and extracted with EtOAc (3×). The combined organics were washed with brine, dried over anhydrous $Na_2SO_4$ and concentrated to dryness. The residue was triturated with hexanes and the solid was collected by vacuum filtration to give the title compound (1.8 g, 64%) as a white solid. LCMS $(M+H)^+$=424.0.

Step 12-3, preparation of 4-(6-chloropyridin-3-yl)-1-[2-cyano-4-(trifluoromethyl)phenyl]piperidine-4-carboxylic acid: To a suspension of methyl 4-(6-chloropyridin-3-yl)-1-[2-cyano-4-(trifluoromethyl)phenyl]piperidine-4-carboxylate (1.8 g, 4.2 mmol) in a mixed solvent of EtOH and water (2:1, 22.5 mL) was added lithium hydroxide (1.0 g, 42 mmol). The mixture was heated at 60° C. for 2 h. The mixture was adjusted to pH 6-7 with 1N HCl (aq). The solution was extracted with EtOAc (3×) and the combined organics were dried over anhydrous $Na_2SO_4$ and concentrated to dryness. The residue was purified by reversed-phase CC to give the title compound (1.5 g, 83%) as an off-white solid. LCMS $(M+H)^+$=409.9.

Step 12-4, preparation of 4-(6-chloropyridin-3-yl)-1-[2-cyano-4-(trifluoromethyl)phenyl]-N-[(3R)-1-methylpyrrolidin-3-yl]piperidine-4-carboxamide: To a solution of 4-(6-chloropyridin-3-yl)-1-[2-cyano-4-(trifluoromethyl)phenyl] piperidine-4-carboxylic acid (500 mg, 1.22 mmol) and HATU (650 mg, 1.71 mmol) in DMF (1 mL) was added DIEA (0.43 mL, 2.4 mmol). After stirring at rt for 5 min, (3R)-1-methylpyrrolidin-3-amine (183 mg, 1.83 mmol) was added to the above HATU-activated solution. The mixture was stirred at rt for 10 min and purified by reversed-phase CC to give the title compound (483 mg, 80.5%) as an off-white solid; LCMS $(M+H)^+$=492.0.

Step 12-5, preparation of 1-[2-cyano-4-(trifluoromethyl) phenyl]-4-[6-(1-methyl-1H-pyrrol-2-yl)pyridin-3-yl]-N-[(3R)-1-methylpyrrolidin-3-yl]piperidine-4-carboxamide: To a mixture of 4-(6-chloropyridin-3-yl)-1-[2-cyano-4-(trifluoromethyl)phenyl]-N-[(3R)-1-methylpyrrolidin-3-yl]piperidine-4-carboxamide (30.0 mg, 0.0610 mmol), 1-methyl-2-(4,4,5,5-tetramethyl-1,3,2-dioxaborolan-2-yl)-1H-pyrrole (63.1 mg, 0.305 mmol), $Pd(amphos)Cl_2$ (17.3 mg, 0.0244 mmol), and potassium carbonate (25.3 mg, 0.183 mmol) in a sealed tube was added 1,4-dioxane (2 mL) and water (0.3 mL). Nitrogen (g) was bubbled through and the resulting mixture was heated at 100° C. for 2 h. The mixture was quenched with water and extracted with EtOAc (2×). The combined organics were concentrated to dryness and the residue was purified by reversed-phase CC to give the title compound (9.1 mg, 28%) as an off-white solid. LCMS $(M+H)^+$=537.5.

The following compounds were prepared similarly to Example 12 with appropriate substituting reagents and substrates at different steps:

| Compound no. | MS $(M + H)^+$ |
|---|---|
| 1-43 | 538.5 |
| 1-52 | 564.5 |
| 1-80 | 570.3 |
| 1-83 | 570.3 |
| 1-84 | 598.4 |
| 1-89 | 590.5 |
| 1-105 | 550.7 |
| 1-114 | 600.5 |
| 1-115 | 537.5 |
| 1-116 | 538.6 |
| 1-137 | 573.5 |
| 1-153 | 562.5 |
| 1-157 | 539.5 |
| 1-158 | 563.6 |
| 1-160 | 546.2 |
| 1-173 | 530.2 |

Example 13: 1-[2-cyano-4-(trifluoromethyl)phenyl]-4-[6-(5-fluoro-2-methoxyphenyl)pyridin-3-yl]-N-[(3R)-1-methylpyrrolidin-3-yl]piperidine-4-carboxamide (Cpd 1-81)

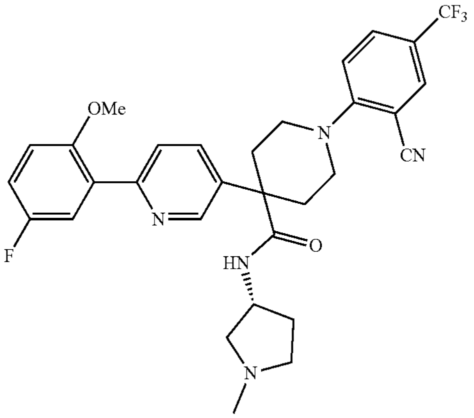 [SMILES: COc1ccc(F)cc1-c1ccc(C2(C(=O)N[C@@H]3CCN(C)C3)CCN(c3ccc(C(F)(F)F)cc3C#N)CC2)cn1]

Step 13-1, preparation of 1-[2-cyano-4-(trifluoromethyl) phenyl]-4-[6-(5-fluoro-2-methoxyphenyl)pyridin-3-yl]-N-[(3R)-1-methylpyrrolidin-3-yl]piperidine-4-carboxamide: To a mixture of 4-(6-chloropyridin-3-yl)-1-[2-cyano-4-(trifluoromethyl)phenyl]-N-[(3R)-1-methylpyrrolidin-3-yl]piperidine-4-carboxamide from Step 12-4 (30.0 mg, 0.0610 mmol), (5-fluoro-2-methoxyphenyl)boronic acid (51.8 mg, 0.305 mmol), $Pd(dtbpf)Cl_2$ (15.9 mg, 0.0244 mmol), and potassium carbonate (25.3 mg, 0.183 mmol) in a sealed tube was added 1,4-dioxane (2 mL) and water (0.3 mL). Nitrogen (g) was bubbled through and the resulting mixture was heated at 80° C. for 3 h. The mixture was quenched with water and extracted with EtOAc (2×). The combined organics were concentrated to dryness and the residue was purified by reversed-phase CC to give the title compound (17.2 mg, 48.5%) as a brown solid. LCMS $(M+H)^+$=582.2.

The following compounds were prepared similarly to Example 13 with appropriate substituting reagents and substrates at different steps:

| Compound no. | MS (M + H)$^+$ |
|---|---|
| 1-31 | 578.2 |
| 1-53 | 576.3 |
| 1-54 | 574.4 |
| 1-55 | 564.5 |
| 1-60 | 562.5 |
| 1-61 | 570.3 |
| 1-62 | 552.2 |
| 1-63 | 592.5 |
| 1-64 | 552.4 |
| 1-65 | 570.3 |
| 1-66 | 548.7 |
| 1-67 | 614.3 |
| 1-68 | 570.3 |
| 1-69 | 596.5 |
| 1-70 | 594.4 |
| 1-71 | 618.5 |
| 1-72 | 596.3 |
| 1-73 | 588.1 |
| 1-74 | 552.4 |
| 1-77 | 602.4 |
| 1-78 | 559.4 |
| 1-79 | 578.4 |
| 1-82 | 582.3 |
| 1-85 | 601.5 |
| 1-86 | 583.2 |
| 1-87 | 600.4 |
| 1-98 | 565.5 |
| 1-99 | 566.5 |
| 1-112 | 554.4 |
| 1-113 | 574.7 |
| 1-117 | 576.7 |
| 1-118 | 563.5 |
| 1-129 | 568.5 |
| 1-130 | 578.4 |
| 1-138 | 554.1 |
| 1-148 | 577.5 |
| 1-151 | 584.2 |
| 1-177 | 549.5 |

Example 14: 1-[2-cyano-4-(trifluoromethyl)phenyl]-4-[6-(1-methyl-1H-pyrrol-2-yl)pyridin-3-yl]-N-[(3S)-1-methylpyrrolidin-3-yl]piperidine-4-carboxamide (Cpd 1-100)

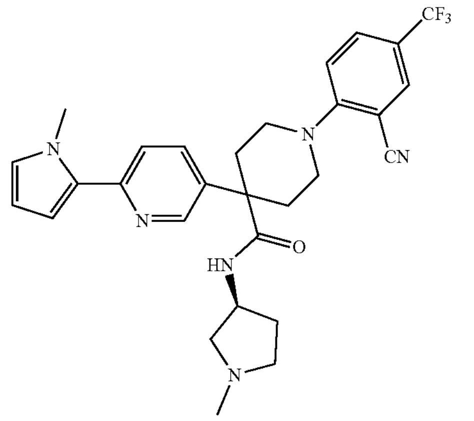 [SMILES: CN1CC[C@H](NC(=O)C2(c3ccc(-c4cccn4C)nc3)CCN(c3ccc(C(F)(F)F)cc3C#N)CC2)C1]

Step 14-1, preparation of 4-(6-chloropyridin-3-yl)-1-[2-cyano-4-(trifluoromethyl)phenyl]-N-[(3S)-1-methylpyrrolidin-3-yl]piperidine-4-carboxamide: To a solution of 4-(6-chloropyridin-3-yl)-1-[2-cyano-4-(trifluoromethyl)phenyl]piperidine-4-carboxylic acid (1.00 g, 2.44 mmol) from Step 12-3 and HATU (1.21 g, 3.17 mmol) in DMF (1 mL) was added DIEA (0.85 mL, 4.9 mmol). After stirring at rt for 5 min, (3S)-1-methylpyrrolidin-3-amine (367 mg, 3.66 mmol) was added to the above HATU-activated solution. The mixture was stirred at rt for 10 min and purified by reversed-phase CC to give the title compound (1.14 g, 94.6%) as a light brown solid; LCMS (M+H)$^+$=492.2.

Step 14-2, preparation of 1-[2-cyano-4-(trifluoromethyl)phenyl]-4-[6-(1-methyl-1H-pyrrol-2-yl)pyridin-3-yl]-N-[(3S)-1-methylpyrrolidin-3-yl]piperidine-4-carboxamide: To a mixture of 4-(6-chloropyridin-3-yl)-1-[2-cyano-4-(trifluoromethyl)phenyl]-N-[(3S)-1-methylpyrrolidin-3-yl]piperidine-4-carboxamide (90.0 mg, 0.183 mmol), 1-methyl-2-(4,4,5,5-tetramethyl-1,3,2-dioxaborolan-2-yl)-1H-pyrrole (189 mg, 0.915 mmol), Pd(amphos)$Cl_2$ (51.8 mg, 0.0732 mmol), potassium carbonate (75.9 mg, 0.549 mmol) in a sealed tube was added 1,4-dioxane (3 mL) and water (0.3 mL). Nitrogen (g) was bubbled through and the resulting mixture was heated at 100° C. for 2 h. The mixture was quenched with water and extracted with EtOAc (2×). The combined organics were concentrated to dryness and the residue was purified by reversed-phase CC to give the title compound (23.5 mg, 23.9%) as an off-white solid. LCMS (M+H)$^+$=537.6.

The following compounds were prepared similarly to Example 14 with appropriate substituting reagents and substrates at different steps. Some examples require a deprotection in the final step:

| Compound no. | MS (M + H)$^+$ |
|---|---|
| 1-119 | 570.4 |
| 1-120 | 538.6 |
| 1-143 | 523.6 |
| 1-146 | 582.3 |
| 1-147 | 568.3 |
| 1-149 | 539.2 |
| 1-187 | 563.3 |
| 1-188 | 563.2 |

Example 15: 1-[2-cyano-4-(trifluoromethyl)phenyl]-4-[6-(5-fluoro-2-methoxyphenyl)pyridin-3-yl]-N-[(3S)-1-methylpyrrolidin-3-yl]piperidine-4-carboxamide (Cpd 1-102)

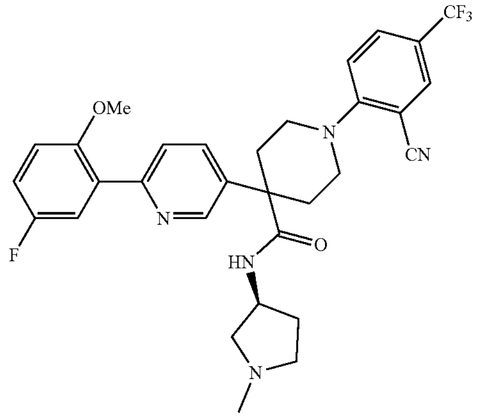 [SMILES: COc1ccc(F)cc1-c1ccc(C2(C(=O)N[C@H]3CCN(C)C3)CCN(c3ccc(C(F)(F)F)cc3C#N)CC2)cn1]

Step 15-1, preparation of 1-[2-cyano-4-(trifluoromethyl)phenyl]-4-[6-(5-fluoro-2-methoxyphenyl)pyridin-3-yl]-N-[(3S)-1-methylpyrrolidin-3-yl]piperidine-4-carboxamide: To a mixture of 4-(6-chloropyridin-3-yl)-1-[2-cyano-4-(trifluoromethyl)phenyl]-N-[(3S)-1-methylpyrrolidin-3-yl]piperidine-4-carboxamide from Step 14-1 (60.0 mg, 0.122 mmol), (5-fluoro-2-methoxyphenyl)boronic acid (104 mg, 0.610 mmol), Pd(dtbpf)$Cl_2$ (31.8 mg, 0.0488 mmol), and potassium carbonate (50.6 mg, 0.366 mmol) in a sealed tube was added 1,4-dioxane (2 mL) and water (0.3 mL). Nitrogen (g) was bubbled through and the resulting mixture was heated at 80° C. for 3 h. The mixture was quenched with water and extracted with EtOAc (2×). The combined organics were concentrated to dryness and the residue was purified by reversed-phase CC to give the title compound (41.9 mg, 59%) as a brown solid. LCMS $(M+H)^+$=582.4.

The following compounds were prepared similarly to Example 15 with appropriate substituting reagents and substrates at different steps:

| Compound no. | MS $(M + H)^+$ |
|---|---|
| 1-30 | 578.2 |
| 1-101 | 578.2 |
| 1-103 | 576.3 |
| 1-104 | 562.4 |
| 1-121 | 574.5 |
| 1-122 | 554.4 |

Example 16: 1-(4-chloro-2-cyanophenyl)-4-[6-(2-ethoxyphenyl)pyridin-3-yl]-N-[(3S)-1-methylpyrrolidin-3-yl]piperidine-4-carboxamide (Cpd 1-90)

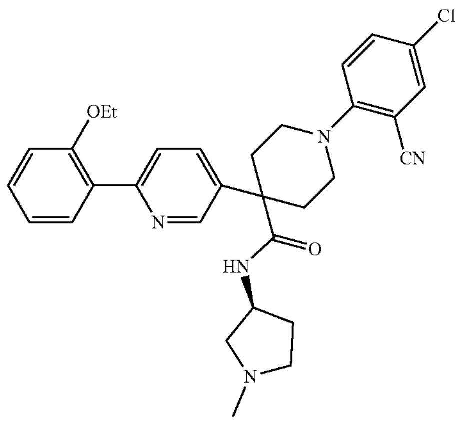

Step 16-1, preparation of ethyl 1-benzyl-4-[6-(2-ethoxyphenyl)pyridin-3-yl]piperidine-4-carboxylate: To a suspension of ethyl 1-benzyl-4-(6-chloropyridin-3-yl)piperidine-4-carboxylate (4.2 g, 12 mmol) from Step 9-1 in 1,4-dioxane (50 mL) and water (5 mL) under nitrogen was added potassium carbonate (3.2 g, 23 mmol), (2-ethoxyphenyl) boronic acid (2.9 g, 17 mmol) and Pd(dtbpf)$Cl_2$ (0.30 g, 0.46 mmol). The mixture was heated at 90° C. for 2 h. The mixture was quenched with water and extracted with EtOAc (2×). The combined organics were concentrated to dryness and the residue was purified by silica gel CC to give the title compound (4.0 g, 77%) as a yellow solid. LCMS $(M+H)^+$=445.2.

Step 16-2, preparation of ethyl 4-[6-(2-ethoxyphenyl) pyridin-3-yl]piperidine-4-carboxylate: To a solution of ethyl 1-benzyl-4-[6-(2-ethoxyphenyl)pyridin-3-yl]piperidine-4-carboxylate (3.5 g, 7.9 mmol) in MeOH (50 mL) was added 10 wt. % of Pd on carbon (160 mg) and 20 wt. % of $Pd(OH)_2$ on carbon (160 mg). The mixture was charged with hydrogen (g) and stirred at rt for 16 h. The mixture was filtered and the filtrate was concentrated to dryness to give the title compound (2.4 g, 86%) as yellow oil. LCMS $(M+H)^+$=355.2.

Step 16-3, preparation of ethyl 1-(4-chloro-2-cyanophenyl)-4-[6-(2-ethoxyphenyl)pyridin-3-yl]piperidine-4-carboxylate: To a mixture of ethyl 4-[6-(2-ethoxyphenyl)pyridin-3-yl]piperidine-4-carboxylate (400 mg, 1.13 mmol), 2-bromo-5-chlorobenzonitrile (320 mg, 1.48 mmol), XPhos (33.3 mg, 0.0699 mmol), $Pd_2(dba)_3$-$CHCl_3$ (35.0 mg, 0.0338 mmol), and cesium carbonate (735 mg, 2.26 mmol) under nitrogen was added toluene (5 mL). The mixture was heated at 90° C. for 2 h. The mixture was filtered and the filtrate was concentrated to dryness. The residue was purified by silica gel CC to give the title compound (290 mg, 52.4%) as yellow oil. LCMS $(M+H)^+$=490.3.

Step 16-4, preparation of 1-(4-chloro-2-cyanophenyl)-4-[6-(2-ethoxyphenyl)pyridin-3-yl]piperidine-4-carboxylic acid: To a suspension of ethyl 1-(4-chloro-2-cyanophenyl)-4-[6-(2-ethoxyphenyl)pyridin-3-yl]piperidine-4-carboxylate (290 mg, 0.59 mmol) in a mixed solvent of EtOH and water (5:1, 6 mL) was added lithium hydroxide (72 mg, 3.0 mmol). The mixture was heated at 60° C. for 2 h. The mixture was diluted with water and adjusted to pH 6-7 with 1N HCl (aq). The mixture was extracted with EtOAc (3×) and the combined organics were dried over anhydrous $Na_2SO_4$ and concentrated to dryness to give the title compound (250 mg, 91.4%) as a yellow solid. LCMS $(M+H)^+$=462.3.

Step 16-5, preparation of 1-(4-chloro-2-cyanophenyl)-4-[6-(2-ethoxyphenyl)pyridin-3-yl]-N-[(3S)-1-methylpyrrolidin-3-yl]piperidine-4-carboxamide: To a solution of 1-(4-chloro-2-cyanophenyl)-4-[6-(2-ethoxyphenyl)pyridin-3-yl] piperidine-4-carboxylic acid (50 mg, 0.11 mmol) and HATU (49 mg, 0.13 mmol) in DMF (0.6 mL) was added DIEA (84 mg, 0.65 mmol). After stirring at rt for 5 min, (3S)-1-Methylpyrrolidin-3-amine (14 mg, 0.14 mmol) was added to the above HATU-activated solution. The mixture was stirred at rt for 1 h and purified by reversed-phase CC to give the title compound (31 mg, 48%) as a white solid. LCMS $(M+H)^+$=544.3.

The following compounds were prepared similarly to Example 16 with appropriate substituting reagents and substrates at different steps:

| Compound no. | MS $(M + H)^+$ |
|---|---|
| 1-93 | 530.3 |
| 1-141 | 588.3 |
| 1-144 | 573.2 |
| 1-145 | 571.3 |
| 1-167 | 579.2 |
| 1-172 | 572.2 |
| 1-281 | 504.3 |
| 1-282 | 534.3 |
| 1-283 | 520.3 |
| 1-284 | 578.3 |
| 1-285 | 563.3 |
| 1-286 | 579.3 |
| 1-287 | 564.3 |
| 1-288 | 594.3 |
| 1-289 | 577.3 |
| 1-290 | 563.3 |
| 1-291 | 593.3 |
| 1-292 | 579.3 |
| 1-293 | 549.3 |
| 1-294 | 565.3 |
| 1-295 | 560.3 |
| 1-296 | 576.3 |
| 1-297 | 532.3 |

-continued

| Compound no. | MS (M + H)+ |
|---|---|
| 1-298 | 518.3 |
| 1-299 | 580.3 |
| 1-300 | 564.3 |
| 1-301 | 550.3 |
| 1-302 | 580.3 |
| 1-303 | 566.3 |
| 1-304 | 536.3 |
| 1-305 | 522.3 |
| 1-306 | 546.3 |
| 1-307 | 562.3 |
| 1-309 | 552.3 |
| 1-310 | 538.3 |
| 1-312 | 592.3 |
| 1-315 | 578.4 |
| 1-317 | 574.4 |
| 1-318 | 556.3 |
| 1-321 | 560.3 |
| 1-322 | 542.2 |

Example 17: 1-(2-cyano-4-fluorophenyl)-4-[6-(2-ethoxyphenyl)pyridin-3-yl]-N-[(3S)-1-methylpyrrolidin-3-yl]piperidine-4-carboxamide (Cpd 1-96)

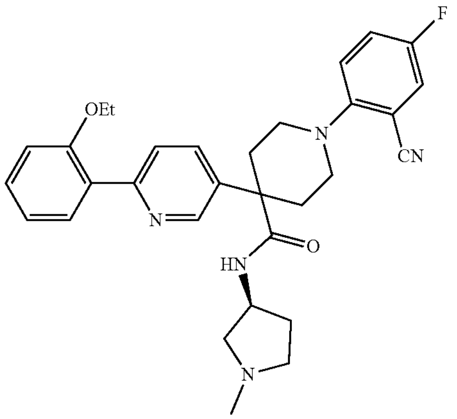 [SMILES: CCOc1ccccc1-c1ccc(C2(C(=O)N[C@H]3CCN(C)C3)CCN(c3ccc(F)cc3C#N)CC2)cn1]

Step 17-1, preparation of 1-benzyl-4-[6-(2-ethoxyphenyl)pyridin-3-yl]piperidine-4-carboxylic acid: To a suspension of ethyl 1-benzyl-4-[6-(2-ethoxyphenyl)pyridin-3-yl]piperidine-4-carboxylate (500 mg, 1.12 mmol) from Step 16-1 in a mixed solvent of EtOH and water (5:1, 6 mL) was added lithium hydroxide (269 mg, 11.2 mmol). The mixture was heated at 60° C. for 1 h. The mixture was diluted with water and adjusted to pH 6-7 with 1N HCl (aq). The mixture was extracted with EtOAc (3×) and the combined organics were dried over anhydrous $Na_2SO_4$ and concentrated to dryness to give the title compound (450 mg, 96.1%) as yellow oil. LCMS $(M+H)^+$=417.3.

Step 17-2, preparation of 1-benzyl-4-[6-(2-ethoxyphenyl)pyridin-3-yl]-N-[(3S)-1-methylpyrrolidin-3-yl]piperidine-4-carboxamide: To a solution of 1-benzyl-4-[6-(2-ethoxyphenyl)pyridin-3-yl]piperidine-4-carboxylic acid (450 mg, 1.08 mmol) and HATU (430 mg, 1.13 mmol) in DMF (5 mL) was added DIEA (450 mg, 3.48 mmol). After stirring at rt for 5 min, (3S)-1-methylpyrrolidin-3-amine (130 mg, 1.30 mmol) was added to the above HATU-activated solution. The mixture was stirred at rt for 1 h and purified by reversed-phase CC to give the title compound (450 mg, 83.5%) as a yellow solid. LCMS $(M+H)^+$=499.4.

Step 17-3, preparation of 4-[6-(2-ethoxyphenyl)pyridin-3-yl]-N-[(3S)-1-methylpyrrolidin-3-yl]piperidine-4-carboxamide: To a solution of 1-benzyl-4-[6-(2-ethoxyphenyl)pyridin-3-yl]-N-[(3S)-1-methylpyrrolidin-3-yl]piperidine-4-carboxamide (430 mg, 0.862 mmol) in MeOH (30 mL) was added 10 wt. % of Pd on carbon (20 mg) and 20 wt. % of $Pd(OH)_2$ on carbon (20 mg). The mixture was charged with hydrogen (g) and stirred at rt for 2 h. The mixture was filtered and the filtrate was concentrated to dryness. The residue was purified by reversed-phase CC to give the title compound (360 mg, 79.9%) as colorless oil. LCMS $(M+H)^+$= 409.3.

Step 17-4, preparation of 1-(2-cyano-4-fluorophenyl)-4-[6-(2-ethoxyphenyl)pyridin-3-yl]-N-[(3S)-1-methylpyrrolidin-3-yl]piperidine-4-carboxamide: To a mixture of 4-[6-(2-ethoxyphenyl)pyridin-3-yl]-N-[(3S)-1-methylpyrrolidin-3-yl]piperidine-4-carboxamide (60 mg, 0.15 mmol), 2-bromo-5-fluorobenzonitrile (50 mg, 0.25 mmol), XPhos (7.0 mg, 0.015 mmol), $Pd_2(dba)_3 \cdot CHCl_3$ (15 mg, 0.014 mmol), and sodium tert-butoxide (45 mg, 0.47 mmol) under nitrogen was added toluene (2 mL). The mixture was heated at 100° C. for 4 h. The mixture was filtered and the filtrate was concentrated to dryness. The residue was purified by reversed-phase CC to give the title compound (8.5 mg, 10%) as a white solid. LCMS $(M+H)^+$=528.3.

The following compounds were prepared similarly to Example 17 with appropriate substituting reagents and substrates at different steps:

| Compound no. | MS (M + H)+ |
|---|---|
| 1-95 | 553.2 |
| 1-97 | 587.3 |
| 1-111 | 562.3 |

Example 18: 1-[2-cyano-4-(trifluoromethyl)phenyl]-4-[6-(2-ethoxyphenyl)pyridin-3-yl]-N-(1-methylazetidin-3-yl)piperidine-4-carboxamide (Cpd 1-76)

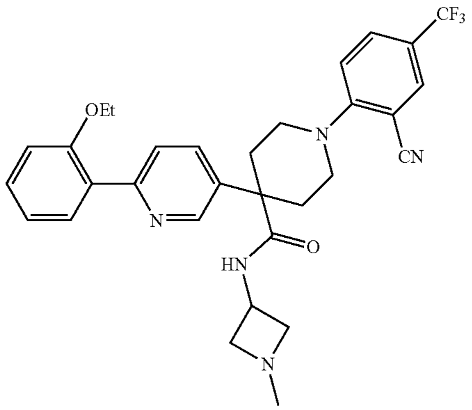 [SMILES: CCOc1ccccc1-c1ccc(C2(C(=O)NC3CN(C)C3)CCN(c3ccc(C(F)(F)F)cc3C#N)CC2)cn1]

Step 18-1, preparation of ethyl 1-[2-cyano-4-(trifluoromethyl)phenyl]-4-[6-(2-ethoxyphenyl)pyridin-3-yl]piperidine-4-carboxylate: To a solution of ethyl 4-[6-(2-ethoxyphenyl)pyridin-3-yl]piperidine-4-carboxylate (0.38 g, 1.1 mmol) from Step 16-2 and 2-fluoro-5-(trifluoromethyl)benzonitrile (0.31 g, 1.6 mmol) in DMSO (5 mL) was added DIEA (0.55 mL, 3.2 mmol). The mixture was heated at 60° C. for 2 h. The mixture was quenched with water and extracted with EtOAc (3×). The combined organics were concentrated to dryness and the residue was purified by reversed-phase CC to give the title compound (0.41 g, 73%) as light yellow oil. LCMS $(M+H)^+$=524.2.

Step 18-2, preparation of 1-[2-cyano-4-(trifluoromethyl) phenyl]-4-[6-(2-ethoxyphenyl)pyridin-3-yl]-N-(1-methyl-azetidin-3-yl)piperidine-4-carboxamide: To a solution of ethyl 1-[2-cyano-4-(trifluoromethyl)phenyl]-4-[6-(2-ethoxyphenyl)pyridin-3-yl]piperidine-4-carboxylate (70 mg, 0.13 mmol) and 1-methylazetidin-3-amine (20 mg, 0.23 mmol) in THE (0.5 mL) under nitrogen was added 1M LiHMDS in THE (0.7 mL, 0.7 mmol). The mixture was stirred at rt for 40 min. The mixture was quenched with saturated $NH_4C_1$ (aq) and extracted with EtOAc (3×). The combined organics were concentrated to dryness and the residue was purified by reversed-phase CC to give the title compound (29 mg, 36%) as a white solid. LCMS $(M+H)^+$=564.3.

Example 19: 1-(4-chloro-2-cyanophenyl)-4-[6-(2-methoxyphenyl)pyridin-3-yl]-N-[(3S)-1-methylpyrrolidin-3-yl]piperidine-4-carboxamide (Cpd 1-91)

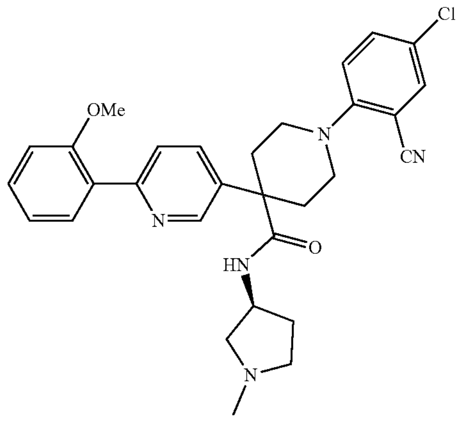 [SMILES: COc1ccccc1-c1ccc(C2(C(=O)N[C@H]3CCN(C)C3)CCN(c3ccc(Cl)cc3C#N)CC2)cn1]

Step 19-1, preparation of ethyl 1-benzyl-4-[6-(2-methoxyphenyl)pyridin-3-yl]piperidine-4-carboxylate: To a mixture of ethyl 1-benzyl-4-(6-chloropyridin-3-yl)piperidine-4-carboxylate (400 mg, 1.11 mmol) from Step 9-1, (2-methoxyphenyl)boronic acid (200 mg, 1.32 mmol), $Pd(amphos)Cl_2$ (60 mg, 0.085 mmol), and potassium carbonate (450 mg, 3.26 mmol) under nitrogen was added 1,4-dioxane (5 mL) and water (0.5 mL). The mixture was heated at 90° C. for 2 h. The mixture was quenched with water and extracted with EtOAc (2×). The combined organics were concentrated to dryness and the residue was purified by silica gel CC to give the title compound (450 mg, 93.8%) as yellow oil. LCMS $(M+H)^+$=431.2.

Step 19-2, preparation of ethyl 4-[6-(2-methoxyphenyl) pyridin-3-yl]piperidine-4-carboxylate: To a solution of ethyl 1-benzyl-4-[6-(2-methoxyphenyl)pyridin-3-yl]piperidine-4-carboxylate (440 mg, 1.02 mmol) in MeOH (30 mL) was added 10 wt. % of Pd on carbon (40 mg) and 20 wt. % of $Pd(OH)_2$ on carbon (40 mg). The mixture was charged with hydrogen (g) and stirred at rt for 2 h. The mixture was filtered and the filtrate was concentrated to dryness to give the title compound (260 mg, 74.8%) as a light brown solid. LCMS $(M+H)^+$=341.2.

Step 19-3, preparation of 1-(4-chloro-2-cyanophenyl)-4-[6-(2-methoxyphenyl)pyridin-3-yl]piperidine-4-carboxylic acid: To a mixture of ethyl 4-[6-(2-methoxyphenyl)pyridin-3-yl]piperidine-4-carboxylate (180 mg, 0.529 mmol), 2-bromo-5-chlorobenzonitrile (180 mg, 0.832 mmol), XPhos (30 mg, 0.063 mmol), $Pd_2(dba)_3 \cdot CHCl_3$ (45 mg, 0.043 mmol), and sodium tert-butoxide (100 mg, 1.04 mmol) under nitrogen was added toluene (2 mL). The mixture was heated at 80° C. for 2 h. The mixture was filtered and the filtrate was concentrated to dryness. The residue was purified by reversed-phase CC to give the title compound (170 mg, 71.8%) as a yellow solid. LCMS $(M+H)^+$=448.2.

Step 19-4, preparation of 1-(4-chloro-2-cyanophenyl)-4-[6-(2-methoxyphenyl)pyridin-3-yl]-N-[(3S)-1-methylpyrrolidin-3-yl]piperidine-4-carboxamide: To a solution of 1-(4-chloro-2-cyanophenyl)-4-[6-(2-methoxyphenyl)pyridin-3-yl]piperidine-4-carboxylic acid (60 mg, 0.13 mmol) and HATU (55 mg, 0.14 mmol) in DMF (2 mL) was added DIEA (70 mg, 0.54 mmol). After stirring at rt for 5 min, (3S)-1-methylpyrrolidin-3-amine (25 mg, 0.25 mmol) was added to the above HATU-activated solution. The mixture was stirred at rt for 1 h and purified by reversed-phase CC to give the title compound (35 mg, 45%) as a white solid. LCMS $(M+H)^+$=530.3.

The following compounds were prepared similarly to Example 19 with appropriate substituting reagents and substrates at different steps:

| Compound no. | MS $(M + H)^+$ |
|---|---|
| 1-92 | 516.2 |
| 1-142 | 574.2 |

Example 20: 1-[2-cyano-4-(trifluoromethyl)phenyl]-4-[6-(2-methoxyphenyl)pyridin-3-yl]-N-(1-methyl-azetidin-3-yl)piperidine-4-carboxamide (Cpd 1-94)

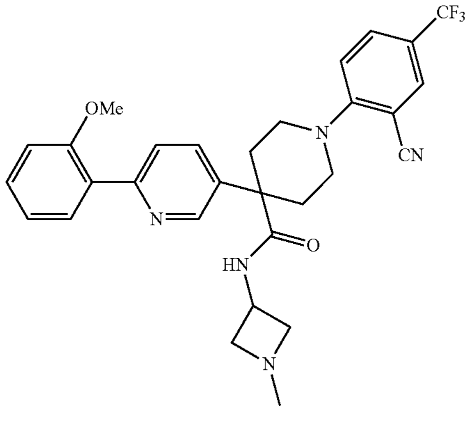 [SMILES: COc1ccccc1-c1ccc(C2(C(=O)NC3CN(C)C3)CCN(c3ccc(C(F)(F)F)cc3C#N)CC2)cn1]

Step 20-1, preparation of ethyl 1-[2-cyano-4-(trifluoromethyl)phenyl]-4-[6-(2-methoxyphenyl)pyridin-3-yl]piperidine-4-carboxylate: To a solution of ethyl 4-[6-(2-methoxyphenyl)pyridin-3-yl]piperidine-4-carboxylate (70 mg, 0.21 mmol) from Step 19-2 and 2-fluoro-5-(trifluoromethyl)benzonitrile (60 mg, 0.32 mmol) in DMSO (2 mL) in a sealed tube was added DIEA (80 mg, 0.62 mmol). The mixture was heated at 60° C. for 1 h. The mixture was purified by reversed-phase CC to give the title compound (60 mg, 57%) as a light brown solid. LCMS $(M+H)^+$=510.3.

Step 20-2, preparation of 1-[2-cyano-4-(trifluoromethyl)phenyl]-4-[6-(2-methoxyphenyl)pyridin-3-yl]piperidine-4-carboxylic acid: To a suspension of ethyl 1-[2-cyano-4-(trifluoromethyl)phenyl]-4-[6-(2-methoxyphenyl)pyridin-3-yl]piperidine-4-carboxylate (60 mg, 0.12 mmol) in a mixed solvent of EtOH and water (5:1, 2.4 mL) was added lithium hydroxide (15 mg, 0.63 mmol). The mixture was heated at 60° C. for 1 h. The mixture was diluted with water and adjusted to pH 6-7 with 1N HCl (aq). The mixture was extracted with EtOAc (3×) and the combined organics were dried over anhydrous $Na_2SO_4$ and concentrated to dryness to give the title compound (55 mg, 97%) as a yellow solid. LCMS $(M+H)^+=482.2$.

Step 20-3, preparation of 1-[2-cyano-4-(trifluoromethyl)phenyl]-4-[6-(2-methoxyphenyl)pyridin-3-yl]-N-(1-methylazetidin-3-yl)piperidine-4-carboxamide: To a solution of 1-[2-cyano-4-(trifluoromethyl)phenyl]-4-[6-(2-methoxyphenyl)pyridin-3-yl]piperidine-4-carboxylic acid (55 mg, 0.11 mmol) and HATU (50 mg, 0.13 mmol) in DMF (2 mL) was added DIEA (50 mg, 0.39 mmol). After stirring at rt for 5 min, 1-methylazetidin-3-amine (15 mg, 0.17 mmol) was added to the above HATU-activated solution. The mixture was stirred at rt for 1 h and purified by reversed-phase CC to give the title compound (47 mg, 69%) as a white solid. LCMS $(M+H)^+=550.3$.

The following compounds were prepared similarly to Example 20 with appropriate substituting reagents and substrates at different steps. Some examples require a deprotection in the final step:

| Compound no. | MS $(M + H)^+$ |
|---|---|
| 1-313 | 581.4 |
| 1-314 | 567.4 |
| 1-316 | 525.4 |
| 1-319 | 599.4 |
| 1-320 | 585.3 |
| 1-323 | 551.3 |
| 1-324 | 557.3 |
| 1-325 | 565.3 |
| 1-326 | 543.3 |
| 1-327 | 594.3 |
| 1-328 | 594.3 |
| 1-329 | 594.3 |
| 1-330 | 594.3 |

Example 21: 2-{4-[2-(dimethylamino)ethoxy]-4-[4-(2-ethoxypyridin-3-yl)phenyl]piperidin-1-yl}-5-(trifluoromethyl)benzonitrile (Cpd 2-1)

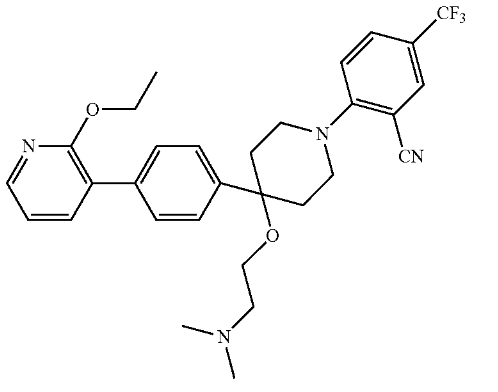 [SMILES: CCOc1ncccc1-c1ccc(C2(OCCN(C)C)CCN(c3ccc(C(F)(F)F)cc3C#N)CC2)cc1]

Step 21-1, preparation of 2-[4-(4-bromophenyl)-4-hydroxypiperidin-1-yl]-5-(trifluoromethyl)benzonitrile: To a solution of 4-(4-bromophenyl)piperidin-4-ol (500 mg, 1.95 mmol) and 2-fluoro-5-(trifluoromethyl)benzonitrile (443 mg, 2.34 mmol) in DMSO (3 mL) in a sealed tube was added DIEA (0.85 mL, 4.9 mmol). The mixture was heated at 130° C. for 5 h. The mixture was purified by reversed-phase CC to give the title compound (779 mg, 93.8%) as a light brown gum. LCMS $(M+H)^+=425.2$.

Step 21-2, preparation of 2-{4-[4-(2-ethoxypyridin-3-yl)phenyl]-4-hydroxypiperidin-1-yl}-5-(trifluoromethyl)benzonitrile: To a mixture of 2-[4-(4-bromophenyl)-4-hydroxypiperidin-1-yl]-5-(trifluoromethyl)benzonitrile (779 mg, 1.83 mmol), (2-ethoxypyridin-3-yl)boronic acid (459 mg, 2.75 mmol), Pd(amphos)$Cl_2$ (130 mg, 0.183 mmol), and potassium carbonate (506 mg, 3.66 mmol) in a sealed tube was added 1,4-dioxane (5 mL) and water (0.5 mL). The mixture was charged with $N_2$ (g) and heated at 100° C. for 1 h. The mixture was quenched with water and extracted with EtOAc (2×). The combined organics were concentrated to dryness and the residue was purified by reversed-phase CC to give the title compound (777 mg, 90.7%) as an off-white solid. LCMS $(M+H)^+=468.1$.

Step 21-3, preparation of 2-{4-[2-(dimethylamino)ethoxy]-4-[4-(2-ethoxypyridin-3-yl)phenyl]piperidin-1-yl}-5-(trifluoromethyl)benzonitrile: To a solution of 2-{4-[4-(2-ethoxypyridin-3-yl)phenyl]-4-hydroxypiperidin-1-yl}-5-(trifluoromethyl)benzonitrile (40.0 mg, 0.0856 mmol) and (2-chloroethyl)dimethylamine hydrochloride (24.6 mg, 0.171 mmol) in DMF (1 mL) at 0° C. was added 60% sodium hydride in mineral oil (34 mg, 0.86 mmol) in portions. The mixture was stirred at rt for 1 h and 50° C. for 1 h. The reaction was not complete but stopped. The mixture was quenched with ice water and extracted with DCM (2×). The combined organics were concentrated to dryness and the residue was purified by reversed-phase CC to give the title compound (19.4 mg, 42.1%) as an off-white solid. LCMS $(M+H)^+=539.5$.

Example 22: 1-[2-cyano-4-(trifluoromethyl)phenyl]-4-[4-(2-ethoxypyridin-3-yl)phenyl]piperidin-4-yl N-[2-(dimethylamino)ethyl]carbamate (Cpd 2-2)

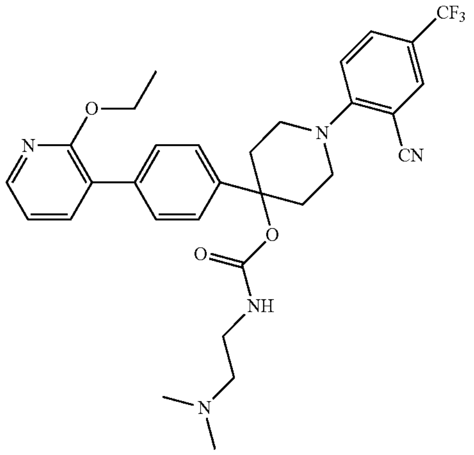 [SMILES: CCOc1ncccc1-c1ccc(C2(OC(=O)NCCN(C)C)CCN(c3ccc(C(F)(F)F)cc3C#N)CC2)cc1]

Step 22-1, preparation of 1-[2-cyano-4-(trifluoromethyl)phenyl]-4-[4-(2-ethoxypyridin-3-yl)phenyl]piperidin-4-yl 1H-imidazole-1-carboxylate: To a suspension of 2-{4-[4-(2-ethoxypyridin-3-yl)phenyl]-4-hydroxypiperidin-1-yl}-5-(trifluoromethyl)benzonitrile (200 mg, 0.428 mmol) from Step 21-2 in THE (3 mL) was added CDI (208 mg, 1.28 mmol). The mixture was stirred at rt for 16 h. The mixture was concentrated to dryness and the residue was purified by silica gel CC to give the title compound (185 mg, 77.1%) as a white solid. LCMS $(M+H)^+$=561.7.

Step 22-2, preparation of 1-[2-cyano-4-(trifluoromethyl)phenyl]-4-[4-(2-ethoxypyridin-3-yl)phenyl]piperidin-4-yl N-[2-(dimethylamino)ethyl]carbamate: To a solution of 1-[2-cyano-4-(trifluoromethyl)phenyl]-4-[4-(2-ethoxypyridin-3-yl)phenyl]piperidin-4-yl 1H-imidazole-1-carboxylate (40.0 mg, 0.0712 mmol) in THE (1 mL) in a sealed tube was added (2-aminoethyl)dimethylamine (12.6 mg g, 0.142 mmol) and DIEA (0.037 mL, 0.21 mmol). The mixture was heated at 100° C. for 16 h. The mixture was concentrated to dryness and the residue was purified by reversed-phase CC to give the title compound (14.9 mg, 36.0%) as a yellow solid. LCMS $(M+H)^+$=582.4.

Example 23: 3-amino-N-{1-[2-cyano-4-(trifluoromethyl)phenyl]-4-[4-(2-ethoxypyridin-3-yl)phenyl]piperidin-4-yl}propanamide (Cpd 2-3)

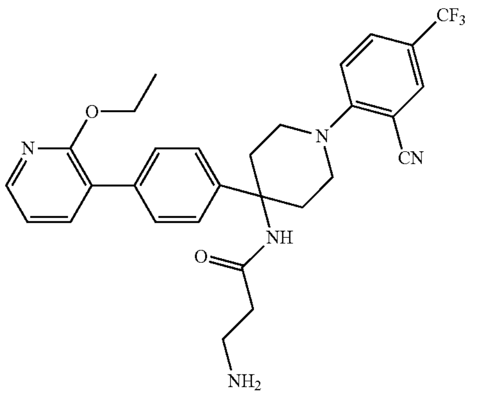 [SMILES: CCOc1ncccc1-c1ccc(C2(NC(=O)CCN)CCN(c3ccc(C(F)(F)F)cc3C#N)CC2)cc1]

Step 23-1, preparation of tert-butyl 4-amino-4-[4-(2-ethoxypyridin-3-yl)phenyl]piperidine-1-carboxylate: To a mixture of tert-butyl 4-amino-4-(4-bromophenyl)piperidine-1-carboxylate (300 mg, 0.844 mmol), (2-ethoxypyridin-3-yl)boronic acid (212 mg, 1.27 mmol), Pd(amphos)$Cl_2$ (59.8 mg, 0.0844 mmol), and potassium carbonate (233 mg, 1.69 mmol) in a sealed tube was added 1,4-dioxane (5 mL) and water (0.5 mL). The mixture was charged with $N_2$ (g) and heated at 100° C. for 1 h. The mixture was quenched with water and extracted with EtOAc (2×). The combined organics were concentrated to dryness and the residue was purified by reversed-phase CC to give the title compound (287 mg, 85.4%) as a brown gum. LCMS $(M+H)^+$=365.2.

Step 23-2, preparation of tert-butyl 4-(3-{[(benzyloxy)carbonyl]amino}propanamido)-4-[4-(2-ethoxypyridin-3-yl)phenyl]piperidine-1-carboxylate: To a solution of 3-{[(benzyloxy)carbonyl]amino}propanoic acid (44.9 mg, 0.201 mmol) and HATU (68.9 mg, 0.181 mmol) in DMF (0.2 mL) was added DIEA (0.053 mL, 0.30 mmol). After stirring at rt for 5 min, tert-butyl 4-amino-4-[4-(2-ethoxypyridin-3-yl)phenyl]piperidine-1-carboxylate (40.0 mg, 0.101 mmol) was added to the above HATU-activated solution. The mixture was stirred at rt for 10 min and purified by reversed-phase CC to give the title compound (47.5 mg, 78.3%) as a white solid. LCMS $(M+H)^+$=603.4.

Step 23-3, preparation of benzyl N-[2-({4-[4-(2-ethoxypyridin-3-yl)phenyl]piperidin-4-yl}carbamoyl)ethyl]carbamate: To a solution of tert-butyl 4-(3-{[(benzyloxy)carbonyl]amino}propanamido)-4-[4-(2-ethoxypyridin-3-yl)phenyl]piperidine-1-carboxylate (47.5 mg, 0.0788 mmol) in DCM (0.1 mL) was added TFA (0.091 mL, 1.2 mmol). The mixture was stirred at rt for 1 h. The mixture was concentrated to dryness and the residue was triturated with saturated $NaHCO_3$ (aq) to give the title compound (35.9 mg, 90.6%) as an off-white solid. LCMS $(M+H)^+$=502.9.

Step 23-4, preparation of benzyl N-[2-({1-[2-cyano-4-(trifluoromethyl)phenyl]-4-[4-(2-ethoxypyridin-3-yl)phenyl]piperidin-4-yl}carbamoyl)ethyl]carbamate: To a solution of benzyl N-[2-({4-[4-(2-ethoxypyridin-3-yl)phenyl]piperidin-4-yl}carbamoyl)ethyl]carbamate (35.9 mg, 0.0714 mmol) and 2-fluoro-5-(trifluoromethyl)benzonitrile (27.0 mg, 0.143 mmol) in DMSO (1 mL) in a sealed tube was added DIEA (0.031 mL, 0.18 mmol). The mixture was heated at 130° C. for 16 h and purified by reversed-phase CC to give the title compound (41.2 mg, 85.9%) as a light brown solid. LCMS $(M+H)^+$=672.1.

Step 23-5, preparation of 3-amino-N-{1-[2-cyano-4-(trifluoromethyl)phenyl]-4-[4-(2-ethoxypyridin-3-yl)phenyl]piperidin-4-yl}propanamide: To benzyl N-[2-({1-[2-cyano-4-(trifluoromethyl)phenyl]-4-[4-(2-ethoxypyridin-3-yl)phenyl]piperidin-4-yl}carbamoyl)ethyl]carbamate (41.2 mg, 0.0613 mmol) was added (methylsulfanyl)benzene (0.030 mL, 0.26 mmol) and TFA (0.15 mL, 2.0 mmol). The mixture was heated at 60° C. for 0.5 h and purified by reversed-phase CC to give the title compound (27.9 mg, 84.6%) as an off-white solid. LCMS $(M+H)^+$=538.0.

Example 24: (2S)—N-{1-[2-cyano-4-(trifluoromethyl)phenyl]-4-[4-(2-ethoxypyridin-3-yl)phenyl]piperidin-4-yl}-1-methylpyrrolidine-2-carboxamide (Cpd 2-11)

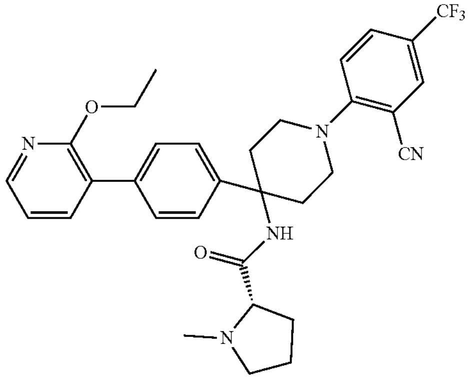 [SMILES: CCOc1ncccc1-c1ccc(C2(NC(=O)[C@@H]3CCCN3C)CCN(c3ccc(C(F)(F)F)cc3C#N)CC2)cc1]

Step 24-1, preparation of tert-butyl 4-{[(benzyloxy)carbonyl]amino}-4-[4-(2-ethoxypyridin-3-yl)phenyl]piperidine-1-carboxylate: To a solution of tert-butyl 4-amino-4-[4-(2-ethoxypyridin-3-yl)phenyl]piperidine-1-carboxylate (237 mg, 0.595 mmol) from Step 23-1 and benzyl 2,5-dioxopyrrolidin-1-yl carbonate (222 mg, 0.892 mmol) in DCM (5 mL) was added DIEA (0.21 mL, 1.2 mmol). The mixture was stirred at rt for 20 min. The mixture was purified by reversed-phase CC to give the title compound (260 mg, 82.2%) as a white solid. LCMS $(M+H)^+$=532.3.

Step 24-2, preparation of benzyl N-{4-[4-(2-ethoxypyridin-3-yl)phenyl]piperidin-4-yl}carbamate bis(2,2,2-trifluoroacetate): To a solution of tert-butyl 4-{[(benzyloxy)carbonyl]amino}-4-[4-(2-ethoxypyridin-3-yl)phenyl]piperidine-1-carboxylate (260 mg, 0.489 mmol) in DCM (0.6 mL) was added TFA (0.56 mL, 7.3 mmol). The mixture was stirred at rt for 0.5 h. The mixture was concentrated to dryness to give the title compound (323 mg, 100%) as a brown gum. LCMS $(M+H)^+$=432.3.

Step 24-3, preparation of benzyl N-{1-[2-cyano-4-(trifluoromethyl)phenyl]-4-[4-(2-ethoxypyridin-3-yl)phenyl]piperidin-4-yl}carbamate: To a solution of benzyl N-{4-[4-(2-ethoxypyridin-3-yl)phenyl]piperidin-4-yl}carbamate bis(2,2,2-trifluoroacetate) (323 mg, 0.489 mmol) and 2-fluoro-5-(trifluoromethyl)benzonitrile (185 mg, 0.979 mmol) in DMSO (1 mL) in a sealed tube was added DIEA (0.43 mL, 2.4 mmol). The mixture was heated at 130° C. for 16 h. The mixture was purified by reversed-phase CC to give the title compound (208 mg, 70.7%) as a brown solid. LCMS $(M+H)^+$=601.7.

Step 24-4, preparation of 2-{4-amino-4-[4-(2-ethoxypyridin-3-yl)phenyl]piperidin-1-yl}-5-(trifluoromethyl)benzonitrile: To benzyl N-{1-[2-cyano-4-(trifluoromethyl)phenyl]-4-[4-(2-ethoxypyridin-3-yl)phenyl]piperidin-4-yl}carbamate (208 mg, 0.346 mmol) was added (methylsulfanyl)benzene (0.050 mL, 0.43 mmol) and TFA (0.25 mL, 3.3 mmol). The mixture was heated at 60° C. for 1 h and purified by reversed-phase CC to give the title compound (121 mg, 75.0%) as an off-white solid. LCMS $(M+H)^+$=467.4.

Step 24-5, preparation of (2S)—N-{1-[2-cyano-4-(trifluoromethyl)phenyl]-4-[4-(2-ethoxypyridin-3-yl)phenyl]piperidin-4-yl}-1-methylpyrrolidine-2-carboxamide: To a solution of (2S)-1-methylpyrrolidine-2-carboxylic acid (16.6 mg, 0.129 mmol) and HATU (44.0 mg, 0.193 mmol) in DMF (0.2 mL) was added DIEA (0.034 mL, 0.19 mmol). After stirring at rt for 5 min, 2-{4-amino-4-[4-(2-ethoxypyridin-3-yl)phenyl]piperidin-1-yl}-5-(trifluoromethyl)benzonitrile (30.0 mg, 0.0643 mmol) was added to the above HATU-activated solution. The mixture was stirred at rt for 10 min and purified by reversed-phase CC to give the title compound (33.8 mg, 91.0%) as a white solid. LCMS $(M+H)^+$=578.3.

The following compounds were prepared similarly to Example 24 with appropriate substituting reagents and substrates at different steps:

| Compound no. | MS $(M + H)^+$ |
|---|---|
| 2-16 | 564.1 |
| 2-17 | 578.2 |

Example 25: N-{1-[2-cyano-4-(trifluoromethyl)phenyl]-4-{2'-ethoxy-[2,3'-bipyridin]-5-yl}piperidin-4-yl}-3-(methylamino)propanamide (Cpd 2-5)

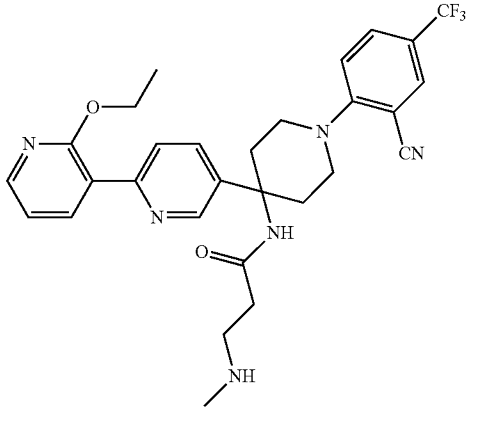 [SMILES: CCOc1ncccc1-c1ccc(C2(NC(=O)CCNC)CCN(c3ccc(C(F)(F)F)cc3C#N)CC2)cn1]

Step 25-1, preparation of benzyl N-{1-[2-cyano-4-(trifluoromethyl)phenyl]-4-{2'-ethoxy-[2,3'-bipyridin]-5-yl}piperidin-4-yl}carbamate: To a solution of 1-[2-cyano-4-(trifluoromethyl)phenyl]-4-{2'-ethoxy-[2,3'-bipyridin]-5-yl}piperidine-4-carboxylic acid from Step 7-5 (1.0 g, 2.0 mmol) in toluene (10 mL) was added TEA (0.3 g, 3 mmol) and DPPA (0.7 g, 3 mmol). The mixture was stirred at rt for 1 h. To this was added benzyl alcohol (2 mL) and 4 Å MS (100 mg). The mixture was heated at 100° C. for 1 h. The mixture was quenched with water and extracted with EtOAc (3×). The combined organics were concentrated to dryness and the residue was purified by silica gel CC to give the title compound (1.0 g, 83%) as a yellow solid. LCMS $(M+H)^+$=602.2.

Step 25-2, preparation of 2-(4-amino-4-{2'-ethoxy-[2,3'-bipyridin]-5-yl}piperidin-1-yl)-5-(trifluoromethyl)benzonitrile: To a solution of benzyl N-{1-[2-cyano-4-(trifluoromethyl)phenyl]-4-{2'-ethoxy-[2,3'-bipyridin]-5-yl}piperidin-4-yl}carbamate (0.98 g, 1.6 mmol) in MeOH (15 mL) was added $Pd(OH)_2$ (100 mg). The mixture was charged with hydrogen (g) and stirred at rt for 1 h. The mixture was filtered and the filtrate was concentrated to dryness to give the title compound (0.74 g, 97%) as a white solid. LCMS $(M+H)^+$=468.2.

Step 25-3, preparation of tert-butyl N-[2-({1-[2-cyano-4-(trifluoromethyl)phenyl]-4-{2'-ethoxy-[2,3'-bipyridin]-5-yl}piperidin-4-yl}carbamoyl)ethyl]-N-methylcarbamate: To a solution of 3-{[(tert-butoxy)carbonyl](methyl)amino}propanoic acid (30 mg, 0.15 mmol) and HATU (49 mg, 0.13 mmol) in DMF (1 mL) was added DIEA (54 mg, 0.42 mmol). After stirring at rt for 5 min, 2-(4-amino-4-{2'-ethoxy-[2,3'-bipyridin]-5-yl}piperidin-1-yl)-5-(trifluoromethyl)benzonitrile (60 mg, 0.13 mmol) was added to the above HATU-activated solution. The mixture was stirred at rt for 2 h and purified by reversed-phase CC to give the title compound (60 mg, 72%) as a white solid. LCMS $(M+H)^+$=653.3.

Step 25-4, preparation of N-{1-[2-cyano-4-(trifluoromethyl)phenyl]-4-{2'-ethoxy-[2,3'-bipyridin]-5-yl}piperidin-4-yl}-3-(methylamino)propanamide: To a solution of tert-butyl N-[2-({1-[2-cyano-4-(trifluoromethyl)phenyl]-4-{2'-ethoxy-[2,3'-bipyridin]-5-yl}piperidin-4-yl}carbamoyl)ethyl]-N-methylcarbamate (60 mg, 0.11 mmol) in DCM (2 mL) was added TFA (0.6 mL). The mixture was stirred at rt for 1 h. The mixture was concentrated to dryness and the residue was purified by reversed-phase CC to give the title compound (42 mg, 83%) as a white solid. LCMS $(M+H)^+$=553.2.

The following compounds were prepared similarly to Example 25 with appropriate substituting reagents and substrates at different steps:

| Compound no. | MS $(M + H)^+$ |
|---|---|
| 2-4 | 539.2 |
| 2-6 | 565.2 |
| 2-8 | 565.2 |
| 2-26 | 553.3 |
| 2-32 | 565.3 |

Example 26: N-{1-[2-cyano-4-(trifluoromethyl)phenyl]-4-{2'-ethoxy-[2,3'-bipyridin]-5-yl}piperidin-4-yl}-3-(dimethylamino)propanamide (Cpd 2-10)

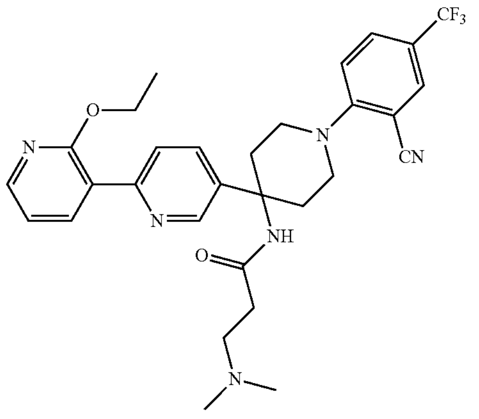 [SMILES: CCOc1ncccc1-c1ccc(C2(NC(=O)CCN(C)C)CCN(c3ccc(C(F)(F)F)cc3C#N)CC2)cn1]

Step 26-1, preparation of N-{1-[2-cyano-4-(trifluoromethyl)phenyl]-4-{2'-ethoxy-[2,3'-bipyridin]-5-yl}piperidin-4-yl}-3-(dimethylamino)propanamide formate: To a solution of N-{1-[2-cyano-4-(trifluoromethyl)phenyl]-4-{2'-ethoxy-[2,3'-bipyridin]-5-yl}piperidin-4-yl}-3-(methylamino)propanamide (55 mg, 0.10 mmol) from Step 25-4 in MeOH (1 mL) was added formaldehyde (10 mg, 0.33 mmol), sodium cyanoborohydride (20 mg, 0.32 mmol) and acetic acid (0.6 mg, 0.01 mmol). The mixture was stirred at rt for 1 h. The mixture was concentrated and purified by reversed-phase CC to give the title compound (27 mg, 44%) as a white solid. LCMS $(M+H)^+$=567.3.

The following compounds were prepared similarly to Example 26 with appropriate substituting reagents and substrates at different steps:

| Compound no. | MS $(M + H)^+$ |
|---|---|
| 2-7 | 579.2 |
| 2-9 | 579.2 |

Example 27: (3R)-1-methylpyrrolidin-3-yl N-{1-[2-cyano-4-(trifluoromethyl)phenyl]-4-[4-(2-ethoxypyridin-3-yl)phenyl]piperidin-4-yl}carbamate (Cpd 2-12)

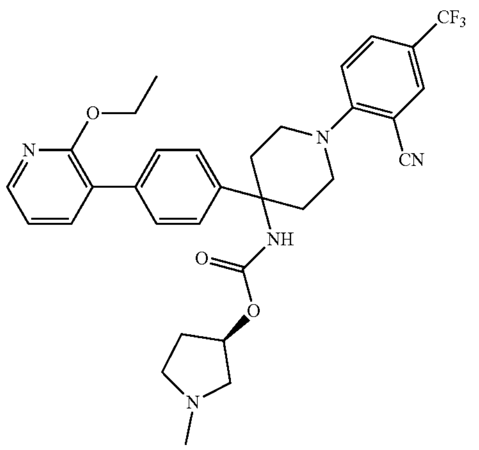 [SMILES: CCOc1ncccc1-c1ccc(C2(NC(=O)O[C@@H]3CCN(C)C3)CCN(c3ccc(C(F)(F)F)cc3C#N)CC2)cc1]

Step 27-1, preparation of (3R)-1-methylpyrrolidin-3-yl N-{1-[2-cyano-4-(trifluoromethyl)phenyl]-4-[4-(2-ethoxypyridin-3-yl)phenyl]piperidin-4-yl}carbamate: To a solution of (3R)-1-methylpyrrolidin-3-ol (7.8 mg, 0.077 mmol) and DIEA (0.056 mL, 0.32 mmol) in DCM (2 mL) at 0° C. was added triphosgene (8.0 mg, 0.027 mmol). The mixture was stirred at 0° C. for 1 h. To this mixture was added 2-{4-amino-4-[4-(2-ethoxypyridin-3-yl)phenyl]piperidin-1-yl}-5-(trifluoromethyl)benzonitrile (30.0 mg, 0.0643 mmol) from Step 24-4. The mixture was stirred at rt for 0.5 h, concentrated and purified by reversed-phase CC to give the title compound (9.3 mg, 24%) as a light yellow solid. LCMS $(M+H)^+$=594.5.

The following compounds were prepared similarly to Example 27 with appropriate substituting reagents and substrates at different steps:

| Compound no. | MS $(M + H)^+$ |
|---|---|
| 2-13 | 594.2 |

Example 28: 2-(4-{2'-ethoxy-[2,3'-bipyridin]-5-yl}-4-[(2-hydroxyethyl)amino]piperidin-1-yl)-5-(trifluoromethyl)benzonitrile (Cpd 2-14)

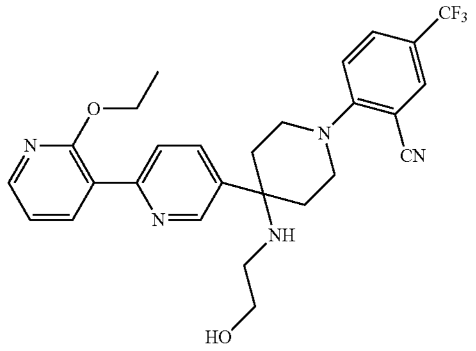 [SMILES: CCOc1ncccc1-c1ccc(C2(NCCO)CCN(c3ccc(C(F)(F)F)cc3C#N)CC2)cn1]

Step 28-1, preparation of 2-[4-({2-[(tert-butyldimethylsilyl)oxy]ethyl}amino)-4-{2'-ethoxy-[2,3'-bipyridin]-5-yl}piperidin-1-yl]-5-(trifluoromethyl)benzonitrile: To a solution of 2-(4-amino-4-{2'-ethoxy-[2,3'-bipyridin]-5-yl}piperidin-1-yl)-5-(trifluoromethyl)benzonitrile (50 mg, 0.11 mmol) from Step 25-2 in MeOH (2 mL) was added 2-[(tert-butyldimethylsilyl)oxy]-acetaldehyde (30 mg, 0.17 mmol), sodium cyanoborohydride (20 mg, 0.32 mmol) and acetic acid (2.0 mg, 0.033 mmol). The mixture was stirred at 30° C. for 2 h. The mixture was quenched with water and extracted with EtOAc (3×). The combined organics were dried over anhydrous $Na_2SO_4$ and concentrated to dryness to give the title compound (30 mg, 45%) as a light yellow solid. LCMS $(M+H)^+$=626.4.

Step 28-2, preparation of 2-(4-{2'-ethoxy-[2,3'-bipyridin]-5-yl}-4-[(2-hydroxyethyl)amino]piperidin-1-yl)-5-(trifluoromethyl)benzonitrile formate: To a solution of 2-[4-({2-[(tert-butyldimethylsilyl)oxy]ethyl}amino)-4-{2'-ethoxy-[2,3'-bipyridin]-5-yl}piperidin-1-yl]-5-(trifluoromethyl)benzonitrile (30 mg, 0.048 mmol) in DCM (3 mL) was added TFA (1 mL). The mixture was stirred at 30° C. for 1 h. The mixture was concentrated to dryness and the residue was purified by reversed-phase CC to give the title compound (24 mg, 88%) as a brown gum. LCMS $(M+H)^+$=512.3.

Example 29: 2-(4-{2'-ethoxy-[2,3'-bipyridin]-5-yl}-4-{[2-(methylamino)ethyl]amino}piperidin-1-yl)-5-(trifluoromethyl)benzonitrile (Cpd 2-15)

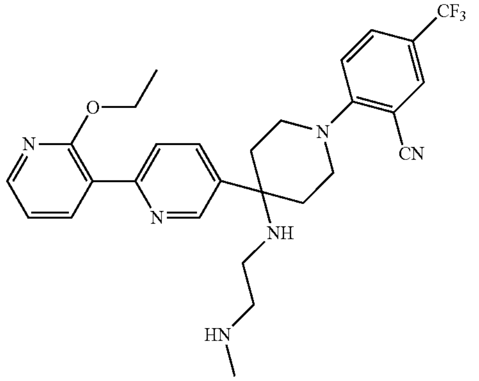 [SMILES: CCOc1ncccc1-c1ccc(C2(NCCNC)CCN(c3ccc(C(F)(F)F)cc3C#N)CC2)cn1]

Step 29-1, preparation of tert-butyl N-[2-({1-[2-cyano-4-(trifluoromethyl)phenyl]-4-{2'-ethoxy-[2,3'-bipyridin]-5-yl}piperidin-4-yl}amino)ethyl]-N-methylcarbamate: To a solution of 2-(4-amino-4-{2'-ethoxy-[2,3'-bipyridin]-5-yl}piperidin-1-yl)-5-(trifluoromethyl)benzonitrile (50 mg, 0.11 mmol) from Step 25-2 in MeOH (2 mL) was added tert-butyl N-methyl-N-(2-oxoethyl)carbamate (30 mg, 0.17 mmol), sodium cyanoborohydride (20 mg, 0.32 mmol) and acetic acid (5.0 mg, 0.083 mmol). The mixture was stirred at 30° C. for 2 h. The mixture was quenched with water and extracted with EtOAc (3×). The combined organics were dried over anhydrous $Na_2SO_4$ and concentrated to dryness to give the title compound (30 mg, 45%) as a yellow solid. LCMS $(M+H)^+$=625.4.

Step 29-2, preparation of 2-(4-{2'-ethoxy-[2,3'-bipyridin]-5-yl}-4-{[2-(methylamino)ethyl]amino}piperidin-1-yl)-5-(trifluoromethyl)benzonitrile formate: To a solution of tert-butyl N-[2-({1-[2-cyano-4-(trifluoromethyl)phenyl]-4-{2'-ethoxy-[2,3'-bipyridin]-5-yl}piperidin-4-yl}amino)ethyl]-N-methylcarbamate (30 mg, 0.048 mmol) in DCM (3 mL) was added TFA (1 mL). The mixture was stirred at 30° C. for 1 h. The mixture was concentrated to dryness and the residue was purified by reversed-phase CC to give the title compound (25 mg, 90%) as a white solid. LCMS $(M+H)^+$=525.2.

Example 30: (3S)-1-methylpyrrolidin-3-yl N-{1-[2-cyano-4-(trifluoromethyl)phenyl]-4-{2'-ethoxy-[2,3'-bipyridin]-5-yl}piperidin-4-yl}carbamate (Cpd 2-18)

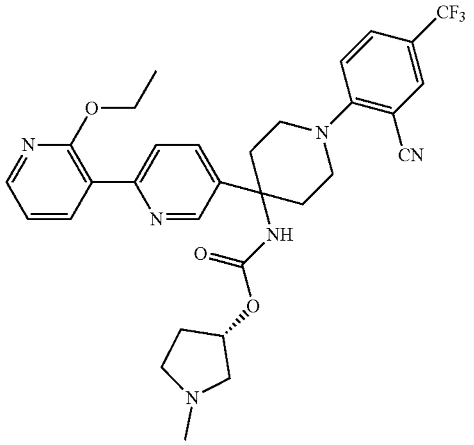 [SMILES: CCOc1ncccc1-c1ccc(C2(NC(=O)O[C@H]3CCN(C)C3)CCN(c3ccc(C(F)(F)F)cc3C#N)CC2)cn1]

Step 30-1, preparation of (3S)-1-methylpyrrolidin-3-yl N-{1-[2-cyano-4-(trifluoromethyl)phenyl]-4-{2'-ethoxy-[2,3'-bipyridin]-5-yl}piperidin-4-yl}carbamate formate: To a solution of 1-[2-cyano-4-(trifluoromethyl)phenyl]-4-{2'-ethoxy-[2,3'-bipyridin]-5-yl}piperidine-4-carboxylic acid (50 mg, 0.10 mmol) from Step 7-5 in toluene (1 mL) was added TEA (0.019 mL, 0.14 mmol) and DPPA (33 mg, 0.12 mmol). The mixture was stirred at rt for 1 h. To this was added (3S)-1-methylpyrrolidin-3-ol (20 mg, 0.20 mmol) and 4 Å MS (100 mg). The mixture was heated at 100° C. for 1 h. The mixture was quenched with water and extracted with EtOAc (3×). The combined organics were concentrated to dryness and the residue was purified by reversed-phase CC to give the title compound (28 mg, 43%) as a white solid. LCMS $(M+H)^+$=595.3.

The following compounds were prepared similarly to Example 30 with appropriate substituting reagents and substrates at different steps:

| Compound no. | MS $(M + H)^+$ |
|---|---|
| 2-22 | 594.4 |
| 2-41 | 553.2 |
| 2-42 | 553.2 |
| 2-49 | 598.2 |
| 2-50 | 598.2 |
| 2-53 | 580.5 |
| 2-54 | 580.5 |
| 2-57 | 568.3 |

Example 31: 1-{1-[2-cyano-4-(trifluoromethyl)phenyl]-4-{2'-ethoxy-[2,3'-bipyridin]-5-yl}piperidin-4-yl}-3-[(3R)-1-methylpyrrolidin-3-yl]urea (Cpd 2-19)

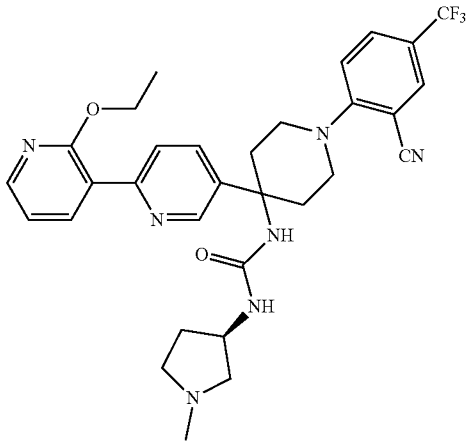 [SMILES: CCOc1ncccc1-c1ccc(C2(NC(=O)N[C@@H]3CCN(C)C3)CCN(c3ccc(C(F)(F)F)cc3C#N)CC2)cn1]

Step 31-1, preparation of 1-{1-[2-cyano-4-(trifluoromethyl)phenyl]-4-{2'-ethoxy-[2,3'-bipyridin]-5-yl}piperidin-4-yl}-3-[(3R)-1-methylpyrrolidin-3-yl]urea bis(2,2,2-trifluoroacetate): To a solution of 2-(4-amino-4-{2'-ethoxy-[2,3'-bipyridin]-5-yl}piperidin-1-yl)-5-(trifluoromethyl) benzonitrile (50 mg, 0.11 mmol) from Step 25-2 in toluene (1 mL) was added triphosgene (13 mg, 0.044 mmol). The mixture was stirred at rt for 2 h. To this mixture was added (3R)-1-methylpyrrolidin-3-amine (22 mg, 0.22 mmol) and TEA (0.045 mL, 0.33 mmol). The mixture was stirred at rt for 1 h. The mixture was concentrated to dryness and purified by reversed-phase CC to give the title compound (12 mg, 14%) as yellow oil. LCMS $(M+H)^+$=594.3.

The following compounds were prepared similarly to Example 31 with appropriate substituting reagents and substrates at different steps:

| Compound no. | MS $(M + H)^+$ |
|---|---|
| 2-20 | 594.3 |
| 2-43 | 552.4 |
| 2-48 | 553.1 |
| 2-51 | 597.3 |
| 2-52 | 597.3 |
| 2-55 | 579.2 |
| 2-56 | 579.2 |
| 2-58 | 567.4 |
| 2-59 | 565.5 |

Example 32: (3R)—N-{1-[2-cyano-4-(trifluoromethyl)phenyl]-4-{2'-ethoxy-[2,3'-bipyridin]-5-yl}piperidin-4-yl}-3-(methylamino)pyrrolidine-1-carboxamide (Cpd 2-21)

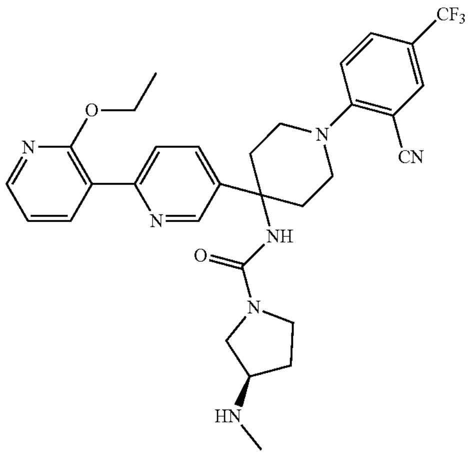 [SMILES: CCOc1ncccc1-c1ccc(C2(NC(=O)N3CC[C@@H](NC)C3)CCN(c3ccc(C(F)(F)F)cc3C#N)CC2)cn1]

Step 32-1, preparation of tert-butyl N-[(3R)-1-({1-[2-cyano-4-(trifluoromethyl)phenyl]-4-{2'-ethoxy-[2,3'-bipyridin]-5-yl}piperidin-4-yl}carbamoyl)pyrrolidin-3-yl]-N-methylcarbamate: To a solution of 2-(4-amino-4-{2'-ethoxy-[2,3'-bipyridin]-5-yl}piperidin-1-yl)-5-(trifluoromethyl) benzonitrile (50 mg, 0.11 mmol) from Step 25-2 in toluene (1 mL) was added triphosgene (13 mg, 0.044 mmol). The mixture was stirred at rt for 2 h. To this mixture was added tert-butyl N-methyl-N-[(3R)-pyrrolidin-3-yl]carbamate (22 mg, 0.22 mmol) and the resulting mixture was stirred at rt for 2 h. The mixture was quenched with water and extracted with EtOAc (3×). The combined organics were concentrated to dryness and purified by silica gel CC to give the title compound (33 mg, 44%) as yellow oil. LCMS $(M+H)^+$=694.5.

Step 32-2, preparation of (3R)—N-{1-[2-cyano-4-(trifluoromethyl)phenyl]-4-{2'-ethoxy-[2,3'-bipyridin]-5-yl}piperidin-4-yl}-3-(methylamino)pyrrolidine-1-carboxamide formate: To a solution of tert-butyl N-[(3R)-1-({1-[2-cyano-4-(trifluoromethyl)phenyl]-4-{2'-ethoxy-[2,3'-bipyridin]-5-yl}piperidin-4-yl}carbamoyl)pyrrolidin-3-yl]-N-methylcarbamate (33 mg, 0.048 mmol) in DCM (1 mL) was added TFA (0.3 mL). The mixture was stirred at rt for 1 h. The mixture was concentrated to dryness and the residue was purified by reversed-phase CC to give the title compound (12 mg, 41%) as a white solid. LCMS $(M+H)^+$=594.3.

The following compounds were prepared similarly to Example 32 with appropriate substituting reagents and substrates at different steps:

| Compound no. | MS $(M + H)^+$ |
|---|---|
| 2-23 | 580.4 |
| 2-24 | 594.3 |

Example 33: N-[1-(4-chloro-2-cyanophenyl)-4-[6-(2-ethoxyphenyl)pyridin-3-yl]piperidin-4-yl]-1-methylazetidine-3-carboxamide (Cpd 2-25)

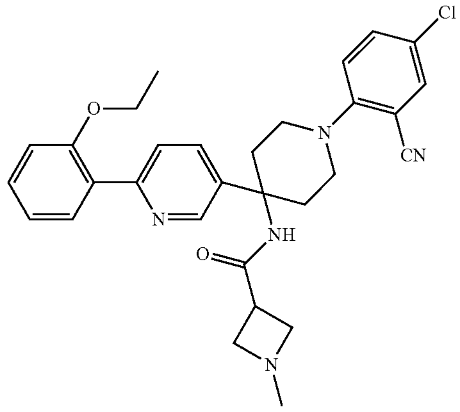 [SMILES: CCOc1ccccc1-c1ccc(C2(NC(=O)C3CN(C)C3)CCN(c3ccc(Cl)cc3C#N)CC2)cn1]

Step 33-1, preparation of ethyl 1-benzyl-4-(6-chloropyridin-3-yl)piperidine-4-carboxylate: To a solution of ethyl 6-chloropyridine-3-carboxylate (9.5 g, 48 mmol) in DMF (100 mL) at 0° C. was added 60% sodium hydride in mineral oil (3.4 g, 0.14 mol) in portions. The mixture was stirred at 0° C. for 0.5 h. To this was added benzylbis(2-bromoethyl) amine (8.3 g, 26 mmol). The mixture was stirred at rt for 2 h. The mixture was quenched with water and extracted with EtOAc (3×). The combined organics were dried over anhydrous $Na_2SO_4$ and concentrated to dryness. The residue was purified by silica gel CC to give the title compound (12 g, 70%) as yellow oil. LCMS $(M+H)^+$=359.2.

Step 33-2, preparation of ethyl 1-benzyl-4-[6-(2-ethoxyphenyl)pyridin-3-yl]piperidine-4-carboxylate: To a suspension of ethyl 1-benzyl-4-(6-chloropyridin-3-yl)piperidine-4-carboxylate (4.2 g, 12 mmol) in 1,4-dioxane (50 mL) and water (5 mL) under nitrogen was added potassium carbonate (3.2 g, 23 mmol), (2-ethoxyphenyl)boronic acid (2.9 g, 17 mmol) and Pd(dtbpf)$Cl_2$ (0.3 g, 0.5 mmol). The mixture was heated at 90° C. for 2 h. The mixture was filtered and the filtrate was concentrated to dryness. The residue was purified by silica gel CC to give the title compound (4.0 g, 77%) as a yellow solid. LCMS $(M+H)^+$=445.2.

Step 33-3, preparation of ethyl 4-[6-(2-ethoxyphenyl) pyridin-3-yl]piperidine-4-carboxylate: To a solution of ethyl 1-benzyl-4-[6-(2-ethoxyphenyl)pyridin-3-yl]piperidine-4-carboxylate (3.5 g, 7.9 mmol) in MeOH (50 mL) was added 10 wt % of Pd on carbon (160 mg) and $Pd(OH)_2$ (160 mg). The mixture was charged with hydrogen (g) and stirred at rt for 16 h. The mixture was filtered and the filtrate was concentrated to dryness to give the title compound (2.4 g, 86%) as yellow oil. LCMS $(M+H)^+$=355.2.

Step 33-4, preparation of ethyl 1-(4-chloro-2-cyanophenyl)-4-[6-(2-ethoxyphenyl)pyridin-3-yl]piperidine-4-carboxylate: To a mixture of ethyl 4-[6-(2-ethoxyphenyl)pyridin-3-yl]piperidine-4-carboxylate (400 mg, 1.13 mmol), 2-bromo-5-chlorobenzonitrile (320 mg, 1.48 mmol), XPhos (33.3 mg, 0.0699 mmol), $Pd_2(dba)_3 \cdot CHCl_3$ (35.0 mg, 0.0338 mmol), and cesium carbonate (735 mg, 2.26 mmol) under nitrogen was added toluene (5 mL). The mixture was heated at 90° C. for 2 h. The mixture was filtered and the filtrate was concentrated to dryness. The residue was purified by silica gel CC to give the title compound (290 mg, 52.4%) as yellow oil. LCMS $(M+H)^+$=490.3.

Step 33-5, preparation of 1-(4-chloro-2-cyanophenyl)-4-[6-(2-ethoxyphenyl)pyridin-3-yl]piperidine-4-carboxylic acid: To a suspension of ethyl 1-(4-chloro-2-cyanophenyl)-4-[6-(2-ethoxyphenyl)pyridin-3-yl]piperidine-4-carboxylate (290 mg, 0.59 mmol) in a mixed solvent of EtOH/water (5:1, 6 mL) was added lithium hydroxide (72 mg, 3.0 mmol). The mixture was heated at 60° C. for 2 h. The mixture was diluted with water and adjusted to pH 6-7 with 1N HCl (aq). The mixture was extracted with EtOAc (3×) and the combined organics were dried over anhydrous $Na_2SO_4$ and concentrated to dryness to give the title compound (250 mg, 91.4%) as a yellow solid. LCMS $(M+H)^+$=462.3.

Step 33-6, preparation of benzyl N-[1-(4-chloro-2-cyanophenyl)-4-[6-(2-ethoxyphenyl)pyridin-3-yl]piperidin-4-yl] carbamate: To a solution of 1-(4-chloro-2-cyanophenyl)-4-[6-(2-ethoxyphenyl)pyridin-3-yl]piperidine-4-carboxylic acid (730 mg, 1.58 mmol) in toluene (10 mL) was added TEA (208 mg, 2.06 mmol) and DPPA (478 mg, 1.74 mmol). The mixture was stirred at rt for 1 h. To this was added benzyl alcohol (513 mg, 4.74 mmol) and 4 Å MS (80 mg). The mixture was heated at 100° C. for 1 h. The mixture was quenched with water and extracted with EtOAc (3×). The combined organics were concentrated to dryness and the residue was purified by silica gel CC to give the title compound (550 mg, 61.4%) as a yellow solid. LCMS $(M+H)^+$=567.3.

Step 33-7, preparation of 2-{4-amino-4-[6-(2-ethoxyphenyl)pyridin-3-yl]piperidin-1-yl}-5-chlorobenzonitrile: To benzyl N-[1-(4-chloro-2-cyanophenyl)-4-[6-(2-ethoxyphenyl)pyridin-3-yl]piperidin-4-yl]carbamate (550 mg, 0.97 mmol) was added TFA (3 mL). The mixture was heated at 70° C. for 5 h. The mixture was concentrated to dryness and triturated with saturated $NaHCO_3$ (aq) to give the title compound (420 mg, 90%) as a light yellow solid. LCMS $(M+H)^+$=433.2.

Step 33-8, preparation of N-[1-(4-chloro-2-cyanophenyl)-4-[6-(2-ethoxyphenyl)pyridin-3-yl]piperidin-4-yl]-1-methylazetidine-3-carboxamide formate: To a solution of 1-methylazetidine-3-carboxylic acid (18 mg, 0.16 mmol) and HATU (60 mg, 0.16 mmol) in DMF (2 mL) was added DIEA (0.081 mL, 0.46 mmol). After stirring at rt for 5 min, 2-{4-amino-4-[6-(2-ethoxyphenyl)pyridin-3-yl]piperidin-1-yl}-5-chlorobenzonitrile (50 mg, 0.12 mmol) was added to the above HATU-activated solution. The mixture was stirred at rt for 1 h. The mixture was purified by reversed-phase CC to give the title compound (28 mg, 42%) as a white solid. LCMS $(M+H)^+$=530.3.

The following compounds were prepared similarly to Example 33 with appropriate substituting reagents and substrates at different steps:

| Compound no. | MS $(M + H)^+$ |
|---|---|
| 2-28 | 544.3 |
| 2-29 | 544.3 |
| 2-30 | 532.3 |
| 2-31 | 518.3 |

Example 34: N-{1-[2-cyano-4-(trifluoromethyl)phenyl]-4-[6-(2-ethoxyphenyl)pyridin-3-yl]piperidin-4-yl}-2-(dimethylamino)acetamide (Cpd 2-34)

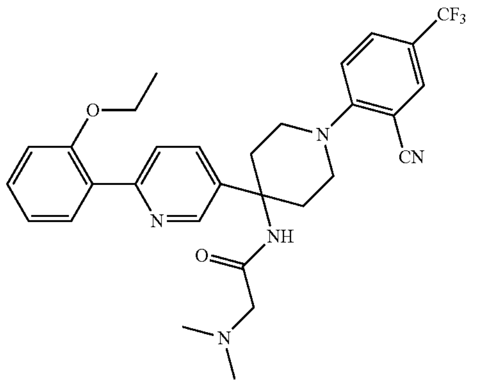 [SMILES: CCOc1ccccc1-c1ccc(C2(NC(=O)CN(C)C)CCN(c3ccc(C(F)(F)F)cc3C#N)CC2)cn1]

Step 34-1, preparation of ethyl 1-[2-cyano-4-(trifluoromethyl)phenyl]-4-[6-(2-ethoxyphenyl)pyridin-3-yl]piperidine-4-carboxylate: To a solution of ethyl 4-[6-(2-ethoxyphenyl)pyridin-3-yl]piperidine-4-carboxylate (800 mg, 2.26 mmol) from Step 33-3 in DMSO (10 mL) was added 2-fluoro-5-(trifluoromethyl)benzonitrile (428 mg, 2.26 mmol) and DIEA (875 mg, 6.77 mmol). The mixture was heated at 60° C. for 1 h. The mixture was filtered and the filtrate was concentrated to dryness. The residue was purified by reversed-phase CC to give the title compound (600 mg, 50.8%) as a yellow solid. LCMS $(M+H)^+$=524.2.

Step 34-2, preparation of 1-[2-cyano-4-(trifluoromethyl)phenyl]-4-[6-(2-ethoxyphenyl)pyridin-3-yl]piperidine-4-carboxylic acid: To a suspension of ethyl 1-[2-cyano-4-(trifluoromethyl)phenyl]-4-[6-(2-ethoxyphenyl)pyridin-3-yl]piperidine-4-carboxylate (600 mg, 1.15 mmol) in a mixed solvent of EtOH/water (5:1, 12 mL) was added lithium hydroxide (138 mg, 5.76 mmol). The mixture was heated at 60° C. for 1 h. The mixture was concentrated to remove organics and the aqueous residue was adjusted to pH 6-7 with 1N HCl (aq). The solution was extracted with EtOAc (3×) and the combined organics were dried over anhydrous $Na_2SO_4$ and concentrated to dryness to give the title compound (570 mg, 100%) as a yellow solid. LCMS $(M+H)^+$=496.1.

Step 34-3, preparation of benzyl N-{1-[2-cyano-4-(trifluoromethyl)phenyl]-4-[6-(2-ethoxyphenyl)pyridin-3-yl]piperidin-4-yl}carbamate: To a solution of 1-[2-cyano-4-(trifluoromethyl)phenyl]-4-[6-(2-ethoxyphenyl)pyridin-3-yl]piperidine-4-carboxylic acid (570 mg, 1.15 mmol) in toluene (8 mL) was added TEA (163 mg, 1.61 mmol) and DPPA (380 mg, 1.38 mmol). The mixture was stirred at rt for 1 h. To this was added benzyl alcohol (1.6 mL) and 4 Å MS (60 mg). The mixture was heated at 100° C. for 1 h. The mixture was quenched with water and extracted with EtOAc (3×). The combined organics were concentrated to dryness and the residue was purified by silica gel CC to give the title compound (550 mg, 79.6%) as a yellow solid. LCMS $(M+H)^+$=601.2.

Step 34-4, preparation of 2-{4-amino-4-[6-(2-ethoxyphenyl)pyridin-3-yl]piperidin-1-yl}-5-(trifluoromethyl)benzonitrile: To benzyl N-{1-[2-cyano-4-(trifluoromethyl)phenyl]-4-[6-(2-ethoxyphenyl)pyridin-3-yl]piperidin-4-yl}carbamate (544 mg, 0.97 mmol) was added TFA (5 mL). The mixture was heated at 70° C. for 7 h. The mixture was concentrated to dryness and the residue was purified by reversed-phase CC to give the title compound (370 mg, 87.6%) as a yellow solid. LCMS $(M+H)^+$=467.1.

Step 34-5, preparation of N-{1-[2-cyano-4-(trifluoromethyl)phenyl]-4-[6-(2-ethoxyphenyl)pyridin-3-yl]piperidin-4-yl}-2-(dimethylamino)acetamide formate: To a solution of 2-(dimethylamino)acetic acid (31 mg, 0.30 mmol) and HATU (65 mg, 0.17 mmol) in DMF (1 mL) was added DIEA (0.091 mL, 0.52 mmol). After stirring at rt for 5 min, 2-{4-amino-4-[6-(2-ethoxyphenyl)pyridin-3-yl]piperidin-1-yl}-5-(trifluoromethyl)benzonitrile (50 mg, 0.11 mmol) was added to the above HATU-activated solution. The mixture was stirred at rt for 1 h. The mixture was purified by reversed-phase CC to give the title compound (40.1 mg, 63.0%) as an off-white solid. LCMS $(M+H)^+$=552.3.

The following compounds were prepared similarly to Example 34 with appropriate substituting reagents and substrates at different steps:

| Compound no. | MS $(M + H)^+$ |
|---|---|
| 2-27 | 578.3 |
| 2-33 | 578.3 |
| 2-35 | 564.3 |
| 2-36 | 566.3 |
| 2-40 | 551.2 |
| 2-44 | 523.4 |
| 2-45 | 523.3 |
| 2-46 | 537.5 |
| 2-47 | 537.5 |
| 2-60 | 564.4 |
| 2-61 | 556.2 |

Example 35: N-[1-(4-chloro-2-cyanophenyl)-4-[6-(2-ethoxyphenyl)pyridin-3-yl]piperidin-4-yl]-1-methylazetidine-3-carboxamide (Cpd 2-37)

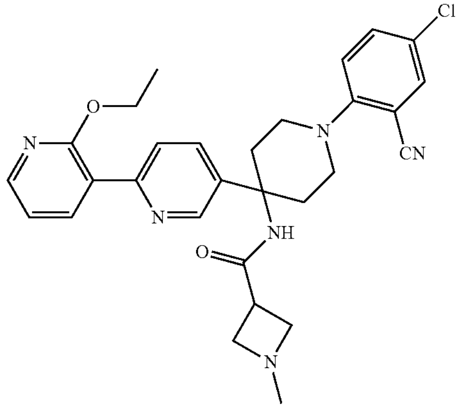 [SMILES: CCOc1ncccc1-c1ccc(C2(NC(=O)C3CN(C)C3)CCN(c3ccc(Cl)cc3C#N)CC2)cn1]

Step 35-1, preparation of ethyl 1-benzyl-4-{2'-ethoxy-[2,3'-bipyridin]-5-yl}piperidine-4-carboxylate: To a suspension of ethyl 1-benzyl-4-(6-chloropyridin-3-yl)piperidine-4-carboxylate (2.0 g, 5.6 mmol) from Step 33-1 in 1,4-dioxane (20 mL) and water (2 mL) under nitrogen was added potassium carbonate (2.3 g, 17 mmol), (2-ethoxypyridin-3-yl)boronic acid (1.4 g, 8.4 mmol) and Pd(dtbpf)$Cl_2$ (0.15 g, 0.23 mmol). The mixture was heated at 90° C. for 2 h. The mixture was filtered and the filtrate was concentrated to dryness. The residue was purified by silica gel CC to give the title compound (2.1 g, 85%) as yellow oil. LCMS $(M+H)^+$=446.3.

Step 35-2, preparation of ethyl 4-{2'-ethoxy-[2,3'-bipyridin]-5-yl}piperidine-4-carboxylate: To a solution of ethyl 1-benzyl-4-{2'-ethoxy-[2,3'-bipyridin]-5-yl}piperidine-4-carboxylate (2.1 g, 4.7 mmol) in MeOH (30 mL) was added 10 wt % of Pd on carbon (200 mg) and $Pd(OH)_2$ (200 mg). The mixture was charged with hydrogen (g) and stirred at rt for 2 h. The mixture was filtered and the filtrate was concentrated to dryness to give the title compound (1.6 g, 96%) as yellow oil. LCMS $(M+H)^+$=356.2.

Step 35-3, preparation of ethyl 1-(4-chloro-2-cyanophenyl)-4-{2'-ethoxy-[2,3'-bipyridin]-5-yl}piperidine-4-carboxylate: To a mixture of ethyl 4-{2'-ethoxy-[2,3'-bipyridin]-5-yl}piperidine-4-carboxylate (1.59 g, 4.47 mmol), 2-bromo-5-chlorobenzonitrile (1.26 g, 5.82 mmol), XPhos (171 mg, 0.359 mmol), $Pd_2(dba)_3{\cdot}CHCl_3$ (185 mg, 0.179 mmol), and cesium carbonate (2.92 g, 8.96 mmol) under nitrogen was added toluene (20 mL). The mixture was heated at 100° C. for 2 h. The mixture was filtered and the filtrate was concentrated to dryness. The residue was purified by silica gel CC to give the title compound (1.3 g, 59%) as a yellow solid. LCMS $(M+H)^+$=491.2.

Step 35-4, preparation of 1-(4-chloro-2-cyanophenyl)-4-{2'-ethoxy-[2,3'-bipyridin]-5-yl}piperidine-4-carboxylic acid: To a suspension of ethyl 1-(4-chloro-2-cyanophenyl)-4-{2'-ethoxy-[2,3'-bipyridin]-5-yl}piperidine-4-carboxylate (1.29 g, 2.63 mmol) in a mixed solvent of EtOH/water (5:1, 18 mL) was added lithium hydroxide (629 mg, 26.3 mmol). The mixture was heated at 60° C. for 1 h. The mixture was adjusted to pH 6-7 with 1N HCl (aq) and extracted with EtOAc (3×) and the combined organics were dried over anhydrous $Na_2SO_4$ and concentrated to dryness to give the title compound (1.1 g, 90%) as a yellow solid. LCMS $(M+H)^+$=463.3.

Step 35-5, preparation of benzyl N-[1-(4-chloro-2-cyanophenyl)-4-{2'-ethoxy-[2,3'-bipyridin]-5-yl}piperidin-4-yl] carbamate: To a solution of 1-(4-chloro-2-cyanophenyl)-4-{2'-ethoxy-[2,3'-bipyridin]-5-yl}piperidine-4-carboxylic acid (800 mg, 1.73 mmol) in toluene (10 mL) was added TEA (245 mg, 2.42 mmol) and DPPA (571 mg, 2.07 mmol). The mixture was stirred at rt for 1 h. To this was added benzyl alcohol (748 mg, 6.92 mmol) and 4 Å MS (80 mg). The mixture was heated at 100° C. for 1 h. The mixture was quenched with water and extracted with EtOAc (3×). The combined organics were concentrated to dryness and the residue was purified by silica gel CC to give the title compound (820 mg, 83.5%) as a yellow solid. LCMS $(M+H)^+$=568.4.

Step 35-6, preparation of 2-(4-amino-4-{2'-ethoxy-[2,3'-bipyridin]-5-yl}piperidin-1-yl)-5-chlorobenzonitrile: To benzyl N-[1-(4-chloro-2-cyanophenyl)-4-{2'-ethoxy-[2,3'-bipyridin]-5-yl}piperidin-4-yl]carbamate (800 mg, 1.41 mmol) was added TFA (10 mL). The mixture was heated at 70° C. for 3 h. The mixture was concentrated to dryness and the residue was purified by reversed-phase CC to give the title compound (450 mg, 73.6%) as a yellow solid. LCMS (M+H)+=434.3.

Step 35-7, preparation of N-[1-(4-chloro-2-cyanophenyl)-4-{2'-ethoxy-[2,3'-bipyridin]-5-yl}piperidin-4-yl]-1-methylazetidine-3-carboxamide formate: To a solution of 1-methylazetidine-3-carboxylic acid (13 mg, 0.11 mmol) and HATU (39 mg, 0.10 mmol) in DMF (0.6 mL) was added DIEA (36 mg, 0.28 mmol). After stirring at rt for 5 min, 2-(4-amino-4-{2'-ethoxy-[2,3'-bipyridin]-5-yl}piperidin-1-yl)-5-chlorobenzonitrile (40 mg, 0.092 mmol) was added to the above HATU-activated solution. The mixture was stirred at rt for 1 h. The mixture was purified by reversed-phase CC to give the title compound (26 mg, 49%) as a light yellow solid. LCMS $(M+H)^+$=531.3.

The following compounds were prepared similarly to Example 35 with appropriate substituting reagents and substrates at different steps:

| Compound no. | MS $(M + H)^+$ |
|---|---|
| 2-38 | 519.3 |
| 2-39 | 545.3 |

Example 36: 1-[2-cyano-4-(trifluoromethyl)phenyl]-4-{2'-cyclopropyl-[2,3'-bipyridin]-5-yl}-N-[(3S)-1-methylpyrrolidin-3-yl]piperidine-4-carboxamide (Compound 1-180)

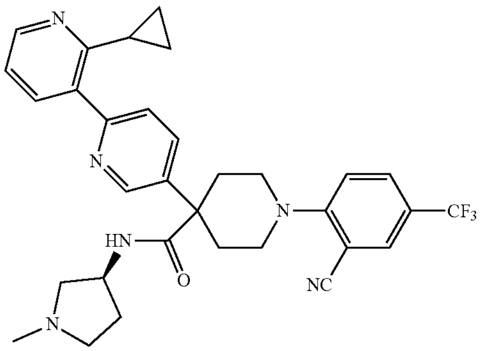 [SMILES: CN1CC[C@H](NC(=O)C2(c3ccc(-c4cccnc4C4CC4)nc3)CCN(c3ccc(C(F)(F)F)cc3C#N)CC2)C1]

Step 36-1, preparation of 3-bromo-2-cyclopropylpyridine: Into a 100-mL vial, was placed 2,3-dibromopyridine (1.5 g, 6.3 mmol), tetrakis(triphenylphosphine)palladium (0) (0.22 g, 0.19 mmol), and THF (10 mL) under $N_2$. The resulting solution was treated with cyclopropylzinc(II) bromide (17 ml, 1.5 Eq) in THF. The reaction was stirred at 65° C. for 2 h. The reaction was cooled to rt and concentrated. The residue was purified by a silica gel column chromatography to afford the title compound (150 mg, 12%) as yellow solid. LCMS $(M+H)^+$=197.9.

Step 36-2, preparation of ethyl 1-[2-cyano-4-(trifluoromethyl)phenyl]-4-[6-(tributylstannyl)pyridin-3-yl]piperidine-4-carboxylate: Into a 20-mL vial, were placed methyl 4-(6-chloropyridin-3-yl)-1-(2-cyano-4-(trifluoromethyl)phenyl) piperidine-4-carboxylate (200 mg, 0.457 mmol) from step 12-2 and dioxane (2 mL). 1,1,1,2,2,2-Hexabutyldistannane (291 mg, 0.502 mmol), $Pd_2(dba)_3{\cdot}CHCl_3$ (23.6 mg, 0.023 mmol), and tricyclohexylphosphonium tetrafluoroborate (16.8 mg, 0.046 mmol) were sequentially added into the solution under $N_2$. The resulting solution was stirred at 120° C. for 4 h. LCMS indicated $\sim_{57}$% desired product which was used in the next step directly without further purification.

Step 36-3, preparation of ethyl 1-[2-cyano-4-(trifluoromethyl)phenyl]-4-{2'-cyclopropyl-[2,3'-bipyridin]-5-yl}piperidine-4-carboxylate: To a solution of ethyl 1-[2-cyano-4-(trifluoromethyl)phenyl]-4-[6-(tributylstannyl) pyridin-3-yl]piperidine-4-carboxylate (316 mg, 0.456 mmol) in dioxane (2 mL) was added 3-bromo-2-cyclopropylpyridine (142 mg, 0.717 mmol), dicyclohexyl(2'4'6'-triisopropyl-[1,1'-biphenyl]-2-yl)phosphane (21.8 mg, 0.046 mmol), and $Pd_2(dba)_3{\cdot}CHCl_3$ (23.6 mg, 0.023 mmol) at rt under $N_2$. The resulting solution was stirred at 120° C. for 1 h. The solid ppts were filtered out. The filtrate was concentrated under vacuum. The residue was purified by a silica gel column chromatography to afford the title compound (96 mg, 40%) as yellow solid. LCMS $(M+H)^+$=520.9.

Step 36-4, preparation of 1-[2-cyano-4-(trifluoromethyl) phenyl]-4-{2'-cyclopropyl-[2,3'-bipyridin]-5-yl}piperidine-4-carboxylic acid: Into a 50-mL round-bottom flask purged, were placed ethyl 1-[2-cyano-4-(trifluoromethyl)phenyl]-4-{2'-cyclopropyl-[2,3'-bipyridin]-5-yl}piperidine-4-carboxylate (96 mg, 0.18 mmol) and EtOH (2 mL)/water (0.4 mL). The solution was treated with LiOH (31 mg, 1.3 mmol) and then stirred at 60° C. for 1 h. The reaction was cooled to rt and neutralized to pH 6-7 with 1N-HCl. The resulting solution was extracted with ethyl acetate (3×). The combined organic layers were washed with brine, dried over anhydrous sodium sulfate and concentrated. This resulted in the title compound (85 mg, 94%) as yellow solid. LCMS $(M+H)^+$=492.9.

Step 36-5, preparation of 1-[2-cyano-4-(trifluoromethyl) phenyl]-4-{2'-cyclopropyl-[2,3'-bipyridin]-5-yl}-N-[(3S)-1-methylpyrrolidin-3-yl]piperidine-4-carboxamide formate: To a solution of 1-[2-cyano-4-(trifluoromethyl)phenyl]-4-{2'-cyclopropyl-[2,3'-bipyridin]-5-yl}piperidine-4-carboxylic acid (45 mg, 0.091 mmol) in DMF (0.6 mL) was added HATU (38 mg, 0.10 mmol) and DIEA (35 mg, 0.27 mmol). After stirring for 5 min, the reaction was treated with (S)-1-methylpyrrolidin-3-amine (10 mg, 0.10 mmol) at rt. The resulting solution was stirred at rt for 1 h. The crude product was further purified by Prep-HPLC to afford the title compound (25 mg, 44%) as off-white solid. LCMS $(M+H)^+$= 575.2.

The following compounds were prepared similarly to Example 36 with appropriate substituting reagents and substrates at different steps:

| Compound no. | MS $(M + H)^+$ |
|---|---|
| 1-181 | 585.2 |
| 1-182 | 565.2 |

Example 37: 1-[2-cyano-4-(trifluoromethyl)phenyl]-4-[6-(1-methyl-1H-pyrrol-2-yl)pyridin-3-yl]-N-[(3S)-pyrrolidin-3-yl]piperidine-4-carboxamide (cod: 1-152)

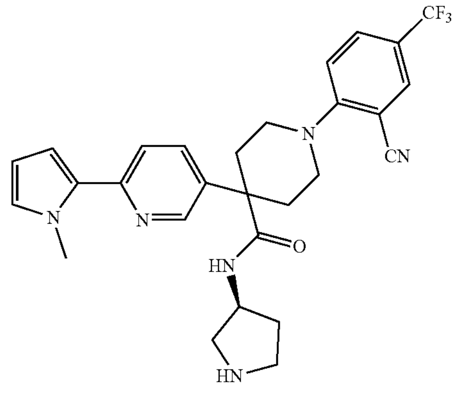 [SMILES: Cn1cccc1-c1ccc(C2(C(=O)N[C@H]3CCNC3)CCN(c3ccc(C(F)(F)F)cc3C#N)CC2)cn1]

Step 37-1, preparation of 1-[2-cyano-4-(trifluoromethyl) phenyl]-4-[6-(1-methyl-1H-pyrrol-2-yl)pyridin-3-yl]piperidine-4-carboxylic acid: To a mixture of 4-(6-chloropyridin-3-yl)-1-[2-cyano-4-(trifluoromethyl)phenyl]piperidine-4-carboxylic acid (1.00 g, 2.44 mmol) from Step 12-3, 1-methyl-2-(4,4,5,5-tetramethyl-1,3,2-dioxaborolan-2-yl)-1H-pyrrole (1.52 g, 7.32 mmol), Pd(amphos)$Cl_2$ (518 mg, 0.732 mmol), and potassium carbonate (1.01 g, 7.32 mmol) in a sealed tube was added 1,4-dioxane (20 mL) and water (3 mL). Nitrogen (g) was bubbled through and the resulting mixture was heated at 90° C. for 2 h. The mixture was quenched with water, acidified with 1N HCl (aq) to pH 2-3 and extracted with EtOAc (2×). The combined organics were dried over anhydrous $MgSO_4$ and concentrated to dryness. The residue was purified by reversed-phase CC to give the title compound (911 mg, 82.1% yield) as a brown solid. LCMS $(M+H)^+$=455.4.

Step 37-2, preparation of tert-butyl (3S)-3-{1-[2-cyano-4-(trifluoromethyl)phenyl]-4-[6-(1-methyl-1H-pyrrol-2-yl) pyridin-3-yl]piperidine-4-amido}pyrrolidine-1-carboxylate: To a solution of 1-[2-cyano-4-(trifluoromethyl)phenyl]-4-[6-(1-methyl-1H-pyrrol-2-yl)pyridin-3-yl]piperidine-4-carboxylic acid (30.0 mg, 0.0660 mmol) and HATU (35.1 mg, 0.0924 mmol) in DMF (0.2 mL) was added DIEA (0.023 mL, 0.13 mmol). After stirring at rt for 5 min, tert-butyl (3S)-3-aminopyrrolidine-1-carboxylate (19.7 mg, 0.106 mmol) was added to the above HATU-activated solution. The mixture was stirred at rt for 10 min and purified by reversed-phase CC to give the title compound (23.9 mg, 58.1% yield) as an off-white solid. LCMS $(M+H)^+$=523.3.

Step 37-3, preparation of 1-[2-cyano-4-(trifluoromethyl) phenyl]-4-[6-(1-methyl-1H-pyrrol-2-yl)pyridin-3-yl]-N-[(3S)-pyrrolidin-3-yl]piperidine-4-carboxamide: To a solution of tert-butyl (3S)-3-{1-[2-cyano-4-(trifluoromethyl) phenyl]-4-[6-(1-methyl-1H-pyrrol-2-yl)pyridin-3-yl] piperidine-4-amido}pyrrolidine-1-carboxylate (23.9 mg, 0.0384 mmol) in DCM (0.05 mL) was added TFA (0.044 mL). The mixture was stirred at rt for 30 min. The mixture was concentrated and the residue was purified by reversed-phase CC to give the title compound (17.3 mg, 86.3% yield) as a light brown solid. LCMS $(M+H)^+$=523.3.

The following compounds were prepared similarly to Example 37 with appropriate substituting reagents and substrates at different steps. Some examples do not require deprotection in the final step.

| Compound no. | MS $(M + H)^+$ |
|---|---|
| 1-206 | 525.4 |
| 1-207 | 539.2 |
| 1-211 | 564.5 |
| 1-212 | 552.0 |
| 1-213 | 550.7 |
| 1-218 | 590.5 |
| 1-219 | 523.6 |
| 1-220 | 537.4 |
| 1-221 | 549.5 |
| 1-229 | 551.5 |
| 1-231 | 537.4 |
| 1-233 | 523.5 |
| 1-234 | 523.3 |
| 1-235 | 523.3 |
| 1-236 | 550.6 |
| 1-237 | 568.3 |
| 1-238 | 568.3 |
| 1-245 | 564.4 |
| 1-246 | 582.3 |
| 1-247 | 582.3 |
| 1-248 | 537.5 |
| 1-253 | 551.4 |
| 1-258 | 509.4 |
| 1-259 | 509.4 |

-continued

| Compound no. | MS (M + H)+ |
|---|---|
| 1-260 | 539.4 |
| 1-261 | 539.2 |
| 1-262 | 567.3 |
| 1-263 | 551.4 |
| 1-264 | 567.2 |
| 1-265 | 539.3 |
| 1-266 | 551.5 |

Example 38: ethyl (3S)-3-{1-[2-cyano-4-(trifluoromethyl)phenyl]-4-[6-(1-methyl-1H-pyrrol-2-yl)pyridin-3-yl]piperidine-4-amido}pyrrolidine-1-carboxylate (cpd: 1-185)

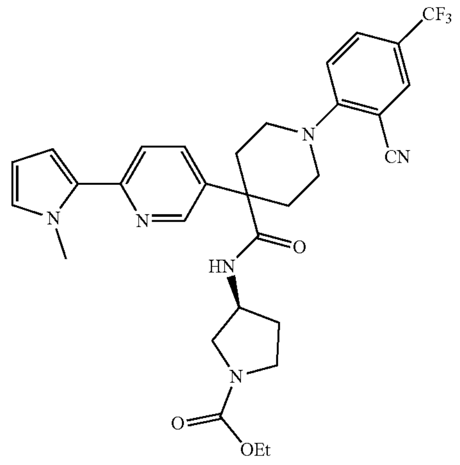 [SMILES: CCOC(=O)N1CC[C@H](NC(=O)C2(c3ccc(-c4cccn4C)nc3)CCN(c3ccc(C(F)(F)F)cc3C#N)CC2)C1]

Step 38-1, preparation of ethyl (3S)-3-{1-[2-cyano-4-(trifluoromethyl)phenyl]-4-[6-(1-methyl-1H-pyrrol-2-yl)pyridin-3-yl]piperidine-4-amido}pyrrolidine-1-carboxylate: To a solution of 1-[2-cyano-4-(trifluoromethyl)phenyl]-4-[6-(1-methyl-1H-pyrrol-2-yl)pyridin-3-yl]-N-[(3S)-pyrrolidin-3-yl]piperidine-4-carboxamide (7.0 mg, 0.013 mmol) from Step 37-3 in DCM (1 mL) was added DIEA (0.005 mL, 0.027 mmol) and ethyl chloroformate (0.002 mL, 0.020 mmol). The mixture was stirred at rt for 30 min. The mixture was concentrated and purified by reversed-phase CC to give the title compound (5.6 mg, 70% yield) as an off-white solid. LCMS $(M+H)^+$=595.4.

The following compounds were prepared similarly to Example 38 with appropriate substituting reagents and substrates at different steps:

| Compound no. | MS (M + H)+ |
|---|---|
| 1-185 | 565.5 |

Example 39: 1-[2-cyano-4-(trifluoromethyl)phenyl]-4-[6-(2-methoxyquinolin-3-yl)pyridin-3-yl]-N-[(3R)-1-methylpyrrolidin-3-yl]piperidine-4-carboxamide (Compound: 1-189)

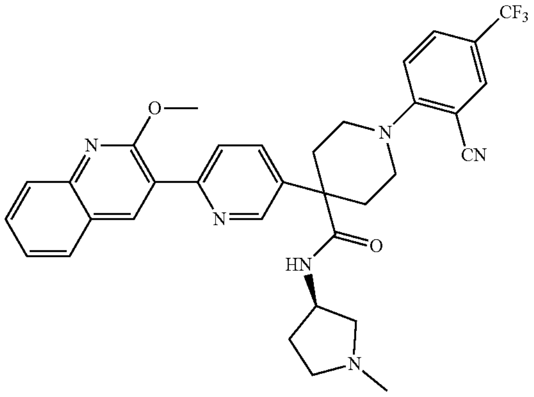 [SMILES: COc1nc2ccccc2cc1-c1ccc(C2(C(=O)N[C@@H]3CCN(C)C3)CCN(c3ccc(C(F)(F)F)cc3C#N)CC2)cn1]

Step 39-1, preparation of 1-[2-cyano-4-(trifluoromethyl)phenyl]-4-[6-(2-methoxyquinolin-3-yl)pyridin-3-yl]-N-[(3R)-1-methylpyrrolidin-3-yl]piperidine-4-carboxamide: To a mixture of 4-(6-chloropyridin-3-yl)-1-[2-cyano-4-(trifluoromethyl)phenyl]-N-[(3R)-1-methylpyrrolidin-3-yl]piperidine-4-carboxamide (30.0 mg, 0.061 mmol) from Step 12-4, (2-methoxyquinolin-3-yl)boronic acid (62.0 mg, 0.300 mmol), Xphos (12.0 mg, 0.024 mmol), potassium carbonate (25.0 mg, 0.180 mmol), and Xphos-Pd-G2 (9.6 mg, 0.012 mmol) in a sealed tube was added 1,4-dioxane (3.0 mL) and water (0.30 mL). Nitrogen (g) was bubbled through and the resulting mixture was heated at 90° C. for 3 h. The mixture was quenched with water and extracted with EtOAc (2×). The organic layers were combined, concentrated and purified by reversed-phase CC to give the title compound (27.3 mg, 73% yield). LCMS $(M+H)^+$=615.2.

The following compounds were prepared similarly to Example 39 with appropriate substituting reagents and substrates at different steps:

| Compound no. | MS (M + H)+ |
|---|---|
| 1-190 | 587.5 |
| 1-191 | 587.4 |

Example 40: 1-[2-fluoro-4-(trifluoromethyl)phenyl]-4-[5-fluoro-6-(1-methyl-1H-pyrrol-2-yl)pyridin-3-yl]-N-[(3S)-1-methylpyrrolidin-3-yl]piperidine-4-carboxamide (Compound 1-192)

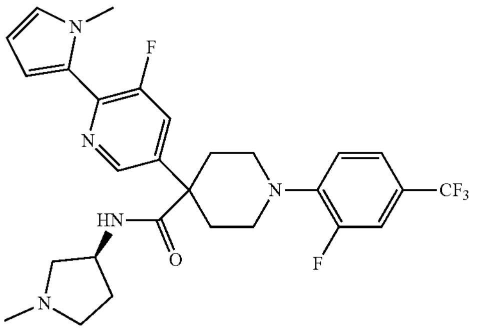 [SMILES: CN1CC[C@H](NC(=O)C2(c3cnc(-c4cccn4C)c(F)c3)CCN(c3ccc(C(F)(F)F)cc3F)CC2)C1]

Step 40-1, preparation of 1-benzyl-4-[5-fluoro-6-(1-methyl-1H-pyrrol-2-yl)pyridine-3-yl]piperidine-4-carbonitrile: A solution of 1-benzyl-4-(6-chloro-5-fluoropyridin-3-yl)piperidine-4-carbonitrile (210 mg, 0.637 mmol) from Step 6-3 in 1,4-dioxane (4 mL) and water (0.4 mL) was stirred in a 50 mL round bottom flask purged and maintained with nitrogen (g). 1-Methyl-2-(4,4,5,5-tetramethyl-1,3,2-dioxaborolan-2-yl)-1H-pyrrole (185 mg, 0.893 mmol), potassium carbonate (264 mg, 1.91 mmol) and RuPhos-Pd-G3 (26.6 mg, 0.0318 mmol) were added. The mixture was heated at 100° C. for 2 h. The mixture was purified by silica gel column chromatography with EtOAc/petroleum ether (1:2) to give the title compound (230 mg, 96.5% yield). LCMS $(M+H)^+$=375.0.

Step 40-2, preparation of 1-benzyl-4-[5-fluoro-6-(1-methyl-1H-pyrrol-2-yl)pyridine-3-yl]piperidine-4-carboxylic acid: A solution of 1-benzyl-4-[5-fluoro-6-(1-methyl-1H-pyrrol-2-yl)pyridine-3-yl]piperidine-4-carbonitrile (230 mg, 0.614 mmol) in EtOH (6 mL) and water (3 mL) was stirred in a 50 mL round bottom flask purged with nitrogen (g). Potassium hydroxide (345 mg, 6.15 mmol) was added and the mixture was stirred at 100° C. for 48 h. The EtOH was removed and the pH of the solution was adjusted to 6-7 with 3N-HCl. The solution was extracted with DCM/MeOH (10:1) (3×15 mL). The organic layers were washed with brine (2×20 mL), dried over anhydrous sodium sulfate and concentrated to give the title compound (200 mg, 82.8% yield). LC/MS $(M+H)^+$=394.0.

Step 40-3, preparation of 1-benzyl-4-[5-fluoro-6-(1-methyl-1H-pyrrol-2-yl)pyridine-3-yl]-N-[(3S)-1-methylpyrrolidin-3-yl]piperidine-4-carboxamide: A solution of 1-benzyl-4-[5-fluoro-6-(1-methyl-1H-pyrrol-2-yl)pyridine-3-yl]piperidine-4-carboxylic acid (230 mg, 0.508 mmol) in DMF (3 mL) was stirred in a 50 mL round bottom flask purged with Nitrogen (g). HATU (232 mg, 0.610 mmol), DIEA (197 mg, 1.52 mmol), and (3S)-1-methylpyrrolidin-3-amine (57.0 mg, 0.569 mmol) were added, and the reaction was stirred at 25° C. for 1 h. The mixture was purified using reversed-phase CC to give the title compound (210 mg, 86.8% yield). LCMS $(M+H)^+$=476.2.

Step 40-4, preparation of 4-[5-fluoro-6-(1-methyl-1H-pyrrol-2-yl)pyridine-3-yl]-N-[(3S)-1-methylpyrrolidin-3-yl]piperidine-4-carboxamide: A solution of 1-benzyl-4-[5-fluoro-6-(1-methyl-1H-pyrrol-2-yl)pyridine-3-yl]-N-[(3S)-1-methylpyrrolidin-3-yl]piperidine-4-carboxamide (210 mg, 0.442 mmol) in MeOH (5 mL) was stirred in a 50 mL round bottom flask purged and maintained with Nitrogen (g). Wet 10% Pd/C (20 mg) and $Pd(OH)_2$ (20.0 mg, 0.014 mmol) were added. The reaction was bubbled with Hydrogen (g) and stirred at 23° C. for 2 h. The solid was filtered out and the mixture was concentrated to give the title compound (130 mg, 76.4% yield). LCMS $(M+H)^+$=386.2.

Step 40-5, preparation of 1-[2-fluoro-4-(trifluoromethyl)phenyl]-4-[5-fluoro-6-(1-methyl-1H-pyrrol-2-yl)pyridin-3-yl]-N-[(3S)-1-methylpyrrolidin-3-yl]piperidine-4-carboxamide: A solution of 4-[5-fluoro-6-(1-methyl-1H-pyrrol-2-yl)pyridine-3-yl]-N-[(3S)-1-methylpyrrolidin-3-yl]piperidine-4-carboxamide (80 mg, 0.21 mmol) in Toluene (1 mL) was stirred in a 10 mL vial. Dicesium carbonate (200 mg, 0.61 mmol), 1-bromo-2-fluoro-4-(trifluoromethyl)benzene (100 mg, 0.41 mmol), $Pd_2(dba)_3{\cdot}CHCl_3$ (13.0 mg, 0.013 mmol), and Xphos (9.9 mg, 0.021 mmol) were added and the reaction was stirred at 100° C. for 16 h. The mixture was purified by reversed-phase CC to give the title compound (17 mg, 14% yield). LCMS $(M+H)^+$=548.3.

Example 41: 4-[6-(2-ethoxypyridin-3-yl)pyridazin-3-yl]-1-[2-fluoro-4-(trifluoromethyl)phenyl]-N-[(3S)-1-methylpyrrolidin-3-yl]piperidine-4-carboxamide (Compound 1-193)

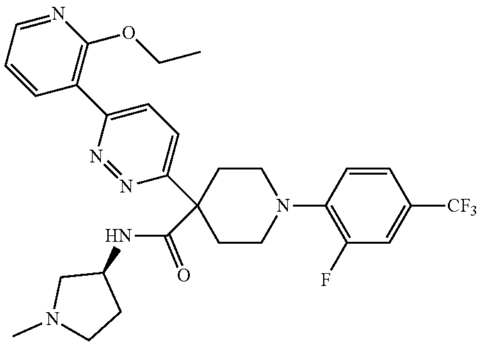 [SMILES: CCOc1ncccc1-c1ccc(C2(C(=O)N[C@H]3CCN(C)C3)CCN(c3ccc(C(F)(F)F)cc3F)CC2)nn1]

Step 41-1, preparation of 3-chloro-6-(2-ethoxypyridin-3-yl)pyridazine: A mixture of 3,6-dichloropyridazine (3.00 g, 20.0 mmol), (2-ethoxypyridin-3-yl)boronic acid (5.00 g, 30.0 mmol), potassium carbonate (8.00 g, 60.0 mmol), and $Pd(dppf)Cl_2$ (1.00 g, 2.00 mmol) were added into a 40 mL vial. 1,4-Dioxane (30 mL) and water (3 mL) were added and nitrogen (g) was bubbled through the resulting mixture. The reaction mixture was stirred at 90° C. for 2 h. The mixture was concentrated and purified by silica gel column chromatography using EtOAc/Petroleum Ether (1:1) to give the title compound (3.3 g, 70% yield). LCMS $(M+H)^+$=236.3.

Step 41-2, preparation of 1-tert-butyl 4-methyl 4-[6-(2-ethoxypyridin-3-yl)pyridazin-3-yl]piperidine-1,4-dicarboxylate: A solution of 3-chloro-6-(2-ethoxypyridin-3-yl)pyridazine (2.00 g, 8.00 mmol) and 1-tert-butyl 4-methyl piperidine-1,4-dicarboxylate (3.00 g, 10.0 mmol) in THF (20 mL) was stirred in a 100 mL round bottom flask. Sodium bis(trimethylsilyl)amide (3.00 g, 20.0 mmol) was added dropwise at 0° C. and the reaction was stirred at 25° C. for 1 h. The reaction was quenched with water (100 mL) and extracted with EtOAc (3×100 mL). The organic layers were combined and washed with brine (2×100 mL). The mixture was dried over anhydrous sodium sulfate, concentrated, and purified by silica gel column chromatography using EtOAc/Petroleum Ether (1:1) to give the title compound (2.0 g, 50% yield). LCMS $(M+H)^+$=443.2.

Step 41-3, preparation of tert-butyl 4-[6-(2-ethoxypyridin-3-yl)pyridazin-3-yl]-4-{[(3S)-1-methylpyrrolidin-3-yl]carbamoyl}piperidine-1-carboxylate: A solution of 1-tert-butyl 4-methyl 4-[6-(2-ethoxypyridin-3-yl)pyridazin-3-yl]piperidine-1,4-dicarboxylate (500 mg, 1.13 mmol) and (3S)-

1-methylpyrrolidin-3-amine (170 mg, 1.69 mmol) in THE (3 mL) was stirred in a 50 mL round bottom flask. Lithium bis(trimethylsilyl)amide (945 mg, 5.65 mmol) was added dropwise and the reaction was stirred at 25° C. for 2 h. The solution was quenched with water (50 mL) and extracted with EtOAc (3×50 mL). The organic layers were combined, washed with brine (2×50 mL), dried over anhydrous sodium sulfate, and concentrated. The mixture was purified with silica gel column chromatography using EtOAc/Petroleum Ether (1:1) to give the title compound (340 mg, 58.9% yield). LCMS $(M+H)^+$=511.3.

Step 41-4, preparation of 4-[6-(2-ethoxypyridin-3-yl) pyridazin-3-yl]-N-[(3S)-1-methylpyrrolidin-3-yl]piperidine-4-carboxamide trifluoroacetate: A solution of tert-butyl 4-[6-(2-ethoxypyridin-3-yl)pyridazin-3-yl]-4-{[(3S)-1-methylpyrrolidin-3-yl]carbamoyl}piperidine-1-carboxylate (340 mg, 0.666 mmol) and TFA (2 mL) in DCM (6 mL) was stirred in a 50 mL round bottom flask at 25° C. for 1 h. The mixture was concentrated to give the title compound (340 mg, 88% yield). LCMS $(M+H)^+$=411.2.

Step 41-5, preparation of 4-[6-(2-ethoxypyridin-3-yl) pyridazin-3-yl]-1-[2-fluoro-4-(trifluoromethyl)phenyl]-N-[(3S)-1-methylpyrrolidin-3-yl]piperidine-4-carboxamide: A solution of 4-[6-(2-ethoxypyridin-3-yl)pyridazin-3-yl]-N-[(3S)-1-methylpyrrolidin-3-yl]piperidine-4-carboxamide trifluoracetate (80 mg, 0.15 mmol) in toluene (3 mL) was stirred in a 8 mL vial under nitrogen (g). Cesium carbonate (150 mg, 0.46 mmol), 1-bromo-2-fluoro-4-(trifluoromethyl) benzene (74 mg, 0.31 mmol), $Pd_2(dba)_3 \cdot CHCl_3$ (14 mg, 0.015 mmol), and Xphos (15 mg, 0.031 mmol) were added and the reaction was stirred at 100° C. for 16 h. The mixture was concentrated and purified by reversed-phase CC to give the title compound (40.2 mg, 33% yield). LCMS $(M+H)^+$=573.2.

The following compounds were prepared similarly to Example 41 with appropriate substituting reagents and substrates at different steps:

| Compound no. | MS $(M + H)^+$ |
|---|---|
| 1-194 | 589.2 |

Example 42: 1-[2-cyano-4-(trifluoromethyl)phenyl]-N-[2-(dimethylamino)ethyl]-4-[5-fluoro-6-(2-methoxyphenyl)pyridin-3-yl]piperidine-4-carboxamide (Compound 1-198)

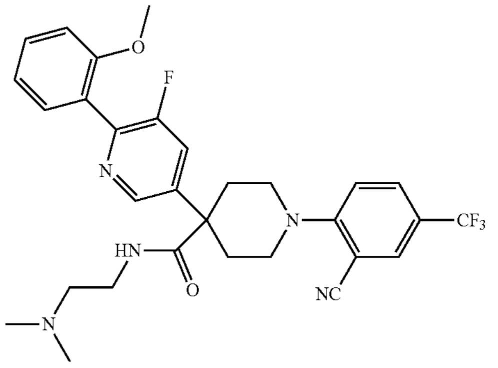 [SMILES: COc1ccccc1-c1ncc(C2(C(=O)NCCN(C)C)CCN(c3ccc(C(F)(F)F)cc3C#N)CC2)cc1F]

Step 42-1, preparation of 1-[2-cyano-4-(trifluoromethyl) phenyl]-N-[2-(dimethylamino)ethyl]-4-[5-fluoro-6-(2-methoxyphenyl)pyridin-3-yl]piperidine-4-carboxamide: A mixture of 1-[2-cyano-4-(trifluoromethyl)phenyl]-4-[5-fluoro-6-(2-methoxyphenyl)pyridin-3-yl]-N-[2-(methylamino)ethyl]piperidine-4-carboxamide (47.4 mg, 0.0853 mmol) (compound 1-196) and polyoxymethylene (51.2 mg, 1.71 mmol) were added to a 4 mL vial. A mixture of sodium cyanoborohydride (53.6 mg, 0.853 mmol) in MeOH (1 mL) was added and the reaction was stirred at 23° C. for 4 h. The reaction was quenched with TFA, neutralized with sat-$NaHCO_3$, and extracted with EtOAc (3×15 mL). The organic layers were combined, concentrated and purified by reversed-phase CC to give the title compound (20.4 mg, 42.0% yield). LCMS $(M+H)^+$=570.3.

The following compounds were prepared similarly to Example 42 with appropriate substituting reagents and substrates at different steps:

| Compound no. | MS $(M + H)^+$ |
|---|---|
| 1-199 | 584.2 |

Example 43: (S)-4-(2'-ethoxy-3-fluoro-[2,3'-bipyridin]-5-yl)-1-(2-fluoro-4-(trifluoromethyl)phenyl)-N-(1-methylpyrrolidin-3-yl)piperidine-4-carboxamide (Compound 1-201)

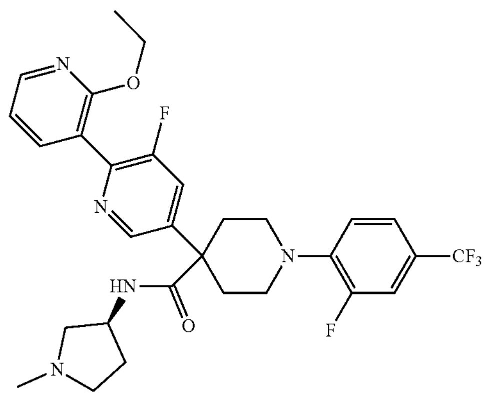 [SMILES: CCOc1ncccc1-c1ncc(C2(C(=O)N[C@H]3CCN(C)C3)CCN(c3ccc(C(F)(F)F)cc3F)CC2)cc1F]

Step 43-1, preparation of 1-benzyl-4-(2'-ethoxy-3-fluoro-[2,3'-bipyridin]-5-yl)piperidine-4-carbonitrile: To a mixture 1-benzyl-4-(6-chloro-5-fluoropyridin-3-yl)piperidine-4-carbonitrile (300 mg, 910 μmol) from Step 6-3, (2-ethoxypyridin-3-yl)boronic acid (304 mg, 1.82 mmol), $Pd(DTBPF)Cl_2$ (59.3 mg, 91.0 μmol), and $K_2CO_3$ (377 mg, 2.73 mmol) in a sealed tube was added 1,4-dioxane (3 mL) and water (0.3 mL). $N_2$ (g) was bubbled through the resulting mixture. The mixture was then heated at 100° C. for 2 h. The mixture was concentrated in vacuo and the crude product was purified by silica gel column chromatography. Pure fractions were combined and concentrated to dryness to give the title compound (330 mg, 87.1%) as yellow oil. LCMS $(M+H)^+$=417.2.

Step 43-2, preparation of 1-benzyl-4-(2'-ethoxy-3-fluoro-[2,3'-bipyridin]-5-yl)piperidine-4-carboxylic acid: To a solution of 1-benzyl-4-(2'-ethoxy-3-fluoro-[2,3'-bipyridin]-5-yl)piperidine-4-carbonitrile (330 mg, 792 μmol) in EtOH (8 mL) was added KOH (445 mg, 7.92 mmol) and water (4.5 mL). The reaction mixture was heated at 100° C. for 24 h. The mixture was acidified with 3 N HCl (aq) to make pH 5. The solid was collected by vacuum filtration, washed with water, and dried under high vacuum to give the title compound (320 mg, 92.7%) as a white solid. LCMS $(M+H)^+$=436.2.

Step 43-3, preparation of (S)-1-benzyl-4-(2'-ethoxy-3-fluoro-[2,3'-bipyridin]-5-yl)-N-(1-methylpyrrolidin-3-yl)piperidine-4-carboxamide: To a solution of 1-benzyl-4-(2'-ethoxy-3-fluoro-[2,3'-bipyridin]-5-yl)piperidine-4-carboxylic acid (320 mg, 735 μmol) and HATU (335 mg, 882 μmol) in DMF (3 mL) was added DIEA (0.39 mL, 2.20 mmol). The reaction mixture was stirred at rt for 15 min. To the above HATU-activated solution was added (S)-1-methylpyrrolidin-3-amine (88.3 mg, 882 μmol) and the reaction was continued to stir at rt for 15 min. The mixture was purified by reversed-phase CC. Pure fractions were combined and concentrated in vacuo to give the title compound (350 mg, 92.1%) as a yellow solid. LCMS $(M+H)^+$=518.2.

Step 43-4, preparation of (S)-4-(2'-ethoxy-3-fluoro-[2,3'-bipyridin]-5-yl)-N-(1-methylpyrrolidin-3-yl)piperidine-4-carboxamide: To a solution of (S)-1-benzyl-4-(2'-ethoxy-3-fluoro-[2,3'-bipyridin]-5-yl)-N-(1-methylpyrrolidin-3-yl) piperidine-4-carboxamide (350 mg, 676 μmol) in MeOH (40 mL) was added $Pd(OH)_2$ (475 mg, 3.38 mmol) and Pd/C (360 mg, 3.38 mmol). The reaction mixture was stirred at 25° C. for 2 h under $H_2$ (g). The mixture was filtered and the filtrate was concentrated to dryness to give the title compound (200 mg, 62%, 90% purity) as a light yellow solid. LCMS $(M+H)^+$=428.2.

Step 43-5, preparation of (S)-4-(2'-ethoxy-3-fluoro-[2,3'-bipyridin]-5-yl)-1-(2-fluoro-4-(trifluoromethyl)phenyl)-N-(1-methylpyrrolidin-3-yl)piperidine-4-carboxamide formate: To a mixture of (S)-4-(2'-ethoxy-3-fluoro-[2,3'-bipyridin]-5-yl)-N-(1-methylpyrrolidin-3-yl)piperidine-4-carboxamide (60 mg, 0.14 mmol), 1-bromo-2-fluoro-4-(trifluoromethyl)benzene (68 mg, 0.28 mmol), XPhos (13 mg, 28 μmol), $Pd_2(dba)_3$ (13 mg, 14 μmol), and cesium carbonate (0.14 g, 0.42 mmol) was added toluene (2 mL). The reaction mixture was heated at 120° C. for 16 h under nitrogen condition. The mixture was concentrated in vacuo and the crude product was purified by reversed-phase CC. Pure fractions were combined and concentrated in vacuo to give the title compound (18.3 mg, 20%) as an off-white solid. LCMS $(M+H)^+$=590.2.

The following compounds were prepared similarly to Example 43 with appropriate substituting reagents and substrates at different steps:

| Compound no. | MS $(M + H)^+$ |
|---|---|
| 1-200 | 589.2 |
| 1-202 | 605.2 |
| 1-203 | 606.2 |
| 1-204 | 593.3 |

Example 44: N-(3-aminopropyl)-1-[2-cyano-4-(trifluoromethyl)phenyl]-4-[6-(1-methyl-1H-pyrrol-2-yl)pyridin-3-yl]piperidine-4-carboxamide (Compound 1-205)

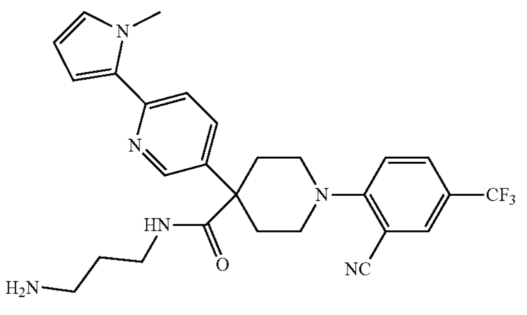 [SMILES: Cn1cccc1-c1ccc(C2(C(=O)NCCCN)CCN(c3ccc(C(F)(F)F)cc3C#N)CC2)cn1]

Step 44-1, preparation of 4-(6-{1-[(tert-butoxy)carbonyl]-1H-pyrrol-2-yl}pyridine-3-yl)-1-[2-cyano-4-(trifluoromethyl)phenyl]piperidine-4-carboxylic acid: A mixture of 4-(6-chloropyridin-3-yl)-1-[2-cyano-4-(trifluoromethyl)phenyl]piperidine-4-carboxylic acid (150 mg, 0.366 mmol) from Step 12-3, {1-[(tert-butoxy)carbonyl]-1H-pyrrol-2-yl}boronic acid (155 mg, 0.732 mmol), potassium carbonate (152 mg, 1.10 mmol), and $Pd(dtbpf)Cl_2$ (47.7 mg, 0.0732 mmol) were placed in a sealed tube. 1,4-Dioxane (3 mL) and water (0.3 mL) were added. Nitrogen (g) was bubbled through and the mixture was stirred at 80° C. for 3 h. The mixture was cooled to room temperature and quenched with water. The solution was extracted with EtOAc and the organic layers were combined and concentrated. The mixture was purified with reversed-phase CC to give the title compound (94.1 mg, 47.6% yield). LCMS $(M+H)^+$=541.6.

Step 44-2, preparation of methyl 4-(6-{1-[(tert-butoxy)carbonyl]-1H-pyrrol-2-yl}pyridine-3-yl)-1-[2-cyano-4-(trifluoromethyl)phenyl]piperidine-4-carboxylate: A solution of 4-(6-{1-[(tert-butoxy)carbonyl]-1H-pyrrol-2-yl}pyridine-3-yl)-1-[2-cyano-4-(trifluoromethyl)phenyl]piperidine-4-carboxylic acid (94.1 mg, 0.174 mmol) in toluene (1.5 mL) and MeOH (1 mL) was stirred. (Diazomethyl)trimethylsilane (39.8 mg, 0.348 mmol) was added dropwise and the mixture was stirred at 25° C. for 30 min. The mixture was quenched with three drops of AcOH, concentrated, and neutralized with sat-$NaHCO_3$ (aq). The solid was collected, washed with water, and dried to give the title compound (73.6 mg, 76.2% yield). LCMS $(M+H)^+$=555.4.

Step 44-3, preparation of methyl 1-[2-cyano-4-(trifluoromethyl)phenyl]-4-[6-(1H-pyrrol-2-yl)pyridine-3-yl]piperidine-4-carboxylate: A solution of methyl 4-(6-{1-[(tert-butoxy)carbonyl]-1H-pyrrol-2-yl}pyridine-3-yl)-1-[2-cyano-4-(trifluoromethyl)phenyl]piperidine-4-carboxylate (73.6 mg, 0.133 mmol) in DCM (0.15 mL) was stirred. TFA (227 mg, 1.99 mmol) was added and the reaction was stirred at 25° C. for 1 h. The mixture was concentrated and purified by reversed-phase CC to give the title compound (60.3 mg, 100% yield). LCMS $(M+H)^+$=455.0.

Step 44-4, preparation of methyl 1-[2-cyano-4-(trifluoromethyl)phenyl]-4-[6-(1-methyl-1H-pyrrol-2-yl)pyridine-3-yl]piperidine-4-carboxylate: A solution of methyl 1-[2-cyano-4-(trifluoromethyl)phenyl]-4-[6-(1H-pyrrol-2-yl) pyridine-3-yl]piperidine-4-carboxylate (60.3 mg, 0.133 mmol) and 60% sodium hydride in mineral oil (10.6 mg, 0.265 mmol) in DMF (1 mL) was stirred at 25° C. for 30 min. Methyl iodide (37.7 mg, 0.265 mmol) was added and the mixture was stirred at 25° C. for 10 min. The mixture was quenched with ice water and the solid was collected, rinsed with water, and dried to give the title compound (57.5 mg, 92.5% yield). LCMS $(M+H)^+$=469.3.

Step 44-5, preparation of 1-[2-cyano-4-(trifluoromethyl) phenyl]-4-[6-(1-methyl-1H-pyrrol-2-yl)pyridine-3-yl]piperidine-4-carboxylic acid: A solution of methyl 1-[2-cyano-4-(trifluoromethyl)phenyl]-4-[6-(1-methyl-1H-pyrrol-2-yl) pyridine-3-yl]piperidine-4-carboxylate (57.5 mg, 0.123 mmol) in THE (1.5 mL), MeOH (0.50 mL), and water (0.50 mL) was stirred. Lithium(I) hydroxide monohydrate (51.5 mg, 1.23 mmol) was added and the mixture was stirred at 25° C. for 16 h. The mixture was concentrated, diluted with water, and acidified using 1N-HCl to pH 3. The solid was collected, rinsed with water, and dried to give the title compound (55.8 mg, 100% yield). LCMS $(M+H)^+$=455.3.

Step 44-6, preparation of tert-butyl N-[3-({1-[2-cyano-4-(trifluoromethyl)phenyl]-4-[6-(1-methyl-1H-pyrrol-2-yl) pyridine-3-yl]piperidin-4-yl}formamido)propyl]carbamate: A solution of 1-[2-cyano-4-(trifluoromethyl)phenyl]-4-[6-

(1-methyl-1H-pyrrol-2-yl)pyridine-3-yl]piperidine-4-carboxylic acid (55.8 mg, 0.123 mmol), HATU (65.4 mg, 0.172 mmol), and DIEA (47.6 mg, 0.368 mmol) in DMF (0.2 mL) was stirred at 25° C. for 5 min. tert-Butyl N-(3-aminopropyl) carbamate (34.2 mg, 0.196 mmol) was added and the mixture was stirred at 25° C. for 10 min. The mixture was purified using reversed-phase CC to give the title compound (43.0 mg, 57.3% yield). LCMS $(M+H)^+$=611.3.

Step 44-7, preparation of N-(3-aminopropyl)-1-[2-cyano-4-(trifluoromethyl)phenyl]-4-[6-(1-methyl-1H-pyrrol-2-yl) pyridin-3-yl]piperidine-4-carboxamide: A solution of tert-butyl N-[3-({1-[2-cyano-4-(trifluoromethyl)phenyl]-4-[6-(1-methyl-1H-pyrrol-2-yl)pyridine-3-yl]piperidin-4-yl}formamido)propyl]carbamate (43.0 mg, 0.0704 mmol) in DCM (0.08 mL) was stirred. TFA (120 mg, 1.06 mmol) was added and the reaction was stirred at 25° C. for 1 h. The mixture was concentrated and purified by reversed-phase CC to give the title compound (34.9 mg, 97.1% yield). LCMS $(M+H)^+$=511.5.

Example 45: 1-[2-cyano-4-(trifluoromethyl)phenyl]-4-[6-(1-ethyl-1H-pyrrol-2-yl)pyridine-3-yl]-N-[(3S)-1-methylpyrrolidin-3-yl]piperidine-4-carboxamide (Compound 1-208)

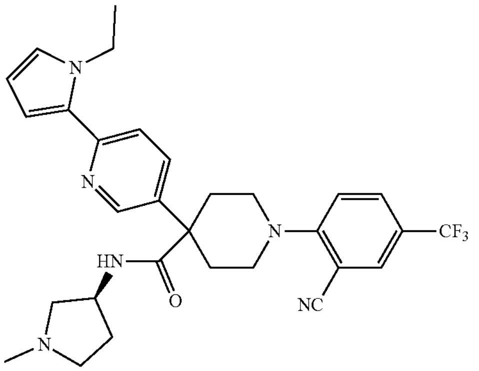 [SMILES: CCn1cccc1-c1ccc(C2(C(=O)N[C@H]3CCN(C)C3)CCN(c3ccc(C(F)(F)F)cc3C#N)CC2)cn1]

Step 45-1, preparation of methyl 4-(6-chloropyridin-3-yl)-1-[2-cyano-4-(trifluoromethyl)phenyl]piperidine-4-carboxylate: A solution of 4-(6-chloropyridin-3-yl)-1-[2-cyano-4-(trifluoromethyl)phenyl]piperidine-4-carboxylic acid (150 mg, 0.366 mmol) from Step 12-3 in Toluene (1.5 mL) and MeOH (1 mL) was stirred. (Diazorethyl)trimethylsilane (83.6 mg, 0.732 mmol) was added dropwise, and the mixture was stirred at 25° C. for 30 min. The mixture was quenched with three drops of AcOH, concentrated, and neutralized with sat-$NaHCO_3$. The solid was collected, washed with water, and dried to give the title compound (150 mg, 96.4% yield). LCMS $(M+H)^+$=424.3.

Step 45-2, preparation of methyl 4-(6-{1-[(tert-butoxy) carbonyl]-1H-pyrrol-2-yl}pyridine-3-yl)-1-[2-cyano-4-(trifluoromethyl)phenyl]piperidine-4-carboxylate: A mixture of methyl 4-(6-chloropyridin-3-yl)-1-[2-cyano-4-(trifluoromethyl)phenyl]piperidine-4-carboxylate (150 mg, 0.353 mmol), {1-[(tert-butoxy)carbonyl]-1H-pyrrol-2-yl}boronic acid (149 mg, 0.706 mmol), dipotassium carbonate (146 mg, 1.06 mmol), and Pd(dtbpf)$Cl_2$ (46.0 mg, 0.0706 mmol) were placed in a sealed tube. 1,4-dioxane (3 mL) and water (0.3 mL) were added, Nitrogen (g) was bubbled through and the mixture was stirred at 80° C. for 3 h. The mixture was cooled to room temperature and quenched with water. The solution was extracted with EtOAc, and the organic layers were combined and concentrated. The mixture was purified with reversed-phase CC to give the title compound (70.9 mg, 36.2% yield). LCMS $(M+H)^+$=555.4.

Step 45-3, preparation of methyl 1-[2-cyano-4-(trifluoromethyl)phenyl]-4-[6-(1H-pyrrol-2-yl)pyridine-3-yl]piperidine-4-carboxylate: A solution of methyl 4-(6-{1-[(tert-butoxy)carbonyl]-1H-pyrrol-2-yl}pyridine-3-yl)-1-[2-cyano-4-(trifluoromethyl)phenyl]piperidine-4-carboxylate (70.9 mg, 0.128 mmol) in DCM (0.2 mL) was stirred. TFA (219 mg, 1.92 mmol) was added and the reaction was stirred at 25° C. for 1 h. The mixture was concentrated and purified by reversed-phase CC to give the title compound (59.5 mg, 102% yield). LCMS $(M+H)^+$=455.3.

Step 45-4, preparation of methyl 1-[2-cyano-4-(trifluoromethyl)phenyl]-4-[6-(1-ethyl-1H-pyrrol-2-yl)pyridine-3-yl]piperidine-4-carboxylate: A solution of methyl 1-[2-cyano-4-(trifluoromethyl)phenyl]-4-[6-(1H-pyrrol-2-yl) pyridine-3-yl]piperidine-4-carboxylate (59.5 mg, 0.131 mmol) and 60% sodium hydride (20.9 mg, 0.524 mmol) in mineral oil in DMF (0.5 mL) was stirred at 25° C. for 30 min. Ethyl iodide (24.5 mg, 0.157 mmol) was added and the mixture was stirred at 25° C. for 10 min. The mixture was quenched with ice water and extracted with EtOAc. The organic layers were combined and concentrated, and the mixture was purified by reversed-phase CC to give the title compound (63.2 mg, 100% yield). LCMS $(M+H)^+$=483.1.

Step 45-5, preparation of 1-[2-cyano-4-(trifluoromethyl) phenyl]-4-[6-(1-ethyl-1H-pyrrol-2-yl)pyridine-3-yl]piperidine-4-carboxylic acid: A solution of methyl 1-[2-cyano-4-(trifluoromethyl)phenyl]-4-[6-(1-ethyl-1H-pyrrol-2-yl) pyridine-3-yl]piperidine-4-carboxylate (63.2 mg, 0.131 mmol) in THE (0.9 mL), MeOH (0.3 mL), and water (0.3 mL) was stirred. Lithium(I) hydrate hydroxide (51.5 mg, 1.23 mmol) was added, and the mixture was stirred at 25° C. for 16 h. The mixture was concentrated, diluted with water, and acidified using 1N-HCl to pH 3. The solid was collected, rinsed with water, and dried to give the title compound (34.1 mg, 55.6% yield). LCMS $(M+H)^+$=469.3.

Step 45-6, preparation of 1-[2-cyano-4-(trifluoromethyl) phenyl]-4-[6-(1-ethyl-1H-pyrrol-2-yl)pyridin-3-yl]-N-[(3S)-1-methylpyrrolidin-3-yl]piperidine-4-carboxamide: A solution of 1-[2-cyano-4-(trifluoromethyl)phenyl]-4-[6-(1-ethyl-1H-pyrrol-2-yl)pyridine-3-yl]piperidine-4-carboxylic acid (34.1 mg, 0.0728 mmol), HATU (38.7 mg, 0.102 mmol), and DIEA (28.2 mg, 0.218 mmol) in DMF (0.3 mL) were stirred at 25° C. for 5 min. (3S)-1-methylpyrrolidin-3-amine (11.7 mg, 0.116 mmol) was added, and the mixture was stirred at 25° C. for 10 min. The mixture was purified using reversed-phase CC to give the title compound (22.6 mg, 56.4% yield). LCMS $(M+H)^+$=551.5.

Example 46: 1-[2-cyano-4-(trifluoromethyl)phenyl]-4-{3,5'-difluoro-2'-methoxy-[2,3'-bipyridin]-5-yl}-N-[(3S)-1-methylpyrrolidin-3-yl]piperidine-4-carboxamide (Compound 1-209)

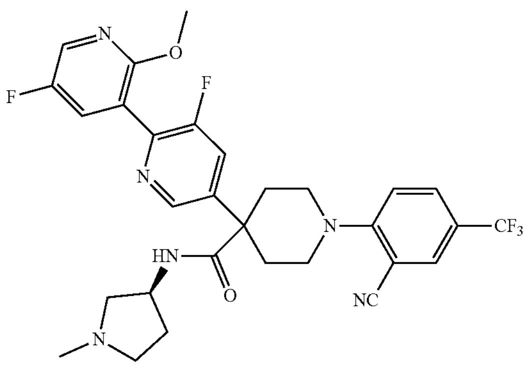 [SMILES: COc1ncc(F)cc1-c1ncc(C2(C(=O)N[C@H]3CCN(C)C3)CCN(c3ccc(C(F)(F)F)cc3C#N)CC2)cc1F]

Step 46-1, preparation of 1-benzyl-4-{3,5'-difluoro-2'-methoxy-[2,3'-bipyridin]-5-yl}piperidine-4-carbonitrile: A solution of 1-benzyl-4-(6-chloro-5-fluoropyridin-3-yl)piperidine-4-carbonitrile (300 mg, 0.910 mmol) from Step 6-3 in 1,4-dioxane (3 mL) and water (0.3 mL) was stirred in a 50 mL round bottom flask, purged and maintained with nitrogen (g). (5-Fluoro-2-methoxypyridin-3-yl)boronic acid (233 mg, 1.36 mmol), potassium carbonate (377 mg, 2.73 mmol), and RuPhos-Pd-G3 (76 mg, 0.091 mmol) were added. The solution was heated at 100° C. for 1 h. The mixture was cooled, quenched with water (40 mL), and extracted with EtOAc (3×40 mL). The organic layers were combined, dried over anhydrous sodium sulfate, and concentrated. The mixture was purified by silica gel column chromatography with EtOAc/Petroleum Ether (1:1) to give the title compound (300 mg, 78.4% yield). LCMS $(M+H)^+$=421.2.

Step 46-2, preparation of 1-benzyl-4-{3,5'-difluoro-2'-methoxy-[2,3'-bipyridin]-5-yl}piperidine-4-carboxylic acid: A solution of 1-benzyl-4-{3,5'-difluoro-2'-methoxy-[2,3'-bipyridin]-5-yl}piperidine-4-carbonitrile (300 mg, 0.714 mmol) in EtOH (6 mL) and water (3 mL) was stirred in a 50 mL round bottom flask. Potassium hydroxide (400 mg, 7.13 mmol) was added, and the mixture was stirred at 100° C. for 24 h. The reaction was quenched with water (10 mL) and the pH of the solution was adjusted to 6-7 with 3N-HCl. The solution was extracted with EtOAc (3×50 mL). The organic layers were dried over anhydrous sodium sulfate and concentrated to give the title compound (300 mg, 95.7% yield). LC/MS $(M+H)^+$=440.2.

Step 46-3, preparation of 1-benzyl-4-{3,5'-difluoro-2'-methoxy-[2,3'-bipyridin]-5-yl}-N-[(3S)-1-methylpyrrolidin-3-yl]piperidine-4-carboxamide: A solution of 1-benzyl-4-{3,5'-difluoro-2'-methoxy-[2,3'-bipyridin]-5-yl}piperidine-4-carboxylic acid (300 mg, 0.683 mmol) and HATU (260 mg, 0.684 mmol) in DMF (3 mL) were stirred at 25° C. for 10 min. (3S)-1-Methylpyrrolidin-3-amine (82 mg, 0.82 mmol) and DIEA (265 mg, 2.05 mmol) were added and the mixture was stirred at 25° C. for 1 h. The reaction was quenched with water (200 mL) and extracted with EtOAc (3×200 mL). The organic layers were combined, dried over anhydrous sodium sulfate, and concentrated. The mixture was purified by silica gel column chromatography with EtOAc/Petroleum Ether (1:1) to give the title compound (280 mg, 78.6% yield). LCMS $(M+H)^+$=522.3.

Step 46-4, preparation of tert-butyl 4-{3,5'-difluoro-2'-methoxy-[2,3'-bipyridin]-5-yl}-4-{[(3S)-1-methylpyrrolidin-3-yl]carbamoyl}piperidine-1-carboxylate: A suspension of 1-benzyl-4-{3,5'-difluoro-2'-methoxy-[2,3'-bipyridin]-5-yl}-N-[(3S)-1-methylpyrrolidin-3-yl]piperidine-4-carboxamide (200 mg, 0.383 mmol), TEA (120 mg, 1.19 mmol), wet 10%-Pd/C (41 mg), $Pd(OH)_2$ (54 mg, 0.38 mmol), and di-tert-butyl dicarbonate (251 mg, 1.15 mmol) in MeOH (10 mL) was stirred in a 50 mL round bottom flask. The flask was flushed with nitrogen (g) three times and then flushed with hydrogen (g). The mixture was stirred at 25° C. for 1 h under hydrogen (g). The solution was diluted with MeOH (10 mL) and filtered. The filtrate was concentrated to give the title compound (180 mg, 73% yield). LCMS $(M+H)^+$=532.3.

Step 46-5, preparation of 4-{3,5'-difluoro-2'-methoxy-[2,3'-bipyridin]-5-yl}-N-[(3S)-1-methylpyrrolidin-3-yl]piperidine-4-carboxamide: A solution of tert-butyl 4-{3,5'-difluoro-2'-methoxy-[2,3'-bipyridin]-5-yl}-4-{[(3S)-1-methylpyrrolidin-3-yl]carbamoyl}piperidine-1-carboxylate (180 mg, 0.339 mmol) in DCM (3 mL) was stirred. TFA (0.6 mL) was added and the reaction was stirred at 25° C. for 1 h. The mixture was concentrated and purified by reversed-phase CC to give the title compound (60 mg, 38% yield). LCMS $(M+H)^+$=432.3.

Step 46-6, preparation of 1-[2-cyano-4-(trifluoromethyl)phenyl]-4-{3,5'-difluoro-2'-methoxy-[2,3'-bipyridin]-5-yl}-N-[(3S)-1-methylpyrrolidin-3-yl]piperidine-4-carboxamide: A solution of 4-{3,5'-difluoro-2'-methoxy-[2,3'-bipyridin]-5-yl}-N-[(3S)-1-methylpyrrolidin-3-yl]piperidine-4-carboxamide (25 mg, 0.058 mmol) in DMSO (1 mL) was stirred in a 8 mL vial. DIEA (22 mg, 0.017 mmol) and 2-fluoro-5-(trifluoromethyl)benzonitrile (22 mg, 0.12 mmol) were added and the mixture was stirred at 70° C. for 1 h. The mixture was purified by reversed-phase CC to give the title compound (4.1 mg, 11% yield). LCMS $(M+H)^+$=601.2.

Example 47: 4-{3,5'-difluoro-2'-methoxy-[2,3'-bipyridin]-5-yl}-1-[2-fluoro-4-(trifluoromethyl)phenyl]-N-[(3S)-1-methylpyrrolidin-3-yl]piperidine-4-carboxamide (Compound 1-210)

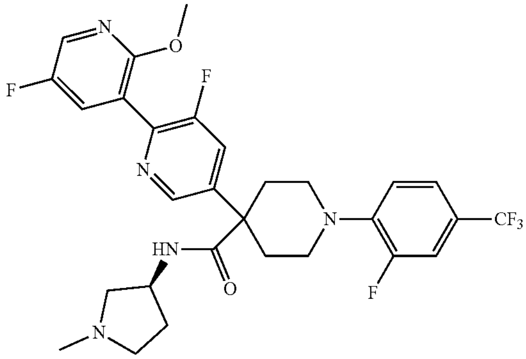 [SMILES: COc1ncc(F)cc1-c1ncc(C2(C(=O)N[C@H]3CCN(C)C3)CCN(c3ccc(C(F)(F)F)cc3F)CC2)cc1F]

Step 47-1, preparation of 4-{3,5'-difluoro-2'-methoxy-[2,3'-bipyridin]-5-yl}-1-[2-fluoro-4-(trifluoromethyl)phenyl]-N-[(3S)-1-methylpyrrolidin-3-yl]piperidine-4-carboxamide: A solution of 4-{3,5'-difluoro-2'-methoxy-[2,3'-bipyridin]-5-yl}-N-[(3S)-1-methylpyrrolidin-3-yl]piperidine-4-carboxamide (25 mg, 0.058 mmol) from Step 46-5 in toluene (1 mL) was stirred in a 8 mL vial, purged and maintained with nitrogen (g). Cesium carbonate (57 mg, 0.17 mmol), 1-bromo-2-fluoro-4-(trifluoromethyl)benzene (28 mg, 0.12 mmol), $Pd_2(dba)_3 \cdot CHCl_3$ (6 mg, 0.006 mmol), and Xphos (10 mg, 0.012 mmol) were added and the reaction was stirred at 100° C. for 16 h. The mixture was purified by reversed-phase CC to give the title compound (6.5 mg, 14% yield). LCMS $(M+H)^+$=594.2.

Example 48: 1-[2-cyano-4-(trifluoromethyl)phenyl]-4-[6-(2-methoxyphenyl)pyridin-3-yl]-N-[2-(methylamino)ethyl]piperidine-4-carboxamide (Compound 1-214)

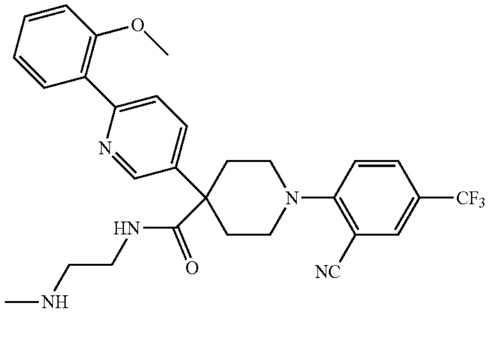 [SMILES: CNCCNC(=O)C1(c2ccc(-c3ccccc3OC)nc2)CCN(c2ccc(C(F)(F)F)cc2C#N)CC1]

Step 48-1, preparation of ethyl 1-benzyl-4-(6-chloropyridin-3-yl)piperidine-4-carboxylate: A solution of ethyl 2-(6-chloropyridin-3-yl)acetate (3.7 g, 19 mmol) and 18-crown-6 (1.0 g, 3.8 mmol) in DMF (40 mL) was stirred in a 50 mL round bottom flask. The flask was flushed three times with nitrogen (g) and cooled to 0° C. 60%-NaH (2.2 mg, 55 mmol) in mineral oil was added and the mixture was stirred at 0° C. for 0.5 h. A solution of N-benzyl-2-bromo-N-(2-bromoethyl)ethan-1-amine (7.2 g, 22 mmol) in DMF was added. The mixture was stirred at 20° C. for 2 h and then quenched with sat-$NH_4C_1$ (50 mL). The resulting solution was extracted with ethyl acetate (3x60 mL). The combined organic layers were washed with brine (3x30 mL), dried over anhydrous sodium sulfate and concentrated under vacuum. The residue was applied onto a silica gel column with ethyl acetate/petroleum ether (1:3). This resulted in the title compound (4.8 g, 72%). LCMS $(M+H)^+$=359.1.

Step 48-2, preparation of ethyl 4-(6-chloropyridin-3-yl) piperidine-4-carboxylate hydrochloride: A solution of ethyl 1-benzyl-4-(6-chloropyridin-3-yl)piperidine-4-carboxylate (1.8 g, 5.0 mmol) in DCM (20 mL) was stirred in a 50 mL round bottom flask. 1-Chloroethyl carbonochloridate (0.95 g, 6.6 mmol) was added and the mixture was stirred at 25° C. for 1 h. The mixture was concentrated to remove DCM. MeOH (20 mL) was added and the mixture was stirred at 70° C. for 1 h. The mixture was concentrated to give the title compound (1.5 g, 78% yield). LCMS $(M+H)^+$=269.1.

Step 48-3, preparation of ethyl 4-(6-chloropyridin-3-yl)-1-[2-cyano-4-(trifluoromethyl)phenyl]piperidine-4-carboxylate: A solution of ethyl 4-(6-chloropyridin-3-yl)piperidine-4-carboxylate hydrochloride (600 mg, 1.6 mmol) in DMSO (6 mL) was stirred in a 20 mL vial. DIEA (1.0 g, 7.7 mmol) and 2-fluoro-5-(trifluoromethyl)benzonitrile (400 mg, 2.1 mmol) were added and the mixture was stirred at 60° C. for 1 h. The solution was quenched with water (30 mL) and extracted with EtOAc (3x40 mL). The organic layers were combined, washed with brine (2x30 mL), dried over anhydrous sodium sulfate, and concentrated. The mixture was purified by silica gel column chromatography EtOAc/Petroleum Ether (1:3) to give the title compound (480 mg, 70% yield). LCMS $(M+H)^+$=438.2.

Step 48-4, preparation of ethyl 1-[2-cyano-4-(trifluoromethyl)phenyl]-4-[6-(2-methoxyphenyl)pyridine-3-yl]piperidine-4-carboxylate: A solution of ethyl 4-(6-chloropyridin-3-yl)-1-[2-cyano-4-(trifluoromethyl)phenyl]piperidine-4-carboxylate (200 mg, 0.457 mmol), (2-methoxyphenyl) boronic acid (85 mg, 0.56 mmol), potassium carbonate (190 mg, 1.37 mmol), and Pd(dtbpf)$Cl_2$ (30 mg, 0.046 mmol) were placed in a sealed tube. 1,4-Dioxane (1 mL) and water (0.1 mL) were added and the mixture was stirred at 100° C. for 2 h. The mixture was cooled to room temperature and concentrated. The mixture was purified with silica gel column chromatography using EtOAc/Petroleum Ether (1:3) to give the title compound (94.1 mg, 47.6% yield). LCMS $(M+H)^+$=510.5.

Step 48-5, preparation of 1-[2-cyano-4-(trifluoromethyl) phenyl]-4-[6-(2-methoxyphenyl)pyridine-3-yl]piperidine-4-carboxylic acid: A solution of ethyl 1-[2-cyano-4-(trifluoromethyl)phenyl]-4-[6-(2-methoxyphenyl)pyridine-3-yl] piperidine-4-carboxylate (150 mg, 0.294 mmol) in EtOH (2 mL) and water (0.40 mL) was stirred in a 8 mL vial. Lithium hydroxide (70 mg, 2.9 mmol) was added and the mixture was stirred at 60° C. for 2 h. The mixture was concentrated, diluted with water (20 mL), and neutralized to pH 6-7 using aq. sodium hydrogen sulfate. The mixture was extracted with EtOAc (3x20 mL) and the organic layers were combined, washed with brine (2x20 mL), dried over anhydrous sodium sulfate, and concentrated to give the title compound (130 mg, 91.7% yield). LCMS $(M+H)^+$=482.3.

Step 48-6, preparation of tert-butyl N-[2-({1-[2-cyano-4-(trifluoromethyl)phenyl]-4-[6-(2-methoxyphenyl)pyridine-3-yl]piperidin-4-yl}formamido)ethyl]-N-methylcarbamate: A solution of 1-[2-cyano-4-(trifluoromethyl)phenyl]-4-[6-(2-methoxyphenyl)pyridine-3-yl]piperidine-4-carboxylic acid (70 mg, 0.15 mmol), HATU (60 mg, 0.16 mmol), and DIEA (70 mg, 0.54 mmol) in DMF (2 mL) was stirred in an 8 mL vial at 20° C. for 5 min. tert-Butyl N-(2-aminoethyl)-N-methylcarbamate (35 mg, 0.20 mmol) was added and the mixture was stirred at 20° C. for 2 h. The reaction was purified using reversed-phase CC to give the title compound (55 mg, 59% yield). LCMS $(M+H)^+$=638.3.

Step 48-7, preparation of 1-[2-cyano-4-(trifluoromethyl) phenyl]-4-[6-(2-methoxyphenyl)pyridin-3-yl]-N-[2-(methylamino)ethyl]piperidine-4-carboxamide: A solution of tert-butyl N-[2-({1-[2-cyano-4-(trifluoromethyl)phenyl]-4-[6-(2-methoxyphenyl)pyridine-3-yl]piperidin-4-yl}formamido)ethyl]-N-methylcarbamate (55 mg, 0.086 mmol) in DCM (3 mL) was stirred in a 50 mL round bottom flask. TFA (1.49 g, 13.1 mmol) was added and the reaction was stirred at 20° C. for 1 h. The mixture was concentrated and purified by reversed-phase CC to give the title compound (44.8 mg, 89.0% yield). LCMS $(M+H)^+$=538.2.

The following compounds were prepared similarly to Example 48 with appropriate substituting reagents and substrates at different steps:

| Compound no. | MS $(M + H)^+$ |
|---|---|
| 1-215 | 511.2 |
| 1-216 | 525.2 |

Example 49: 1-[2-cyano-4-(trifluoromethyl)phenyl]-4-[6-(2-methoxyphenyl)pyridine-3-yl]-N-{[(2S)-1-methylazetidin-2-yl]methyl}piperidine-4-carboxamide (Compound 1-217)

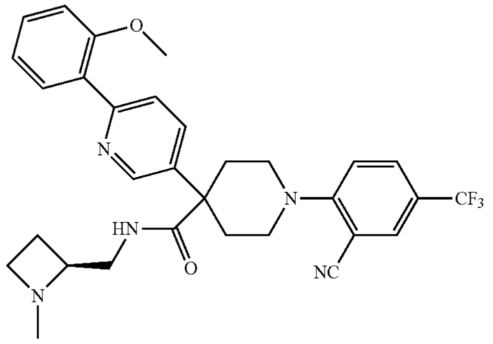 [SMILES: COc1ccccc1-c1ccc(C2(C(=O)NC[C@@H]3CCN3C)CCN(c3ccc(C(F)(F)F)cc3C#N)CC2)cn1]

Step 49-1, preparation of 1-[2-cyano-4-(trifluoromethyl) phenyl]-4-[6-(2-methoxyphenyl)pyridine-3-yl]piperidine-4-carboxylic acid: A mixture of 4-(6-chloropyridin-3-yl)-1-[2-cyano-4-(trifluoromethyl)phenyl]piperidine-4-carboxylic acid (200.0 mg, 0.4881 mmol) from Step 12-3, (2-methoxyphenyl)boronic acid (111.2 mg, 0.7321 mmol), potassium carbonate (202.3 mg, 1.464 mmol), and Pd(amphos)$Cl_2$ (69.12 mg, 0.09761 mmol) were placed in a sealed tube. 1,4-Dioxane (3 mL) and water (0.3 mL) were added. Nitrogen (g) was bubbled through and the mixture was stirred at 90° C. for 2 h. The mixture was cooled to room temperature, quenched with water and EtOAc, and acidified to pH 2-3 using 1N-HCl. The solution was extracted with EtOAc (2×), and the organic layers were combined, dried over anhydrous magnesium sulfate, and concentrated. The mixture was purified with reversed-phase CC to give the title compound (113.8 mg, 48.43% yield). LCMS $(M+H)^+$=482.3.

Step 49-2, preparation of tert-butyl (2S)-2-[({1-[2-cyano-4-(trifluoromethyl)phenyl]-4-[6-(2-methoxyphenyl)pyridine-3-yl]piperidin-4-yl}formamido)methyl]azetidine-1-carboxylate: A solution of 1-[2-cyano-4-(trifluoromethyl)phenyl]-4-[6-(2-methoxyphenyl)pyridine-3-yl]piperidine-4-carboxylic acid (40.0 mg, 0.0831 mmol), HATU (44.2 mg, 0.116 mmol), and DIEA (53.7 mg, 0.415 mmol) in DMF (0.2 mL) was stirred at 25° C. for 5 min. tert-Butyl (2S)-2-(aminomethyl)azetidine-1-carboxylate (24.8 mg, 0.133 mmol) was added and the mixture was stirred at 25° C. for 10 min. The reaction was purified using reversed-phase CC to give the title compound (33.8 mg, 62.6% yield). LCMS $(M+H)^+$=650.1.

Step 49-3, preparation of N-{[(2S)-azetidin-2-yl]methyl}-1-[2-cyano-4-(trifluoromethyl)phenyl]-4-[6-(2-methoxyphenyl)pyridine-3-yl]piperidine-4-carboxamide: A solution of tert-butyl (2S)-2-[({1-[2-cyano-4-(trifluoromethyl)phenyl]-4-[6-(2-methoxyphenyl)pyridine-3-yl]piperidin-4-yl}formamido)methyl]azetidine-1-carboxylate (33.8 mg, 0.0520 mmol) in DCM (0.06 mL) was stirred. TFA (89.0 mg, 0.780 mmol) was added and the reaction was stirred at 25° C. for 1 h. The mixture was concentrated and purified by reversed-phase CC to give the title compound (23.8 mg, 83.2% yield). LCMS $(M+H)^+$=550.7.

Step 49-4, preparation of 1-[2-cyano-4-(trifluoromethyl)phenyl]-4-[6-(2-methoxyphenyl)pyridin-3-yl]-N-{1[(2S)-1-methylazetidin-2-yl]methyl}piperidine-4-carboxamide: A solution of N-{[(2S)-azetidin-2-yl]methyl}-1-[2-cyano-4-(trifluoromethyl)phenyl]-4-[6-(2-methoxyphenyl)pyridine-3-yl]piperidine-4-carboxamide (21.4 mg, 0.0389 mmol) in MeOH (3 mL) was stirred. Polyoxymethylene (24.5 mg, 0.0389 mmol) and sodium cyanoborohydride (24.5 mg, 0.389 mmol) were added, and the reaction was stirred at 25° C. for 1.5 h. The reaction was quenched with TFA, neutralized with sat-$NaHCO_3$, and extracted with EtOAc (2×). The organic layers were combined, concentrated and purified by reversed-phase CC to give the title compound (4.2 mg, 19% yield). LCMS $(M+H)^+$=564.3.

The following compounds were prepared similarly to Example 49 with appropriate substituting reagents and substrates at different steps:

| Compound no. | MS $(M + H)^+$ |
|---|---|
| 1-232 | 551.4 |
| 1-239 | 551.5 |
| 1-240 | 551.4 |
| 1-241 | 537.5 |
| 1-242 | 582.4 |
| 1-243 | 582.2 |
| 1-244 | 564.3 |
| 1-249 | 596.4 |
| 1-250 | 596.4 |
| 1-251 | 563.5 |
| 1-252 | 590.4 |
| 1-275 | 555.4 |

Example 50: 4-{2'-ethoxy-[2,3'-bipyridin]-5-yl}-1-[2-fluoro-4-(trifluoromethyl)phenyl]-N-[2-(methylamino)ethyl]piperidine-4-carboxamide (Compound 1-223)

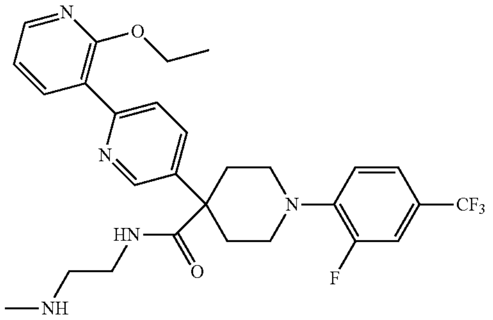 [SMILES: CCOc1ncccc1-c1ccc(C2(C(=O)NCCNC)CCN(c3ccc(C(F)(F)F)cc3F)CC2)cn1]

Step 50-1, preparation of 1-tert-butyl 4-ethyl 4-(6-chloropyridin-3-yl)piperidine-1,4-dicarboxylate: A solution of ethyl 4-(6-chloropyridin-3-yl)piperidine-4-carboxylate (3.0 g, 11 mmol) from Step 48-2, TEA (3.5 g, 35 mmol) and di-tert-butyl dicarbonate (5.0 g, 23 mmol) in DCM was stirred in a 50 mL round bottom flask, purged with nitrogen (g). The mixture was stirred at 25° C. for 1 h. The mixture was concentrated and purified by silica gel column chromatography using EtOAc/Petroleum Ether (1:3) to give the title compound (3.5 g, 85% yield). LCMS $(M+H)^+$=369.2.

Step 50-2, preparation of 1-tert-butyl 4-ethyl 4-{2'-ethoxy-[2,3'-bipyridin]-5-yl}piperidine-1,4-dicarboxylate: A solution of 1-tert-butyl 4-ethyl 4-(6-chloropyridin-3-yl)piperidine-1,4-dicarboxylate (550 mg, 1.49 mmol) in 1,4-dioxane (10 mL) and water (1 mL) was stirred in a 50 mL round bottom flask, purged and maintained with nitrogen (g). (2-Ethoxypyridin-3-yl)boronic acid (500 mg, 2.99 mmol), potassium carbonate (600 mg, 4.34 mmol), and $Pd(dtbpf)Cl_2$ (80 mg, 0.082 mmol) were added and the mixture was stirred at 100° C. for 1 h. The mixture was concentrated and purified with silica gel column chromatography using EtOAc/Petroleum Ether (1:3) to give the title compound (550 mg, 81.0% yield). LCMS (M+H)+=456.3.

Step 50-3, preparation of ethyl 4-{2'-ethoxy-[2,3'-bipyridin]-5-yl}piperidine-4-carboxylate trifluoroacetate: A solution of 1-tert-butyl 4-ethyl 4-{2'-ethoxy-[2,3'-bipyridin]-5-yl}piperidine-1,4-dicarboxylate (550.0 mg, 1.207 mmol) in DCM (5 mL) was stirred in a 50 mL round bottom flask. TFA (1 mL) was added and the reaction was stirred at 25° C. for 1 h. The mixture was concentrated to give the title compound (600.0 mg, 95% yield). LCMS $(M+H)^+$=356.3.

Step 50-4, preparation of ethyl 4-{2'-ethoxy-[2,3'-bipyridin]-5-yl}-1-[2-fluoro-4-(trifluoromethyl)phenyl]piperidine-4-carboxylate: A solution of ethyl 4-{2'-ethoxy-[2,3'-bipyridin]-5-yl}piperidine-4-carboxylate trifluoroacetate (550 mg, 1.49 mmol) in toluene (10 mL) was stirred in a 50 mL round bottom flask, purged and maintained with nitrogen (g). Cesium carbonate (1.000 g, 3.069 mmol), 1-bromo-2-fluoro-4-(trifluoromethyl)benzene (300 mg, 1.23 mmol), $Pd_2(dba)_3{\cdot}CHCl_3$ (60 mg, 0.066 mmol), and XPhos (60 mg, 0.13 mmol) were added and the reaction was stirred at 100° C. for 16 h. The mixture was concentrated and purified by silica gel column chromatography using EtOAc/Petroleum Ether (1:3) to give the title compound (220 mg, 67% yield). LCMS $(M+H)^+$=534.2.

Step 50-5, preparation of 4-{2'-ethoxy-[2,3'-bipyridin]-5-yl}-1-[2-fluoro-4-(trifluoromethyl)phenyl]piperidine-4-carboxylic acid: A solution of ethyl 4-{2'-ethoxy-[2,3'-bipyridin]-5-yl}-1-[2-fluoro-4-(trifluoromethyl)phenyl]piperidine-4-carboxylate (220 mg, 0.425 mmol) in EtOH (10 mL) and water (5 mL) was stirred in a 50 mL round bottom flask. Lithium hydroxide (100 mg, 4.18 mmol) was added, and the mixture was stirred at 60° C. for 1 h. The mixture was concentrated, diluted with water (10 mL), and neutralized to pH 6-7 using aq. sodium hydrogen sulfate. The mixture was extracted with EtOAc (3×20 mL) and the organic layers were combined, washed with brine (2×30 mL), dried over anhydrous sodium sulfate and concentrated to give the title compound (200 mg, 96.1% yield). LCMS $(M+H)^+$=490.3.

Step 50-6, preparation of tert-butyl N-{2-[(4-{2'-ethoxy-[2,3'-bipyridin]-5-yl}-1-[2-fluoro-4-(trifluoromethyl)phenyl]piperidin-4-yl)formamido]ethyl}-N-methylcarbamate: A solution of 4-{2'-ethoxy-[2,3'-bipyridin]-5-yl}-1-[2-fluoro-4-(trifluoromethyl)phenyl]piperidine-4-carboxylic acid (60 mg, 0.12 mmol), HATU (60 mg, 0.16 mmol) and DIEA (60 mg, 0.46 mmol) in DMF (2 mL) was stirred in a 50 mL round bottom flask at 25° C. for 20 min. tert-Butyl N-(2-aminoethyl)-N-methylcarbamate (40 mg, 0.23 mmol) was added, and the mixture was stirred at 25° C. for 1 h. The reaction was purified using reversed-phase CC to give the title compound (40 mg, 51% yield). LCMS $(M+H)^+$=646.4.

Step 50-7, preparation of 4-{2'-ethoxy-[2,3'-bipyridin]-5-yl}-1-[2-fluoro-4-(trifluoromethyl)phenyl]-N-[2-(methylamino)ethyl]piperidine-4-carboxamide ditrifluoroacetate: A solution of tert-butyl N-{2-[(4-{2'-ethoxy-[2,3'-bipyridin]-5-yl}-1-[2-fluoro-4-(trifluoromethyl)phenyl]piperidin-4-yl)formamido]ethyl}-N-methylcarbamate (40 mg, 0.062 mmol) in DCM (2 mL) was stirred. TFA (1 mL) was added and the reaction was stirred at 25° C. for 1 h. The mixture was concentrated, and water and acetonitrile were added. The compound was freeze-dried to give the title compound (34.4 mg, 72.0% yield). LCMS $(M+H)^+$=546.3.

The following compounds were prepared similarly to Example 50 with appropriate substituting reagents and substrates at different steps. Some examples do not require deprotection in the final step.

| Compound no. | MS $(M + H)^+$ |
|---|---|
| 1-222 | 560.2 |
| 1-224 | 576.2 |
| 1-225 | 562.3 |
| 1-226 | 559.2 |
| 1-227 | 545.3 |
| 1-228 | 575.2 |
| 1-230 | 561.2 |
| 1-254 | 545.3 |
| 1-255 | 561.3 |
| 1-256 | 531.3 |
| 1-257 | 547.3 |
| 1-271 | 546.3 |
| 1-272 | 532.3 |
| 1-273 | 562.3 |
| 1-274 | 548.3 |
| 1-276 | 518.3 |

Example 51: rac-1-[2-cyano-4-(trifluoromethyl)phenyl]-N-[(3S,4R)-4-methoxy-1-methylpyrrolidin-3-yl]-4-[6-(1-methyl-1H-pyrrol-2-yl)pyridin-3-yl]piperidine-4-carboxamide (Compound 1-267)

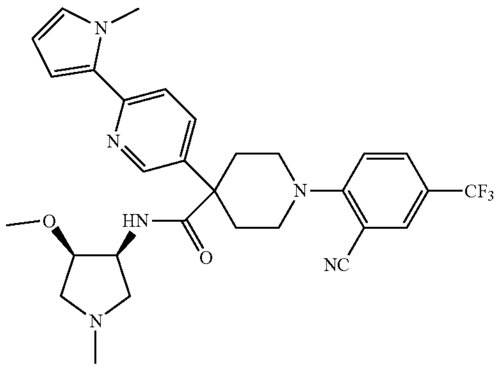 [SMILES: CO[C@@H]1CN(C)C[C@@H]1NC(=O)C1(c2ccc(-c3cccn3C)nc2)CCN(c2ccc(C(F)(F)F)cc2C#N)CC1]

Step 51-1, preparation of methyl 4-(6-chloropyridin-3-yl)piperidine-4-carboxylate: A solution of methyl 1-benzyl-4-(6-chloropyridin-3-yl)piperidine-4-carboxylate (6.01 g, 17.4 mmol) from Step 7-1 was stirred in DCM (120 mL) in a 250 ml round bottom flask. 1-chloroethyl carbonochloridate (7.47 g, 52.3 mmol) was added and the mixture was stirred at 25° C. for 4 h. The mixture was concentrated to remove DCM. MeOH (120 mL) was added and the mixture was stirred at 70° C. for 1 h. The mixture was concentrated, diluted with water, neutralized with sat-$NaHCO_3$, and extracted with EtOAc (3×15 mL). The mixture was then extracted with 25% IPA in DCM (10×20 mL). The layers of 25% IPA in DCM were combined, dried over anhydrous sodium sulfate, and concentrated to give the title compound (4.44 g, 100% yield). LCMS $(M+H)^+$=255.4.

Step 51-2, preparation of methyl 4-(6-chloropyridin-3-yl)-1-[2-cyano-4-(trifluoromethyl)phenyl]piperidine-4-carboxylate: A solution of methyl 4-(6-chloropyridin-3-yl)piperidine-4-carboxylate (4.44 g, 17.4 mmol) in DMSO (10 mL) was stirred in a sealed tube. 2-fluoro-5-(trifluoromethyl)benzonitrile (4.94 g, 26.1 mmol) and DIEA (6.76 g, 52.3 mmol) were added, and the mixture was stirred at 90° C. for 1.5 h. The mixture was diluted with water and extracted with DCM (4×20 mL). The organic layers were combined, concentrated, and purified by reversed-phase CC to give the title compound (1.71 g, 23.1% yield). LCMS $(M+H)^+$=424.3.

Step 51-3, preparation of methyl 1-[2-cyano-4-(trifluoromethyl)phenyl]-4-[6-(1-methyl-1H-pyrrol-2-yl)pyridin-3-yl]piperidine-4-carboxylate: A solution of methyl 4-(6-chloropyridin-3-yl)-1-[2-cyano-4-(trifluoromethyl)phenyl]piperidine-4-carboxylate (1.00 g, 2.37 mmol), 1-methyl-2-(4,4,5,5-tetramethyl-1,3,2-dioxaborolan-2-yl)-1H-pyrrole (2.21 g, 10.5 mmol), Pd(amphos)$Cl_2$ (754 mg, 1.05 mmol), and potassium carbonate (1.47 g, 10.5 mmol) in a sealed tube was added 1,4-dioxane (25 mL) and water (2.5 mL). Nitrogen (g) was bubbled through and the mixture was stirred at 90° C. for 4 h. The mixture was quenched with water and extracted with EtOAc (3×). The combined organics were dried over anhydrous $MgSO_4$ and concentrated. The residue was purified by silica gel column chromatography using EtOAc/Hexanes (1:3) to give the title compound (412 mg, 37.1% yield) as a brown solid. LCMS $(M+H)^+$=469.5.

Step 51-4, preparation of 1-[2-cyano-4-(trifluoromethyl)phenyl]-4-[6-(1-methyl-1H-pyrrol-2-yl)pyridin-3-yl]piperidine-4-carboxylic acid: A solution of methyl 1-[2-cyano-4-(trifluoromethyl)phenyl]-4-[6-(1-methyl-1H-pyrrol-2-yl)pyridin-3-yl]piperidine-4-carboxylate (412 mg, 0.879 mmol) in EtOH (5 mL) and water (2.5 mL) was stirred in a 40 mL vial. Lithium(I) hydrate hydroxide (369 mg, 8.79 mmol) was added, and the mixture was stirred at 60° C. for 1 h. The mixture was concentrated, diluted with water (5 mL), and acidified using 1N-HCl to pH 4. The solution was extracted with EtOAc (3×15 mL) and the organic layers were combined, washed with brine, dried over anhydrous magnesium sulfate, and concentrated to give the title compound (394 mg, 98.6% yield). LCMS $(M+H)^+$=455.3.

Step 51-5, preparation of rac-tert-butyl (3R,4S)-3-{1-[2-cyano-4-(trifluoromethyl)phenyl]-4-[6-(1-methyl-1H-pyrrol-2-yl)pyridin-3-yl]piperidine-4-amido}-4-methoxypyrrolidine-1-carboxylate: A solution of 1-[2-cyano-4-(trifluoromethyl)phenyl]-4-[6-(1-methyl-1H-pyrrol-2-yl)pyridin-3-yl]piperidine-4-carboxylic acid (40.9 mg, 0.0899 mmol), HATU (47.9 mg, 0.126 mmol) and DIEA (20.7 mg, 0.180 mmol) in DMF (0.25 mL) was stirred at 23° C. for 5 min. rac-tert-butyl (3R,4S)-3-amino-4-methoxypyrrolidine-1-carboxylate (27.3 mg, 0.135 mmol) was added and the reaction was stirred at 23° C. for 30 min. The mixture was purified by reversed-phase CC to give the title compound (49.6 mg, 86.4% yield). LCMS $(M+H)^+$=653.5.

Step 51-6, preparation of rac-1-[2-cyano-4-(trifluoromethyl)phenyl]-N-[(3S,4R)-4-methoxypyrrolidin-3-yl]-4-[6-(1-methyl-1H-pyrrol-2-yl)pyridin-3-yl]piperidine-4-carboxamide: A solution of rac-tert-butyl (3R,4S)-3-{1-[2-cyano-4-(trifluoromethyl)phenyl]-4-[6-(1-methyl-1H-pyrrol-2-yl)pyridin-3-yl]piperidine-4-amido}-4-methoxypyrrolidine-1-carboxylate (49.6 mg, 76.0 mmol) in DCM (0.25 mL) was stirred in a 4 mL vial. TFA (125 mg, 1.14 mmol) was added and the reaction was stirred at 23° C. for 6 h. The mixture was concentrated, neutralized with sat-$NaHCO_3$, and extracted with EtOAc (3×10 mL). The organic layers were combined, dried over anhydrous magnesium sulfate and concentrated to give the title compound (38.5 mg, 91.7% yield). LCMS $(M+H)^+$=553.0.

Step 51-7, preparation of rac-1-[2-cyano-4-(trifluoromethyl)phenyl]-N-[(3S,4R)-4-methoxy-1-methylpyrrolidin-3-yl]-4-[6-(1-methyl-1H-pyrrol-2-yl)pyridin-3-yl]piperidine-4-carboxamide: A mixture of rac-1-[2-cyano-4-(trifluoromethyl)phenyl]-N-[(3S,4R)-4-methoxypyrrolidin-3-yl]-4-[6-(1-methyl-1H-pyrrol-2-yl)pyridin-3-yl]piperidine-4-carboxamide (38.5 mg, 0.0697 mmol) and polyoxymethylene (41.8 mg, 1.39 mmol) were added to a 4 mL vial. A solution of sodium cyanoborohydride (43.8 mg, 0.697 mmol) in MeOH (1 mL) was added and the reaction was stirred at 23° C. for 2 h. The reaction was quenched with TFA, neutralized with sat-$NaHCO_3$, and extracted with EtOAc (3×15 mL). The organic layers were combined, concentrated and purified by reversed-phase CC to give the title compound (22.1 mg, 56.0% yield). LCMS $(M+H)^+$=567.4.

The following compounds were prepared similarly to Example 51 with appropriate substituting reagents and substrates at different steps:

| Compound no. | MS $(M + H)^+$ |
|---|---|
| 1-268 | 567.3 |
| 1-269 | 553.2 |
| 1-270 | 553.2 |
| 1-277 | 569.4 |
| 1-278 | 569.4 |
| 1-279 | 587.3 |
| 1-280 | 587.4 |

-continued

Example 52: N-{1-[2-cyano-4-(trifluoromethyl)phenyl]-4-[5-fluoro-6-(2-methoxyphenyl)pyridin-3-yl]piperidin-4-yl}-3-(methylamino)propanamide (Compound 2-63)

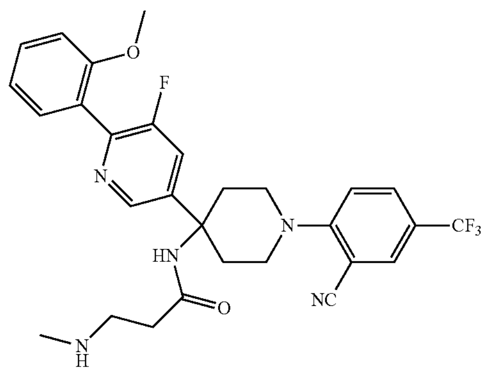 [SMILES: CNCCC(=O)NC1(c2cnc(-c3ccccc3OC)c(F)c2)CCN(c2ccc(C(F)(F)F)cc2C#N)CC1]

Step 52-1, preparation of 1-benzyl-4-(5-fluoro-6-(2-methoxyphenyl)pyridin-3-yl)piperidine-4-carbonitrile: To a mixture 1-benzyl-4-(6-chloro-5-fluoropyridin-3-yl)piperidine-4-carbonitrile (3.00 g, 9.10 mmol) from Step 6-3, (2-methoxyphenyl)boronic acid (1.66 g, 10.9 mmol), $Pd(DTBPF)Cl_2$ (592.9 mg, 909.8 μmol), and $K_2CO_3$ (3.77 g, 27.3 mmol) in a sealed tube was added 1,4-dioxane (30 mL) and water (3 mL). $N_2$ (g) was bubbled through the resulting mixture. The mixture was then heated at 100° C. for 2.5 h. The reaction was not complete and thus more (2-methoxyphenyl)boronic acid (0.3 eq), $Pd(DTBPF)Cl_2$ (0.03 eq), and $K_2CO_3$ (0.3 eq) were added. The reaction was continued to heat at 100° C. for 1.5 h under nitrogen condition. The mixture was quenched with water and extracted with EtOAc (2×). The combined organics were concentrated in vacuo and the crude product was purified by reversed-phased CC. Pure fractions were combined and concentrated to dryness to give the title compound (1.76 g, 48.1%). LCMS $(M+H)^+$=402.3.

Step 52-2, preparation of 1-benzyl-4-(5-fluoro-6-(2-methoxyphenyl)pyridin-3-yl)piperidine-4-carboxylic acid: To a solution of 1-benzyl-4-(5-fluoro-6-(2-methoxyphenyl)pyridin-3-yl)piperidine-4-carbonitrile (1.76 g, 4.38 mmol) in EtOH (20 mL) was added KOH (2.46 g, 43.8 mmol) and water (20 mL). The reaction mixture was heated at 100° C. for 23 h. The reaction was not complete and thus more KOH (3.3 eq) was added. The reaction was continued to heat at 100° C. for 18 h. The mixture was diluted with water and acidified with 1 N HCl (aq) to make pH 5. The solid was collected by vacuum filtration, washed with water, and dried under high vacuum to give the title compound (1.54 g, 83.7%) as a yellow solid. LCMS $(M+H)^+$=421.4.

Step 52-3, preparation of 4-(5-fluoro-6-(2-methoxyphenyl)pyridin-3-yl)piperidine-4-carboxylic acid: To a solution of 1-benzyl-4-(5-fluoro-6-(2-methoxyphenyl)pyridin-3-yl)piperidine-4-carboxylic acid (500 mg, 1.19 mmol) in MeOH (5 mL) was added ammonium formate (750 mg, 11.9 mmol)

and Pd/C (540 mg, 238 μmol). The reaction mixture was heated at 80° C. for 1 h. The mixture was filtered through Celite and the filtrate was concentrated to dryness to give the title compound (185.6 mg, 47.2%). LCMS $(M+H)^+$=331.3.

Step 52-4, preparation of 1-(2-cyano-4-(trifluoromethyl) phenyl)-4-(5-fluoro-6-(2-methoxyphenyl)pyridin-3-yl)piperidine-4-carboxylic acid: To a solution of 4-(5-fluoro-6-(2-methoxyphenyl)pyridin-3-yl)piperidine-4-carboxylic acid (185.6 mg, 561.8 μmol) and 2-fluoro-5-(trifluoromethyl) benzonitrile (159.4 mg, 842.7 μmol) in DMSO (3.5 mL) in a sealed tube was added DIEA (0.29 mL, 1.69 mmol). The mixture was heated at 90° C. for 1.5 h. The mixture was purified by reversed-phase CC. Pure fractions were combined and concentrated in vacuo to give the title compound (101.5 mg, 36.2%) as a white solid. LCMS $(M+H)^+$=500.1.

Step 52-5, preparation of benzyl (1-(2-cyano-4-(trifluoromethyl)phenyl)-4-(5-fluoro-6-(2-methoxyphenyl)pyridin-3-yl)piperidin-4-yl)carbamate: To a solution of 1-(2-cyano-4-(trifluoromethyl)phenyl)-4-(5-fluoro-6-(2-methoxyphenyl)pyridin-3-yl)piperidine-4-carboxylic acid (101.5 mg, 203.2 μmol) in toluene (3 mL) under nitrogen was added TEA (51 μL, 36.8 μmol) and diphenyl phosphorazidate (69.9 μL, 325.1 μmol). The mixture was stirred at rt for 1 h. To this mixture was then added phenylmethanol (42.3 μL, 406.4 μmol) and the resulting mixture was heated at 100° C. for 1 h. The reaction was not complete and thus more phenylmethanol (1 eq) was added. The reaction was continued to heat at 100° C. for 1 h. The mixture was quenched with water (20 mL) and extracted with EtOAc (2×). The combined organics were concentrated in vacuo and the crude product was purified by reversed-phase CC. Pure fractions were combined and concentrated in vacuo to give the title compound (62.2 mg, 50.6%). LCMS $(M+H)^+$=605.2.

Step 52-6, preparation of 2-(4-amino-4-(5-fluoro-6-(2-methoxyphenyl)pyridin-3-yl)piperidin-1-yl)-5-(trifluoromethyl)benzonitrile: To benzyl (1-(2-cyano-4-(trifluoromethyl)phenyl)-4-(5-fluoro-6-(2-methoxyphenyl)pyridin-3-yl)piperidin-4-yl)carbamate (62.2 mg, 103 μmol) was added TFA (0.50 mL, 6.5 mmol). The mixture was heated at 70° C. for 10 h. The mixture was concentrated to dryness and the residue was purified by reversed-phase CC. Pure fractions were combined and concentrated in vacuo to give the title compound (34.6 mg, 71.5%). LCMS $(M+H)^+$=471.2.

Step 52-7, preparation of tert-butyl N-[2-({1-[2-cyano-4-(trifluoromethyl)phenyl]-4-[5-fluoro-6-(2-methoxyphenyl) pyridin-3-yl]piperidin-4-yl}carbamoyl)ethyl]-N-methylcarbamate: To a solution of 3-{[(tert-butoxy)carbonyl](methyl) amino}propanoic acid (11 mg, 0.054 mmol) and HATU (19 mg, 0.051 mmol) in DMF (0.5 mL) was added DIEA (14 mg, 0.011 mmol). The mixture was stirred at rt for 5 min. To 2-{4-amino-4-[5-fluoro-6-(2-methoxyphenyl)pyridin-3-yl] piperidin-1-yl}-5-(trifluoromethyl)benzonitrile (17 mg, 0.036 mmol) was added the above HATU-activated solution. The resulting mixture was stirred at rt for 30 min. The mixture was purified by reversed-phase CC. Pure fractions were combined and concentrated in vacuo to give the title compound (9.9 mg, 42%). LCMS $(M+H)^+$=656.4.

Step 52-8, preparation of N-{1-[2-cyano-4-(trifluoromethyl)phenyl]-4-[5-fluoro-6-(2-methoxyphenyl)pyridin-3-yl]piperidin-4-yl}-3-(methylamino)propanamide: To a solution of tert-butyl N-[2-({1-[2-cyano-4-(trifluoromethyl) phenyl]-4-[5-fluoro-6-(2-methoxyphenyl)pyridin-3-yl] piperidin-4-yl}carbamoyl)ethyl]-N-methylcarbamate (9.9 mg, 15 μmol) in DCM (0.25 mL) was added TFA (12 μL, 0.15 mmol). The mixture was heated at 70° C. for 10 h. The mixture was concentrated to dryness and the residue was stirred at rt for 1.5 h. The reaction was not complete. More TFA (12 μL, 0.15 mmol) was added and the reaction was continued to stir at rt for 2 h. The mixture was concentrated in vacuo to dryness and the residue was purified by reversed-phase CC. Pure fractions were combined and concentrated in vacuo to give the title compound (5.7 mg, 68%). LCMS $(M+H)^+$=556.3.

Example 53: N-{1-[2-cyano-4-(trifluoromethyl) phenyl]-4-[5-fluoro-6-(2-methoxyphenyl)pyridin-3-yl]piperidin-4-yl}-3-(dimethylamino)propanamide (Compound 2-62)

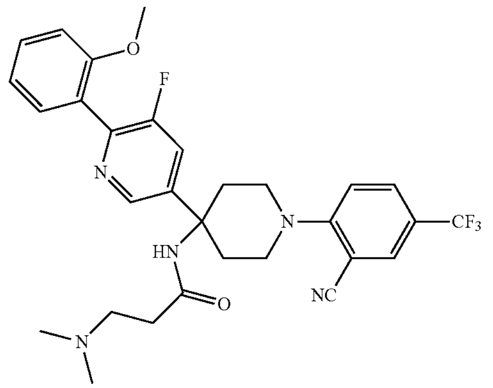 [SMILES: COc1ccccc1-c1ncc(C2(NC(=O)CCN(C)C)CCN(c3ccc(C(F)(F)F)cc3C#N)CC2)cc1F]

Step 53-1, preparation of N-{1-[2-cyano-4-(trifluoromethyl)phenyl]-4-[5-fluoro-6-(2-methoxyphenyl)pyridin-3-yl]piperidin-4-yl}-3-(dimethylamino)propanamide: A mixture of N-{1-[2-cyano-4-(trifluoromethyl)phenyl]-4-[5-fluoro-6-(2-methoxyphenyl)pyridin-3-yl]piperidin-4-yl}-3-(methylamino)propanamide (5.7 mg, 0.010 mmol) from Step 52-8 and polyoxymethylene (6.2 mg, 0.21 mmol) were added to a 4 mL vial. A solution of sodium cyanoborohydride (6.4 mg, 0.10 mmol) in MeOH (1 mL) was added and the reaction was stirred at 23° C. for 2 h. The reaction was quenched with TFA, neutralized with sat-$NaHCO_3$, and extracted with EtOAc (3×15 mL). The organic layers were combined, concentrated and purified by reversed-phase CC to give the title compound (3.1 mg, 53% yield). LCMS $(M+H)^+$=570.3.

Example 54: N-[2-(dimethylamino)ethyl]-4-[6-(2-ethoxypyridin-3-yl)pyridazin-3-yl]-1-[2-fluoro-4-(trifluoromethyl)phenyl]piperidine-4-carboxamide (Compound 1-335)

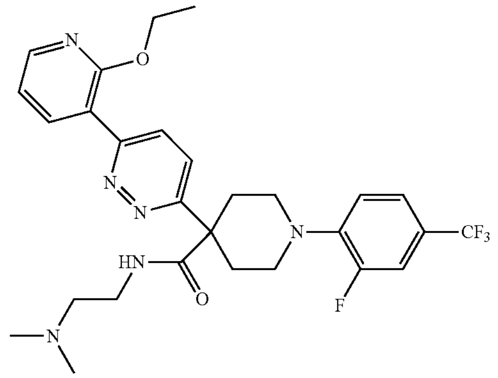 [SMILES: CCOc1ncccc1-c1ccc(C2(C(=O)NCCN(C)C)CCN(c3ccc(C(F)(F)F)cc3F)CC2)nn1]

Step 54-1, preparation of methyl 4-(6-(2-ethoxypyridin-3-yl)pyridazin-3-yl)piperidine-4-carboxylate: To a solution of 1-(tert-butyl) 4-methyl 4-(6-(2-ethoxypyridin-3-yl)

pyridazin-3-yl)piperidine-1,4-dicarboxylate (100 mg, 226 μmol) from Step 41-2 in DCM (1 mL) was added TFA (222 mg, 2.26 mmol). The resulting mixture was stirred at rt for 1 h. The mixture was concentrated in vacuo and the residue was triturated with saturated $Na_2CO_3$ (aq) (30 mL) and extracted with DCM (2×). The combined organics were dried over anhydrous $Na_2SO_4$, filtered, and concentrated in vacuo to dryness to give the crude title compound (96 mg, 120% yield) as yellow oil, which was used in the next step without further purification. LCMS $(M+H)^+$=343.4.

Step 54-2, preparation of methyl 4-(6-(2-ethoxypyridin-3-yl)pyridazin-3-yl)-1-(2-fluoro-4-(trifluoromethyl)phenyl) piperidine-4-carboxylate: To a mixture of methyl 4-(6-(2-ethoxypyridin-3-yl)pyridazin-3-yl)piperidine-4-carboxylate (80 mg, 0.23 mmol), cesium carbonate (0.23 g, 0.71 mmol), 1-bromo-2-fluoro-4-(trifluoromethyl)benzene (85 mg, 0.35 mmol), dicyclohexyl(2',4',6'-triisopropyl-[1,1'-biphenyl]-2-yl)phosphane (11 mg, 23 μmol), and $Pd_2(dba)_3$ (21 mg, 23 μmol) was added toluene (1 mL) under $N_2$ (g). The resulting suspension was heated at 100° C. for 4 h. The reaction mixture was concentrated in vacuo and the residue was purified by reversed-phase CC to give the title compound (72 mg, 61% yield) as a yellow solid. LCMS $(M+H)^+$=505.4.

Step 54-3, preparation of N-(2-(dimethylamino)ethyl)-4-(6-(2-ethoxypyridin-3-yl)pyridazin-3-yl)-1-(2-fluoro-4-(trifluoromethyl)phenyl)piperidine-4-carboxamide bis(2,2,2-trifluoroacetate): To a solution of methyl 4-(6-(2-ethoxypyridin-3-yl)pyridazin-3-yl)-1-(2-fluoro-4-(trifluoromethyl)phenyl)piperidine-4-carboxylate (67 mg, 0.13 mmol) in THF (0.05 mL) was added N,N-dimethylethylamine (59 mg, 0.66 mmol). The mixture was cooled to −15° C. and then to this was added 1M LiHMDS in THE (2.7 mL, 2.7 mmol). The resulting mixture was stirred at −15° C. for 1 h. The mixture was quenched with MeOH (2.5 mL) and the crude was further purified by reversed-phase CC to give the title compound (35.8 mg, 34% yield) as yellow oil. LCMS $(M+H)^+$=561.3.

Example A-1: Parenteral Pharmaceutical Composition

To prepare a parenteral pharmaceutical composition suitable for administration by injection (subcutaneous, intravenous), 1-100 mg of a water-soluble salt of a compound Formula (I), or a pharmaceutically acceptable salt or solvate thereof, is dissolved in sterile water and then mixed with 10 mL of 0.9% sterile saline. A suitable buffer is optionally added as well as optional acid or base to adjust the pH. The mixture is incorporated into a dosage unit form suitable for administration by injection

Example A-2: Oral Solution

To prepare a pharmaceutical composition for oral delivery, a sufficient amount of a compound of Formula (I), or a pharmaceutically acceptable salt thereof, is added to water (with optional solubilizer(s), optional buffer(s) and taste masking excipients) to provide a 20 mg/mL solution.

Example A-3: Oral Tablet

A tablet is prepared by mixing 20-50% by weight of a compound of Formula (I), or a pharmaceutically acceptable salt thereof, 20-50% by weight of microcrystalline cellulose, 1-10% by weight of low-substituted hydroxypropyl cellulose, and 1-10% by weight of magnesium stearate or other appropriate excipients. Tablets are prepared by direct compression. The total weight of the compressed tablets is maintained at 100-500 mg.

Example A-4: Oral Capsule

To prepare a pharmaceutical composition for oral delivery, 10-500 mg of a compound of Formula (I), or a pharmaceutically acceptable salt thereof, is mixed with starch or other suitable powder blend. The mixture is incorporated into an oral dosage unit such as a hard gelatin capsule, which is suitable for oral administration.

In another embodiment, 10-500 mg of a compound of Formula (I), or a pharmaceutically acceptable salt thereof, is placed into Size 4 capsule, or size 1 capsule (hypromellose or hard gelatin) and the capsule is closed.

Example A-5: Topical Gel Composition

To prepare a pharmaceutical topical gel composition, a compound of Formula (I), or a pharmaceutically acceptable salt thereof, is mixed with hydroxypropyl celluose, propylene glycol, isopropyl myristate and purified alcohol USP. The resulting gel mixture is then incorporated into containers, such as tubes, which are suitable for topical administration.

Example B-1: MC2R Assays

Membrane Preparation:

Crude membrane fractions are prepared from CRE-bla-CHO-$K_1$ cells stably expressing hMC2 receptor and hMRAP accessory protein (Thermo Fisher). The cells are grown to 85-100% confluence on standard tissue culture dishes in GlutaMax DMEM growth media (Gibco) with following additives: 10% dialyzed FBS (Gemini), 0.1 mM NEAA (Gibco), 25 mM HEPES (Gibco), 5 μg/mL blasticidin (Goldbio), 100 μg/mL zeocin (Invitrogen), 600 μg/mL hygromycin (Goldbio). To prepare membranes, cells are scraped and collected in 1× Dulbecco's phosphate buffered saline (Corning) and then pelleted at 1000 RPM's. The cell pellet is reconstituted in membrane preparation buffer (20 mM HEPES, 6 mM $MgCl_2$ and 1 mM EGTA, protease inhibitor tablets (Pierce) adjusted to pH 7.4), homogenized using a dounce homogenizer, and the resulting membrane fraction is pelleted by centrifugation at 12,000 RPM's. The membrane pellet is resuspended in membrane preparation buffer, snap freezed and stored at −80° C. for later use.

Binding Assay for hMC2 Antagonists Protocol:

The hMC2 membrane binding assay utilizes the following components: radiolabel $[^{125}I]$ACTH (1-39) Tyr23 (PerkinElmer), wheatgerm agglutinin coated PVT SPA beads (PerkinElmer), crude hMC2R membranes, and compounds. Briefly hMC2R membranes are incubated with SPA beads in binding assay buffer (50 mM HEPES, 5 mM $MgCl_2$, 1 mM $CaCl_2$), 0.20% BSA, protease inhibitor tablets (Pierce) adjusted to pH7.4) prior to assay initiation. A dose response of compound (the final concentration of compound are typically 0-10,000 nM), SPA membranes, and $[^{125}]$ACTH (1-39) Tyr23 at a final concentration of 0.2 nM is plated in a 96-well assay plate and allowed to incubate 1.5 hours at room temperature. Assay plates are read using a Top Count NXT and $K_i$ values for compounds are determined using a GraphPad Prism 6 non-linear regression analysis.

Illustrative binding affinities of selective compounds are described in Table A. The potencies are divided into four criteria: + means that $K_1$ is between 1,000 nM and 10,000 nM; ++ means that $K_1$ is between 100 nM and 1,000 nM; +++ means $K_1$ is between 10 nM and 100 nM; ++++ means K is below 10 nM.

TABLE A

| Cpd No. | MC2R binding potency |
|---|---|
| 1-1 | ++++ |
| 1-2 | ++++ |
| 1-3 | +++ |
| 1-4 | +++ |
| 1-5 | +++ |
| 1-6 | +++ |
| 1-7 | ++++ |
| 1-8 | ++++ |
| 1-9 | ++++ |
| 1-10 | ++++ |
| 1-11 | ++++ |
| 1-12 | ++++ |
| 1-13 | ++++ |
| 1-14 | ++++ |
| 1-15 | +++ |
| 1-16 | ++++ |
| 1-17 | ++++ |
| 1-18 | ++++ |
| 1-19 | ++++ |
| 1-20 | ++++ |
| 1-21 | ++++ |
| 1-22 | ++++ |
| 1-23 | ++++ |
| 1-24 | ++++ |
| 1-25 | +++ |
| 1-26 | ++++ |
| 1-27 | +++ |
| 1-28 | ++++ |
| 1-29 | +++ |
| 1-30 | ++++ |
| 1-31 | ++++ |
| 1-32 | +++ |
| 1-33 | ++++ |
| 1-34 | ++++ |
| 1-35 | ++++ |
| 1-36 | ++++ |
| 1-37 | ++++ |
| 1-38 | ++++ |
| 1-39 | ++++ |
| 1-40 | ++++ |
| 1-41 | ++++ |
| 1-42 | ++++ |
| 1-43 | ++++ |
| 1-44 | ++++ |
| 1-45 | ++++ |
| 1-46 | ++++ |
| 1-47 | ++++ |
| 1-48 | ++++ |
| 1-51 | ++++ |
| 1-52 | ++++ |
| 1-53 | +++ |
| 1-54 | +++ |
| 1-55 | ++++ |
| 1-56 | ++++ |
| 1-57 | ++++ |
| 1-58 | ++++ |
| 1-59 | ++++ |
| 1-60 | ++++ |
| 1-61 | ++++ |
| 1-62 | ++++ |
| 1-63 | ++++ |
| 1-64 | ++++ |
| 1-65 | +++ |
| 1-66 | ++++ |
| 1-67 | +++ |
| 1-68 | ++++ |
| 1-69 | ++++ |
| 1-70 | +++ |
| 1-71 | ++++ |
| 1-72 | ++++ |
| 1-73 | ++++ |

TABLE A-continued

| Cpd No. | MC2R binding potency |
|---|---|
| 1-74 | ++++ |
| 1-75 | ++++ |
| 1-76 | ++++ |
| 1-77 | ++++ |
| 1-78 | ++++ |
| 1-79 | ++++ |
| 1-80 | ++++ |
| 1-81 | ++++ |
| 1-82 | ++++ |
| 1-83 | ++++ |
| 1-84 | +++ |
| 1-85 | ++++ |
| 1-86 | ++++ |
| 1-87 | ++++ |
| 1-88 | ++++ |
| 1-89 | ++++ |
| 1-90 | ++++ |
| 1-91 | ++++ |
| 1-92 | ++++ |
| 1-93 | ++++ |
| 1-94 | ++++ |
| 1-95 | ++++ |
| 1-96 | ++++ |
| 1-97 | ++++ |
| 1-98 | ++++ |
| 1-99 | ++++ |
| 1-100 | ++++ |
| 1-101 | ++++ |
| 1-102 | ++++ |
| 1-103 | ++++ |
| 1-104 | ++++ |
| 1-105 | +++ |
| 1-106 | ++++ |
| 1-107 | ++++ |
| 1-108 | ++++ |
| 1-109 | ++++ |
| 1-110 | ++++ |
| 1-111 | ++++ |
| 1-112 | ++++ |
| 1-113 | ++++ |
| 1-114 | ++++ |
| 1-115 | +++ |
| 1-116 | ++++ |
| 1-117 | ++++ |
| 1-118 | ++++ |
| 1-119 | ++++ |
| 1-120 | ++++ |
| 1-121 | ++++ |
| 1-122 | ++++ |
| 1-123 | ++++ |
| 1-124 | ++++ |
| 1-125 | ++++ |
| 1-126 | ++++ |
| 1-127 | ++++ |
| 1-128 | ++++ |
| 1-129 | +++ |
| 1-130 | ++++ |
| 1-131 | ++++ |
| 1-132 | ++++ |
| 1-133 | ++++ |
| 1-134 | ++++ |
| 1-135 | ++++ |
| 1-136 | ++++ |
| 1-137 | +++ |
| 1-138 | ++++ |
| 1-139 | ++++ |
| 1-140 | ++++ |
| 1-141 | ++++ |
| 1-142 | ++++ |
| 1-143 | ++++ |
| 1-144 | ++++ |
| 1-145 | ++++ |
| 1-146 | ++++ |
| 1-147 | ++++ |
| 1-148 | +++ |
| 1-149 | ++++ |

TABLE A-continued

| Cpd No. | MC2R binding potency |
|---|---|
| 1-150 | +++ |
| 1-151 | ++++ |
| 1-152 | ++++ |
| 1-153 | +++ |
| 1-154 | ++++ |
| 1-155 | ++++ |
| 1-156 | ++++ |
| 1-157 | +++ |
| 1-158 | ++++ |
| 1-159 | +++ |
| 1-160 | ++++ |
| 1-161 | ++++ |
| 1-162 | ++++ |
| 1-163 | ++++ |
| 1-164 | +++ |
| 1-165 | +++ |
| 1-166 | ++++ |
| 1-167 | ++++ |
| 1-168 | ++++ |
| 1-169 | ++++ |
| 1-170 | ++++ |
| 1-171 | ++++ |
| 1-172 | ++++ |
| 1-173 | ++++ |
| 1-174 | ++++ |
| 1-175 | ++++ |
| 1-176 | +++ |
| 1-177 | ++ |
| 1-178 | +++ |
| 1-179 | ++++ |
| 1-180 | ++++ |
| 1-181 | +++ |
| 1-182 | +++ |
| 1-183 | ++++ |
| 1-184 | ++ |
| 1-185 | ++ |
| 1-186 | ++++ |
| 1-187 | ++++ |
| 1-188 | +++ |
| 1-189 | ++++ |
| 1-190 | +++ |
| 1-191 | +++ |
| 1-192 | ++++ |
| 1-193 | ++++ |
| 1-194 | ++++ |
| 1-195 | ++++ |
| 1-196 | ++++ |
| 1-197 | ++++ |
| 1-198 | ++++ |
| 1-199 | ++++ |
| 1-200 | ++++ |
| 1-201 | ++++ |
| 1-202 | ++++ |
| 1-203 | ++++ |
| 1-204 | ++++ |
| 1-205 | +++ |
| 1-206 | +++ |
| 1-207 | ++++ |
| 1-208 | ++++ |
| 1-209 | ++++ |
| 1-210 | ++++ |
| 1-211 | ++++ |
| 1-212 | ++++ |
| 1-213 | ++++ |
| 1-214 | ++++ |
| 1-215 | ++++ |
| 1-216 | ++++ |
| 1-217 | ++++ |
| 1-218 | ++++ |
| 1-219 | ++++ |
| 1-220 | ++++ |
| 1-221 | +++ |
| 1-222 | ++++ |
| 1-223 | ++++ |
| 1-224 | ++++ |
| 1-225 | ++++ |

TABLE A-continued

| Cpd No. | MC2R binding potency |
|---|---|
| 1-226 | ++++ |
| 1-227 | ++++ |
| 1-228 | ++++ |
| 1-229 | +++ |
| 1-230 | ++++ |
| 1-231 | ++++ |
| 1-232 | ++++ |
| 1-233 | +++ |
| 1-234 | +++ |
| 1-235 | +++ |
| 1-236 | ++++ |
| 1-237 | ++++ |
| 1-238 | ++++ |
| 1-239 | +++ |
| 1-240 | +++ |
| 1-241 | ++++ |
| 1-242 | ++++ |
| 1-243 | ++++ |
| 1-244 | ++++ |
| 1-245 | ++++ |
| 1-246 | ++++ |
| 1-247 | ++++ |
| 1-248 | ++++ |
| 1-249 | ++++ |
| 1-250 | ++++ |
| 1-251 | +++ |
| 1-252 | +++ |
| 1-253 | ++++ |
| 1-254 | ++++ |
| 1-255 | ++++ |
| 1-256 | ++++ |
| 1-257 | ++++ |
| 1-258 | ++++ |
| 1-259 | +++ |
| 1-260 | ++++ |
| 1-261 | ++++ |
| 1-262 | ++++ |
| 1-263 | +++ |
| 1-264 | +++ |
| 1-265 | ++++ |
| 1-266 | ++++ |
| 1-267 | ++++ |
| 1-268 | ++++ |
| 1-269 | ++++ |
| 1-270 | ++++ |
| 1-271 | ++++ |
| 1-272 | ++++ |
| 1-273 | ++++ |
| 1-274 | ++++ |
| 1-275 | ++++ |
| 1-276 | ++++ |
| 1-277 | ++++ |
| 1-278 | ++++ |
| 1-279 | ++ |
| 1-280 | ++ |
| 1-281 | ++++ |
| 1-282 | ++++ |
| 1-283 | ++++ |
| 1-284 | ++++ |
| 1-285 | ++++ |
| 1-286 | ++++ |
| 1-287 | ++++ |
| 1-288 | ++++ |
| 1-289 | ++++ |
| 1-290 | ++++ |
| 1-291 | ++++ |
| 1-292 | ++++ |
| 1-293 | ++++ |
| 1-294 | +++ |
| 1-295 | ++++ |
| 1-296 | ++++ |
| 1-297 | ++++ |
| 1-298 | ++++ |
| 1-299 | ++++ |
| 1-300 | ++++ |
| 1-301 | ++++ |

TABLE A-continued

| Cpd No. | MC2R binding potency |
|---|---|
| 1-302 | ++++ |
| 1-303 | ++++ |
| 1-304 | ++++ |
| 1-305 | ++++ |
| 1-306 | ++++ |
| 1-307 | ++++ |
| 1-308 | ++++ |
| 1-309 | ++++ |
| 1-310 | ++++ |
| 1-311 | ++++ |
| 1-312 | ++++ |
| 1-313 | ++++ |
| 1-314 | ++++ |
| 1-315 | ++++ |
| 1-316 | ++++ |
| 1-317 | ++++ |
| 1-318 | ++++ |
| 1-319 | ++++ |
| 1-320 | ++++ |
| 1-321 | ++++ |
| 1-322 | ++++ |
| 1-323 | ++++ |
| 1-324 | ++++ |
| 1-325 | ++++ |
| 1-326 | ++++ |
| 1-327 | +++ |
| 1-328 | +++ |
| 1-329 | ++++ |
| 1-330 | +++ |
| 1-331 | ++++ |
| 1-332 | ++++ |
| 1-333 | ++++ |
| 1-334 | ++++ |
| 1-335 | ++++ |
| 2-1 | +++ |
| 2-2 | +++ |
| 2-3 | +++ |
| 2-4 | ++++ |
| 2-5 | ++++ |
| 2-6 | ++++ |
| 2-7 | ++++ |
| 2-8 | ++++ |
| 2-9 | ++++ |
| 2-10 | ++++ |
| 2-11 | +++ |
| 2-12 | +++ |
| 2-13 | +++ |
| 2-14 | +++ |
| 2-15 | +++ |
| 2-16 | +++ |
| 2-17 | +++ |
| 2-18 | ++++ |
| 2-19 | ++++ |
| 2-20 | ++++ |
| 2-21 | ++++ |
| 2-22 | ++++ |
| 2-23 | ++++ |
| 2-24 | ++++ |
| 2-25 | ++++ |
| 2-26 | ++++ |
| 2-27 | ++++ |
| 2-28 | ++++ |
| 2-29 | ++++ |
| 2-30 | ++++ |
| 2-31 | ++++ |
| 2-32 | ++++ |
| 2-33 | ++++ |
| 2-34 | ++++ |
| 2-35 | ++++ |
| 2-36 | ++++ |
| 2-37 | ++++ |
| 2-38 | ++++ |
| 2-39 | ++++ |
| 2-40 | ++++ |
| 2-41 | ++++ |
| 2-42 | ++++ |

TABLE A-continued

| Cpd No. | MC2R binding potency |
|---|---|
| 2-43 | ++++ |
| 2-44 | ++++ |
| 2-45 | ++++ |
| 2-46 | ++++ |
| 2-47 | ++++ |
| 2-48 | ++++ |
| 2-49 | ++++ |
| 2-50 | ++++ |
| 2-51 | ++++ |
| 2-52 | ++++ |
| 2-53 | ++++ |
| 2-54 | ++++ |
| 2-55 | ++++ |
| 2-56 | ++++ |
| 2-57 | ++++ |
| 2-58 | ++++ |
| 2-59 | +++ |
| 2-60 | ++++ |
| 2-61 | ++++ |
| 2-62 | ++++ |
| 2-63 | ++++ |

The examples and embodiments described herein are for illustrative purposes only and various modifications or changes suggested to persons skilled in the art are to be included within the spirit and purview of this application and scope of the appended claims.

What is claimed is:

1. A compound of Formula (IIa) or Formula (IIb), or a pharmaceutically acceptable salt thereof:

Formula (IIa)

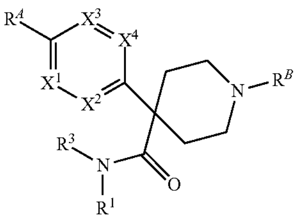

Formula (IIb)

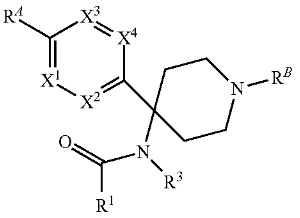

wherein:

$R^A$ is unsubstituted or substituted monocyclic 6-membered heteroaryl, unsubstituted or substituted phenyl, or unsubstituted or substituted monocyclic 5-membered heteroaryl, wherein if $R^A$ is substituted then $R^A$ is substituted with 1, 2, 3 or 4 groups selected from $R^a$, $R^b$, and $R^c$;

$R^a$, $R^b$, and $R^c$ are independently selected from the group consisting of hydrogen, halogen, —$OR^4$, —CN, —$N(R^4)_2$, —C(═O)$R^7$, unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted $C_3$-$C_6$ cycloalkyl, unsubstituted or substituted $C_2$-$C_7$ heterocycloalkyl, unsubstituted or substituted phenyl, and unsubstituted or substituted heteroaryl, wherein any substituted group of $R^a$, $R^b$, and $R^c$ is substituted with one or more $R^6$ groups;

or one $R^a$ and one $R^b$, when present on adjacent atoms of $R^A$, are taken together with the intervening atoms connecting $R^a$ to $R^b$ to form a 5- to 6-membered monocyclic carbocycle or 5- to 6-membered monocyclic heterocycle, wherein the carbocycle or heterocycle is unsubstituted or substituted with one or more $R^6$ groups;

wherein, if $R^a$, $R^b$, and $R^c$ is attached to the N atom of a heteroaryl, then it is hydrogen, —C(═O)$R^7$, unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted $C_3$-$C_6$ cycloalkyl, or unsubstituted or substituted $C_2$-$C_7$ heterocycloalkyl;

$R^B$ is an unsubstituted or substituted phenyl or unsubstituted or substituted monocyclic 6-membered heteroaryl, wherein if $R^B$ is substituted then $R^B$ is substituted with 1, 2, 3 or 4 groups selected from $R^d$, $R^e$, and $R^f$;

$R^d$, $R^e$, and $R^f$ are independently selected from the group consisting of hydrogen, halogen, —$OR^4$, —CN, —$N(R^4)_2$, —C(═O)$R^7$, —C(═O)$N(R^4)_2$, unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted $C_3$-$C_6$ cycloalkyl, unsubstituted or substituted $C_2$-$C_7$ heterocycloalkyl, unsubstituted or substituted phenyl, and unsubstituted or substituted heteroaryl, wherein any substituted group of $R^d$, $R^e$, and $R^f$ is substituted with one or more $R^6$ groups;

wherein, if $R^d$, $R^e$, and $R^f$ is attached to the N atom of a heteroaryl, then it is hydrogen, —C(═O)$R^7$, unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted $C_3$-$C_6$ cycloalkyl, or unsubstituted or substituted $C_2$-$C_7$ heterocycloalkyl;

$X^1$ is $CR^{11}$ or N;

$X^2$ is $CR^{12}$ or N;

$X^3$ is $CR^{13}$ or N;

$X^4$ is $CR^{14}$ or N;

$R^{11}$, $R^{12}$, $R^{13}$, and $R^{14}$ are each independently hydrogen, halogen, unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted $C_3$-$C_6$cycloalkyl, —CN, —$OR^4$, —$SR^4$, —$CO_2R^4$, —C(═O)$N(R^4)_2$, or —$N(R^4)_2$;

$R^1$ is unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted $C_3$-$C_6$ cycloalkyl, unsubstituted or substituted $C_2$-$C_7$ heterocycloalkyl, unsubstituted or substituted —($C_1$-$C_6$ alkyl)-($C_3$-$C_6$ cycloalkyl), or unsubstituted or substituted —($C_1$-$C_6$ alkyl)-($C_2$-$C_7$ heterocycloalkyl), wherein any substituted group of $R^1$ is substituted with one or more halogen, unsubstituted or substituted $C_1$-$C_6$ alkyl, unsubstituted or substituted monocyclic heterocycle, —$N(R^4)_2$, —$OR^5$, —CN, —$CO_2R^5$, —C(═O)$N(R^4)_2$, —$SR^5$, —S(═O)$R^7$, —S(═O)$_2R^7$, —$NR^4$C(═O)$R^5$, —$NR^4SO_2R^7$, —$SO_2R^7$, or —$SO_2N(R^4)_2$;

each $R^3$ is independently hydrogen, unsubstituted or substituted $C_1$-$C_6$ alkyl, unsubstituted or substituted $C_3$-$C_6$ cycloalkyl, or unsubstituted or substituted $C_2$-$C_7$ heterocycloalkyl;

each $R^4$ is independently selected from the group consisting of hydrogen, unsubstituted or substituted $C_1$-$C_6$ alkyl, unsubstituted or substituted $C_3$-$C_6$ cycloalkyl, unsubstituted or substituted $C_1$-$C_6$fluoroalkyl, unsubstituted or substituted aryl, and unsubstituted or substituted heteroaryl;

or two $R^4$ are taken together with the nitrogen atom to which they are attached to form an unsubstituted or substituted 3- to 6-membered monocyclic heterocycle;

each $R^5$ is independently selected from the group consisting of hydrogen, substituted $C_1$-$C_6$ alkyl, unsubstituted or substituted $C_3$-$C_6$ cycloalkyl, unsubstituted or substituted $C_1$-$C_6$fluoroalkyl, unsubstituted or substituted aryl, and unsubstituted or substituted heteroaryl;

each $R^6$ is independently hydrogen, halogen, unsubstituted or substituted $C_1$-$C_4$alkyl, unsubstituted or substituted $C_1$-$C_4$alkoxy, unsubstituted or substituted $C_1$-$C_4$fluoroalkyl, unsubstituted or substituted $C_1$-$C_4$fluoroalkoxy, unsubstituted or substituted monocyclic carbocycle, unsubstituted or substituted monocyclic heterocycle, —CN, —OH, —$CO_2R^5$, —$CH_2CO_2R^5$, —C(═O)$N(R^4)_2$, —C(═O)$N(R^4)OR^5$, —$CH_2$C(═O)$N(R^4)_2$, —$N(R^4)_2$, —$CH_2N(R^4)_2$, —$C(R^5)_2N(R^4)_2$, —$NR^4$C(═O)$R^5$, —$CH_2NR^4$C(═O)$R^5$, —$NR^4$C(═O)$N(R^3)_2$, —$NR^4$C(═O)$N(R^4)_2$, $C(R^5)$═$N(R^4)$—$OR^5$, —$SR^5$, —S(═O)$R^7$, —$SO_2R^7$, or —$SO_2N(R^4)_2$; and each $R^7$ is independently selected from the group consisting substituted $C_1$-$C_6$ alkyl, unsubstituted or substituted $C_3$-$C_6$ cycloalkyl, unsubstituted or substituted $C_1$-$C_6$fluoroalkyl, unsubstituted or substituted phenyl, and unsubstituted or substituted heteroaryl.

2. The compound of claim 1, or a pharmaceutically acceptable salt thereof, wherein:

$R^A$ is

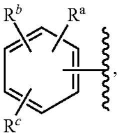,
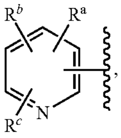,
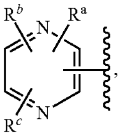,
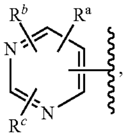, or
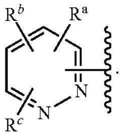.

and $R^B$ is

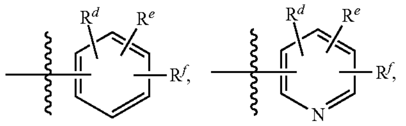

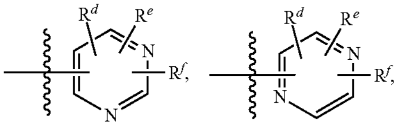

or

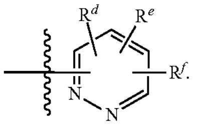

3. The compound of claim 1, or a pharmaceutically acceptable salt thereof, wherein the compound has the structure of Formula (IVa), or a pharmaceutically acceptable salt thereof:

Formula (IVa)

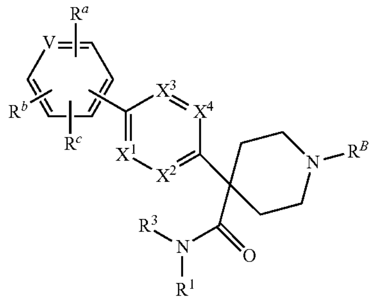

wherein V is CH, $CR^a$, $CR^b$, or N.

4. The compound of claim 1, or a pharmaceutically acceptable salt thereof, wherein the compound has the structure of Formula (VIa), Formula (VIc), Formula (VIb), Formula (VId), Formula (VIIb) or Formula (VIIe), or a pharmaceutically acceptable salt thereof:

Formula (VIa)

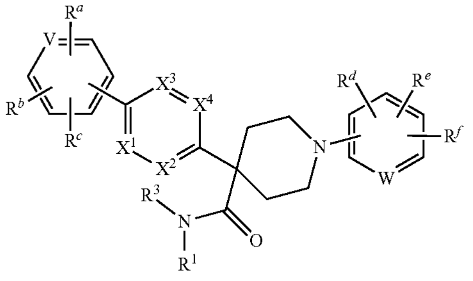

Formula (VIc)

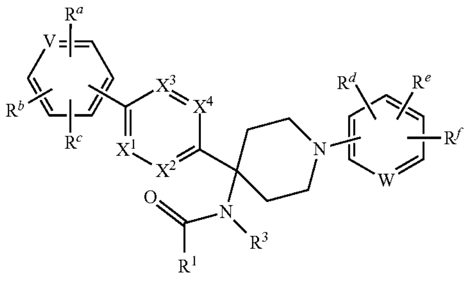

Formula (VIb)

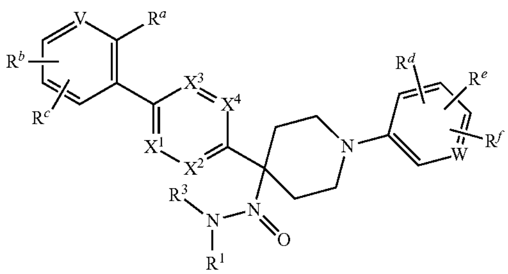

-continued

Formula (VId)

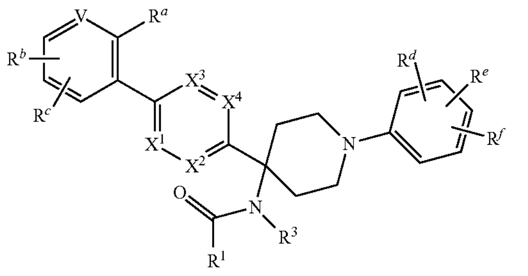

Formula (VIIb)

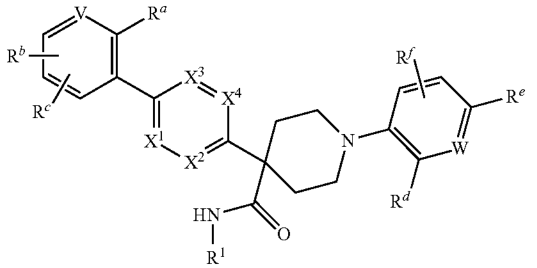

Formula (VIIe)

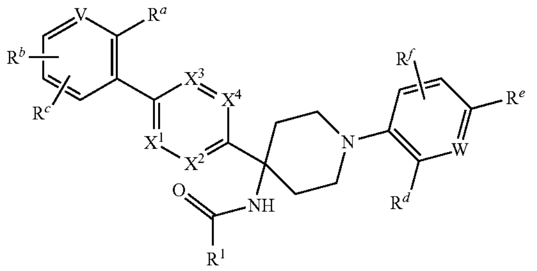

wherein V is CH, $CR^a$, $CR^b$, or N; and W is CH, $CR^d$, $CR^e$, or N.

5. The compound of claim 4, or a pharmaceutically acceptable salt thereof, wherein:

$R^1$ is unsubstituted or substituted $C_1$-$C_6$ alkyl, unsubstituted or substituted $C_1$-$C_6$ heteroalkyl containing 1 N atom, wherein any substituted group of $R^1$ is substituted with one or more halogen, unsubstituted or substituted $C_1$-$C_6$ alkyl, unsubstituted or substituted monocyclic heterocycle, $—N(R^4)_2$, $—OR^5$, —CN, $—CO_2R^3$, $—C(=O)N(R^4)_2$, $—SR^5$, $—S(=O)R^7$, $—S(=O)_2R^7$, $—NR^4C(=O)R^5$, $—NR^4SO_2R^7$, $—SO_2R^7$, or $—SO_2N(R^4)_2$;

or $R^1$ is unsubstituted or substituted monocyclic 4-, 5- or 6-membered heterocycle containing 1-4 N atoms and 0 or 1 O or S atoms;

or $R^1$ is unsubstituted or substituted bridged $C_2$-$C_7$ heterocycloalkyl containing 1-2 N atoms;

or $R^1$ is unsubstituted or substituted —($C_1$-$C_6$ alkyl)-($C_2$-$C_7$ heterocycloalkyl), wherein the heterocycloalkyl is an unsubstituted or substituted monocyclic 4-, 5- or 6-membered heterocycloalkyl containing 1-4 N atoms and 0 or 1 O or S atoms.

6. The compound of claim 5, or a pharmaceutically acceptable salt thereof, wherein:

$R^1$ is unsubstituted or substituted $C_1$-$C_6$ heteroalkyl containing 1 N atom;

or $R^1$ is unsubstituted or substituted monocyclic 4-, 5- or 6-membered heterocycle containing 1-4 N atoms and 0 or 1 O or S atoms;

or $R^1$ is unsubstituted or substituted —($C_1$-$C_6$ alkyl)-($C_2$-$C_7$ heterocycloalkyl), wherein the heterocycloalkyl is an unsubstituted or substituted monocyclic 4-, 5- or 6-membered heterocycloalkyl containing 1-4 N atoms and 0 or 1 O or S atoms.

7. The compound of claim 4, or a pharmaceutically acceptable salt thereof, wherein:

$X^1$ is CH, CF, or N;

$X^2$ is CH, CF, or N;

$X^3$ is CH, CF, or N; and $X^4$ is CH, CF, or N.

8. The compound of claim 7, or a pharmaceutically acceptable salt thereof, wherein:

$X^1$ is N;

$X^2$ is CH;

$X^3$ is CH or CF; and $X^4$ is CH.

9. The compound of claim 1, or a pharmaceutically acceptable salt thereof, wherein:

$R^a$ is selected from the group consisting of hydrogen, halogen, $—OR^4$, —CN, $—N(R^4)_2$, $—C(=O)R^7$, unsubstituted or substituted $C_1$-$C_6$ alkyl, unsubstituted or substituted $C_1$-$C_6$ fluoroalkyl, unsubstituted or substituted $C_1$-$C_6$ heteroalkyl, and unsubstituted or substituted $C_3$-$C_6$ cycloalkyl, wherein any substituted group of $R^a$ is substituted with one or more $R^6$ groups;

$R^b$ and $R^c$ are independently selected from the group consisting of hydrogen, halogen, —$OR^4$, —CN, —$N(R^4)_2$, —C(═O)$R^7$, unsubstituted or substituted $C_1$-$C_6$ alkyl, unsubstituted or substituted $C_1$-$C_6$ fluoroalkyl, and unsubstituted or substituted $C_1$-$C_6$ heteroalkyl, wherein any substituted group of $R^b$ and $R^c$ is substituted with one or more $R^6$ groups;

wherein, if $R^a$, $R^b$, or $R^c$ is attached to the N atom of a heteroaryl, then it is hydrogen, —C(═O)$R^7$, or unsubstituted or substituted $C_1$-$C_6$ alkyl;

$R^d$ is selected from the group consisting of hydrogen, halogen, —$OR^4$, —CN, —$N(R^4)_2$, unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted $C_3$-$C_6$ cycloalkyl, unsubstituted or substituted $C_2$-$C_7$ heterocycloalkyl, unsubstituted or substituted phenyl, unsubstituted or substituted monocyclic heteroaryl, and unsubstituted or substituted bicyclic heteroaryl, wherein any substituted group of $R^d$ is substituted with one or more $R^6$ groups; and $R^e$ and $R^f$ are independently selected from the group consisting of hydrogen, halogen, —$OR^4$, —CN, —$N(R^4)_2$, unsubstituted or substituted $C_1$-$C_6$ alkyl, unsubstituted or substituted $C_1$-$C_6$ fluoroalkyl, and unsubstituted or substituted $C_1$-$C_6$ heteroalkyl;

wherein, if $R^d$, $R^e$, or $R^f$ is attached to the N atom of a heteroaryl, then it is hydrogen, —C(═O)$R^7$, or unsubstituted or substituted $C_1$-$C_6$ alkyl.

10. The compound of claim 1, or a pharmaceutically acceptable salt thereof, wherein:

$R^a$ is selected from the group consisting of hydrogen, F, Cl, Br, —CN, —OH, —$OCH_3$, —$OCH_2CH_3$, —C(O)$CH_3$, —C(O)$CH_2CH_3$, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)(CH_2CH_3)$, —$C(CH_3)_3$, —$CH_2CH_2CH(CH_3)_2$, —$CH_2OH$, —$CH_2CN$, —$CH_2F$, —$CHF_2$, —$CF_3$, —$CH_2CH_2OH$, —$CH_2CH_2CN$, —$CH_2CH_2F$, —$CH_2CHF_2$, —$CH_2CF_3$, —$CH_2OCH_3$, —$CH_2CH_2OCH_3$, —$CH_2NH_2$, —$CH_2NHCH_3$, —$CH_2N(CH_3)_2$, —$CH_2CH_2NH_2$, —$CH_2CH_2NHCH_3$, —$CH_2CH_2N(CH_3)_2$, cyclopropyl, cyclobutyl, cyclopentyl, and cyclohexyl;

$R^b$ and $R^c$ are independently selected from the group consisting of hydrogen, F, Cl, Br, —CN, —OH, —$OCH_3$, —$OCH_2CH_3$, —C(O)$CH_3$, —C(O)$CH_2CH_3$, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)(CH_2CH_3)$, —$C(CH_3)_3$, —$CH_2CH_2CH(CH_3)_2$, —$CH_2OH$, —$CH_2CN$, —$CH_2F$, —$CHF_2$, —$CF_3$, —$CH_2CH_2OH$, —$CH_2CH_2CN$, —$CH_2CH_2F$, —$CH_2CHF_2$, —$CH_2CF_3$, —$CH_2OCH_3$, —$CH_2CH_2OCH_3$, —$CH_2NH_2$, —$CH_2NHCH_3$, —$CH_2N(CH_3)_2$, —$CH_2CH_2NH_2$, —$CH_2CH_2NHCH_3$, and —$CH_2CH_2N(CH_3)_2$;

wherein, if $R^a$, $R^b$, or $R^c$ is attached to the N atom of a heteroaryl, then it is hydrogen, —C(O)$CH_3$, —C(O)$CH_2CH_3$, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)(CH_2CH_3)$, —$C(CH_3)_3$, —$CH_2CH_2CH(CH_3)_2$, —$CH_2OH$, —$CH_2CN$, —$CH_2F$, —$CHF_2$, —$CF_3$, —$CH_2CH_2OH$, —$CH_2CH_2CN$, —$CH_2CH_2F$, —$CH_2CHF_2$, —$CH_2CF_3$, —$CH_2OCH_3$, —$CH_2CH_2OCH_3$, —$CH_2NH_2$, —$CH_2NHCH_3$, —$CH_2N(CH_3)_2$, —$CH_2CH_2NH_2$, —$CH_2CH_2NHCH_3$, and —$CH_2CH_2N(CH_3)_2$;

$R^d$ is selected from the group consisting of hydrogen, F, Cl, Br, —CN, —OH, —$OCH_3$, —$OCH_2CH_3$, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)(CH_2CH_3)$, —$C(CH_3)_3$, —$CH_2CH_2CH(CH_3)_2$, —$CH_2OH$, —$CH_2CN$, —$CH_2F$, —$CHF_2$, —$CF_3$, —$CH_2CH_2OH$, —$CH_2CH_2CN$, —$CH_2CH_2F$, —$CH_2CHF_2$, —$CH_2CF_3$, —$CH_2OCH_3$, —$CH_2CH_2OCH_3$, —$CH_2NH_2$, —$CH_2NHCH_3$, —$CH_2N(CH_3)_2$, —$CH_2CH_2NH_2$, —$CH_2CH_2NHCH_3$, —$CH_2CH_2N(CH_3)_2$, unsubstituted or substituted cyclopropyl, unsubstituted or substituted cyclobutyl, unsubstituted or substituted cyclopentyl, unsubstituted or substituted cyclohexyl, unsubstituted or substituted $C_2$-$C_7$ heterocycloalkyl, unsubstituted or substituted phenyl, unsubstituted or substituted monocyclic heteroaryl, and unsubstituted or substituted bicyclic heteroaryl, wherein any substituted group of $R^d$ is substituted with one or more $R^6$ groups; and $R^e$ and $R^f$ are independently selected from the group consisting of hydrogen, F, Cl, Br, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)(CH_2CH_3)$, —$C(CH_3)_3$, —$CH_2CH_2CH(CH_3)_2$, —$CH_2OH$, —$CH_2CN$, —$CH_2F$, —$CHF_2$, —$CF_3$, —CN, —OH, —$OCH_3$, and —$OCH_2CH_3$;

wherein, if $R^d$, $R^e$, or $R^f$ is attached to the N atom of a heteroaryl, then it is hydrogen, —C(O)$CH_3$, —C(O)$CH_2CH_3$, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)(CH_2CH_3)$, —$C(CH_3)_3$, —$CH_2CH_2CH(CH_3)_2$, —$CH_2OH$, —$CH_2CN$, —$CH_2F$, —$CHF_2$, —$CF_3$, —$CH_2CH_2OH$, —$CH_2CH_2CN$, —$CH_2CH_2F$, —$CH_2CHF_2$, —$CH_2CF_3$, —$CH_2OCH_3$, —$CH_2CH_2OCH_3$, —$CH_2NH_2$, —$CH_2NHCH_3$, —$CH_2N(CH_3)_2$, —$CH_2CH_2NH_2$, —$CH_2CH_2NHCH_3$, and —$CH_2CH_2N(CH_3)_2$.

11. The compound of claim 1, or a pharmaceutically acceptable salt thereof, wherein:

$R^A$ is unsubstituted or substituted pyridinyl, unsubstituted or substituted phenyl, or unsubstituted or substituted pyrrolyl, wherein if $R^A$ is substituted then $R^A$ is substituted with 1, or 2 groups selected from $R^a$, $R^b$, and $R^c$;

$R^B$ is unsubstituted or substituted phenyl or unsubstituted or substituted pyridinyl, wherein if $R^B$ is substituted then $R^B$ is substituted with 1, 2, or 3 groups selected from $R^d$, $R^e$, and $R^f$;

$X^1$ is CH or N;

$X^2$ is CH or N;

$X^3$ is $CR^{13}$ or N;

$X^4$ is CH or N;

$R^{11}$, $R^{12}$, $R^{13}$, and $R^{14}$ are each independently hydrogen, F, Cl, —$CH_3$, $CF_3$, —CN, —$OR^4$, or —$N(R^4)_2$;

$R^1$ is unsubstituted or substituted $C_1$-$C_6$ heteroalkyl containing 1 N atom, wherein any substituted group of $R^1$ is substituted with one or more halogen, $C_1$-$C_4$ alkyl, —$N(R^4)_2$, or —$OR^5$;

or $R^1$ is unsubstituted or substituted azetidinyl, unsubstituted or substituted pyrrolidinyl, or unsubstituted or substituted piperidinyl;

or $R^1$ is unsubstituted or substituted bridged $C_2$-$C_7$ heterocycloalkyl containing 1-2 N atoms;

or $R^1$ is unsubstituted or substituted —($C_1$-$C_6$ alkyl)-($C_2$-$C_7$ heterocycloalkyl), wherein the heterocycloalkyl is an unsubstituted or substituted monocyclic 4-, 5- or 6-membered heterocycloalkyl containing 1-2 N atoms.

12. The compound of claim 1, or a pharmaceutically acceptable salt thereof, wherein:

$R^A$ is

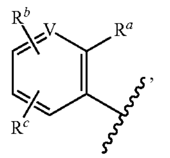

or $R^A$ is

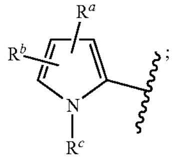

or $R^A$ is

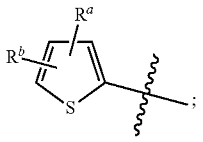

where V is CH or N;

$R^a$ is selected from the group consisting of hydrogen, halogen, —$OR^4$, —CN, unsubstituted or substituted $C_1$-$C_6$ alkyl, unsubstituted or substituted $C_1$-$C_6$ fluoroalkyl, and unsubstituted or substituted $C_3$-$C_6$ cycloalkyl; and $R^b$ and $R^c$ are independently selected from the group consisting of hydrogen, halogen, —$OR^4$, —CN, unsubstituted or substituted $C_1$-$C_6$ alkyl, and unsubstituted or substituted $C_1$-$C_6$ fluoroalkyl;

$R^B$ is

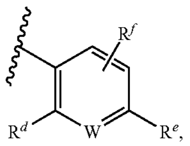

where W is CH or N;

$R^d$ is selected from the group consisting of hydrogen, halogen, —$OR^4$, —CN, unsubstituted or substituted $C_1$-$C_6$ alkyl, unsubstituted or substituted $C_1$-$C_6$ fluoroalkyl, and unsubstituted or substituted $C_3$-$C_6$ cycloalkyl; and $R^e$ and $R^f$ are independently selected from the group consisting of hydrogen, halogen, —$OR^4$, —CN, unsubstituted or substituted $C_1$-$C_6$ alkyl, and unsubstituted or substituted $C_1$-$C_6$ fluoroalkyl;

$X^1$ is CH, CF, or N;

$X^2$ is CH, CF, or N;

$X^3$ is CH, CF, or N;

$X^4$ is CH, CF, or N;

$R^1$ is unsubstituted or substituted $C_1$-$C_6$ alkyl, unsubstituted or substituted $C_1$-$C_6$ heteroalkyl containing 1 N atom, wherein any substituted group of $R^1$ is substituted with one or more halogen, unsubstituted or substituted $C_1$-$C_6$ alkyl, unsubstituted or substituted monocyclic heterocycle, —$N(R^4)_2$, —$OR^5$, —CN, —$CO_2R^5$, —$C(=O)N(R^4)_2$, —$SR^5$ —$S(=O)R^7$, —$S(=O)_2R^7$, —$NR_4C(=O)R^5$, —$NR^4SO_2R^7$, —$SO_2R^7$, or —$SO_2N(R^4)_2$;

or $R^1$ is unsubstituted or substituted monocyclic 4-, 5- or 6-membered heterocycle containing 1-4 N atoms and 0 or 1 O or S atoms;

or $R^1$ is unsubstituted or substituted bridged $C_2$-$C_7$ heterocycloalkyl containing 1-2 N atoms;

or $R^1$ is unsubstituted or substituted —($C_1$-$C_6$ alkyl)-($C_2$-$C_7$ heterocycloalkyl), wherein the heterocycloalkyl is an unsubstituted or substituted monocyclic 4-, 5- or 6-membered heterocycloalkyl containing 1-2 N atoms.

13. The compound of claim 1, or a pharmaceutically acceptable salt thereof, wherein:

$R^A$ is

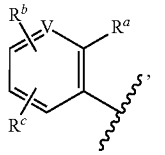

where V is CH or N;

$R^a$ is selected from the group consisting of hydrogen, F, Cl, Br, —CN, —$OCH_3$, —$OCH_2CH_3$, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)(CH_2CH_3)$, —$C(CH_3)_3$, —$CH_2F$, —$CHF_2$, and —$CF_3$; and $R^b$ and $R^c$ are independently selected from the group consisting of hydrogen, F, Cl, —$CH_3$, —$CH_2F$, —$CHF_2$, —$CF_3$, —CN, and —$OCH_3$;

$R^B$ is

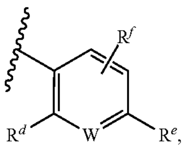

where W is CH or N;

$R^d$ is selected from the group consisting of hydrogen, F, Cl, Br, —CN, —$OCH_3$, —$OCH_2CH_3$, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$), —$C(CH_3)_3$, —$CH_2F$, —$CHF_2$, and —$CF_3$;

$R^e$ and $R^f$ are independently selected from the group consisting of hydrogen, F, Cl, Br, —$CH_3$, —$CH_2F$, —$CHF_2$, —$CF_3$, —CN, —OH, and —$OCH_3$;

$X^1$ is CH or N;

$X^2$ is CH or N;

$X^3$ is CH, CF, or N;

$X^4$ is CH or N;

$R^1$ is unsubstituted or substituted $C_1$-$C_6$ alkyl, unsubstituted or substituted $C_1$-$C_6$ heteroalkyl containing 1 N atom, wherein any substituted group of $R^1$ is substituted with one or more halogen, unsubstituted or substituted $C_1$-$C_6$ alkyl, unsubstituted or substituted monocyclic heterocycle, —$N(R^4)_2$, —$OR^5$, —CN, —$CO_2R^5$, —C(═O)$N(R^4)_2$, —$SR^5$, —S(═O)$R^7$, —S(═O)$_2R^7$, —$NR^4C$(═O)$R^5$, —$NR^4SO_2R^7$, —$SO_2R^7$, or —$SO_2N(R^4)_2$;

or $R^1$ is unsubstituted or substituted monocyclic 4-, 5- or 6-membered heterocycle containing 1-4 N atoms and 0 or 1 O or S atoms;

or $R^1$ is unsubstituted or substituted bridged $C_2$-$C_7$ heterocycloalkyl containing 1-2 N atoms;

or $R^1$ is unsubstituted or substituted —($C_1$-$C_6$ alkyl)-($C_2$-$C_7$ heterocycloalkyl), wherein the heterocycloalkyl is an unsubstituted or substituted monocyclic 4-, 5- or 6-membered heterocycloalkyl containing 1-2 N atoms.

14. The compound of claim 1, or a pharmaceutically acceptable salt thereof, wherein:

$R^A$ is unsubstituted or substituted 6-membered or 5-membered heteroaryl containing 1 or 2 N atoms or unsubstituted or substituted phenyl, wherein if $R^A$ is substituted then $R^A$ is substituted with 1 or 2 groups selected from $R^a$, $R^b$, and $R^c$;

$R^a$ is selected from the group consisting of hydrogen, halogen, —$OR^4$, —CN, —$N(R^4)_2$, —C(═O)$R^7$, unsubstituted or substituted $C_1$-$C_6$ alkyl, unsubstituted or substituted $C_1$-$C_6$ fluoroalkyl, unsubstituted or substituted $C_1$-$C_6$ heteroalkyl, and unsubstituted or substituted $C_3$-$C_6$ cycloalkyl, wherein any substituted group of $R^a$ is substituted with one or more $R^6$ groups; and $R^b$ and $R^c$ are independently selected from the group consisting of hydrogen, halogen, —$OR^4$, —CN, —$N(R^4)_2$, —C(═O)$R^7$, unsubstituted or substituted $C_1$-$C_6$ alkyl, unsubstituted or substituted $C_1$-$C_6$ fluoroalkyl, and unsubstituted or substituted $C_1$-$C_6$ heteroalkyl, wherein any substituted group of $R^b$ and $R^c$ is substituted with one or more $R^6$ groups;

wherein, if $R^a$, $R^b$, or $R^c$ is attached to the N atom of a heteroaryl, then it is hydrogen, —C(═O)$R^7$, or unsubstituted or substituted $C_1$-$C_6$ alkyl;

$R^B$ is unsubstituted or substituted phenyl or unsubstituted or substituted 5- or 6-membered heteroaryl containing 1 or 2 N atoms, wherein if $R^B$ is substituted then $R^B$ is substituted with 1, 2, or 3 groups selected from $R^d$, $R^e$, and $R^f$, $R^d$ is selected from the group consisting of hydrogen, halogen, —$OR^4$, —CN, —$N(R^4)_2$, unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted $C_3$-$C_6$ cycloalkyl, unsubstituted or substituted $C_2$-$C_7$ heterocycloalkyl, unsubstituted or substituted phenyl, unsubstituted or substituted monocyclic heteroaryl, and unsubstituted or substituted bicyclic heteroaryl, wherein any substituted group of $R^d$ is substituted with one or more $R^6$ groups; and $R^e$ and $R^f$ are independently selected from the group consisting of hydrogen, halogen, —$OR^4$, —CN, —$N(R^4)_2$, unsubstituted or substituted $C_1$-$C_6$ alkyl, unsubstituted or substituted $C_1$-$C_6$ fluoroalkyl, and unsubstituted or substituted $C_1$-$C_6$ heteroalkyl;

wherein, if $R^d$, $R^e$, or $R^f$ is attached to the N atom of a heteroaryl, then it is hydrogen, —C(═O)$R^7$, or unsubstituted or substituted $C_1$-$C_6$ alkyl;

$X^1$ is $CR^{11}$ or N;

$X^2$ is $CR^{12}$ or N;

$X^3$ is CH;

$X^4$ is CH;

$R^{11}$ and $R^{12}$ are each independently hydrogen, halogen, $C_1$-$C_6$ alkyl, $C_1$-$C_6$ fluoroalkyl, or $C_1$-$C_6$ heteroalkyl, —CN, —$OR^4$, or —$N(R^4)_2$; and $R^1$ is unsubstituted or substituted $C_1$-$C_6$ alkyl, unsubstituted or substituted $C_1$-$C_6$ heteroalkyl containing 1 N atom, wherein any substituted group of $R^1$ is substituted with one or more halogen, unsubstituted or substituted $C_1$-$C_6$ alkyl, unsubstituted or substituted monocyclic heterocycle, —$N(R^4)_2$, —$OR^5$, —CN, —$CO_2R^5$, —C(═O)$N(R^4)_2$, —$SR^5$, —S(═O)$R^7$, —S(═O)$_2R^7$, —$NR^4C$(═O)$R^5$, —$NR^4SO_2R^7$, —$SO_2R^7$, or —$SO_2N(R^4)_2$;

or $R^1$ is unsubstituted or substituted monocyclic 4-, 5- or 6-membered heterocycle containing 1-4 N atoms and 0 or 1 O or S atoms;

or $R^1$ is unsubstituted or substituted bridged $C_2$-$C_7$ heterocycloalkyl containing 1-2 N atoms;

or $R^1$ is unsubstituted or substituted —($C_1$-$C_6$ alkyl)-($C_2$-$C_7$heterocycloalkyl), wherein the heterocycloalkyl is an unsubstituted or substituted monocyclic 4-, 5- or 6-membered heterocycloalkyl containing 1-2 N atoms.

15. The compound of claim 14, or a pharmaceutically acceptable salt thereof, wherein:

$R^A$ is unsubstituted or substituted pyridinyl, unsubstituted or substituted phenyl, or unsubstituted or substituted pyrrolyl, wherein if $R^A$ is substituted then $R^A$ is substituted with 1 or 2 groups selected from $R^a$, $R^b$, and $R^e$;

wherein, if $R^a$, $R^b$, and $R^c$ is attached to the N atom of a heteroaryl, then it is hydrogen, —C(═O)$R^7$, or unsubstituted or substituted $C_1$-$C_6$ alkyl;

$R^B$ is unsubstituted or substituted phenyl or unsubstituted or substituted pyridinyl, wherein if $R^B$ is substituted then $R^B$ is substituted with 1, 2, or 3 groups selected from $R^d$, $R^e$, and $R^f$;

$X^1$ is $CR^{11}$ or N;

$X^2$ is $CR^{12}$ or N;

$R^{11}$ and $R^{12}$ are each independently hydrogen, F, Cl, —$CH_3$, $CF_3$, —CN, —$OR^4$, or —$N(R^4)_2$;

$R^1$ is unsubstituted or substituted $C_1$-$C_6$ heteroalkyl containing 1 N atom, wherein any substituted group of $R^1$ is substituted with one or more halogen, $C_1$-$C_4$ alkyl, —$N(R^4)_2$, or —$OR^5$;

or $R^1$ is unsubstituted or substituted azetidinyl, unsubstituted or substituted pyrrolidinyl, or unsubstituted or substituted piperidinyl;

or $R^1$ is unsubstituted or substituted bridged $C_2$-$C_7$ heterocycloalkyl containing 1-2 N atoms;

or $R^1$ is unsubstituted or substituted —($C_1$-$C_6$ alkyl)-($C_2$-$C_7$ heterocycloalkyl), wherein the $C_2$-$C_7$ heterocycloalkyl is an unsubstituted or substituted monocyclic 4-, 5- or 6-membered heterocycloalkyl containing 1-2 N atoms.

16. A compound that is:

1-1: 1-[2-cyano-4-(trifluoromethyl)phenyl]-4-[4-(2-ethoxypyridin-3-yl)phenyl]-N-[(3R)-1-methylpyrrolidin-3-yl]piperidine-4-carboxamide;

1-2: 1-[2-cyano-4-(trifluoromethyl)phenyl]-4-[4-(2-ethoxypyridin-3-yl)phenyl]-N-[(3R)-pyrrolidin-3-yl]piperidine-4-carboxamide;

1-3: N-(2-aminoethyl)-1-[2-cyano-4-(trifluoromethyl)phenyl]-4-[4-(2-ethoxypyridin-3-yl)phenyl]piperidine-4-carboxamide;

1-4: N-[(2R)-2-aminopropyl]-1-[2-cyano-4-(trifluoromethyl)phenyl]-4-[4-(2-ethoxypyridin-3-yl)phenyl]piperidine-4-carboxamide;

1-5: N-(3-aminopropyl)-1-[2-cyano-4-(trifluoromethyl)phenyl]-4-[4-(2-ethoxypyridin-3-yl)phenyl]piperidine-4-carboxamide;

1-6: N-[(2S)-2-aminopropyl]-1-[2-cyano-4-(trifluoromethyl)phenyl]-4-[4-(2-ethoxypyridin-3-yl)phenyl]piperidine-4-carboxamide;

1-7: 1-[2-cyano-4-(trifluoromethyl)phenyl]-4-[4-(2-ethoxypyridin-3-yl)phenyl]-N-[2-(methylamino)ethyl]piperidine-4-carboxamide;

1-8: 1-[2-cyano-4-(trifluoromethyl)phenyl]-N-[2-(dimethylamino)ethyl]-4-[4-(2-ethoxypyridin-3-yl)phenyl]piperidine-4-carboxamide;

1-9: 1-[2-cyano-4-(trifluoromethyl)phenyl]-4-{2'-ethoxy-[2,3'-bipyridin]-5-yl}-N-[(3R)-1-methylpyrrolidin-3-yl]piperidine-4-carboxamide;

1-10: 1-[2-cyano-4-(trifluoromethyl)phenyl]-4-{2'-ethoxy-[2,3'-bipyridin]-5-yl}-N-[(3R)-pyrrolidin-3-yl]piperidine-4-carboxamide;

1-11: 1-[2-cyano-4-(trifluoromethyl)phenyl]-4-{2'-ethoxy-[2,3'-bipyridin]-5-yl}-N-[(3S)-1-methylpyrrolidin-3-yl]piperidine-4-carboxamide;

1-12: 1-[2-cyano-4-(trifluoromethyl)phenyl]-4-{2'-ethoxy-[2,3'-bipyridin]-5-yl}-N-[(3S)-pyrrolidin-3-yl]piperidine-4-carboxamide;

1-13: N-(2-aminoethyl)-1-[2-cyano-4-(trifluoromethyl)phenyl]-4-{2'-ethoxy-[2,3'-bipyridin]-5-yl}piperidine-4-carboxamide;

1-14: 1-[2-cyano-4-(trifluoromethyl)phenyl]-4-{2'-ethoxy-[2,3'-bipyridin]-5-yl}-N-[2-(methylamino)ethyl]piperidine-4-carboxamide;

1-15: 1-[2-cyano-4-(trifluoromethyl)phenyl]-N-[2-(dimethylamino)ethyl]-4-{2'-ethoxy-[2,3'-bipyridin]-5-yl}piperidine-4-carboxamide;

1-16: N-[(2S)-2-aminopropyl]-1-[2-cyano-4-(trifluoromethyl)phenyl]-4-{2'-ethoxy-[2,3'-bipyridin]-5-yl}piperidine-4-carboxamide;

1-17: N-[(2R)-2-amino-3-hydroxypropyl]-1-[2-cyano-4-(trifluoromethyl)phenyl]-4-{2'-ethoxy-[2,3'-bipyridin]-5-yl}piperidine-4-carboxamide;

1-18: 1-[2-cyano-4-(trifluoromethyl)phenyl]-4-{2'-ethoxy-[2,3'-bipyridin]-5-yl}-N-[(1-methylazetidin-3-yl)methyl]piperidine-4-carboxamide;

1-19: 1-[2-cyano-4-(trifluoromethyl)phenyl]-4-{2'-ethoxy-[2,3'-bipyridin]-5-yl}-N-(1-methylazetidin-3-yl)piperidine-4-carboxamide;

1-20: N-[(3S)-1-azabicyclo[2.2.2]octan-3-yl]-1-[2-cyano-4-(trifluoromethyl)phenyl]-4-{2'-ethoxy-[2,3'-bipyridin]-5-yl}piperidine-4-carboxamide;

1-21: 1-[2-cyano-4-(trifluoromethyl)phenyl]-4-{2'-ethoxy-[3,3'-bipyridin]-6-yl}-N-[(3R)-pyrrolidin-3-yl]piperidine-4-carboxamide;

1-22: 1-[2-cyano-4-(trifluoromethyl)phenyl]-4-{2'-ethoxy-[3,3'-bipyridin]-6-yl}-N-[(3R)-1-methylpyrrolidin-3-yl]piperidine-4-carboxamide;

1-23: 1-[2-cyano-6-(trifluoromethyl)pyridin-3-yl]-4-[4-(2-ethoxypyridin-3-yl)phenyl]-N-[(3R)-1-methylpyrrolidin-3-yl]piperidine-4-carboxamide;

1-24: 1-[2-cyano-6-(trifluoromethyl)pyridin-3-yl]-4-{2'-ethoxy-[2,3'-bipyridin]-5-yl}-N-[(3R)-1-methylpyrrolidin-3-yl]piperidine-4-carboxamide;

1-25: 3-(4-{2'-ethoxy-[2,3'-bipyridin]-5-yl}-4-{[(3R)-1-methylpyrrolidin-3-yl]carbamoyl}piperidin-1-yl)-6-(trifluoromethyl)pyridine-2-carboxamide;

1-26: 1-[2-cyano-6-(trifluoromethyl)pyridin-3-yl]-4-{2'-ethoxy-[2,3'-bipyridin]-5-yl}-N-[(3S)-1-methylpyrrolidin-3-yl]piperidine-4-carboxamide;

1-27: 3-(4-{2'-ethoxy-[2,3'-bipyridin]-5-yl}-4-{[(3S)-1-methylpyrrolidin-3-yl]carbamoyl}piperidin-1-yl)-6-(trifluoromethyl)pyridine-2-carboxamide;

1-28: N-[(2S)-2-amino-3-hydroxypropyl]-1-[2-cyano-4-(trifluoromethyl)phenyl]-4-{2'-ethoxy-[2,3'-bipyridin]-5-yl}piperidine-4-carboxamide;

1-29: 1-[2-chloro-6-cyano-4-(trifluoromethyl)phenyl]-4-[4-(2-ethoxypyridin-3-yl)phenyl]-N-[(3R)-1-methylpyrrolidin-3-yl]piperidine-4-carboxamide;

1-30: 1-[2-cyano-4-(trifluoromethyl)phenyl]-4-[6-(2-ethoxyphenyl)pyridin-3-yl]-N-[(3S)-1-methylpyrrolidin-3-yl]piperidine-4-carboxamide;

1-31: 1-[2-cyano-4-(trifluoromethyl)phenyl]-4-[6-(2-ethoxyphenyl)pyridin-3-yl]-N-[(3R)-1-methylpyrrolidin-3-yl]piperidine-4-carboxamide;

1-32: 1-(2-cyanophenyl)-4-{2'-ethoxy-[2,3'-bipyridin]-5-yl}-N-[(3S)-1-methylpyrrolidin-3-yl]piperidine-4-carboxamide;

1-33: 4-{2'-ethoxy-[2,3'-bipyridin]-5-yl}-N-[(3S)-1-methylpyrrolidin-3-yl]-1-[4-(trifluoromethyl)phenyl]piperidine-4-carboxamide;

1-34: 1-(4-chloro-2-cyanophenyl)-4-{2'-ethoxy-[2,3'-bipyridin]-5-yl}-N-[(3S)-1-methylpyrrolidin-3-yl]piperidine-4-carboxamide;

1-35: 4-{2'-ethoxy-[2,3'-bipyridin]-5-yl}-N-[(3S)-1-methylpyrrolidin-3-yl]-1-[5-(trifluoromethyl)pyridin-2-yl]piperidine-4-carboxamide;

1-36: 1-(4-acetyl-2-cyanophenyl)-4-{2'-ethoxy-[2,3'-bipyridin]-5-yl}-N-[(3S)-1-methylpyrrolidin-3-yl]piperidine-4-carboxamide;

1-37: 1-[2-cyano-4-(difluoromethyl)phenyl]-4-{2'-ethoxy-[2,3'-bipyridin]-5-yl}-N-[(3S)-1-methylpyrrolidin-3-yl]piperidine-4-carboxamide;

1-38: 1-[4-cyano-2-(trifluoromethyl)phenyl]-4-(2'-ethoxy-[2,3'-bipyridin]-5-yl)-N-[(3S)-1-methylpyrrolidin-3-yl]piperidine-4-carboxamide;

1-39: 1-[2-cyano-4-(trifluoromethoxy)phenyl]-4-{2'-ethoxy-[2,3'-bipyridin]-5-yl}-N-[(3S)-1-methylpyrrolidin-3-yl]piperidine-4-carboxamide;

1-40: 1-(2,4-dicyanophenyl)-4-{2'-ethoxy-[2,3'-bipyridin]-5-yl}-N-[(3S)-1-methylpyrrolidin-3-yl]piperidine-4-carboxamide;

1-41: 1-[2-cyano-4-(trifluoromethyl)phenyl]-4-{2'-ethoxy-[2,3'-bipyridin]-5-yl}-N-[(3S,4S)*-4-hydroxy-1-methylpyrrolidin-3-yl]piperidine-4-carboxamide;

1-42: 1-[3-cyano-5-(trifluoromethyl)pyridin-2-yl]-4-{2'-ethoxy-[2,3'-bipyridin]-5-yl}-N-[(3S)-1-methylpyrrolidin-3-yl]piperidine-4-carboxamide;

1-43: 1-[2-cyano-4-(trifluoromethyl)phenyl]-4-[6-(1-methyl-1H-pyrazol-5-yl)pyridin-3-yl]-N-[(3R)-1-methylpyrrolidin-3-yl]piperidine-4-carboxamide;

1-44: 1-[2-cyano-4-(trifluoromethyl)phenyl]-4-{2'-ethoxy-[2,3'-bipyridin]-5-yl}-N-[(2R)-3-hydroxy-2-(methylamino)propyl]piperidine-4-carboxamide;

1-45: 1-[2-cyano-4-(trifluoromethyl)phenyl]-N-[(2R)-2-(dimethylamino)-3-hydroxypropyl]-4-{2'-ethoxy-[2,3'-bipyridin]-5-yl}piperidine-4-carboxamide;

1-46: 1-[2-cyano-4-(trifluoromethyl)phenyl]-4-{2'-ethoxy-[2,3'-bipyridin]-5-yl}-N-[(3R,4R)*-4-hydroxy-1-methylpyrrolidin-3-yl]piperidine-4-carboxamide;

1-47: 1-[2-cyano-4-(trifluoromethyl)phenyl]-4-{2'-ethoxy-[2,3'-bipyridin]-5-yl}-N-[(2S)-3-hydroxy-2-(methylamino)propyl]piperidine-4-carboxamide;

1-48: 1-[2-cyano-4-(trifluoromethyl)phenyl]-N-[(2S)-2-(dimethylamino)-3-hydroxypropyl]-4-{2'-ethoxy-[2,3'-bipyridin]-5-yl}piperidine-4-carboxamide;

1-51: 1-[2-cyano-4-(trifluoromethyl)phenyl]-4-[5-(2-ethoxypyridin-3-yl)pyrazin-2-yl]-N-[(3R)-1-methylpyrrolidin-3-yl]piperidine-4-carboxamide;

1-52: 1-[2-cyano-4-(trifluoromethyl)phenyl]-4-[6-(2-methoxyphenyl)pyridin-3-yl]-N-[(3R)-1-methylpyrrolidin-3-yl]piperidine-4-carboxamide;

1-53: 1-[2-cyano-4-(trifluoromethyl)phenyl]-4-[6-(2,3-dihydro-1-benzofuran-7-yl)pyridin-3-yl]-N-[(3R)-1-methylpyrrolidin-3-yl]piperidine-4-carboxamide;

1-54: 4-[6-(1-benzofuran-7-yl)pyridin-3-yl]-1-[2-cyano-4-(trifluoromethyl)phenyl]-N-[(3R)-1-methylpyrrolidin-3-yl]piperidine-4-carboxamide;

1-55: 1-[2-cyano-4-(trifluoromethyl)phenyl]-4-{6-[2-(hydroxymethyl)phenyl]pyridin-3-yl}-N-[(3R)-1-methylpyrrolidin-3-yl]piperidine-4-carboxamide;

1-56: 1-[2-cyano-4-(trifluoromethyl)phenyl]-4-[6-(2-ethoxypyridin-3-yl)pyridazin-3-yl]-N-[(3S)-1-methylpyrrolidin-3-yl]piperidine-4-carboxamide;

1-57: 1-[2-cyano-4-(trifluoromethyl)phenyl]-4-[6-(2-ethoxypyridin-3-yl)pyridazin-3-yl]-N-[(3R)-1-methylpyrrolidin-3-yl]piperidine-4-carboxamide;

1-58: 1-[2-cyano-4-(trifluoromethyl)phenyl]-4-[5-(2-ethoxypyridin-3-yl)pyrazin-2-yl]-N-[(3S)-1-methylpyrrolidin-3-yl]piperidine-4-carboxamide;

1-59: 1-[2-cyano-4-(1,1-difluoroethyl)phenyl]-4-{2'-ethoxy-[2,3'-bipyridin]-5-yl}-N-[(3S)-1-methylpyrrolidin-3-yl]piperidine-4-carboxamide;

1-60: 1-[2-cyano-4-(trifluoromethyl)phenyl]-4-[6-(2-ethylphenyl)pyridin-3-yl]-N-[(3R)-1-methylpyrrolidin-3-yl]piperidine-4-carboxamide;

1-61: 1-[2-cyano-4-(trifluoromethyl)phenyl]-4-[6-(2,3-difluorophenyl)pyridin-3-yl]-N-[(3R)-1-methylpyrrolidin-3-yl]piperidine-4-carboxamide;

1-62: 1-[2-cyano-4-(trifluoromethyl)phenyl]-4-[6-(1-ethyl-1H-pyrazol-5-yl)pyridin-3-yl]-N-[(3R)-1-methylpyrrolidin-3-yl]piperidine-4-carboxamide;

1-63: 1-[2-cyano-4-(trifluoromethyl)phenyl]-N-[(3R)-1-methylpyrrolidin-3-yl]-4-[6-(2-propoxyphenyl)pyridin-3-yl]piperidine-4-carboxamide;

1-64: 1-[2-cyano-4-(trifluoromethyl)phenyl]-4-[6-(3-fluorophenyl)pyridin-3-yl]-N-[(3R)-1-methylpyrrolidin-3-yl]piperidine-4-carboxamide;

1-65: 1-[2-cyano-4-(trifluoromethyl)phenyl]-4-[6-(3,5-difluorophenyl)pyridin-3-yl]-N-[(3R)-1-methylpyrrolidin-3-yl]piperidine-4-carboxamide;

1-66: 1-[2-cyano-4-(trifluoromethyl)phenyl]-4-[6-(2-methylphenyl)pyridin-3-yl]-N-[(3R)-1-methylpyrrolidin-3-yl]piperidine-4-carboxamide;

1-67: 1-[2-cyano-4-(trifluoromethyl)phenyl]-4-[6-(2,2-difluoro-2H-1,3-benzodioxol-4-yl)pyridin-3-yl]-N-[(3R)-1-methylpyrrolidin-3-yl]piperidine-4-carboxamide;

1-68: 1-[2-cyano-4-(trifluoromethyl)phenyl]-4-[6-(2,5-difluorophenyl)pyridin-3-yl]-N-[(3R)-1-methylpyrrolidin-3-yl]piperidine-4-carboxamide;

1-69: 1-[2-cyano-4-(trifluoromethyl)phenyl]-4-[6-(2-ethoxy-5-fluorophenyl)pyridin-3-yl]-N-[(3R)-1-methylpyrrolidin-3-yl]piperidine-4-carboxamide;

1-70: 1-[2-cyano-4-(trifluoromethyl)phenyl]-4-{6-[1-(3-methylbutyl)-1H-pyrazol-5-yl]pyridin-3-yl}-N-[(3R)-1-methylpyrrolidin-3-yl]piperidine-4-carboxamide;

1-71: 1-[2-cyano-4-(trifluoromethyl)phenyl]-N-[(3R)-1-methylpyrrolidin-3-yl]-4-{6-[2-(trifluoromethoxy)phenyl]pyridin-3-yl}piperidine-4-carboxamide;

1-72: 1-[2-cyano-4-(trifluoromethyl)phenyl]-4-[6-(2-ethoxy-3-fluorophenyl)pyridin-3-yl]-N-[(3R)-1-methylpyrrolidin-3-yl]piperidine-4-carboxamide;

1-73: 1-[2-cyano-4-(trifluoromethyl)phenyl]-4-[6-(1-methyl-1H-indazol-7-yl)pyridin-3-yl]-N-[(3R)-1-methylpyrrolidin-3-yl]piperidine-4-carboxamide;

1-74: 1-[2-cyano-4-(trifluoromethyl)phenyl]-4-[6-(2-fluorophenyl)pyridin-3-yl]-N-[(3R)-1-methylpyrrolidin-3-yl]piperidine-4-carboxamide;

1-75: 1-[2-cyano-4-(trifluoromethyl)phenyl]-4-[4-(2-ethoxypyridin-3-yl)-3-fluorophenyl]-N-[(3R)-1-methylpyrrolidin-3-yl]piperidine-4-carboxamide;

1-76: 1-[2-cyano-4-(trifluoromethyl)phenyl]-4-[6-(2-ethoxyphenyl)pyridin-3-yl]-N-(1-methylazetidin-3-yl)piperidine-4-carboxamide;

1-77: 1-[2-cyano-4-(trifluoromethyl)phenyl]-N-[(3R)-1-methylpyrrolidin-3-yl]-4-{6-[2-(trifluoromethyl)phenyl]pyridin-3-yl}piperidine-4-carboxamide;

1-78: 1-[2-cyano-4-(trifluoromethyl)phenyl]-4-[6-(2-cyanophenyl)pyridin-3-yl]-N-[(3R)-1-methylpyrrolidin-3-yl]piperidine-4-carboxamide;

1-79: 1-[2-cyano-4-(trifluoromethyl)phenyl]-4-{6-[2-(methoxymethyl)phenyl]pyridin-3-yl}-N-[(3R)-1-methylpyrrolidin-3-yl]piperidine-4-carboxamide;

1-80: 1-[2-cyano-4-(trifluoromethyl)phenyl]-4-[6-(3-methoxythiophen-2-yl)pyridin-3-yl]-N-[(3R)-1-methylpyrrolidin-3-yl]piperidine-4-carboxamide;

1-81: 1-[2-cyano-4-(trifluoromethyl)phenyl]-4-[6-(5-fluoro-2-methoxyphenyl)pyridin-3-yl]-N-[(3R)-1-methylpyrrolidin-3-yl]piperidine-4-carboxamide;

1-82: 1-[2-cyano-4-(trifluoromethyl)phenyl]-4-[6-(3-fluoro-2-methoxyphenyl)pyridin-3-yl]-N-[(3R)-1-methylpyrrolidin-3-yl]piperidine-4-carboxamide;

1-83: 1-[2-cyano-4-(trifluoromethyl)phenyl]-4-[6-(2-methoxythiophen-3-yl)pyridin-3-yl]-N-[(3R)-1-methylpyrrolidin-3-yl]piperidine-4-carboxamide;

1-84: 1-[2-cyano-4-(trifluoromethyl)phenyl]-4-{6-[2-(1,1-difluoroethyl)phenyl]pyridin-3-yl}-N-[(3R)-1-methylpyrrolidin-3-yl]piperidine-4-carboxamide;

1-85: 1-[2-cyano-4-(trifluoromethyl)phenyl]-4-[2'-(difluoromethoxy)-[2,3'-bipyridin]-5-yl]-N-[(3R)-1-methylpyrrolidin-3-yl]piperidine-4-carboxamide;

1-86: 1-[2-cyano-4-(trifluoromethyl)phenyl]-4-{5'-fluoro-2'-methoxy-[2,3'-bipyridin]-5-yl}-N-[(3R)-1-methylpyrrolidin-3-yl]piperidine-4-carboxamide;

1-87: 1-[2-cyano-4-(trifluoromethyl)phenyl]-4-[6-(3,5-difluoro-2-methoxyphenyl)pyridin-3-yl]-N-[(3R)-1-methylpyrrolidin-3-yl]piperidine-4-carboxamide;

1-88: 1-[2-cyano-4-(trifluoromethyl)phenyl]-4-[6-(1-methyl-1H-pyrrol-2-yl)pyridin-3-yl]-N-[(3R)-1-methylpyrrolidin-3-yl]piperidine-4-carboxamide;

1-89: 1-[2-cyano-4-(trifluoromethyl)phenyl]-4-[6-(2-cyclopropoxyphenyl)pyridin-3-yl]-N-[(3R)-1-methylpyrrolidin-3-yl]piperidine-4-carboxamide;

1-90: 1-(4-chloro-2-cyanophenyl)-4-[6-(2-ethoxyphenyl)pyridin-3-yl]-N-[(3S)-1-methylpyrrolidin-3-yl]piperidine-4-carboxamide;

1-91: 1-(4-chloro-2-cyanophenyl)-4-[6-(2-methoxyphenyl)pyridin-3-yl]-N-[(3S)-1-methylpyrrolidin-3-yl]piperidine-4-carboxamide;

1-92: 1-(4-chloro-2-cyanophenyl)-4-[6-(2-methoxyphenyl)pyridin-3-yl]-N-(1-methylazetidin-3-yl)piperidine-4-carboxamide;

1-93: 1-(4-chloro-2-cyanophenyl)-4-[6-(2-ethoxyphenyl)pyridin-3-yl]-N-(1-methylazetidin-3-yl)piperidine-4-carboxamide;

1-94: 1-[2-cyano-4-(trifluoromethyl)phenyl]-4-[6-(2-methoxyphenyl)pyridin-3-yl]-N-(1-methylazetidin-3-yl)piperidine-4-carboxamide;

1-95: 1-(2,4-dichlorophenyl)-4-[6-(2-ethoxyphenyl)pyridin-3-yl]-N-[(3S)-1-methylpyrrolidin-3-yl]piperidine-4-carboxamide;

1-96: 1-(2-cyano-4-fluorophenyl)-4-[6-(2-ethoxyphenyl)pyridin-3-yl]-N-[(3S)-1-methylpyrrolidin-3-yl]piperidine-4-carboxamide;

1-97: 1-[2-chloro-4-(trifluoromethyl)phenyl]-4-[6-(2-ethoxyphenyl)pyridin-3-yl]-N-[(3S)-1-methylpyrrolidin-3-yl]piperidine-4-carboxamide;

1-98: 1-[2-cyano-4-(trifluoromethyl)phenyl]-4-{2'-methoxy-[2,3'-bipyridin]-5-yl}-N-[(3R)-1-methylpyrrolidin-3-yl]piperidine-4-carboxamide;

1-99: 1-[2-cyano-4-(trifluoromethyl)phenyl]-4-[6-(5-fluoro-2-methylphenyl)pyridin-3-yl]-N-[(3R)-1-methylpyrrolidin-3-yl]piperidine-4-carboxamide;

1-100: 1-[2-cyano-4-(trifluoromethyl)phenyl]-4-[6-(1-methyl-1H-pyrrol-2-yl)pyridin-3-yl]-N-[(3S)-1-methylpyrrolidin-3-yl]piperidine-4-carboxamide;

1-101: 1-[2-cyano-4-(trifluoromethyl)phenyl]-4-[6-(3-fluoro-2-methoxyphenyl)pyridin-3-yl]-N-[(3S)-1-methylpyrrolidin-3-yl]piperidine-4-carboxamide;

1-102: 1-[2-cyano-4-(trifluoromethyl)phenyl]-4-[6-(5-fluoro-2-methoxyphenyl)pyridin-3-yl]-N-[(3S)-1-methylpyrrolidin-3-yl]piperidine-4-carboxamide;

1-103: 1-[2-cyano-4-(trifluoromethyl)phenyl]-4-{5'-fluoro-2'-methoxy-[2,3'-bipyridin]-5-yl}-N-[(3S)-1-methylpyrrolidin-3-yl]piperidine-4-carboxamide;

1-104: 1-[2-cyano-4-(trifluoromethyl)phenyl]-4-[6-(2-ethylphenyl)pyridin-3-yl]-N-[(3S)-1-methylpyrrolidin-3-yl]piperidine-4-carboxamide;

1-105: 1-[2-cyano-4-(trifluoromethyl)phenyl]-4-[6-(4-methylpyrimidin-5-yl)pyridin-3-yl]-N-[(3R)-1-methylpyrrolidin-3-yl]piperidine-4-carboxamide;

1-106: 1-[2-cyano-4-(trifluoromethyl)phenyl]-4-[2-(2-ethoxypyridin-3-yl)pyrimidin-5-yl]-N-[(3S)-1-methylpyrrolidin-3-yl]piperidine-4-carboxamide;

1-107: 1-[2-cyano-4-(trifluoromethyl)phenyl]-4-[2-(2-ethoxypyridin-3-yl)pyrimidin-5-yl]-N-[(3R)-1-methylpyrrolidin-3-yl]piperidine-4-carboxamide;

1-108: 1-[2-cyano-4-(trifluoromethyl)phenyl]-4-{2'-ethoxy-3-fluoro-[2,3'-bipyridin]-5-yl}-N-[(3R)-1-methylpyrrolidin-3-yl]piperidine-4-carboxamide;

1-109: 1-[2-cyano-4-(trifluoromethyl)phenyl]-4-{2'-ethoxy-3-fluoro-[2,3'-bipyridin]-5-yl}-N-[(3S)-1-methylpyrrolidin-3-yl]piperidine-4-carboxamide;

1-110: 1-[2-cyano-6-(trifluoromethyl)pyridin-3-yl]-4-{2'-ethoxy-3-fluoro-[2,3'-bipyridin]-5-yl}-N-[(3S)-1-methylpyrrolidin-3-yl]piperidine-4-carboxamide;

1-111: 1-(4-chloro-2-cyano-6-fluorophenyl)-4-[6-(2-ethoxyphenyl)pyridin-3-yl]-N-[(3S)-1-methylpyrrolidin-3-yl]piperidine-4-carboxamide;

1-112: 1-[2-cyano-4-(trifluoromethyl)phenyl]-N-[(3R)-1-methylpyrrolidin-3-yl]-4-[6-(2-methylthiophen-3-yl)pyridin-3-yl]piperidine-4-carboxamide;

1-113: 1-[2-cyano-4-(trifluoromethyl)phenyl]-4-[6-(2-cyclopropylphenyl)pyridin-3-yl]-N-[(3R)-1-methylpyrrolidin-3-yl]piperidine-4-carboxamide;

1-114: 1-[2-cyano-4-(trifluoromethyl)phenyl]-4-{6-[2-(difluoromethoxy)phenyl]pyridin-3-yl}-N-[(3R)-1-methylpyrrolidin-3-yl]piperidine-4-carboxamide;

1-115: 1-[2-cyano-4-(trifluoromethyl)phenyl]-4-[6-(1-methyl-1H-pyrrol-3-yl)pyridin-3-yl]-N-[(3R)-1-methylpyrrolidin-3-yl]piperidine-4-carboxamide;

1-116: 1-[2-cyano-4-(trifluoromethyl)phenyl]-4-[6-(2-methylfuran-3-yl)pyridin-3-yl]-N-[(3R)-1-methylpyrrolidin-3-yl]piperidine-4-carboxamide;

1-117: 1-[2-cyano-4-(trifluoromethyl)phenyl]-N-[(3R)-1-methylpyrrolidin-3-yl]-4-[6-(2-propylphenyl)pyridin-3-yl]piperidine-4-carboxamide;

1-118: 1-[2-cyano-4-(trifluoromethyl)phenyl]-4-{2'-ethyl-[2,3'-bipyridin]-5-yl}-N-[(3R)-1-methylpyrrolidin-3-yl]piperidine-4-carboxamide;

1-119: 1-[2-cyano-4-(trifluoromethyl)phenyl]-4-[6-(2-methoxythiophen-3-yl)pyridin-3-yl]-N-[(3S)-1-methylpyrrolidin-3-yl]piperidine-4-carboxamide;

1-120: 1-[2-cyano-4-(trifluoromethyl)phenyl]-4-[6-(2-methylfuran-3-yl)pyridin-3-yl]-N-[(3S)-1-methylpyrrolidin-3-yl]piperidine-4-carboxamide;

1-121: 1-[2-cyano-4-(trifluoromethyl)phenyl]-4-[6-(2-cyclopropylphenyl)pyridin-3-yl]-N-[(3S)-1-methylpyrrolidin-3-yl]piperidine-4-carboxamide;

1-122: 1-[2-cyano-4-(trifluoromethyl)phenyl]-N-[(3S)-1-methylpyrrolidin-3-yl]-4-[6-(2-methylthiophen-3-yl)pyridin-3-yl]piperidine-4-carboxamide;

1-123: 1-[2-cyano-4-(trifluoromethyl)phenyl]-4-[6-(2-ethoxyphenyl)-5-fluoropyridin-3-yl]-N-[(3R)-1-methylpyrrolidin-3-yl]piperidine-4-carboxamide;

1-124: 1-[2-cyano-4-(trifluoromethyl)phenyl]-4-[6-(2-ethoxyphenyl)-5-fluoropyridin-3-yl]-N-[(3S)-1-methylpyrrolidin-3-yl]piperidine-4-carboxamide;

1-125: 1-[2-cyano-6-(trifluoromethyl)pyridin-3-yl]-4-[6-(2-ethoxyphenyl)-5-fluoropyridin-3-yl]-N-[(3S)-1-methylpyrrolidin-3-yl]piperidine-4-carboxamide;

1-126: 1-[2-cyano-4-(trifluoromethyl)phenyl]-4-[5-fluoro-6-(2-methoxyphenyl)pyridin-3-yl]-N-[(3R)-1-methylpyrrolidin-3-yl]piperidine-4-carboxamide;

1-127: 1-[2-cyano-4-(trifluoromethyl)phenyl]-4-[5-fluoro-6-(2-methoxyphenyl)pyridin-3-yl]-N-[(3S)-1-methylpyrrolidin-3-yl]piperidine-4-carboxamide;

1-128: 1-[2-cyano-6-(trifluoromethyl)pyridin-3-yl]-4-[5-fluoro-6-(2-methoxyphenyl)pyridin-3-yl]-N-[(3S)-1-methylpyrrolidin-3-yl]piperidine-4-carboxamide;

1-129: 1-[2-cyano-4-(trifluoromethyl)phenyl]-4-[6-(3-fluoro-2-hydroxyphenyl)pyridin-3-yl]-N-[(3R)-1-methylpyrrolidin-3-yl]piperidine-4-carboxamide;

1-130: 1-[2-cyano-4-(trifluoromethyl)phenyl]-4-[6-(2-methoxy-5-methylphenyl)pyridin-3-yl]-N-[(3R)-1-methylpyrrolidin-3-yl]piperidine-4-carboxamide;

1-131: 1-[2-cyano-4-(trifluoromethyl)phenyl]-4-{3-fluoro-2'-methoxy-[2,3'-bipyridin]-5-yl}-N-[(3R)-1-methylpyrrolidin-3-yl]piperidine-4-carboxamide;

1-132: 1-[2-cyano-4-(trifluoromethyl)phenyl]-4-{3-fluoro-2'-methoxy-[2,3'-bipyridin]-5-yl}-N-[(3S)-1-methylpyrrolidin-3-yl]piperidine-4-carboxamide;

1-133: 1-[2-cyano-6-(trifluoromethyl)pyridin-3-yl]-4-{3-fluoro-2'-methoxy-[2,3'-bipyridin]-5-yl}-N-[(3S)-1-methylpyrrolidin-3-yl]piperidine-4-carboxamide;

1-134: 1-(4-chloro-2-cyanophenyl)-4-[6-(2-ethoxyphenyl)pyridazin-3-yl]-N-[(3S)-1-methylpyrrolidin-3-yl]piperidine-4-carboxamide;

1-135: 1-(4-chloro-2-cyanophenyl)-4-[6-(2-ethoxyphenyl)pyridazin-3-yl]-N-(1-methylazetidin-3-yl)piperidine-4-carboxamide;

1-136: 1-[2-cyano-4-(trifluoromethyl)phenyl]-4-[6-(2-ethoxyphenyl)pyridazin-3-yl]-N-(1-methylazetidin-3-yl)piperidine-4-carboxamide;

1-137: 1-[2-cyano-4-(trifluoromethyl)phenyl]-4-{6-[2-(cyanomethyl)phenyl]pyridin-3-yl}-N-[(3R)-1-methylpyrrolidin-3-yl]piperidine-4-carboxamide;

1-138: 1-[2-cyano-4-(trifluoromethyl)phenyl]-N-[(3R)-1-methylpyrrolidin-3-yl]-4-[6-(4-methylthiophen-3-yl)pyridin-3-yl]piperidine-4-carboxamide;

1-139: 1-(4-chloro-2-cyanophenyl)-4-[6-(2-ethoxypyridin-3-yl)pyridazin-3-yl]-N-[(3S)-1-methylpyrrolidin-3-yl]piperidine-4-carboxamide;

1-140: 1-[2-cyano-4-(trifluoromethyl)phenyl]-4-[6-(2-ethoxypyridin-3-yl)pyridazin-3-yl]-N-(1-methylazetidin-3-yl)piperidine-4-carboxamide;

1-141: 1-[2-chloro-4-(trifluoromethyl)phenyl]-4-{2'-ethoxy-[2,3'-bipyridin]-5-yl}-N-[(3S)-1-methylpyrrolidin-3-yl]piperidine-4-carboxamide;

1-142: 1-[2-chloro-4-(trifluoromethyl)phenyl]-4-{2'-methoxy-[2,3'-bipyridin]-5-yl}-N-[(3S)-1-methylpyrrolidin-3-yl]piperidine-4-carboxamide;

1-143: 1-[2-cyano-4-(trifluoromethyl)phenyl]-N-[(3S)-1-methylpyrrolidin-3-yl]-4-[6-(1H-pyrrol-2-yl)pyridin-3-yl]piperidine-4-carboxamide;

1-144: 1-[2-chloro-4-(trifluoromethyl)phenyl]-4-[6-(2-methoxyphenyl)pyridin-3-yl]-N-[(3S)-1-methylpyrrolidin-3-yl]piperidine-4-carboxamide;

1-145: 4-[6-(2-ethoxyphenyl)pyridin-3-yl]-1-[2-fluoro-4-(trifluoromethyl)phenyl]-N-[(3S)-1-methylpyrrolidin-3-yl]piperidine-4-carboxamide;

1-146: 4-[6-(2-acetylthiophen-3-yl)pyridin-3-yl]-1-[2-cyano-4-(trifluoromethyl)phenyl]-N-[(3S)-1-methylpyrrolidin-3-yl]piperidine-4-carboxamide;

1-147: 1-[2-cyano-4-(trifluoromethyl)phenyl]-4-[6-(2-ethylthiophen-3-yl)pyridin-3-yl]-N-[(3S)-1-methylpyrrolidin-3-yl]piperidine-4-carboxamide;

1-148: 4-[6-(2-cyano-3-fluorophenyl)pyridin-3-yl]-1-[2-cyano-4-(trifluoromethyl)phenyl]-N-[(3S)-1-methylpyrrolidin-3-yl]piperidine-4-carboxamide;

1-149: 1-[2-cyano-4-(trifluoromethyl)phenyl]-4-[6-(3-methyl-1,2-oxazol-4-yl)pyridin-3-yl]-N-[(3S)-1-methylpyrrolidin-3-yl]piperidine-4-carboxamide;

1-150: 1-[3-chloro-5-(trifluoromethyl)pyridin-2-yl]-4-{2'-ethoxy-[2,3'-bipyridin]-5-yl}-N-[(3S)-1-methylpyrrolidin-3-yl]piperidine-4-carboxamide;

1-151: 1-[2-cyano-4-(trifluoromethyl)phenyl]-4-{6-[2-(difluoromethyl)phenyl]pyridin-3-yl}-N-[(3S)-1-methylpyrrolidin-3-yl]piperidine-4-carboxamide;

1-152: 1-[2-cyano-4-(trifluoromethyl)phenyl]-4-[6-(1-methyl-1H-pyrrol-2-yl)pyridin-3-yl]-N-[(3S)-pyrrolidin-3-yl]piperidine-4-carboxamide;

1-153: 4-[6-(5-cyano-1-methyl-1H-pyrrol-2-yl)pyridin-3-yl]-1-[2-cyano-4-(trifluoromethyl)phenyl]-N-[(3R)-1-methylpyrrolidin-3-yl]piperidine-4-carboxamide;

1-154: 1-[2-chloro-4-(trifluoromethyl)phenyl]-4-{5'-fluoro-2'-methoxy-[2,3'-bipyridin]-5-yl}-N-[(3S)-1-methylpyrrolidin-3-yl]piperidine-4-carboxamide;

1-155: 1-[2-chloro-4-(trifluoromethyl)phenyl]-4-[6-(5-fluoro-2-methoxyphenyl)pyridin-3-yl]-N-[(3S)-1-methylpyrrolidin-3-yl]piperidine-4-carboxamide;

1-156: 1-[2-chloro-4-(trifluoromethyl)phenyl]-4-[6-(2-ethylphenyl)pyridin-3-yl]-N-[(3S)-1-methylpyrrolidin-3-yl]piperidine-4-carboxamide;

1-157: 1-[2-cyano-4-(trifluoromethyl)phenyl]-4-[6-(5-methyl-1,2-oxazol-4-yl)pyridin-3-yl]-N-[(3R)-1-methylpyrrolidin-3-yl]piperidine-4-carboxamide;

1-158: 1-[2-cyano-4-(trifluoromethyl)phenyl]-4-[6-(1-cyclopropyl-1H-pyrrol-2-yl)pyridin-3-yl]-N-[(3S)-1-methylpyrrolidin-3-yl]piperidine-4-carboxamide;

1-159: 4-[4-(2-ethoxypyridin-3-yl)phenyl]-1-[2-methoxy-4-(trifluoromethyl)phenyl]-N-[(3R)-1-methylpyrrolidin-3-yl]piperidine-4-carboxamide;

1-160: 1-[2-chloro-4-(trifluoromethyl)phenyl]-4-[6-(1-methyl-1H-pyrrol-2-yl)pyridin-3-yl]-N-[(3S)-1-methylpyrrolidin-3-yl]piperidine-4-carboxamide;

1-161: 1-[2-cyano-4-(trifluoromethyl)phenyl]-4-[5-fluoro-6-(1-methyl-1H-pyrrol-2-yl)pyridin-3-yl]-N-[(3S)-1-methylpyrrolidin-3-yl]piperidine-4-carboxamide;

1-162: 1-[2-chloro-4-(trifluoromethyl)phenyl]-4-[5-fluoro-6-(1-methyl-1H-pyrrol-2-yl)pyridin-3-yl]-N-[(3S)-1-methylpyrrolidin-3-yl]piperidine-4-carboxamide;

1-163: 1-(4-chloro-2-cyanophenyl)-4-[5-fluoro-6-(1-methyl-1H-pyrrol-2-yl)pyridin-3-yl]-N-[(3S)-1-methylpyrrolidin-3-yl]piperidine-4-carboxamide;

1-164: 4-[4-(2-ethoxypyridin-3-yl)phenyl]-1-[2-methyl-4-(trifluoromethyl)phenyl]-N-[(3R)-1-methylpyrrolidin-3-yl]piperidine-4-carboxamide;

1-165: 1-[3-chloro-4-(trifluoromethyl)phenyl]-4-[4-(2-ethoxypyridin-3-yl)phenyl]-N-[(3R)-1-methylpyrrolidin-3-yl]piperidine-4-carboxamide;

1-166: 1-[2-cyano-4-(trifluoromethyl)phenyl]-4-[6-(2-methoxyphenyl)pyridin-3-yl]-N-[(3S)-1-methylpyrrolidin-3-yl]piperidine-4-carboxamide;

1-167: 1-[2-chloro-4-(trifluoromethyl)phenyl]-4-[6-(2-methoxythiophen-3-yl)pyridin-3-yl]-N-[(3S)-1-methylpyrrolidin-3-yl]piperidine-4-carboxamide;

1-168: 1-[2-cyano-4-(trifluoromethyl)phenyl]-4-[6-(1-methyl-1H-pyrrol-2-yl)pyridazin-3-yl]-N-[(3S)-1-methylpyrrolidin-3-yl]piperidine-4-carboxamide;

1-169: 1-[2-chloro-4-(trifluoromethyl)phenyl]-4-[6-(1-methyl-1H-pyrrol-2-yl)pyridazin-3-yl]-N-[(3S)-1-methylpyrrolidin-3-yl]piperidine-4-carboxamide;

1-170: 1-(4-chloro-2-cyanophenyl)-4-[6-(1-methyl-1H-pyrrol-2-yl)pyridazin-3-yl]-N-[(3S)-1-methylpyrrolidin-3-yl]piperidine-4-carboxamide;

1-171: 1-[2-fluoro-4-(trifluoromethyl)phenyl]-4-[6-(1-methyl-1H-pyrrol-2-yl)pyridazin-3-yl]-N-[(3S)-1-methylpyrrolidin-3-yl]piperidine-4-carboxamide;

1-172: 1-[2-chloro-4-(trifluoromethyl)phenyl]-4-{2'-ethyl-[2,3'-bipyridin]-5-yl}-N-[(3S)-1-methylpyrrolidin-3-yl]piperidine-4-carboxamide;

1-173: 1-[2-fluoro-4-(trifluoromethyl)phenyl]-4-[6-(1-methyl-1H-pyrrol-2-yl)pyridin-3-yl]-N-[(3S)-1-methylpyrrolidin-3-yl]piperidine-4-carboxamide;

1-174: 4-[6-(2-ethoxyphenyl)pyridazin-3-yl]-1-[2-fluoro-4-(trifluoromethyl)phenyl]-N-[(3S)-1-methylpyrrolidin-3-yl]piperidine-4-carboxamide;

1-175: 1-[2-chloro-4-(trifluoromethyl)phenyl]-4-[6-(2-ethoxyphenyl)pyridazin-3-yl]-N-[(3S)-1-methylpyrrolidin-3-yl]piperidine-4-carboxamide;

1-176: 4-{[2,2'-bipyridin]-5-yl}-1-[2-cyano-4-(trifluoromethyl)phenyl]-N-[(3S)-1-methylpyrrolidin-3-yl]piperidine-4-carboxamide;

1-177: 1-[2-cyano-4-(trifluoromethyl)phenyl]-4-{3'-methyl-[2,2'-bipyridin]-5-yl}-N-[(3R)-1-methylpyrrolidin-3-yl]piperidine-4-carboxamide;

1-178: 1-[2-cyano-4-(trifluoromethyl)phenyl]-4-{3'-methoxy-[2,2'-bipyridin]-5-yl}-N-[(3S)-1-methylpyrrolidin-3-yl]piperidine-4-carboxamide;

1-179: 1-[2-cyano-4-(trifluoromethyl)phenyl]-4-(2'-methoxy-[2,3'-bipyridin]-5-yl)-N-[(3S)-1-methylpyrrolidin-3-yl]piperidine-4-carboxamide;

1-180: 1-[2-cyano-4-(trifluoromethyl)phenyl]-4-{2'-cyclopropyl-[2,3'-bipyridin]-5-yl}-N-[(3S)-1-methylpyrrolidin-3-yl]piperidine-4-carboxamide;

1-181: 1-[2-cyano-4-(trifluoromethyl)phenyl]-4-[2'-(difluoromethyl)-[2,3'-bipyridin]-5-yl]-N-[(3S)-1-methylpyrrolidin-3-yl]piperidine-4-carboxamide;

1-182: 1-[2-cyano-4-(trifluoromethyl)phenyl]-4-[6-(5-cyclopropyl-1,3-oxazol-4-yl)pyridin-3-yl]-N-[(3S)-1-methylpyrrolidin-3-yl]piperidine-4-carboxamide;

1-183: 1-[2-cyano-4-(trifluoromethyl)phenyl]-4-[6-(2-methoxyphenyl)pyridazin-3-yl]-N-[(3S)-1-methylpyrrolidin-3-yl]piperidine-4-carboxamide;

1-184: ethyl (3S)-3-{1-[2-cyano-4-(trifluoromethyl)phenyl]-4-[6-(1-methyl-1H-pyrrol-2-yl)pyridin-3-yl]piperidine-4-amido}pyrrolidine-1-carboxylate;

1-185: N-[(3S)-1-acetylpyrrolidin-3-yl]-1-[2-cyano-4-(trifluoromethyl)phenyl]-4-[6-(1-methyl-1H-pyrrol-2-yl)pyridin-3-yl]piperidine-4-carboxamide;

1-186: 4-{2'-ethoxy-[2,3'-bipyridin]-5-yl}-1-[2-fluoro-4-(trifluoromethyl)phenyl]-N-[(3S)-1-methylpyrrolidin-3-yl]piperidine-4-carboxamide;

1-187: N-[(3S)-1-azabicyclo[2.2.2]octan-3-yl]-1-[2-cyano-4-(trifluoromethyl)phenyl]-4-[6-(1-methyl-1H-pyrrol-2-yl)pyridin-3-yl]piperidine-4-carboxamide;

1-188: N-[(3R)-1-azabicyclo[2.2.2]octan-3-yl]-1-[2-cyano-4-(trifluoromethyl)phenyl]-4-[6-(1-methyl-1H-pyrrol-2-yl)pyridin-3-yl]piperidine-4-carboxamide;

1-189: 1-[2-cyano-4-(trifluoromethyl)phenyl]-4-[6-(2-methoxyquinolin-3-yl)pyridin-3-yl]-N-[(3R)-1-methylpyrrolidin-3-yl]piperidine-4-carboxamide;

1-190: 1-[2-cyano-4-(trifluoromethyl)phenyl]-4-[6-(1-methyl-1H-indol-7-yl)pyridin-3-yl]-N-[(3R)-1-methylpyrrolidin-3-yl]piperidine-4-carboxamide;

1-191: 1-[2-cyano-4-(trifluoromethyl)phenyl]-4-[6-(1-methyl-1H-indol-2-yl)pyridin-3-yl]-N-[(3R)-1-methylpyrrolidin-3-yl]piperidine-4-carboxamide;

1-192: 1-[2-fluoro-4-(trifluoromethyl)phenyl]-4-[5-fluoro-6-(1-methyl-1H-pyrrol-2-yl)pyridin-3-yl]-N-[(3S)-1-methylpyrrolidin-3-yl]piperidine-4-carboxamide;

1-193: 4-[6-(2-ethoxypyridin-3-yl)pyridazin-3-yl]-1-[2-fluoro-4-(trifluoromethyl)phenyl]-N-[(3S)-1-methylpyrrolidin-3-yl]piperidine-4-carboxamide;

1-194: 1-[2-chloro-4-(trifluoromethyl)phenyl]-4-[6-(2-ethoxypyridin-3-yl)pyridazin-3-yl]-N-[(3S)-1-methylpyrrolidin-3-yl]piperidine-4-carboxamide;

1-195: 1-[2-cyano-4-(trifluoromethyl)phenyl]-4-[5-fluoro-6-(5-fluoro-2-methoxyphenyl)pyridin-3-yl]-N-[(3S)-1-methylpyrrolidin-3-yl]piperidine-4-carboxamide;

1-196: 1-[2-cyano-4-(trifluoromethyl)phenyl]-4-[5-fluoro-6-(2-methoxyphenyl)pyridin-3-yl]-N-[2-(methylamino)ethyl]piperidine-4-carboxamide;

1-197: 1-[2-cyano-4-(trifluoromethyl)phenyl]-4-[5-fluoro-6-(2-methoxyphenyl)pyridin-3-yl]-N-[3-(methylamino)propyl]piperidine-4-carboxamide;

1-198: 1-[2-cyano-4-(trifluoromethyl)phenyl]-N-[2-(dimethylamino)ethyl]-4-[5-fluoro-6-(2-methoxyphenyl)pyridin-3-yl]piperidine-4-carboxamide;

1-199: 1-[2-cyano-4-(trifluoromethyl)phenyl]-N-[3-(dimethylamino)propyl]-4-[5-fluoro-6-(2-methoxyphenyl)pyridin-3-yl]piperidine-4-carboxamide;

1-200: 4-[6-(2-ethoxyphenyl)-5-fluoropyridin-3-yl]-1-[2-fluoro-4-(trifluoromethyl)phenyl]-N-[(3S)-1-methylpyrrolidin-3-yl]piperidine-4-carboxamide;

1-201: 4-{2'-ethoxy-3-fluoro-[2,3'-bipyridin]-5-yl}-1-[2-fluoro-4-(trifluoromethyl)phenyl]-N-[(3S)-1-methylpyrrolidin-3-yl]piperidine-4-carboxamide;

1-202: 1-[2-chloro-4-(trifluoromethyl)phenyl]-4-[6-(2-ethoxyphenyl)-5-fluoropyridin-3-yl]-N-[(3S)-1-methylpyrrolidin-3-yl]piperidine-4-carboxamide;

1-203: 1-[2-chloro-4-(trifluoromethyl)phenyl]-4-{2'-ethoxy-3-fluoro-[2,3'-bipyridin]-5-yl}-N-[(3S)-1-methylpyrrolidin-3-yl]piperidine-4-carboxamide;

1-204: 1-[2-fluoro-4-(trifluoromethyl)phenyl]-4-[5-fluoro-6-(5-fluoro-2-methoxyphenyl)pyridin-3-yl]-N-[(3S)-1-methylpyrrolidin-3-yl]piperidine-4-carboxamide;

1-205: N-(3-aminopropyl)-1-[2-cyano-4-(trifluoromethyl)phenyl]-4-[6-(1-methyl-1H-pyrrol-2-yl)pyridin-3-yl]piperidine-4-carboxamide;

1-206: 1-[2-cyano-4-(trifluoromethyl)phenyl]-4-[6-(1-methyl-1H-pyrrol-2-yl)pyridin-3-yl]-N-[3-(methylamino)propyl]piperidine-4-carboxamide;

1-207: 1-[2-cyano-4-(trifluoromethyl)phenyl]-N-[3-(dimethylamino)propyl]-4-[6-(1-methyl-1H-pyrrol-2-yl)pyridin-3-yl]piperidine-4-carboxamide;

1-208: 1-[2-cyano-4-(trifluoromethyl)phenyl]-4-[6-(1-ethyl-1H-pyrrol-2-yl)pyridin-3-yl]-N-[(3S)-1-methylpyrrolidin-3-yl]piperidine-4-carboxamide;

1-209: 1-[2-cyano-4-(trifluoromethyl)phenyl]-4-{3,5'-difluoro-2'-methoxy-[2,3'-bipyridin]-5-yl}-N-[(3S)-1-methylpyrrolidin-3-yl]piperidine-4-carboxamide;

1-210: 4-{3,5'-difluoro-2'-methoxy-[2,3'-bipyridin]-5-yl}-1-[2-fluoro-4-(trifluoromethyl)phenyl]-N-[(3S)-1-methylpyrrolidin-3-yl]piperidine-4-carboxamide;

1-211: 1-[2-cyano-4-(trifluoromethyl)phenyl]-4-[6-(2-methoxyphenyl)pyridin-3-yl]-N-[(1-methylazetidin-3-yl)methyl]piperidine-4-carboxamide;

1-212: 1-[2-cyano-4-(trifluoromethyl)phenyl]-N-[2-(dimethylamino)ethyl]-4-[6-(2-methoxyphenyl)pyridin-3-yl]piperidine-4-carboxamide;

1-213: N-{[(2S)-azetidin-2-yl]methyl}-1-[2-cyano-4-(trifluoromethyl)phenyl]-4-[6-(2-methoxyphenyl)pyridin-3-yl]piperidine-4-carboxamide;

1-214: 1-[2-cyano-4-(trifluoromethyl)phenyl]-4-[6-(2-methoxyphenyl)pyridin-3-yl]-N-[2-(methylamino)ethyl]piperidine-4-carboxamide;

1-215: 1-[2-cyano-4-(trifluoromethyl)phenyl]-4-[6-(1-methyl-1H-pyrrol-2-yl)pyridin-3-yl]-N-[2-(methylamino)ethyl]piperidine-4-carboxamide;

1-216: 1-[2-cyano-4-(trifluoromethyl)phenyl]-N-[2-(dimethylamino)ethyl]-4-[6-(1-methyl-1H-pyrrol-2-yl)pyridin-3-yl]piperidine-4-carboxamide;

1-217: 1-[2-cyano-4-(trifluoromethyl)phenyl]-4-[6-(2-methoxyphenyl)pyridin-3-yl]-N-{[(2S)-1-methylazetidin-2-yl]methyl}piperidine-4-carboxamide;

1-218: N-[(3S)-1-azabicyclo[2.2.2]octan-3-yl]-1-[2-cyano-4-(trifluoromethyl)phenyl]-4-[6-(2-methoxyphenyl)pyridin-3-yl]piperidine-4-carboxamide;

1-219: 1-[2-cyano-4-(trifluoromethyl)phenyl]-4-[6-(1-methyl-1H-pyrrol-2-yl)pyridin-3-yl]-N-(1-methylazetidin-3-yl)piperidine-4-carboxamide;

1-220: 1-[2-cyano-4-(trifluoromethyl)phenyl]-4-[6-(1-methyl-1H-pyrrol-2-yl)pyridin-3-yl]-N-[(1-methylazetidin-3-yl)methyl]piperidine-4-carboxamide;

1-221: N—{(1-azabicyclo[2.2.1]heptan-4-yl}-1-[2-cyano-4-(trifluoromethyl)phenyl]-4-[6-(1-methyl-1H-pyrrol-2-yl)pyridin-3-yl]piperidine-4-carboxamide;

1-222: N-[2-(dimethylamino)ethyl]-4-{2'-ethoxy-[2,3'-bipyridin]-5-yl}-1-[2-fluoro-4-(trifluoromethyl)phenyl]piperidine-4-carboxamide;

1-223: 4-{2'-ethoxy-[2,3'-bipyridin]-5-yl}-1-[2-fluoro-4-(trifluoromethyl)phenyl]-N-[2-(methylamino)ethyl]piperidine-4-carboxamide;

1-224: 1-[2-chloro-4-(trifluoromethyl)phenyl]-N-[2-(dimethylamino)ethyl]-4-{2'-ethoxy-[2,3'-bipyridin]-5-yl}piperidine-4-carboxamide;

1-225: 1-[2-chloro-4-(trifluoromethyl)phenyl]-4-(2'-ethoxy-[2,3'-bipyridin]-5-yl)-N-[2-(methylamino)ethyl]piperidine-4-carboxamide;

1-226: N-[2-(dimethylamino)ethyl]-4-[6-(2-ethoxyphenyl)pyridin-3-yl]-1-[2-fluoro-4-(trifluoromethyl)phenyl]piperidine-4-carboxamide;

1-227: 4-[6-(2-ethoxyphenyl)pyridin-3-yl]-1-[2-fluoro-4-(trifluoromethyl)phenyl]-N-[2-(methylamino)ethyl]piperidine-4-carboxamide;

1-228: 1-[2-chloro-4-(trifluoromethyl)phenyl]-N-[2-(dimethylamino)ethyl]-4-[6-(2-ethoxyphenyl)pyridin-3-yl]piperidine-4-carboxamide;

1-229: 1-[2-cyano-4-(trifluoromethyl)phenyl]-4-[6-(1-methyl-1H-pyrrol-2-yl)pyridin-3-yl]-N-{[(2S)-1-methylpyrrolidin-2-yl]methyl}piperidine-4-carboxamide;

1-230: 1-[2-chloro-4-(trifluoromethyl)phenyl]-4-[6-(2-ethoxyphenyl)pyridin-3-yl]-N-[2-(methylamino)ethyl]piperidine-4-carboxamide;

1-231: 1-[2-cyano-4-(trifluoromethyl)phenyl]-4-[6-(1-methyl-1H-pyrrol-2-yl)pyridin-3-yl]-N-{[(2R)-pyrrolidin-2-yl]methyl}piperidine-4-carboxamide;

1-232: 1-[2-cyano-4-(trifluoromethyl)phenyl]-4-[6-(1-methyl-1H-pyrrol-2-yl)pyridin-3-yl]-N-{[(2R)-1-methylpyrrolidin-2-yl]methyl}piperidine-4-carboxamide;

1-233: 1-[2-cyano-4-(trifluoromethyl)phenyl]-4-[6-(1-methyl-1H-pyrrol-2-yl)pyridin-3-yl]-N-[(1S,3S)-3-aminocyclobutyl]piperidine-4-carboxamide;

1-234: 1-[2-cyano-4-(trifluoromethyl)phenyl]-4-[6-(1-methyl-1H-pyrrol-2-yl)pyridin-3-yl]-N-[(1R,3R)-3-aminocyclobutyl]piperidine-4-carboxamide;

1-235: N-{[(2S)-azetidin-2-yl]methyl}-1-[2-cyano-4-(trifluoromethyl)phenyl]-4-[6-(1-methyl-1H-pyrrol-2-yl)pyridin-3-yl]piperidine-4-carboxamide;

1-236: N-{[(2R)-azetidin-2-yl]methyl}-1-[2-cyano-4-(trifluoromethyl)phenyl]-4-[6-(2-methoxyphenyl)pyridin-3-yl]piperidine-4-carboxamide;

1-237: 1-[2-cyano-4-(trifluoromethyl)phenyl]-N-[(3R,4S)-4-fluoropyrrolidin-3-yl]-4-[6-(2-methoxyphenyl)pyridin-3-yl]piperidine-4-carboxamide;

1-238: 1-[2-cyano-4-(trifluoromethyl)phenyl]-N-[(3R,4R)-4-fluoropyrrolidin-3-yl]-4-[6-(2-methoxyphenyl)pyridin-3-yl]piperidine-4-carboxamide;

1-239: 1-[2-cyano-4-(trifluoromethyl)phenyl]-4-[6-(1-methyl-1H-pyrrol-2-yl)pyridin-3-yl]-N-[(1S,3S)-3-(dimethylamino)cyclobutyl]piperidine-4-carboxamide;

1-240: 1-[2-cyano-4-(trifluoromethyl)phenyl]-4-[6-(1-methyl-1H-pyrrol-2-yl)pyridin-3-yl]-N-[(1R,3R)-3-(dimethylamino)cyclobutyl]piperidine-4-carboxamide;

1-241: 1-[2-cyano-4-(trifluoromethyl)phenyl]-4-[6-(1-methyl-1H-pyrrol-2-yl)pyridin-3-yl]-N-{[(2S)-1-methylazetidin-2-yl]methyl}piperidine-4-carboxamide;

1-242: 1-[2-cyano-4-(trifluoromethyl)phenyl]-N-[(3R,4S)-4-fluoro-1-methylpyrrolidin-3-yl]-4-[6-(2-methoxyphenyl)pyridin-3-yl]piperidine-4-carboxamide;

1-243: 1-[2-cyano-4-(trifluoromethyl)phenyl]-N-[(3R,4R)-4-fluoro-1-methylpyrrolidin-3-yl]-4-[6-(2-methoxyphenyl)pyridin-3-yl]piperidine-4-carboxamide;

1-244: 1-[2-cyano-4-(trifluoromethyl)phenyl]-4-[6-(2-methoxyphenyl)pyridin-3-yl]-N-{[(2R)-1-methylazetidin-2-yl]methyl}piperidine-4-carboxamide;

1-245: N-[2-(azetidin-1-yl)ethyl]-1-[2-cyano-4-(trifluoromethyl)phenyl]-4-[6-(2-methoxyphenyl)pyridin-3-yl]piperidine-4-carboxamide;

1-246: 1-[2-cyano-4-(trifluoromethyl)phenyl]-N-{[(2S,4S)-4-fluoropyrrolidin-2-yl]methyl}-4-[6-(2-methoxyphenyl)pyridin-3-yl]piperidine-4-carboxamide;

1-247: 1-[2-cyano-4-(trifluoromethyl)phenyl]-N-{[(2S,4R)-4-fluoropyrrolidin-2-yl]methyl}-4-[6-(2-methoxyphenyl)pyridin-3-yl]piperidine-4-carboxamide;

1-248: N-[2-(azetidin-1-yl)ethyl]-1-[2-cyano-4-(trifluoromethyl)phenyl]-4-[6-(1-methyl-1H-pyrrol-2-yl)pyridin-3-yl]piperidine-4-carboxamide;

1-249: 1-[2-cyano-4-(trifluoromethyl)phenyl]-N-{[(2S,4S)-4-fluoro-1-methylpyrrolidin-2-yl]methyl}-4-[6-(2-methoxyphenyl)pyridin-3-yl]piperidine-4-carboxamide;

1-250: 1-[2-cyano-4-(trifluoromethyl)phenyl]-N-{[(2S,4R)-4-fluoro-1-methylpyrrolidin-2-yl]methyl}-4-[6-(2-methoxyphenyl)pyridin-3-yl]piperidine-4-carboxamide;

1-251: rac-1-[2-cyano-4-(trifluoromethyl)phenyl]-4-[6-(1-methyl-1H-pyrrol-2-yl)pyridin-3-yl]-N-[(1S,2S,4R)-7-methyl-7-azabicyclo[2.2.1]heptan-2-yl]piperidine-4-carboxamide;

1-252: rac-1-[2-cyano-4-(trifluoromethyl)phenyl]-4-[6-(2-methoxyphenyl)pyridin-3-yl]-N-[(1S,2S,4R)-7-methyl-7-azabicyclo[2.2.1]heptan-2-yl]piperidine-4-carboxamide;

1-253: 1-[2-cyano-4-(trifluoromethyl)phenyl]-N-[(3S)-1,3-dimethylpyrrolidin-3-yl]-4-[6-(1-methyl-1H-pyrrol-2-yl)pyridin-3-yl]piperidine-4-carboxamide;

1-254: N-[2-(dimethylamino)ethyl]-1-[2-fluoro-4-(trifluoromethyl)phenyl]-4-[6-(2-methoxyphenyl)pyridin-3-yl]piperidine-4-carboxamide;

1-255: 1-[2-chloro-4-(trifluoromethyl)phenyl]-N-[2-(dimethylamino)ethyl]-4-[6-(2-methoxyphenyl)pyridin-3-yl]piperidine-4-carboxamide;

1-256: 1-[2-fluoro-4-(trifluoromethyl)phenyl]-4-[6-(2-methoxyphenyl)pyridin-3-yl]-N-[2-(methylamino)ethyl]piperidine-4-carboxamide;

1-257: 1-[2-chloro-4-(trifluoromethyl)phenyl]-4-[6-(2-methoxyphenyl)pyridin-3-yl]-N-[2-(methylamino)ethyl]piperidine-4-carboxamide;

1-258: rac-N-[(1R,2S)-2-aminocyclopropyl]-1-[2-cyano-4-(trifluoromethyl)phenyl]-4-[6-(1-methyl-1H-pyrrol-2-yl)pyridin-3-yl]piperidine-4-carboxamide;

1-259: rac-N-[(1R,2R)-2-aminocyclopropyl]-1-[2-cyano-4-(trifluoromethyl)phenyl]-4-[6-(1-methyl-1H-pyrrol-2-yl)pyridin-3-yl]piperidine-4-carboxamide;

1-260: 1-[2-cyano-4-(trifluoromethyl)phenyl]-N-[(2R)-1-(dimethylamino)propan-2-yl]-4-[6-(1-methyl-1H-pyrrol-2-yl)pyridin-3-yl]piperidine-4-carboxamide;

1-261: 1-[2-cyano-4-(trifluoromethyl)phenyl]-N-[(2S)-1-(dimethylamino)propan-2-yl]-4-[6-(1-methyl-1H-pyrrol-2-yl)pyridin-3-yl]piperidine-4-carboxamide;

1-262: 1-[2-cyano-4-(trifluoromethyl)phenyl]-N-{3-[(dimethylamino)methyl]oxetan-3-yl}-4-[6-(1-methyl-1H-pyrrol-2-yl)pyridin-3-yl]piperidine-4-carboxamide;

1-263: 1-[2-cyano-4-(trifluoromethyl)phenyl]-N-{[1-(dimethylamino)cyclopropyl]methyl}-4-[6-(1-methyl-1H-pyrrol-2-yl)pyridin-3-yl]piperidine-4-carboxamide;

1-264: 1-[2-cyano-4-(trifluoromethyl)phenyl]-N-[(3S,4S)-4-(dimethylamino)oxolan-3-yl]-4-[6-(1-methyl-1H-pyrrol-2-yl)pyridin-3-yl]piperidine-4-carboxamide;

1-265: 1-[2-cyano-4-(trifluoromethyl)phenyl]-N-{2-[ethyl(methyl)amino]ethyl}-4-[6-(1-methyl-1H-pyrrol-2-yl)pyridin-3-yl]piperidine-4-carboxamide;

1-266: 1-[2-cyano-4-(trifluoromethyl)phenyl]-N-{2-[cyclopropyl(methyl)amino]ethyl}-4-[6-(1-methyl-1H-pyrrol-2-yl)pyridin-3-yl]piperidine-4-carboxamide;

1-267: rac-1-[2-cyano-4-(trifluoromethyl)phenyl]-N-[(3S,4R)-4-methoxy-1-methylpyrrolidin-3-yl]-4-[6-(1-methyl-1H-pyrrol-2-yl)pyridin-3-yl]piperidine-4-carboxamide;

1-268: rac-1-[2-cyano-4-(trifluoromethyl)phenyl]-N-[(3R,4R)-4-methoxy-1-methylpyrrolidin-3-yl]-4-[6-(1-methyl-1H-pyrrol-2-yl)pyridin-3-yl]piperidine-4-carboxamide;

1-269: 1-[2-cyano-4-(trifluoromethyl)phenyl]-N-[(3R,4R)-4-hydroxy-1-methylpyrrolidin-3-yl]-4-[6-(1-methyl-1H-pyrrol-2-yl)pyridin-3-yl]piperidine-4-carboxamide;

1-270: 1-[2-cyano-4-(trifluoromethyl)phenyl]-N-[(3S,4S)-4-hydroxy-1-methylpyrrolidin-3-yl]-4-[6-(1-methyl-1H-pyrrol-2-yl)pyridin-3-yl]piperidine-4-carboxamide;

1-271: N-[2-(dimethylamino)ethyl]-1-[2-fluoro-4-(trifluoromethyl)phenyl]-4-{2'-methoxy-[2,3'-bipyridin]-5-yl}piperidine-4-carboxamide;

1-272: 1-[2-fluoro-4-(trifluoromethyl)phenyl]-4-(2'-methoxy-[2,3'-bipyridin]-5-yl)-N-[2-(methylamino)ethyl]piperidine-4-carboxamide;

1-273: 1-[2-chloro-4-(trifluoromethyl)phenyl]-N-[2-(dimethylamino)ethyl]-4-{2'-methoxy-[2,3'-bipyridin]-5-yl}piperidine-4-carboxamide;

1-274: 1-[2-chloro-4-(trifluoromethyl)phenyl]-4-(2'-methoxy-[2,3'-bipyridin]-5-yl)-N-[2-(methylamino)ethyl]piperidine-4-carboxamide;

1-275: 1-[2-cyano-4-(trifluoromethyl)phenyl]-N-[(2R)-2-(dimethylamino)-3-hydroxypropyl]-4-[6-(1-methyl-1H-pyrrol-2-yl)pyridin-3-yl]piperidine-4-carboxamide;

1-276: N-[2-(dimethylamino)ethyl]-1-[2-fluoro-4-(trifluoromethyl)phenyl]-4-[6-(1-methyl-1H-pyrrol-2-yl)pyridin-3-yl]piperidine-4-carboxamide;

1-277: 1-[2-cyano-4-(trifluoromethyl)phenyl]-N-{[(2S,4S)-4-fluoro-1-methylpyrrolidin-2-yl]methyl}-4-[6-(1-methyl-1H-pyrrol-2-yl)pyridin-3-yl]piperidine-4-carboxamide;

1-278: 1-[2-cyano-4-(trifluoromethyl)phenyl]-N-{[(2S,4R)-4-fluoro-1-methylpyrrolidin-2-yl]methyl}-4-[6-(1-methyl-1H-pyrrol-2-yl)pyridin-3-yl]piperidine-4-carboxamide;

1-279: 1-[2-cyano-4-(trifluoromethyl)phenyl]-N-{[(2S)-4,4-difluoro-1-methylpyrrolidin-2-yl]methyl}-4-[6-(1-methyl-1H-pyrrol-2-yl)pyridin-3-yl]piperidine-4-carboxamide;

1-280: 1-[2-cyano-4-(trifluoromethyl)phenyl]-N-{[(2R)-4,4-difluoro-1-methylpyrrolidin-2-yl]methyl}-4-[6-(1-methyl-1H-pyrrol-2-yl)pyridin-3-yl]piperidine-4-carboxamide;

1-281: 1-[2-fluoro-4-(trifluoromethyl)phenyl]-4-[6-(1-methyl-1H-pyrrol-2-yl)pyridin-3-yl]-N-[2-(methylamino)ethyl]piperidine-4-carboxamide;

1-282: 1-[2-chloro-4-(trifluoromethyl)phenyl]-N-[2-(dimethylamino)ethyl]-4-[6-(1-methyl-1H-pyrrol-2-yl)pyridin-3-yl]piperidine-4-carboxamide;

1-283: 1-[2-chloro-4-(trifluoromethyl)phenyl]-4-[6-(1-methyl-1H-pyrrol-2-yl)pyridin-3-yl]-N-[2-(methylamino)ethyl]piperidine-4-carboxamide;

1-284: N-[2-(dimethylamino)ethyl]-4-{2'-ethoxy-3-fluoro-[2,3'-bipyridin]-5-yl}-1-[2-fluoro-4-(trifluoromethyl)phenyl]piperidine-4-carboxamide;

1-285: N-[2-(dimethylamino)ethyl]-1-[2-fluoro-4-(trifluoromethyl)phenyl]-4-[5-fluoro-6-(2-methoxyphenyl)pyridin-3-yl]piperidine-4-carboxamide;

1-286: 1-[2-chloro-4-(trifluoromethyl)phenyl]-N-[2-(dimethylamino)ethyl]-4-[5-fluoro-6-(2-methoxyphenyl)pyridin-3-yl]piperidine-4-carboxamide;

1-287: 4-{2'-ethoxy-3-fluoro-[2,3'-bipyridin]-5-yl}-1-[2-fluoro-4-(trifluoromethyl)phenyl]-N-[2-(methylamino)ethyl]piperidine-4-carboxamide;

1-288: 1-[2-chloro-4-(trifluoromethyl)phenyl]-N-[2-(dimethylamino)ethyl]-4-{2'-ethoxy-3-fluoro-[2,3'-bipyridin]-5-yl}piperidine-4-carboxamide;

1-289: N-[2-(dimethylamino)ethyl]-4-[6-(2-ethoxyphenyl)-5-fluoropyridin-3-yl]-1-[2-fluoro-4-(trifluoromethyl)phenyl]piperidine-4-carboxamide;

1-290: 4-[6-(2-ethoxyphenyl)-5-fluoropyridin-3-yl]-1-[2-fluoro-4-(trifluoromethyl)phenyl]-N-[2-(methylamino)ethyl]piperidine-4-carboxamide;

1-291: 1-[2-chloro-4-(trifluoromethyl)phenyl]-N-[2-(dimethylamino)ethyl]-4-[6-(2-ethoxyphenyl)-5-fluoropyridin-3-yl]piperidine-4-carboxamide;

1-292: 1-[2-chloro-4-(trifluoromethyl)phenyl]-4-[6-(2-ethoxyphenyl)-5-fluoropyridin-3-yl]-N-[2-(methylamino)ethyl]piperidine-4-carboxamide;

1-293: 1-[2-fluoro-4-(trifluoromethyl)phenyl]-4-[5-fluoro-6-(2-methoxyphenyl)pyridin-3-yl]-N-[2-(methylamino)ethyl]piperidine-4-carboxamide;

1-294: 1-[2-chloro-4-(trifluoromethyl)phenyl]-4-[5-fluoro-6-(2-methoxyphenyl)pyridin-3-yl]-N-[2-(methylamino)ethyl]piperidine-4-carboxamide;

1-295: N-[(2S)-1-(dimethylamino)propan-2-yl]-1-[2-fluoro-4-(trifluoromethyl)phenyl]-4-{2'-methoxy-[2,3'-bipyridin]-5-yl}piperidine-4-carboxamide;

1-296: 1-[2-chloro-4-(trifluoromethyl)phenyl]-N-[(2S)-1-(dimethylamino)propan-2-yl]-4-{2'-methoxy-[2,3'-bipyridin]-5-yl}piperidine-4-carboxamide;

1-297: N-[(2S)-1-(dimethylamino)propan-2-yl]-1-[2-fluoro-4-(trifluoromethyl)phenyl]-4-[6-(1-methyl-1H-pyrrol-2-yl)pyridin-3-yl]piperidine-4-carboxamide;

1-298: 1-[2-fluoro-4-(trifluoromethyl)phenyl]-4-[6-(1-methyl-1H-pyrrol-2-yl)pyridin-3-yl]-N-[(2S)-1-(methylamino)propan-2-yl]piperidine-4-carboxamide;

1-299: 1-[2-chloro-4-(trifluoromethyl)phenyl]-4-{2'-ethoxy-3-fluoro-[2,3'-bipyridin]-5-yl}-N-[2-(methylamino)ethyl]piperidine-4-carboxamide;

1-300: N-[2-(dimethylamino)ethyl]-4-{3-fluoro-2'-methoxy-[2,3'-bipyridin]-5-yl}-1-[2-fluoro-4-(trifluoromethyl)phenyl]piperidine-4-carboxamide;

1-301: 4-{3-fluoro-2'-methoxy-[2,3'-bipyridin]-5-yl}-1-[2-fluoro-4-(trifluoromethyl)phenyl]-N-[2-(methylamino)ethyl]piperidine-4-carboxamide;

1-302: 1-[2-chloro-4-(trifluoromethyl)phenyl]-N-[2-(dimethylamino)ethyl]-4-{3-fluoro-2'-methoxy-[2,3'-bipyridin]-5-yl}piperidine-4-carboxamide;

1-303: 1-[2-chloro-4-(trifluoromethyl)phenyl]-4-{3-fluoro-2'-methoxy-[2,3'-bipyridin]-5-yl}-N-[2-(methylamino)ethyl]piperidine-4-carboxamide;

1-304: N-[2-(dimethylamino)ethyl]-1-[2-fluoro-4-(trifluoromethyl)phenyl]-4-[5-fluoro-6-(1-methyl-1H-pyrrol-2-yl)pyridin-3-yl]piperidine-4-carboxamide;

1-305: 1-[2-fluoro-4-(trifluoromethyl)phenyl]-4-[5-fluoro-6-(1-methyl-1H-pyrrol-2-yl)pyridin-3-yl]-N-[2-(methylamino)ethyl]piperidine-4-carboxamide;

1-306: 1-[2-fluoro-4-(trifluoromethyl)phenyl]-4-{2'-methoxy-[2,3'-bipyridin]-5-yl}-N-[(2S)-1-(methylamino)propan-2-yl]piperidine-4-carboxamide;

1-307: 1-[2-chloro-4-(trifluoromethyl)phenyl]-4-{2'-methoxy-[2,3'-bipyridin]-5-yl}-N-[(2S)-1-(methylamino)propan-2-yl]piperidine-4-carboxamide;

1-308: 1-[2-cyano-4-(trifluoromethyl)phenyl]-N-[2-(dimethylamino)ethyl]-4-{2'-ethoxy-3-fluoro-[2,3'-bipyridin]-5-yl}piperidine-4-carboxamide;

1-309: 1-[2-chloro-4-(trifluoromethyl)phenyl]-N-[2-(dimethylamino)ethyl]-4-[5-fluoro-6-(1-methyl-1H-pyrrol-2-yl)pyridin-3-yl]piperidine-4-carboxamide;

1-310: 1-[2-chloro-4-(trifluoromethyl)phenyl]-4-[5-fluoro-6-(1-methyl-1H-pyrrol-2-yl)pyridin-3-yl]-N-[2-(methylamino)ethyl]piperidine-4-carboxamide;

1-311: 1-[2-cyano-4-(trifluoromethyl)phenyl]-4-{2'-ethoxy-3-fluoro-[2,3'-bipyridin]-5-yl}-N-[2-(methylamino)ethyl]piperidine-4-carboxamide;

1-312: N-[(2S)-1-(dimethylamino)propan-2-yl]-4-{2'-ethoxy-3-fluoro-[2,3'-bipyridin]-5-yl}-1-[2-fluoro-4-(trifluoromethyl)phenyl]piperidine-4-carboxamide;

1-313: 1-[2-cyano-4-(trifluoromethyl)phenyl]-N-[(2S)-1-(dimethylamino)propan-2-yl]-4-{2'-ethoxy-[2,3'-bipyridin]-5-yl}piperidine-4-carboxamide;

1-314: 1-[2-cyano-4-(trifluoromethyl)phenyl]-4-{2'-ethoxy-[2,3'-bipyridin]-5-yl}-N-[(2S)-1-(methylamino)propan-2-yl]piperidine-4-carboxamide;

1-315: 4-{2'-ethoxy-3-fluoro-[2,3'-bipyridin]-5-yl}-1-[2-fluoro-4-(trifluoromethyl)phenyl]-N-[(2S)-1-(methylamino)propan-2-yl]piperidine-4-carboxamide;

1-316: 1-[2-cyano-4-(trifluoromethyl)phenyl]-4-[6-(1-methyl-1H-pyrrol-2-yl)pyridin-3-yl]-N-[(2S)-1-(methylamino)propan-2-yl]piperidine-4-carboxamide;

1-317: N-[(2S)-1-(dimethylamino)propan-2-yl]-4-{2'-ethoxy-[2,3'-bipyridin]-5-yl}-1-[2-fluoro-4-(trifluoromethyl)phenyl]piperidine-4-carboxamide;

1-318: 1-(2,4-dichlorophenyl)-N-[(2S)-1-(dimethylamino)propan-2-yl]-4-{2'-ethoxy-[2,3'-bipyridin]-5-yl}piperidine-4-carboxamide;

1-319: 1-[2-cyano-4-(trifluoromethyl)phenyl]-N-[(2S)-1-(dimethylamino)propan-2-yl]-4-{2'-ethoxy-3-fluoro-[2,3'-bipyridin]-5-yl}piperidine-4-carboxamide;

1-320: 1-[2-cyano-4-(trifluoromethyl)phenyl]-4-{2'-ethoxy-3-fluoro-[2,3'-bipyridin]-5-yl}-N-[(2S)-1-(methylamino)propan-2-yl]piperidine-4-carboxamide;

1-321: 4-{2'-ethoxy-[2,3'-bipyridin]-5-yl}-1-[2-fluoro-4-(trifluoromethyl)phenyl]-N-[(2S)-1-(methylamino)propan-2-yl]piperidine-4-carboxamide;

1-322: 1-(2,4-dichlorophenyl)-4-{2'-ethoxy-[2,3'-bipyridin]-5-yl}-N-[(2S)-1-(methylamino)propan-2-yl]piperidine-4-carboxamide;

1-323: 1-(4-chloro-2-cyanophenyl)-4-{2'-ethoxy-3-fluoro-[2,3'-bipyridin]-5-yl}-N-[(2S)-1-(methylamino)propan-2-yl]piperidine-4-carboxamide;

1-324: 1-[2-cyano-4-(trifluoromethyl)phenyl]-N-[(2S)-1-(dimethylamino)propan-2-yl]-4-[5-fluoro-6-(1-methyl-1H-pyrrol-2-yl)pyridin-3-yl]piperidine-4-carboxamide;

1-325: 1-(4-chloro-2-cyanophenyl)-N-[(2S)-1-(dimethylamino)propan-2-yl]-4-{2'-ethoxy-3-fluoro-[2,3'-bipyridin]-5-yl}piperidine-4-carboxamide;

1-326: 1-[2-cyano-4-(trifluoromethyl)phenyl]-4-[5-fluoro-6-(1-methyl-1H-pyrrol-2-yl)pyridin-3-yl]-N-[(2S)-1-(methylamino)propan-2-yl]piperidine-4-carboxamide;

1-327: 1-[2-cyano-4-(trifluoromethyl)phenyl]-4-[6-(2-methoxyphenyl)pyridin-3-yl]-N-{[(2S)-4-methylmorpholin-2-yl]methyl}piperidine-4-carboxamide;

1-328: 1-[2-cyano-4-(trifluoromethyl)phenyl]-4-[6-(2-methoxyphenyl)pyridin-3-yl]-N-{[(3S)-4-methylmorpholin-3-yl]methyl}piperidine-4-carboxamide;

1-329: 1-[2-cyano-4-(trifluoromethyl)phenyl]-4-[6-(2-methoxyphenyl)pyridin-3-yl]-N-{[(3R)-4-methylmorpholin-3-yl]methyl}piperidine-4-carboxamide;

1-330: 1-[2-cyano-4-(trifluoromethyl)phenyl]-4-[6-(2-methoxyphenyl)pyridin-3-yl]-N-{[(2R)-4-methylmorpholin-2-yl]methyl}piperidine-4-carboxamide;

1-331: 1-[2-cyano-4-(trifluoromethyl)phenyl]-N-[2-(dimethylamino)ethyl]-4-[6-(2-ethoxypyridin-3-yl)pyridazin-3-yl]piperidine-4-carboxamide;

1-332: 1-[2-cyano-4-(trifluoromethyl)phenyl]-N-[(2S)-2-(dimethylamino)propyl]-4-{2'-ethoxy-[2,3'-bipyridin]-5-yl}piperidine-4-carboxamide;

1-333: 1-[2-cyano-4-(trifluoromethyl)phenyl]-N-[(2R)-2-(dimethylamino)propyl]-4-{2'-ethoxy-[2,3'-bipyridin]-5-yl}piperidine-4-carboxamide;

1-334: 1-[2-cyano-4-(trifluoromethyl)phenyl]-N-[(2R)-2-(dimethylamino)-3-hydroxypropyl]-4-{2'-ethoxy-3-fluoro-[2,3'-bipyridin]-5-yl}piperidine-4-carboxamide;

1-335: N-[2-(dimethylamino)ethyl]-4-[6-(2-ethoxypyridin-3-yl)pyridazin-3-yl]-1-[2-fluoro-4-(trifluoromethyl)phenyl]piperidine-4-carboxamide;

2-1: 2-{4-[2-(dimethylamino)ethoxy]-4-[4-(2-ethoxypyridin-3-yl)phenyl]piperidin-1-yl}-5-(trifluoromethyl)benzonitrile;

2-2: 1-[2-cyano-4-(trifluoromethyl)phenyl]-4-[4-(2-ethoxypyridin-3-yl)phenyl]piperidin-4-yl N-[2-(dimethylamino)ethyl]carbamate;

2-3: 3-amino-N-{1-[2-cyano-4-(trifluoromethyl)phenyl]-4-[4-(2-ethoxypyridin-3-yl)phenyl]piperidin-4-yl}propanamide;

2-4: 3-amino-N-{1-[2-cyano-4-(trifluoromethyl)phenyl]-4-{2'-ethoxy-[2,3'-bipyridin]-5-yl}piperidin-4-yl}propanamide;

2-5: N-{1-[2-cyano-4-(trifluoromethyl)phenyl]-4-{2'-ethoxy-[2,3'-bipyridin]-5-yl}piperidin-4-yl}-3-(methylamino)propanamide;

2-6: (3R)—N-{1-[2-cyano-4-(trifluoromethyl)phenyl]-4-{2'-ethoxy-[2,3'-bipyridin]-5-yl}piperidin-4-yl}pyrrolidine-3-carboxamide;

2-7: (3R)—N-{1-[2-cyano-4-(trifluoromethyl)phenyl]-4-{2'-ethoxy-[2,3'-bipyridin]-5-yl}piperidin-4-yl}-1-methylpyrrolidine-3-carboxamidev;

2-8: (3S)—N-{1-[2-cyano-4-(trifluoromethyl)phenyl]-4-{2'-ethoxy-[2,3'-bipyridin]-5-yl}piperidin-4-yl}pyrrolidine-3-carboxamide;

2-9: (3S)—N-{1-[2-cyano-4-(trifluoromethyl)phenyl]-4-{2'-ethoxy-[2,3'-bipyridin]-5-yl}piperidin-4-yl}-1-methylpyrrolidine-3-carboxamide;

2-10: N-{1-[2-cyano-4-(trifluoromethyl)phenyl]-4-{2'-ethoxy-[2,3'-bipyridin]-5-yl}piperidin-4-yl}-3-(dimethylamino)propanamide;

2-11: (2S)—N-{1-[2-cyano-4-(trifluoromethyl)phenyl]-4-[4-(2-ethoxypyridin-3-yl)phenyl]piperidin-4-yl}-1-methylpyrrolidine-2-carboxamide;

2-12: (3R)-1-methylpyrrolidin-3-yl N-{1-[2-cyano-4-(trifluoromethyl)phenyl]-4-[4-(2-ethoxypyridin-3-yl)phenyl]piperidin-4-yl}carbamate;

2-13: (3S)-1-methylpyrrolidin-3-yl N-{1-[2-cyano-4-(trifluoromethyl)phenyl]-4-[4-(2-ethoxypyridin-3-yl)phenyl]piperidin-4-yl}carbamate;

2-14: 2-(4-{2'-ethoxy-[2,3'-bipyridin]-5-yl}-4-[(2-hydroxyethyl)amino]piperidin-1-yl)-5-(trifluoromethyl)benzonitrile;

2-15: 2-(4-{2'-ethoxy-[2,3'-bipyridin]-5-yl}-4-{[2-(methylamino)ethyl]amino}piperidin-1-yl)-5-(trifluoromethyl)benzonitrile;

2-16: N-{1-[2-cyano-4-(trifluoromethyl)phenyl]-4-[4-(2-ethoxypyridin-3-yl)phenyl]piperidin-4-yl}-1-methylazetidine-3-carboxamide;

2-17: (2R)—N-{1-[2-cyano-4-(trifluoromethyl)phenyl]-4-[4-(2-ethoxypyridin-3-yl)phenyl]piperidin-4-yl}-1-methylpyrrolidine-2-carboxamide;

2-18: (3S)-1-methylpyrrolidin-3-yl N-{1-[2-cyano-4-(trifluoromethyl)phenyl]-4-{2'-ethoxy-[2,3'-bipyridin]-5-yl}piperidin-4-yl}carbamate;

2-19: 1-{1-[2-cyano-4-(trifluoromethyl)phenyl]-4-{2'-ethoxy-[2,3'-bipyridin]-5-yl}piperidin-4-yl}-3-[(3R)-1-methylpyrrolidin-3-yl]urea;

2-20: 1-{1-[2-cyano-4-(trifluoromethyl)phenyl]-4-{2'-ethoxy-[2,3'-bipyridin]-5-yl}piperidin-4-yl}-3-[(3S)-1-methylpyrrolidin-3-yl]urea;

2-21: (3R)—N-{1-[2-cyano-4-(trifluoromethyl)phenyl]-4-{2'-ethoxy-[2,3'-bipyridin]-5-yl}piperidin-4-yl}-3-(methylamino)pyrrolidine-1-carboxamide;

2-22: (3R)-1-methylpyrrolidin-3-yl N-{1-[2-cyano-4-(trifluoromethyl)phenyl]-4-{2'-ethoxy-[2,3'-bipyridin]-5-yl}piperidin-4-yl}carbamate;

2-23: N-{1-[2-cyano-4-(trifluoromethyl)phenyl]-4-{2'-ethoxy-[2,3'-bipyridin]-5-yl}piperidin-4-yl}-3-(methylamino)azetidine-1-carboxamide;

2-24: (3S)—N-{1-[2-cyano-4-(trifluoromethyl)phenyl]-4-{2'-ethoxy-[2,3'-bipyridin]-5-yl}piperidin-4-yl}-3-(methylamino)pyrrolidine-1-carboxamide;

2-25: N-[1-(4-chloro-2-cyanophenyl)-4-[6-(2-ethoxyphenyl)pyridin-3-yl]piperidin-4-yl]-1-methylazetidine-3-carboxamide;

2-26: N-{1-[2-cyano-4-(trifluoromethyl)phenyl]-4-{2'-ethoxy-[2,3'-bipyridin]-5-yl}piperidin-4-yl}-2-(dimethylamino)acetamide;

2-27: (3S)—N-{1-[2-cyano-4-(trifluoromethyl)phenyl]-4-[6-(2-ethoxyphenyl)pyridin-3-yl]piperidin-4-yl}-1-methylpyrrolidine-3-carboxamide;

2-28: (3S)—N-[1-(4-chloro-2-cyanophenyl)-4-[6-(2-ethoxyphenyl)pyridin-3-yl]piperidin-4-yl]-1-methylpyrrolidine-3-carboxamide;

2-29: (3R)—N-[1-(4-chloro-2-cyanophenyl)-4-[6-(2-ethoxyphenyl)pyridin-3-yl]piperidin-4-yl]-1-methylpyrrolidine-3-carboxamide;

2-30: N-[1-(4-chloro-2-cyanophenyl)-4-[6-(2-ethoxyphenyl)pyridin-3-yl]piperidin-4-yl]-3-(dimethylamino)propanamide;

2-31: N-[1-(4-chloro-2-cyanophenyl)-4-[6-(2-ethoxyphenyl)pyridin-3-yl]piperidin-4-yl]-2-(dimethylamino)acetamide;

2-32: N-{1-[2-cyano-4-(trifluoromethyl)phenyl]-4-{2'-ethoxy-[2,3'-bipyridin]-5-yl}piperidin-4-yl}-1-methylazetidine-3-carboxamide;

2-33: (3R)—N-{1-[2-cyano-4-(trifluoromethyl)phenyl]-4-[6-(2-ethoxyphenyl)pyridin-3-yl]piperidin-4-yl}-1-methylpyrrolidine-3-carboxamide;

2-34: N-{1-[2-cyano-4-(trifluoromethyl)phenyl]-4-[6-(2-ethoxyphenyl)pyridin-3-yl]piperidin-4-yl}-2-(dimethylamino)acetamide;

2-35: N-{1-[2-cyano-4-(trifluoromethyl)phenyl]-4-[6-(2-ethoxyphenyl)pyridin-3-yl]piperidin-4-yl}-1-methylazetidine-3-carboxamide;

2-36: N-{1-[2-cyano-4-(trifluoromethyl)phenyl]-4-[6-(2-ethoxyphenyl)pyridin-3-yl]piperidin-4-yl}-3-(dimethylamino)propanamide;

2-37: N-[1-(4-chloro-2-cyanophenyl)-4-{2'-ethoxy-[2,3'-bipyridin]-5-yl}piperidin-4-yl]-1-methylazetidine-3-carboxamide;

2-38: N-[1-(4-chloro-2-cyanophenyl)-4-{2'-ethoxy-[2,3'-bipyridin]-5-yl}piperidin-4-yl]-2-(dimethylamino)acetamide;

2-39: (3S)—N-[1-(4-chloro-2-cyanophenyl)-4-{2'-ethoxy-[2,3'-bipyridin]-5-yl}piperidin-4-yl]-1-methylpyrrolidine-3-carboxamide;

2-40: N-{1-[2-cyano-4-(trifluoromethyl)phenyl]-4-{2'-methoxy-[2,3'-bipyridin]-5-yl}piperidin-4-yl}-1-methylazetidine-3-carboxamide;

2-41: (3R)-1-methylpyrrolidin-3-yl N-{1-[2-cyano-4-(trifluoromethyl)phenyl]-4-[6-(1-methyl-1H-pyrrol-2-yl)pyridin-3-yl]piperidin-4-yl}carbamate;

2-42: (3S)-1-methylpyrrolidin-3-yl N-{-[2-cyano-4-(trifluoromethyl)phenyl]-4-[6-(1-methyl-1H-pyrrol-2-yl)pyridin-3-yl]piperidin-4-yl}carbamate;

2-43: 1-(1-[2-cyano-4-(trifluoromethyl)phenyl]-4-[6-(1-methyl-1H-pyrrol-2-yl)pyridin-3-yl]piperidin-4-yl)-3-[(3S)-1-methylpyrrolidin-3-yl]urea;

2-44: (3S)—N-{1-[2-cyano-4-(trifluoromethyl)phenyl]-4-[6-(1-methyl-1H-pyrrol-2-yl)pyridin-3-yl]piperidin-4-yl}pyrrolidine-3-carboxamide;

2-45: N-(1-[2-cyano-4-(trifluoromethyl)phenyl]-4-[6-(1-methyl-1H-pyrrol-2-yl)pyridin-3-yl]piperidin-4-yl)-1-methylazetidine-3-carboxamide;

2-46: (3S)—N-{1-[2-cyano-4-(trifluoromethyl)phenyl]-4-[6-(1-methyl-1H-pyrrol-2-yl)pyridin-3-yl]piperidin-4-yl}-1-methylpyrrolidine-3-carboxamide; and 2-47: (3R)—N-{1-[2-cyano-4-(trifluoromethyl)phenyl]-4-[6-(1-methyl-1H-pyrrol-2-yl)pyridin-3-yl]piperidin-4-yl}-1-methylpyrrolidine-3-carboxamide;

2-48: 1-{1-[2-cyano-4-(trifluoromethyl)phenyl]-4-[6-(1-methyl-1H-pyrrol-2-yl)pyridin-3-yl]piperidin-4-yl}-3-[(3R)-1-methylpyrrolidin-3-yl]urea;

2-49: (3S)-1-methylpyrrolidin-3-yl N-{1-[2-cyano-4-(trifluoromethyl)phenyl]-4-[5-fluoro-6-(2-methoxyphenyl)pyridin-3-yl]piperidin-4-yl}carbamate;

2-50: (3R)-1-methylpyrrolidin-3-yl N-{1-[2-cyano-4-(trifluoromethyl)phenyl]-4-[5-fluoro-6-(2-methoxyphenyl)pyridin-3-yl]piperidin-4-yl}carbamate;

2-51: 1-{1-[2-cyano-4-(trifluoromethyl)phenyl]-4-[5-fluoro-6-(2-methoxyphenyl)pyridin-3-yl]piperidin-4-yl}-3-[(3S)-1-methylpyrrolidin-3-yl]urea;

2-52: 1-{1-[2-cyano-4-(trifluoromethyl)phenyl]-4-[5-fluoro-6-(2-methoxyphenyl)pyridin-3-yl]piperidin-4-yl}-3-[(3R)-1-methylpyrrolidin-3-yl]urea;

2-53: (3S)-1-methylpyrrolidin-3-yl N-{1-[2-cyano-4-(trifluoromethyl)phenyl]-4-[6-(2-methoxyphenyl)pyridin-3-yl]piperidin-4-yl}carbamate;

2-54: (3R)-1-methylpyrrolidin-3-yl N-{1-[2-cyano-4-(trifluoromethyl)phenyl]-4-[6-(2-methoxyphenyl)pyridin-3-yl]piperidin-4-yl}carbamate;

2-55: 1-{1-[2-cyano-4-(trifluoromethyl)phenyl]-4-[6-(2-methoxyphenyl)pyridin-3-yl]piperidin-4-yl}-3-[(3S)-1-methylpyrrolidin-3-yl]urea;

2-56: 1-{1-[2-cyano-4-(trifluoromethyl)phenyl]-4-[6-(2-methoxyphenyl)pyridin-3-yl]piperidin-4-yl}-3-[(3R)-1-methylpyrrolidin-3-yl]urea;

2-57: 2-(dimethylamino)ethyl N-{1-[2-cyano-4-(trifluoromethyl)phenyl]-4-[6-(2-methoxyphenyl)pyridin-3-yl]piperidin-4-yl}carbamate;

2-58: 1-{1-[2-cyano-4-(trifluoromethyl)phenyl]-4-[6-(2-methoxyphenyl)pyridin-3-yl]piperidin-4-yl}-3-[2-(dimethylamino)ethyl]urea;

2-59: 1-{1-[2-cyano-4-(trifluoromethyl)phenyl]-4-[6-(2-methoxyphenyl)pyridin-3-yl]piperidin-4-yl}-3-(1-methylazetidin-3-yl)urea;

2-60: (3R)—N-{1-[2-cyano-4-(trifluoromethyl)phenyl]-4-[6-(2-methoxyphenyl)pyridin-3-yl]piperidin-4-yl}-1-methylpyrrolidine-3-carboxamide;

2-61: N-{1-[2-cyano-4-(trifluoromethyl)phenyl]-4-[5-fluoro-6-(2-methoxyphenyl)pyridin-3-yl]piperidin-4-yl}-2-(dimethylamino)acetamide;

2-62: N-{1-[2-cyano-4-(trifluoromethyl)phenyl]-4-[5-fluoro-6-(2-methoxyphenyl)pyridin-3-yl]piperidin-4-yl}-3-(dimethylamino)propanamide;

2-63: N-{1-[2-cyano-4-(trifluoromethyl)phenyl]-4-[5-fluoro-6-(2-methoxyphenyl)pyridin-3-yl]piperidin-4-yl}-3-(methylamino)propanamide;

2-64: N-{1-[2-cyano-4-(trifluoromethyl)phenyl]-4-[6-(2-ethoxypyridin-3-yl)pyridazin-3-yl]piperidin-4-yl}-3-(dimethylamino)propanamide;

or a pharmaceutically acceptable salt thereof.

17. A pharmaceutical composition comprising a compound of claim 1, or a pharmaceutically acceptable salt thereof, and at least one pharmaceutically acceptable excipient.

18. A method of treating Cushing's syndrome, ectopic Cushing's syndrome, congenital adrenal hyperplasia (CAH), or for reducing the secretion of adrenocorticotropic hormone (ACTH) in a mammal comprising administering a compound of claim 1, or a pharmaceutically acceptable salt thereof, to the mammal in need thereof.

19. A compound that is N-{1-[2-cyano-4-(trifluoromethyl)phenyl]-4-[5-fluoro-6-(2-methoxyphenyl)pyridin-3-yl]piperidin-4-yl}-3-(dimethylamino)propenamide, which has the following structure:

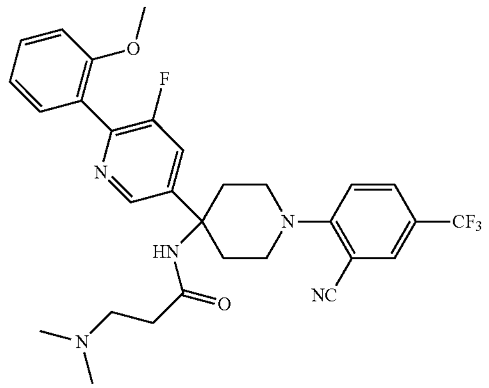 [SMILES: COc1ccccc1-c1ncc(C2(NC(=O)CCN(C)C)CCN(c3ccc(C(F)(F)F)cc3C#N)CC2)cc1F]

or a pharmaceutically acceptable salt thereof.

20. A pharmaceutical composition comprising a compound of claim 19, or a pharmaceutically acceptable salt thereof, and at least one pharmaceutically acceptable excipient.

21. A method of treating Cushing's syndrome, ectopic Cushing's syndrome, congenital adrenal hyperplasia (CAH), or for reducing the secretion of adrenocorticotropic hormone (ACTH) in a mammal comprising administering a compound of claim 19, or a pharmaceutically acceptable salt thereof, to the mammal in need thereof.

* * * * *